(12) United States Patent
Hornberger

(10) Patent No.: US 11,957,759 B1
(45) Date of Patent: Apr. 16, 2024

(54) RAPIDLY ACCELERATED FIBROSARCOMA (RAF) DEGRADING COMPOUNDS AND ASSOCIATED METHODS OF USE

(71) Applicant: Arvinas Operations, Inc., New Haven, CT (US)

(72) Inventor: Keith R. Hornberger, Southbury, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 18/243,177

(22) Filed: Sep. 7, 2023

Related U.S. Application Data

(60) Provisional application No. 63/525,770, filed on Jul. 10, 2023, provisional application No. 63/451,822, filed on Mar. 13, 2023, provisional application No. 63/404,228, filed on Sep. 7, 2022.

(51) Int. Cl.
 *A61K 47/55* (2017.01)
 *A61K 47/54* (2017.01)

(52) U.S. Cl.
 CPC ............ *A61K 47/55* (2017.08); *A61K 47/545* (2017.08)

(58) Field of Classification Search
 CPC .............................. A61K 47/55; A61K 47/545
 USPC .......................................................... 544/284
 See application file for complete search history.

(56) References Cited

U.S. PATENT DOCUMENTS

| | | |
|---|---|---|
| 6,268,391 B1 | 7/2001 | Dickerson et al. |
| 6,306,663 B1 | 10/2001 | Kenten et al. |
| 6,670,348 B1 | 12/2003 | Rosen et al. |
| 7,030,141 B2 | 4/2006 | Bigge et al. |
| 7,041,298 B2 | 5/2006 | Deshaies et al. |
| 7,208,157 B2 | 4/2007 | Dashaies et al. |
| 7,244,851 B2 | 7/2007 | Cohen et al. |
| 7,345,081 B2 | 3/2008 | Cohen et al. |
| 7,419,975 B2 | 9/2008 | Palermo et al. |
| 7,517,906 B2 | 4/2009 | Condon et al. |
| 7,915,293 B2 | 3/2011 | Ramesh |
| 9,447,070 B2 | 9/2016 | Muller et al. |
| 9,500,653 B2 | 11/2016 | Crews et al. |
| 9,632,089 B2 | 4/2017 | Crews et al. |
| 10,723,717 B2 | 7/2020 | Crew et al. |
| 11,173,211 B2 | 11/2021 | Crew et al. |
| 11,266,653 B2 | 3/2022 | Cooke |
| 11,338,012 B2 | 5/2022 | Wang et al. |
| 11,414,404 B2 | 8/2022 | Barbour et al. |
| 2003/0096841 A1 | 5/2003 | Robarge et al. |
| 2006/0128632 A1 | 6/2006 | Sharma et al. |
| 2008/0051432 A1 | 2/2008 | Zhang |
| 2008/0214501 A1 | 9/2008 | Pan et al. |
| 2008/0269140 A1 | 10/2008 | Wang et al. |
| 2010/0203012 A1 | 8/2010 | Laurent et al. |
| 2011/0195043 A1 | 8/2011 | Sun et al. |
| 2011/0230457 A1 | 9/2011 | Berghausen et al. |
| 2012/0270800 A1 | 10/2012 | Verdine et al. |
| 2013/0029993 A1 | 1/2013 | Stadtmueller |
| 2014/0088143 A1 | 3/2014 | Jain |
| 2014/0235629 A1 | 8/2014 | Bartberger et al. |
| 2014/0243372 A1 | 8/2014 | Rew |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0141470 A1 | 5/2015 | Garraway et al. |
| 2015/0259288 A1 | 9/2015 | Nam et al. |
| 2015/0291562 A1 | 10/2015 | Crew et al. |
| 2015/0344473 A1 | 12/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |

(Continued)

FOREIGN PATENT DOCUMENTS

| | | |
|---|---|---|
| CN | 1844118 A | 10/2006 |
| CN | 102050793 A | 5/2011 |

(Continued)

OTHER PUBLICATIONS

Ammar et al. European Journal of Medicinal Chemistry 158 (2018) 144-166, "Recent advances of RAF (rapidly accelerated fibrosarcoma) inhibitors as anti-cancer agents" (Year: 2018).*

(Continued)

*Primary Examiner* — Jared Barsky
*Assistant Examiner* — Liyuan Mou
(74) *Attorney, Agent, or Firm* — McCarter & English, LLP; Michael J. DeGrazia; James M. Alburger

(57) ABSTRACT

Provided herein are bifunctional compounds having the chemical structure I:

PTM-L-CLM    (I):

or pharmaceutically acceptable salts thereof, which find utility as modulators of Rapidly Accelerated Fibrosarcoma (Raf, such as c-Raf, A-Raf, and/or B-RAF) and are useful in the treatment of a variety of Raf mediated conditions or diseases, such as cancer, specifically lung cancer, skin cancer, or colorectal cancer.

6 Claims, 5 Drawing Sheets

(56) References Cited

U.S. PATENT DOCUMENTS

| | | |
|---|---|---|
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2018/0353501 A1 | 12/2018 | Crew et al. |
| 2019/0151295 A1 | 5/2019 | Crew et al. |
| 2020/0129627 A1 | 4/2020 | Crew et al. |
| 2021/0087171 A1 | 3/2021 | Fan et al. |
| 2022/0125936 A1 | 4/2022 | Sicheri et al. |
| 2022/0144809 A1 | 5/2022 | Dong et al. |
| 2022/0217979 A1 | 7/2022 | Tsuruda et al. |
| 2023/0000994 A1 | 1/2023 | Crew et al. |
| 2023/0081501 A1 | 3/2023 | Hornberger et al. |

FOREIGN PATENT DOCUMENTS

| | | |
|---|---|---|
| CN | 103159736 A | 6/2013 |
| CN | 103688176 A | 3/2014 |
| CN | 108276352 A | 7/2018 |
| CN | 114805303 A | 7/2022 |
| EP | 2985285 A1 | 2/2016 |
| JP | 2004-525889 A | 8/2004 |
| JP | 2010-502627 A | 1/2010 |
| JP | 2020-189891 A | 11/2020 |
| KR | 20180011759 A | 2/2018 |
| RU | 2008112221 A | 10/2009 |
| RU | 2418800 C2 | 5/2011 |
| RU | 2448101 C2 | 4/2012 |
| RU | 2011121567 A | 12/2012 |
| RU | 2012138709 A | 3/2014 |
| WO | WO-1998/003502 A1 | 1/1998 |
| WO | WO-2000/066119 A1 | 11/2000 |
| WO | WO-2002/048115 A2 | 6/2002 |
| WO | WO-2002/066512 A1 | 8/2002 |
| WO | WO-2002/096873 A1 | 12/2002 |
| WO | WO-2002/100845 A1 | 12/2002 |
| WO | WO-2003/033480 A1 | 4/2003 |
| WO | WO-2004/113307 A1 | 12/2004 |
| WO | WO-2005/016326 A2 | 2/2005 |
| WO | WO-2005/042502 A1 | 5/2005 |
| WO | WO-2005/097791 A1 | 10/2005 |
| WO | WO-2006/024834 A1 | 3/2006 |
| WO | WO-2006/069063 A1 | 6/2006 |
| WO | WO-2006/084015 A2 | 8/2006 |
| WO | WO-2006/090143 A1 | 8/2006 |
| WO | WO-2006/113942 A2 | 10/2006 |
| WO | WO-2007/056167 A2 | 5/2007 |
| WO | WO-2007/101347 A1 | 9/2007 |
| WO | WO-2007/106670 A2 | 9/2007 |
| WO | WO-2007/115289 A2 | 10/2007 |
| WO | WO-2007/130626 A2 | 11/2007 |
| WO | WO-2008/011392 A2 | 1/2008 |
| WO | WO-2008/014236 A1 | 1/2008 |
| WO | WO-2008/044688 A1 | 4/2008 |
| WO | WO-2008/109057 A1 | 9/2008 |
| WO | WO-2008/128121 A1 | 10/2008 |
| WO | WO-2008/128171 A2 | 10/2008 |
| WO | WO-2008/134679 A1 | 11/2008 |
| WO | WO-2009/015254 A1 | 1/2009 |
| WO | WO-2009/060292 A2 | 5/2009 |
| WO | WO-2010/063784 A1 | 6/2010 |
| WO | WO-2010/107485 A1 | 9/2010 |
| WO | WO-2010/141805 A1 | 12/2010 |
| WO | WO-2011/008260 A2 | 1/2011 |
| WO | WO-2011/045258 A1 | 4/2011 |
| WO | WO-2012/003281 A2 | 1/2012 |
| WO | WO-2012/007409 A1 | 1/2012 |
| WO | WO-2012/040527 A2 | 3/2012 |
| WO | WO-2012/078559 A2 | 6/2012 |
| WO | WO-2012/090104 A1 | 7/2012 |
| WO | WO-2012/118492 A1 | 9/2012 |
| WO | WO-2013/071035 A1 | 5/2013 |
| WO | WO-2013/071039 A1 | 5/2013 |
| WO | WO-2013/097224 A1 | 7/2013 |
| WO | WO-2013/106643 A2 | 7/2013 |
| WO | WO-2013/106646 A2 | 7/2013 |
| WO | WO-2013/170147 A1 | 11/2013 |
| WO | WO-2013/175417 A1 | 11/2013 |
| WO | WO-2013/178570 A1 | 12/2013 |
| WO | WO-2014/011712 A1 | 1/2014 |
| WO | WO-2014/020502 A2 | 2/2014 |
| WO | WO-2014/025759 A1 | 2/2014 |
| WO | WO-2014/038606 A1 | 3/2014 |
| WO | WO-2014/047024 A1 | 3/2014 |
| WO | WO-2014/055461 A1 | 4/2014 |
| WO | WO-2014/074658 A1 | 5/2014 |
| WO | WO-2014/100065 A1 | 6/2014 |
| WO | WO-2014/100071 A2 | 6/2014 |
| WO | WO-2014/107713 A1 | 7/2014 |
| WO | WO-2014/108452 A1 | 7/2014 |
| WO | WO-2014/123418 A1 | 8/2014 |
| WO | WO-2014/134201 A1 | 9/2014 |
| WO | WO-2014/151863 A1 | 9/2014 |
| WO | WO-2014/182643 A2 | 11/2014 |
| WO | WO-2015/000868 A1 | 1/2015 |
| WO | WO-2015/006524 A1 | 1/2015 |
| WO | WO-2015/040169 A1 | 3/2015 |
| WO | WO-2015/097621 A2 | 7/2015 |
| WO | WO-2015/160845 A2 | 10/2015 |
| WO | WO-2016/045765 A1 | 3/2016 |
| WO | WO-2016/105518 A1 | 6/2016 |
| WO | WO-2016/118666 A1 | 7/2016 |
| WO | WO-2016/146985 A1 | 9/2016 |
| WO | WO-2016/149668 A1 | 9/2016 |
| WO | WO-2016/151144 A1 | 9/2016 |
| WO | WO-2016/169989 A1 | 10/2016 |
| WO | WO-2016/172134 A2 | 10/2016 |
| WO | WO-2016/197114 A1 | 12/2016 |
| WO | WO-2017/007612 A1 | 1/2017 |
| WO | WO-2017/011590 A1 | 1/2017 |
| WO | WO-2017/024317 A2 | 2/2017 |
| WO | WO-2017/024318 A1 | 2/2017 |
| WO | WO-2017/024319 A1 | 2/2017 |
| WO | WO-2017/030814 A1 | 2/2017 |
| WO | WO-2017/046036 A1 | 3/2017 |
| WO | WO-2017/079267 A1 | 5/2017 |
| WO | WO-2017/117473 A1 | 7/2017 |
| WO | WO-2017/117474 A1 | 7/2017 |
| WO | WO-2017/161119 A1 | 9/2017 |
| WO | WO-2017/176957 A1 | 10/2017 |
| WO | WO-2017/176958 A1 | 10/2017 |
| WO | WO-2017/185023 A1 | 10/2017 |
| WO | WO-2017/185031 A1 | 10/2017 |
| WO | WO-2017/185034 A1 | 10/2017 |
| WO | WO-2017/185036 A1 | 10/2017 |
| WO | WO-2017/197051 A1 | 11/2017 |
| WO | WO-2017/197055 A1 | 11/2017 |
| WO | WO-2017/197056 A1 | 11/2017 |
| WO | WO-2017/223415 A1 | 12/2017 |
| WO | WO-2017/223452 A1 | 12/2017 |
| WO | WO-2018/052949 A1 | 3/2018 |
| WO | WO-2018/064589 A1 | 4/2018 |
| WO | WO-2018/098275 A1 | 5/2018 |
| WO | WO-2018/098280 A1 | 5/2018 |
| WO | WO-2018/098288 A1 | 5/2018 |
| WO | WO-2018/106870 A1 | 6/2018 |
| WO | WO-2018/119448 A1 | 6/2018 |
| WO | WO-2018/148440 A1 | 8/2018 |
| WO | WO-2018/200981 A1 | 11/2018 |
| WO | WO-2020/051564 A1 | 3/2020 |
| WO | WO-2020/203763 A1 | 10/2020 |
| WO | WO-2020/261156 A1 | 12/2020 |
| WO | WO-2021/16055 A1 | 1/2021 |

(56) References Cited

FOREIGN PATENT DOCUMENTS

| | | |
|---|---|---|
| WO | WO-2021/25052 A1 | 2/2021 |
| WO | WO-2021/061644 A1 | 4/2021 |
| WO | WO-2021/116050 A1 | 6/2021 |
| WO | WO-2021/129653 A1 | 7/2021 |
| WO | WO-2021/207532 A1 | 10/2021 |
| WO | WO-2021/224927 A1 | 11/2021 |
| WO | 2021/255212 A1 | 12/2021 |
| WO | 2021/255213 A1 | 12/2021 |
| WO | WO-2021/250521 A1 | 12/2021 |
| WO | WO-2022/011204 A1 | 1/2022 |
| WO | 2022/061348 A1 | 3/2022 |
| WO | WO-2022/047145 A1 | 3/2022 |
| WO | WO-2022/098544 A1 | 5/2022 |
| WO | 2022/129260 A1 | 6/2022 |
| WO | WO-2022/129259 A1 | 6/2022 |
| WO | 2022/258584 A1 | 12/2022 |
| WO | 2022/258612 A1 | 12/2022 |
| WO | 2022/259157 A1 | 12/2022 |
| WO | WO-2022/258600 A1 | 12/2022 |
| WO | WO-2022/261250 A1 | 12/2022 |
| WO | 2023/076991 A1 | 5/2023 |
| WO | 2023/078881 A1 | 5/2023 |

OTHER PUBLICATIONS

Ahn et al., HIF-1alpha peptide derivatives with modifications at the hydroxyproline residue as activators of HIF-1alpha. Bioorg Med Chem Lett. Aug. 1, 2009;19(15):4403-5.

Ardecky et al., Design, synthesis and evaluation of inhibitor of apoptosis protein (IAP) antagonists that are highly selective for the BIR2 domain of XIAP. Bioorg Med Chem Lett. Jul. 15, 2013;23(14):4253-7.

Arora et al., Design, synthesis and characterisation of a novel type II B-RAF paradox breaker inhibitor. Eur J Med Chem. Mar. 15, 2023;250:115231, 44 pages. Pre-publication edition.

Asano et al., Design, stereoselective synthesis, and biological evaluation of novel tri-cyclic compounds as inhibitor of apoptosis proteins (IAP) antagonists. Bioorg Med Chem. Sep. 15, 2013;21(18):5725-37.

Avery et al., Onco-immunomodulatory properties of pharmacological interference with RAS-RAF-MEK-ERK pathway hyperactivation. Front Oncol. Jul. 27, 2022;12:931774, 30 pages.

Bargagna-Mohan et al., Use of PROTACS as molecular probes of angiogenesis. Bioorg Med Chem Lett. Jun. 2, 2005;15(11):2724-7.

Bondeson et al., Catalytic in vivo protein knockdown by small-molecule PROTACs. Nat Chem Biol. Aug. 2015;11(8):611-7.

Bondeson et al., Lessons in PROTAC Design from Selective Degradation with a Promiscuous Warhead. Cell Chem Biol. Jan. 18, 2018;25(1):78-87.e5.

Bondeson et al., Targeted Protein Degradation by Small Molecules. Annu Rev Pharmacol Toxicol. Jan. 6, 2017;57:107-123.

Buckley et al., HaloPROTACS: Use of Small Molecule PROTACs to Induce Degradation of Halo Tag Fusion Proteins. ACS Chem Biol. Aug. 21, 2015;10(8):1831-7.

Buckley et al., Small-molecule inhibitors of the interaction between the E3 ligase VHL and HIF1a. Angew Chem Int Ed Engl. Nov. 12, 2012;51(46):11463-7.

Buckley et al., Targeting the von Hippel-Lindau E3 ubiquitin ligase using small molecules to disrupt the VHL/HIF-1a interaction. J Am Chem Soc. Mar. 14, 2012;134(10):4465-8.

Burslem et al., Small-Molecule Modulation of Protein Homeostasis. Chem Rev. Sep. 13, 2017;117(17):11269-11301.

Burslem et al., The Advantages of Targeted Protein Degradation Over Inhibition: An RTK Case Study. Cell Chem Biol. Jan. 1, 20188;25(1):67-77.e3.

Capitosti et al., Thalidomide analogues demonstrate dual inhibition of both angiogenesis and prostate cancer. Bioorg Med Chem. Jan. 15, 2004;12(2):327-36.

Carmony et al., PROTAC-induced proteolytic targeting. Methods Mol Biol. 2012;832:627-38.

CAS Registry No. 1004933-70-3, STN, dated Feb. 21, 2008, 1 page.
CAS Registry No. 1226974-40-8, STN, dated Jun. 4, 2010, 1 page.
CAS Registry No. 1542127-97-8, STN, dated Feb. 11, 2014, 5 pages.
CAS Registry No. 871986-52-6, 1 page, Jan. 16, 2006.

Chan et al., Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) Bet Inhibitor Scaffolds. J Med Chem. Jan. 25, 2018;61(2):504-513.

Chene, Inhibiting the p53-MDM2 interaction: an important target for cancer therapy. Nat Rev Cancer. Feb. 2003;3(2):102-9.

Churcher, Protac-Induced Protein Degradation in Drug Discovery: Breaking the Rules or Just Making New Ones? J Med Chem. Jan. 25, 2018;61(2):444-452.

Cohen et al., Antagonists of inhibitor of apoptosis proteins based on thiazole amide isosteres. Bioorg Med Chem Lett. Apr. 1, 2010;20(7):2229-33.

Cohen et al., Orally bioavailable antagonists of inhibitor of apoptosis proteins based on an azabicyclooctane scaffold. J Med Chem. Mar. 26, 2009;52(6):1723-30.

Contino-Pepin et al., Preliminary biological evaluations of new thalidomide analogues for multiple sclerosis application. Bioorg Med Chem Lett. Feb. 1, 2009;19(3):878-81.

Corson et al., Design and Applications of Bifunctional Small Molecules: Why Two Heads Are Better Than One. ACS Chem Biol. Nov. 21, 2008;3(11):677-692.

Crew et al., Identification and Characterization of Von Hippel-Lindau-Recruiting Proteolysis Targeting Chimeras (PROTACs) of TANK-Binding Kinase 1. J Med Chem. Jan. 25, 2018;61(2):583-598.

Crews. Targeting the undruggable proteome: the small molecules of my dreams. Chem Biol. Jun. 25, 2010;17(6):551-5.

Cromm et al., Targeted Protein Degradation: from Chemical Biology to Drug Discovery. Cell Chem Biol. Sep. 21, 2017;24(9):1181-1190.

Cyrus et al., Impact of linker length on the activity of PROTACs. Mol Biosyst. Feb. 2011;7(2):359-64.

Cyrus et al., Jostling for position: optimizing linker location in the design of estrogen receptor-targeting PROTACs. ChemMedChem. Jul. 5, 2010;5(7):979-85.

Cyrus et al., Two-headed PROTAC: an effective new tool for targeted protein degradation. Chembiochem. Jul. 26, 2010;11(11):1531-4.

Di et al., Reactivation of p53 by inhibiting Mdm2 E3 ligase: a novel antitumor approach. Curr Cancer Drug Targets. Oct. 2011;11(8):987-94.

Ding et al., Discovery of RG7388, a potent and selective p53-MDM2 inhibitor in clinical development. J Med Chem. Jul. 25, 2013;56(14):5979-83.

Dixon et al., Identifying druggable disease-modifying gene products. Curr Opin Chem Biol. Dec. 2009;13(5-6):549-55.

Fischer et al., Structure of the DDB1-CRBN E3 ubiquitin ligase in complex with thalidomide. Nature. Aug. 7, 2014;512(7512):49-53.

Flygare et al., Small-molecule pan-IAP antagonists: a patent review. Expert Opin Ther Pat. Feb. 2010;20(2):251-67.

Gadd et al., Structural basis of PROTAC cooperative recognition for selective protein degradation. Nat Chem Biol. May 2017;13(5):514-521.

Galdeano et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem. Oct. 23, 2014;57(20):8657-63.

Golub et al., Molecular classification of cancer: class discovery and class prediction by gene expression monitoring. Science. Oct. 15, 1999;286(5439):531-7.

Gosink et al., Redirecting the specificity of ubiquitination by modifying ubiquitin-conjugating enzymes. Proc Natl Acad Sci U S A. Sep. 26, 1995;92(20):9117-21.

Grasso et al., Chemically Linked Vemurafenib Inhibitors Promote an Inactive BRAFV600E Conformation. ACS Chem Biol. Oct. 21, 2016;11(10):2876-2888.

(56) References Cited

OTHER PUBLICATIONS

Graves et al., The dynamic nature of the kinome. Biochem J. Feb. 15, 2013;450(1):1-8.

Han et al., Discovery of ARD-69 as a Highly Potent Proteolysis Targeting Chimera (PROTAC) Degrader of Androgen Receptor (AR) for the Treatment of Prostate Cancer. J Med Chem. Jan. 24, 2019;62(2):941-964.

Han et al., Discovery of Selective Small Molecule Degraders of BRAF-V600E. J Med Chem Apr. 23, 2020;63(8):4069-4080. Pre-publication edition.

Hansen et al., Potent and selective pyrazole-based inhibitors of B-Raf kinase. Bioorg Med Chem Lett. Aug. 15, 2008;18(16):4692-5.

Haupt et al., Mdm2 promotes the rapid degradation of p53. Nature. May 1997 15;387(6630):296-9.

Hennessy et al., Discovery of aminopiperidine-based Smac mimetics as IAP antagonists. Bioorg Med Chem Lett. Feb. 15, 2012;22(4):1690-4.

Hines et al., Posttranslational protein knockdown coupled to receptor tyrosine kinase activation with phosphoPROTACs. Proc Natl Acad Sci U S A. May 28, 2013;110(22):8942-7.

Hird et al., Structure-based design and synthesis of tricyclic IAP (Inhibitors of Apoptosis Proteins) inhibitors. Bioorg Med Chem Lett. Apr. 1, 2014;24(7):1820-4.

Hon et al., Structural basis for the recognition of hydroxyproline in HIF-1 alpha by pVHL. Nature. Jun. 27, 2002;417(6892):975-8.

Hu et al., Discovery of ERD-308 as a Highly Potent Proteolysis Targeting Chimera (PROTAC) Degrader of Estrogen Receptor (ER). J Med Chem. Feb. 14, 2019;62(3):1420-1442.

Huang et al., A Chemoproteomic Approach to Query the Degradable Kinome Using a Multi-kinase Degrader. Cell Chem Biol. Jan. 18, 2018;25(1):88-99.e6.

Huang et al., Drugging the undruggables: exploring the ubiquitin system for drug development. Cell Res. Apr. 2016;26(4):484-98.

Hughes et al., Molecular recognition of ternary complexes: a new dimension in the structure-guided design of chemical degraders. Essays Biochem. Nov. 8, 2017;61(5):505-516.

Ishikawa et al., Design and synthesis of novel human epidermal growth factor receptor 2 (HER2)/epidermal growth factor receptor (EGFR) dual inhibitors bearing a pyrrolo[3,2-d]pyrimidine scaffold. J Med Chem. Dec. 8, 2011;54(23):8030-50.

Itoh et al., Development of target protein-selective degradation inducer for protein knockdown. Bioorg Med Chem. May 15, 2011;19(10):3229-41.

Itoh et al., Protein knockdown using methyl bestatin-ligand hybrid molecules: design and synthesis of inducers of ubiquitination-mediated degradation of cellular retinoic acid-binding proteins. J Am Chem Soc. Apr. 28, 2010;132(16):5820-6.

Ivan et al., HIFalpha targeted for VHL-mediated destruction by proline hydroxylation: implications for 02 sensing. Science. Apr. 20, 2001;292(5516):464-8.

Jang et al., Targeted Degradation of Proteins by PROTACs. Curr Protoc Chem Biol. Jun. 1, 2010;2(2):71-87.

Kim et al., Design, synthesis and biological evaluation of benzyl 2-(1H-imidazole-1-yl) pyrimidine analogues as selective and potent Raf inhibitors. Bioorg Med Chem Lett. Aug. 1, 2014;24(15):3600-4.

Kim et al., Discovery of tetrahydroisoquinoline-based bivalent heterodimeric IAP antagonists. Bioorg Med Chem Lett. Nov. 1, 2014;24(21):5022-9.

Knott, Compounds containing sulphur chromophores. Part I. The action of bases on heterocyclic sulphide quarternary salts. Journal of the Chemical Society. 1955, pp. 916-927.

Knott, Compounds containing sulphur chromophores. Part V. Complex Cyanines. The Journal of the Chemical Society. 1955;949-954.

Kronke et al., Lenalidomide causes selective degradation of IKZF1 and IKZF3 in multiple myeloma cells. Science. Jan. 17, 2014;343(6168):301-5.

Lackey et al., The discovery of potent cRaf1 kinase inhibitors. Bioorg Med Chem Lett. Feb. 7, 2000;10(3):223-6.

Lai et al., Induced protein degradation: an emerging drug discovery paradigm. Nat Rev Drug Discov. Feb. 2017;16(2):101-114.

Lai et al., Modular PROTAC Design for the Degradation of Oncogenic BCR-ABL. Angew Chem Int Ed Engl. Jan. 11, 2016;55(2):807-10.

Lala et al., Role of nitric oxide in tumor progression: lessons from experimental tumors. Cancer Metastasis Rev. Mar. 1998;17(1):91-106.

Lebraud et al., Protein Degradation by In-Cell Self-Assembly of Proteolysis Targeting Chimeras. ACS Cent Sci. Dec. 28, 2016;2(12):927-934.

Lee et al., Targeted degradation of the aryl hydrocarbon receptor by the PROTAC approach: a useful chemical genetic tool. Chembiochem. Nov. 23, 2007;8(17):2058-62.

Levine et al., Targeting the androgen receptor with steroid conjugates. J Med Chem. Oct. 23, 2014;57(20):8224-37.

Li et al., Single Polymer-drug Conjugate Carrying Two Drugs for Fixed-dose Codelivery. Medicinal Chemistry, 2014;4(10):676-683.

Liu et al., Design and biological characterization of hybrid compounds of curcumin and thalidomide for multiple myeloma. Org Biomol Chem. Aug. 7, 2013;11(29):4757-63.

Lopez-Girona et al., Cereblon is a direct protein target for immunomodulatory and antiproliferative activities of lenalidomide and pomalidomide. Leukemia. Nov. 2012;26(11):2326-35.

Lu et al., Hijacking the E3 Ubiquitin Ligase Cereblon to Efficiently Target BRD4. Chem Biol. Jun. 18, 2015;22(6):755-63.

Lu et al., The myeloma drug lenalidomide promotes the cereblon-dependent destruction of Ikaros proteins. Science. Jan. 17, 2014;343(6168):305-9.

Mahalingam et al., Targeting HSP90 for cancer therapy. Br J Cancer. May 19, 2009;100(10):1523-9.

Maniaci et al., Homo-PROTACs: bivalent small-molecule dimerizers of the VHL E3 ubiquitin ligase to induce self-degradation. Nat Commun. Oct. 10, 2017;8(1):830, 14 pages.

Mannhold et al., IAP antagonists: promising candidates for cancer therapy. Drug Discov Today. Mar. 2010; 15(5-6):210-9.

MedlinePlus, Cancer. Retrieved online at: www.nlm.nih.gov/medlineplus/cancer.html. 10 page, Jun. 27, 2007.

Min et al., Structure of an HIF-1alpha-pVHL complex: hydroxyproline recognition in signaling. Science. Jun. 7, 2002;296(5574):1886-9.

Miyazaki et al., Discovery of DS-5272 as a promising candidate: A potent and orally active p53-MDM2 interaction inhibitor. Bioorg Med Chem. May 15, 2015;23(10):2360-7.

Muller et al., Amino-substituted thalidomide analogs: potent inhibitors of TNF-alpha production. Bioorg Med Chem Lett. Jun. 7, 1999;9(11):1625-30.

Ndubaku et al., Antagonism of c-IAP and XIAP proteins is required for efficient induction of cell death by small-molecule IAP antagonists. ACS Chem Biol. Jul. 17, 2009;4(7):557-66.

Neklesa et al., Greasy tags for protein removal. Nature. Jul. 18, 2012;487(7407):308-9.

Neklesa et al., Targeted protein degradation by PROTACs. Pharmacol Ther. Jun. 2017;174:138-144.

Nikolovska-Coleska et al., Interaction of a cyclic, bivalent smac mimetic with the x-linked inhibitor of apoptosis protein. Biochemistry. Sep. 16, 2008;47(37):9811-24.

Noguchi-Yachide, BET Bromodomain as a Target of Epigenetic Therapy. Chem Pharm Bull (Tokyo). 2016;64(6):540-7.

Ohoka et al., SNIPER(TACC3) induces cytoplasmic vacuolization and sensitizes cancer cells to Bortezomib. Cancer Sci. May 2017;108(5):1032-1041.

Oost et al., Discovery of potent antagonists of the antiapoptotic protein XIAP for the treatment of cancer. J Med Chem. Aug. 26, 2004;47(18):4417-26.

Ottis et al., Assessing Different E3 Ligases for Small Molecule Induced Protein Ubiquitination and Degradation. ACS Chem Biol. Oct. 20, 2017;12(10):2570-2578.

Ottis et al., Proteolysis-Targeting Chimeras: Induced Protein Degradation as a Therapeutic Strategy. ACS Chem Biol. Apr. 21, 20171;12(4):892-898.

Perez et al., Discovery of potent heterodimeric antagonists of inhibitor of apoptosis proteins (IAPs) with sustained antitumor activity. J Med Chem. Feb. 12, 2015;58(3):1556-62.

(56) References Cited

OTHER PUBLICATIONS

Posternak et al., Functional characterization of a PROTAC directed against BRAF mutant V600E. Nat Chem Biol. Nov. 2020;16(11):1170-1178.
Poulikakos et al., RAF inhibitors transactivate RAF dimers and ERK signalling in cells with wild-type BRAF. Nature. Mar. 18, 2010;464(7287):427-30.
Powell et al., Chemically Induced Degradation of Anaplastic Lymphoma Kinase (ALK). J Med Chem. May 10, 2018;61(9):4249-4255.
Puppala et al., Development of an aryl hydrocarbon receptor antagonist using the proteolysis-targeting chimeric molecules approach: a potential tool for chemoprevention. Mol Pharmacol. Apr. 2008;73(4):1064-71.
Raina et al., Chemical inducers of targeted protein degradation. J Biol Chem. Apr. 9, 2010;285(15):11057-60.
Raina et al., PROTAC-induced BET protein degradation as a therapy for castration-resistant prostate cancer. Proc Natl Acad Sci U S A. Jun. 28, 2016;113(26):7124-9.
Raina et al., Targeted protein knockdown using small molecule degraders. Curr Opin Chem Biol. Aug. 2017;39:46-53.
Remillard et al., Degradation of the BAF Complex Factor BRD9 by Heterobifunctional Ligands. Angew Chem Int Ed Engl. May 15, 2017;56(21):5738-5743.
Rew et al., Discovery of AM-7209, a potent and selective 4-amidobenzoic acid inhibitor of the MDM2-p53 interaction. J Med Chem. Dec. 26, 2014;57(24):10499-511.
Rodriguez-Gonzalez et al., Targeting steroid hormone receptors for ubiquitination and degradation in breast and prostate cancer. Oncogene. Dec. 4, 2008;27(57):7201-11.
Rotili et al., Photoactivable peptides for identifying enzyme-substrate and protein-protein interactions. Chem Commun (Camb). Feb. 7, 2011;47(5):1488-90.
Ruchelman et al., Isosteric analogs of lenalidomide and pomalidomide: synthesis and biological activity. Bioorg Med Chem Lett. Jan. 1, 2013;23(1):360-5.
Sakamoto et al., Development of Protacs to target cancer-promoting proteins for ubiquitination and degradation. Mol Cell Proteomics. Dec. 2003;2(12):1350-8.
Sakamoto et al., Protacs: chimeric molecules that target proteins to the Skp1-Cullin-F box complex for ubiquitination and degradation. Proc Natl Acad Sci U S A. Jul. 17, 2001;98(15):8554-9.
Salami et al., Waste disposal-An attractive strategy for cancer therapy. Science. Mar. 17, 2017;355(6330):1163-1167.
Schiedel et al., Chemically Induced Degradation of Sirtuin 2 (Sirt2) by a Proteolysis Targeting Chimera (PROTAC) Based on Sirtuin Rearranging Ligands (SirReals). J Med Chem. Jan. 25, 2018;61(2):482-491.
Schneekloth et al., Chemical genetic control of protein levels: selective in vivo targeted degradation. J Am Chem Soc. Mar. 31, 2004;126(12):3748-54.
Schneekloth et al., Targeted intracellular protein degradation induced by a small molecule: En route to chemical proteomics. Bioorg Med Chem Lett. Nov. 15, 2008;18(22):5904-8.
Shangary et al., Temporal activation of p53 by a specific MDM2 inhibitor is selectively toxic to tumors and leads to complete tumor growth inhibition. Proc Natl Acad Sci U S A. Mar. 11, 2008;105(10):3933-8.
Smith et al., Targeted Intracellular Protein Degradation Induced by a Small Molecule: En Route to Chemical Proteomics. Bioorg Med Chem Lett. Nov. 15, 2008;18(22):5904-5908.
Stanton et al., Chemically induced proximity in biology and medicine. Science. Mar. 9, 2018;359:1117.
Stanton et al., Chemically induced proximity in biology and medicine. Science. Mar. 9, 2018;359(6380):eaao5902, 9 pages.
Stewart et al., Efforts toward elucidating Thalidomide's molecular target: an expedient synthesis of the first Thalidomide biotin analogue. Org Biomol Chem. Sep. 21, 2010;8(18):4059-62.
STN Accession No. 1957:56724, Compounds containing sulfur Chromophores v. Complex cyanines. 1 page, (2017).
STN Registry No. 1004933-70-3, 2-Pyrrolidinecarboxamide, N-(4-bromo-2-fluorophenyl)-4-hydroxy-1-(2-naphthalenylsulfonyl). 1 page, Feb. 21, 2008.
Stoppler, Endometriosis, Endometriosis definition and facts. Retrieved online at: http://www.medicinenet.com/endometriosis/article.htm. 7 pages, retrieved on Apr. 5, 2017.
Stoppler, Endometriosis, What about surgery for Endometriosis. Retrieved online at: http://www.medicinenet.com/endometriosis/article.htm. 7 pages, retrieved on Apr. 5, 2017.
Sun et al., BET protein proteolysis targeting chimera (PROTAC) exerts potent lethal activity against mantle cell lymphoma cells. Leukemia. Feb. 2018;32(2):343-352.
Sun et al., Discovery of AMG 232, a potent, selective, and orally bioavailable MDM2-p53 inhibitor in clinical development. J Med Chem. Feb. 27, 2014;57(4):1454-72.
Sun et al., Potent bivalent Smac mimetics: effect of the linker on binding to inhibitor of apoptosis proteins (IAPs) and anticancer activity. J Med Chem. May 12, 2011;54(9):3306-18.
Takeuchi et al., Receptor tyrosine kinases and targeted cancer therapeutics. Biol Pharm Bull. 2011;34(12):1774-80.
Takle et al., The identification of potent and selective imidazole-based inhibitors of B-Raf kinase. Bioorg Med Chem Lett. Jan. 15, 2006;16(2):378-81.
Toure et al., Small-Molecule PROTACS: New Approaches to Protein Degradation. Angew Chem Int Ed Engl. Feb. 5, 2016;55(6):1966-73.
Turk et al., Binding of thalidomide to alpha1-acid glycoprotein may be involved in its inhibition of tumor necrosis factor alpha production. Proc Natl Acad Sci U S A. Jul. 23, 1996;93(15):7552-6.
Vallee et al., ricyclic series of heat shock protein 90 (Hsp90) inhibitors part I: discovery of tricyclic imidazo[4,5-c]pyridines as potent inhibitors of the Hsp90 molecular chaperone. J Med Chem. Oct. 27, 2011;54(20):7206-19.
Vamos et al., Expedient synthesis of highly potent antagonists of inhibitor of apoptosis proteins (IAPs) with unique selectivity for ML-IAP. ACS Chem Biol. Apr. 19, 2013;8(4):725-32.
Van Molle et al., Dissecting fragment-based lead discovery at the von Hippel-Lindau protein:hypoxia inducible factor 1a protein-protein interface. Chem Biol. Oct. 26, 2012;19(10):1300-12.
Vassilev et al., In vivo activation of the p53 pathway by small-molecule antagonists of MDM2. Science. Feb. 6, 2004;303(5659):844-8.
Vazquez et al., The genetics of the p53 pathway, apoptosis and cancer therapy. Nat Rev Drug Discov. Dec. 2008;7(12):979-87.
Vu et al., Discovery of RG7112: A Small-Molecule MDM2 Inhibitor in Clinical Development. ACS Med Chem Lett. Apr. 2, 2013;4(5):466-9.
Waizenegger et al., A Novel RAF Kinase Inhibitor with DFG-Out-Binding Mode: High Efficacy in BRAF-Mutant Tumor Xenograft Models in the Absence of Normal Tissue Hyperproliferation. Mol Cancer Ther. Mar. 2016; 15(3):354-65.
Wang et al., Discovery of novel second mitochondria-derived activator of caspase mimetics as selective inhibitor of apoptosis protein inhibitors. J Pharmacol Exp Ther. May 2014;349(2):319-29.
Wenglowsky et al., Highly potent and selective 3-N-methylquinazoline-4(3H)-one based inhibitors of B-Raf(V600E) kinase. Bioorg Med Chem Lett. Apr. 15, 2014;24(8):1923-7.
Wichmann et al., Preclinical Characterization of a Next-Generation Brain Permeable, Paradox Breaker BRAF Inhibitor. Clin Cancer Res. Feb. 15, 2022;28(4):770-780.
Winter et al., Phthalimide conjugation as a strategy for in vivo target protein degradation. Science. Jun. 19, 2015;348(6241):1376-81.
Yao et al., BRAF Mutants Evade ERK-Dependent Feedback by Different Mechanisms that Determine Their Sensitivity to Pharmacologic Inhibition. Cancer Cell. Sep. 14, 2015;28(3):370-83.
Yao et al., Tumours with class 3 BRAF mutants are sensitive to the inhibition of activated RAS. Nature. Aug. 10, 2017;548(7666):234-238.
Zengerle et al., Selective Small Molecule Induced Degradation of the BET Bromodomain Protein BRD4. ACS Chem Biol. Aug. 21, 2015;10(8):1770-7.
Zhang et al., RAF inhibitors that evade paradoxical MAPK pathway activation. Nature. Oct. 22, 2015;526(7574):583-6.

(56) References Cited

OTHER PUBLICATIONS

Zhang et al., Small-molecule MDM2-p53 inhibitors: recent advances. Future Med Chem. 2015;7(5):631-45.

Zhang et al., Targeted degradation of proteins by small molecules: a novel tool for functional proteomics. Comb Chem High Throughput Screen. Nov. 2004;7(7):689-97.

Zhao et al., Small-molecule inhibitors of the MDM2-p53 protein-protein interaction (MDM2 Inhibitors) in clinical trials for cancer treatment. J Med Chem. Feb. 12, 2015;58(3):1038-52.

Zhou et al., Discovery of a Small-Molecule Degrader of Bromodomain and Extra-Terminal (BET) Proteins with Picomolar Cellular Potencies and Capable of Achieving Tumor Regression. J Med Chem. Jan. 25, 2018;61(2):462-481.

International Search Report and Written Opinion for Application No. PCT/US2019/050114, dated Jan. 2, 2020, 10 pages.

Liang et al., The Discovery and Characterization of CFT-18442: A Potent, Selective, and Orally Bioavailable Degrader of BRAF V600E. 16th Winter Conference on Medicinal & Bioorganic Chemistry. 1 page, Feb. 1, 2023.

U.S. Appl. No. 15/853,166, filed Dec. 22, 2017, U.S. Pat. No. 10,723,717, Issued.

U.S. Appl. No. 16/563,842, filed Sep. 7, 2019, U.S. Pat. No. 11,173,211, Issued.

U.S. Appl. No. 17/387,621, filed Jul. 28, 2021, 2023-0000994, Published.

U.S. Appl. No. 17/459,179, filed Aug. 27, 2021, 2023-0081501, Published.

International Search Report and Written Opinion for Application No. PCT/US2023/032225, dated Jan. 3, 2024, 15 pages.

\* cited by examiner

RAPIDLY ACCELERATED FIBROSARCOMA (RAF) DEGRADING COMPOUNDS AND ASSOCIATED METHODS OF USE

RELATED APPLICATIONS

This application claims the benefit of priority to U.S. provisional application No. 63/404,228, filed Sep. 7, 2022, U.S. provisional application No. 63/451,822, filed Mar. 13, 2023, and U.S. provisional application No. 63/525,770, filed Jul. 10, 2023, the entire contents of each of which are incorporated herein by reference.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands that bind to these ligases. For example, since the discovery of nutlins, the first small molecule E3 ligase inhibitors, additional compounds have been reported that target E3 ligases.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

An ongoing need exists in the art for effective treatments for disease associated with overexpression or aggregation of Rapidly Accelerated Fibrosarcoma (RAF), or the overactivation of RAF (such as constitutively active RAF). For example, current B-RAF inhibitors (such as, vemurafenib and daB-RAFenib) may target V600 mutant B-RAF. Thus, a need exists for diseases or disorders (such as, melanoma, lung cancer, pancreatic cancer, and/or colorectal cancers) that have different B-RAF mutations that are insensitive to currently marketed agents. Furthermore, resistance mutations can emerge in response to B-RAF/MEK inhibitor therapy. For example, the p61 splice variant can emerge in melanoma patients treated with B-RAF/MEK inhibitor therapy, which leaves these patients with no clinical options. Currently marketed agents also bind to and cause paradoxical activation of wild-type B-RAF, which results in clinical complications. In addition, the family of hypoactive Class III B-RAF mutants that signal through heterodimerization with CRaf, constitute 40% of B-RAF mutations in non-small cell lung cancer (NSCLC), and also appear sporadically across other cancers, cannot be targeted with any currently approved or clinical-stage B-RAF inhibitors. Class I B-RAF mutants (V600E, V600K, V600D) have high kinase activity, are Ras and dimerization independent, and are sensitive to vemurafenib. Class II B-RAF mutants have high to intermediate kinase activity, are Ras-independent and dimerization dependent, and are insensitive to vemurafenib. Class III B-RAF mutants have varying levels of kinase activity (e.g., some Class III B-RAF mutants have high levels of kinase activity while other mutants have no kinase activity), are Ras and dimerization dependent, and are insensitive to vemurafenib.

Thus, non-specific effects and the inability to target and modulate RAF remain an obstacle to the development of effective treatments. As such, an ongoing need exists in the art for effective treatments for RAF-related disease and disorders.

SUMMARY

Provided herein are hetero-bifunctional compounds that function to recruit Rapidly Accelerated Fibrosarcoma (RAF) protein or a mutated version thereof to an E3 ubiquitin ligase for targeted ubiquitination and subsequent proteasomal degradation. Such compounds include those having the chemical structure:

PTM-L-CLM wherein PTM is a RAF targeting moiety, CLM is an E3 ubiquitin ligase binding moiety that binds a cereblon E3 ubiquitin ligase, and L is a chemical linking moiety covalently coupling the CLM to the PTM.

Pharmaceutical compositions comprising these hetero-bifunctional compounds, methods for their preparation, and methods of treating RAF related conditions using the disclosed hetero-bifunctional compounds are also included Methods of treating conditions responsive to the modulation of RAF using the disclosed compounds, pharmaceutically acceptable salts, and compositions thereof are also included.

DETAILED DESCRIPTION

1. General Description of Compounds

Figure 1:
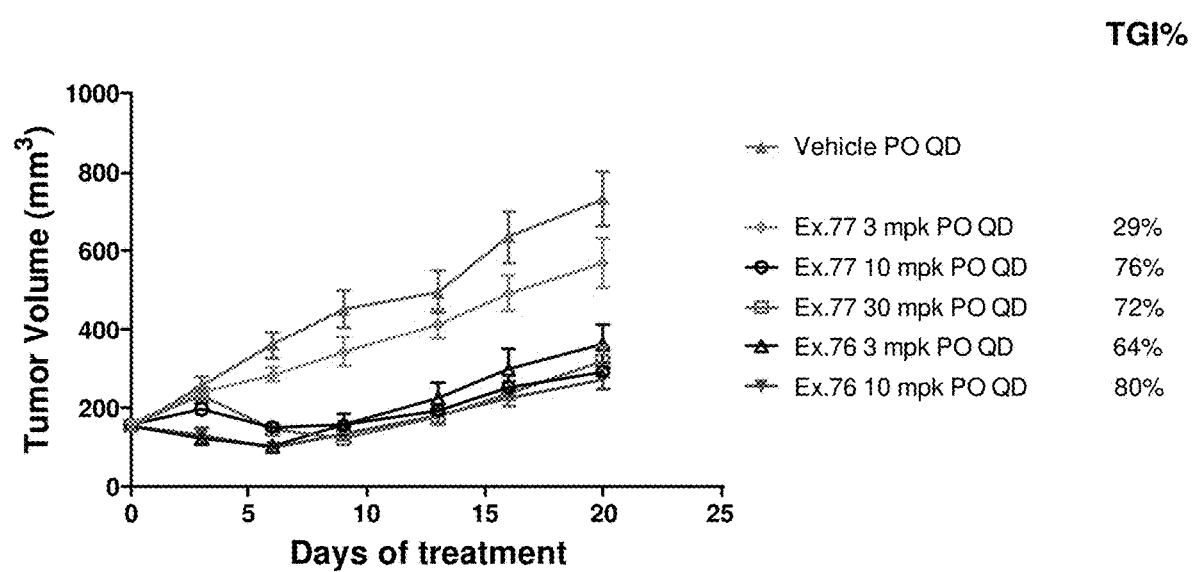
FIG. 1 shows tumor growth inhibition results in H1666 tumors using compounds 76 and 77 of the present disclosure.

In a first embodiment, provided herein is compound having the chemical structure I:

PTM-L-CLM;  (I)

or a pharmaceutically acceptable salt thereof, wherein:
(a) PTM is a small molecule Rapidly Accelerated Fibrosarcoma (RAF) targeting moiety such as e.g., one represented by the chemical structure:

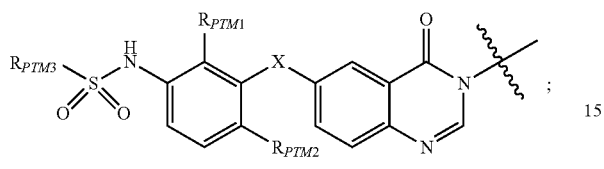
(PTM)

wherein:
X is O or NH;
$R_{PTM1}$ is selected from hydrogen, halo, $C_{1-4}$alkyl, and cyano;
$R_{PTM2}$ is selected from hydrogen, optionally substituted $C_{1-4}$ alkyl, and optionally substituted $C_{1-4}$ alkoxy;
$R_{PTM3}$ is selected from optionally substituted $C_{1-4}$ alkyl, —NH (optionally substituted $C_{1-4}$ alkyl), —N(optionally substituted $C_{1-4}$ alkyl)$_2$, optionally substituted cycloalkyl, and optionally substituted heterocycly; and
∿ indicates the point of attachment to the chemical linking moiety (L);

(b) CLM is an E3 ubiquitin ligase binding moiety that binds a cereblon E3 ubiquitin ligase such as e.g., one represented by the chemical structure:

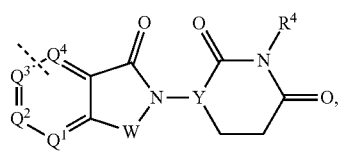
(CLMI)

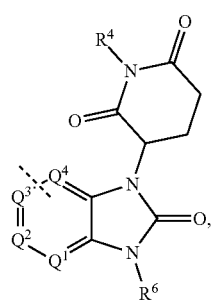
(CLMII)

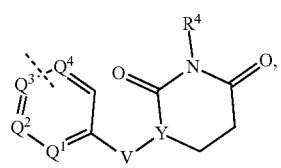
(CLMIII)

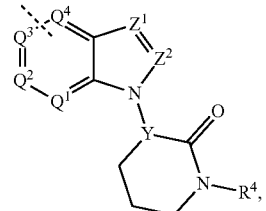
(CLMIV)

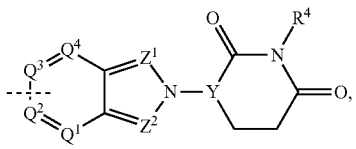
(CLMV)

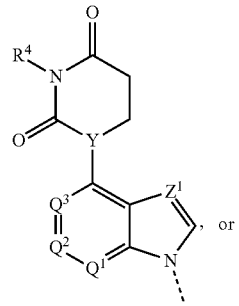
(CLVI)

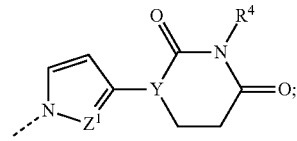
(CLMVII)

wherein:
W is $CH_2$ or C(O);
Y is N or $CR^5$;
$Q^1$, $Q^2$, $Q^3$, $Q^4$, and $Q^5$ are each independently CH, $CR^w$ or N;
$Z^1$ and $Z^2$ are each independently CH, $CR^x$ or N; V is absent or is $NR^y$ or $C(O)NR^z$;
$R^4$, $R^5$, and $R^6$ are each independently hydrogen or optionally substituted $C_{1-4}$ alkyl;
$R^w$ and $R^x$ are each independently selected from halo, optionally substituted $C_{1-4}$ alkyl, optionally substituted $C_{1-4}$ alkoxy, cyano, OH, —NH (optionally substituted $C_{1-4}$ alkyl), and —NH (optionally substituted $C_{1-4}$ alkyl)$_2$;
$R^y$ and $R^z$ are each independently hydrogen or optionally substituted $C_{1-6}$ alkyl, optionally substituted cycloalkyl, or optionally substituted heterocyclyl; and
the dashed line indicates the part of the structure to which the chemical linking moiety (L) is attached; and
(c) L is a chemical linking moiety covalently coupling the CLM to the PTM.

Alternatively, as part of the first embodiment, provided herein is compound having the chemical structure I:

PTM-L-CLM;  (I)

or a pharmaceutically acceptable salt thereof, wherein:
(a) PTM is a small molecule Rapidly Accelerated Fibrosarcoma (RAF) targeting moiety such as e.g., one represented by the chemical structure:

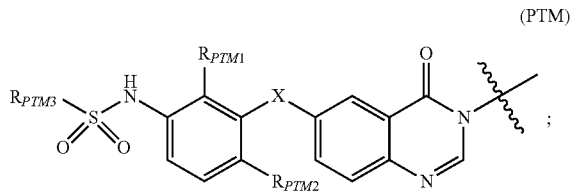

(PTM)

wherein:

X is O or NH;

$R_{PTM1}$ is selected from hydrogen, halo, and cyano;

$R_{PTM2}$ is selected from hydrogen, optionally substituted $C_{1-4}$ alkyl, and optionally substituted $C_{1-4}$ alkoxy;

$R_{PTM3}$ is selected from optionally substituted $C_{1-4}$ alkyl, —NH (optionally substituted $C_{1-4}$ alkyl), —N(optionally substituted $C_{1-4}$ alkyl)$_2$, optionally substituted cycloalkyl, and optionally substituted heterocyclyl; and 〜 indicates the point of attachment to the chemical linking moiety (L);

(b) CLM is an E3 ubiquitin ligase binding moiety that binds a cereblon E3 ubiquitin ligase such as e.g., one represented by the chemical structure:

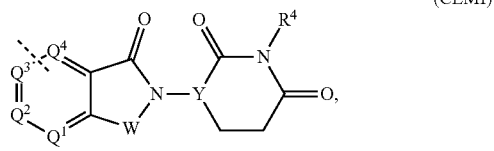
(CLMI)

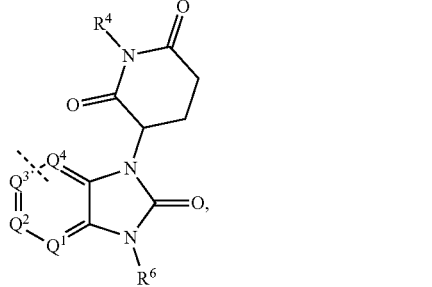
(CLMII)

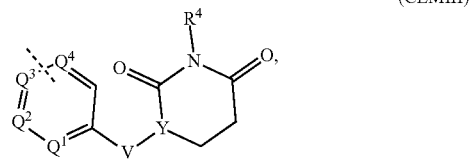
(CLMIII)

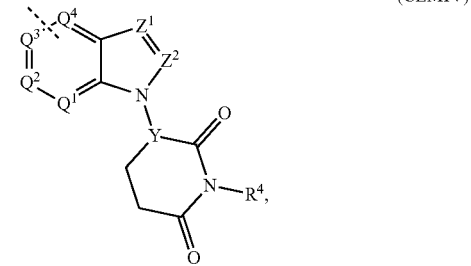
(CLMIV)

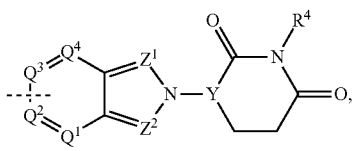
(CLMV)

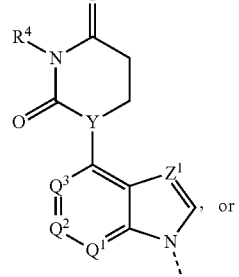
(CLMVI)

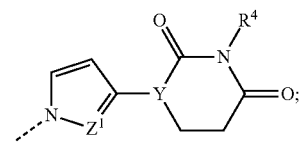
(CLMVII)

wherein:

W is $CH_2$ or C(O);

Y is N or $CR^5$;

$Q^1$, $Q^2$, $Q^3$, $Q^4$, and $Q^5$ are each independently CH, $CR^w$ or N;

$Z^1$ and $Z^2$ are each independently CH, $CR^x$ or N;

V is absent or is $NR^y$ or $C(O)NR^z$;

$R^4$, $R^5$, and $R^6$ are each independently hydrogen or optionally substituted $C_{1-4}$ alkyl;

$R^w$ and $R^x$ are each independently selected from halo, optionally substituted $C_{1-4}$ alkyl, optionally substituted $C_{1-4}$ alkoxy, cyano, OH, —NH (optionally substituted $C_{1-4}$ alkyl), and —NH (optionally substituted $C_{1-4}$ alkyl)$_2$;

$R^y$ and $R^z$ are each independently hydrogen or optionally substituted $C_{1-6}$ alkyl, optionally substituted cycloalkyl, or optionally substituted heterocyclyl; and the dashed line indicates the part of the structure to which the chemical linking moiety (L) is attached; and (c) L is a chemical linking moiety covalently coupling the CLM to the PTM.

2. Definitions

In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element, unless otherwise indicated.

All transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

When a range of carbon atoms is used herein, for example, $C_1$-$C_6$ or $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The terms "halo" and "halogen" refer to an atom selected from fluorine (fluoro, F), chlorine (chloro, $C_1$), bromine (bromo, Br), and iodine (iodo, I).

The term "alkyl" when used alone or as part of a larger moiety, such as "haloalkyl", "hydroxyalkyl" and the like, means saturated straight-chain or branched monovalent hydrocarbon radical having, unless otherwise specified, from 1 to 20 carbon atoms such as $C_{1-10}$, $C_{1-6}$, or $C_{1-4}$. A $C_{1-6}$ alkyl includes e.g., methyl, ethyl, propyl (e.g., n-propyl, isopropyl), butyl (e.g., n-butyl, tert-butyl, sec-butyl, isobutyl), pentyl (e.g., n-pentyl, 3-pentanyl, amyl, neopentyl, 3-methyl-2-butanyl, tertiary amyl), and hexyl (e.g., n-hexyl). It will be understood that when specified, optional substituents on an alkyl group may be present on any substitutable position.

The term "haloalkyl" includes mono, poly, and perhaloalkyl groups where the halogens are independently selected from fluorine, chlorine, bromine, and iodine.

The term "hydroxyalkyl" includes mono, poly, and perhydroxy alkyl groups where one or more hydrogen atoms are replaced by OH.

The term "alkoxy" refers to an alkyl radical attached through an oxygen linking atom, represented by -Oalkyl. Non-limiting examples include methoxy, ethoxy, propoxy, 2-propoxy, butoxy, tert-butoxy, pentyloxy, and hexyloxy. It will be understood that when specified, optional substituents on an alkoxy group may be present on any substitutable position The term "haloalkoxy" includes mono, poly, and perhaloalkoxy groups where the halogens are independently selected from fluorine, chlorine, bromine, and iodine.

The term "heteroaryl" refers to, unless otherwise specified, a 5-16 membered aromatic radical containing 1-4 heteroatoms selected from N, O, and S. In some instances, nitrogen atoms in a heteroaryl may be quarternized. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, etc. Bi-cyclic heteroaryls include groups in which a monocyclic heteroaryl ring is fused to one or more aryl or heteroaryl rings. Nonlimiting examples include indolyl, benzooxazolyl, benzooxodiazolyl, indazolyl, benzimidazolyl, benzthiazolyl, benzothiopheneyl, quinolinyl, quinazolinyl, quinoxalinyl, pyrrolopyridinyl, pyrrolopyrimidinyl, pyrrolopyridinyl, thienopyridinyl, thienopyrimidinyl, indolizinyl, purinyl, cinnolinyl, naphthyridinyl, and pteridinyl. It will be understood that when specified, optional substituents on a heteroaryl group may be present on any substitutable position and, include, e.g., the position at which the heteroaryl is attached (where valency permits).

The term "heterocyclyl" means, unless otherwise specified, a 4- to 12-membered saturated or partially unsaturated heterocyclic ring containing 1 to 4 heteroatoms independently selected from N, O, and S. A heterocyclyl ring can be attached to its pendant group at any heteroatom or carbon atom that results in a stable structure. A heterocyclyl group may be mono- or bicyclic (e.g., a bridged, fused, or spiro bicyclic ring). Examples of monocyclic saturated or partially unsaturated heterocyclic radicals include, without limitation, azetidinyl, tetrahydrofuranyl, tetrahydrothienyl, terahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, tetrahydropyrimidinyl, dihydrooxadizolyl, and dihydroisoxazolyl. Bi-cyclic heterocyclyl groups include, e.g., unsaturated heterocyclic radicals fused to another unsaturated heterocyclic radical, cycloalkyl, aryl, or heteroaryl ring, such as for example, benzodioxolyl, dihydrobenzodioxinyl, dihydrobenzofuranyl, dihydrobenzothiophenyl, 5-oxa-2,6-diazaspiro[3.4]oct-6-enyl, 6-thia-2,7-diazaspiro[3.4]octanyl, 2,6-diazaspiro[3.3]heptanyl, spiro[indoline-3,3'-pyrrolidine]-yl, thiochromanyl, 7-azaspiro[3.5]nonanyl, 6-azaspiro[3.4]octanyl and the like. It will be understood that when specified, optional substituents on a heterocyclyl group may be present on any substitutable position and, include, e.g., the position at which the heterocyclyl group is attached.

The term "spiro" refers to two rings that shares one ring atom (e.g., carbon).

The term "fused" refers to two rings that share two adjacent ring atoms with one another.

The term "bridged" refers to two rings that share three adjacent ring atoms with one another.

The term "cycloalkyl" refers to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl group is attached.

The term "optionally substituted" means that one or more hydrogens of the designated moiety may be replaced with a suitable substituent. Unless otherwise indicated, an "optionally substituted" group may have a suitable substituent at each substitutable position of the group as valency permits. Optional substituents include, but are not limited to, one or more groups selected from cyano (—CN), halo, imino (=NH), nitro (—NO$_2$), oxo (=O), —C(O)R$^i$, —C(O)OR$^i$, —C(O)NR$^{ii}$R$^{iii}$, —C(O)SR$^i$, —C(NR$^i$)NR$^{ii}$R$^{iii}$, —C(S)R$^i$, —C(S)OR$^i$, —C(S)NR$^{ii}$R$^{iii}$, —OR$^i$, —OC(O)R$^i$, —OC(O)OR$^i$, —OC(O)NR$^{ii}$R$^{iii}$, —OC(O)SR$^i$, —OC(NR$^i$)NR$^{ii}$R$^{iii}$, —OC(S)R$^i$, —OC(S)OR$^i$, —OC(S)NR$^{ii}$R$^{iii}$, —OP(O)(OR$^{ii}$)OR$^{iii}$, —OS(O)R$^i$, —OS(O)$_2$R$^i$, —OS(O)NR$^{ii}$R$^{iii}$, —OS(O)$_2$NR$_{ii}$R$^{iii}$, —NR$^{ii}$R$^{iii}$, —NR$^i$C(O)R$^{iv}$, NR$^i$C(O)OR$^{iv}$, NR$^i$C(O)NR$^{ii}$R$^{iii}$, —NR$^a$C(O)SR$^{iv}$, —NR$^i$C(NR$^{iv}$)NR$^{ii}$R$^{iii}$, —NR$^i$C(S)R$^{iv}$, —NR$^i$C(S)OR$^{iv}$, —NR$^i$C(S)NR$^{ii}$R$^{iii}$, —NR$^i$S(O)R$^{iv}$, —NR$^i$S(O)$_2$R$^{iv}$, —NR$^i$S(O)NR$^{ii}$R$^{iii}$, —NR$^i$S(O)$_2$NR$^{ii}$R$^{iv}$, —SR$^i$, —S(O)R$^i$, —S(O)$_2$R$^i$, —S(O)NR$^{ii}$R$^{iv}$, —S(O)$_2$NR$^{ii}$R$^{iv}$, alkyl, heteroalkyl, alkenyl, alkynyl, cycloalkyl, aryl, heteroaryl, and heterocyclyl, wherein said alkyl, heteroalkyl, alkenyl, alkynyl, cycloalkyl, aryl, heteroaryl, and heterocyclyl are each further optionally substituted with one or more, in one embodiment, one, two, three, or four, substituents Q$^a$, wherein each R$^i$, R$^{ii}$, R$^{iii}$, and R$^{iv}$ is independently alkyl, heteroalkyl, alkenyl, alkynyl, cycloalkyl, aryl, heteroaryl, or heterocyclyl, each of which is optionally substituted with one or more, in one embodiment, one, two, three, or four, substituents Q$^a$ or R$^{ii}$ and R$^{iii}$ together with the N atom to which they are attached form heterocyclyl optionally substituted with one or more, in one embodiment, one, two, three, or four, substituents Q$^a$, wherein each Q$^a$ is independently selected from cyano, halo, imino, nitro, oxo, alkyl, heteroalkyl, alkenyl, alkynyl, cycloalkyl, $C_{6-14}$ aryl, heteroaryl, heterocyclyl, —C(O)R$^v$, —C(O)OR$^v$, —C(O)NR$^{vi}$R$^{vii}$, —C(O)SR$^v$, —C(NR$^v$)NR$^{vi}$R$^{vii}$, —C(S)R$^v$, —C(S)OR$^v$, —C(S)NR$^{vi}$R$^{vii}$, —OR$^v$, —OC(O)R$^v$, —OC(O)OR$^v$, —OC(O)NR$^{vi}$R$^{vii}$, —OC(O)SR$^v$, —OC(NR$^v$)NR$^{vi}$R$^{vii}$, —OC(S)R$^v$, —OC(S)OR$^v$, —OC(S)NR$^{vi}$R$^{vii}$, —OP(O)(OR$^v$)OR$^{vi}$, —OS(O)R$^v$, —OS(O)$_2$R$^v$, —OS(O)NR$^{vi}$R$^{vii}$, —OS(O)$_2$NR$^{vi}$R$^{vii}$, —NR$^{vi}$R$^{vii}$ —NR$^v$C(O)R$^{viii}$, —NR$^e$C(O)OR$^{vi}$, —NR$^v$C(O)NR$^{vi}$R$^{vii}$, —NR$^v$C(O)SR$^{vi}$, —NR$^v$C(NR$^{viii}$)NR$^{vi}$R$^{vii}$, —NR$^v$C(S)R$^{vi}$R$^{viii}$, —NR$^v$C(S)OR$^{vi}$, —NR$^v$C(S)NR$^{vi}$R$^{vii}$, —NR$^v$S(O)R$^{viii}$, —NR$^v$S(O)$_2$R$^{viii}$, —NR$^v$S(O)NR$^{vi}$R$^{vii}$, —NR$^v$S(O)$_2$NR$^{vi}$R$^{vii}$, —SR$^v$, —S(O)R$^v$, —S(O)$_2$R$^v$, —S(O)NR$^{vi}$R$^{vii}$, and —S(O)$_2$NR$^{vi}$R$^{vii}$; wherein each R$^v$, R$^{vi}$, R$^{vii}$, and R$^{viii}$ is independently alkyl, alkenyl, alkynyl, cycloalkyl, aryl, aralkyl, heteroaryl, or heterocyclyl; or (iii) R$^{vi}$ and R$^{vii}$ together with the N atom to which they are attached form heterocyclyl.

Unless otherwise indicated, the term "compound" refers to any hetero-bifunctional compound described herein. In certain aspects, where specified, one or more hydrogen atoms on a disclosed compound may be replaced with deuterium. Such deuterated compounds may have one or more improved pharmacokinetic or pharmacodynamic properties (e.g., longer half-life) compared to the equivalent "un-deuterated" compound.

One or more of the compounds described herein may exist in various tautomeric forms and are part of the present disclosure. The terms "tautomers" or "tautomeric" refer to two or more interconvertible compounds/substituents resulting from at least one formal migration of a hydrogen atom and at least one change in valency. All such isomeric forms of such compounds are expressly included. Thus, when a compound herein is represented by a structural formula or designated by a chemical name herein, all tautomeric forms which may exist for the compound are encompassed by the structural formula.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. A "geometric isomer" refers to isomers that differ in the orientation of substituent group in relationship to a carbon-carbon double bond, a cycloalkyl ring, or a bridged bicyclic system. Atoms (other than H) on each side of a carbon-carbon double bond may be in an E (substituents are on opposite sides of the carbon-carbon double bond) or Z (substituents are oriented on the same side) configuration. "Cis" refers to substituents oriented on the same side of the ring, whereas "trans" refers to substituents oriented on opposite sides of the ring.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9%. "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When a geometric isomer is depicted by name or structure, the enrichment of the indicated isomer relative to the opposite isomer is greater than 50%, 60%, 70%, 80%, 90%, 99% or 99.9%. "Enrichment of the indicated isomer relative to the opposite isomer" is a mole percent and is determined by dividing the number of compounds with the indicated geometrical configuration by the total number of all of the compounds with the same or opposite geometrical configuration in a mixture.

When a disclosed compound is named or depicted by structure without indicating stereochemistry, it is understood that the name or the structure encompasses one of the possible stereoisomers or geometric isomers free of the others, or a mixture of the encompassed stereoisomers or geometric isomers. R*" and "S*" denote the relative configurations of substituents around one or more chiral carbon atoms, i.e. the compound is a single enantiomer, but the absolute configuration is unknown.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

The terms "effective amount" and "therapeutically effective amount" of a compound described herein refers to an amount sufficient to induce a particular response in the subject, e.g., to provide a therapeutic benefit in the treatment of a condition described herein. The therapeutically effective amount of a compound of the disclosure or a pharmaceutically acceptable salt thereof may vary depending upon the intended application (in vitro or in vivo), the subject and disease condition being treated, e.g., the weight and age of the subject, the severity of the disease condition, the manner of administration and the like. Therapeutically effective amounts or doses of the compounds and pharmaceutically acceptable salts of the compounds described herein may be ascertained by routine methods such as modeling, dose escalation studies or clinical trials, and by taking into consideration factors such as, e.g., the mode or route of administration or drug delivery, the pharmacokinetics of the compound or salt, the severity and course of the disease or disorder, the subject's previous or ongoing therapy, the subject's health status and response to drugs, and the judgment of the treating physician. An illustrative example of a dose for a subject is in the range of from about 0.001 mg to about 1000 mg of compound (per day, in single or divided dosage units (e.g., BID, TID, QID).

The terms "condition", "disease", and "disorder" are used interchangeably herein and mean an abnormal condition that negatively affects the structure or function of all or part of a subject, and that is not immediately due to any external injury. In some embodiments, a disease is a medical condition, illness or sickness that is associated with one or more specific signs and symptoms.

The terms "administer," "administering," and "administration" refer to providing, implanting, absorbing, ingesting, injecting, inhaling, or otherwise introducing a compound described herein, or a pharmaceutically acceptable salt or pharmaceutical composition thereof, to, in or on a subject.

The term "ubiquitin ligase" refers to a family of proteins that facilitate the transfer of one or more ubiquitins to a specific substrate protein. Addition of a chain of several ubiquitins (poly-ubiquitination) targets the substrate protein for degradation. For example, cereblon is an E3 ubiquitin ligase that alone, or in combination with an E2 ubiquitin-conjugating enzyme, can ultimately cause the attachment of a chain of four ubiquitins to a lysine residue on the target protein, thereby targeting the protein for degradation by the proteasome. The ubiquitin ligase is involved in poly-ubiquitination such that a first ubiquitin is attached to a lysine on the target protein; a second ubiquitin is attached to the first; a third is attached to the second, and a fourth is attached to the third. Such poly-ubiquitination marks proteins for degradation by the proteasome.

Unless otherwise indicated, the term "RAF" includes both wild-type RAF and mutant forms therefore.

A "RAF related condition" refers to a condition that is responsive to the modulation of RAF such as e.g., conditions which are modulated by degrading the RAF protein (e.g., B-RAF). RAF (e.g., B-RAF) related conditions may arise from protein expression, overexpression, mutation, misfolding, or dysregulation (e.g., the amount of protein expressed in a patient is elevated).

3. Compounds and Compositions

In a second embodiment, $R_{PTM2}$ in the compound having the chemical structure I, or a pharmaceutically acceptable salt thereof, is selected from hydrogen, halo, halo$C_{1-4}$ alkyl, $C_{1-4}$ alkoxy, and halo$C_{1-4}$ alkoxy; $R_{PTM3}$ is selected from $C_{1-4}$ alkyl, halo$C_{1-4}$ alkyl, cyano$C_{1-4}$ alkyl, hydroxy$C_{1-4}$ alkyl, —NH($C_{1-4}$ alkyl), —N($C_{1-4}$ alkyl)$_2$, cycloalkyl, and heterocyclyl, where said cycloalkyl, and heterocyclyl are each optionally substituted with 1 to 3 groups selected from halo, oxo, $C_{1-4}$ alkyl, halo$C_{1-4}$ alkyl, $C_{1-4}$ alkoxy, halo$C_{1-4}$ alkoxy, and cyano; $R^4$ and $R^5$ are each independently hydrogen or $C_{1-4}$ alkyl; $R^w$ and $R^x$ are each independently selected from halo, $C_{1-4}$ alkyl, halo$C_{1-4}$ alkyl, $C_{1-4}$ alkoxy, halo$C_{1-4}$ alkoxy, cyano, OH, —NH($C_{1-4}$ alkyl), and —NH($C_{1-4}$ alkyl)$_2$; and $R^y$ and $R^z$ are each independently hydrogen or $C_{1-4}$ alkyl, wherein the remaining variables are as described above for chemical structure I.

In a third embodiment, X in the compound having the chemical structure I, or a pharmaceutically acceptable salt thereof, is O, wherein the remaining variables are as described above for chemical structure I and the second embodiment.

In a fourth embodiment, $R_{PTM1}$ in the compound having the chemical structure I, or a pharmaceutically acceptable salt thereof, is cyano, wherein the remaining variables are as described above for chemical structure I and the second or third embodiment. Alternatively, as part of the fourth embodiment, $R_{PTM1}$ in the compound having the chemical structure I, or a pharmaceutically acceptable salt thereof, is cyano, —$CH_3$, —$CH_2CH_3$, F, or —Cl, wherein the remaining variables are as described above for chemical structure I and the second or third embodiment.

In a fifth embodiment, $R_{PTM2}$ in the compound having the chemical structure I, or a pharmaceutically acceptable salt thereof, is halo, wherein the remaining variables are as described above for chemical structure I and any one of the second to fourth embodiments. Alternatively, as part of a fifth embodiment, $R_{PTM2}$ in the compound having the chemical structure I, or a pharmaceutically acceptable salt thereof, is fluoro, wherein the remaining variables are as described above for chemical structure I and any one of the second to fourth embodiments.

In a sixth embodiment, $R_{PTM3}$ in the compound having the chemical structure I, or a pharmaceutically acceptable salt thereof, is heterocyclyl optionally substituted with 1 to 3 groups selected from halo, oxo, $C_{1-6}$ alkyl, halo$C_{1-6}$ alkyl, $C_{1-6}$ alkoxy, halo$C_{1-6}$ alkoxy, and cyano, wherein the remaining variables are as described above for chemical structure I and any one of the second to fifth embodiments. Alternatively, as part of a sixth embodiment, $R_{PTM3}$ in the compound having the chemical structure I, or a pharmaceutically acceptable salt thereof, is an N-linked heterocyclyl optionally substituted with 1 to 3 groups selected from halo, oxo, $C_{1-6}$ alkyl, halo$C_{1-6}$ alkyl, $C_{1-6}$ alkoxy, halo$C_{1-6}$ alkoxy, and cyano, wherein the remaining variables are as described above for chemical structure I and any one of the second to fifth embodiments. Alternatively, as part of a sixth embodiment, $R_{PTM3}$ in the compound having the chemical structure I, or a pharmaceutically acceptable salt thereof, is pyrrolidinyl optionally substituted with 1 to 3 groups selected from halo, oxo, $C_{1-6}$ alkyl, halo$C_{1-6}$ alkyl, $C_{1-6}$ alkoxy, halo$C_{1-6}$ alkoxy, and cyano, wherein the remaining variables are as described above for chemical structure I and any one of the second to fifth embodiments. In another alternative, as part of a sixth embodiment, $R_{PTM3}$ in the compound having the chemical structure I, or a pharmaceutically acceptable salt thereof, is pyrrolidinyl optionally substituted with 1 to 3 halo, wherein the remaining variables are as described above for chemical structure I and any one of the second to fifth embodiments.

In a seventh embodiment, the PTM in the compound having the chemical structure I, or a pharmaceutically acceptable salt thereof, is represented by the chemical structure:

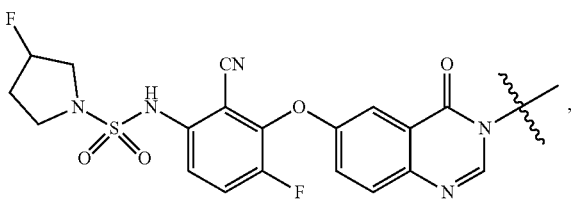 [SMILES: *n1cnc2ccc(Oc3c(F)ccc(NS(=O)(=O)N4CCC(F)C4)c3C#N)cc2c1=O]

wherein the remaining variables are as described above for chemical structure I and any one of the second to sixth embodiments. Alternatively, as part of a seventh embodiment, the PTM in the compound having the chemical structure I, or a pharmaceutically acceptable salt thereof, is represented by the chemical structure:

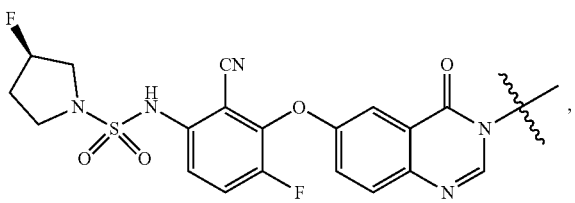 [SMILES: *n1cnc2ccc(Oc3c(F)ccc(NS(=O)(=O)N4CC[C@@H](F)C4)c3C#N)cc2c1=O]

wherein the remaining variables are as described above for chemical structure I and any one of the second to sixth embodiments.

In an eighth embodiment, the CLM in the compound having the chemical structure I, or a pharmaceutically acceptable salt thereof, is represented by the chemical structure:

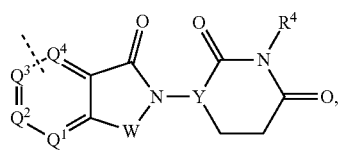
(CLMI)

or

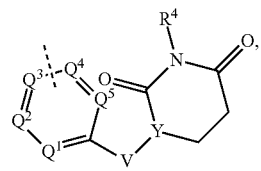
(CLMIII)

wherein the remaining variables are as described above for chemical structure I and any one of the second to seventh embodiments. Alternatively, as part of the eighth embodiment, the CLM in the compound having the chemical structure I, or a pharmaceutically acceptable salt thereof, is represented by the chemical structure:

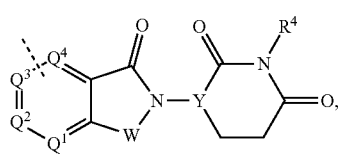
(CLMI)

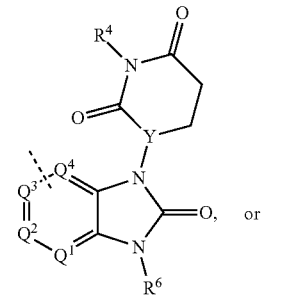
(CLMII)

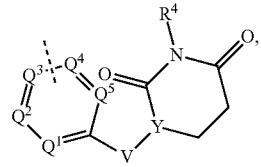
(CLMIII)

wherein the remaining variables are as described above for chemical structure I and any one of the second to seventh embodiments. Alternatively, as part of the eighth embodiment, the CLM in the compound having the chemical structure I, or a pharmaceutically acceptable salt thereof, is represented by the chemical structure:

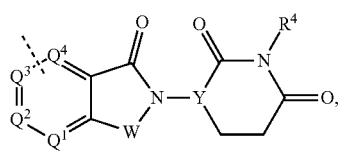
(CLMI)

wherein the remaining variables are as described above for chemical structure I and any one of the second to seventh embodiments. Alternatively, as part of the eighth embodiment, the CLM in the compound having the chemical structure I, or a pharmaceutically acceptable salt thereof, is represented by the chemical structure:

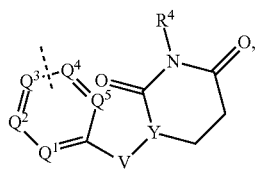
(CLMIII)

wherein the remaining variables are as described above for chemical structure I and any one of the second to seventh embodiments. Alternatively, as part of the eighth embodiment, the CLM in the compound having the chemical structure I, or a pharmaceutically acceptable salt thereof, is represented by the chemical structure:

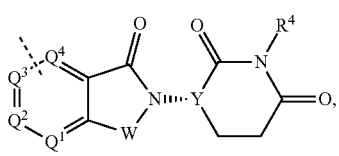
(CLMI')

wherein Y is CH, and the remaining variables are as described above for chemical structure I and any one of the second to seventh embodiments.

In a ninth embodiment, $R^4$ in the compound having the chemical structure I, or a pharmaceutically acceptable salt thereof, is hydrogen, wherein the remaining variables are as described above for chemical structure I and any one of the second to eighth embodiments.

In a tenth embodiment, Y in the compound having the chemical structure I, or a pharmaceutically acceptable salt thereof, is CH, wherein the remaining variables are as described above for chemical structure I and any one of the second to ninth embodiments.

In an eleventh embodiment, $R^y$ and $R^z$ in the compound having the chemical structure I, or a pharmaceutically acceptable salt thereof, are each hydrogen, wherein the remaining variables are as described above for chemical structure I and any one of the second to tenth embodiments.

In a twelfth embodiment, $Q^1$, $Q^2$, $Q^3$, $Q^4$, and $Q^5$ in the compound having the chemical structure I, or a pharmaceutically acceptable salt thereof, are each independently CH or $CR^w$, wherein the remaining variables are as described above for chemical structure I and any one of the second to eleventh embodiments.

In a thirteenth embodiment, $Q^3$, $Q^4$, and $Q^5$ are each CH for the CLM represented by the chemical structure CLMI and CLMIII, wherein the remaining variables are as described above for chemical structure I and any one of the second to twelfth embodiments.

In a fourteenth embodiment, $Q^1$ and $Q^2$ are each $CR^w$ for the CLM represented by the chemical structure CLMIII, wherein the remaining variables are as described above for chemical structure I and any one of the second to thirteenth embodiments. In an alternative fourteenth embodiment, $Q^1$ is CH and $Q^2$ is $CR^w$ for the CLM represented by the chemical structure CLMIII, wherein the remaining variables are as described above for chemical structure I and any one of the second to thirteenth embodiments.

In a fifteenth embodiment, $Q^1$ is $CR^w$ and $Q^2$ is CH for the CLM represented by the chemical structure CLMI, wherein the remaining variables are as described above for chemical structure I and any one of the second to fourteenth embodiments. In an alternative, as part of the fifteenth embodiment, $Q^1$ is CH and $Q^2$ is $CR^w$ for the CLM represented by the chemical structure CLMI, wherein the remaining variables are as described above for chemical structure I and any one of the second to fourteenth embodiments. Alternatively, as part of the fifteenth embodiment, $Q^1$, $Q^2$, and $Q^3$ is CH and $Q^4$ is $CR^w$ for the CLM represented by the chemical structure CLMII, wherein the remaining variables are as described above for chemical structure I and any one of the second to fourteenth embodiments.

In a sixteenth embodiment, $R^w$ in the compound having the chemical structure I, or a pharmaceutically acceptable salt thereof, is selected from halo and $C_{1-4}$ alkoxy, wherein the remaining variables are as described above for chemical structure I and any one of the second to fifteenth embodiments. Alternatively, as part of the sixteenth embodiment, $R^w$ in the compound having the chemical structure I, or a pharmaceutically acceptable salt thereof, is selected from halo, $C_{1-4}$alkyl, and $C_{1-4}$ alkoxy, wherein the remaining variables are as described above for chemical structure I and any one of the second to fifteenth embodiments.

In a seventeenth embodiment, the CLM in the compound having the chemical structure I, or a pharmaceutically acceptable salt thereof, is represented by the chemical structure:

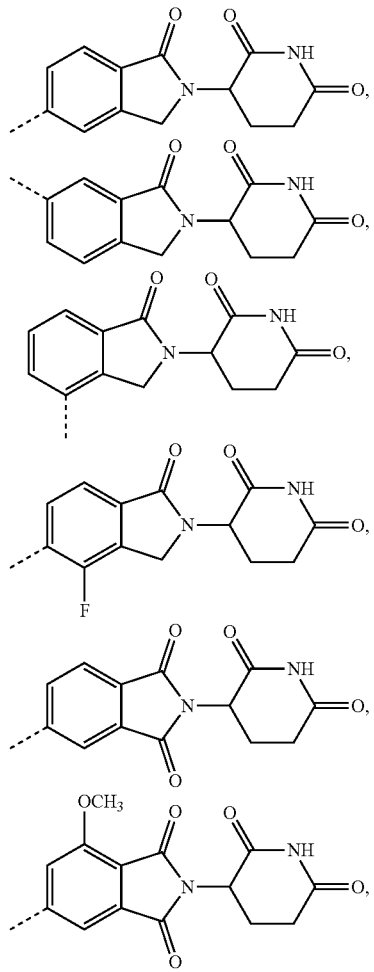

17
-continued
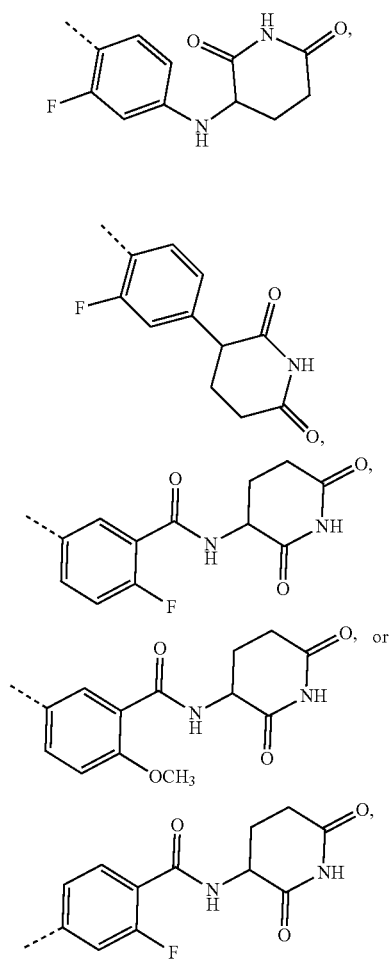
wherein the remaining variables are as described above for chemical structure I and any one of the second to sixteenth embodiments. In an alternative seventeenth embodiment, the CLM in the compound having the chemical structure I, or a pharmaceutically acceptable salt thereof, is represented by the chemical structure:
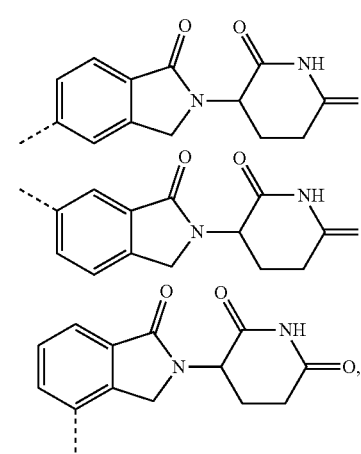
18
-continued
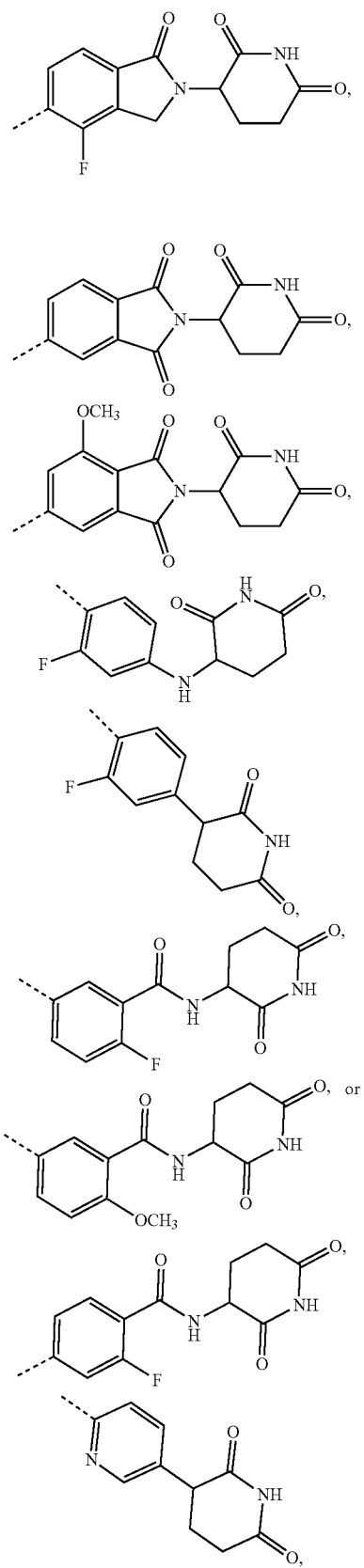

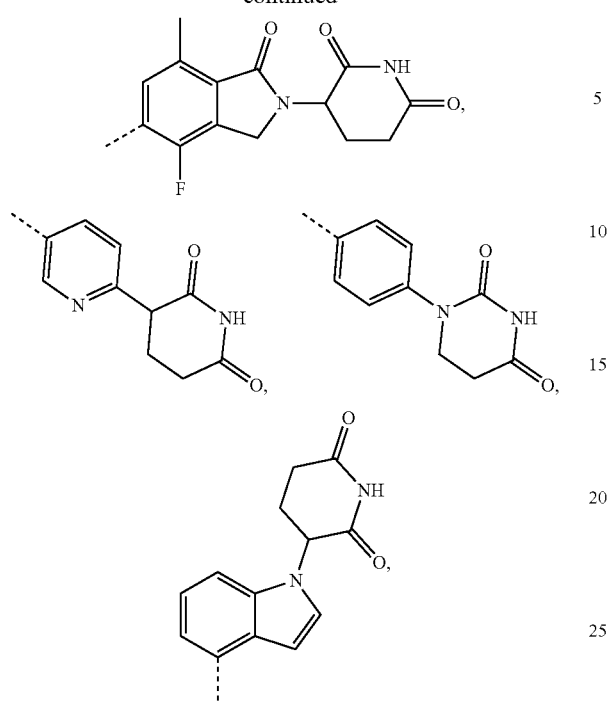
wherein the remaining variables are as described above for chemical structure I and any one of the second to sixteenth embodiments. In an alternative seventeenth embodiment, the CLM in the compound having the chemical structure I, or a pharmaceutically acceptable salt thereof, is represented by the chemical structure:
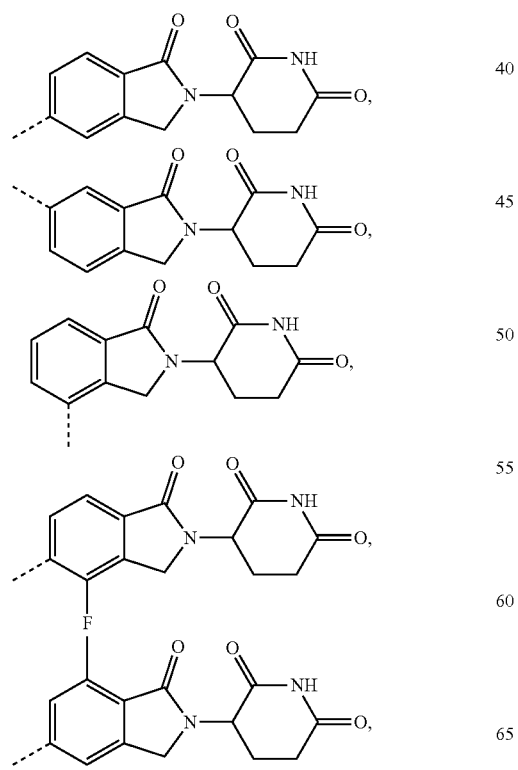
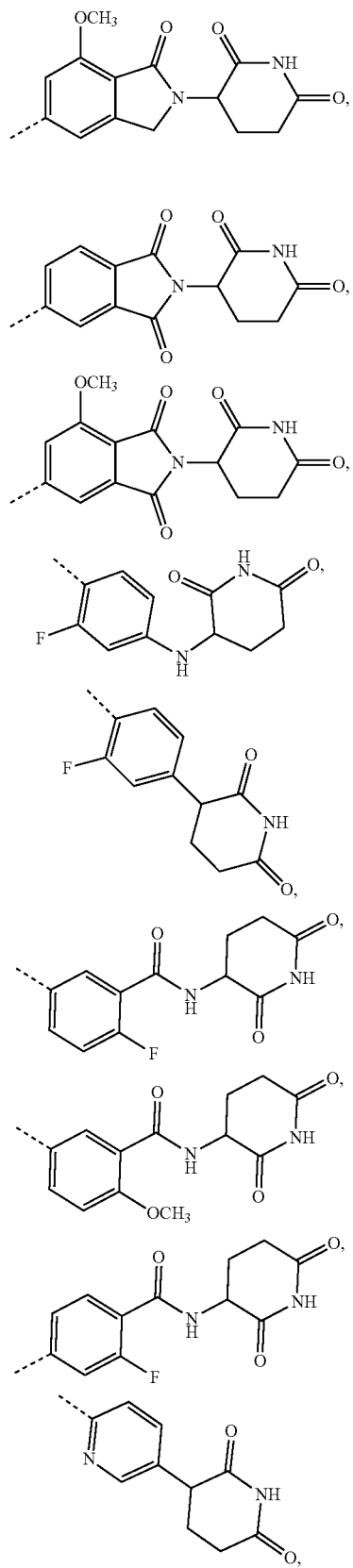

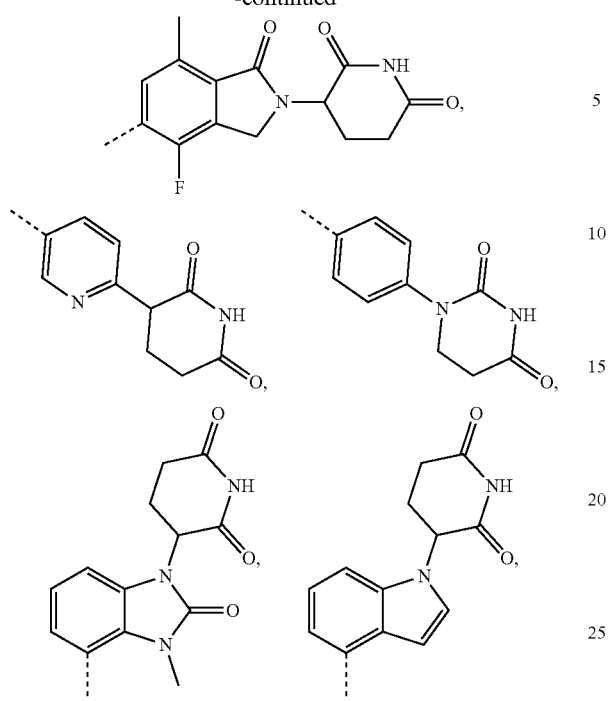
wherein the remaining variables are as described above for chemical structure I and any one of the second to sixteenth embodiments. In an alternative seventeenth embodiment, the CLM in the compound having the chemical structure I, or a pharmaceutically acceptable salt thereof, is represented by the chemical structure:
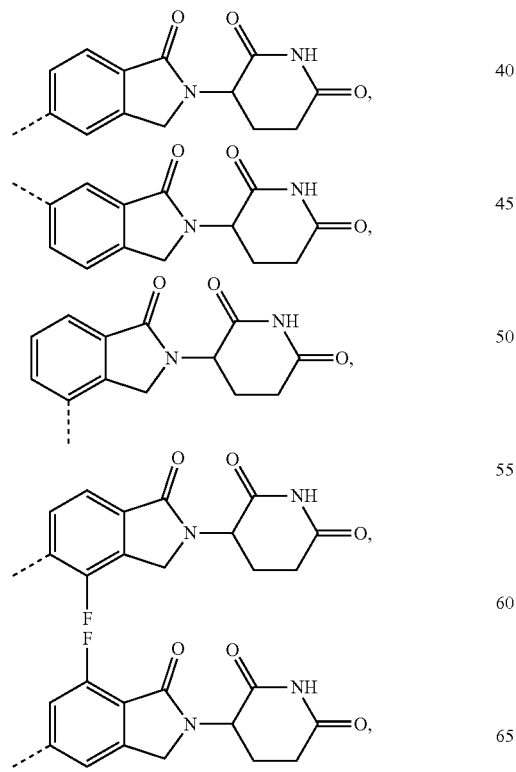
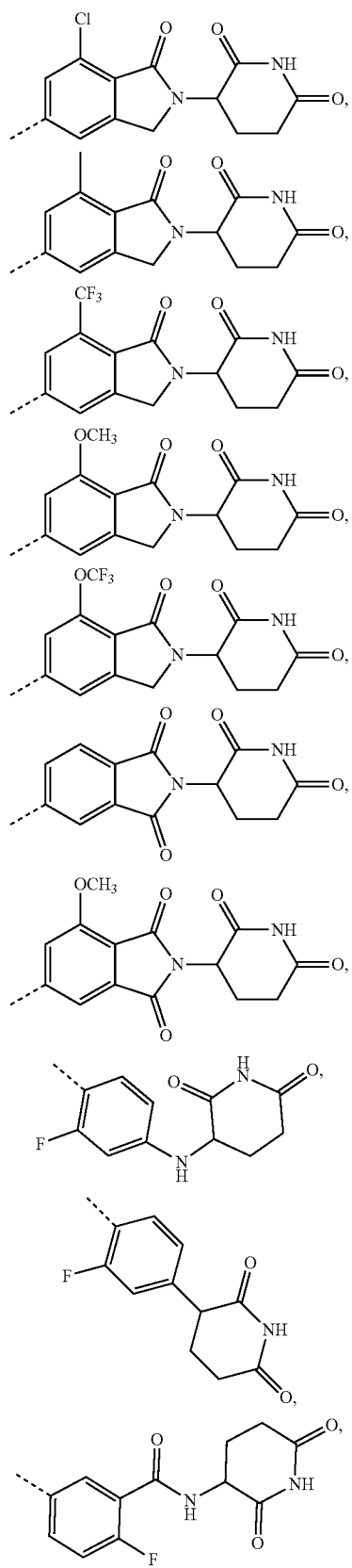

-continued

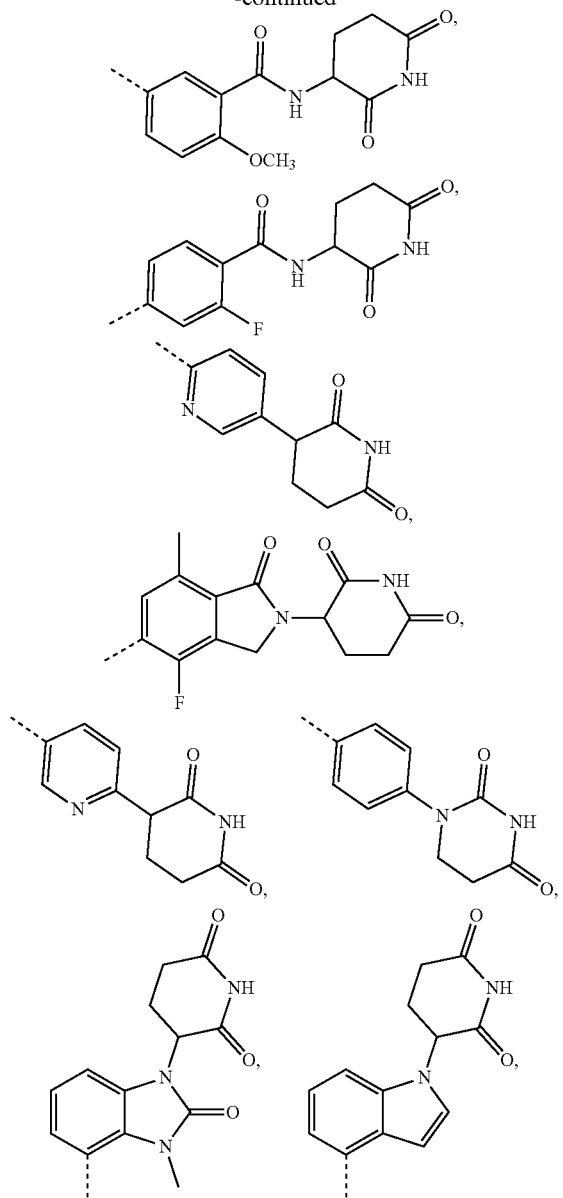

wherein the remaining variables are as described above for chemical structure I and any one of the second to sixteenth embodiments. In another alternative seventeenth embodiment, the CLM in the compound having the chemical structure I, or a pharmaceutically acceptable salt thereof, is represented by the chemical structure:

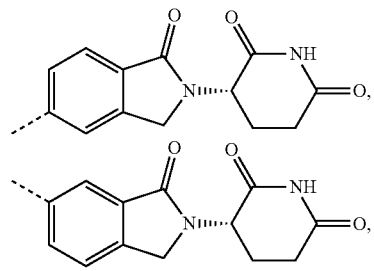

-continued

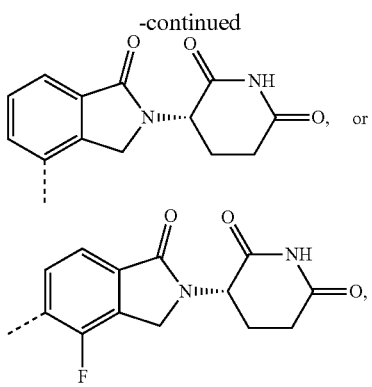

wherein the remaining variables are as described above for chemical structure I and any one of the second to sixteenth embodiments. In yet another alternative seventeenth embodiment, the CLM in the compound having the chemical structure I, or a pharmaceutically acceptable salt thereof, is represented by the chemical structure:

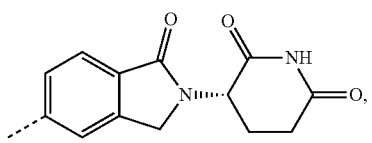

wherein the remaining variables are as described above for chemical structure I and any one of the second to sixteenth embodiments.

In yet another alternative seventeenth embodiment, the CLM in the compound having the chemical structure I, or a pharmaceutically acceptable salt thereof, is represented by the chemical structure:

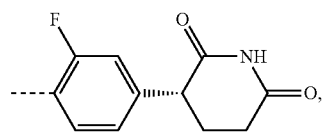

wherein the remaining variables are as described above for chemical structure I and any one of the second to sixteenth embodiments.

In an eighteenth embodiment, the chemical linking moiety (L) in the compound having the chemical structure I, or a pharmaceutically acceptable salt thereof, is represented by the chemical structure A, B, or C:

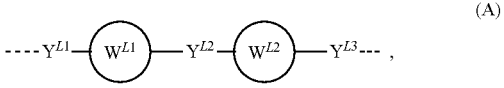

(A)

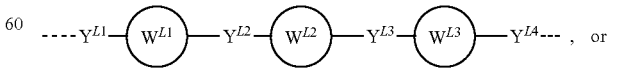

(B)

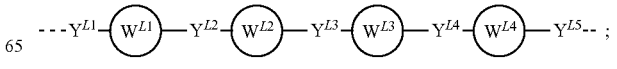

(C)

wherein: $Y^{L1}$, $Y^{L2}$, $Y^{L3}$, $Y^{L4}$ and $Y^{L5}$ are each independently absent or selected from O, NH, N($C_{1-4}$ alkyl), and an optionally substituted $C_{1-6}$ alkylene, wherein said $C_{1-6}$ alkylene may also be optionally interrupted by one or more O, NH, and N($C_{1-4}$ alkyl), and wherein two hydrogens on the same carbon of said $C_{1-6}$ alkylene may be taken together to form oxo; and $W^{L1}$, $W^{L2}$, $W^{L3}$, and $W^{L4}$ are each independently selected from phenyl, heterocyclyl, heteroaryl, and cycloalkyl, each of which are optionally substituted, wherein the remaining variables are as described above for chemical structure I and any one of the second to seventeenth embodiments. In an alternative eighteenth embodiment, the chemical linking moiety (L) in the compound having the chemical structure I, or a pharmaceutically acceptable salt thereof, is represented by the chemical structure A, B, or C:

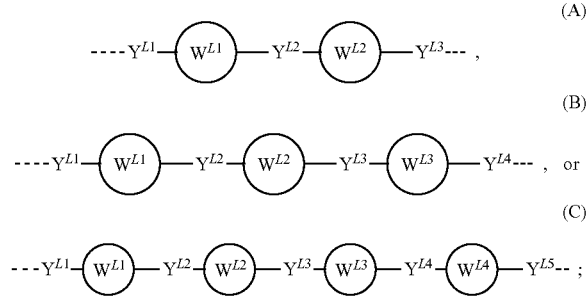

wherein: $Y^{L1}$, $Y^{L2}$, $Y^{L3}$, $Y^{L4}$, and $Y^{L5}$ are each independently absent or selected from O, NH, N($C_{1-4}$ alkyl), and an optionally substituted $C_{1-6}$ alkylene, wherein said $C_{1-6}$ alkylene may also be optionally interrupted by one or more O, NH, and N($C_{1-4}$ alkyl), and wherein two hydrogens on the same carbon of said $C_{1-6}$ alkylene may be taken together to form oxo or $C_{3-6}$cycloalkyl; and $W^{L1}$, $W^{L2}$, $W^{L3}$, and $W^{L4}$ are each independently selected from phenyl, heterocyclyl, heteroaryl, and cycloalkyl, each of which are optionally substituted, wherein the remaining variables are as described above for chemical structure I and any one of the second to seventeenth embodiments. In an alternative eighteenth embodiment, the chemical linking moiety (L) in the compound having the chemical structure I, or a pharmaceutically acceptable salt thereof, is represented by the chemical structure A, B, or C:

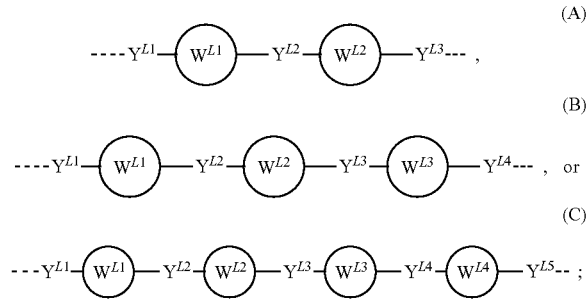

wherein: $Y^{L1}$, $Y^{L2}$, $Y^{L3}$, $Y^{L4}$, and $Y^{L5}$ are each independently absent or selected from O, NH, N($C_{1-4}$ alkyl), and an optionally substituted $C_{1-6}$ alkylene, wherein said $C_{1-6}$ alkylene may also be optionally interrupted by one or more O, NH, and $NR^{NY}$, and wherein two hydrogens on the same carbon of said $C_{1-6}$ alkylene may be taken together to form oxo or $C_{3-6}$cycloalkyl; $R^{NY}$ is $C_{1-4}$alkyl optionally substituted by $C_{1-3}$alkoxy or oxo; and $W^{L1}$, $W^{L2}$, $W^{L3}$, and WM are each independently selected from phenyl, heterocyclyl, heteroaryl, and cycloalkyl, each of which are optionally substituted, wherein the remaining variables are as described above for chemical structure I and any one of the second to seventeenth embodiments.

In a nineteenth embodiment, $Y^{L1}$, $Y^{L2}$, $Y^{L3}$, $Y^{L4}$, and $Y^{L5}$ in the chemical structure A, B, or C are each independently absent or selected from O, NH, N($C_{1-4}$ alkyl), and a $C_{1-6}$ alkylene optionally interrupted by one or more O, NH, and N($C_{1-4}$ alkyl), and wherein two hydrogens on the same carbon of said $C_{1-6}$ alkylene may be taken together to form oxo; $W^{L1}$, $W^{L2}$, $W^{L3}$, and WM are each independently selected from phenyl, heterocyclyl, heteroaryl, and cycloalkyl, each of which are optionally substituted with 1 to 4 groups selected from $R^M$; and $R^M$ is selected from halo, OH, cyano, oxo, $C_{1-4}$ alkyl, $C_{1-4}$ haloalkyl, $C_{1-4}$ hydroxyalkyl, $C_{1-4}$ alkoxy, and $C_{1-4}$ haloalkoxy, wherein the remaining variables are as described above for chemical structure I and any one of the second to eighteenth embodiments. In a nineteenth embodiment, $Y^{L1}$, $Y^{L2}$, $y^{L3}$, $Y^{L4}$, and $Y^{L5}$ in the chemical structure A, B, or C are each independently absent or selected from O, NH, N($C_{1-4}$ alkyl), and a $C_{1-6}$ alkylene optionally interrupted by one or more O, NH, and N($C_{1-4}$ alkyl), and wherein two hydrogens on the same carbon of said $C_{1-6}$ alkylene may be taken together to form oxo ot $C_{3-4}$cycloalkyl; $W^L$, $W^{L2}$, $W^{L3}$, and WM are each independently selected from phenyl, heterocyclyl, heteroaryl, and cycloalkyl, each of which are optionally substituted with 1 to 4 groups selected from $R^M$; and $R^M$ is selected from halo, OH, cyano, oxo, $C_{1-4}$ alkyl, $C_{1-4}$ haloalkyl, $C_{1-4}$ hydroxyalkyl, $C_{1-4}$ alkoxy, and $C_{1-4}$ haloalkoxy, wherein the remaining variables are as described above for chemical structure I and any one of the second to eighteenth embodiments.

In a twentieth embodiment, $Y^{L1}$ in the chemical structure A, B, or C is absent, wherein the remaining variables are as described above for chemical structure I and any one of the second to nineteenth embodiments.

In a twenty-first embodiment, $W^{L1}$ in the chemical structure A, B, or C is selected from phenyl, 4- to 7-membered heterocyclyl, and 5- to 7-membered heteroaryl, each of which are optionally substituted with 1 to 3 groups selected from $R^M$, wherein the remaining variables are as described above for chemical structure I and any one of the second to twentieth embodiments. Alternatively, as part of the twenty-first embodiment, $W^{L1}$ in the chemical structure A, B, or C is selected from phenyl, 4- to 7-membered heterocyclyl, and 5- to 10-membered heteroaryl, each of which are optionally substituted with 1 to 3 groups selected from $R^M$, wherein the remaining variables are as described above for chemical structure I and any one of the second to twentieth embodiments. Alternatively, as part of a twenty-first embodiment, $W^{L1}$ in the chemical structure A, B, or C is selected from phenyl, piperidinyl, pyridinyl, and pyrimidinyl, each of which are optionally substituted with 1 to 3 groups selected from $R^M$, wherein the remaining variables are as described above for chemical structure I and any one of the second to twentieth embodiments. In an alternative twenty-first embodiment, $W^{L1}$ in the chemical structure A, B, or C is selected from pyrazoyl, thiophenyl, phenyl, piperidinyl, pyridinyl, pyridazinyl, pyrazinyl, and pyrimidinyl, each of which are optionally substituted with 1 to 3 groups selected from $R^M$, wherein the remaining variables are as described above for chemical structure I and any one of the second to twentieth embodiments. Alternatively, as part of a twenty-first embodiment, $W^{L1}$ in the chemical structure A, B, or C is selected from pyrazoyl, thiophenyl, phenyl, piperidinyl, pyridinyl, 1-oxa-8-azaspiro[4.5]decanyl, pyridazinyl, pyrazinyl, and pyrimidinyl, each of which are optionally substituted with 1 to 3 groups selected from $R^M$, wherein the remaining variables are as described above for chemical structure I and any one of the second to twentieth embodiments.

In a twenty-second embodiment, $Y^{L2}$ in the chemical structure A, B, or C is absent or selected from NH and a $C_{1-6}$ alkylene, wherein the remaining variables are as described above for chemical structure I and any one of the second to twenty-first embodiments. In an alternative twenty-second embodiment, $Y^{L2}$ in the chemical structure A, B, or C is absent or selected from NH and a $C_{1-6}$ alkylene, wherein two hydrogens on the same carbon of said $C_{1-6}$ alkylene may be taken together to form $C_{3-4}$cycloalkyl, and wherein the remaining variables are as described above for chemical structure I and any one of the second to twenty-first embodiments.

In a twenty-third embodiment, $W^{L2}$ in the chemical structure A, B, or C is selected from 4- to 11-membered heterocyclyl and cycloalkyl, each of which are optionally substituted with 1 to 3 groups selected from $R^M$, wherein the remaining variables are as described above for chemical structure I and any one of the second to twenty-second embodiments. Alternatively, as part of a twenty-third embodiment, $W^{L2}$ in the chemical structure A, B, or C is selected from piperidinyl, piperazinyl, azetidinyl, morpholinyl, 2,6-diazaspiro[3.3]heptanyl, 3,9-diazaspiro[5.5]undecanyl, 2,7-diazaspiro[3.5]nonanyl, cyclobutyl, and cyclohexyl, each of which are optionally substituted with 1 to 3 groups selected from $R^M$, wherein the remaining variables are as described above for chemical structure I and any one of the second to twenty-second embodiments. In an alternative twenty-third embodiment, $W^{L2}$ in the chemical structure A, B, or C is selected from pyrrolidinyl, piperidinyl, piperazinyl, azetidinyl, morpholinyl, 2-azaspiro[3.3]heptanyl, 2,6-diazaspiro[3.3]heptanyl, 3,9-diazaspiro[5.5]undecanyl, 2,7-diazaspiro[3.5]nonanyl, cyclobutyl, and cyclohexyl, each of which are optionally substituted with 1 to 3 groups selected from $R^M$, wherein the remaining variables are as described above for chemical structure I and any one of the second to twenty-second embodiments. In an alternative twenty-second embodiment, $W^{L2}$ in the chemical structure A, B, or C is selected from piperidinyl, piperazinyl, pyrrolidinyl, azetidinyl, morpholinyl, 7-azaspiro[3.5]nonanyl, 2,6-diazaspiro[3.3]heptanyl, 3,9-diazaspiro[5.5]undecanyl, 2,7-diazaspiro[3.5]nonanyl, cyclobutyl, and cyclohexyl, each of which are optionally substituted with 1 to 3 groups selected from $R^M$, wherein the remaining variables are as described above for chemical structure I and any one of the second to twenty-second embodiments.

In a twenty-fourth embodiment, $Y^{L3}$ in the chemical structure A, B, or C is absent or selected from O and a $C_{1-6}$ alkylene, wherein said $C_{1-6}$ alkylene may be optionally interrupted by O, NH, and $N(C_{1-4}$ alkyl), and wherein two hydrogens on the same carbon of said $C_{1-6}$ alkylene may be taken together to form oxo, wherein the remaining variables are as described above for chemical structure I and any one of the second to twenty-third embodiments.

In a twenty-fifth embodiment, $W^{L3}$ in the chemical structure A, B, or C is selected from 4- to 7-membered heterocyclyl, cycloalkyl, and 5- to 7-membered heteroaryl, each of which are optionally substituted with 1 to 3 groups selected from $R^M$, wherein the remaining variables are as described above for chemical structure I and any one of the second to twenty-fourth embodiments. In an alternative twenty-fifth embodiment, $W^{L3}$ in the chemical structure A, B, or C is selected from 4- to 11-membered heterocyclyl, cycloalkyl, and 5- to 7-membered heteroaryl, each of which are optionally substituted with 1 to 3 groups selected from $R^M$, wherein the remaining variables are as described above for chemical structure I and any one of the second to twenty-fourth embodiments. Alternatively, as part of a twenty-fifth embodiment, $W^{L3}$ in the chemical structure A, B, or C is selected from piperidinyl, azetidinyl, piperazinyl, cyclohexyl, cyclobutyl, and pyrimidinyl, each of which are optionally substituted with 1 to 3 groups selected from $R^M$, wherein the remaining variables are as described above for chemical structure I and any one of the second to twenty-fourth embodiments. Alternatively, as part of the twenty-fifth embodiment, $W^{L3}$ in the chemical structure A, B, or C is selected from pyrrolidinyl, piperidinyl, azetidinyl, piperazinyl, 2,6-diazaspiro[3.3]heptanyl, 2-azaspiro[3.3]heptanyl, 2,7-diazaspiro[3.5]nonanyl, 3,9-diazaspiro[5.5]undecanyl, cyclohexyl, cyclobutyl, and pyrimidinyl, each of which are optionally substituted with 1 to 3 groups selected from $R^M$, wherein the remaining variables are as described above for chemical structure I and any one of the second to twenty-fourth embodiments. Alternatively, as part of the twenty-fifth embodiment, $W^{L3}$ in the chemical structure A, B, or C is selected from pyrrolidinyl, piperidinyl, azetidinyl, piperazinyl, 2,6-diazaspiro[3.3]heptanyl, 2-azaspiro[3.3]heptanyl, 2,7-diazaspiro[3.5]nonanyl, 2-azaspiro[3.5]nonanyl, 3-azaspiro[5.5]undecanyl, 3,9-diazaspiro[5.5]undecanyl, cyclohexyl, cyclobutyl, and pyrimidinyl, each of which are optionally substituted with 1 to 3 groups selected from $R^M$, wherein the remaining variables are as described above for chemical structure I and any one of the second to twenty-fourth embodiments. Alternatively, as part of the twenty-fifth embodiment, $W^{L3}$ in the chemical structure A, B, or C is selected from pyrrolidinyl, piperidinyl, azetidinyl, piperazinyl, 2,6-diazaspiro[3.3]heptanyl, 2-azaspiro[3.3]heptanyl, 2,7-diazaspiro[3.5]nonanyl, 3,9-diazaspiro[5.5]undecanyl, cyclohexyl, cyclobutyl, and pyrimidinyl, each of which are optionally substituted with 1 to 3 groups selected from $R^M$, wherein the remaining variables are as described above for chemical structure I and any one of the second to twenty-fourth embodiments.

In a twenty-sixth embodiment, $Y^L$ in the chemical structure A, B, or C is absent or selected from O, NH, and a $C_{1-6}$ alkylene, wherein the remaining variables are as described above for chemical structure I and any one of the second to twenty-fifth embodiments. Alternatively, as part of the twenty-sixth embodiment, $Y^L$ in the chemical structure A, B, or C is absent or selected from O, NH, NCH₃, and a $C_{1-6}$ alkylene, wherein the remaining variables are as described above for chemical structure I and any one of the second to twenty-fifth embodiments.

In a twenty-seventh embodiment, WM in the chemical structure A, B, or C is 4- to 7-membered heterocyclyl optionally substituted with 1 to 3 groups selected from $R^M$, wherein the remaining variables are as described above for chemical structure I and any one of the second to twenty-sixth embodiments. Alternatively, as part of a twenty-seventh embodiment, WM in the chemical structure A, B, or C is selected from piperidinyl and piperazinyl, each of which are optionally substituted with 1 to 3 groups selected from $R^M$, wherein the remaining variables are as described above for chemical structure I and any one of the second to twenty-sixth embodiments.

In a twenty-eighth embodiment, $Y^{L5}$ in the chemical structure A, B, or C is absent or is a $C_{1-6}$ alkylene, wherein the remaining variables are as described above for chemical structure I and any one of the second to twenty-seventh embodiments.

In a twenty-ninth embodiment, $R^M$ in the chemical structure A, B, or C is $C_{1-4}$ alkoxy or OH, wherein the remaining variables are as described above for chemical structure I and any one of the second to twenty-eighth embodiments. In an alternative twenty-ninth embodiment, $R^M$ in the chemical structure A, B, or C is $C_{1-4}$ alkoxy, halo, or OH, wherein the remaining variables are as described above for chemical structure I and any one of the second to twenty-eighth embodiments.

In a thirtieth embodiment, the chemical linking moiety (L) in the compound having the chemical structure I, or a pharmaceutically acceptable salt thereof, is represented by the structure:

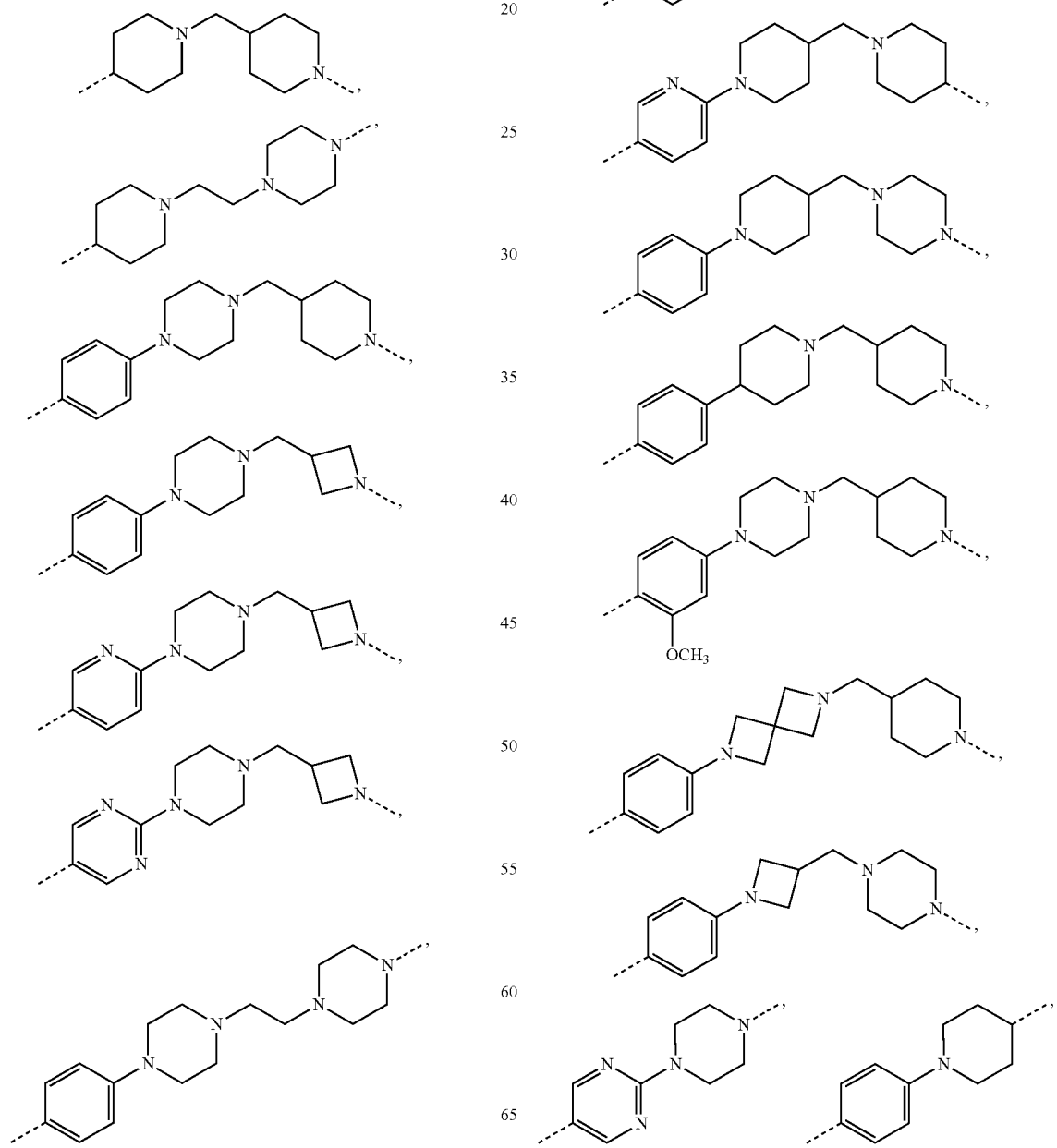

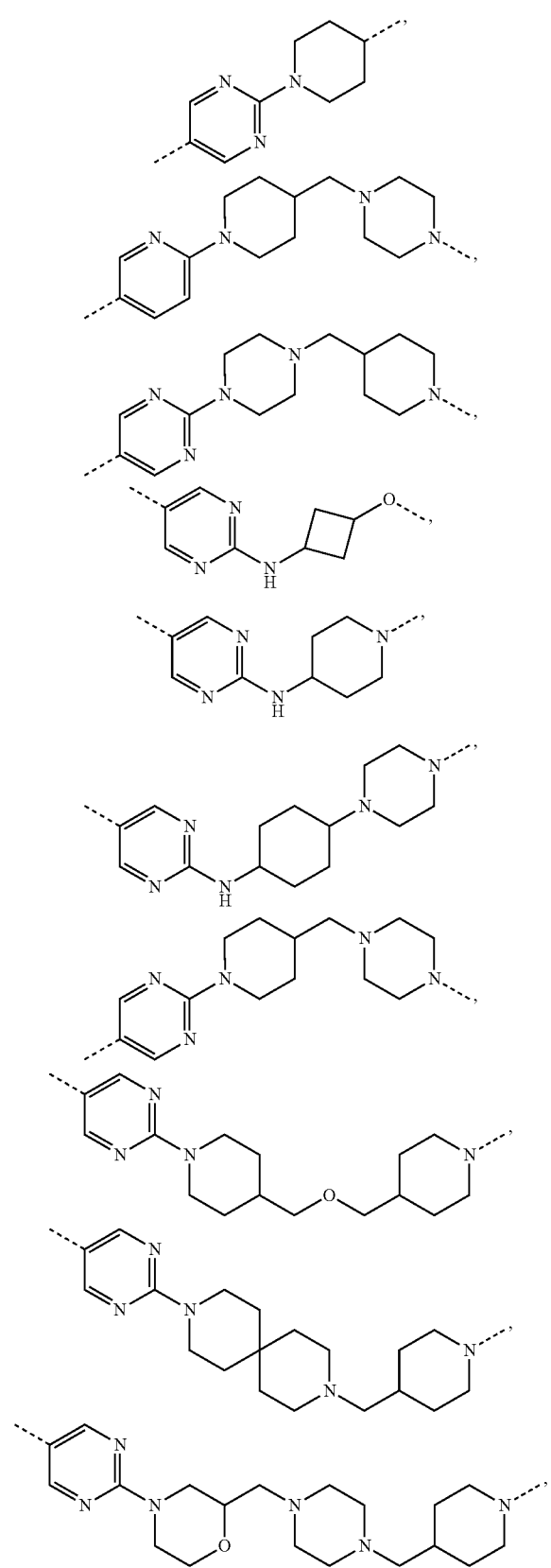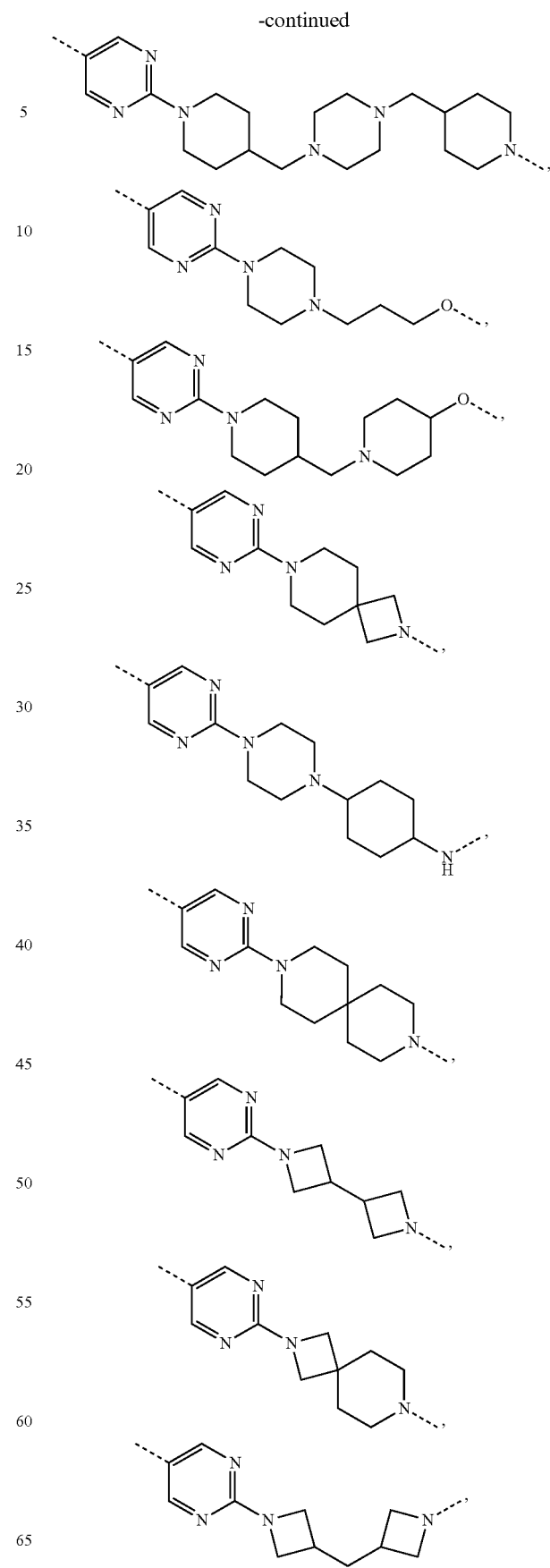

-continued

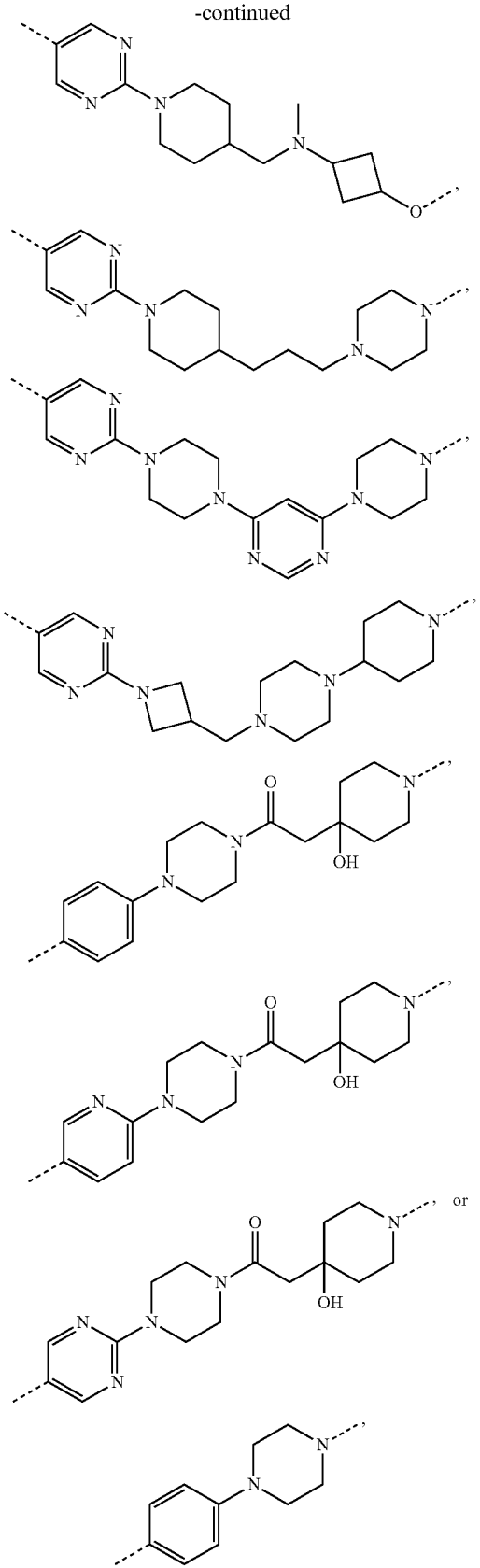

wherein the dashed lines indicate the point of attachment to the PTM and CLM and wherein the remaining variables are as described above for chemical structure I and any one of the second to twenty-ninth embodiments. In an alternative thirtieth embodiment, the chemical linking moiety (L) in the compound having the chemical structure I, or a pharmaceutically acceptable salt thereof, is represented by the structure:

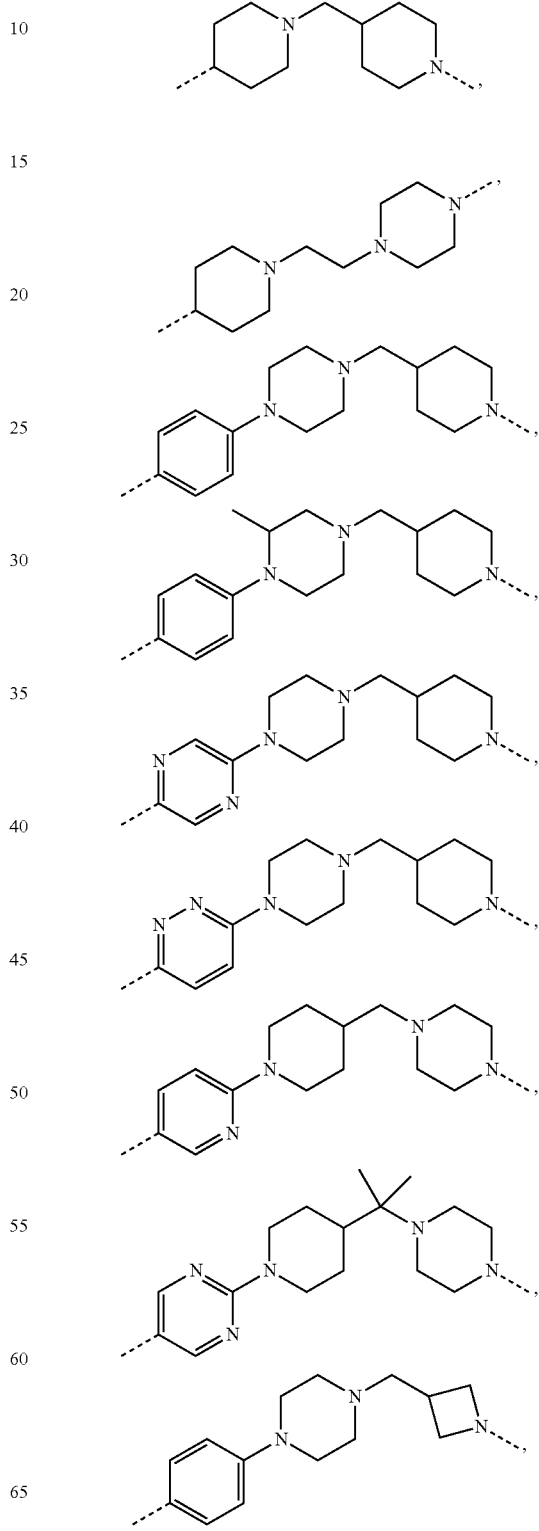

-continued
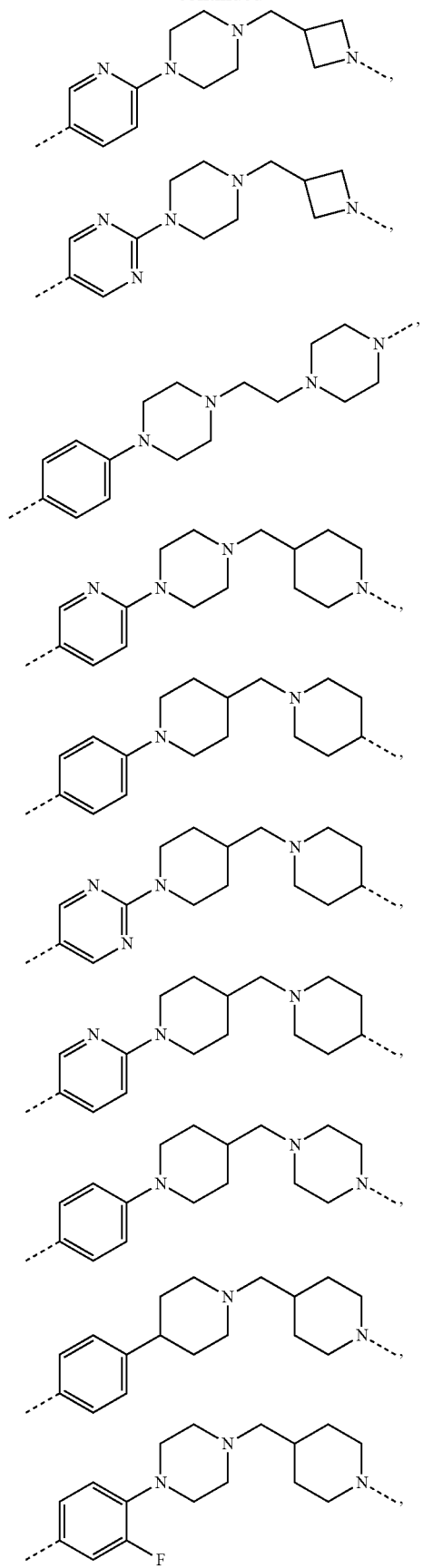
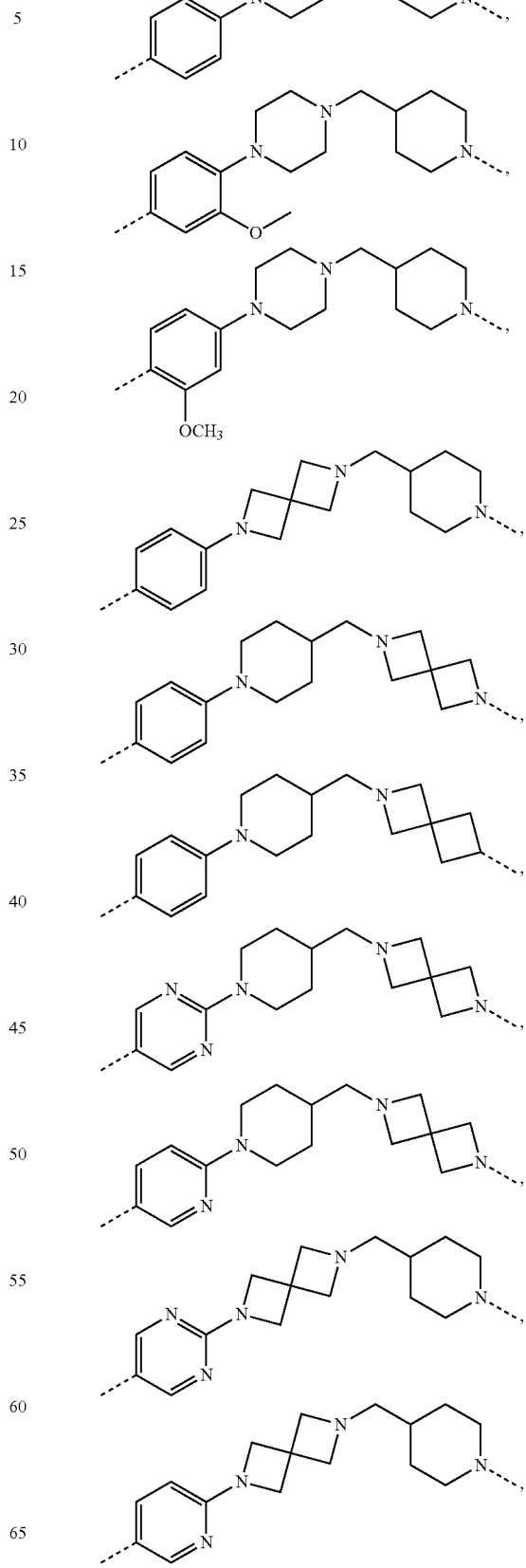

-continued
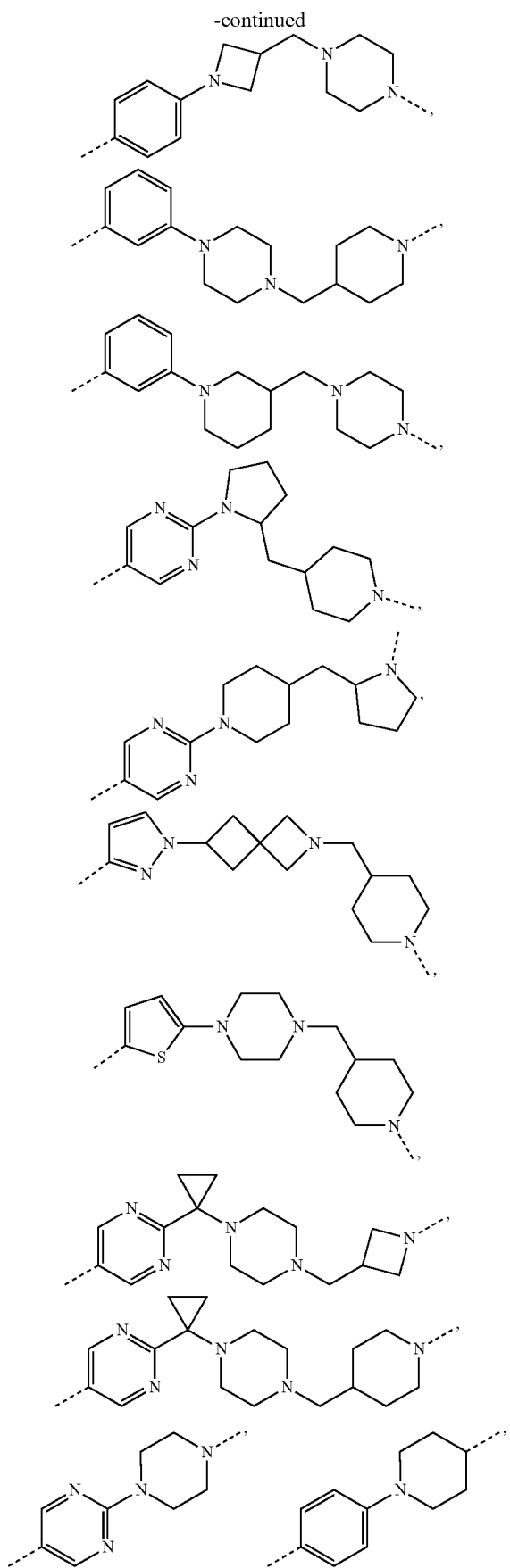
-continued
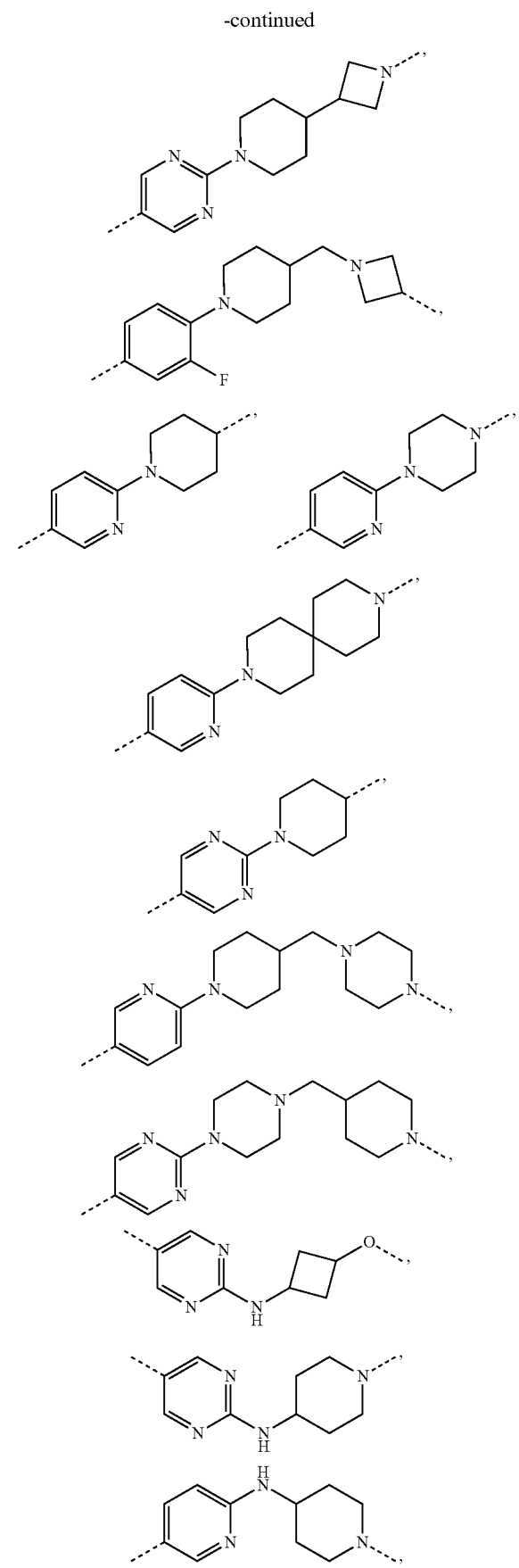

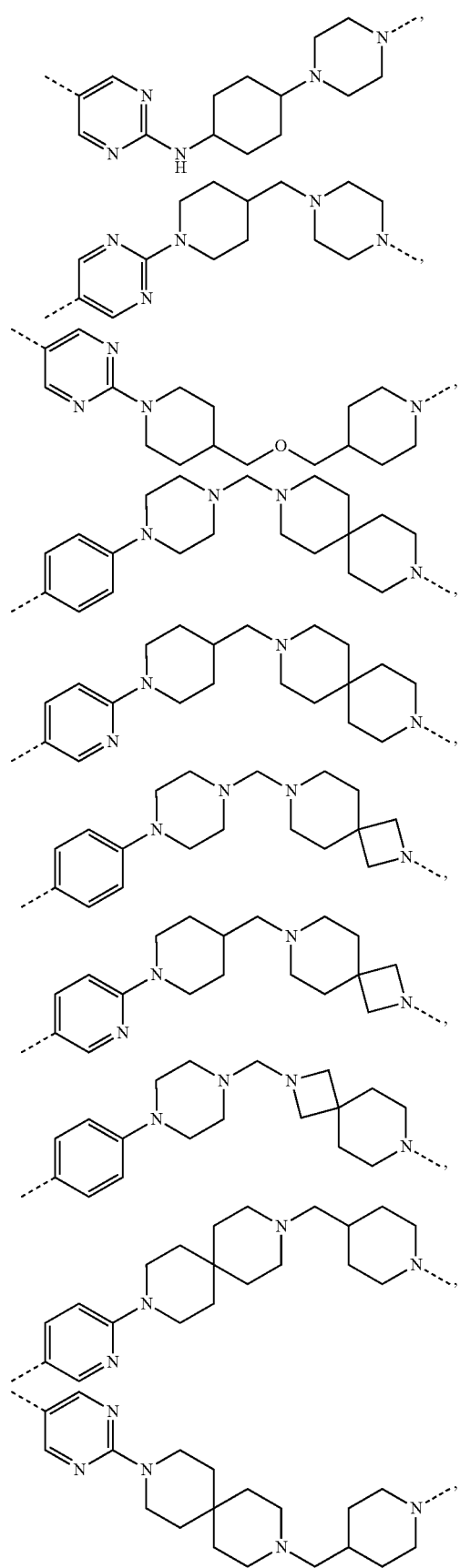
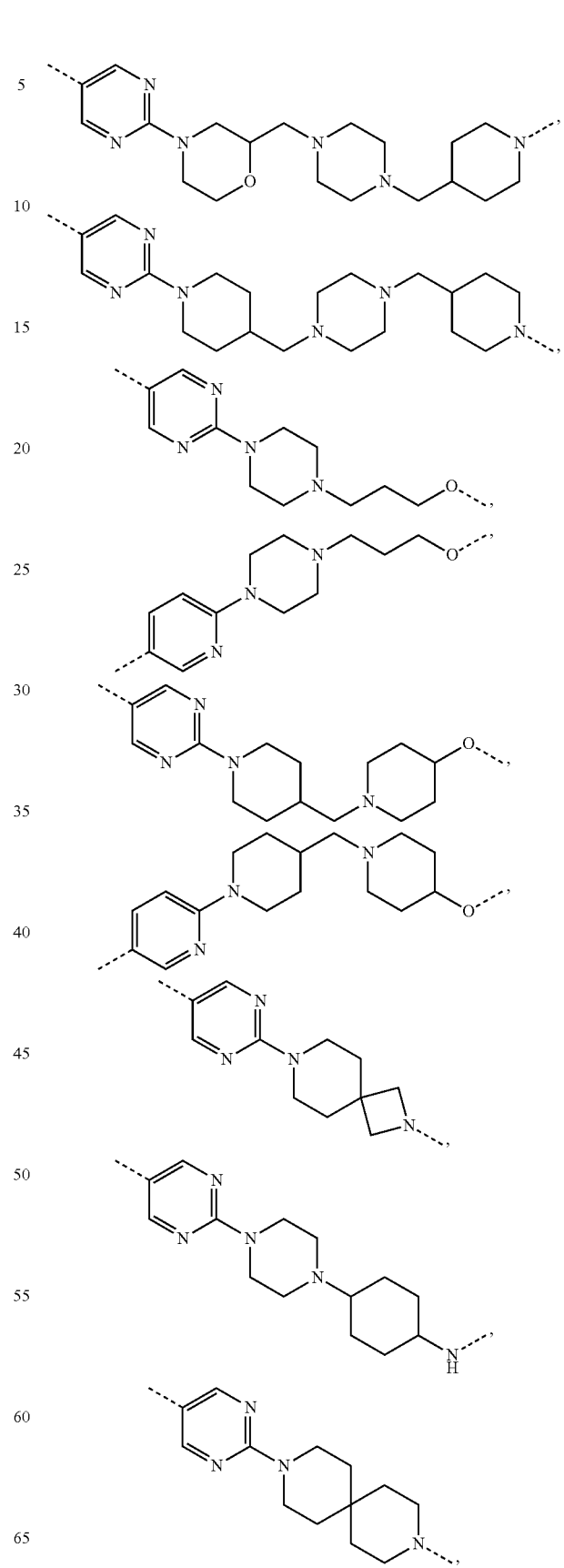

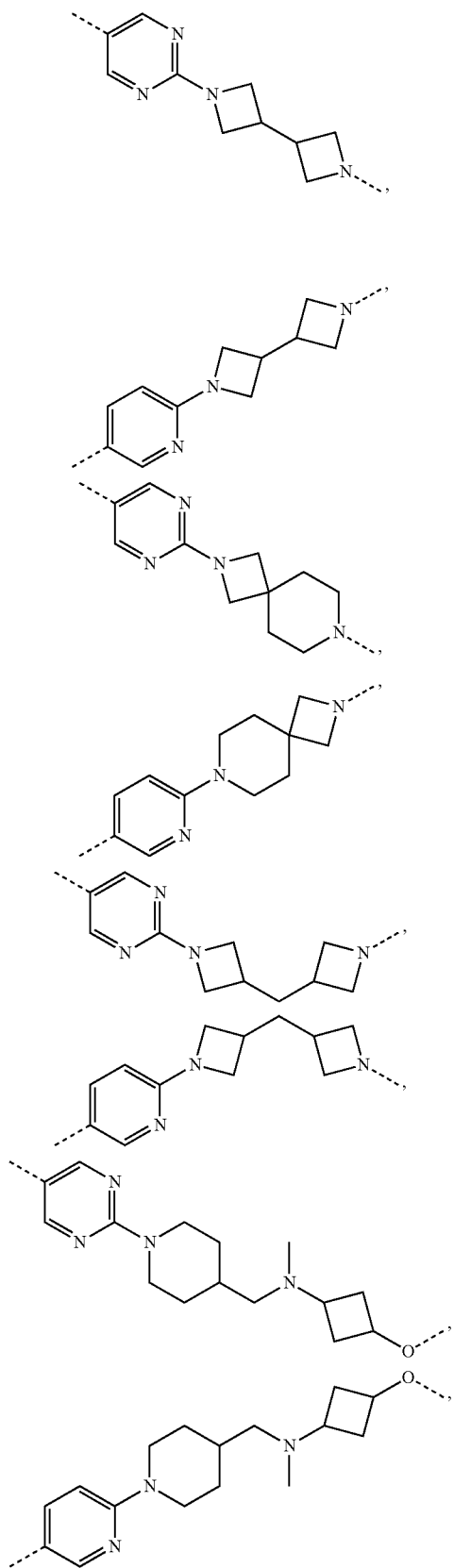
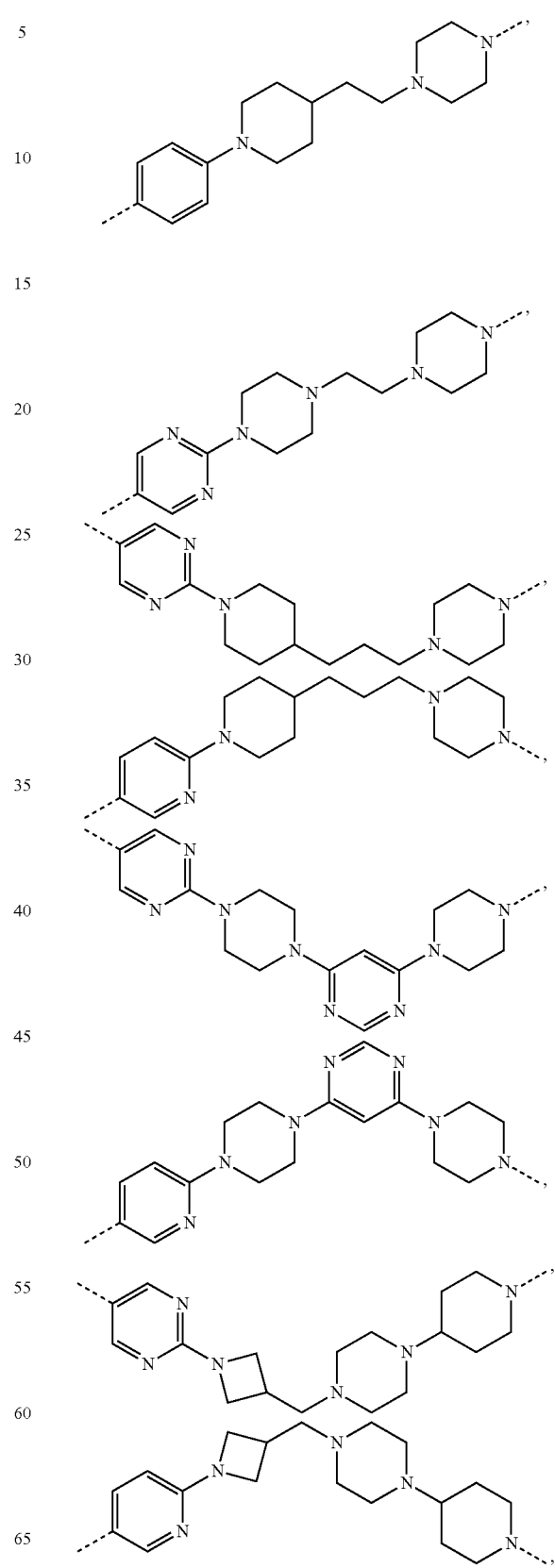

-continued

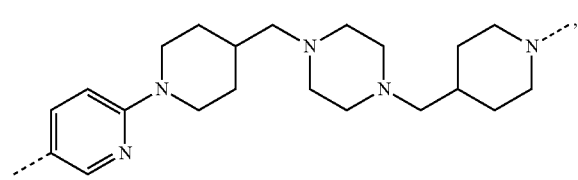

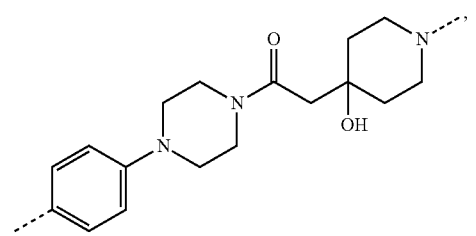

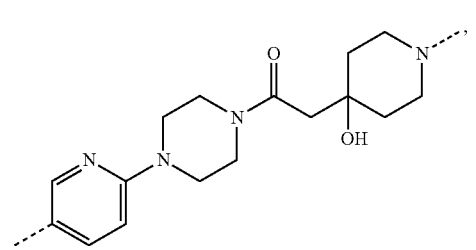

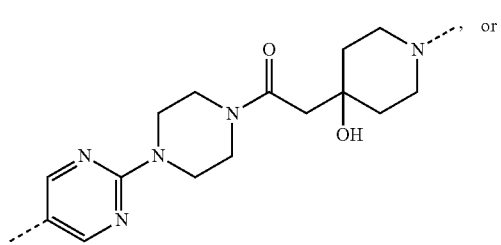, or

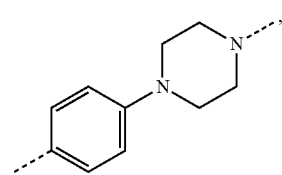

wherein the dashed lines indicate the point of attachment to the PTM and CLM and wherein the remaining variables are as described above for chemical structure I and any one of the second to twenty-ninth embodiments. In an alternative thirtieth embodiment, the chemical linking moiety (L) in the compound having the chemical structure I, or a pharmaceutically acceptable salt thereof, is represented by the structure:

-continued

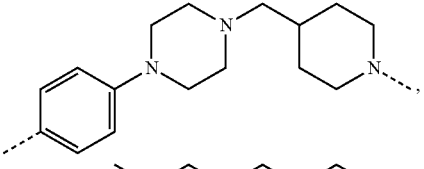

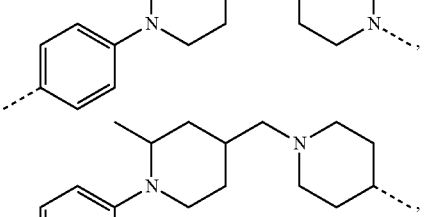

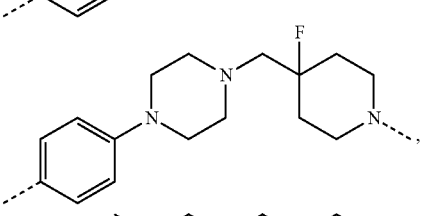

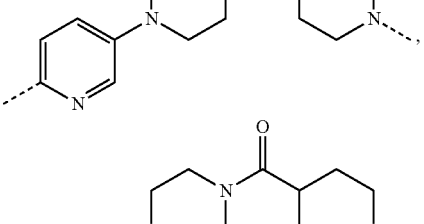

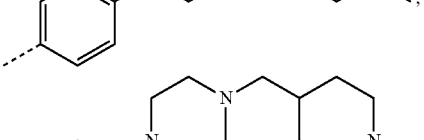

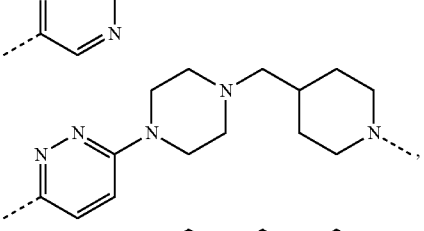

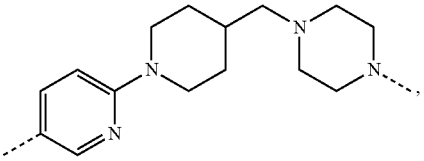

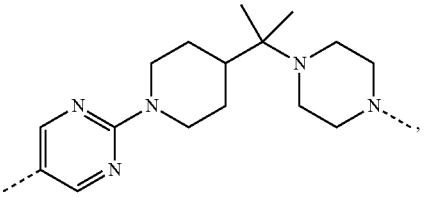

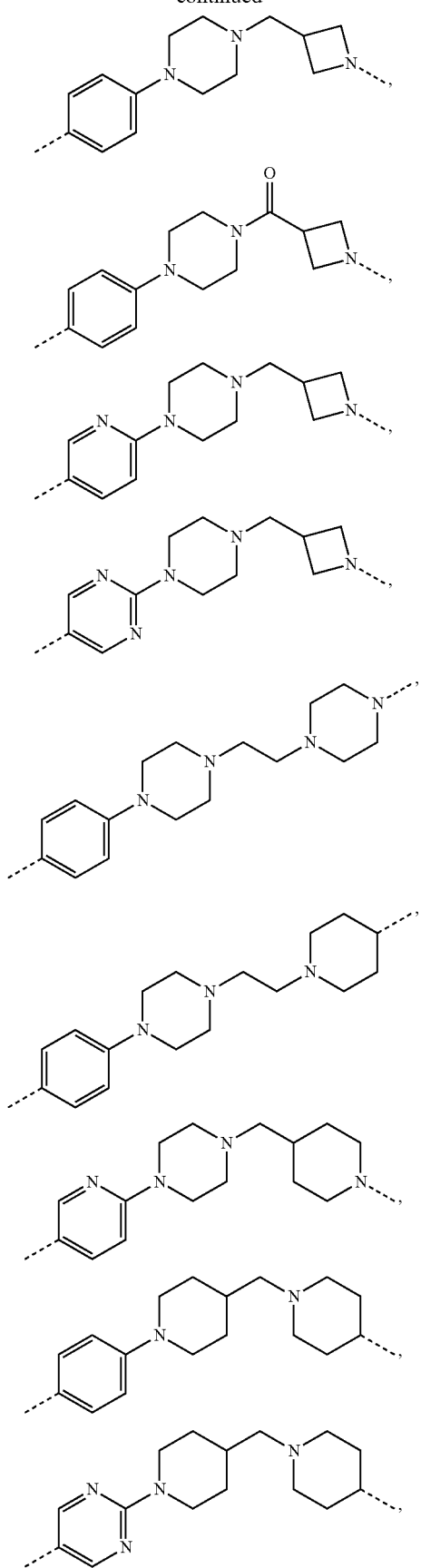
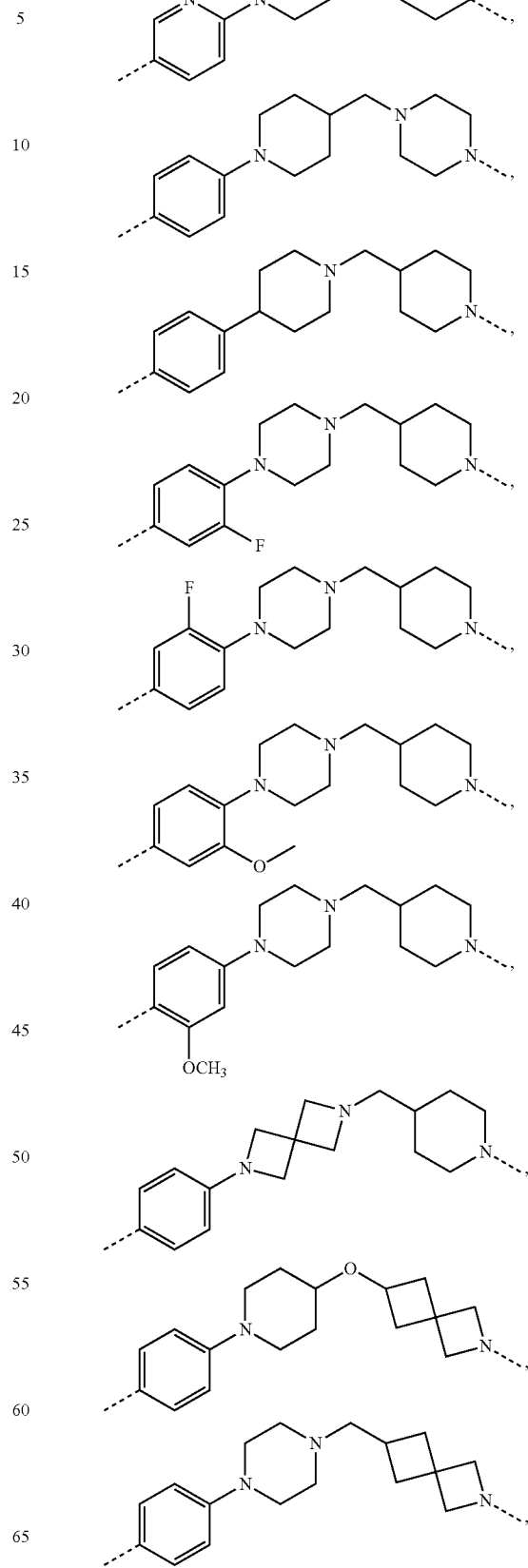

-continued
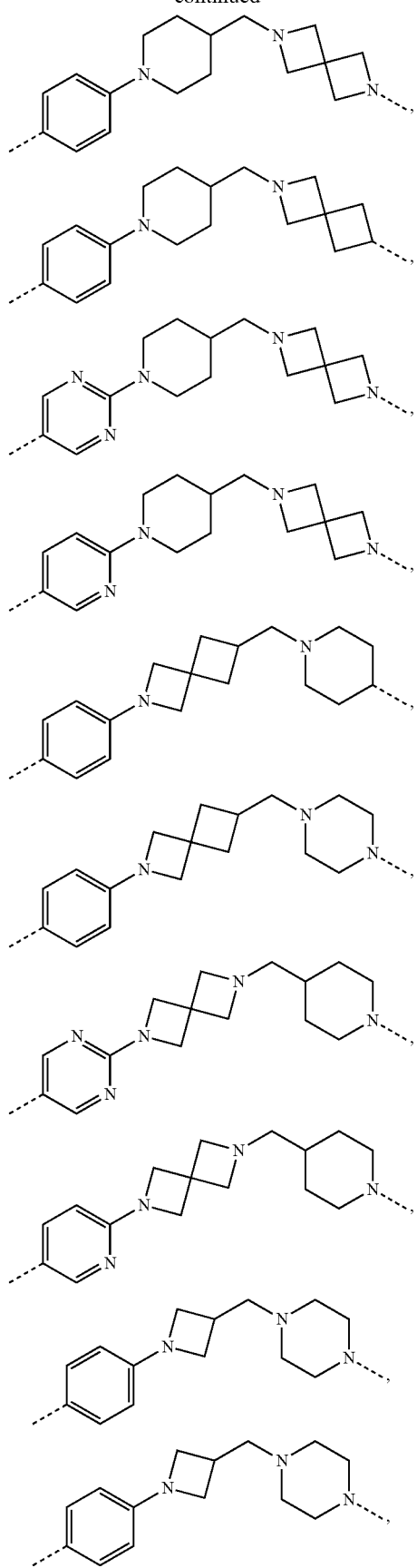
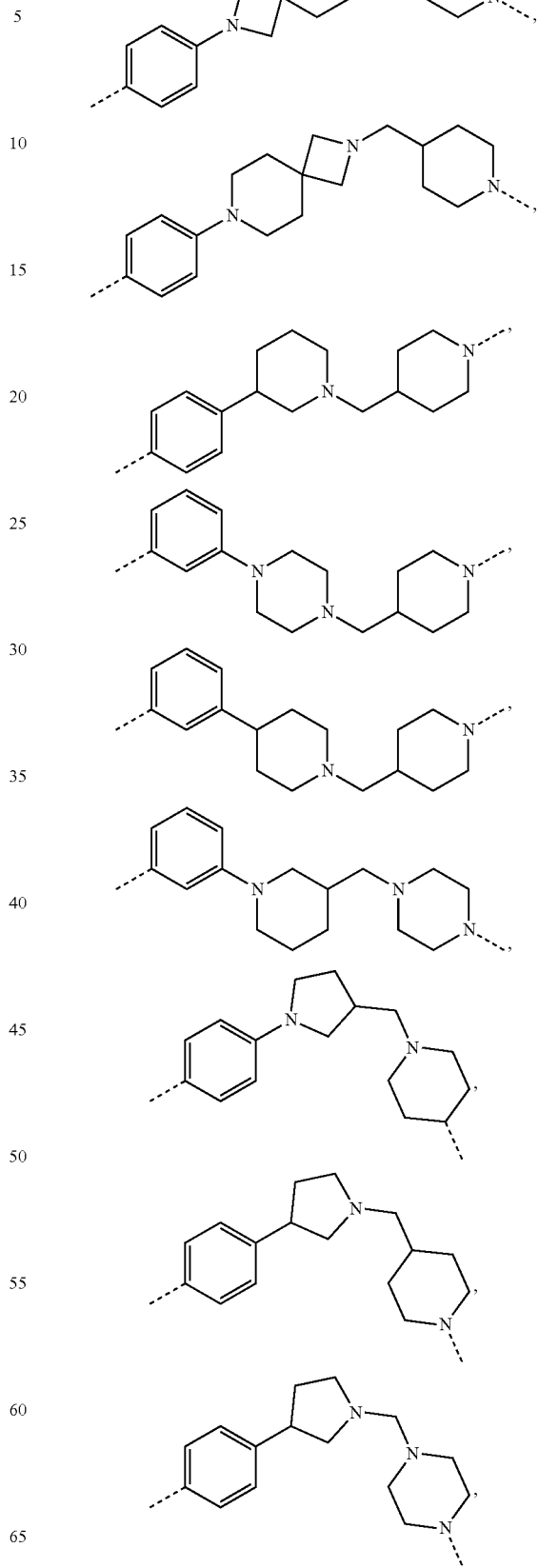

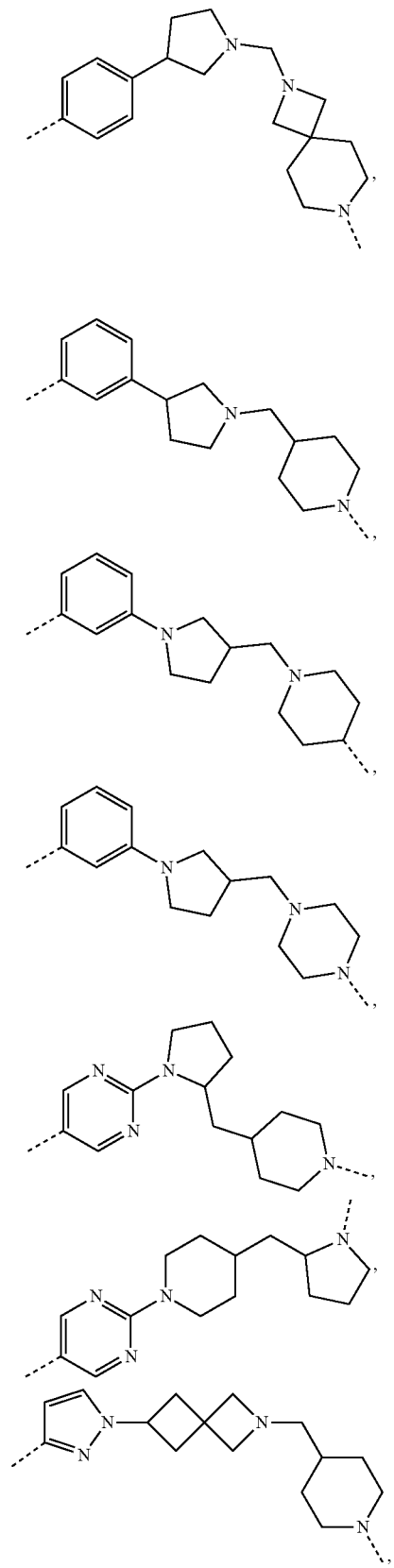
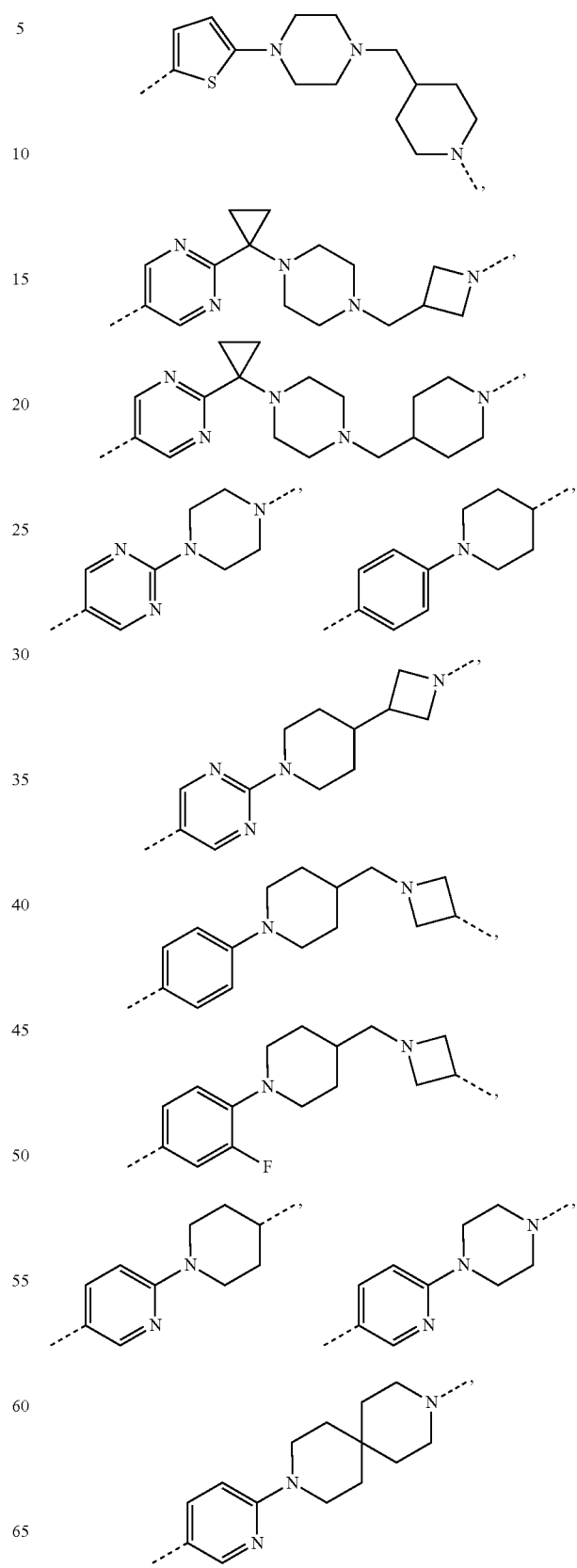

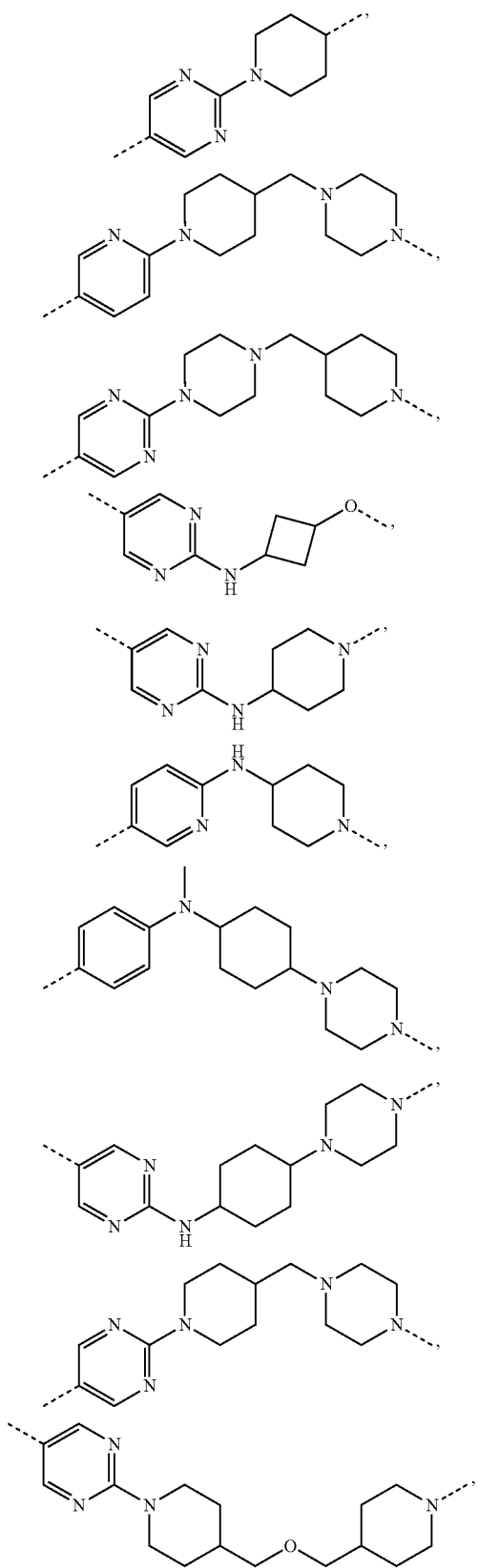
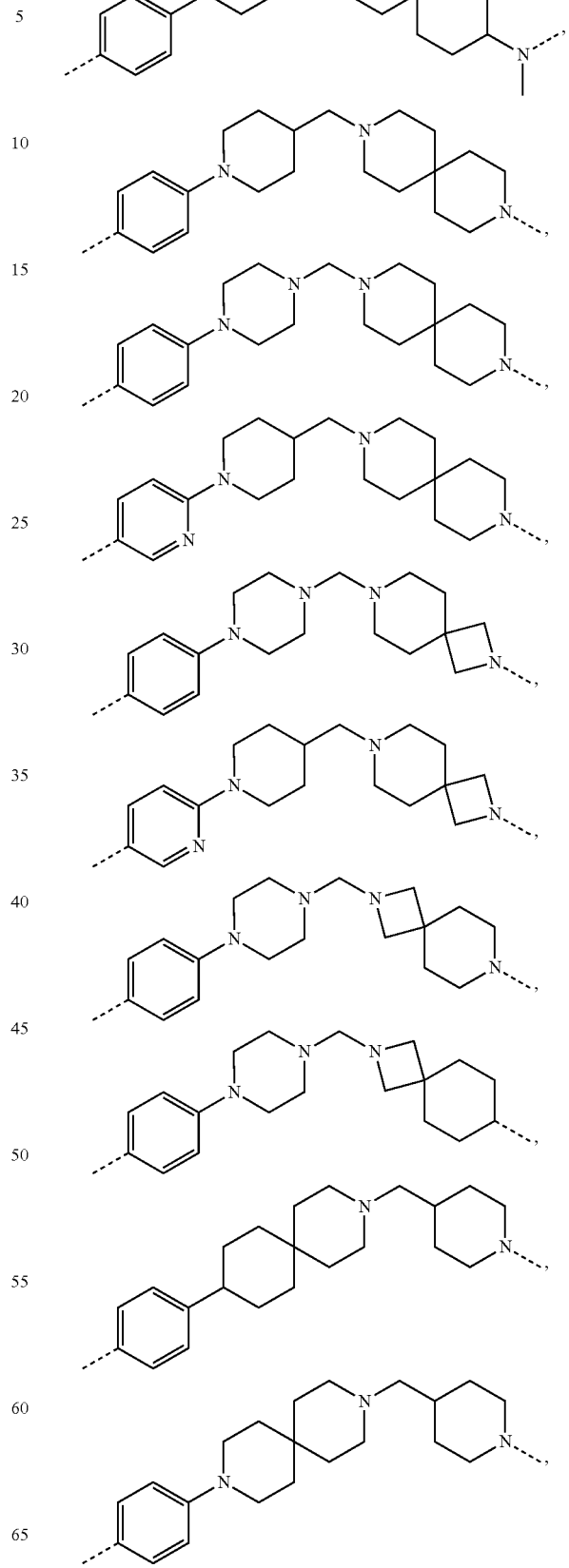

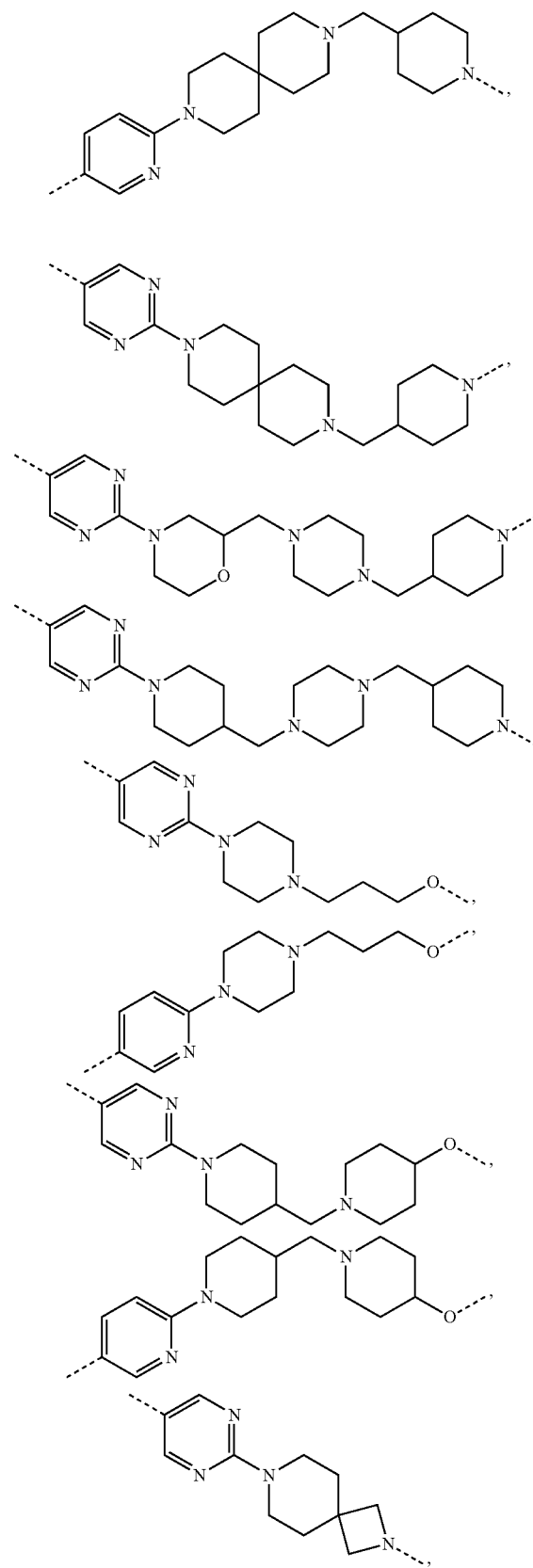
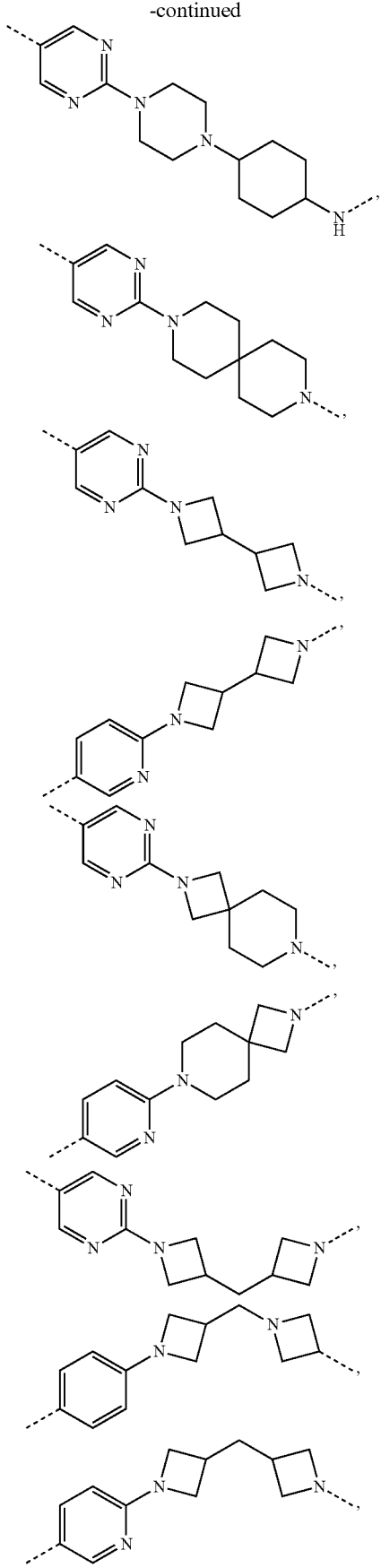

-continued
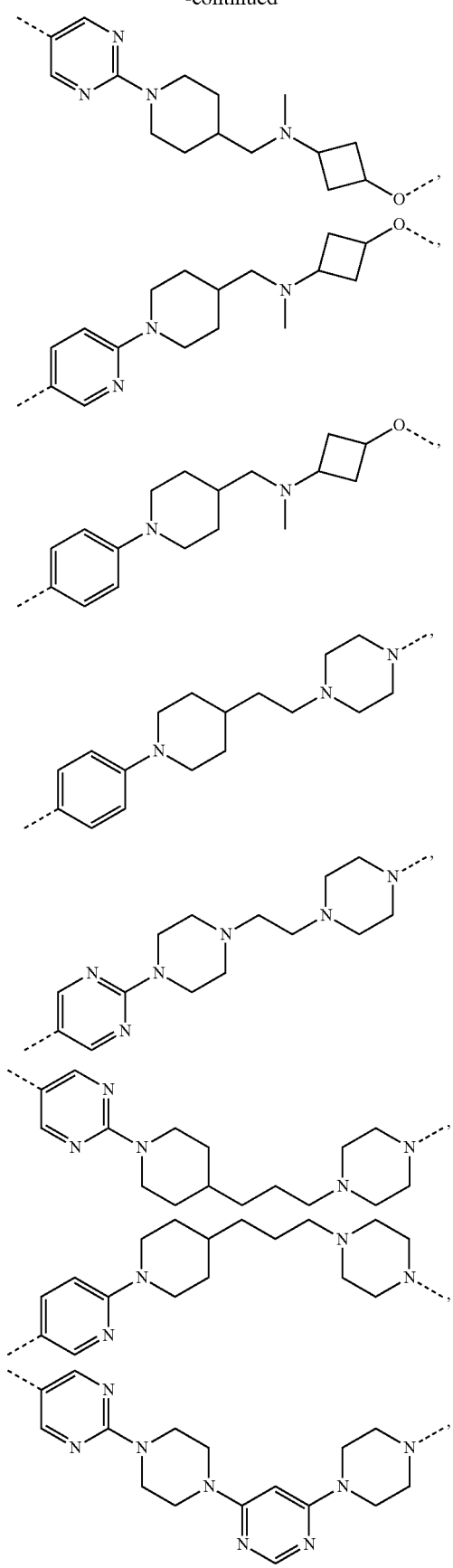
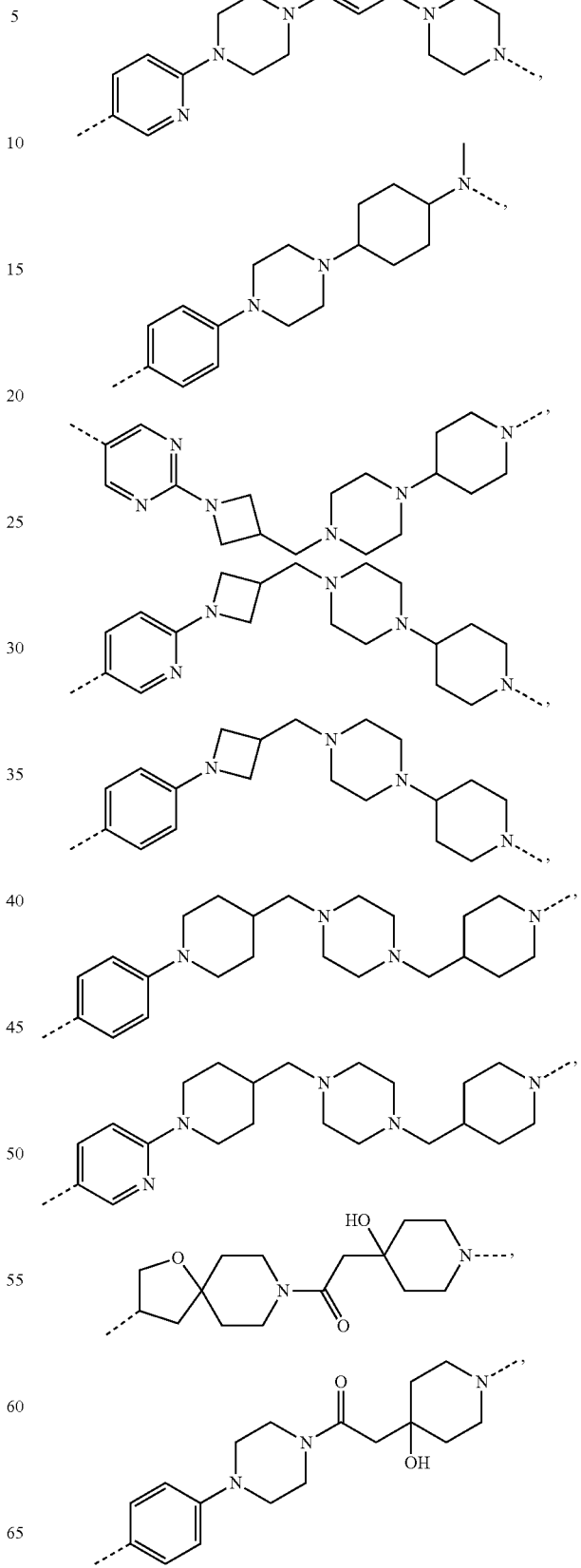

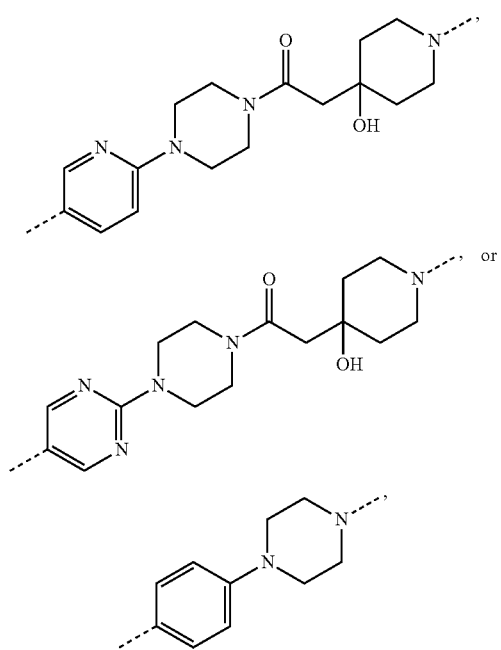

wherein the dashed lines indicate the point of attachment to the PTM and CLM and wherein the remaining variables are as described above for chemical structure I and any one of the second to twenty-ninth embodiments. In an alternative thirtieth embodiment, the chemical linking moiety (L) in the compound having the chemical structure I, or a pharmaceutically acceptable salt thereof, is represented by the structure:

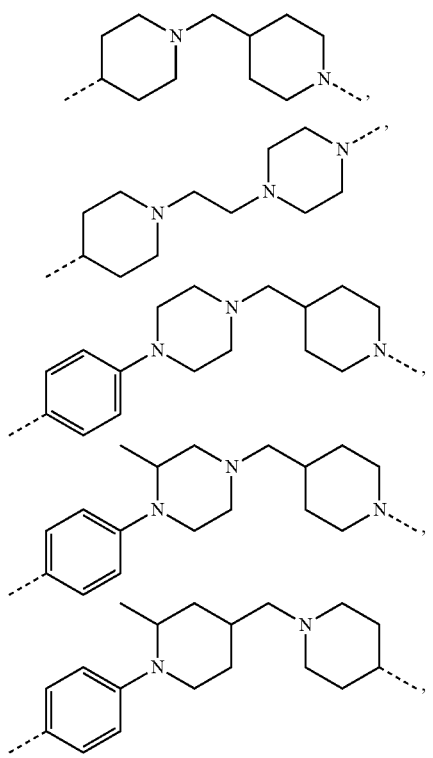

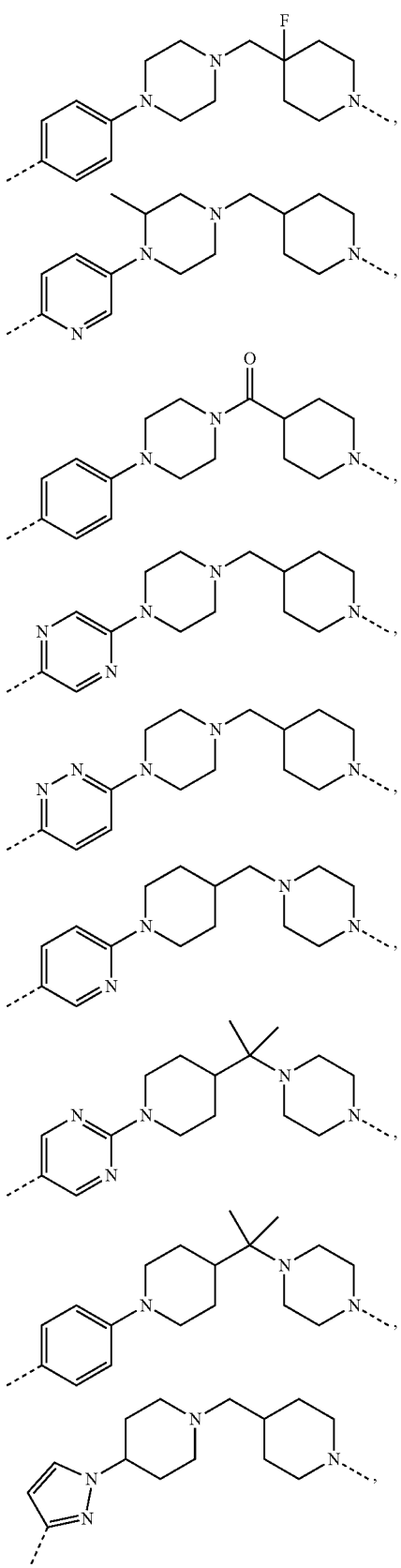

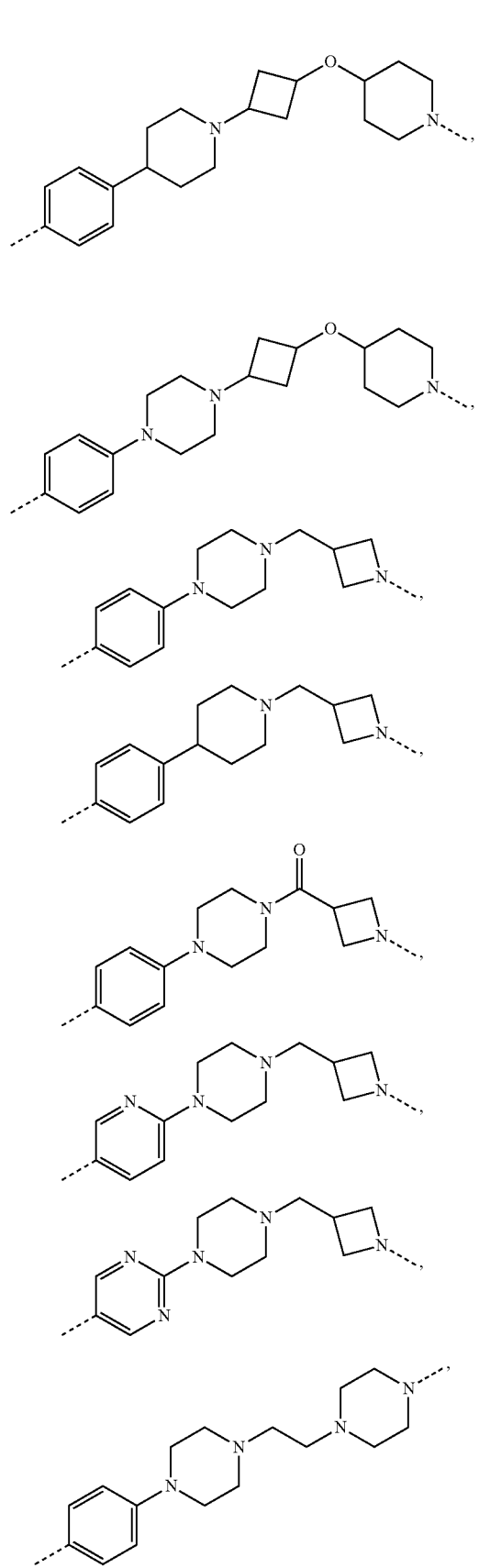

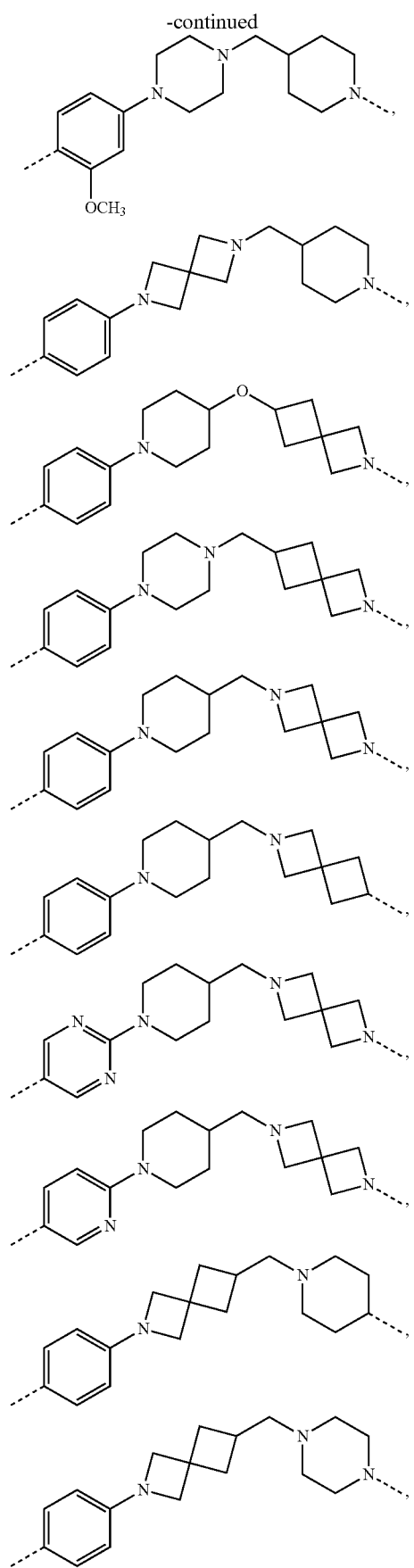

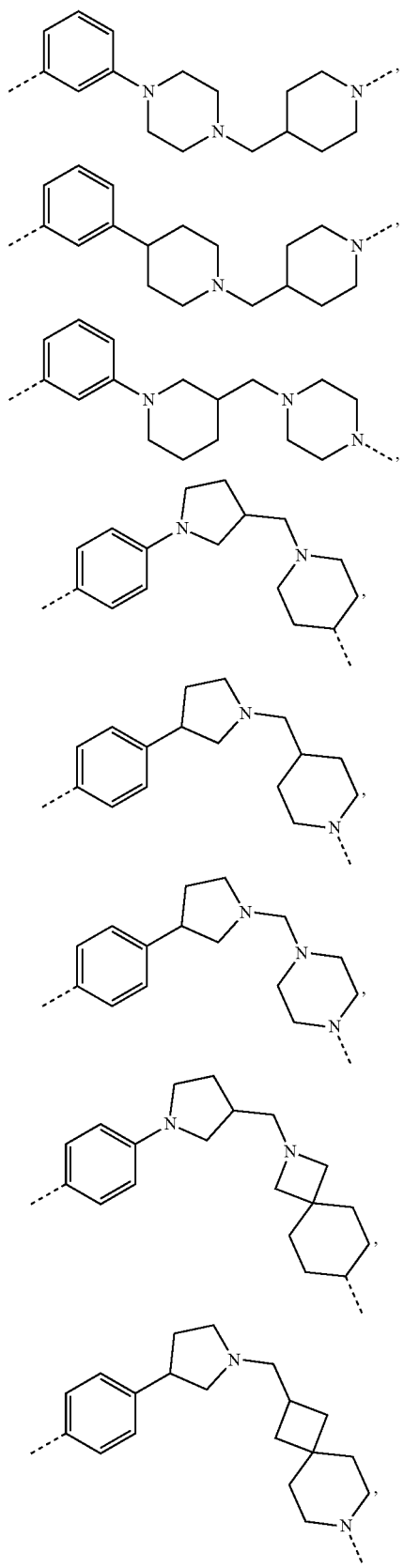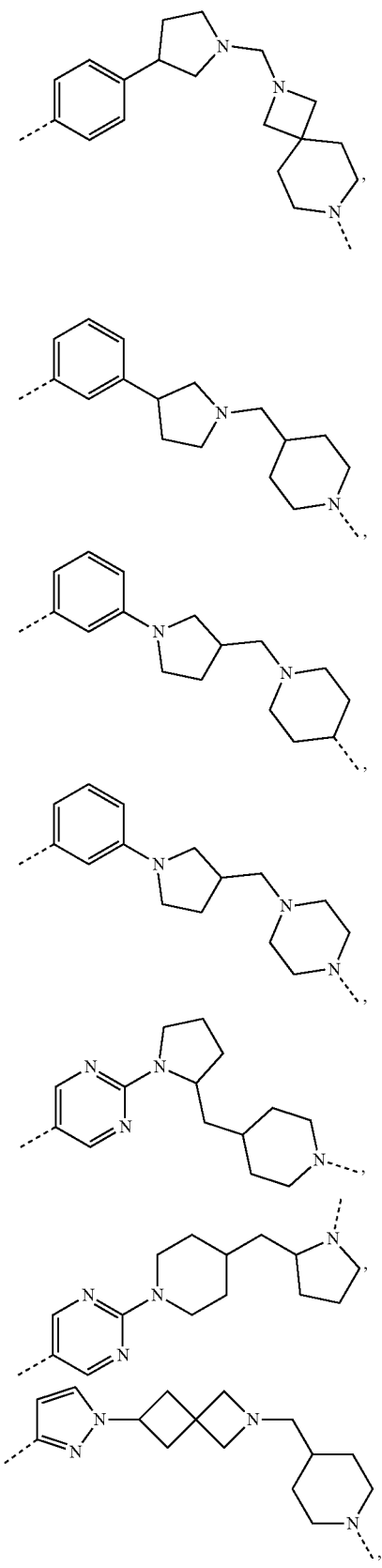

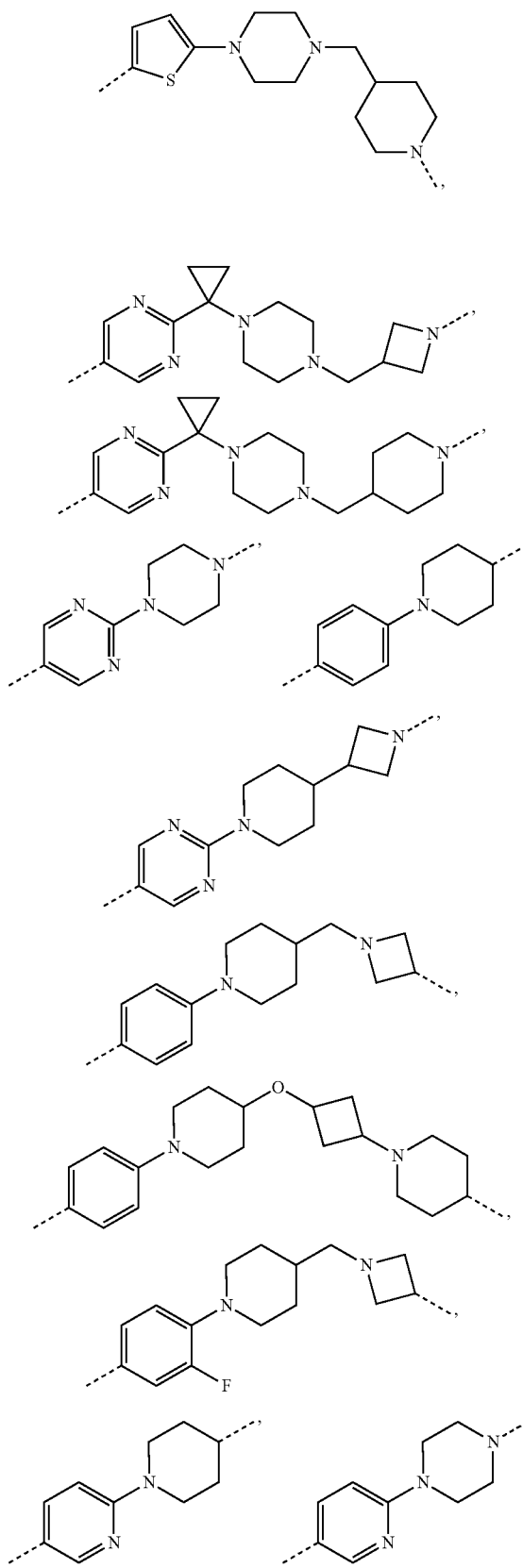
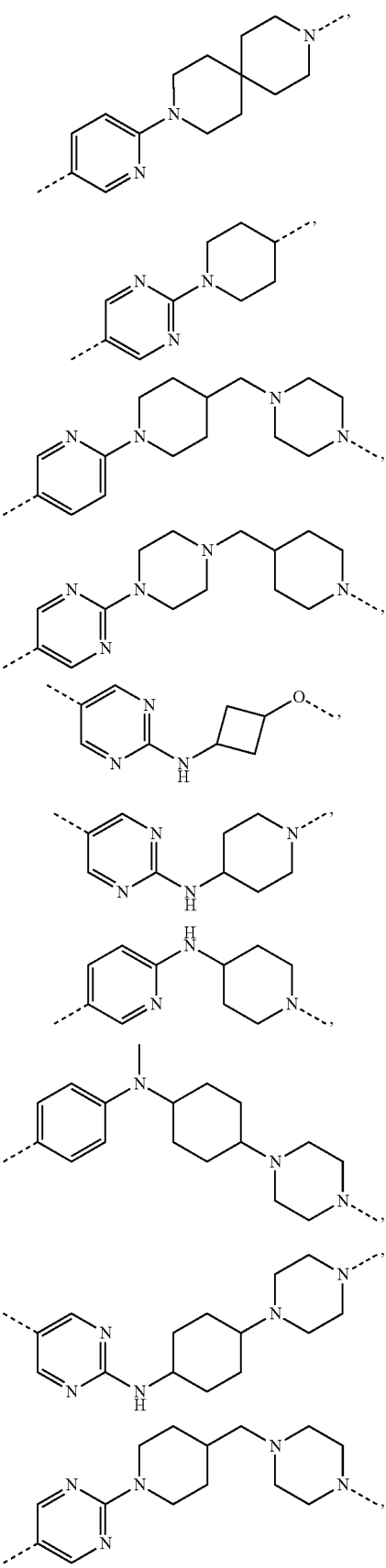

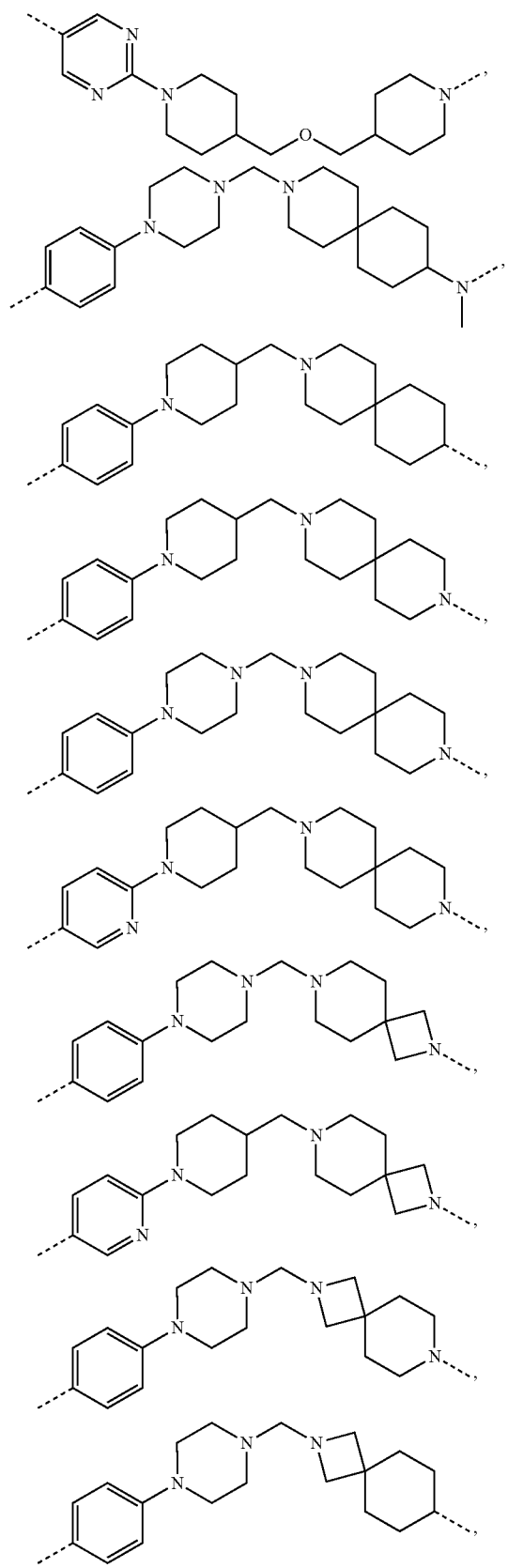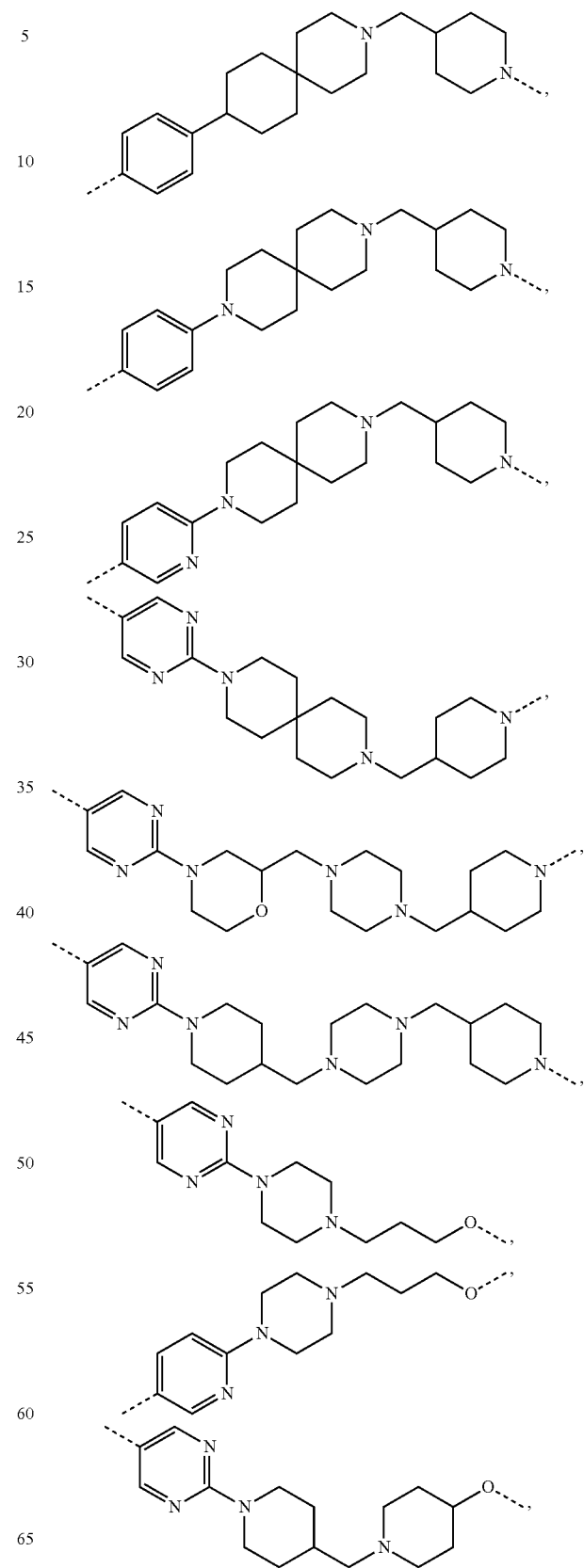

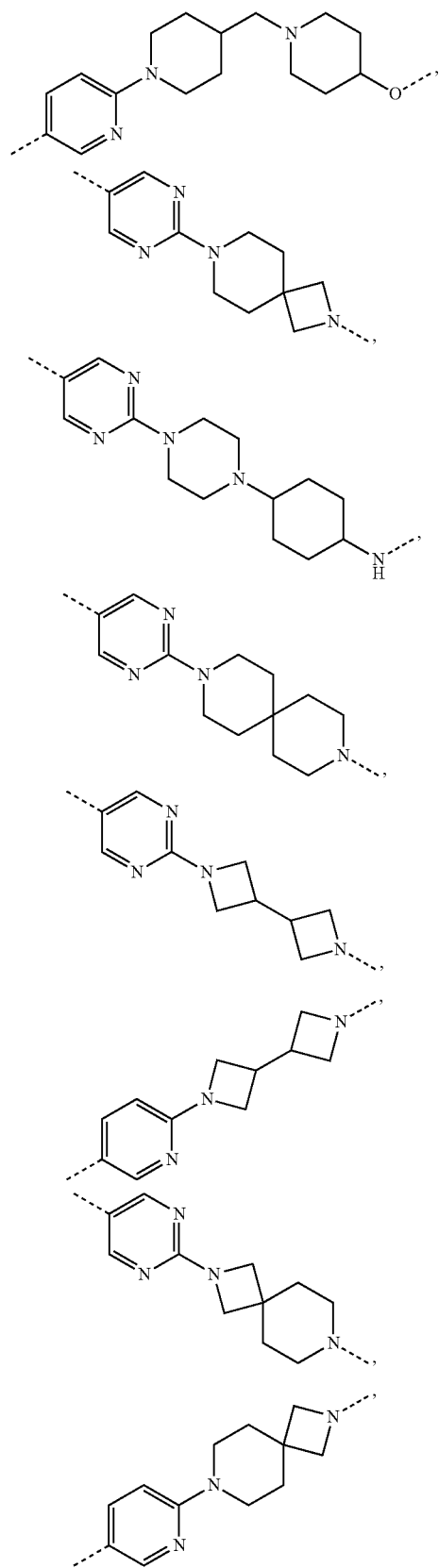
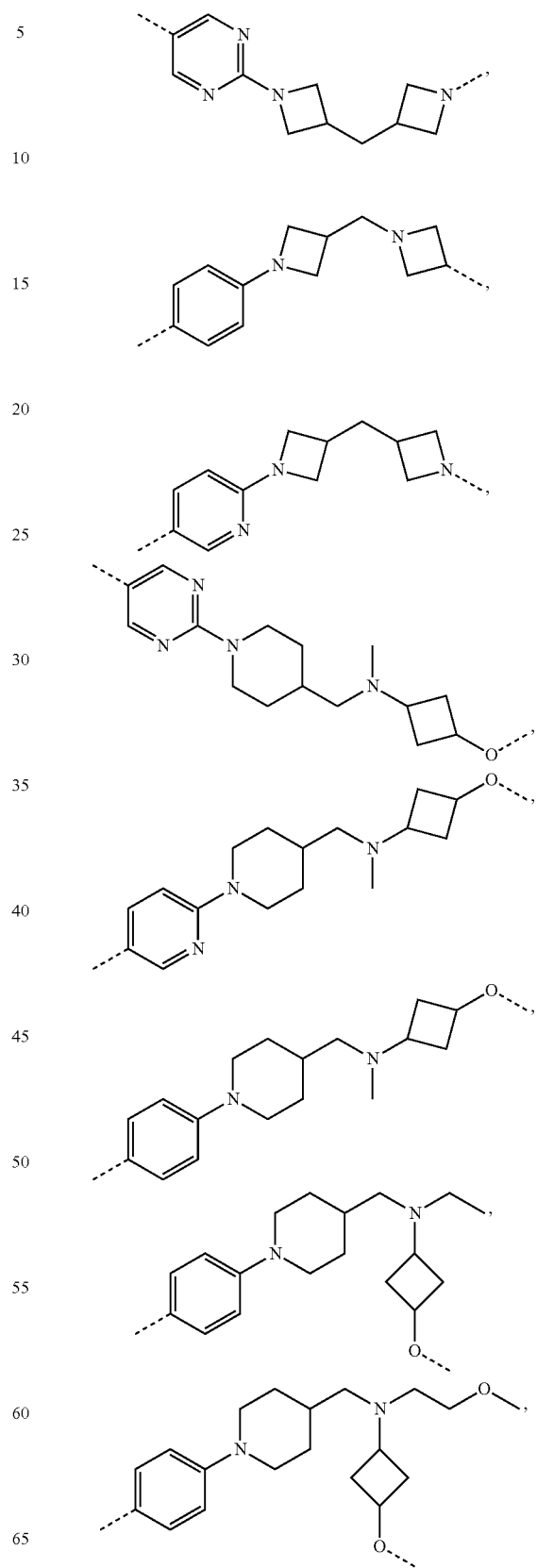

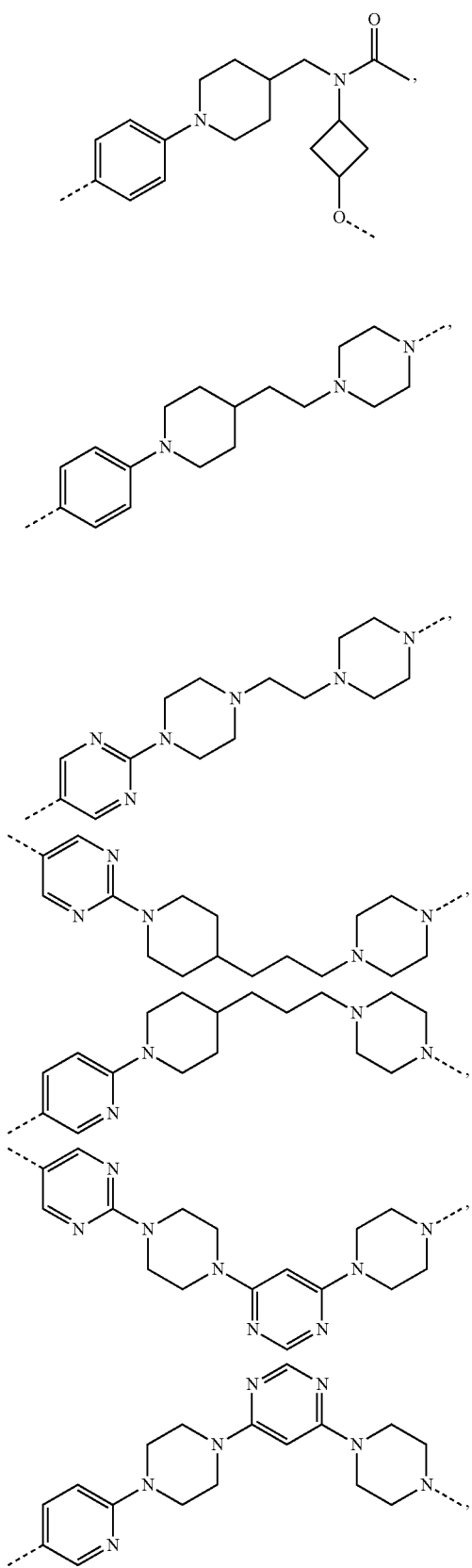
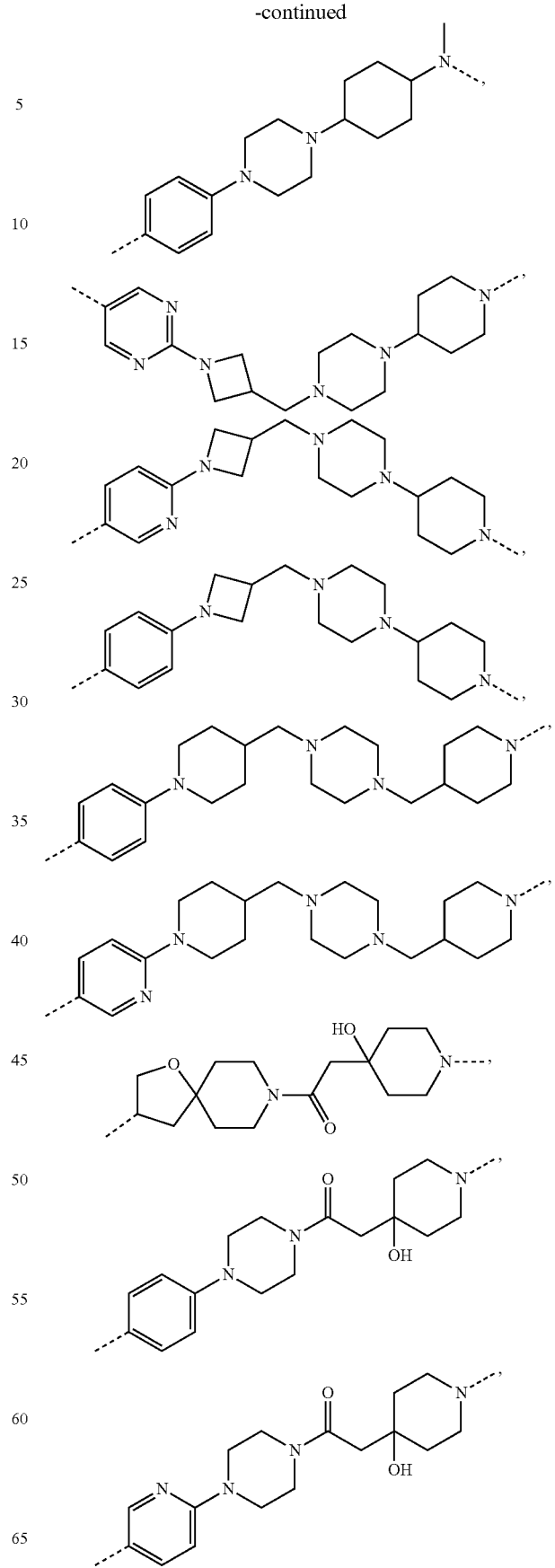

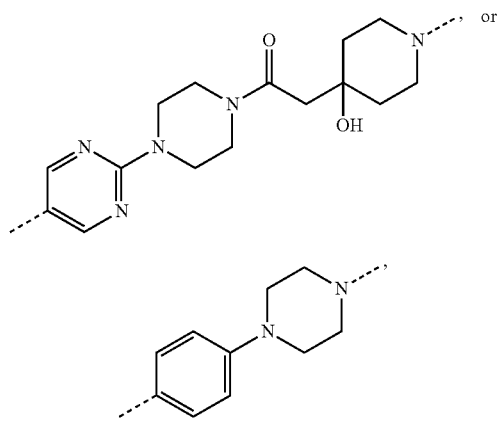

wherein the dashed lines indicate the point of attachment to the PTM and CLM and wherein the remaining variables are as described above for chemical structure I and any one of the second to twenty-ninth embodiments.

In a thirty-first embodiment, the chemical linking moiety (L) in the compound having the chemical structure I, or a pharmaceutically acceptable salt thereof, is represented by the structure:

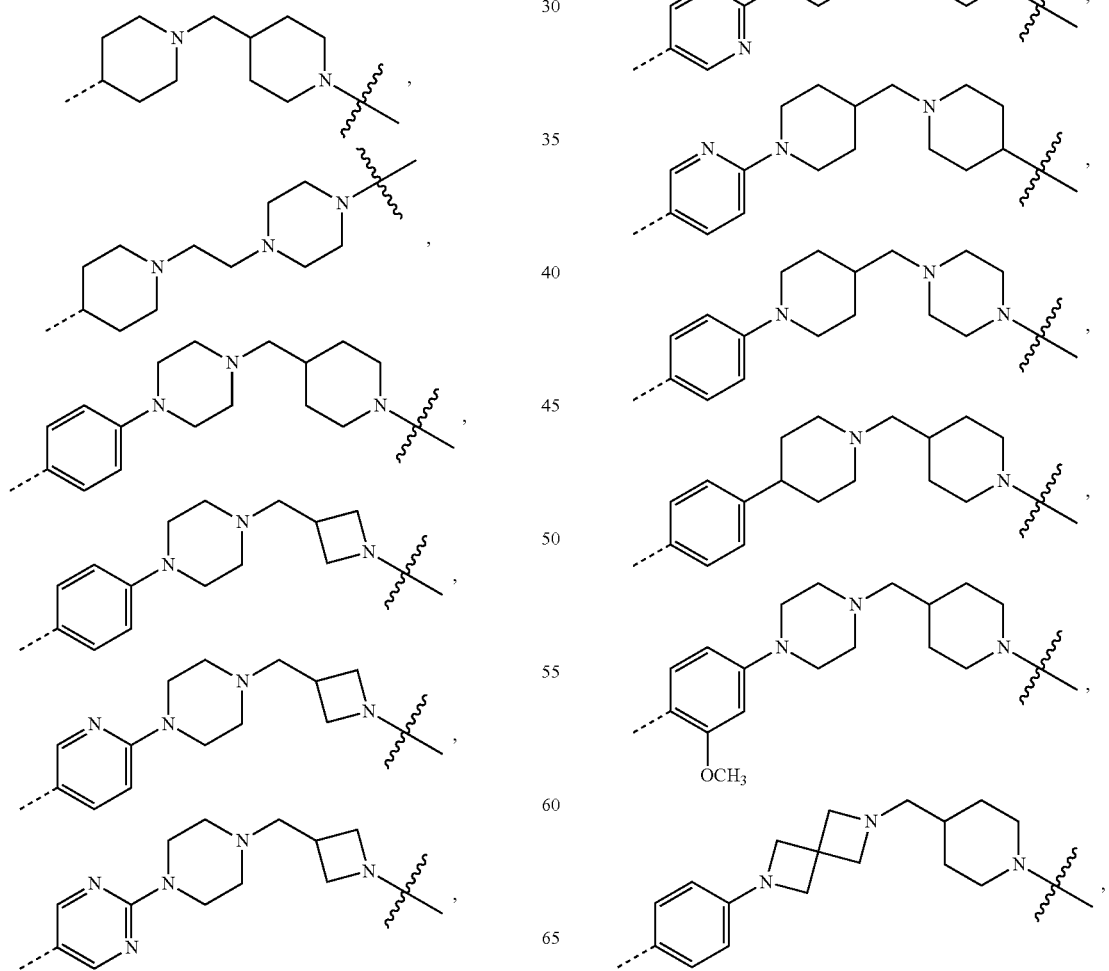

-continued
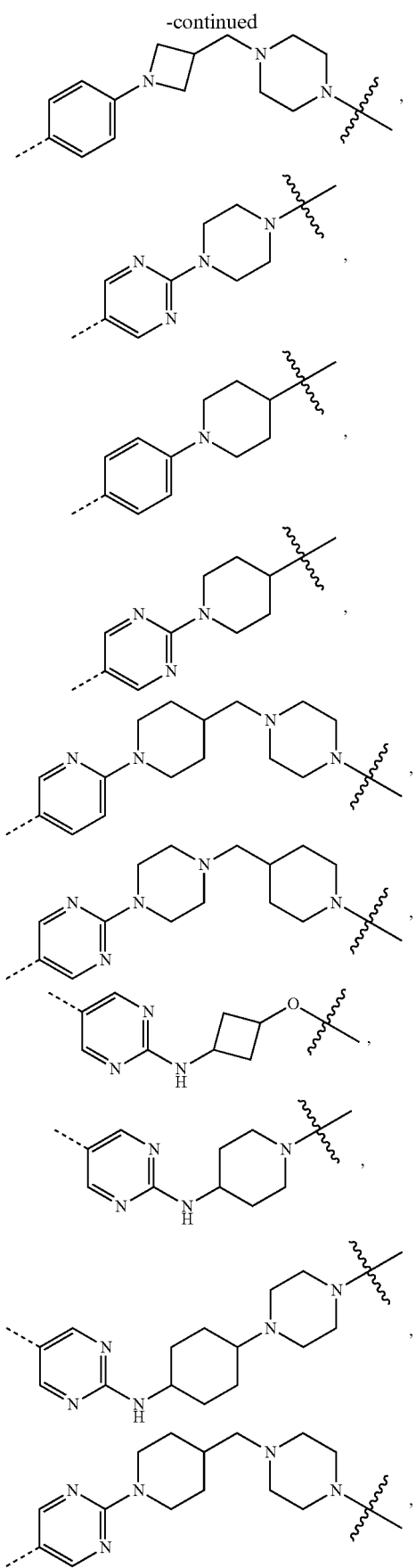
-continued
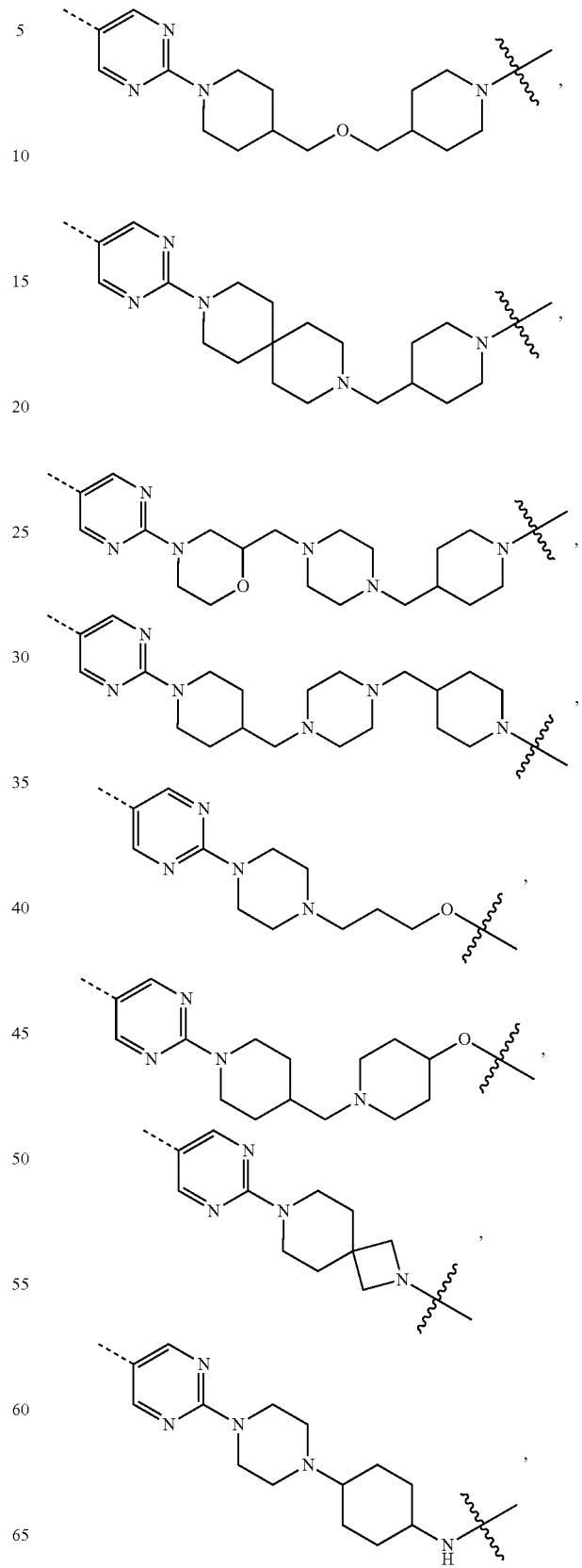

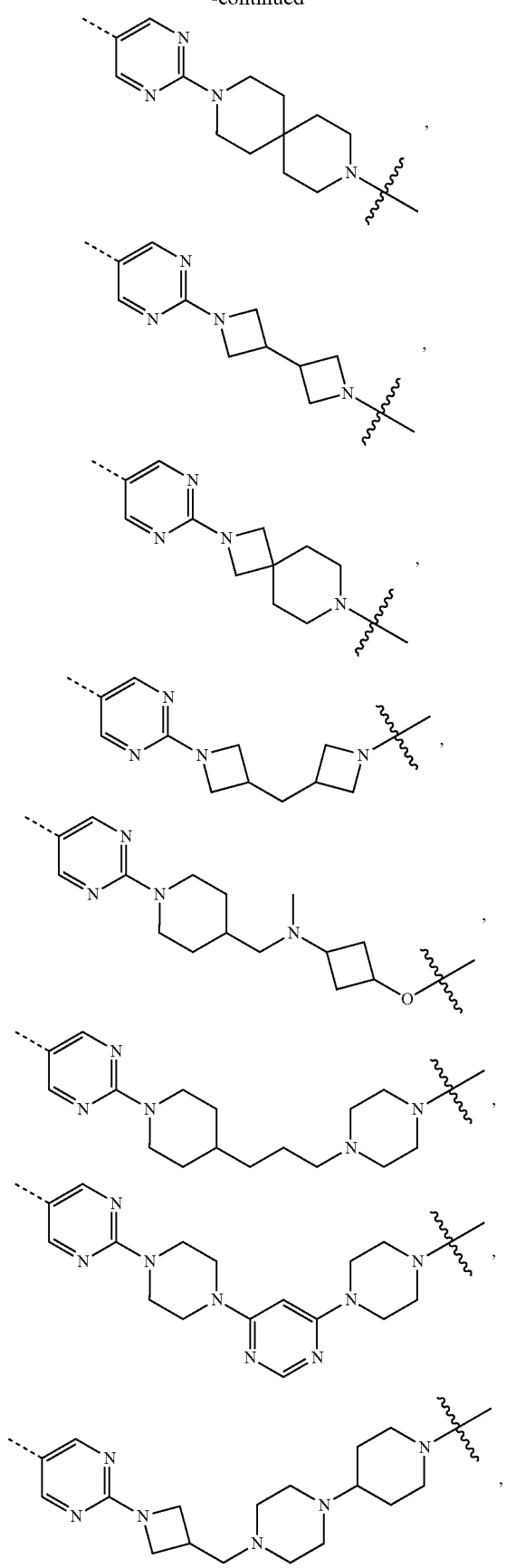

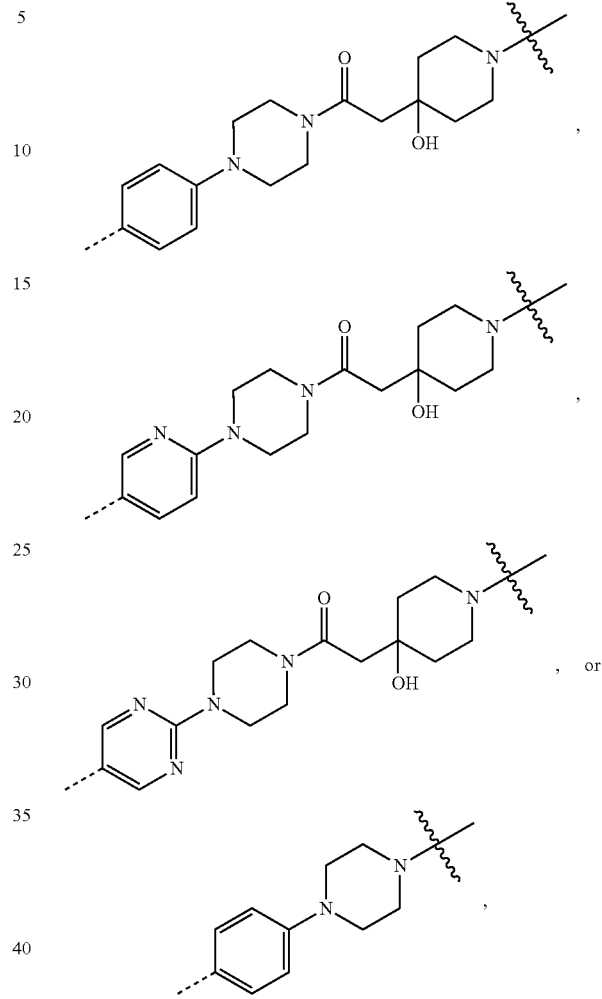

wherein the dashed lines indicate the point of attachment to the PTM and ⁓ indicates the point of attachment to the CLM and wherein the remaining variables are as described above for chemical structure I and any one of the second to twenty-ninth embodiments. In an alternative thirty-first embodiment, the chemical linking moiety (L) in the compound having the chemical structure I, or a pharmaceutically acceptable salt thereof, is represented by the structure:

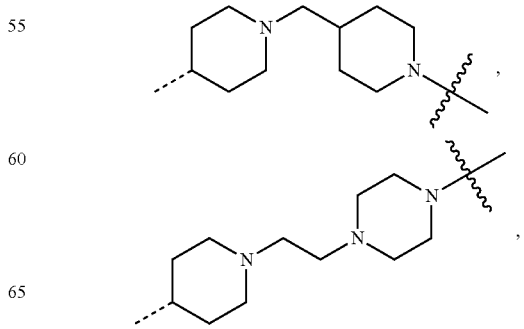

-continued
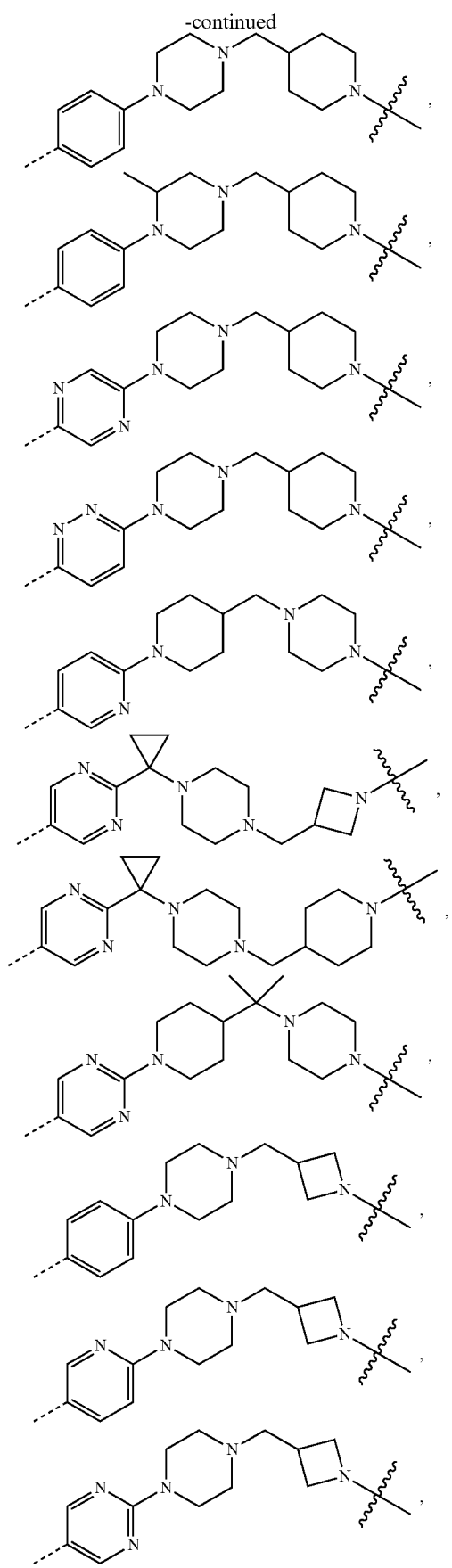
-continued
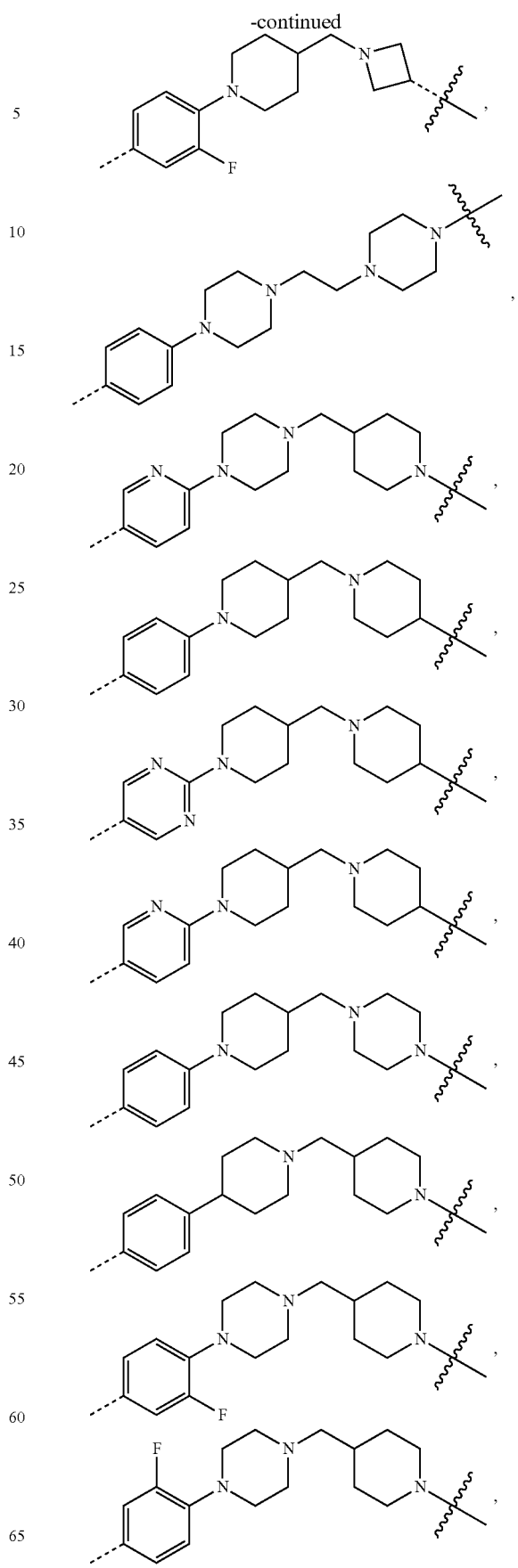

-continued
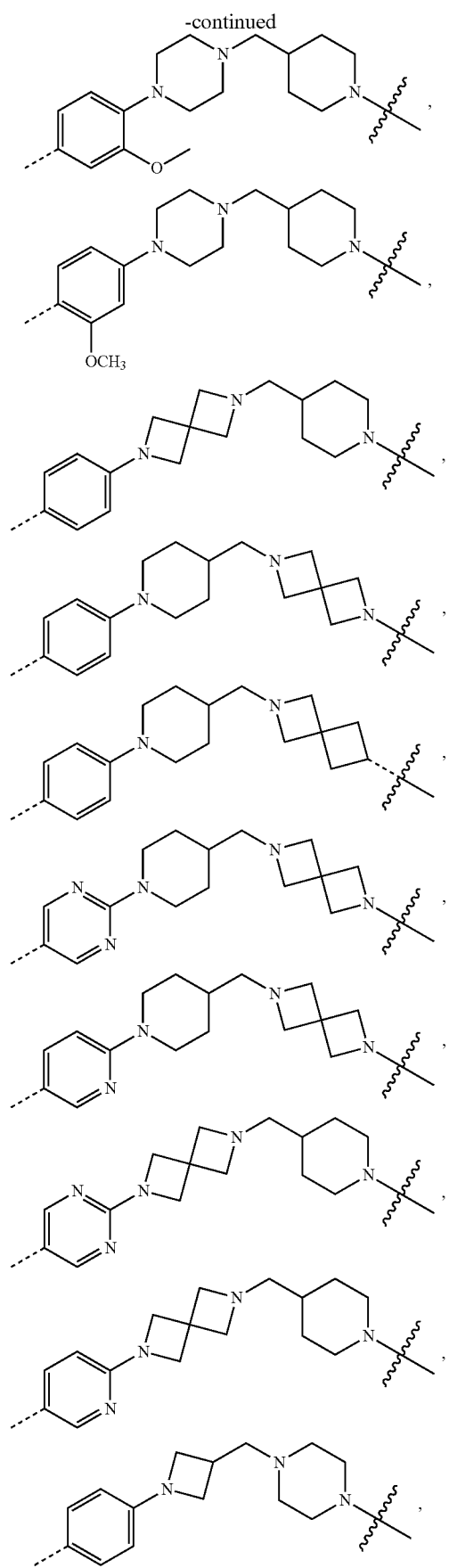
-continued
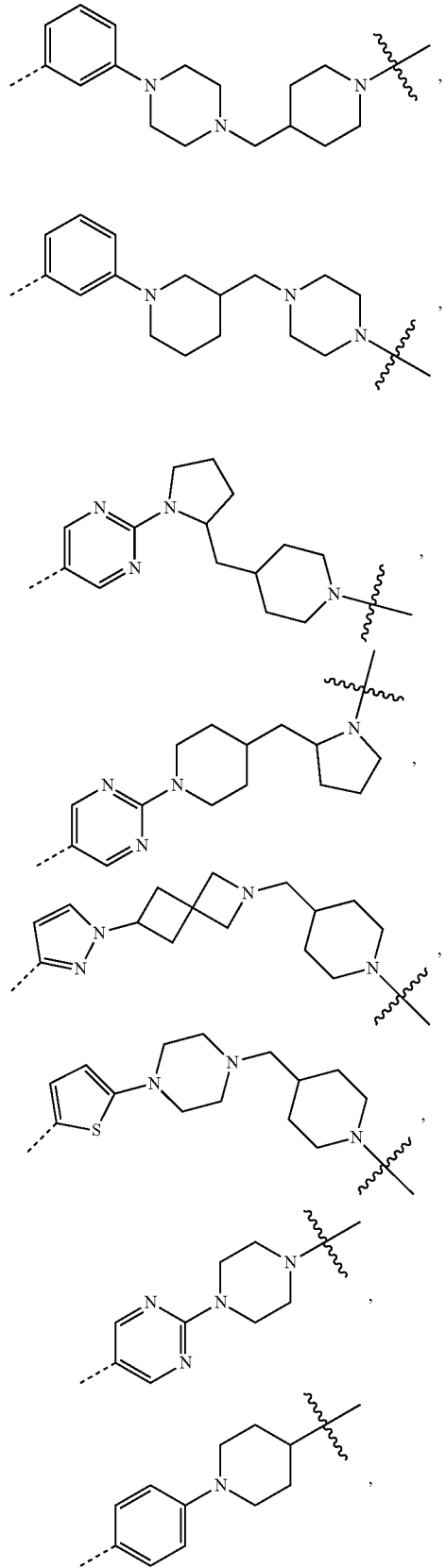

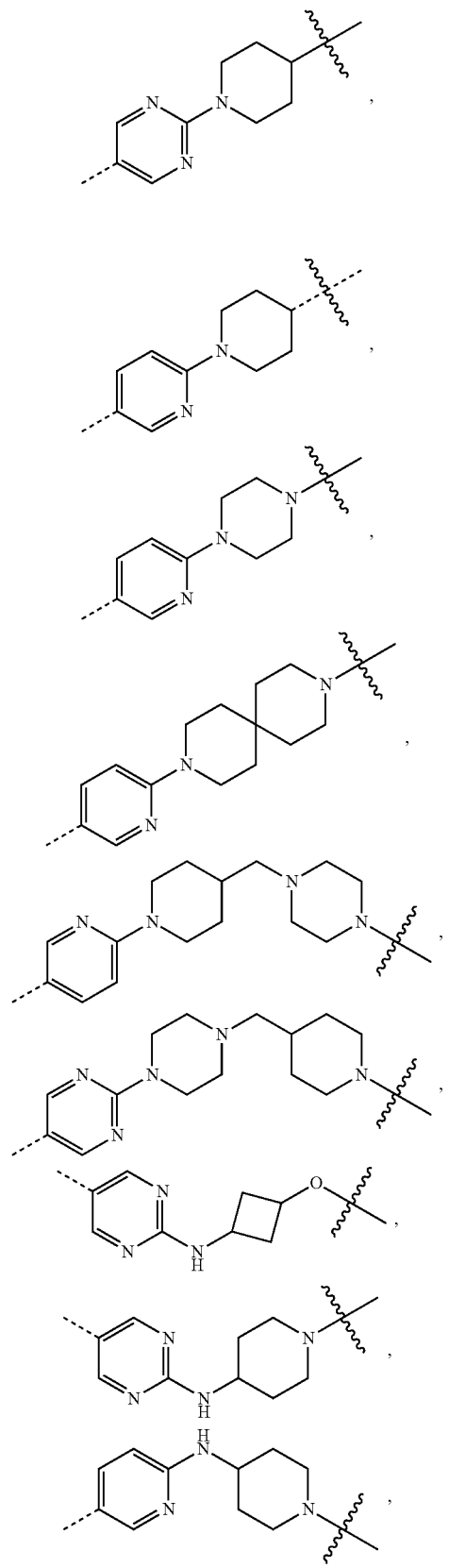
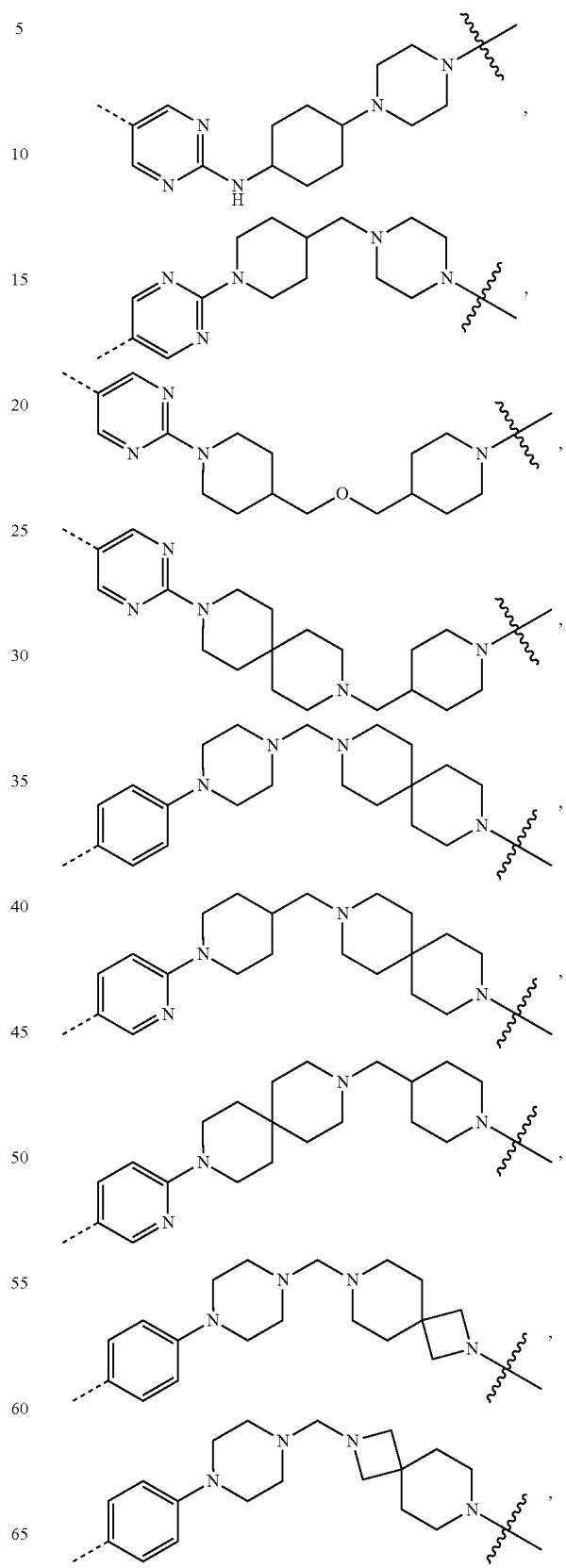

85
-continued
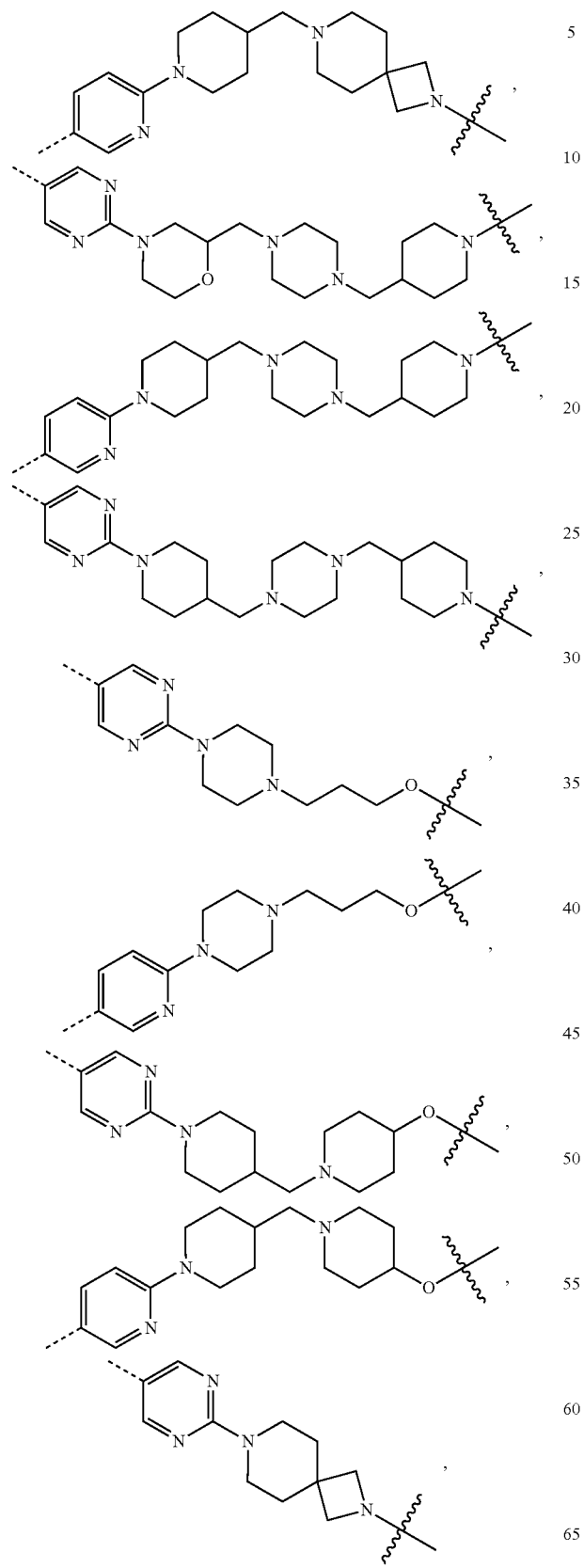
86
-continued
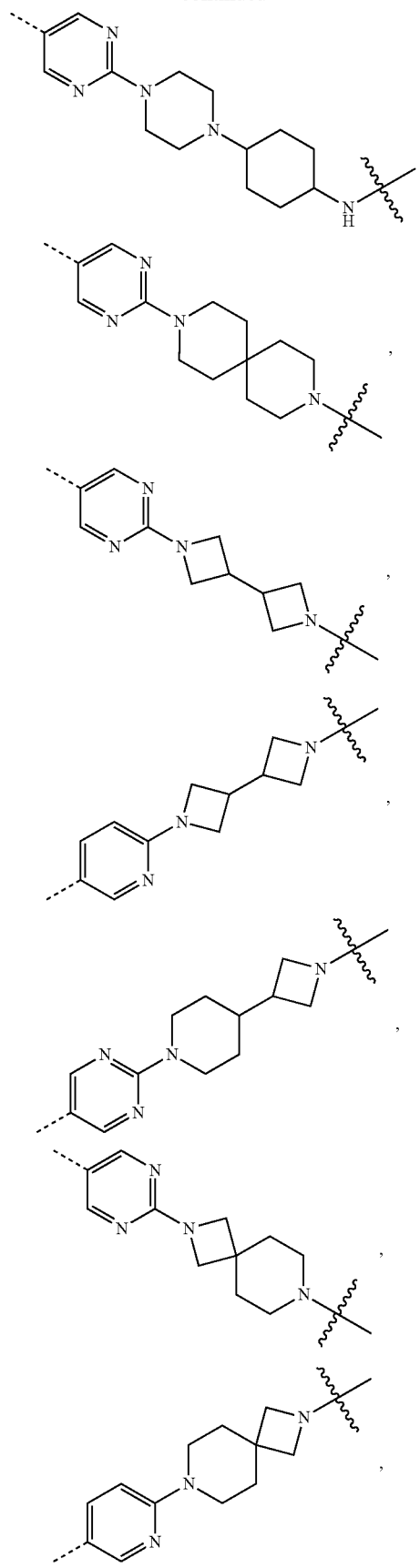

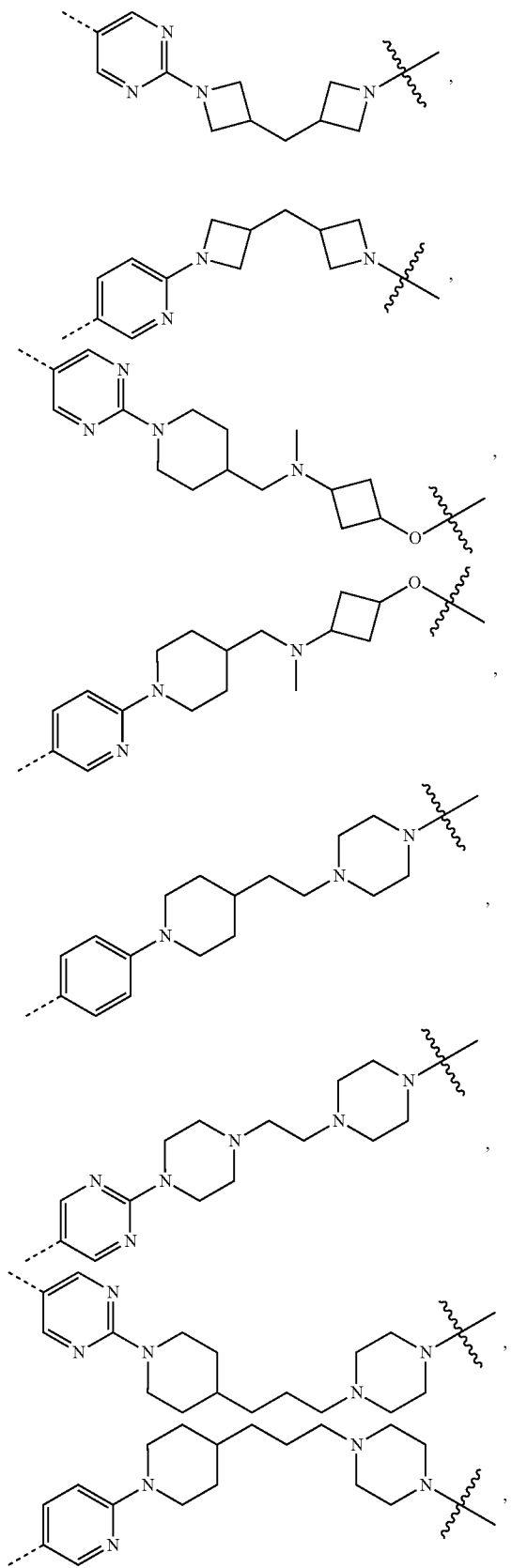
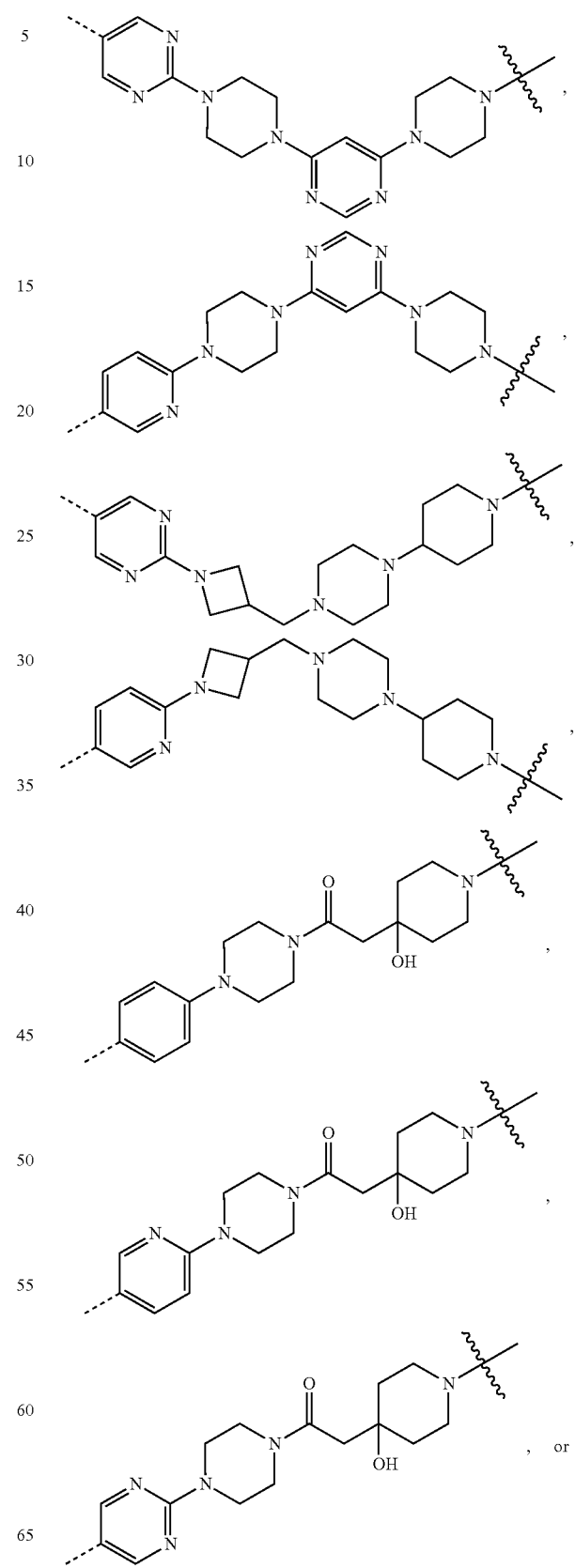

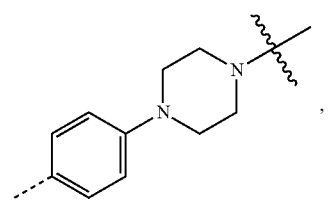

wherein the dashed lines indicate the point of attachment to the PTM and ⁓ indicates the point of attachment to the CLM and wherein the remaining variables are as described above for chemical structure I and any one of the second to twenty-ninth embodiments. In an alternative thirty-first embodiment, the chemical linking moiety (L) in the compound having the chemical structure I, or a pharmaceutically acceptable salt thereof, is represented by the structure:

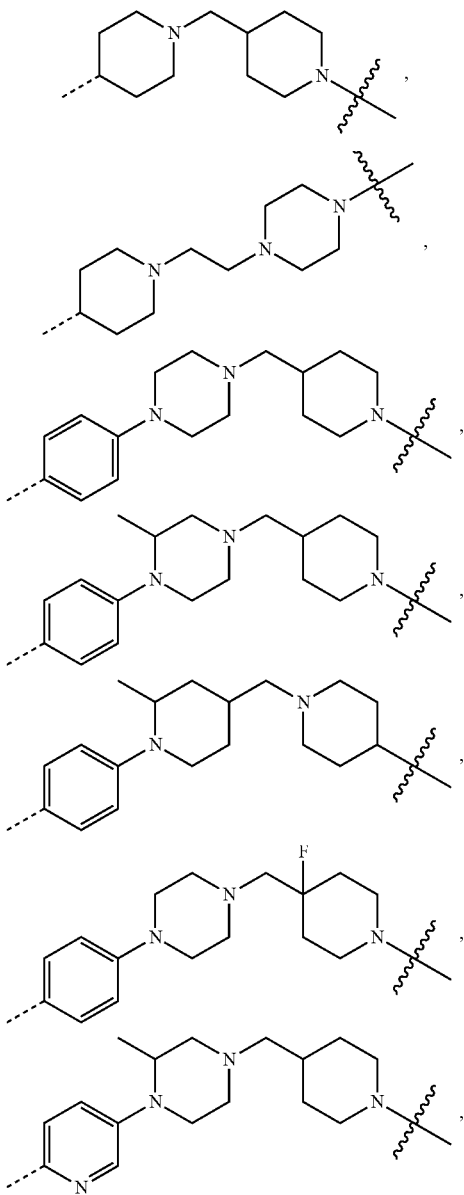

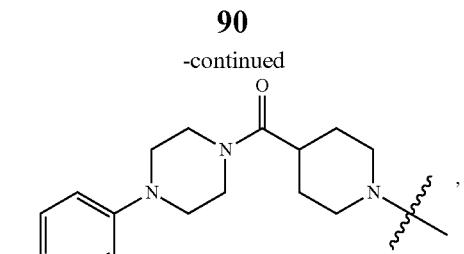
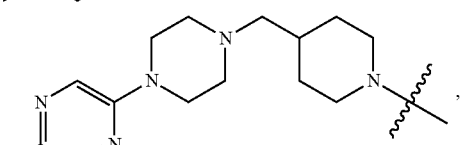
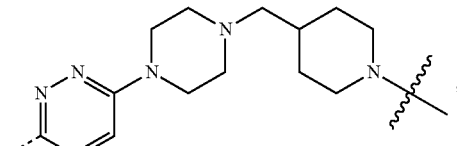
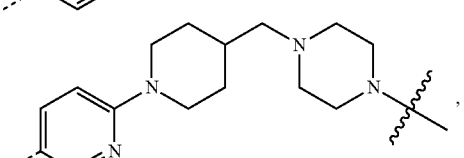
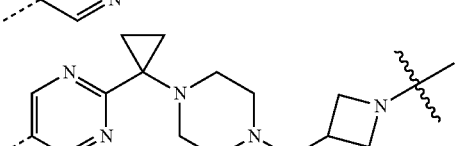
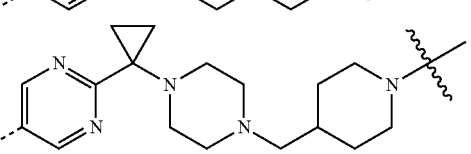
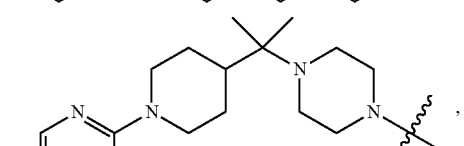
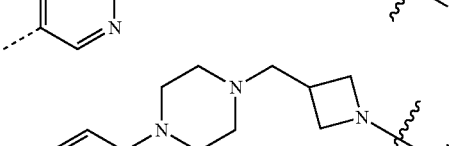
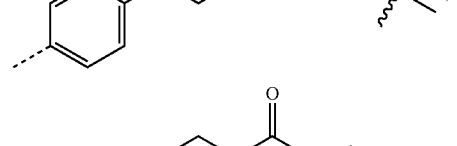
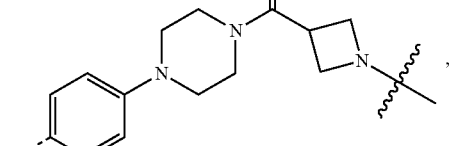
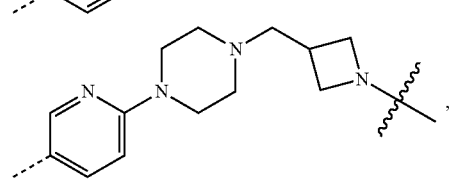
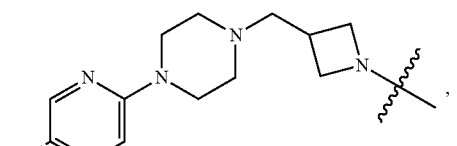

-continued
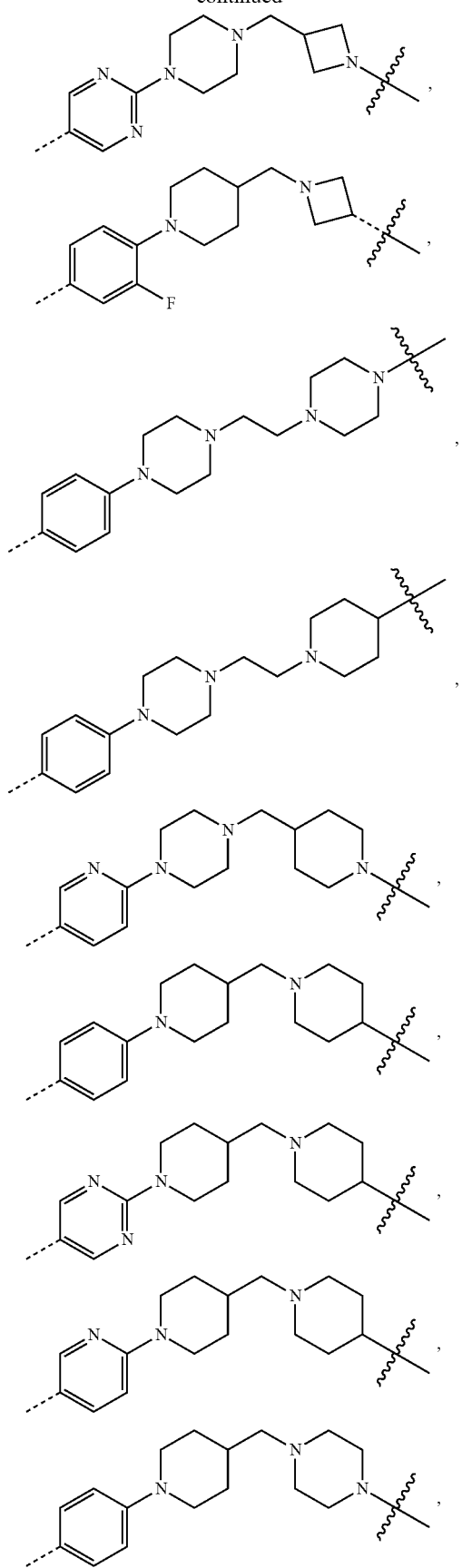
-continued
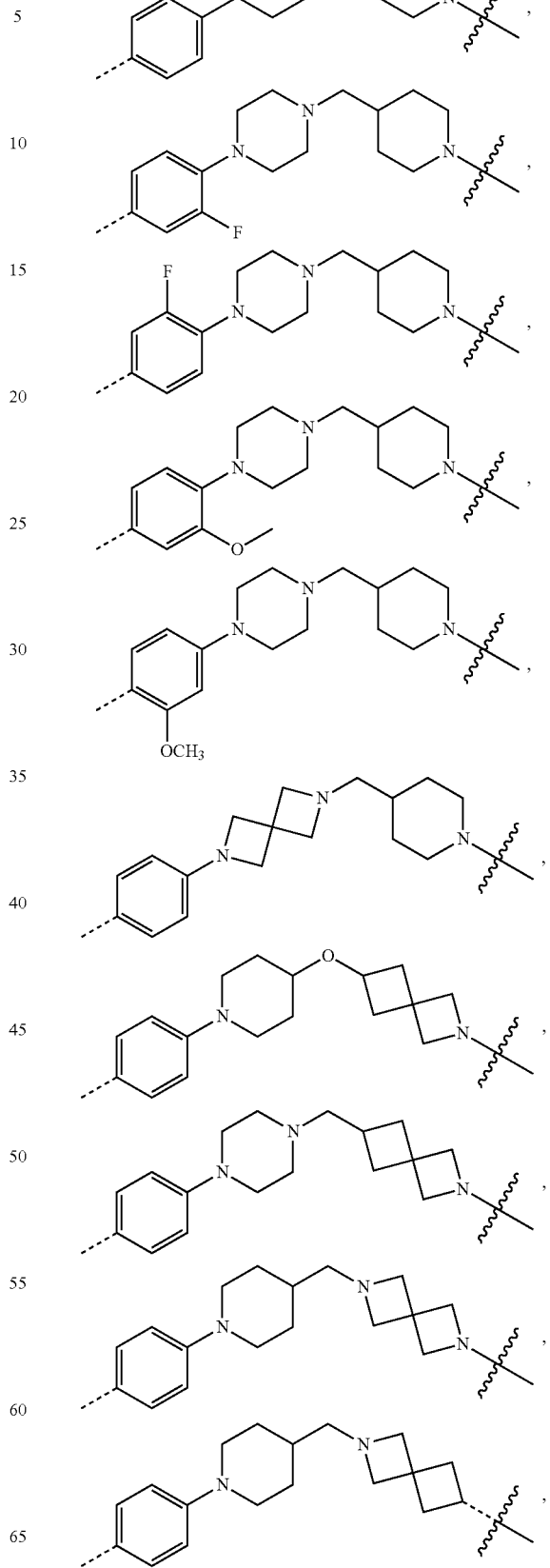

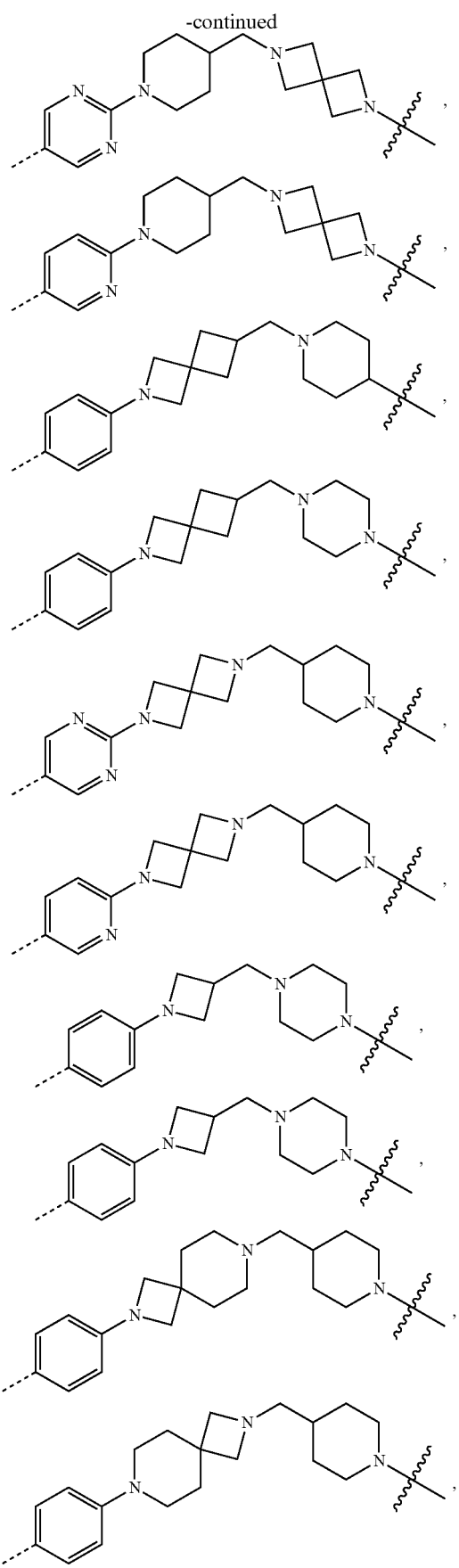
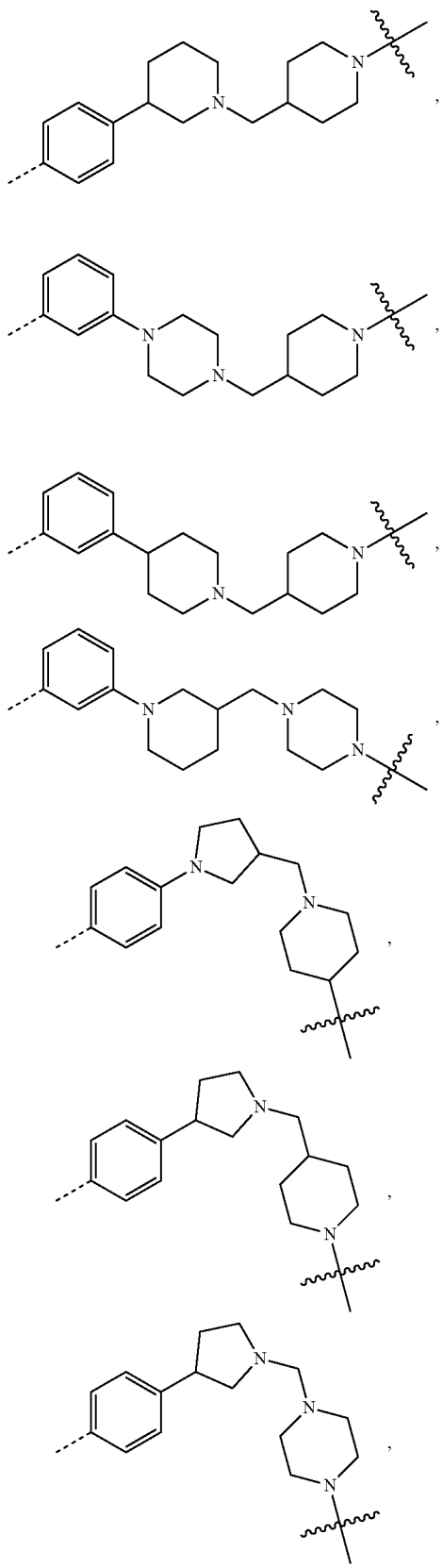

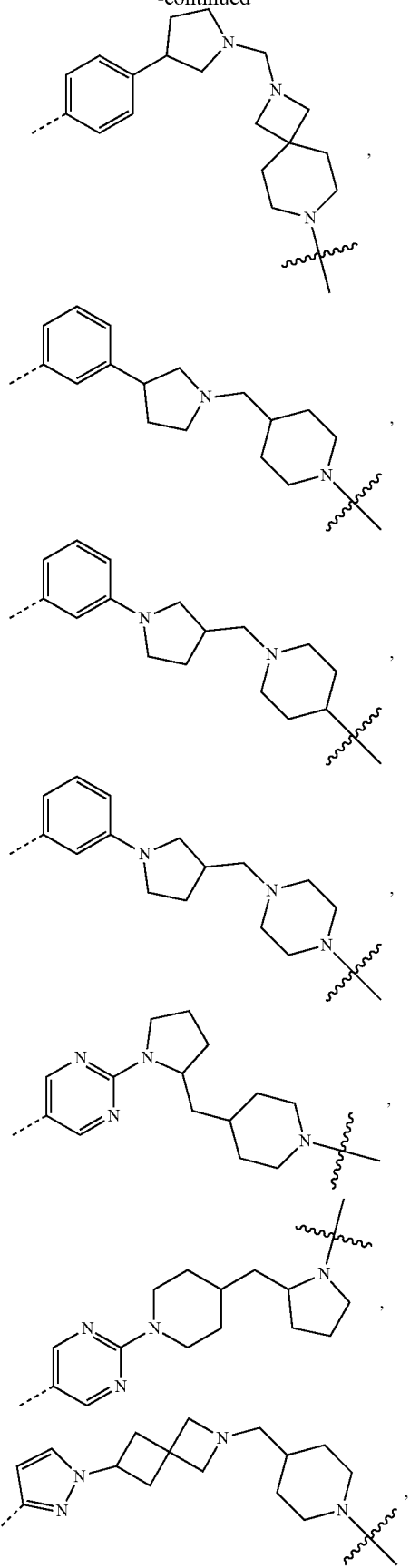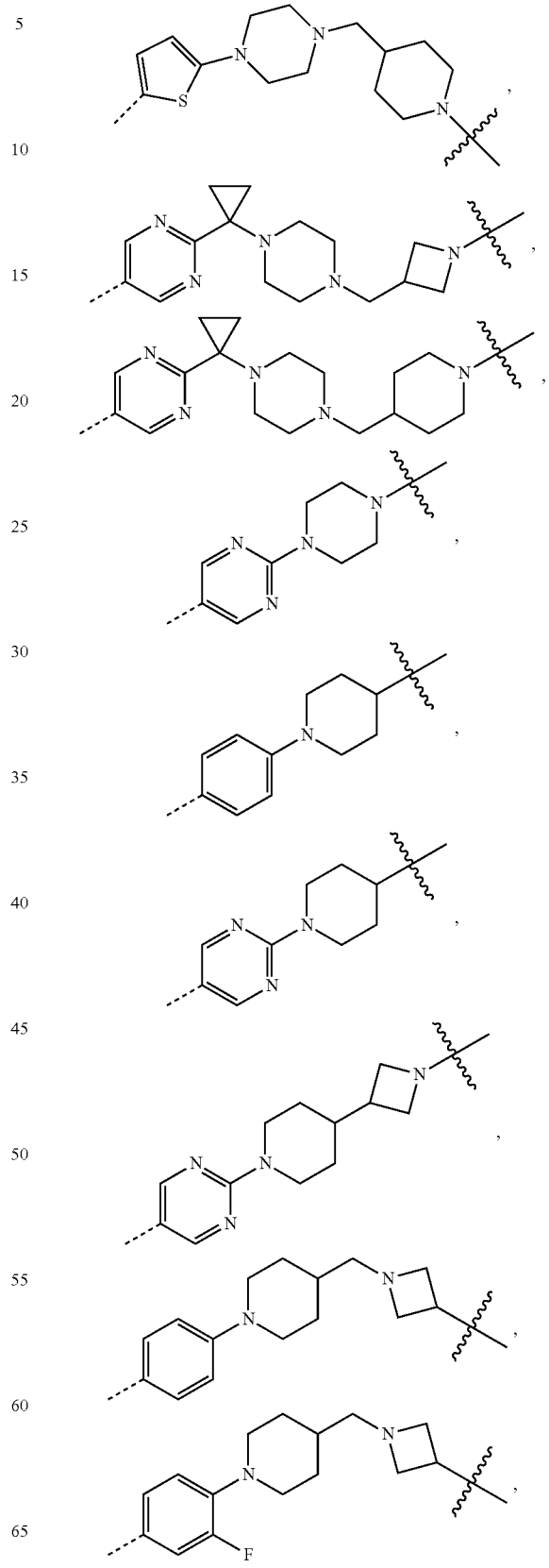

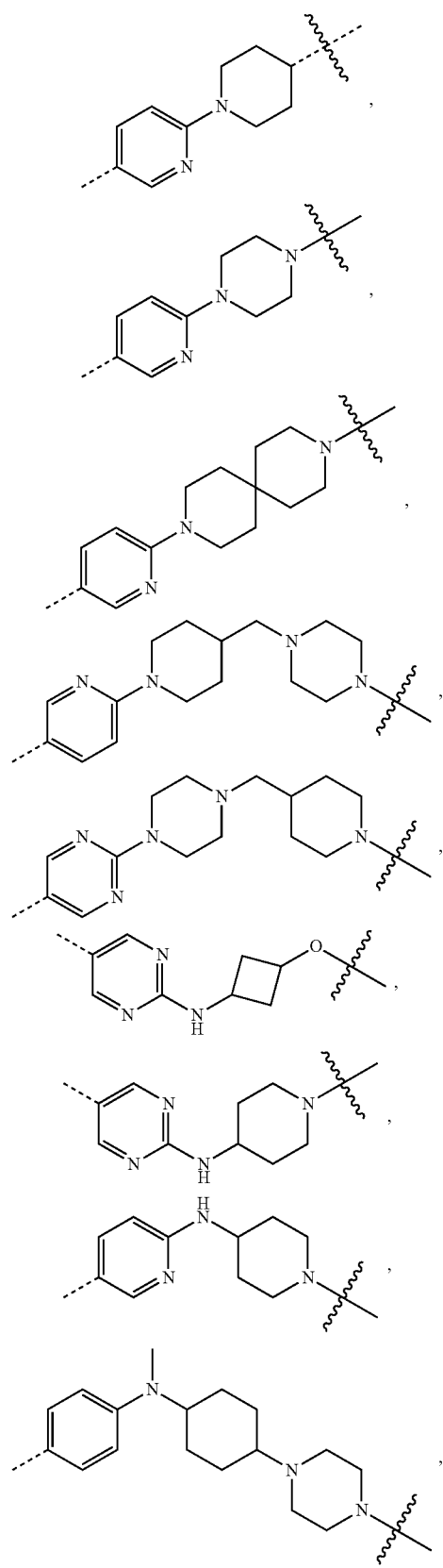
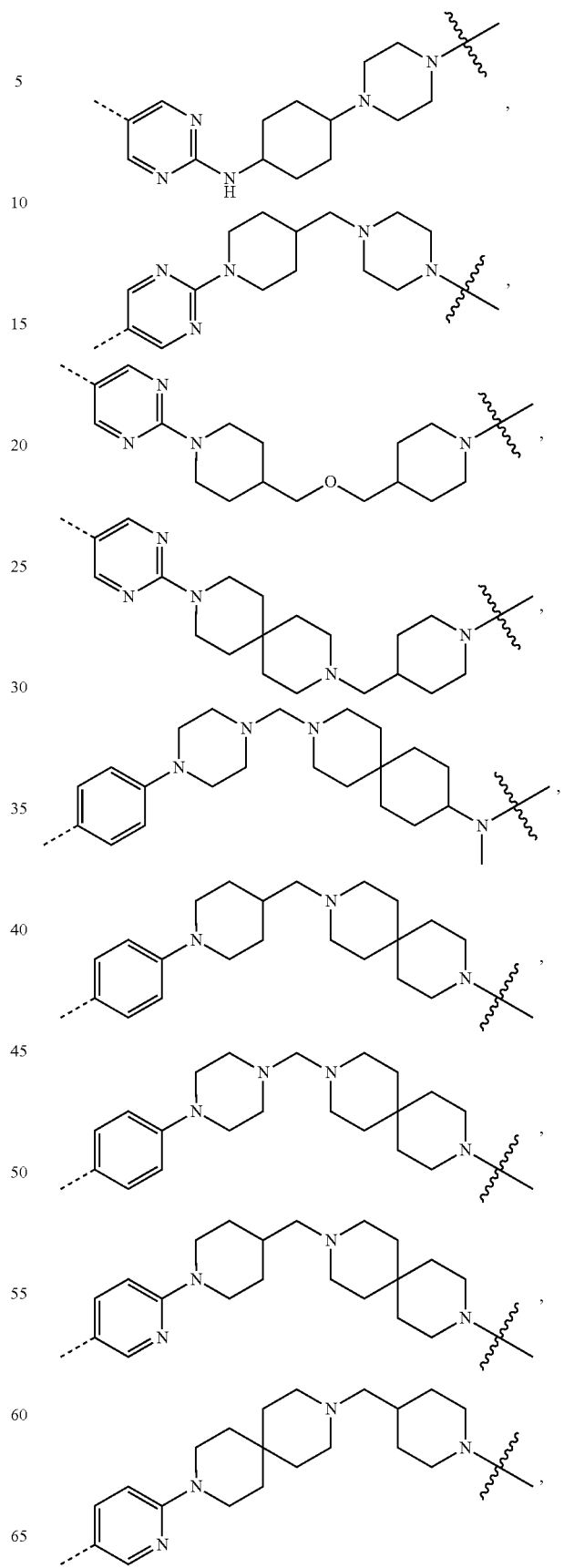

99
-continued
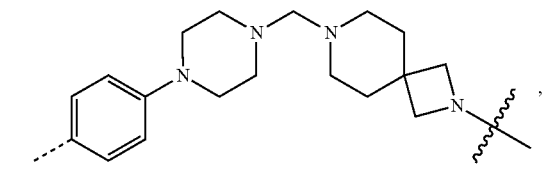,
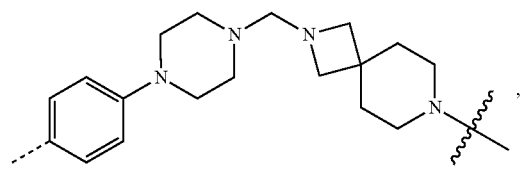,
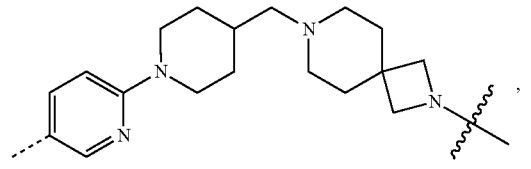,
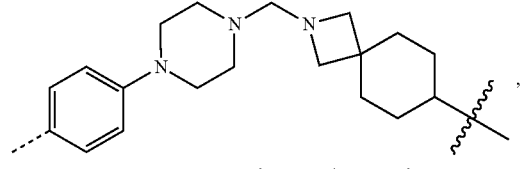,
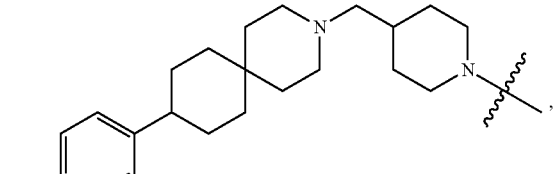,
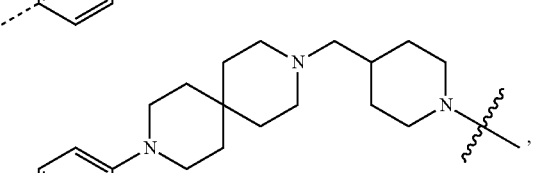,
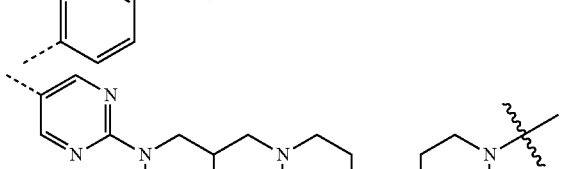,
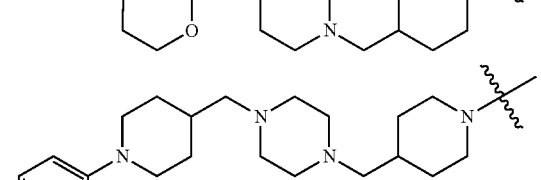,
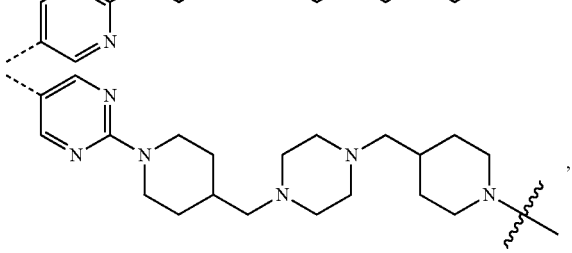,
100
-continued
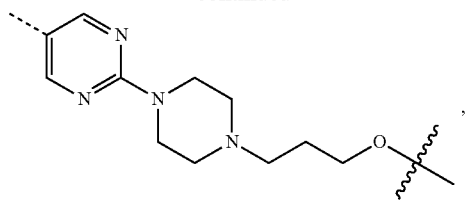,
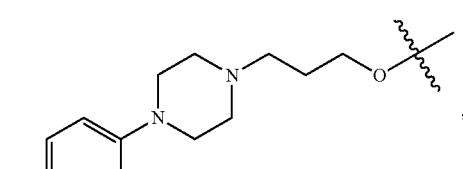,
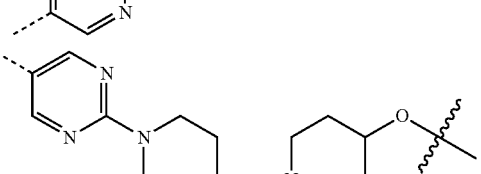,
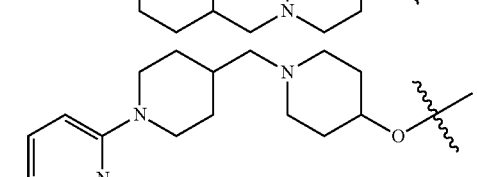,
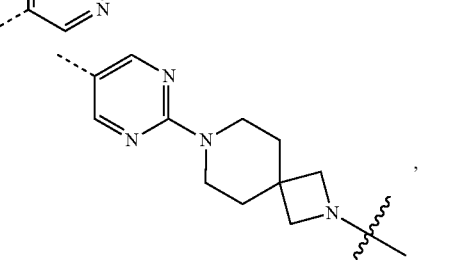,
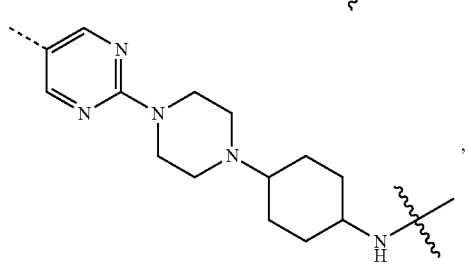,
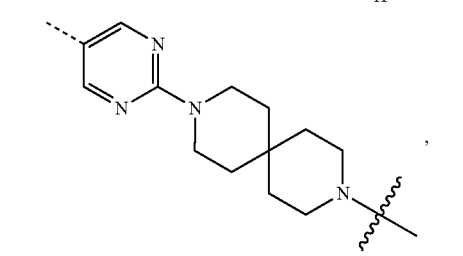,
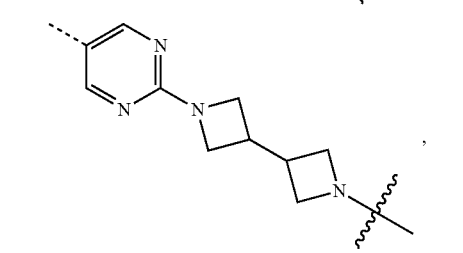,

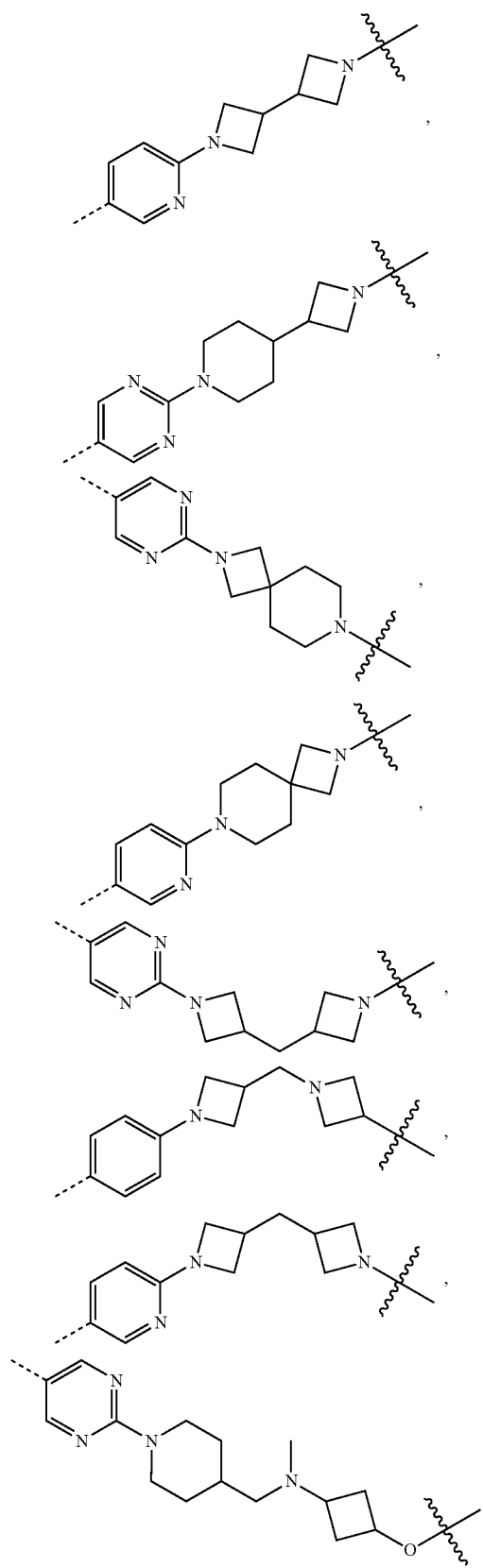
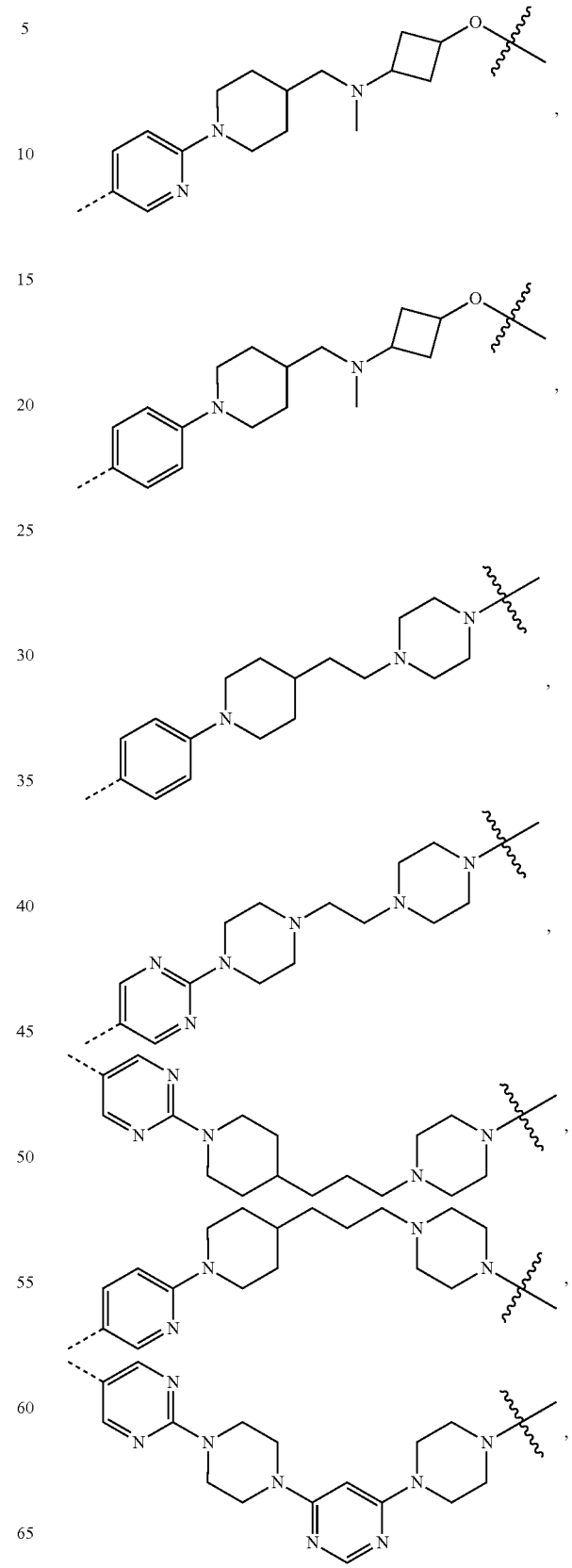

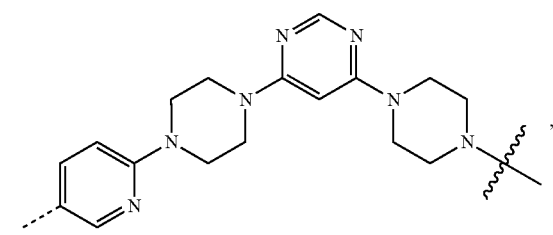

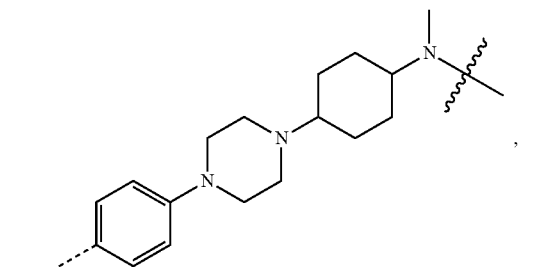

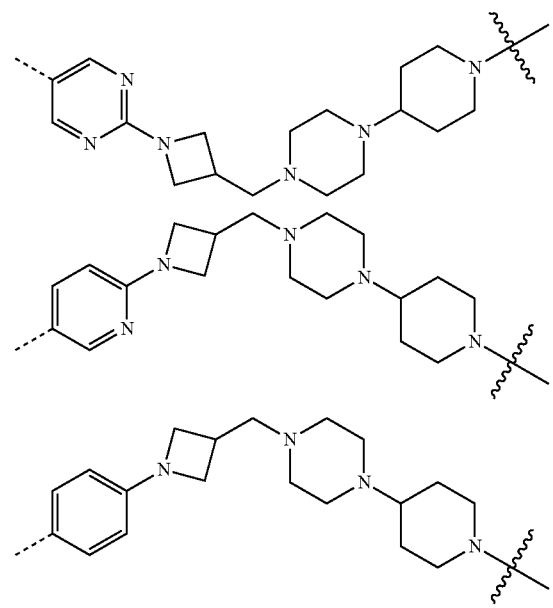

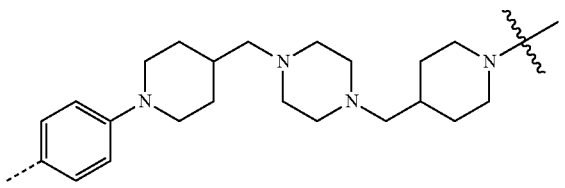

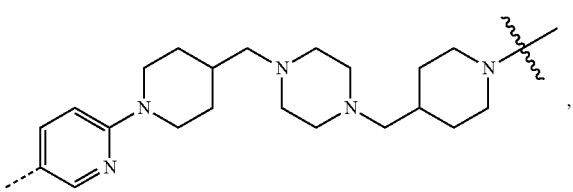

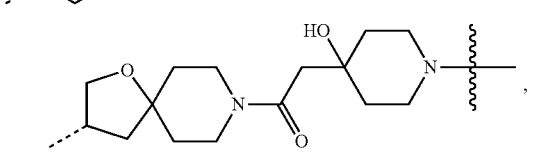

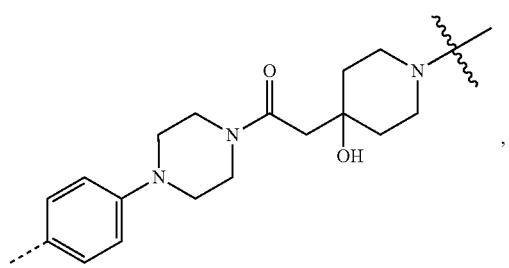

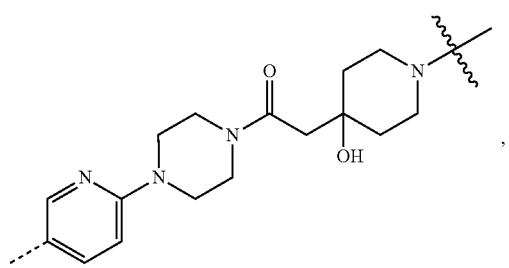

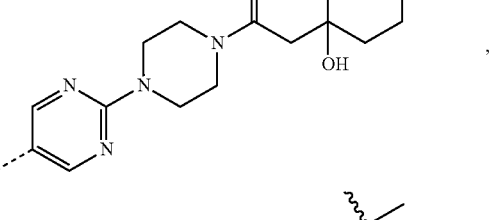

, or

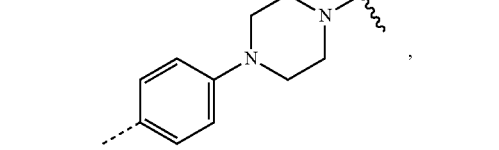

wherein the dashed lines indicate the point of attachment to the PTM and ⁓ indicates the point of attachment to the CLM and wherein the remaining variables are as described above for chemical structure I and any one of the second to twenty-ninth embodiments. In an alternative thirty-first embodiment, the chemical linking moiety (L) in the compound having the chemical structure I, or a pharmaceutically acceptable salt thereof, is represented by the structure:

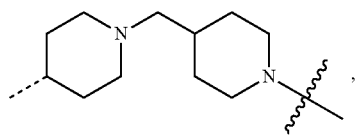

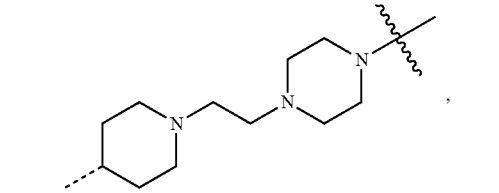

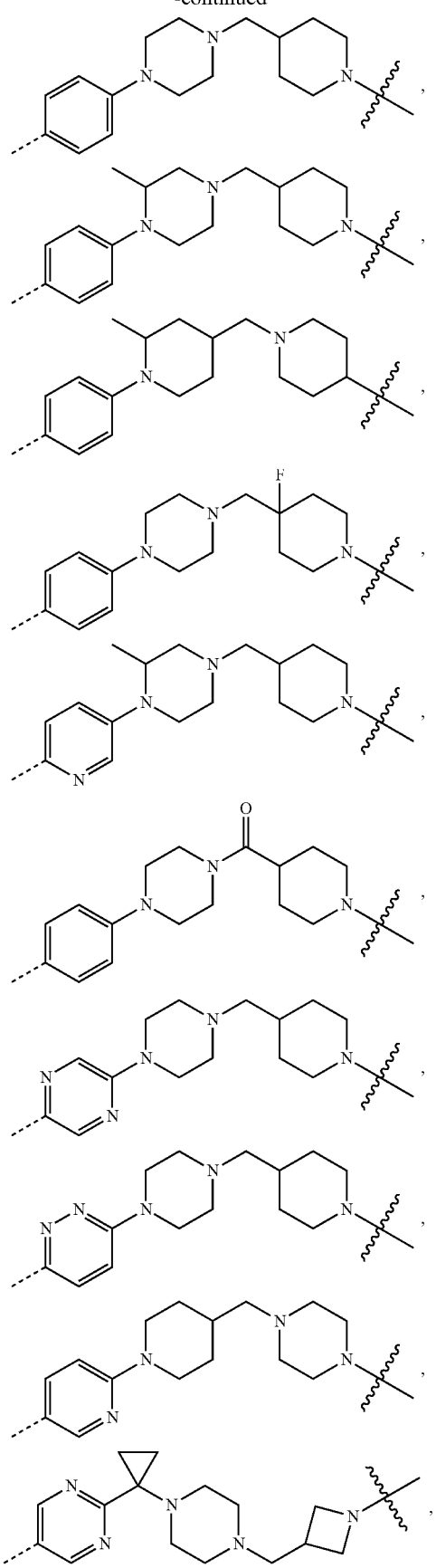
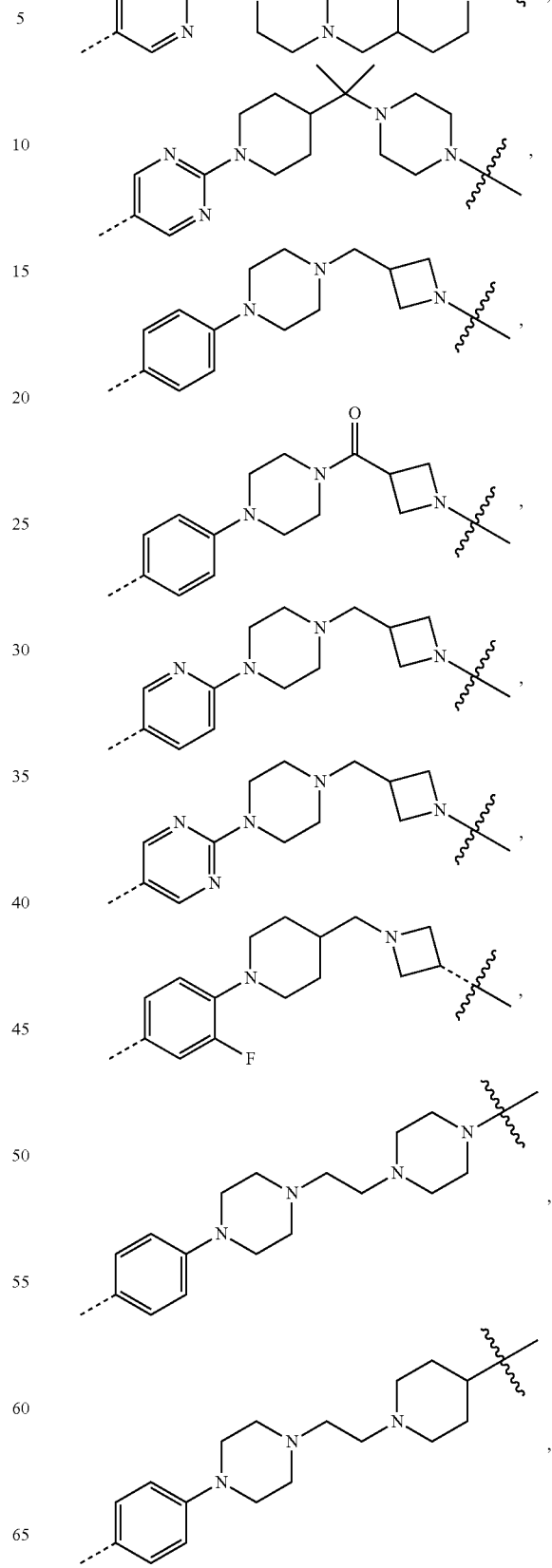

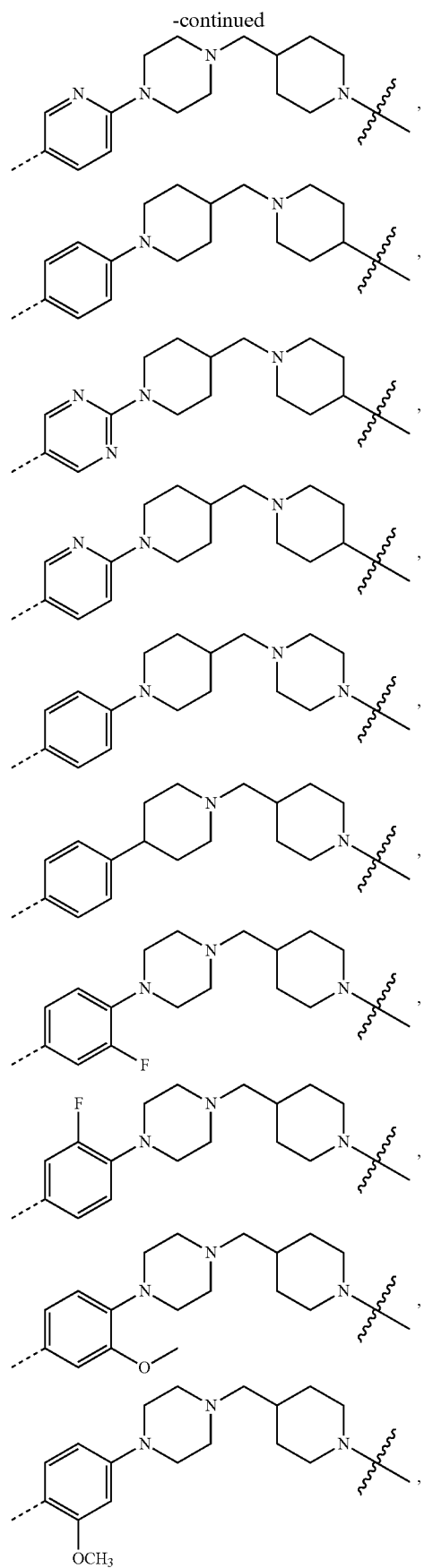
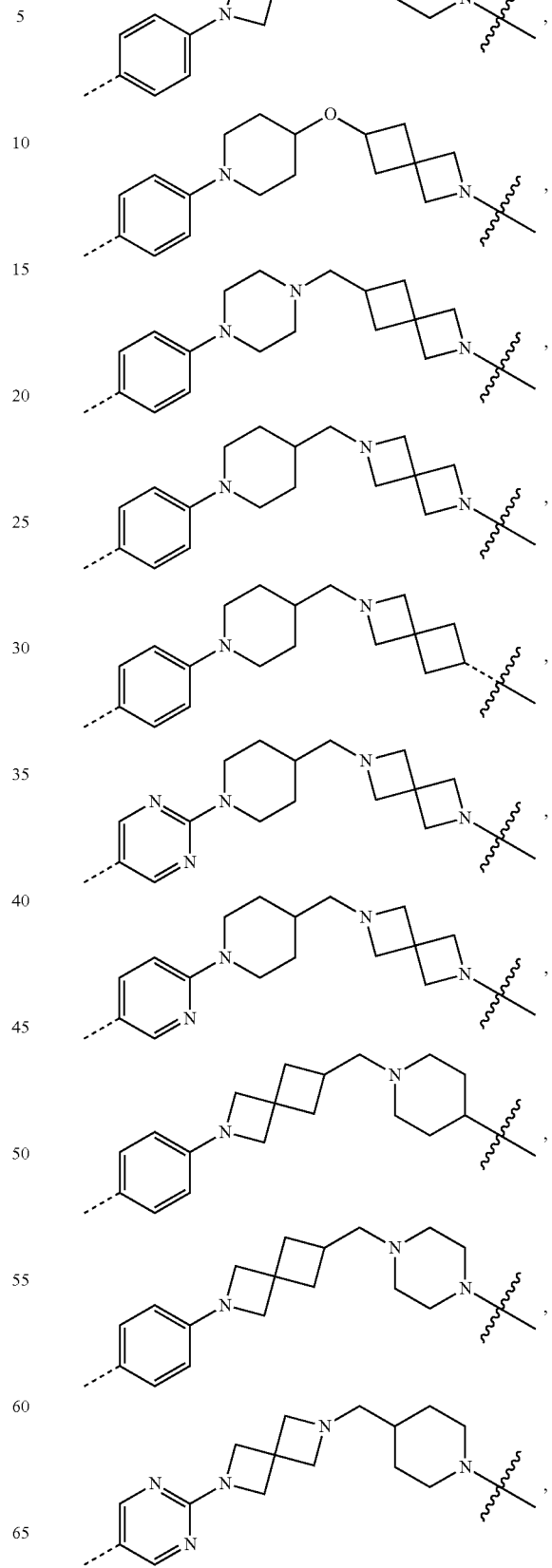

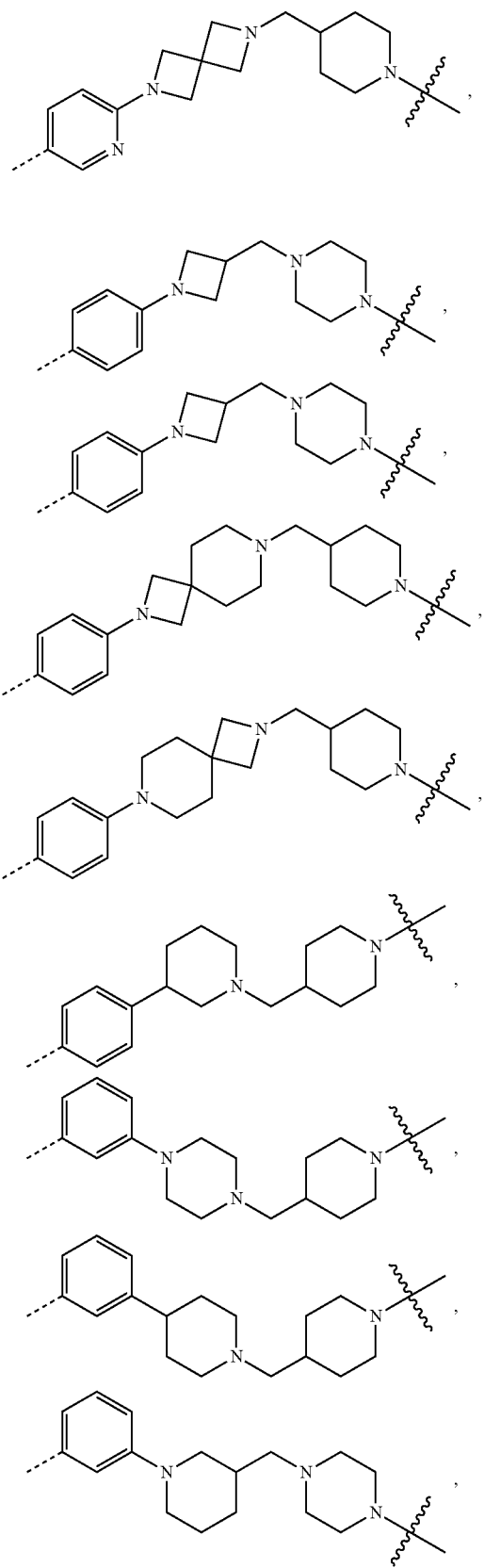
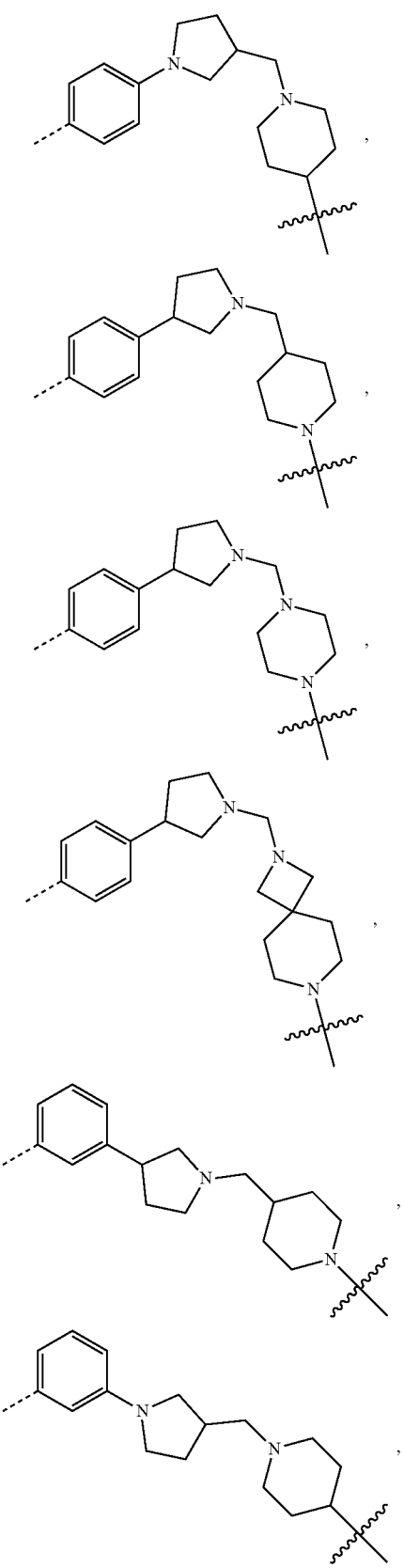

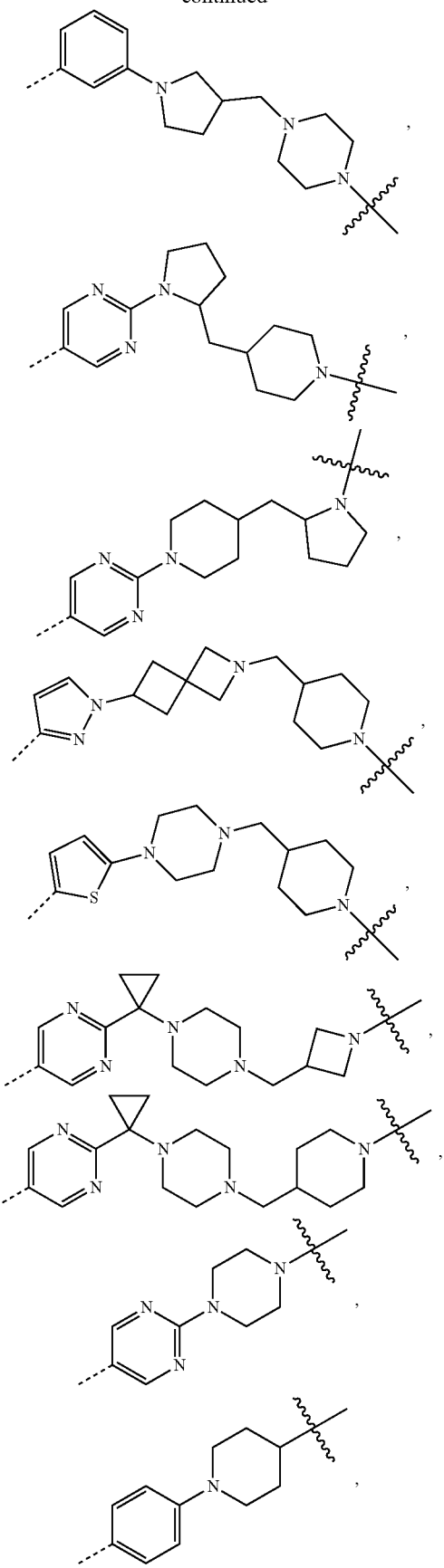
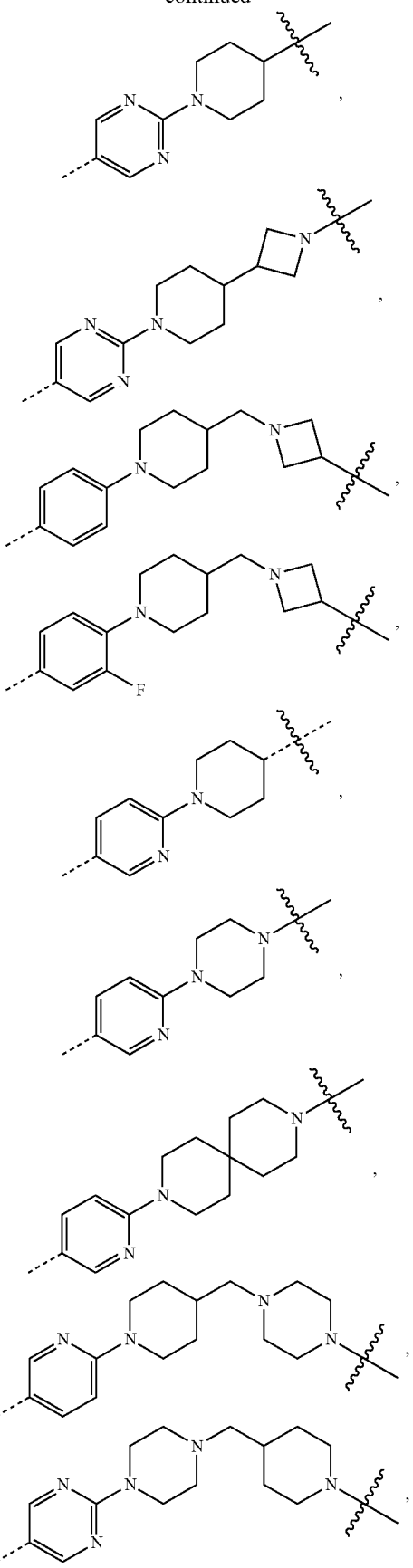

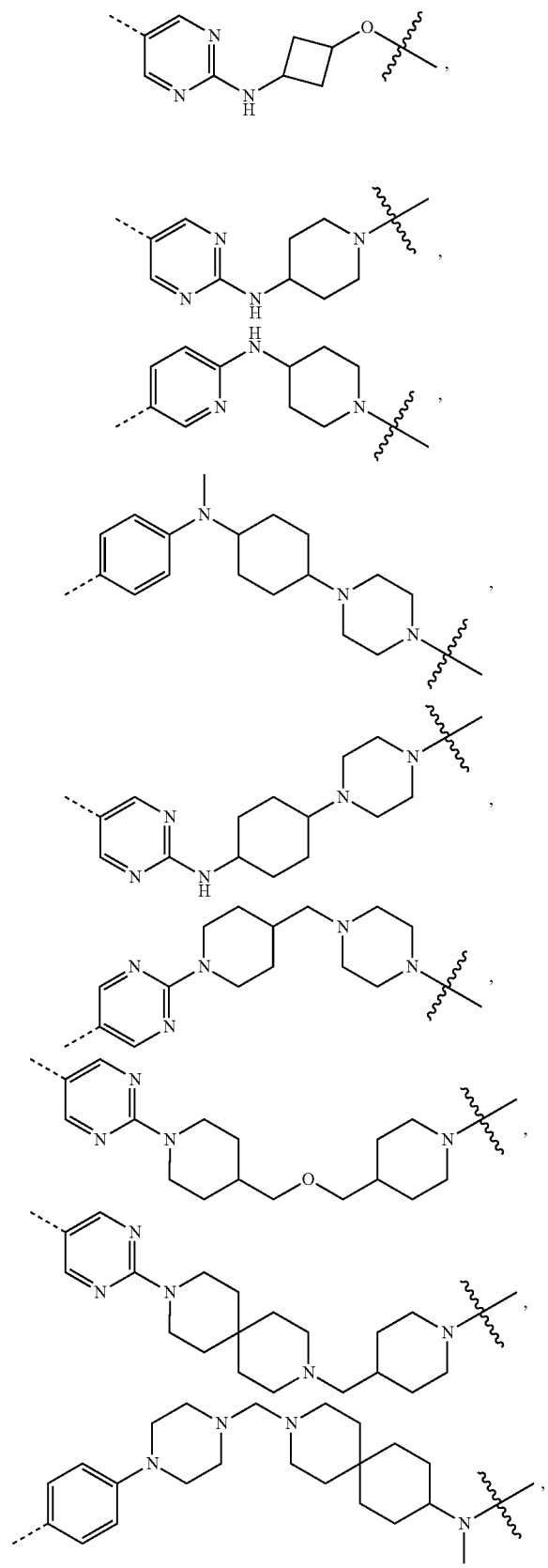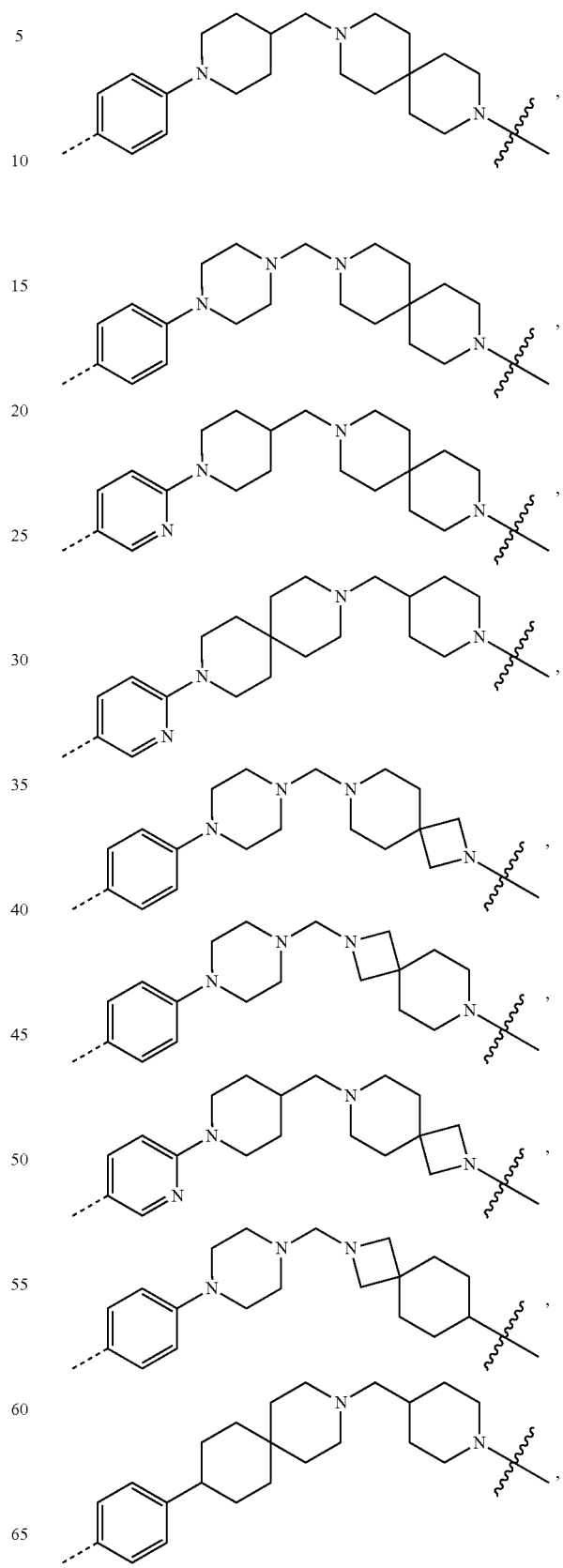

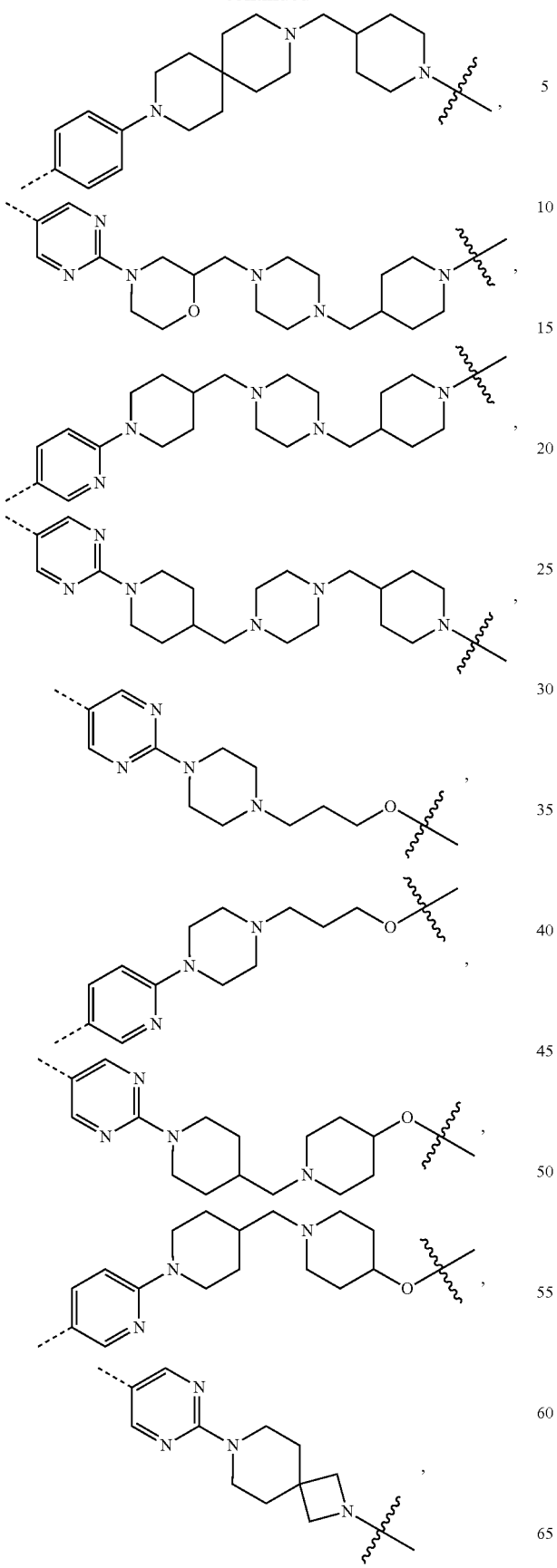
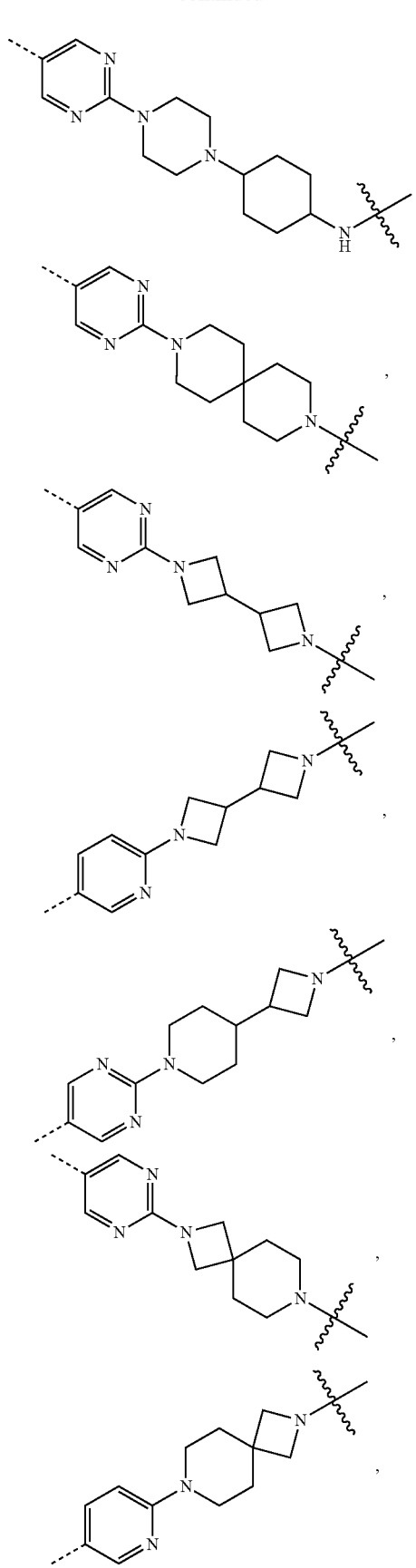

117
-continued
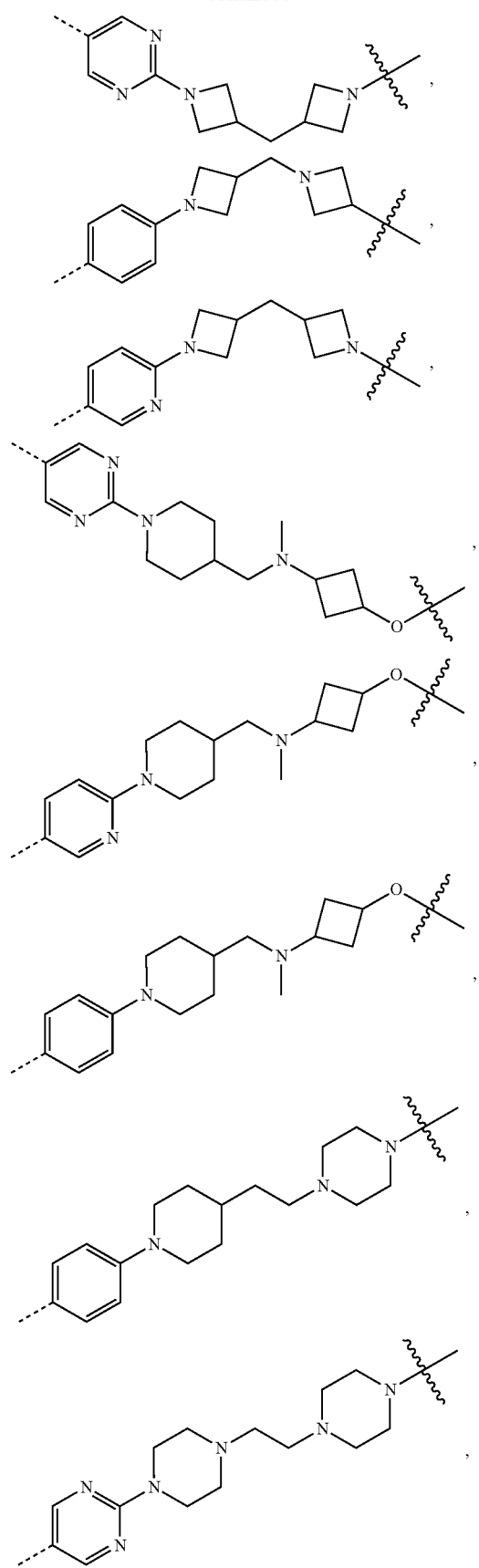
118
-continued
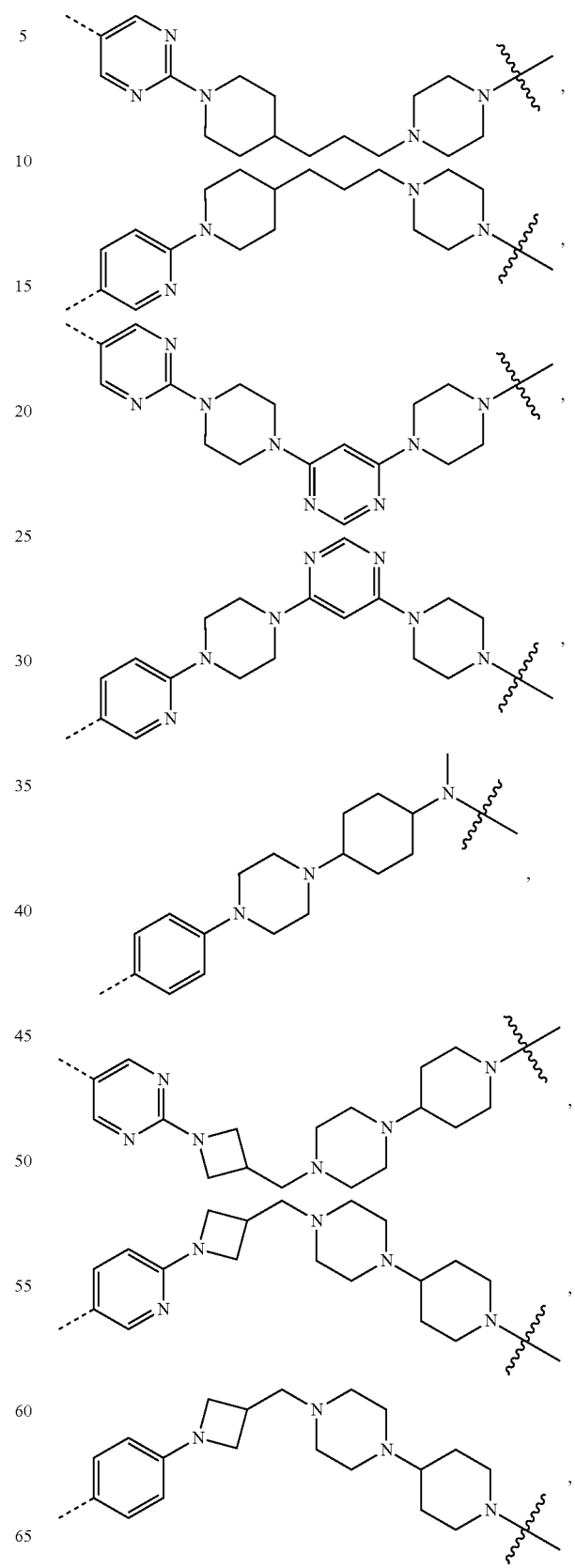

-continued

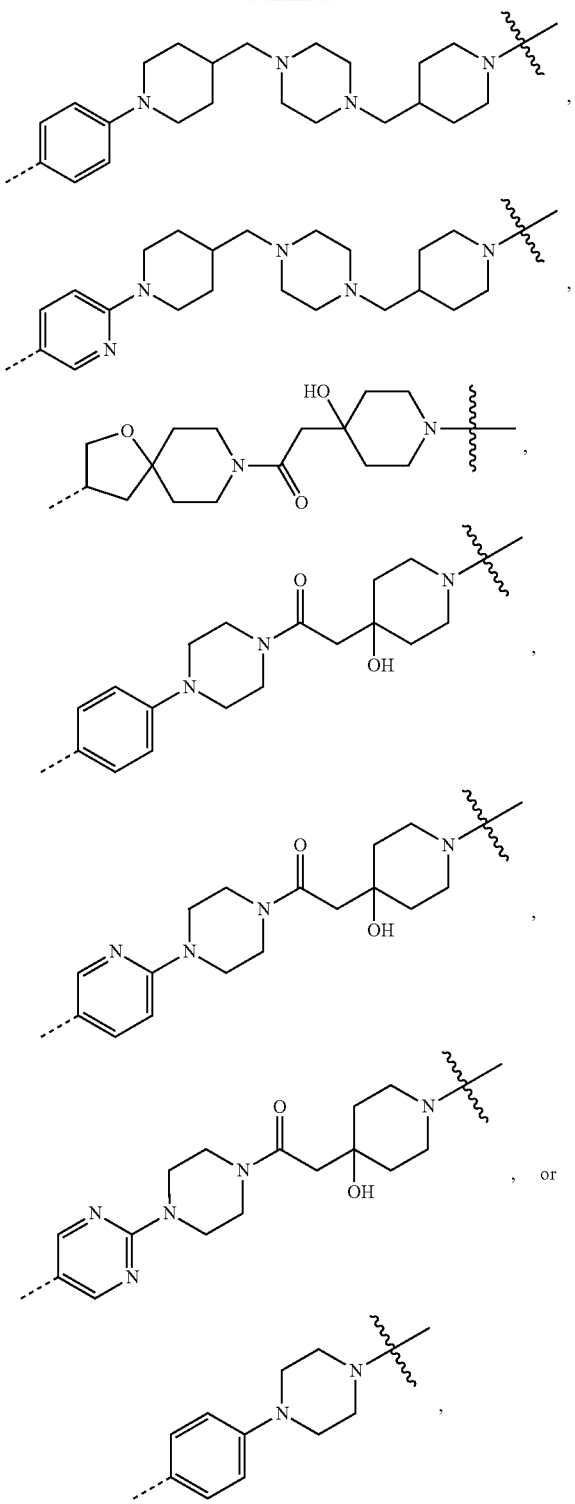

, or wherein the dashed lines indicate the point of attachment to the PTM and ⁓ indicates the point of attachment to the CLM and wherein the remaining variables are as described above for chemical structure I and any one of the second to twenty-ninth embodiments.

Compounds having the chemical structure I are further described in the Exemplification and are included in the present disclosure. Pharmaceutically acceptable salts thereof as well as the neutral forms of the compounds described herein are also included.

Also provided herein are pharmaceutical compositions comprising a described compound or a pharmaceutically acceptable salt of a described compound, or pharmaceutical compositions comprising a described compound or a pharmaceutically acceptable salt of a compound described herein; and a pharmaceutically acceptable carrier.

4. Uses and Administration

The compounds and compositions described herein are generally useful for treating a RAF (e.g., B-RAF) related condition. Thus, in one aspect, provided are methods of treating a RAF (e.g., B-RAF) related condition in a subject in need thereof comprising administering to the subject a therapeutically effective amount of a compound described herein, or a pharmaceutically acceptable salt thereof, or a pharmaceutical composition comprising a disclosed compound or pharmaceutically acceptable salt thereof.

Also provided is the use of a compound described herein, or a pharmaceutically acceptable salt thereof, or a pharmaceutical composition comprising a disclosed compound or pharmaceutically acceptable salt thereof, for the manufacture of a medicament for treating a RAF (e.g., B-RAF) related condition. Also provided is a compound described herein, or a pharmaceutically acceptable salt thereof, or a pharmaceutical composition comprising a disclosed compound or pharmaceutically acceptable salt thereof, for use in treating a RAF (e.g., B-RAF) related condition.

In one aspect, the RAF (e.g., B-RAF) related conditions are those which are modulated by degrading the RAF (e.g., B-RAF) protein.

In certain aspects, the RAF (e.g., B-RAF) related condition is a cancer.

In certain aspects, the RAF (e.g., B-RAF) related condition is a cancer selected from brain cancer, eye cancer, breast cancer, prostate cancer, oral cancer, ovarian cancer, lung cancer, colorectal cancer, liver cancer, endometrial cancer, cholangiocarcinoma, endometrial cancer, lymphatic cancer, gastric cancer, esophageal cancer, reproductive cancer, thyroid cancer, skin cancer, and hematologic cancer. In other aspects, the RAF (e.g., B-RAF) related condition is a cancer selected from renal cell carcinoma, pancreatic cancer, colorectal cancer, lung cancer, ovarian cancer, breast cancer, thyroid cancer, pilocytic astrocytoma, prostate cancer, gastric cancer, hepatocellular carcinoma, and melanoma. In other aspects, the RAF (e.g., B-RAF) related condition is a cancer selected from pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer. In other aspects, the RAF (e.g., B-RAF) related condition is a cancer selected from lung cancer, skin cancer or colorectal cancer. In other aspects, the RAF (e.g., B-RAF) related condition is lung cancer. In other aspects, the lung cancer is non-small cell lung cancer. In other aspects, the skin cancer is melanoma.

In certain aspects, the RAF (e.g., B-RAF) related condition is selected from cardiofaciocutaneous syndrome, neurofibromatosis type 1, Costello syndrome, Noonan Syndrome, LEOPARD (Lentigo, Electrocardiographic abnormalities, Ocular hypertelorism, Pulmonary stenosis, Abnormal genitalia, Retarded growth, Deafness) syndrome.

The compounds, the pharmaceutically acceptable salts of the compounds, and the pharmaceutical compositions described herein may be administered orally, parenterally, by inhalation spray, topically, rectally, nasally, buccally, vaginally or via an implanted reservoir. Preparations for such pharmaceutical compositions are well-known in the art. See, e.g., Anderson, Philip O.; Knoben, James E.; Troutman, William G., eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of the compounds, the pharmaceutically acceptable salts of the compounds, and the pharmaceutical compositions described herein are included herein. In one aspect, the compounds, the pharmaceutically acceptable salts of the compounds, and the pharmaceutical compositions described herein are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

EXAMPLES

General Synthetic Approach

General synthetic schemes for preparing the described compounds are described below. These schemes are illustrative and are not meant to limit the possible techniques one skilled in the art may use to prepare the compounds described herein.

Starting materials and reagents used in these examples, when not prepared by a procedure described herein, are generally either commercially available, or are reported in the chemical literature, or may be prepared by using procedures described in the chemical literature.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Synthetic Procedures

General Synthetic Scheme

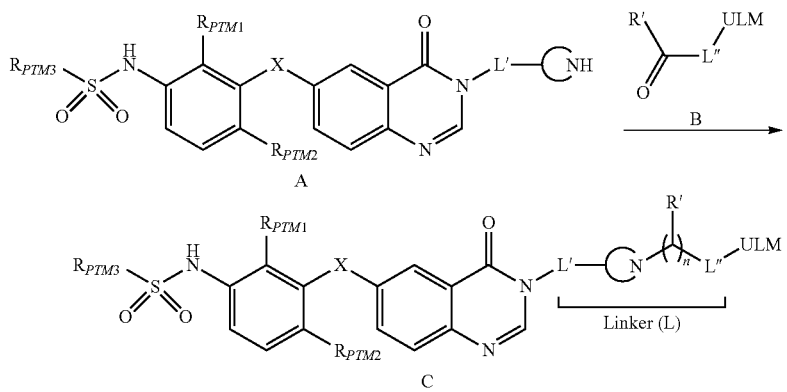

A compound of formula A may be reacted with a compound of formula B to afford a compound of formula C under conditions suitable for a reductive amination reaction, e.g. sodium triacetoxyborohydride and triethylamine or diisopropylethylamine; or sodium cyanoborohydride, sodium acetate, and acetic acid; in a suitable solvent such as isopropanol/dichloromethane, dimethylsulfoxide/dichloromethane, dichloromethane, dichloroethane, or dimethylsulfoxide/dichloroethane at room temperature. As needed, mixtures of enantiomers or diastereomers of may be resolved into their constituent enantiomers or diastereomers using techniques known to one skilled in the art, including but not limited to preparative high performance liquid chromatography or preparative supercritical fluid chromatography. L', L", R', and

each represent a portion of linker (L), n is 1, and

represents an ring system having a basic primary or secondary amine capable of undergoing the specified reaction to form part of the linker. All other variables are as defined herein. It will be further apparent to one skilled in the art that the positions of

in formula A and C(O)R' in formula B may be reversed throughout the synthetic sequence, such that the positions of

and

are reversed in formula C.

Scheme 1'

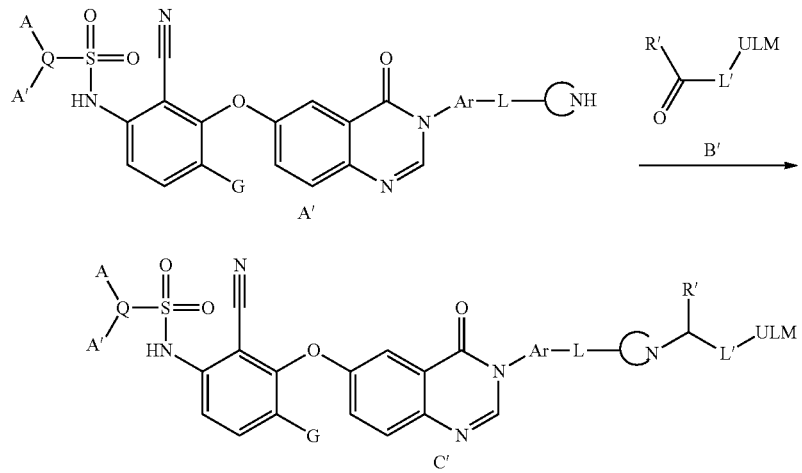

A compound of formula A' may be reacted with a compound of formula B' to afford a compound of formula C' under conditions suitable for a reductive amination reaction, e.g. sodium triacetoxyborohydride and triethylamine or diisopropylethylamine; or sodium cyanoborohydride, sodium acetate, and acetic acid; in a suitable solvent such as isopropanol/dichloromethane, dimethylsulfoxide/dichloromethane, dichloromethane, dichloroethane, or dimethylsulfoxide/dichloroethane at room temperature. As needed, mixtures of enantiomers or diastereomers of any compounds A', B', or C' may be resolved into their constituent enantiomers or diastereomers using techniques known to one skilled in the art, including but not limited to preparative high performance liquid chromatography or preparative supercritical fluid chromatography. Herein Q is N or CH; A and A' are each independently H, substituted alkyl, or optionally fused into a ring with Q, which may have further optional substitutions; G is H, halogen, substituted alkyl, or substituted alkoxy; Ar represents an optional aromatic or heteroaromatic ring system with one or more optional substituents; L represents an optional linker or portion of a linker;

represents a primary or secondary amine, optionally cyclized into a 4 to 8 membered heterocyclic ring and/or fused to Ar when L is absent; R' is either H or alkyl, and when R' is alkyl it may optionally be tied into a ring with L'; L' is an optional linker or portion of a linker; n is 1; and ULM is:

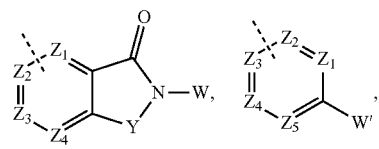

-continued

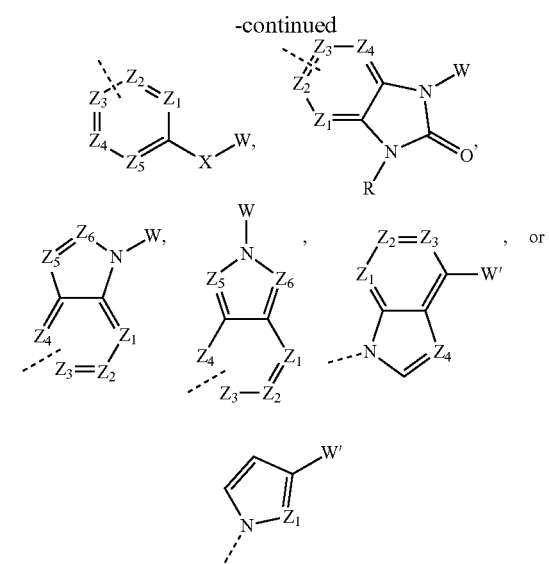

wherein W is

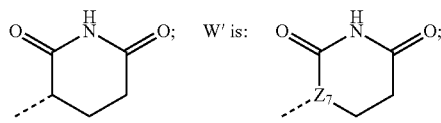

each $Z_1$, $Z_2$, $Z_3$, $Z_4$, $Z_5$, $Z_6$, and $Z_7$ is independently selected from N or CR; $Z'_1$ is NR or CHR; X is NR or C(O)NR; Y is $CH_2$ or C=O; and R is H or an optional substituent.

It will further be apparent to one skilled in the art that the positions of

in compound A' and C(O)R' in compound B' may be reversed throughout the synthetic sequence, such that the positions of

and

are reversed in compound C'.

It will also be apparent to one skilled in the art that a compound of formula III may be transformed into a different compound of formula III. For example, in cases where

represents a secondary amine, this amine may be further modified by reductive amination or acylation to produce a tertiary amine or amide, respectively.

Scheme 2

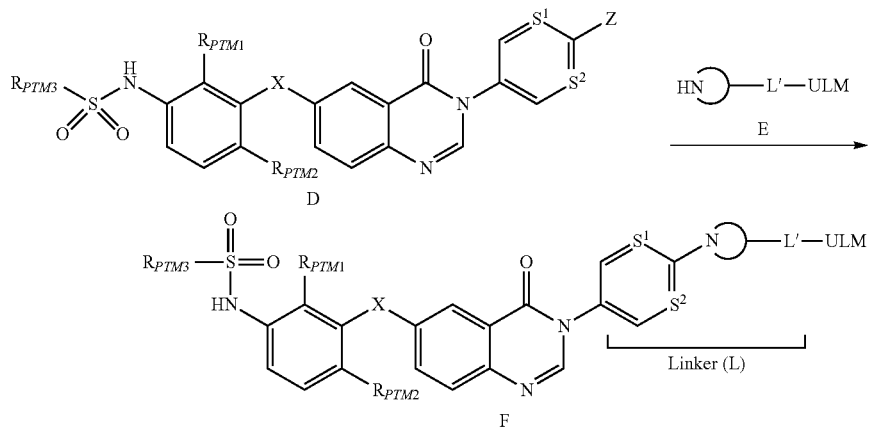

A compound of formula D may be reacted with a compound of formula E to afford a compound of formula F under conditions suitable for a nucleophilic aromatic substitution reaction, e.g. diisopropylethylamine or potassium carbonate in DMSO at 80 to 100° C. or in acetonitrile at 80° C. As needed, mixtures of enantiomers or diastereomers may be resolved into their constituent enantiomers or diastereomers using techniques known to one skilled in the art, including but not limited to preparative high performance liquid chromatography or preparative supercritical fluid chromatography. $S^1$ and $S^2$ are each independently N or CH, where the aryl ring containing $S^1$ and $S^2$, L', and

each represent a portion of linker (L). All other variables are as defined herein.

Scheme 2'

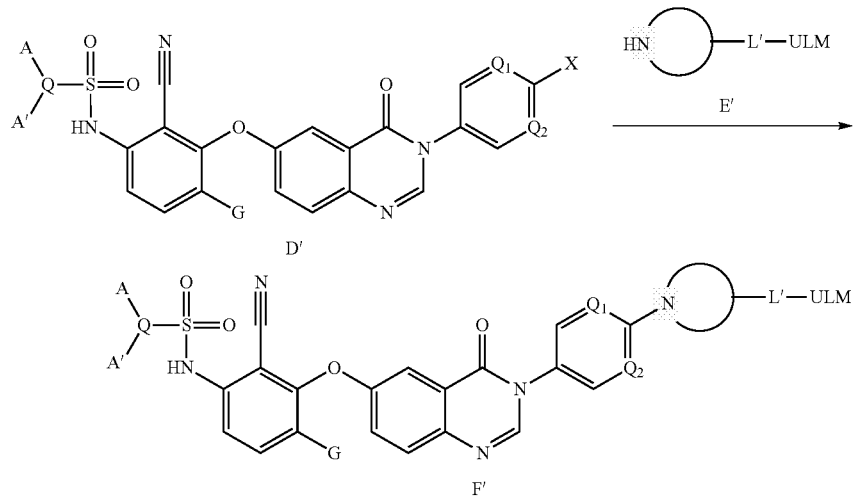

A compound of formula D' may be reacted with a compound of formula E' to afford a compound of formula F' under conditions suitable for a nucleophilic aromatic substitution reaction, e.g. diisopropylethylamine or potassium carbonate in DMSO at 80 to 100° C. or in acetonitrile at 80° C. As needed, mixtures of enantiomers or diastereomers of any compounds D', E', or F' may be resolved into their constituent enantiomers or diastereomers using techniques known to one skilled in the art, including but not limited to preparative high performance liquid chromatography or preparative supercritical fluid chromatography. Herein Q is N or CH; A and A' are each independently H, substituted alkyl, or optionally fused into a ring with Q, which may have further optional substitutions; G is H, halogen, substituted alkyl, or substituted alkoxy; $Q_1$ and $Q_2$ are each independently CR' or N, where at least one of $Q_1$ and $Q_2$ is N and R' represents an optional substituent; X is a suitable leaving group, including but not limited to F, $C_1$, or methylsulfonyl;

represents a primary or secondary amine, optionally cyclized into a 4 to 8 membered heterocyclic ring; L' is an optional linker or portion of a linker; and ULM is as defined in Scheme 1 or 1'.

Scheme 3

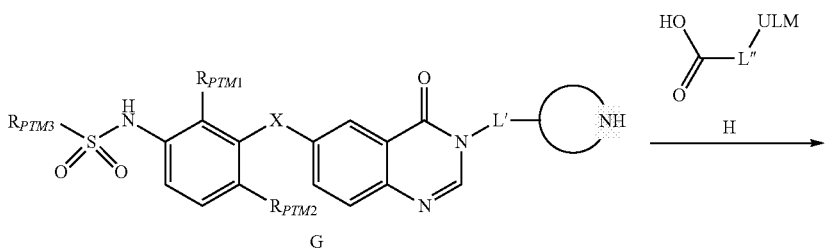

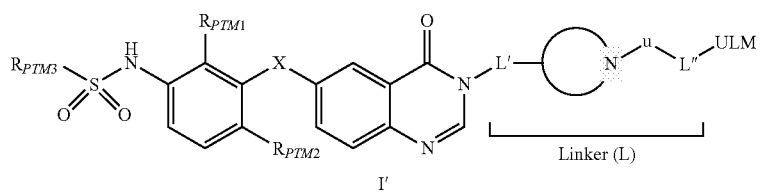

A compound of formula G may alternatively be reacted with a compound of formula H to afford a compound of formula I' under conditions suitable for an amide coupling reaction, e.g. N-methylimidazole and chloro-N,N,N',N'-tetramethylformamidinium hexafluorophosphate in N,N-dimethylformamide; or (benzotriazol-1-yloxy)tris(dimethylamino)phosphonium hexafluorophosphate and diisopropylethylamine in N,N-dimethylformamide. As needed, mixtures of enantiomers or diastereomers may be resolved into their constituent enantiomers or diastereomers using techniques known to one skilled in the art, including but not limited to preparative high performance liquid chromatography or preparative supercritical fluid chromatography. L', L", u, and

each represent a portion of linker (L). All other variables are as defined herein. It will further be apparent to one skilled in the art that the positions of

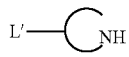

and L"-CO$_2$H may be reversed.

Scheme 3'

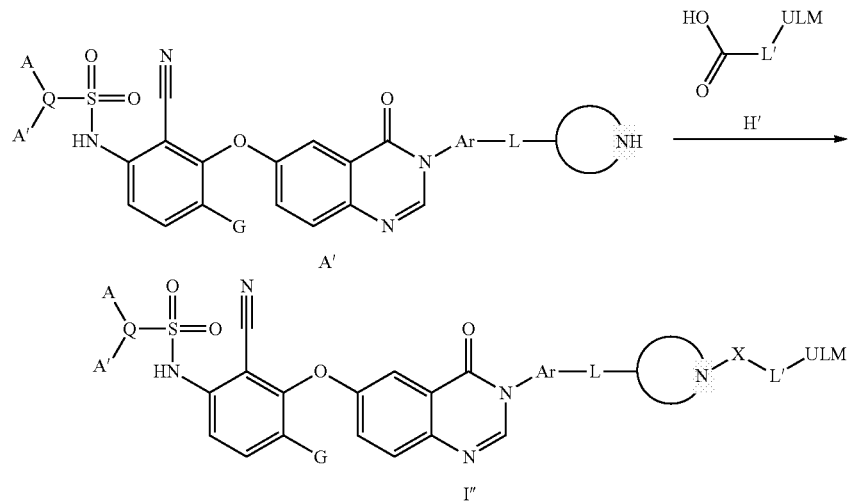

A compound of formula A' may alternatively be reacted with a compound of formula H' to afford a compound of formula I" under conditions suitable for an amide coupling reaction, e.g. N-methylimidazole and chloro-N,N,N',N'-tetramethylformamidinium hexafluorophosphate in N,N-dimethylformamide; or (benzotriazol-1-yloxy)tris(dimethylamino)phosphonium hexafluorophosphate and diisopropylethylamine in N,N-dimethylformamide. As needed, mixtures of enantiomers or diastereomers of any compounds A', H', or I" may be resolved into their constituent enantiomers or diastereomers using techniques known to one skilled in the art, including but not limited to preparative high performance liquid chromatography or preparative supercritical fluid chromatography. Herein Q is N or CH; A and A' are each independently H, substituted alkyl, or optionally fused into a ring with Q, which may have further optional substitutions; G is H, halogen, substituted alkyl, or substituted alkoxy; Ar represents an optional aromatic or heteroaromatic ring system with one or more optional substituents; L represents an optional linker or portion of a linker;

represents a primary or secondary amine, optionally cyclized into a 4 to 8 membered heterocyclic ring and/or fused to Ar when L is absent; L' is an optional linker or portion of a linker; X is C=O; and ULM is as defined in Scheme 1 or 1'.

It will further be apparent to one skilled in the art that the positions of

in compound A' and C(O)OH in compound H' may be reversed throughout the synthetic sequence, such that the positions of

and X are reversed in compound I".

Scheme 4

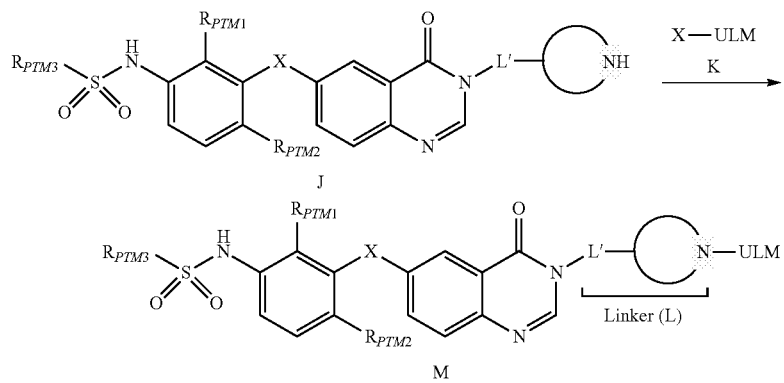

A compound of formula J may alternatively be reacted with a compound of formula K to afford a compound of formula M under conditions suitable for Hartwig-Buchwald amination reaction, e.g. [1,3-bis(2,6-di-3-pentylphenyl)imidazol-2-ylidene](3-chloropyridyl)dichloropalladium(II) or dichloro[1,3-bis(2,6-di-4-heptylphenyl)imidazol-2-ylidene](3-chloropyridyl)palladium(II) and cesium carbonate in dimethylsulfoxide at 100° C. As needed, mixtures of enantiomers or diastereomers may be resolved into their constituent enantiomers or diastereomers using techniques known to one skilled in the art, including but not limited to preparative high performance liquid chromatography or preparative supercritical fluid chromatography. X represents a functional group capable of undergoing palladium-catalyzed oxidative addition, e.g. an iodide, bromide, chloride, or trifluoromethanesulfonate. L',

and

each represent a portion of linker (L). All other variables are as defined herein.

It will further be apparent to one skilled in the art that the positions of

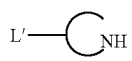

may be reversed.

Scheme 4'

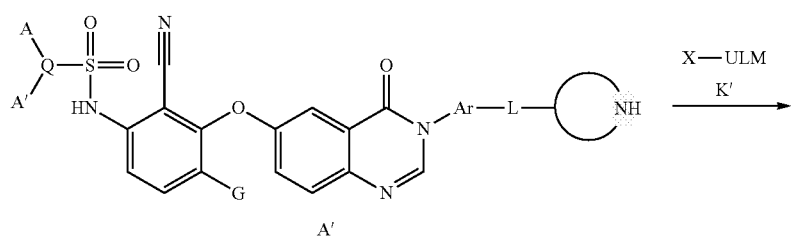

-continued

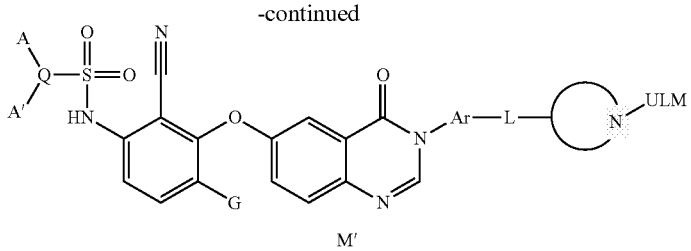

A compound of formula A' may alternatively be reacted with a compound of formula K' to afford a compound of formula M' under conditions suitable for Hartwig-Buchwald amination reaction, e.g. [1,3-bis(2,6-di-3-pentylphenyl)imidazol-2-ylidene](3-chloropyridyl)dichloropalladium(II) or dichloro[1,3-bis(2,6-di-4-heptylphenyl)imidazol-2-ylidene](3-chloropyridyl)palladium(II) and cesium carbonate in dimethylsulfoxide at 100° C. As needed, mixtures of enantiomers or diastereomers of any compounds A', K', or M' may be resolved into their constituent enantiomers or diastereomers using techniques known to one skilled in the art, including but not limited to preparative high performance liquid chromatography or preparative supercritical fluid chromatography. Herein Q is N or CH; A and A' are each independently H, substituted alkyl, or optionally fused into a ring with Q, which may have further optional substitutions; G is H, halogen, substituted alkyl, or substituted alkoxy; Ar represents an optional aromatic or heteroaromatic ring system with one or more optional substituents; L represents an optional linker or portion of a linker;

represents a primary or secondary amine, optionally cyclized into a 4 to 8 membered heterocyclic ring and/or fused to Ar when L is absent; X represents a functional group capable of undergoing palladium-catalyzed oxidative addition, e.g. an iodide, bromide, chloride, or trifluoromethanesulfonate; and ULM is as defined in Scheme 1 or 1'.

Intermediate 1: (3R)—N-[2-cyano-4-fluoro-3-[4-oxo-3-(4-piperidyl)quinazolin-6-yl]oxy-phenyl]-3-fluoro-pyrrolidine-1-sulfonamide Step 1: (3R)-3-fluoropyrrolidine-1-sulfonamide

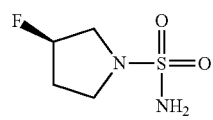

To a solution of (3R)-3-fluoropyrrolidine hydrochloride (5.00 g, 39.8 mmol) in 1,4-dioxane (25 mL) was added sulfamide (2.0 mL, 33 mmol,) and triethylamine (9.2 mL, 66 mmol). The mixture was stirred at 120° C. for 15 h, then concentrated. The residue was purified by flash silica gel chromatography (80% ethyl acetate/petroleum ether) to afford (3R)-3-fluoropyrrolidine-1-sulfonamide (4.3 g, 77%) as a white solid.

Step 2: tert-butyl 4-[(2-amino-5-hydroxy-benzoyl)amino]piperidine-1-carboxylate

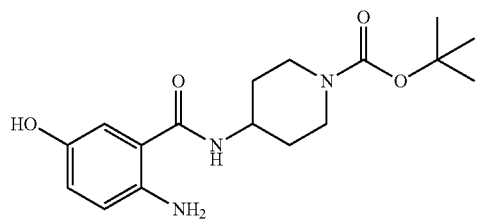 [SMILES: CC(C)(C)OC(=O)N1CCC(NC(=O)c2cc(O)ccc2N)CC1]

To a solution of 2-amino-5-hydroxy-benzoic acid (500 mg, 3.3 mmol) in N,N-dimethylformamide (15 mL) was added triethylamine (1.3 mL, 9.8 mmol), 1-(3-dimethylaminopropyl)-3-ethylcarbodiimide hydrochloride (938 mg, 4.9 mmol) and hydroxybenzotriazole (529 mg, 3.9 mmol). The mixture was stirred at 20° C. for 0.5 h. Then tert-butyl 4-aminopiperidine-1-carboxylate (653 mg, 3.3 mmol) was added, the mixture was stirred at 20° C. for 11.5 h. The reaction was diluted with water (20 mL) and extracted with dichloromethane (3×20 mL). The combined organic layers were washed with brine (3×30 mL), dried over anhydrous sodium sulfate, filtered, and concentrated. The residue was purified by preparative HPLC (mobile phase: [0.2% formic acid in water-acetonitrile]; B %: 5%-35%, 10 min) to afford tert-butyl 4-[(2-amino-5-hydroxy-benzoyl)amino]piperidine-1-carboxylate (140 mg, 12%) as a brown solid. MS (ESI) m/z: 336.0 [M+H]$^+$.

Step 3: 4-(6-hydroxy-4-oxo-quinazolin-3-yl)piperidine-1-carbaldehyde

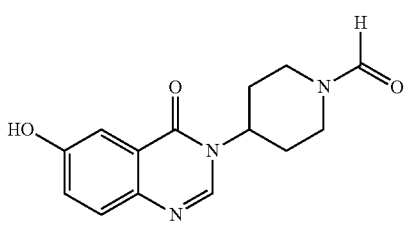 [SMILES: O=CN1CCC(n2cnc3ccc(O)cc3c2=O)CC1]

Tert-butyl 4-[(2-amino-5-hydroxy-benzoyl)amino]piperidine-1-carboxylate (1 g, 3 mmol) was dissolved in acetic acid (25 mL). The reaction was stirred at 110° C. for 12 h, then concentrated to afford 4-(6-hydroxy-4-oxo-quinazolin-3-yl) piperidine-1-carbaldehyde (730 mg, 89%) as a brown oil, which was used in the next step without further purification. MS (ESI) m/z: 274.1 [M+H]$^+$.

Step 4: 6-hydroxy-3-(4-piperidyl)quinazolin-4-one

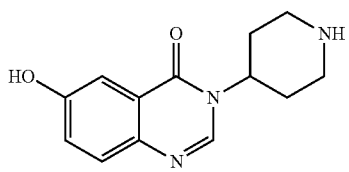 [SMILES: O=c1c2cc(O)ccc2ncn1C1CCNCC1]

To a solution of 4-(6-hydroxy-4-oxo-quinazolin-3-yl)piperidine-1-carbaldehyde (730 mg, 2.7 mmol) in 1,4-dioxane (15 mL) was added 1 M hydrochloric acid (14.6 mL). The mixture was stirred at 100° C. for 16 h, then concentrated to afford 6-hydroxy-3-(4-piperidyl) quinazolin-4-one (650 mg, crude) as a white solid. MS (ESI) m/z: 245.8 [M+H]$^+$.

Step 5: tert-butyl 4-(6-hydroxy-4-oxo-quinazolin-3-yl)piperidine-1-carboxylate

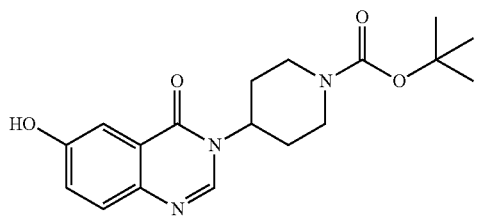 [SMILES: CC(C)(C)OC(=O)N1CCC(n2cnc3ccc(O)cc3c2=O)CC1]

To a solution of 6-hydroxy-3-(4-piperidyl)quinazolin-4-one (400 mg, 1.6 mmol) in dichloromethane (40 mL) was added triethylamine (0.7 mL, 5 mmol) and di-tert-butyldicarbonate (355 mg, 1.6 mmol). The mixture was stirred at 20° C. for 12 h. The reaction mixture was diluted with water (50 mL) and extracted with dichloromethane (3×50 mL). The combined organic layers were washed with brine (3×70 mL), dried over anhydrous sodium sulfate, filtered, and concentrated. The residue was purified by flash silica gel chromatography (0 to 5% methanol/dichloromethane) to afford tert-butyl 4-(6-hydroxy-4-oxo-quinazolin-3-yl)piperidine-1-carboxylate (400 mg, 71%) as a white solid. MS (ESI) m/z: 345.9 [M+H]$^+$.

Step 6: tert-butyl 4-[6-(2-cyano-3,6-difluoro-phenoxy)-4-oxo-quinazolin-3-yl]piperidine-1-carboxylate

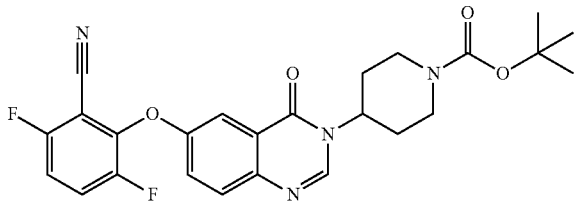 [SMILES: CC(C)(C)OC(=O)N1CCC(n2cnc3ccc(Oc4c(F)ccc(F)c4C#N)cc3c2=O)CC1]

To a solution of tert-butyl 4-(6-hydroxy-4-oxo-quinazolin-3-yl)piperidine-1-carboxylate (400 mg, 1.2 mmol) in N,N-dimethylformamide (10 mL) was added cesium carbonate (433 mg, 1.3 mmol) and 2,3,6-trifluorobenzonitrile (236 mg, 1.5 mmol). The mixture was stirred at 20° C. for 12 h. The reaction mixture was diluted with water (30 mL) and extracted with dichloromethane (3×15 mL). The combined organic layers were washed with brine (3×8 mL), dried over anhydrous sodium sulfate, filtered, and concentrated. The residue was purified by flash silica gel chromatography (0-8% ethyl acetate/petroleum ether) to afford tert-butyl 4-[6-(2-cyano-3,6-difluoro-phenoxy)-4-oxo-quinazolin-3-yl]piperidine-1-carboxylate (440 mg, 78%) as a yellow solid. MS (ESI) m/z: 483.1 [M+H]$^+$.

Step 7: tert-butyl 4-[6-[2-cyano-6-fluoro-3-[[(3R)-3-fluoropyrrolidin-1-yl]sulfonylamino]phenoxy]-4-oxo-quinazolin-3-yl]piperidine-1-carboxylate

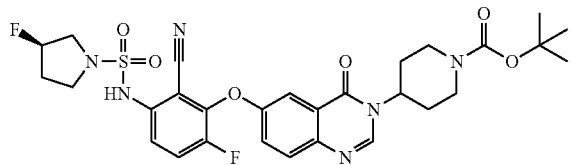 [SMILES: CC(C)(C)OC(=O)N1CCC(n2cnc3ccc(Oc4c(F)ccc(NS(=O)(=O)N5CC[C@@H](F)C5)c4C#N)cc3c2=O)CC1]

To a solution of (3R)-3-fluoropyrrolidine-1-sulfonamide (292 mg, 1.7 mmol) in N,N-dimethylformamide (5 mL) was added cesium carbonate (594 mg, 1.8 mmol). The mixture was stirred at 50° C. for 0.5 h. Then cooled to 20° C. and tert-butyl 4-[6-(2-cyano-3,6-difluoro-phenoxy)-4-oxo-quinazolin-3-yl]piperidine-1-carboxylate (400 mg, 0.8 mmol) in N,N-dimethylformamide (10 mL) was added to the mixture, stirred at 100° C. for 11.5 h. The reaction mixture was diluted with water (30 mL) and extracted with dichloromethane (3×30 mL). The combined organic layers were washed with brine (3×50 mL), dried over anhydrous sodium sulfate, filtered, and concentrated. The residue was purified by flash silica gel chromatography (0-2% methanol/dichloromethane) to afford tert-butyl 4-[6-[2-cyano-6-fluoro-3-[[(3R)-3-fluoropyrrolidin-1-yl]sulfonylamino]phenoxy]-4-oxo-quinazolin-3-yl]piperidine-1-carboxylate (30 mg, 57%) as white solid. MS (ESI) m/z: 631.2 [M+H]$^+$.

Step 8: (3R)—N-[2-cyano-4-fluoro-3-[4-oxo-3-(4-piperidyl)quinazolin-6-yl]oxy-phenyl]-3-fluoro-pyrrolidine-1-sulfonamide

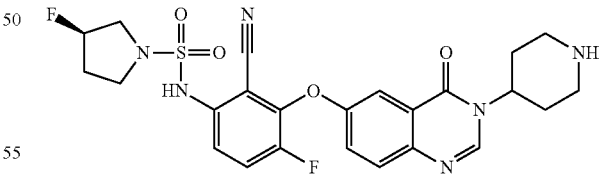

To a solution of tert-butyl 4-[6-[2-cyano-6-fluoro-3-[[(3R)-3-fluoropyrrolidin-1-yl]sulfonylamino]phenoxy]-4-oxo-quinazolin-3-yl]piperidine-1-carboxylate (280 mg, 0.4 mmol) in dichloromethane (6 mL) was added 4 M hydrochloride in 1,4-dioxane (8 mL). The mixture was stirred at 20° C. for 1 h, then concentrated to afford (3R)—N-[2-cyano-4-fluoro-3-[4-oxo-3-(4-piperidyl)quinazolin-6-yl] oxy-phenyl]-3-fluoro-pyrrolidine-1-sulfonamide hydrochloride (270 mg, crude) as a white solid. MS (ESI) m/z: 530.16 [M+H]$^+$.

Intermediate 2: (3R)—N-[3-[3-(4-bromophenyl)-4-oxo-quinazolin-6-yl]oxy-2-cyano-4-fluoro-phenyl]-3-fluoro-pyrrolidine-1-sulfonamide

Step 1: N-(4-bromophenyl)-5-hydroxy-2-nitro-benzamide

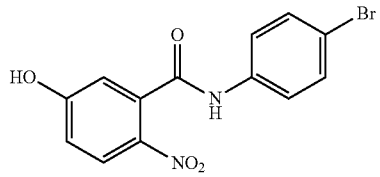

To a solution of 5-hydroxy-2-nitro-benzoic acid (10 g, 55 mmol) and 4-bromoaniline (9.39 g, 55 mmol) in pyridine (150 mL) was added 1-(3-dimethylaminopropyl)-3-ethylcarbodiimide hydrochloride (15.70 g, 82 mmol), the mixture was stirred at 80° C. for 1 h. Water (500 mL) was poured into the mixture and stirred for 10 min. The precipitate was collected by filtration, then purified by column chromatography (petroleum ether/ethyl acetate=1/0 to 1/1) to afford N-(4-bromophenyl)-5-hydroxy-2-nitro-benzamide (4 g, 21%) as a yellow solid. MS (ESI) m/z: 338.6 [M+H]$^+$.

Step 2: 2-amino-N-(4-bromophenyl)-5-hydroxy-benzamide

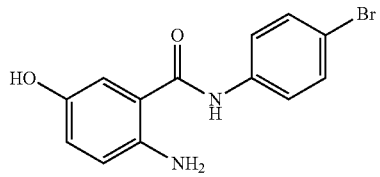 [SMILES: O=C(Nc1ccc(Br)cc1)c1cc(O)ccc1[N+](=O)[O-]]

To a solution of N-(4-bromophenyl)-5-hydroxy-2-nitro-benzamide (4.0 g, 12 mmol) in ethanol (40 mL) and tetrahydrofuran (40 mL) was added iron (3.3 g, 59 mmol), hydrochloric acid (12 M, 0.9 mL) and ammonium chloride (1.9 g, 36 mmol). The mixture was stirred at 40° C. for 12 h. The reaction mixture was filtered, and concentrated. The residue was purified by column chromatography (petroleum ether/ethyl acetate=20/1 to 1/1) to afford 2-amino-N-(4-bromophenyl)-5-hydroxy-benzamide (3.2 g, 87%) as a yellow solid. MS (ESI) m/z: 308.8 [M+H]$^+$.

Step 3: 3-(4-bromophenyl)-6-hydroxy-quinazolin-4-one

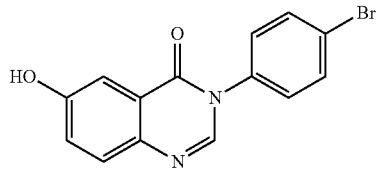 [SMILES: O=c1c2cc(O)ccc2ncn1-c1ccc(Br)cc1]

2-amino-N-(4-bromophenyl)-5-hydroxy-benzamide (5.0 g, 16 mmol) was suspended in formic acid (70 mL). The mixture was stirred at 110° C. for 12 h, then concentrated under reduced pressure. The crude product was triturated with ethyl acetate (2×50 mL) to afford 3-(4-bromophenyl)-6-hydroxy-quinazolin-4-one (3.5 g, 67%) as a white solid. MS (ESI) m/z: 318.5 [M+H]$^+$.

Step 4: 2-[3-(4-bromophenyl)-4-oxo-quinazolin-6-yl]oxy-3,6-difluoro-benzonitrile

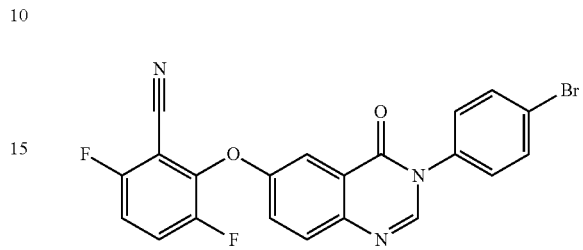

To a solution of 3-(4-bromophenyl)-6-hydroxy-quinazolin-4-one (3.5 g, 11 mmol) in N,N-dimethylformamide (70 mL) was added cesium carbonate (4.14 g, 13 mmol) and 2,3,6-trifluorobenzonitrile (2.25 g, 14 mmol). The mixture was stirred at 20° C. for 12 h. Water (100 mL) was poured into the mixture and stirred for 1 min. The aqueous phase was extracted with ethyl acetate (3×50 mL). The combined organic phase was washed with brine (2×50 mL), dried over anhydrous sodium sulfate, filtered, and concentrated. The residue was purified by column chromatography (petroleum ether/ethyl acetate=20/1 to 1/1) to afford 2-[3-(4-bromophenyl)-4-oxo-quinazolin-6-yl]oxy-3,6-difluoro-benzonitrile (4.5 g, 89%) as a white solid. MS (ESI) m/z: 455.8 [M+H]$^+$.

Step 5: (3R)—N-[3-[3-(4-bromophenyl)-4-oxo-quinazolin-6-yl]oxy-2-cyano-4-fluoro-phenyl]-3-fluoro-pyrrolidine-1-sulfonamide

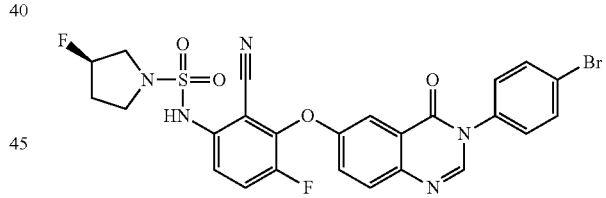

To a solution of (3R)-3-fluoropyrrolidine-1-sulfonamide (3.5 g, 21 mmol) in N,N-dimethylformamide (50 mL) was added cesium carbonate (7.1 g, 22 mmol). The mixture was stirred at 50° C. for 0.5 h, then cooled to 20° C. and 2-[3-(4-bromophenyl)-4-oxo-quinazolin-6-yl]oxy-3,6-difluoro-benzonitrile (4.5 g, 10 mmol) in N,N-dimethylformamide (10 mL) was added to the mixture and stirred at 100° C. for 11.5 h. Water (100 mL) was poured into the mixture and stirred for 1 min. The aqueous phase was extracted with ethyl acetate (3×100 mL). The combined organic phase was washed with brine (2×100 mL), dried over anhydrous sodium sulfate, filtered, and concentrated. The residue was purified by preparative HPLC (mobile phase: [0.2% formic acid in water-acetonitrile]; B %: 30%-60%, 25 min) to afford (3R)—N-[3-[3-(4-bromophenyl)-4-oxo-quinazolin-6-yl]oxy-2-cyano-4-fluoro-phenyl]-3-fluoro-pyrrolidine-1-sulfonamide (2.76 g, 44%) as a yellow solid. MS (ESI) m/z: 604.2 [M+H]$^+$; $^1$H NMR (400 MHz, DMSO-$d_6$) δ 10.35 (s, 1H), 8.32 (s, 1H), 7.91-7.81 (m, 2H), 7.80-7.70 (m, 3H), 7.57-

7.48 (m, 3H), 7.43 (d, J=3.2 Hz, 1H), 5.43-5.20 (m, 1H), 3.53 (s, 1H), 3.50-3.40 (m, 2H), 3.39-3.35 (m, 1H), 2.19-1.98 (m, 3H).

Intermediate 3: (3R)—N-[2-cyano-4-fluoro-3-[4-oxo-3-(4-piperazin-1-ylphenyl)quinazolin-6-yl]oxyphenyl]-3-fluoro-pyrrolidine-1-sulfonamide Step 1: tert-butyl 4-[4-[(5-hydroxy-2-nitro-benzoyl)amino]phenyl]piperazine-1-carboxylate

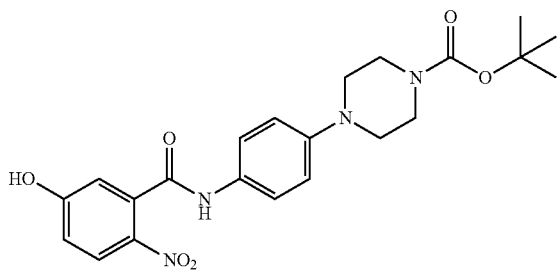

To a solution of tert-butyl 4-(4-aminophenyl)piperazine-1-carboxylate hydrochloride (9.43 g, 30 mmol) and 5-hydroxy-2-nitro-benzoic acid (5.5 g, 30 mmol) in pyridine (100 mL) was added 1-(3-dimethylaminopropyl)-3-ethylcarbodiimide hydrochloride (8.64 g, 45 mmol). The mixture was stirred at 80° C. for 2 h, then concentrated. The crude product was triturated with water (30 mL), then purified by flash silica gel chromatography (5% dichloromethane/methanol) to afford tert-butyl 4-[4-[(5-hydroxy-2-nitro-benzoyl)amino]phenyl]piperazine-1-carboxylate (7.2 g, 54%) as a black solid. MS (ESI) m/z: 443.0 [M+H]$^+$.

Step 2: tert-butyl 4-[4-[(2-amino-5-hydroxy-benzoyl)amino]phenyl]piperazine-1-carboxylate

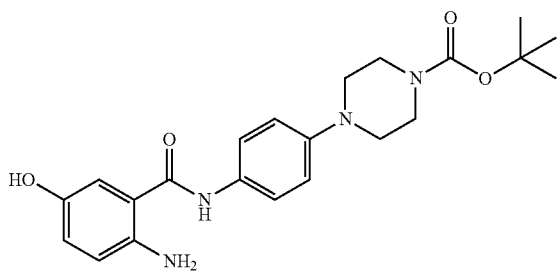 [SMILES: CC(C)(C)OC(=O)N1CCN(c2ccc(NC(=O)c3cc(O)ccc3N)cc2)CC1]

To a solution of tert-butyl 4-[4-[(5-hydroxy-2-nitro-benzoyl)amino]phenyl]piperazine-1-carboxylate (6.2 g, 14 mmol) in ethanol (40 mL), tetrahydrofuran (40 mL) and water (25 mL) was added iron powder (4.7 g, 84 mmol), ammonium chloride (3.0 g, 56 mmol) and hydrochloric acid (12 M, 2 mL). The mixture was stirred at 60° C. for 12 h, then filtered and concentrated. The residue was purified by flash silica gel chromatography (3-4% dichloromethane/methanol) to afford tert-butyl 4-[4-[(2-amino-5-hydroxy-benzoyl)amino]phenyl]piperazine-1-carboxylate (2.27 g, 39%) as a dark brown solid. MS (ESI) m/z: 413.0 [M+H]$^+$.

Step 3: 4-[4-(6-hydroxy-4-oxo-quinazolin-3-yl)phenyl]piperazine-1-carbaldehyde

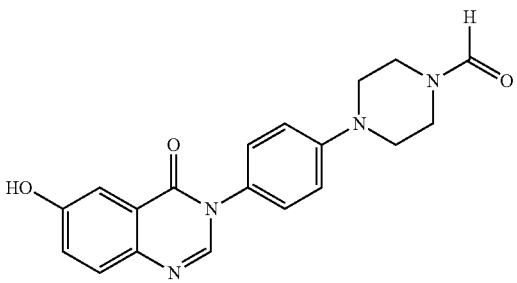 [SMILES: O=CN1CCN(c2ccc(-n3cnc4ccc(O)cc4c3=O)cc2)CC1]

A mixture of tert-butyl 4-[4-[(2-amino-5-hydroxy-benzoyl)amino]phenyl]piperazine-1-carboxylate (470 mg, 1.1 mmol) and formic acid (8 mL) was stirred at 110° C. for 12 h, then concentrated to afford 4-[4-(6-hydroxy-4-oxo-quinazolin-3-yl)phenyl]piperazine-1-carbaldehyde (390 mg, crude) as a black solid, which was used in the next step without further purification. MS (ESI) m/z: 350.8 [M+H]$^+$.

Step 4: 6-hydroxy-3-(4-piperazin-1-ylphenyl)quinazolin-4-one

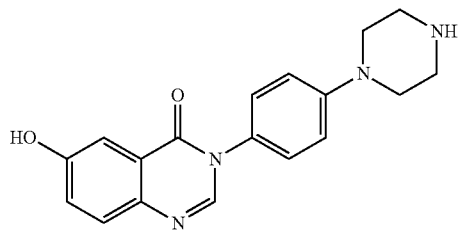 [SMILES: O=c1c2cc(O)ccc2ncn1-c1ccc(N2CCNCC2)cc1]

To a solution of 4-[4-(6-hydroxy-4-oxo-quinazolin-3-yl)phenyl]piperazine-1-carbaldehyde (390 mg, 1.1 mmol) in 1,4-dioxane (5 mL) was added 1 M hydrochloric acid (5 mL). The mixture was stirred at 100° C. for 12 h, then concentrated to afford 6-hydroxy-3-(4-piperazin-1-ylphenyl)quinazolin-4-one (355 mg, crude) as a black solid, which was used in the next step without further purification. MS (ESI) m/z: 323.2 [M+H]$^+$.

Step 5: tert-butyl 4-[4-(6-hydroxy-4-oxo-quinazolin-3-yl)phenyl]piperazine-1-carboxylate

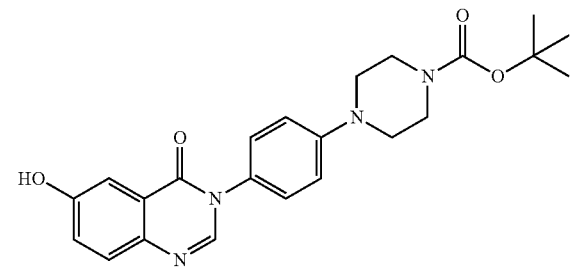 [SMILES: CC(C)(C)OC(=O)N1CCN(c2ccc(-n3cnc4ccc(O)cc4c3=O)cc2)CC1]

To a solution of 6-hydroxy-3-(4-piperazin-1-ylphenyl)quinazolin-4-one (355 mg, 1.1 mmol) in dichloromethane (5 mL) was added triethylamine (0.5 mL, 3 mmol) and tert-butoxycarbonyl tert-butyl carbonate (240 mg, 1.1 mmol). The mixture was stirred at 25° C. for 12 h. Diluted with water (10 mL) and extracted with dichloromethane (3×10 mL). The combined organic layers were washed with brine (2×10 mL), dried over anhydrous sodium sulfate, filtered, and concentrated. The residue was purified by flash silica gel chromatography (3% dichloromethane/methanol) to afford tert-butyl 4-[4-(6-hydroxy-4-oxo-quinazolin-3-yl)phenyl]piperazine-1-carboxylate (225 mg, 48%) as a dark brown solid. MS (ESI) m/z: 423.3 [M+H]+.

Step 6: tert-butyl 4-[4-[6-(2-cyano-3,6-difluoro-phenoxy)-4-oxo-quinazolin-3-yl]phenyl]piperazine-1-carboxylate

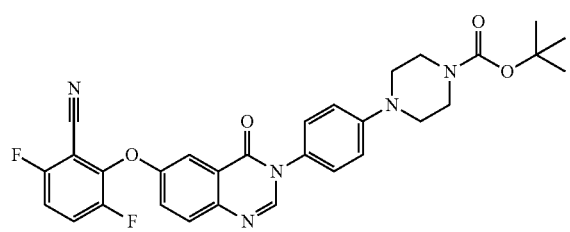 [SMILES: CC(C)(C)OC(=O)N1CCN(c2ccc(-n3cnc4ccc(Oc5c(F)ccc(F)c5C#N)cc4c3=O)cc2)CC1]

To a solution of tert-butyl 4-[4-(6-hydroxy-4-oxo-quinazolin-3-yl)phenyl]piperazine-1-carboxylate (225 mg, 0.5 mmol) in N,N-dimethylformamide (5 mL) was added cesium carbonate (199 mg, 0.6 mmol) and 2,3,6-trifluorobenzonitrile (108 mg, 0.7 mmol). The mixture was stirred at 25° C. for 12 h, diluted with water (10 mL) and extracted with ethyl acetate (3×10 mL). The combined organic layers were washed with brine (3×10 mL), dried over anhydrous sodium sulfate, filtered, and concentrated. The residue was purified by flash silica gel chromatography (5% dichloromethane/methanol) to afford tert-butyl 4-[4-[6-(2-cyano-3,6-difluoro-phenoxy)-4-oxo-quinazolin-3-yl]phenyl]piperazine-1-carboxylate (279 mg, 93%) as a brown oil. MS (ESI) m/z: 560.4 [M+H]+.

Step 7: tert-butyl 4-[4-[6-[2-cyano-6-fluoro-3-[[(3R)-3-fluoropyrrolidin-1-yl]sulfonylamino]phenoxy]-4-oxo-quinazolin-3-yl]phenyl]piperazine-1-carboxylate To a solution of (3R)-3-fluoropyrrolidine-1-sulfonamide (176 mg, 1.1 mmol) in N,N-dimethylformamide (1 mL) was added cesium carbonate (357 mg, 1.1 mmol). The mixture was stirred at 50° C. for 0.5 h. The mixture was cooled to 20° C. and tert-butyl 4-[4-[6-(2-cyano-3,6-difluoro-phenoxy)-4-oxo-quinazolin-3-yl]phenyl]piperazine-1-carboxylate (279 mg, 0.5 mmol) in N,N-dimethylformamide (2 mL) was added to the mixture, the mixture was stirred at 100° C. for 11.5 h. The residue was diluted with water (5 mL) and extracted with ethyl acetate (3×5 mL). The combined organic layers were washed with brine (3×5 mL), dried over anhydrous sodium sulfate, filtered, and concentrated. The residue was purified by preparative HPLC (mobile phase: [0.2% formic acid in water-acetonitrile]; B %: 54%-84%, 10 min) to afford tert-butyl 4-[4-[6-[2-cyano-6-fluoro-3-[[(3R)-3-fluoropyrrolidin-1-yl]sulfonylamino]phenoxy]-4-oxo-quinazolin-3-yl]phenyl]piperazine-1-carboxylate (200 mg, 56%) as a yellow solid. MS (ESI) m/z: 708.2 [M+H]+.

Step 8: (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide

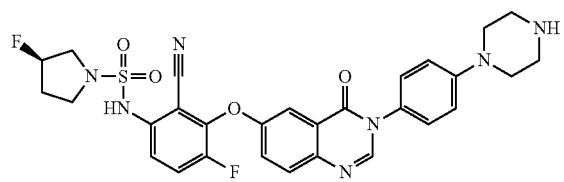

To a solution of tert-butyl 4-[4-[6-[2-cyano-6-fluoro-3-[[(3R)-3-fluoropyrrolidin-1-yl] sulfonylamino]phenoxy]-4-oxo-quinazolin-3-yl]phenyl]piperazine-1-carboxylate (200 mg, 0.3 mmol) in dichloromethane (1 mL) was added 4 M hydrochloric acid in 1,4-dioxane (2 mL). The mixture was stirred at 25° C. for 1 h, then concentrated to afford (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide hydrochloride (171 mg, crude) as a white solid, which was used in the next step without further purification. MS (ESI) m/z: 608.1 [M+H]+.

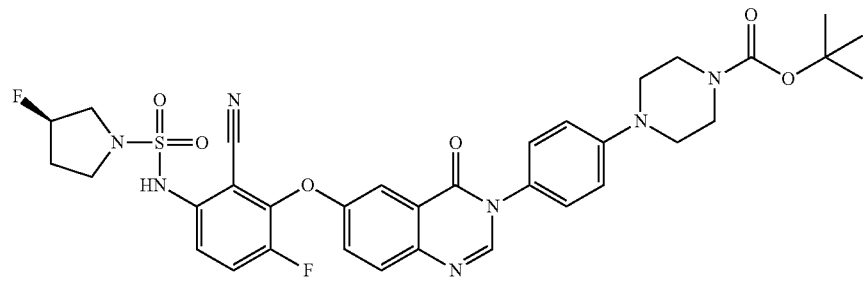 [SMILES: CC(C)(C)OC(=O)N1CCN(c2ccc(-n3cnc4ccc(Oc5c(F)ccc(NS(=O)(=O)N6CC[C@@H](F)C6)c5C#N)cc4c3=O)cc2)CC1]

Intermediate 4: (3R)—N-[2-cyano-4-fluoro-3-[3-[4-(4-formyl-1-piperidyl)phenyl]-4-oxo-quinazolin-6-yl]oxy-phenyl]-3-fluoro-pyrrolidine-1-sulfonamide Step 1: (3R)—N-[2-cyano-3-[3-[4-[4-(dimethoxymethyl)-1-piperidyl]phenyl]-4-oxo-quinazolin-6-yl]oxy-4-fluoro-phenyl]-3-fluoro-pyrrolidine-1-sulfonamide

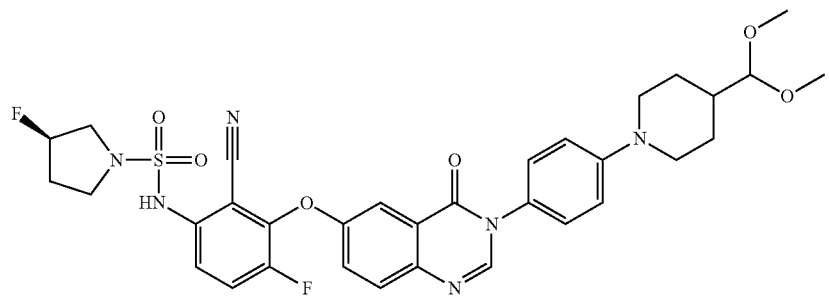 [SMILES: COC(OC)C1CCN(c2ccc(-n3cnc4ccc(Oc5c(F)ccc(NS(=O)(=O)N6CC[C@@H](F)C6)c5C#N)cc4c3=O)cc2)CC1]

To a solution of (3R)—N-[3-[3-(4-bromophenyl)-4-oxo-quinazolin-6-yl]oxy-2-cyano-4-fluoro-phenyl]-3-fluoro-pyrrolidine-1-sulfonamide (200 mg, 0.3 mmol) and 4-(dimethoxymethyl)piperidine (68 mg, 0.4 mmol) in 1,4-dioxane (3 mL) was added cesium carbonate (324 mg, 1.0 mmol) and RuPhos Pd G4 (28 mg, 0.03 mmol). The mixture was stirred at 90° C. for 12 h, then diluted with water (30 mL) and extracted with tetrahydrofuran (3×20 mL). The combined organic layers were washed with brine (3×40 mL), dried over anhydrous sodium sulfate, filtered, and concentrated. The residue was purified by flash silica gel chromatography (0-1% methanol:dichloromethane). Then the crude product was further purified by preparative thin layer chromatography (methanol:dichloromethane=20:1) to give (3R)—N-[2-cyano-3-[3-[4-[4-(dimethoxymethyl)-1-piperidyl]phenyl]-4-oxo-quinazolin-6-yl]oxy-4-fluoro-phenyl]-3-fluoro-pyrrolidine-1-sulfonamide (100 mg, 44%) as a light yellow oil. MS (ESI) m/z: 681.2 [M+H]⁺.

Step 2: (3R)—N-[2-cyano-4-fluoro-3-[3-[4-(4-formyl-1-piperidyl)phenyl]-4-oxo-quinazolin-6-yl]oxy-phenyl]-3-fluoro-pyrrolidine-1-sulfonamide

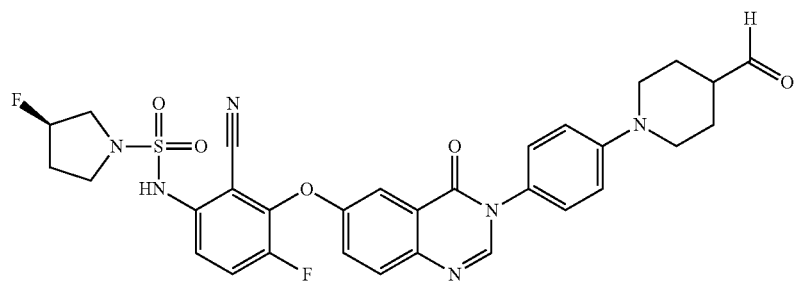 [SMILES: N#Cc1c(NS(=O)(=O)N2CC[C@@H](F)C2)ccc(F)c1Oc1ccc2ncn(-c3ccc(N4CCC(C=O)CC4)cc3)c(=O)c2c1]

To a solution of (3R)—N-[2-cyano-3-[3-[4-[4-(dimethoxymethyl)-1-piperidyl]phenyl]-4-oxo-quinazolin-6-yl]oxy-4-fluoro-phenyl]-3-fluoro-pyrrolidine-1-sulfonamide (50 mg, 0.1 mmol) in dichloromethane (0.5 mL) was added trifluoroacetic acid (0.1 mL). The mixture was stirred at 20° C. for 1 h, then concentrated in vacuum to afford (3R)—N-[2-cyano-4-fluoro-3-[3-[4-(4-formyl-1-piperidyl)phenyl]-4-oxo-quinazolin-6-yl]oxy-phenyl]-3-fluoro-pyrrolidine-1-sulfonamide (40 mg, 86%) as a brown oil, which was used in the next step without further purification. MS (ESI) m/z: 635.1 [M+H]⁺.

Intermediate 5: (3R)—N-(2-cyano-4-fluoro-3-{[3-(2-methanesulfonylpyrimidin-5-yl)-4-oxoquinazolin-6-yl]oxy}phenyl)-3-fluoropyrrolidine-1-sulfonamide Step 1: 6-hydroxy-3-[2-(methylsulfanyl)pyrimidin-5-yl]quinazolin-4-one

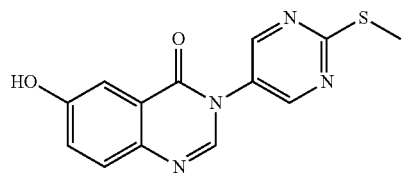 [SMILES: CSc1ncc(-n2cnc3ccc(O)cc3c2=O)cn1]

To a stirred mixture of 2-amino-5-hydroxybenzoic acid (6.0 g, 39 mmol) and 2-(methylsulfanyl)pyrimidin-5-amine (6.0 g, 43 mmol) in acetic acid (60 mL) was added trimethyl orthoformate (16.0 g, 151 mmol) at room temperature under nitrogen atmosphere. The resulting mixture was stirred for 3 h at 120° C. under nitrogen. Then cooled to room temperature, suspended in water (1000 mL). The precipitates were collected by filtration and washed with water (2×200 mL). The resulting solid was dried in an oven at 60° C. to afford 6-hydroxy-3-[2-(methylsulfanyl)pyrimidin-5-yl]quinazolin-4-one (9.2 g, 82%) as a light yellow solid. ¹H NMR (300 MHz, DMSO-d₆) δ 10.32 (s, 1H), 8.88 (d, J=1.1 Hz, 2H), 8.25 (d, J=1.1 Hz, 1H), 7.63 (d, J=8.8 Hz, 1H), 7.50 (d, J=2.7 Hz, 1H), 7.46-7.26 (m, 1H), 2.59 (s, 3H); MS (ESI): m/z 287.05 [M+H]⁺.

Step 2: 3,6-difluoro-2-({3-[2-(methylsulfanyl)pyrimidin-5-yl]-4-oxoquinazolin-6-yl}oxy)benzonitrile

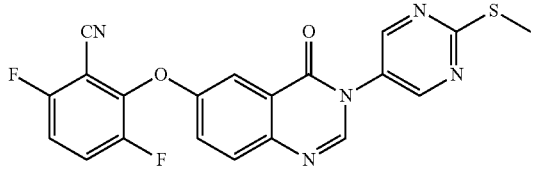 [SMILES: CSc1ncc(-n2cnc3ccc(Oc4c(F)ccc(F)c4C#N)cc3c2=O)cn1]

To a stirred mixture of 6-hydroxy-3-[2-(methylsulfanyl)pyrimidin-5-yl]quinazolin-4-one (9.0 g, 31 mmol) and 2,3,6-trifluorobenzonitrile (7.4 g, 47 mmol) in N,N-dimethylformamide (100 mL) was added cesium carbonate (16 g, 49 mmol) at room temperature under nitrogen atmosphere. The resulting mixture was stirred overnight at 40° C., then cooled to room temperature, diluted with water (200 mL), and extracted with ethyl acetate (3×200 mL). The combined organic layers were washed with brine (2×100 mL), dried over anhydrous sodium sulfate, filtered, and concentrated. The residue was purified by trituration with ethyl acetate/petroleum ether (100 mL/100 mL) to afford 3,6-difluoro-2-({3-[2-(methylsulfanyl)pyrimidin-5-yl]-4-oxoquinazolin-6-yl}oxy)benzonitrile (12.2 g, 92%) as an off-white solid. ¹H NMR (300 MHz, CDCl₃) δ 8.56 (s, 1H), 7.94 (s, 1H), 7.81-7.78 (m, 1H), 7.59 (s, 2H), 7.44-7.36 (m, 1H), 7.07-7.03 (m, 1H), 2.56 (s, 3H); MS (ESI): m/z 424.10 [M+H]⁺.

Step 3: (3R)—N-[2-cyano-4-fluoro-3-({3-[2-(methylsulfanyl)pyrimidin-5-yl]-4-oxoquinazolin-6-yl}oxy)phenyl]-3-fluoropyrrolidine-1-sulfonamide

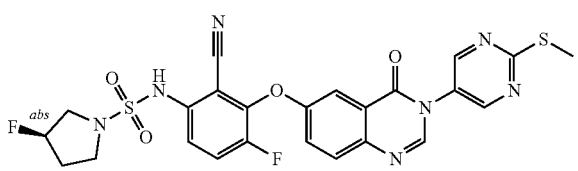 [SMILES: CSc1ncc(-n2cnc3ccc(Oc4c(F)ccc(NS(=O)(=O)N5CC[C@@H](F)C5)c4C#N)cc3c2=O)cn1]

A mixture of (3R)-3-fluoropyrrolidine-1-sulfonamide (12 g, 71.3 mmol) and cesium carbonate (20 g, 262.7 mmol) in N,N-dimethylformamide (150 mL) was stirred for 30 min at 40° C. under N2 atmosphere. Then 3,6-difluoro-2-({3-[2-(methylsulfanyl)pyrimidin-5-yl]-4-oxoquinazolin-6-yl}oxy)benzonitrile (12.2 g, 28.8 mmol) was added, The resulting mixture was stirred overnight at 90° C. under nitrogen. The mixture was allowed to cool to room temperature, diluted with water (200 mL), and extracted with ethyl acetate (3×200 mL). The combined organic layers were washed with brine (3×100 mL), dried over anhydrous sodium sulfate, filtered and concentrated. The residue was purified by reversed-phase flash chromatography (mobile phase: acetonitrile in water (10 mM ammonium bicarbonate), 20% to 50% gradient in 20 min) to afford (3R)—N-[2-cyano-4-fluoro-3-({3-[2-(methylsulfanyl)pyrimidin-5-yl]-4-oxoquinazolin-6-yl}oxy)phenyl]-3-fluoropyrrolidine-1-sulfonamide (4.6 g, 29%) as an off-white oil. MS (ESI): m/z 572.20 [M+H]⁺.

Step 4: (3R)—N-(2-cyano-4-fluoro-3-{[3-(2-methanesulfonylpyrimidin-5-yl)-4-oxoquinazolin-6-yl]oxy}phenyl)-3-fluoropyrrolidine-1-sulfonamide

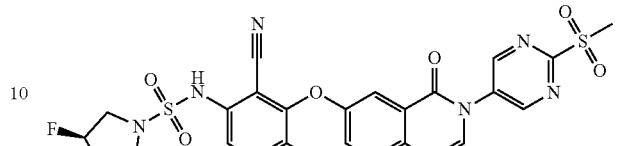

To a stirred solution of (3R)—N-[2-cyano-4-fluoro-3-({3-[2-(methylsulfanyl)pyrimidin-5-yl]-4-oxoquinazolin-6-yl}oxy)phenyl]-3-fluoropyrrolidine-1-sulfonamide (4.6 g, 8.1 mmol) in tetrahydrofuran/water (5:1, 200 mL) was added potassium peroxymonosulfate (14.7 g, 24 mmol) in portions at room temperature under nitrogen atmosphere. The resulting mixture was stirred for 1 h, then quenched by water (250 mL), extracted with ethyl acetate (3×250 mL). The combined organic layers were washed with brine (150 mL), dried over anhydrous sodium sulfate, filtered and concentrated. The residue was purified by silica gel column chromatography (petroleum ether/ethyl acetate=1:1) to afford the crude product, which was further purified by trituration with ethyl acetate/petroleum ether (20 mL/100 mL) to afford (3R)—N-(2-cyano-4-fluoro-3-{[3-(2-methanesulfonylpyrimidin-5-yl)-4-oxoquinazolin-6-yl]oxy}phenyl)-3-fluoropyrrolidine-1-sulfonamide (1.6 g, 33%) as an off-white solid. ¹H NMR (400 MHz, DMSO-d₆) δ 10.37 (s, 1H), 9.37 (s, 2H), 8.53 (s, 1H), 7.94-7.84 (m, 2H), 7.80 (m, 1H), 7.54 (m, 1H), 7.49 (d, J=3.0 Hz, 2H), 5.39-5.26 (dd, 1H), 3.54 (d, J=2.0 Hz, 4H), 3.51-3.40 (m, 2H), 3.44-3.35 (s, 3H); MS (ESI): m/z 601.95 [M−H]—.

Intermediate 6: (3R)—N-[2-cyano-4-fluoro-3-[3-(6-fluoro-3-pyridyl)-4-oxo-quinazolin-6-yl]oxy-phenyl]-3-fluoro-pyrrolidine-1-sulfonamide Step 1: 6-methoxy-1H-3,1-benzoxazine-2,4-dione

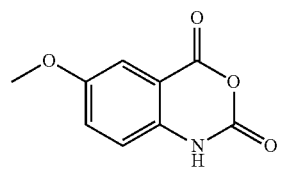

To a solution of 2-amino-5-methoxy-benzoic acid (19.0 g, 114 mmol) in tetrahydrofuran (1 L) was added triethylamine (15.8 mL, 114 mmol,) and cooled to 0° C. Then (2,2,2-trichloroacetyl) 2,2,2-trichloroacetate (23.7 mL, 130 mmol,) was added portion-wise and the mixture was stirred at 25° C. for 18 h. Water (38 mL) was added to the mixture at 0° C. and the solvent was removed under reduced pressure to afford 6-methoxy-1H-3,1-benzoxazine-2,4-dione (20 g, 91%) as a gray solid, which was used in the next step without further purification. MS (ESI) m/z: 193.7 [M+H]⁺.

Step 2: 3-(6-fluoro-3-pyridyl)-6-methoxy-quinazolin-4-one

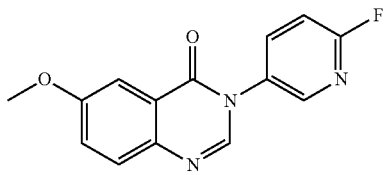 [SMILES: COc1ccc2ncn(-c3ccc(F)nc3)c(=O)c2c1]

To a solution of 6-methoxy-1H-3,1-benzoxazine-2,4-dione (20.0 g, 104 mmol) in trimethoxymethane (200 mL) was added 6-fluoropyridin-3-amine (11.6 g, 104 mmol). The mixture was stirred at 100° C. for 16 h, then concentrated under reduced pressure. The crude product was triturated with acetonitrile (50 mL) at 25° C. for 60 min, filtered to afford 3-(6-fluoro-3-pyridyl)-6-methoxy-quinazolin-4-one (12 g, 42%) as a white solid. MS (ESI) m/z: 271.9 [M+H]+.

Step 3: 3-(6-fluoro-3-pyridyl)-6-hydroxy-quinazolin-4-one

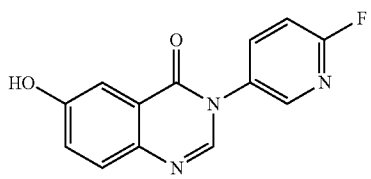 [SMILES: O=c1c2cc(O)ccc2ncn1-c1ccc(F)nc1]

To a solution of 3-(6-fluoro-3-pyridyl)-6-methoxy-quinazolin-4-one (6.0 g, 22 mmol) in dichloromethane (40 mL) was added boron tribromide (8.5 mL, 89 mmol,). The mixture was stirred at 0° C. for 0.5 h, then 25° C. for 1 h, and concentrated under reduced pressure. The crude product was triturated with water (3×50 mL) at 25° C. for 2 h, filtered to afford 3-(6-fluoro-3-pyridyl)-6-hydroxy-quinazolin-4-one (2.8 g, 49%) as a white solid. MS (ESI) m/z: 257.5 [M+H]+.

Step 4: 3,6-difluoro-2-[3-(6-fluoro-3-pyridyl)-4-oxo-quinazolin-6-yl]oxy-benzonitrile

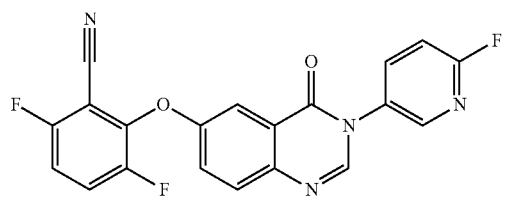 [SMILES: N#Cc1c(F)ccc(F)c1Oc1ccc2ncn(-c3ccc(F)nc3)c(=O)c2c1]

To a solution of 3-(6-fluoro-3-pyridyl)-6-hydroxy-quinazolin-4-one (2.8 g, 11 mmol) in N,N-dimethylformamide (30 mL) was added cesium carbonate (4.08 g, 12 mmol) and 2,3,6-trifluorobenzonitrile (1.71 g, 11 mmol). The mixture was stirred at 25° C. for 12 h. Water (30 mL) was poured into the mixture and stirred for 1 min. The aqueous phase was extracted with ethyl acetate (3×30 mL). The combined organic phase was washed with brine (3×90 mL), dried over anhydrous sodium sulfate, filtered, and concentrated. The residue was purified by flash silica gel chromatography (20-30% ethyl acetate/petroleum ether) to afford 3,6-difluoro-2-[3-(6-fluoro-3-pyridyl)-4-oxo-quinazolin-6-yl]oxy-benzonitrile (3.4 g, 79%) as a white solid. MS (ESI) m/z: 395.0 [M+H]+; 1H NMR (400 MHz, DMSO-d6) δ 8.47 (d, J=2.4 Hz, 1H), 8.39 (s, 1H), 8.27-8.21 (m, 1H), 7.97 (dt, J=5.2, 10.0 Hz, 1H), 7.89-7.84 (m, 1H), 7.82-7.77 (m, 1H), 7.63 (d, J=2.8 Hz, 1H), 7.58 (dt, J=3.6, 8.8 Hz, 1H), 7.43 (dd, J=2.8, 8.8 Hz, 1H).

Step 5: (3R)—N-[2-cyano-4-fluoro-3-[3-(6-fluoro-3-pyridyl)-4-oxo-quinazolin-6-yl]oxy-phenyl]-3-fluoro-pyrrolidine-1-sulfonamide

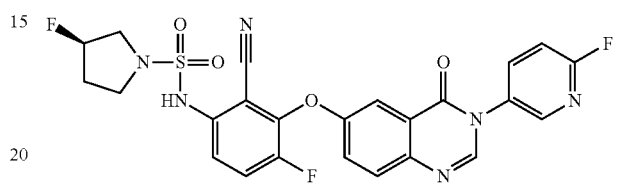

To a solution of 3,6-difluoro-2-[3-(6-fluoro-3-pyridyl)-4-oxo-quinazolin-6-yl]oxy-benzonitrile (3.40 g, 8.6 mmol) in N,N-dimethylformamide (35 mL) was added cesium carbonate (8.43 g, 26 mmol) and (3R)-3-fluoropyrrolidine-1-sulfonamide (2.90 g, 17 mmol). The mixture was stirred at 80° C. for 12 h, then cooled to room temperature. The pH of the reaction mixture was adjusted to 3 with 1 M aqueous hydrochloric acid (40 mL). Water (100 mL) was poured into the mixture and stirred for 1 min. The aqueous phase was extracted with ethyl acetate (3×150 mL). The combined organic phase was washed with brine (2×300 mL), dried over anhydrous sodium sulfate, filtered, and concentrated. The residue was purified by preparative HPLC (mobile phase: [0.2% formic acid in water-acetonitrile]; B %: 35%-63%, 22 min), the crude product was further purified by preparative HPLC (mobile phase: [10 mM ammonium bicarbonate in water-acetonitrile]; B %: 14%-44%, 8 min) to afford (3R)—N-[2-cyano-4-fluoro-3-[3-(6-fluoro-3-pyridyl)-4-oxo-quinazolin-6-yl]oxy-phenyl]-3-fluoro-pyrrolidine-1-sulfonamide (761.7 mg, 15%) as an off-white solid. MS (ESI) m/z: 842.8 [M+H]+; 1H NMR (400 MHz, CDCl3) δ 8.31 (d, J=2.0 Hz, 1H), 8.05 (s, 1H), 7.93 (ddd, J=2.8, 6.4, 8.8 Hz, 1H), 7.85 (d, J=8.8 Hz, 1H), 7.68-7.58 (m, 3H), 7.44 (t, J=9.6 Hz, 1H), 7.16 (dd, J=3.2, 8.8 Hz, 1H), 6.95 (s, 1H), 5.35-5.14 (m, 1H), 3.76-3.49 (m, 4H), 2.41-2.25 (m, 1H), 2.20-1.96 (m, 1H).

Intermediate 7: (3R)—N-[2-cyano-4-fluoro-3-({4-oxo-3-[6-(piperazin-1-yl)pyridin-3-yl]quinazolin-6-yl}oxy)phenyl]-3-fluoropyrrolidine-1-sulfonamide Step 1: tert-butyl 4-[5-(6-hydroxy-4-oxoquinazolin-3-yl)pyridin-2-yl]piperazine-1-carboxylate

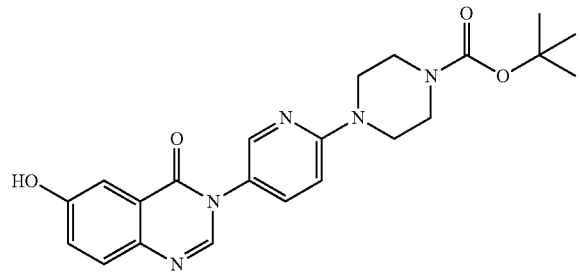 [SMILES: CC(C)(C)OC(=O)N1CCN(c2ccc(-n3cnc4ccc(O)cc4c3=O)cn2)CC1]

To a stirred mixture of 2-amino-5-hydroxybenzoic acid (5.0 g, 33 mmol) and trimethyl orthoformate (20.0 g, 188 mmol) in pyridine (50 mL) was added tert-butyl-4-(5-aminopyridin-2-yl)piperazine-1-carboxylate (10.0 g, 36 mmol) dropwise at room temperature. The resulting mixture was stirred overnight at 120° C., then cooled to room temperature, and concentrated. The residue was diluted with water (200 mL) and extracted with ethyl acetate (3×200 mL). The combined organic layers were washed with brine (2×100 mL), dried over anhydrous sodium sulfate, filtered, and concentrated. The residue was purified by silica gel column chromatography (petroleum ether/ethyl acetate=1:1) to afford tert-butyl 4-[5-(6-hydroxy-4-oxoquinazolin-3-yl)pyridin-2-yl]piperazine-1-carboxylate (5.1 g, 37%) as a brown solid. $^1$H NMR (300 MHz, CDCl$_3$) δ 8.11 (d, J=2.7 Hz, 1H), 7.90 (s, 1H), 7.62 (d, J=8.8 Hz, 1H), 7.57-7.47 (m, 1H), 7.33-7.23 (m, 1H), 6.69 (d, J=9.1 Hz, 1H), 3.61-3.47 (m, 7H), 1.43 (s, 8H), 1.19 (s, 2H), 0.84-0.73 (m, 2H); MS (ESI): m/z 424.20 [M+H]$^+$.

Step 2: tert-butyl 4-{5-[6-(2-cyano-3,6-difluorophenoxy)-4-oxoquinazolin-3-yl]pyridin-2-yl}piperazine-1-carboxylate

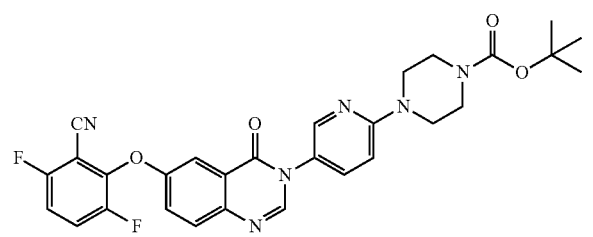 [SMILES: CC(C)(C)OC(=O)N1CCN(c2ccc(-n3cnc4ccc(Oc5c(F)ccc(F)c5C#N)cc4c3=O)cn2)CC1]

To a stirred mixture of tert-butyl 4-[5-(6-hydroxy-4-oxoquinazolin-3-yl)pyridin-2-yl]piperazine-1-carboxylate (5.0 g, 12 mmol) and cesium carbonate (6.0 g, 18 mmol) in N,N-dimethylformamide (60 mL) was added 2,3,6-trifluorobenzonitrile (3.0 g, 19 mmol) at room temperature, then stirred overnight at 40° C. The reaction was cooled to room temperature, diluted with water (200 mL) and extracted with ethyl acetate (3×200 mL). The combined organic layers were washed with brine (2×100 mL), dried over anhydrous sodium sulfate, filtered, and concentrated. The residue was purified by silica gel column chromatography (petroleum ether/ethyl acetate=1:1) to afford tert-butyl 4-{5-[6-(2-cyano-3,6-difluorophenoxy)-4-oxoquinazolin-3-yl]pyridin-2-yl}piperazine-1-carboxylate (6.5 g, 98%) as a purple solid. $^1$H NMR (300 MHz, CDCl$_3$) δ 8.10 (d, J=2.7 Hz, 1H), 7.96 (s, 1H), 7.75 (d, J=8.8 Hz, 1H), 7.61-7.46 (m, 3H), 7.46-7.30 (m, 1H), 7.11-6.89 (m, 1H), 6.69 (d, J=9.1 Hz, 1H), 3.62-3.47 (m, 6H), 2.89 (s, 2H), 1.43 (s, 7H), 1.19 (s, 1H), 0.78 (t, J=7.6 Hz, 1H); MS (ESI): m/z 561.25 [M+H]$^+$.

Step 3: (3R)—N-[2-cyano-4-fluoro-3-({4-oxo-3-[6-(piperazin-1-yl)pyridin-3-yl]quinazolin-6-yl}oxy)phenyl]-3-fluoropyrrolidine-1-sulfonamide

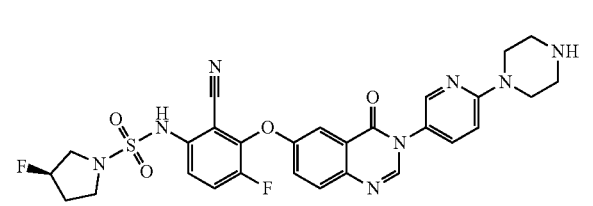 [SMILES: N#Cc1c(NS(=O)(=O)N2CC[C@@H](F)C2)ccc(F)c1Oc1ccc2ncn(-c3ccc(N4CCNCC4)nc3)c(=O)c2c1]

To a stirred mixture of tert-butyl 4-{5-[6-(2-cyano-6-fluoro-3-{[(3R)-3-fluoropyrrolidin-1-ylsulfonyl]amino}phenoxy)-4-oxoquinazolin-3-yl]pyridin-2-yl}piperazine-1-carboxylate (1.5 g, 2.1 mmol) in tetrahydrofuran (15 mL) was added 4 N hydrochloric acid in 1,4-dioxane (15 mL) at room temperature. The resulting mixture was stirred for 2 h, then concentrated under reduced pressure to afford (3R)—N-[2-cyano-4-fluoro-3-({4-oxo-3-[6-(piperazin-1-yl)pyridin-3-yl]quinazolin-6-yl}oxy)phenyl]-3-fluoropyrrolidine-1-sulfonamide hydrochloride (1.3 g, 95%) as a pink solid. MS (ESI): m/z 609.45 [M+H]$^+$; $^1$H NMR (400 MHz, DMSO-d$_6$) δ 10.47 (s, 1H), 8.38 (d, J=1.2 Hz, 1H), 8.31 (d, J=2.6 Hz, 1H), 7.93-7.82 (m, 3H), 7.85-7.61 (m, 1H), 7.60-7.51 (m, 1H), 7.44 (d, J=3.0 Hz, 1H), 7.18 (d, J=9.2 Hz, 1H), 3.75-3.53 (m, 1H), 3.53 (d, J=17.6 Hz, 1H), 3.52-3.41 (m, 1H), 3.45-3.25 (m, 2H), 3.29-3.20 (m, 2H), 2.90 (s, 1H), 2.73 (s, 1H), 2.23-2.05 (m, 4H), 1.79-1.70 (m, 1H), 1.41-1.32 (m, 1H), 1.29-1.12 (m, 1H).

Intermediate 8: tert-butyl 4-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}piperazine-1-carboxylate Step 1: tert-butyl 4-(5-nitropyrimidin-2-yl)piperazine-1-carboxylate

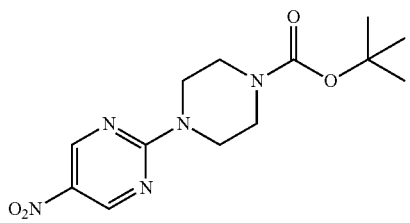

To a solution of 2-chloro-5-nitropyrimidine (20.0 g, 125 mmol) in N,N-dimethylformamide (400 mL) was added tert-butyl piperazine-1-carboxylate (25.7 g, 138 mmol) under nitrogen atmosphere, followed by the addition of triethylamine (38.0 g, 376 mmol) in portions at room temperature. The resulting mixture was stirred overnight at 90° C. under nitrogen. The mixture was allowed to cool to room temperature, diluted with water (1000 mL). The precipitate was collected by filtration and washed with water (3×200 mL). The resulting solid was dried in an oven at 60° C. for 3 h to afford tert-butyl 4-(5-nitropyrimidin-2-yl)piperazine-1-carboxylate (34.2 g, 88%) as a light yellow solid. $^1$H NMR (400 MHz, CDCl$_3$) δ 9.00 (s, 2H), 3.92 (s, 4H), 3.46 (s, 4H), 1.42 (s, 9H); MS (ESI): m/z 328.10 [M+H$_2$O]$^+$.

Step 2: tert-butyl 4-(5-aminopyrimidin-2-yl)piperazine-1-carboxylate

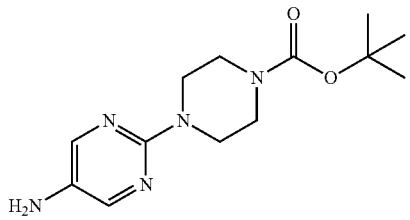 [SMILES: CC(C)(C)OC(=O)N1CCN(c2ncc([N+](=O)[O-])cn2)CC1]

To a solution of tert-butyl 4-(5-nitropyrimidin-2-yl)piperazine-1-carboxylate (10.3 g, 33 mmol) in methanol (150 mL) was added 10% palladium on carbon (5 g) under nitrogen atmosphere. The mixture was degassed and purged with hydrogen for three times, then stirred at room temperature for 3 h under hydrogen. The mixture was filtered through a Celite pad and concentrated under reduced pressure to afford tert-butyl 4-(5-aminopyrimidin-2-yl)piperazine-1-carboxylate (7.5 g, 81%) as a light yellow solid. $^1$H NMR (300 MHz, CDCl$_3$) δ 7.91 (s, 1H), 4.16 (m, 2H), 3.64-3.54 (m, 4H), 3.52-3.37 (m, 4H), 3.10 (s, 1H), 1.41 (s, 8H), 1.39 (s, 1H); MS (ESI): m/z 280.05 [M+H]$^+$.

Step 3: tert-butyl-4-[5-(6-hydroxy-4-oxoquinazolin-3-yl)pyrimidin-2-yl]piperazine-1-carboxylate

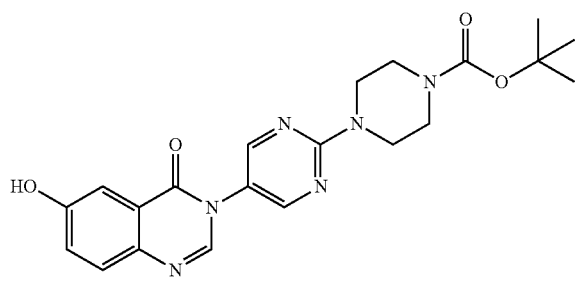 [SMILES: CC(C)(C)OC(=O)N1CCN(c2ncc(-n3cnc4ccc(O)cc4c3=O)cn2)CC1]

To a stirred mixture of tert-butyl 4-(5-aminopyrimidin-2-yl)piperazine-1-carboxylate (5.0 g, 18 mmol) and 2-amino-5-hydroxybenzoic acid (2.5 g, 16 mmol) in pyridine (60 mL) was added trimethyl orthoformate (10 g, 94 mmol) at room temperature. The resulting mixture was stirred overnight at 120° C., then cooled to room temperature and concentrated. The residue was diluted with water (100 mL) and extracted with ethyl acetate (3×200 mL). The combined organic layers were washed with brine (100 mL), dried over anhydrous sodium sulfate, filtered, and concentrated. The residue was purified by trituration with ethyl acetate (100 mL) and petroleum ether (100 mL) to afford tert-butyl-4-[5-(6-hydroxy-4-oxoquinazolin-3-yl)pyrimidin-2-yl]piperazine-1-carboxylate (5.5 g, 72%) as a yellow solid. MS (ESI): m/z 425.25 [M+H]$^+$.

Step 4: tert-butyl 4-{5-[6-(2-cyano-3,6-difluorophenoxy)-4-oxoquinazolin-3-yl]pyrimidin-2-yl}piperazine-1-carboxylate

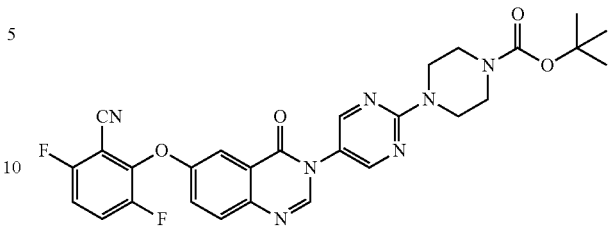

To a stirred solution of tert-butyl 4-[5-(6-hydroxy-4-oxoquinazolin-3-yl)pyrimidin-2-yl]piperazine-1-carboxylate (5.5 g, 13 mmol) and 2,3,6-trifluorobenzonitrile (3.1 g, 20 mmol) in N,N-dimethylformamide (60 mL) was added cesium carbonate (6.5 g, 20 mmol) at room temperature. The resulting mixture was stirred overnight at 40° C., then cooled to room temperature and diluted with water (100 mL), extracted with ethyl acetate (3×200 mL). The combined organic layers were washed with brine (1×100 mL), dried over anhydrous sodium sulfate, filtered, and concentrated. The residue was purified by trituration with ethyl acetate (200 mL) and petroleum ether (100 mL) to afford tert-butyl 4-{5-[6-(2-cyano-3,6-difluorophenoxy)-4-oxoquinazolin-3-yl]pyrimidin-2-yl}piperazine-1-carboxylate (6.11 g, 84%) as a yellow solid. $^1$H NMR (300 MHz, CDCl$_3$) δ 8.29 (s, 2H), 7.93 (d, J=12.5 Hz, 2H), 7.81-7.72 (m, 1H), 7.61-7.50 (m, 2H), 7.46-7.30 (m, 1H), 7.12-6.97 (m, 1H), 5.23 (s, 1H), 3.87-3.72 (m, 4H), 3.46 (t, J=5.3 Hz, 4H), 2.89 (s, 3H), 2.81 (d, J=0.6 Hz, 3H), 1.19 (s, 1H); MS (ESI): m/z 562.25 [M+H]$^+$.

Step 5: tert-butyl 4-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}piperazine-1-carboxylate

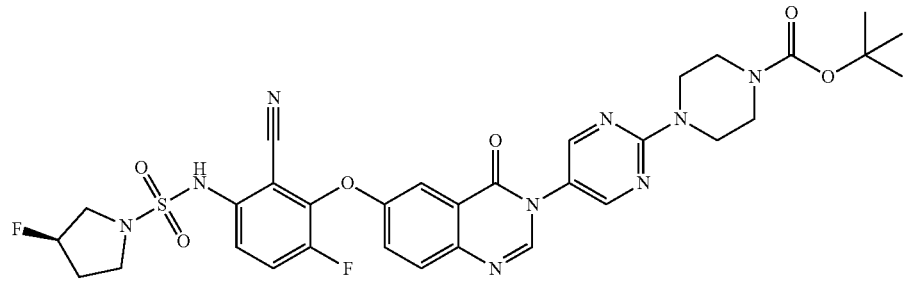 [SMILES: CC(C)(C)OC(=O)N1CCN(c2ncc(-n3cnc4ccc(Oc5c(F)ccc(NS(=O)(=O)N6CC[C@@H](F)C6)c5C#N)cc4c3=O)cn2)CC1]

To a stirred mixture of tert-butyl 4-{5-[6-(2-cyano-3,6-difluorophenoxy)-4-oxoquinazolin-3-yl]pyrimidin-2-yl}piperazine-1-carboxylate (3.0 g, 5 mmol) and (3R)-3-fluoropyrrolidine-1-sulfonamide (1.4 g, 8 mmol) in N,N-dimethylformamide (40 mL) was added cesium carbonate (3.0 g, 9 mmol) at room temperature. The resulting mixture was stirred for 3 h at 90° C., cooled to room temperature and diluted with water (100 mL). The mixture was extracted with ethyl acetate (3×200 mL). The combined organic layers were washed with brine (2×100 mL), dried over anhydrous sodium sulfate, filtered, and concentrated. The residue was purified by reversed-phase flash chromatography (acetonitrile in water (10 mM ammonium bicarbonate), 20% to 50% gradient in 20 min) to afford tert-butyl 4-{5-[6-(2-cyano-6-fluoro-3-{[(3R)-3-fluoropyrrolidin-1-ylsulfonyl]amino}phenoxy)-4-oxoquinazolin-3-yl]pyrimidin-2- yl}piperazine-1-carboxylate (1.8 g, 47%) as a light yellow solid. MS (ESI): m/z 710.30 [M+H]⁺.

Step 6: tert-butyl-4-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}piperazine-1-carboxylate

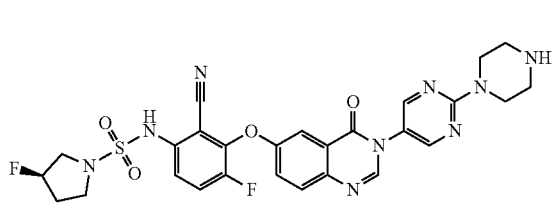 [SMILES: N#Cc1c(NS(=O)(=O)N2CC[C@@H](F)C2)ccc(F)c1Oc1ccc2ncn(-c3cnc(N4CCNCC4)nc3)c(=O)c2c1]

To a stirred mixture of tert-butyl 4-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}piperazine-1-carboxylate (1.9 g, 2.7 mmol) in tetrahydrofuran (15 mL) was added 4 N hydrochloric acid in 1,4-dioxane (9.5 mL) at room temperature. The reaction was stirred for 2 h, then concentrated to afford (3R)—N-[2-cyano-4-fluoro-3-({4-oxo-3-[2-(piperazin-1-yl)pyrimidin-5-yl]quinazolin-6-yl}oxy)phenyl]-3-fluoropyrrolidine-1-sulfonamide hydrochloride (1.5 g, 92%) as a light brown solid. ¹H NMR (400 MHz, DMSO-d₆) δ 10.43 (s, 1H), 9.54 (s, 2H), 8.61 (s, 2H), 8.36 (s, 1H), 7.93-7.81 (m, 2H), 7.79-7.65 (m, 1H), 7.58-7.50 (m, 1H), 7.43 (d, J=3.0 Hz, 1H), 5.39 (q, J=2.4 Hz, 2H), 3.73-3.61 (m, 1H), 3.59-3.51 (m, 2H), 3.49-3.30 (m, 4H), 3.23-3.14 (m, 4H), 1.81-1.69 (m, 1H); MS (ESI): m/z 610.15 [M+H]⁺.

Intermediate 9: (3R)—N-{2-cyano-4-fluoro-3-[(4-oxo-3-{2-[1-(piperazin-1-yl)cyclopropyl]pyrimidin-5-yl}quinazolin-6-yl)oxy]phenyl}-3-fluoropyrrolidine-1-sulfonamide Step 1: benzyl N-(1-cyanocyclopropyl)carbamate

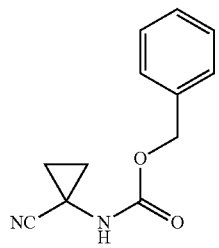 [SMILES: N#CC1(NC(=O)OCc2ccccc2)CC1]

To a stirred mixture of 1-aminocyclopropane-1-carbonitrile hydrochloride (50.0 g, 422 mmol) in tetrahydrofuran (300 mL) and water (100 mL) was added sodium bicarbonate (89.00 g, 1054 mmol) and benzyl chloroformate (64.8 g, 379 mmol) in portions at 10° C. under nitrogen atmosphere. The resulting mixture was stirred overnight at room temperature under nitrogen atmosphere. The reaction was extracted with ethyl acetate (3×300 mL). The combined organic layers were washed with brine (2×100 mL), dried over anhydrous sodium sulfate, filtered, and concentrated under reduced pressure. The residue was triturated with petroleum ether (100 mL) to afford benzyl N-(1-cyanocyclopropyl)carbamate (65 g, 71%) as a white solid. 1H NMR (300 MHz, DMSO-d6) δ 7.38-7.25 (m, 5H), 5.84 (s, 1H), 5.13 (s, 2H), 2.05-2.02 (m, 2H), 1.31-1.11 (m, 2H).

Step 2: 1-[[(benzyloxy)carbonyl]amino]cyclopropane-1-carboximidate

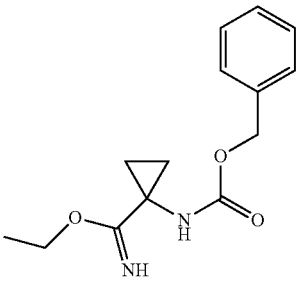 [SMILES: CCOC(=N)C1(NC(=O)OCc2ccccc2)CC1]

To a stirred solution of benzyl N-(1-cyanocyclopropyl)carbamate (61.0 g, 282 mmol) in ethanol (400 mL) was added 4 M hydrochloric acid in 1,4-dioxane (400 mL). The resulting solution was stirred for 3 d at room temperature, then concentrated. The residue was triturated with petroleum ether/ethyl acetate (1:5, 2×200 mL) to afford 1-[[(benzyloxy)carbonyl]amino]cyclopropane-1-carboximidate (52 g, crude) as a white solid. MS (ESI): m/z 263.00[M+H]⁺. Step 3: benzyl N-(1-carbamimidoylcyclopropyl)carbamate

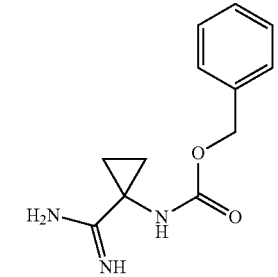 [SMILES: N=C(N)C1(NC(=O)OCc2ccccc2)CC1]

To a solution of ethyl 1-[[(benzyloxy)carbonyl]amino]cyclopropane-1-carboximidate (55.0 g, 210 mmol) in methanol (300 mL) was added 7 M ammonia in methanol (500 mL) at 10° C. The reaction was stirred for 16 h at room temperature, then concentrated. The residue was triturated with petroleum ether/ethyl acetate (1:5, 2×150 mL) to afford benzyl N-(1-carbamimidoylcyclopropyl)carbamate (43.3 g, crude) as a white solid. MS (ESI): m/z 433.95 [M+H]⁺. Step 4: benzyl N-[1-(5-chloropyrimidin-2-yl)cyclopropyl]carbamate

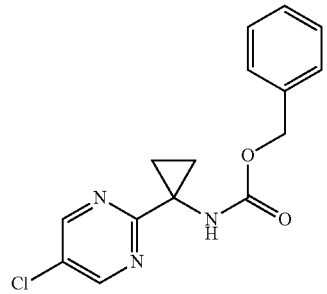 [SMILES: O=C(NC1(c2ncc(Cl)cn2)CC1)OCc1ccccc1]

To a mixture of benzyl N-(1-carbamimidoylcyclopropyl)carbamate (130 g, 557 mmol) and (Z)—N-(2-chloro-3-(dimethylamino)allylidene)-N-methylmethanaminium (340.0 g, 1114 mmol) in N,N-dimethylacetamide (1500 mL) was added 4-methylmorpholine (150 mL). The reaction was stirred overnight at 75° C. The mixture was cooled to room temperature, diluted with water (2000 mL) and extracted with ethyl acetate (3×1000 mL). The combined organic layers were washed with brine (4×300 mL), dried over anhydrous sodium sulfate, filtered, and concentrated. The residue was purified by silica gel column chromatography (petroleum ether/ethyl acetate=1:1) to afford benzyl N-[1-(5-chloropyrimidin-2-yl)cyclopropyl]carbamate (83.5 g, 49%) as a brown solid. 1H NMR (300 MHz, CDCl$_3$) δ 8.55 (s, 2H), 7.44-7.32 (m, 5H), 5.70-5.25 (s, 1H), 5.17 (s, 2H), 1.95 (s, 2H), 1.55-1.45 (s, 2H); MS (ESI): m/z 304.00 [M+H]$^+$.

Step 5:
1-(5-chloropyrimidin-2-yl)cyclopropan-1-amine

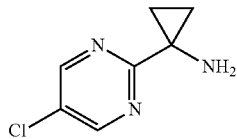 [SMILES: NC1(c2ncc(Cl)cn2)CC1]

A solution of benzyl N-[1-(5-chloropyrimidin-2-yl)cyclopropyl]carbamate (35.0 g, 115 mmol) and trifluoroacetic acid (300 mL) was stirred overnight at 60° C., then concentrated under reduced pressure. The residue was dissolved in tetrahydrofuran (200 mL) and water (50 mL), adjusted the pH to 13 with sodium hydroxide solid, and stirred for 2 h at room temperature. The mixture was diluted with water (200 mL), adjusted the pH to 7-8 with aqueous hydrochloric acid solution. The resulting mixture was extracted with ethyl acetate (3×250 mL). The combined organic layers were washed with brine (3×25 mL), dried over anhydrous sodium sulfate, filtered, and concentrated. The residue was purified by silica gel column chromatography (petroleum ether/ethyl acetate=2.5:1) to afford 1-(5-chloropyrimidin-2-yl)cyclopropan-1-amine (15.2 g, 78%) as a light yellow solid. 1H NMR (400 MHz, DMSO-d6) δ 8.83 (s, 1H), 3.46 (s, 1H), 2.57 (s, 2H), 1.30 (m, 1H), 1.13 (m, 1H); MS (ESI): m/z 170.15 [M+H]$^+$.

Step 6: tert-butyl N,N-bis(2-oxoethyl)carbamate

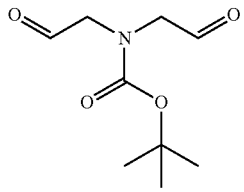

To a mixture of tert-butyl N,N-bis(2-hydroxyethyl)carbamate (15 g, 73 mmol) in tetrahydrofuran (30 mL) and water (10 mL) was added sodium periodate (21.9 g, 102 mmol), the reaction was stirred overnight at room temperature. The mixture was diluted with water (20 mL) and extracted with ethyl acetate (3×100 mL). The combined organic layers were washed with brine (3×15 mL), dried over anhydrous sodium sulfate, filtered, and concentrated. The residue was dissolved in dichloromethane (30 mL), magnesium sulfate (26.39 g, 219 mmol) was added in portions and the resulting mixture was stirred overnight at room temperature. The mixture was filtered, washed with dichloromethane (2×20 mL). The filtrate was concentrated under reduced pressure to afford tert-butyl N,N-bis(2-oxoethyl)carbamate (14.5 g, 99%) as an off-white oil. MS (ESI): m/z 224.10 [M+Na]$^+$. Step 7: tert-butyl 4-[1-(5-chloropyrimidin-2-yl)cyclopropyl]piperazine-1-carboxylate

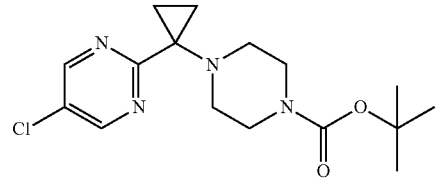 [SMILES: CC(C)(C)OC(=O)N1CCN(C2(c3ncc(Cl)cn3)CC2)CC1]

To a mixture of 1-(5-chloropyrimidin-2-yl)cyclopropan-1-amine (7.2 g, 42 mmol) in methanol (40 mL), tetrahydrofuran (10 mL) and acetic acid (1 mL) was added tert-butyl N,N-bis(2-oxoethyl)carbamate (17.08 g, 85 mmol) and sodium triacetoxyborohydride (6.67 g, 106 mmol). The reaction was stirred overnight at room temperature. The mixture was diluted with water (60 mL) and extracted with dichloromethane (3×100 mL). The combined organic layers were washed with brine (2×35 mL), dried over anhydrous sodium sulfate, filtered, and concentrated. The residue was purified by silica gel column chromatography (petroleum ether/ethyl acetate=2:1) to afford tert-butyl 4-[1-(5-chloropyrimidin-2-yl)cyclopropyl]piperazine-1-carboxylate (6.3 g, 43%) as a yellow solid. MS (ESI): m/z 339.10 [M+H]+.
Step 8: tert-butyl 4-(1-{5-[(diphenylmethylidene)amino]pyrimidin-2-yl}cyclopropyl)piperazine-1-carboxylate

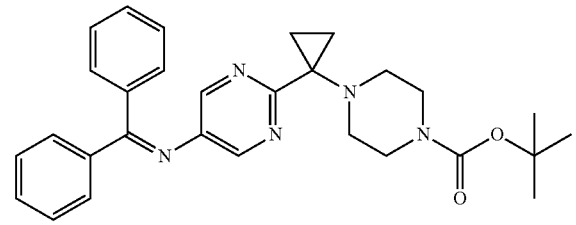 [SMILES: CC(C)(C)OC(=O)N1CCN(C2(c3ncc(N=C(c4ccccc4)c4ccccc4)cn3)CC2)CC1]

A mixture of tert-butyl 4-[1-(5-chloropyrimidin-2-yl)cyclopropyl]piperazine-1-carboxylate (1 g, 3 mmol), dichloro[1,3-bis(2,6-di-3-pentylphenyl)imidazol-2-ylidene](3-chloropyridyl)palladium(II) (0.12 g, 0.1 mmol), cesium carbonate (2.4 g, 7 mmol) and diphenylmethanimine (0.8 g, 4 mmol) in 1,4-dioxane (15 mL) was stirred for 3 h at 110° C. under nitrogen atmosphere. The mixture was cooled to room temperature, diluted with water (40 mL) and extracted with ethyl acetate (3×100 mL). The combined organic layers were washed with brine (2×20 mL), dried over anhydrous sodium sulfate, filtered, and concentrated. The residue was purified by silica gel column chromatography (petroleum ether/ethyl acetate=1:1) to afford tert-butyl 4-(1-{5-[(diphenylmethylidene)amino]pyrimidin-2-yl}cyclopropyl)piperazine-1-carboxylate (1.14 g, 79%) as a white solid. MS (ESI): m/z 484.35[M+H]+. Step 9: tert-butyl 4-[1-(5-aminopyrimidin-2-yl)cyclopropyl]piperazine-1-carboxylate

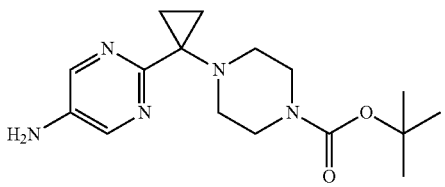 [SMILES: CC(C)(C)OC(=O)N1CCN(C2(c3ncc(N)cn3)CC2)CC1]

A mixture of tert-butyl 4-(1-{5-[(diphenylmethylidene)amino]pyrimidin-2-yl}cyclopropyl)piperazine-1-carboxylate (6.8 g, 14 mmol), hydroxylamine hydrochloride (4.4 g, 63 mmol) and methanol (50 mL) was stirred for 5 h at room temperature, then concentrated. The residue was diluted with water (60 mL) and extracted with ethyl acetate (3×100 mL). The combined organic layers were washed with brine (15 mL), dried over anhydrous sodium sulfate, filtered, and concentrated. The residue was purified by silica gel column chromatography (petroleum ether/ethyl acetate=1:1) to afford tert-butyl 4-[1-(5-aminopyrimidin-2-yl)cyclopropyl] piperazine-1-carboxylate (4.2 g, 93%) as a white solid. 1H NMR (300 MHz, DMSO-d6) δ 8.00 (s, 2H), 5.30 (s, 2H), 3.20 (m, 1H), 2.90 (m, 4H), 1.38 (s, 9H), 1.07-0.87 (m, 4H); MS (ESI): m/z 320.25 [M+H]⁺. Step 10: tert-butyl 4-{1-[5-(6-hydroxy-4-oxoquinazolin-3-yl)pyrimidin-2-yl]cyclopropyl}piperazine-1-carboxylate

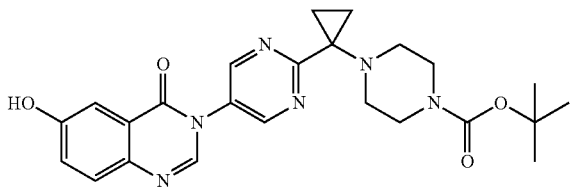 [SMILES: CC(C)(C)OC(=O)N1CCN(C2(c3ncc(-n4cnc5ccc(O)cc5c4=O)cn3)CC2)CC1]

A mixture of tert-butyl 4-[1-(5-aminopyrimidin-2-yl)cyclopropyl]piperazine-1-carboxylate (4.7 g, 15 mmol), triethyl orthoformate (18.74 g, 176 mmol) and acetic acid (100 mL) was stirred for 28 h at 60° C. The reaction was cooled to room temperature, diluted with water (80 mL) and extracted with ethyl acetate (3×60 mL). The combined organic layers were washed with brine (5×20 mL), dried over anhydrous sodium sulfate, filtered, and concentrated under reduced pressure. The residue was purified by silica gel column chromatography (petroleum ether/ethyl acetate=1:1) to afford tert-butyl 4-{1-[5-(6-hydroxy-4-oxoquinazolin-3-yl)pyrimidin-2-yl]cyclopropyl}piperazine-1-carboxylate (4.2 g, 61%) as a yellow solid. MS (ESI): m/z 465.15 [M+H]+. Step 11: tert-butyl 4-(1-{5-[6-(2-cyano-3,6-difluorophenoxy)-4-oxoquinazolin-3-yl]pyrimidin-2-yl}cyclopropyl)piperazine-1-carboxylate

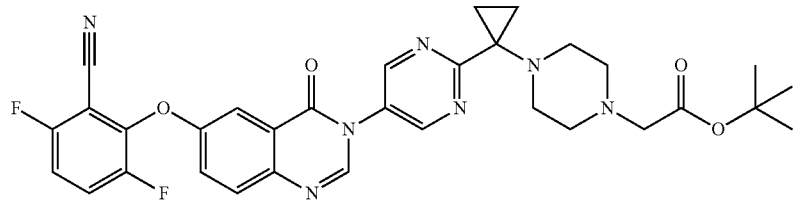 [SMILES: CC(C)(C)OC(=O)CN1CCN(C2(c3ncc(-n4cnc5ccc(Oc6c(F)ccc(F)c6C#N)cc5c4=O)cn3)CC2)CC1]

To a stirred solution of tert-butyl 4-{1-[5-(6-hydroxy-4-oxoquinazolin-3-yl)pyrimidin-2-yl]cyclopropyl}piperazine-1-carboxylate (4.2 g, 9 mmol) in N,N-dimethylmethanamide (45 mL) was added cesium carbonate (7.36 g, 23 mmol). The mixture was stirred for 0.5 h at 40° C. Then 2,3,6-trifluorobenzonitrile (2.13 g, 14 mmol) was added in portions and the reaction was stirred overnight at 40° C. The mixture was cooled to room temperature, diluted with water (60 mL) and extracted with ethyl acetate (3×100 mL). The combined organic layers were washed with brine (2×20 mL), dried over anhydrous sodium sulfate, filtered, and concentrated. The residue was triturated with petroleum ether (20 mL) to afford tert-butyl 4-(1-{5-[6-(2-cyano-3,6-difluorophenoxy)-4-oxoquinazolin-3-yl]pyrimidin-2-yl}cyclopropyl)piperazine-1-carboxylate (2.1 g, 39%) as a brown yellow solid. 1H NMR (300 MHz, DMSO-d6) δ 10.34 (s, 1H), 8.90 (s, 2H), 8.41 (s, 1H), 7.98-7.62 (m, 6H), 7.52 (m, 1H), 7.46 (m, 1H), 5.41 (m, 1H), 5.23 (s, 1H), 4.23 (m, 2H), 4.03 (m, 7H), 3.55 (s, 1H), 3.52-3.41 (m, 2H), 3.46-3.34 (m, 5H), 3.12 (s, 4H), 2.89 (s, 1H), 2.73 (m, 2H), 2.55-2.46 (m, 2H), 2.29-2.16 (m, 7H); MS (ESI): m/z 602.40 [M+H]⁺. Step 12: tert-butyl 4-(1-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}cyclopropyl)piperazine-1-carboxylate

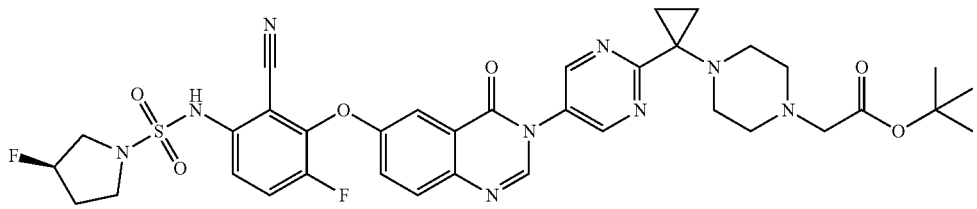 [SMILES: CC(C)(C)OC(=O)CN1CCN(C2(c3ncc(-n4cnc5ccc(Oc6c(F)ccc(NS(=O)(=O)N7CC[C@@H](F)C7)c6C#N)cc5c4=O)cn3)CC2)CC1]

A mixture of (3R)-3-fluoropyrrolidine-1-sulfonamide (2.73 g, 16 mmol) and cesium carbonate (5.28 g, 16 mmol) was stirred for 1 h at 50° C. Then tert-butyl 4-(1-{5-[6-(2-cyano-3,6-difluorophenoxy)-4-oxoquinazolin-3-yl]pyrimidin-2-yl}cyclopropyl)piperazine-1-carboxylate (3.9 g, 6 mmol) was added in portions, the resulting mixture was stirred overnight at 80° C. The reaction was cooled to room temperature, diluted with water (60 mL) and extracted with ethyl acetate (3×70 mL). The combined organic layers were washed with brine (3×20 mL), dried over anhydrous sodium sulfate, filtered, and concentrated. The residue was purified by reversed-phase flash chromatography (mobile phase: acetonitrile in water (10 mM ammonium bicarbonate), 15% to 56% in 50 min) to afford tert-butyl 4-(1-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}cyclopropyl)piperazine-1-carboxylate (2.8 g, 57%) as a brown solid. MS (ESI): m/z 750.45 [M+H]$^+$. Step 13: (3R)—N-{2-cyano-4-fluoro-3-[(4-oxo-3-{2-[1-(piperazin-1-yl)cyclopropyl]pyrimidin-5-yl}quinazolin-6-yl)oxy]phenyl}-3-fluoropyrrolidine-1-sulfonamide

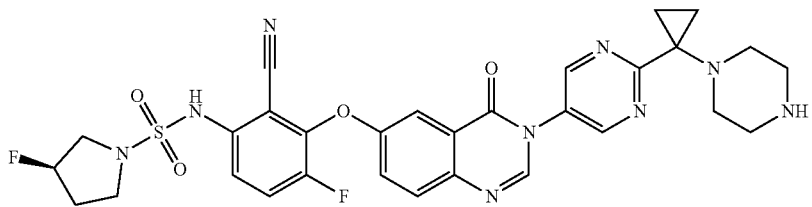 [SMILES: N#Cc1c(NS(=O)(=O)N2CC[C@@H](F)C2)ccc(F)c1Oc1ccc2ncn(-c3cnc(C4(N5CCNCC5)CC4)nc3)c(=O)c2c1]

A solution of tert-butyl 4-(1-{5-[6-(2-cyano-6-fluoro-3-{[(3R)-3-fluoropyrrolidin-1-ylsulfonyl]amino}phenoxy)-4-oxoquinazolin-3-yl]pyrimidin-2-yl}cyclopropyl)piperazine-1-carboxylate (400 mg, 0.5 mmol) and 4 M hydrochloric acid in 1,4-dioxane (15 mL) was stirred for 2 h at room temperature under nitrogen atmosphere. The reaction was concentrated to afford (3R)—N-{2-cyano-4-fluoro-3-[(4-oxo-3-{2-[1-(piperazin-1-yl)cyclopropyl]pyrimidin-5-yl}quinazolin-6-yl)oxy]phenyl}-3-fluoropyrrolidine-1-sulfonamide hydrochloride (365 mg, crude) as a white solid. MS (ESI): m/z 650.45 [M+H]$^+$.

The following intermediates may be prepared by a procedure analogous to Intermediate 3

| Structure | MS |
|---|---|
| Intermediate 11 | 578.50 [M + H]$^+$ HCl |
| Intermediate 12 | 610.15 [M + H]$^+$ HCl |
| Intermediate 13 | 609.35 [M + H]$^+$ HCl |

-continued
| Structure | MS |
|---|---|
| 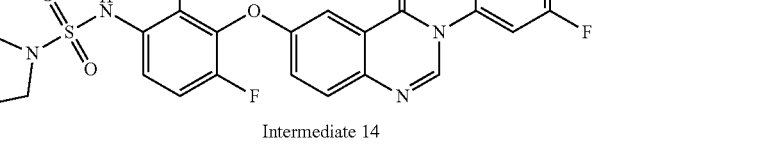 Intermediate 14 | 625.7 [M + H]+ HCl |
| 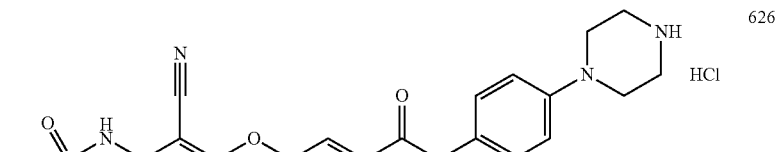 Intermediate 15 | 626.10 [M + H]+ HCl |
| 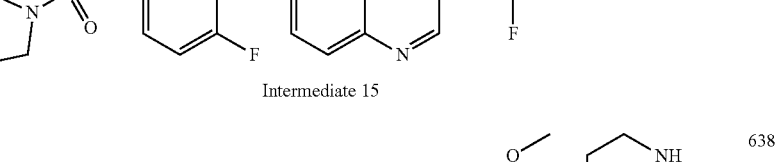 Intermediate 16 | 638.35 [M + H]+ HCl |
| 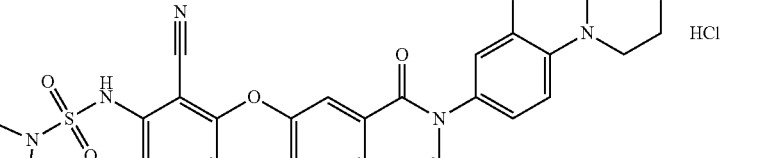 Intermediate 17 | 625.7 [M + H]+ HCl |
| 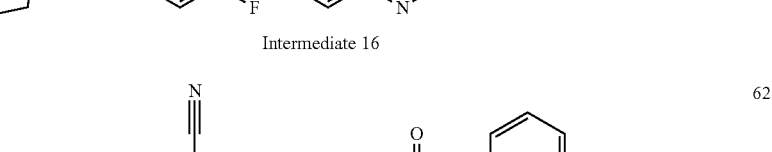 Intermediate 18 | 612.05 [M + H]+ |
| 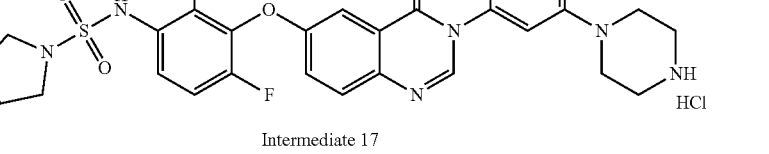 Intermediate 19 | 597.30 [M + H]+ HCl |

-continued

| Structure | MS |
|---|---|
| 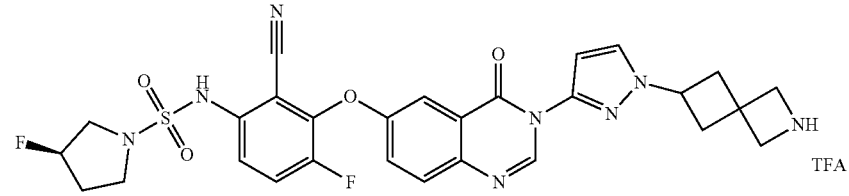  Intermediate 20 | 609.20 [M + H]+ TFA |
| 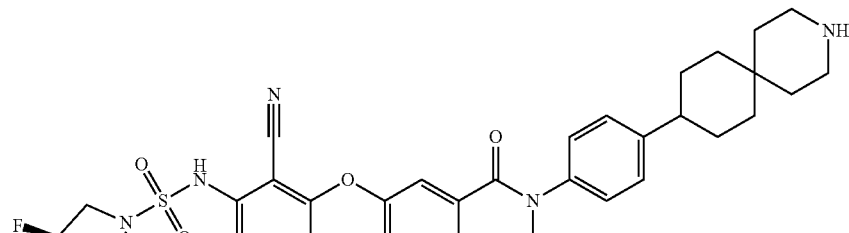  Intermediate 31 | N/A |

Intermediate 10: (3R)—N-{2-cyano-4-fluoro-3-[(3-{4-[(2S)-2-methylpiperazin-1-yl]phenyl}-4-oxoquinazolin-6-yl)oxy]phenyl}-3-fluoropyrrolidine-1l-sulfonamide Step 1: (3S)-4-{4-[6-(2-cyano-6-fluoro-3-{[(3R)-3-fluoropyrrolidin-1-ylsulfonyl]amino}phenoxy)-4-oxoquinazolin-3-yl]phenyl}-3-methylpiperazine-1-carboxylate To a stirred mixture of (3R)—N-(3-{[3-(4-bromophenyl)-4-oxoquinazolin-6-yl]oxy}-2-cyano-4-fluorophenyl)-3-fluoropyrrolidine-1-sulfonamide (600 mg, 1 mmol) and tert-butyl (3S)-3-methylpiperazine-1-carboxylate (199 mg, 1 mmol) in 1,4-dioxane (15 mL) was added cesium carbonate (974 mg, 3 mmol) and (2-dicyclohexylphosphino-2',6'-diisopropoxy-1,1'-biphenyl)[2-(2'-amino-1,1'-biphenyl)]palladium(II) methanesulfonate (83 mg, 0.1 mmol). The reaction was stirred overnight at 90° C., then cooled to room temperature. The mixture was diluted with water (10 mL) and extracted with ethyl acetate (2×100 mL). The combined organic layers were washed with water (2×20 mL), dried over anhydrous sodium sulfate, filtered, and concentrated. The residue was purified by silica gel column chromatography (petroleum ether/ethyl acetate=1:1) to afford tert-butyl (3S)-4-{4-[6-(2-cyano-6-fluoro-3-{[(3R)-3-fluoropyrrolidin-1-ylsulfonyl]amino}phenoxy)-4-oxoquinazolin-3-yl]phenyl}-3-methylpiperazine-1-carboxylate (300 mg, 42%) as a white solid. 1H NMR (400 MHz, DMSO-d6) δ 10.35 (s,

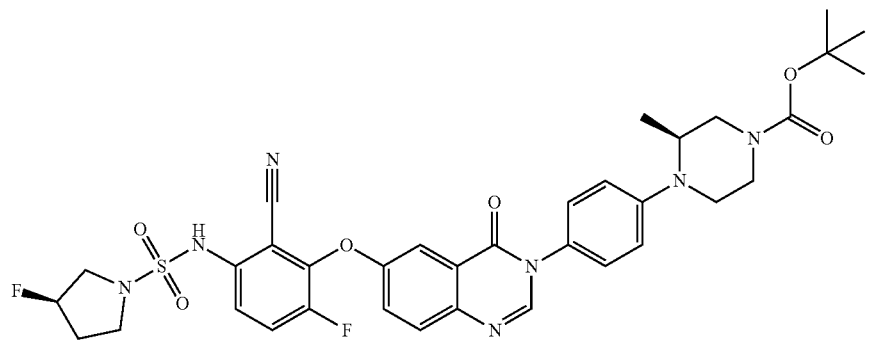 [SMILES: C[C@H]1CN(C(=O)OC(C)(C)C)CCN1c1ccc(-n2cnc3ccc(Oc4c(F)ccc(NS(=O)(=O)N5CC[C@@H](F)C5)c4C#N)cc3c2=O)cc1]

1H), 8.27 (s, 1H), 7.42 (d, J=3.0 Hz, 4H), 7.33 (d, J=8.5 Hz, 5H), 7.01 (d, J=8.8 Hz, 3H), 5.76 (s, 2H), 5.39-5.20 (d, J=76 Hz, 1H), 4.09 (s, 4H), 3.84-3.74 (m, 1H), 3.46 (s, 4H), 2.99 (s, 2H), 2.29-2.19 (m, 2H), 2.19-2.10 (m, 2H), 1.43 (s, 9H), 1.22-1.07 (m, 2H), 0.96 (d, J=6.4 Hz, 2H); MS (ESI): m/z 722.1 [M+H]+. Step 2: (3R)—N-{2-cyano-4-fluoro-3-[(3-{4-[(2S)-2-methylpiperazin-1-yl]phenyl}-4-oxoquinazolin-6-yl)oxy]phenyl}-3-fluoropyrrolidine-1-sulfonamide

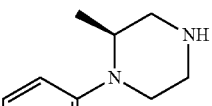
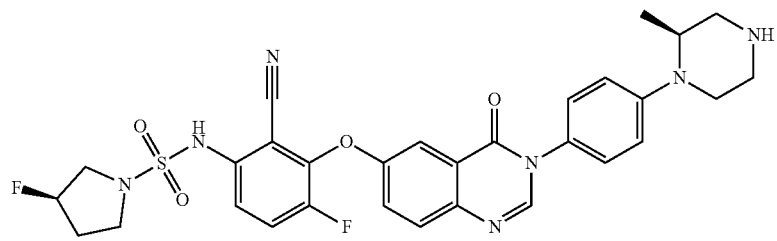 [SMILES: C[C@H]1CNCCN1c1ccc(-n2cnc3ccc(Oc4c(F)ccc(NS(=O)(=O)N5CC[C@@H](F)C5)c4C#N)cc3c2=O)cc1]

A solution of tert-butyl (3S)-4-{4-[6-(2-cyano-6-fluoro-3-{[(3R)-3-fluoropyrrolidin-1-ylsulfonyl]amino}phenoxy)-4-oxoquinazolin-3-yl]phenyl}-3-methylpiperazine-1-carboxylate (160 mg, 0.2 mmol) and 4 M hydrochloric acid in 1,4-dioxane (10 mL) was stirred for 2 h at room temperature. The reaction was concentrated under reduced pressure. The residue was triturated with ethyl acetate (5 mL) to afford (3R)—N-{2-cyano-4-fluoro-3-[(3-{4-[(2S)-2-methylpiperazin-1-yl]phenyl}-4-oxoquinazolin-6-yl)oxy]phenyl}-3-fluoropyrrolidine-1-sulfonamide hydrochloride (130 mg, 89%) as a white solid.

The following intermediates may be prepared by a procedure analogous to Intermediate 4

| Structure | MS |
|---|---|
| Intermediate 21 | 635.15 [M + H]⁺ |
| Intermediate 22 | 635.30 [M + H]⁺ |
| Intermediate 23 | 649.2 [M + H]⁺ |

| Structure | MS |
|---|---|
| 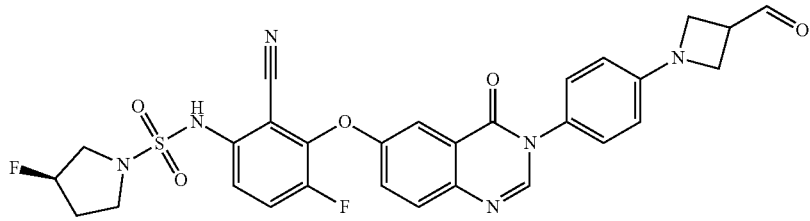<br>Intermediate 32 | 607.25 [M + H]⁺ |
| 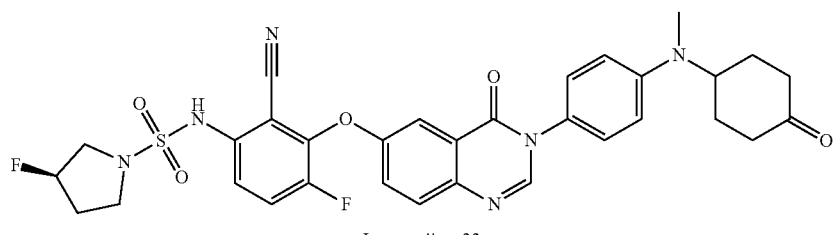<br>Intermediate 33 | 649.2 [M + H]⁺ |
| 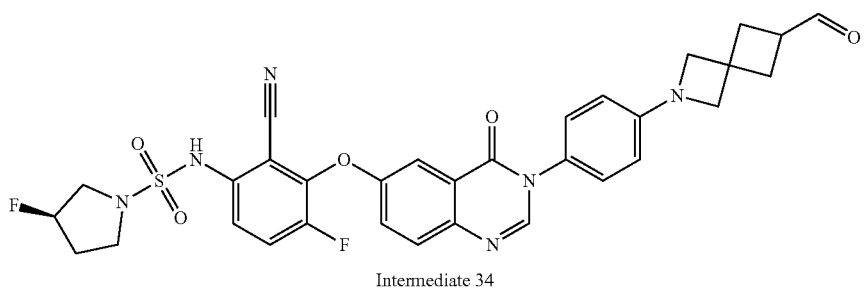 [SMILES: N#Cc1c(NS(=O)(=O)N2CC[C@@H](F)C2)ccc(F)c1Oc1ccc2ncn(-c3ccc(N4CC5(CC(C=O)C5)C4)cc3)c(=O)c2c1]<br>Intermediate 34 | 647.2 [M + H]⁺ |
| 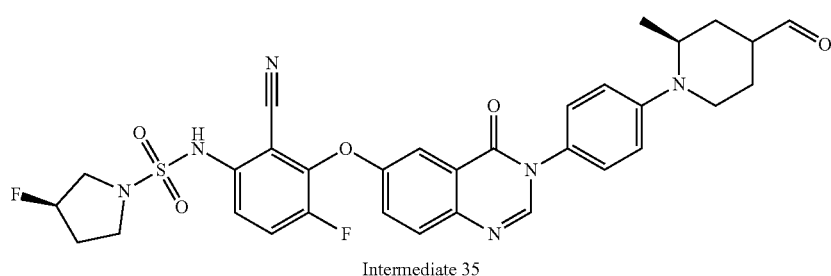 [SMILES: C[C@H]1CC(C=O)CCN1c1ccc(-n2cnc3ccc(Oc4c(F)ccc(NS(=O)(=O)N5CC[C@@H](F)C5)c4C#N)cc3c2=O)cc1]<br>Intermediate 35 | 649.3 [M + H]⁺ |
| 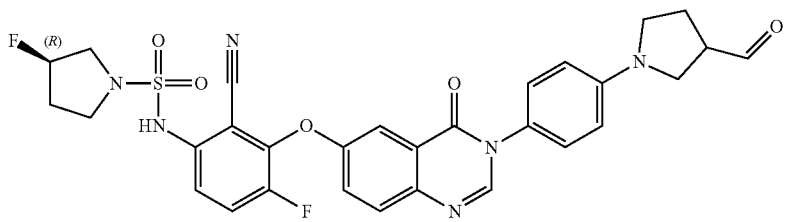<br>Intermediate 36 | 621.1 [M + H]⁺ |

| Structure | MS |
|---|---|
| 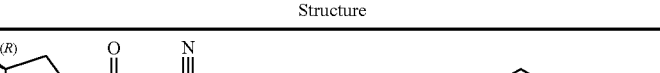<br>Intermediate 37 | 621.0 [M + H]⁺ |
Intermediate 24: 6-{[ethyl(methyl)sulfamoyl]amino}-3-fluoro-2-({4-oxo-3-[4-(piperazin-1-yl)phenyl]quinazolin-6-yl}oxy)benzonitrile
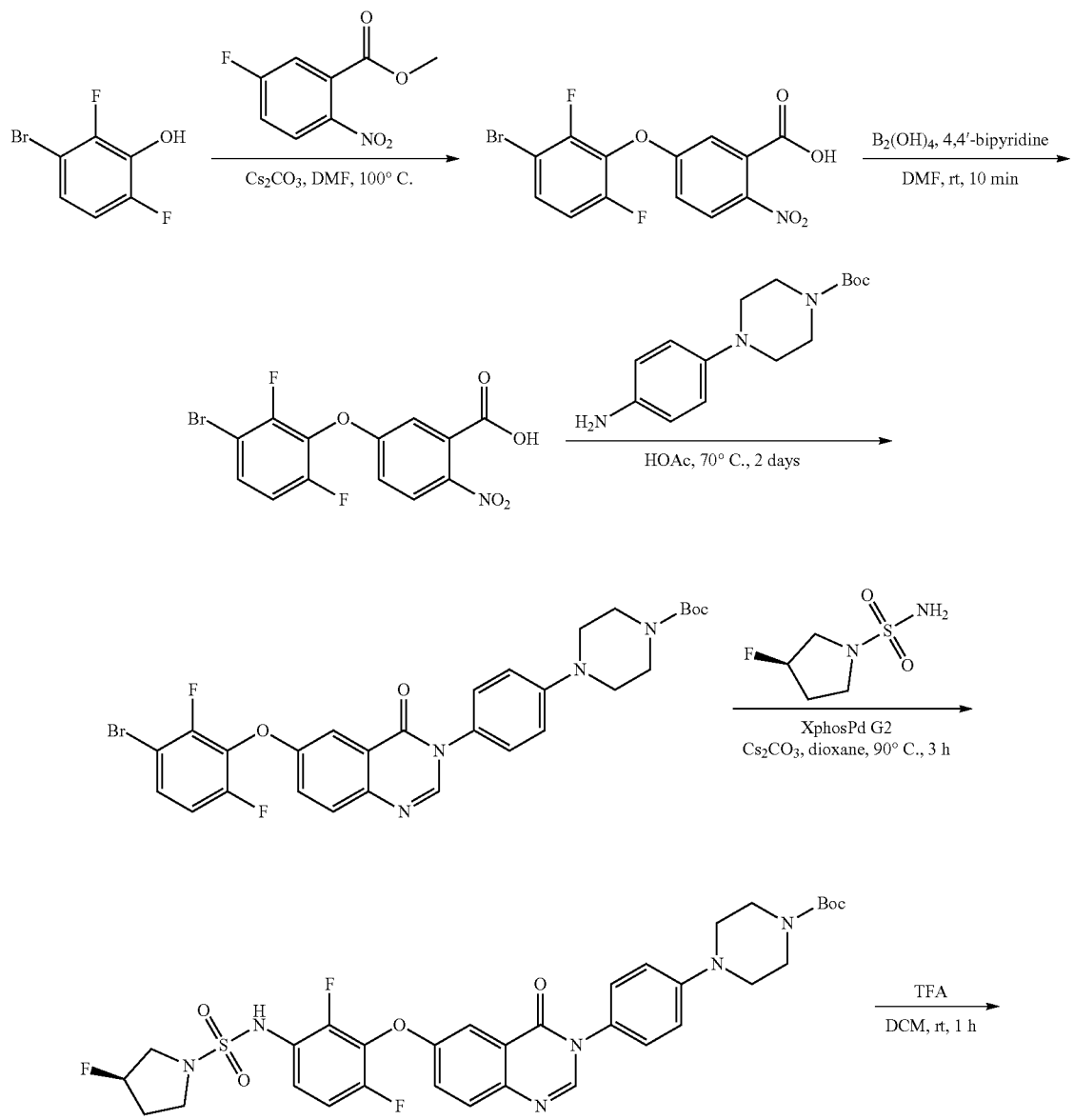

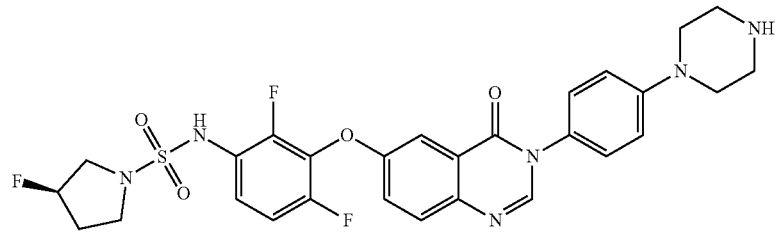

-continued

Step 1: ethyl(methyl)sulfamoylamine

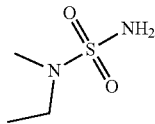

To a stirred mixture of N-ethylmethylamine (22.14 g, 374 mmol) in 1,4-dioxane (1600 mL) was added sulfamide (30.0 g, 312 mmol) and triethylamine (63.18 g, 624 mmol) over 5 min at room temperature. The resulting mixture was stirred for 12 h at 110° C. in a sealed pressure reactor. The reaction was allowed to cool to room temperature and concentrated under reduced pressure. The residue was diluted with water (600 mL) and extracted with dichloromethane (5×600 mL). The combined organic layers were dried over sodium sulfate, filtered, and concentrated. The residue was purified by silica gel column chromatography (petroleum ether/ethyl acetate=2:1) to afford ethyl(methyl)sulfamoylamine (27.3 g, 63%) as a brown oil. $^1$H NMR (300 MHz, DMSO-$d_6$) δ 6.59 (s, 2H), 2.98 (m, 2H), 2.61 (s, 3H), 1.08 (s, 3H); MS (ESI): m/z 139.20 [M+H]$^+$.

Step 2: tert-butyl 4-{4-[6-(2-cyano-3-{[ethyl(methyl)sulfamoyl]amino}-6-fluorophenoxy)-4-oxoquinazolin-3-yl]phenyl}piperazine-1-carboxylate

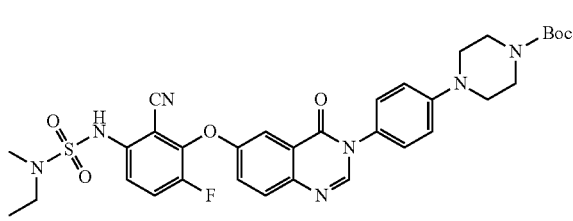 [SMILES: CCN(C)S(=O)(=O)Nc1ccc(F)c(Oc2ccc3ncn(-c4ccc(N5CCN(C(=O)OC(C)(C)C)CC5)cc4)c(=O)c3c2)c1C#N]

To a stirred mixture of ethyl(methyl)sulfamoylamine (5.26 g, 38 mmol) in N, N-dimethylformamide (120 mL) was added cesium carbonate (10.34 g, 32 mmol). The mixture was stirred for 1 h at 50° C., followed by the addition of tert-butyl 4-{4-[6-(2-cyano-3,6-difluorophenoxy)-4-oxoquinazolin-3-yl]phenyl}piperazine-1-carboxylate (7.1 g, 13 mmol) dropwise at 50° C. The mixture was stirred for 12 h at 90° C., then cooled to room temperature. The reaction was diluted with water (200 mL) and extracted with ethyl acetate (3×200 mL). The combined organic layers were washed with brine (3×20 mL), dried over anhydrous sodium sulfate, filtered, and concentrated. The residue was purified by reversed-phase flash column chromatography (15%-60% acetonitrile in water [10 mmol/L ammonium bicarbonate] in 45 min) to afford tert-butyl 4-{4-[6-(2-cyano-3-{[ethyl(methyl)sulfamoyl]amino}-6-fluorophenoxy)-4-oxoquinazolin-3-yl]phenyl}piperazine-1-carboxylate (3.3 g, 38%) as an off-white solid. $^1$H NMR (300 MHz, DMSO-$d_6$) δ 10.18 (s, 1H), 8.26 (s, 1H), 7.94-7.78 (m, 2H), 7.73 (m, 1H), 7.50 m, 1H), 7.43-7.30 (m, 3H), 7.07 (m, 2H), 3.48 (m, 4H), 3.17 (m, 6H), 2.79 (s, 3H), 1.43 (s, 9H), 1.04 (m, 3H); MS (ESI): m/z 678.35 [M+H]$^+$.

Step 3: 6-{[ethyl(methyl)sulfamoyl]amino}-3-fluoro-2-({4-oxo-3-[4-(piperazin-1-yl)phenyl]quinazolin-6-yl}oxy)benzonitrile

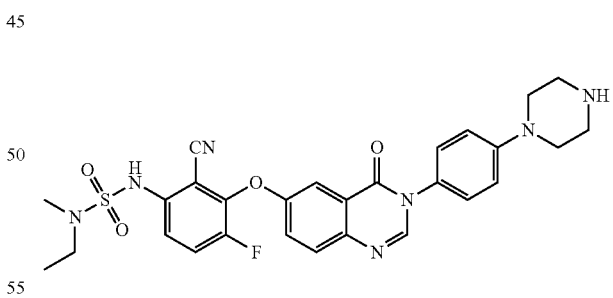

A mixture of tert-butyl 4-{4-[6-(2-cyano-3-{[ethyl(methyl)sulfamoyl]amino}-6-fluorophenoxy)-4-oxoquinazolin-3-yl]phenyl}piperazine-1-carboxylate (1.43 g, 2 mmol) in 4 M hydrochloric acid in 1,4-dioxane (60 mL) was stirred for 3 h at room temperature. The resulting was concentrated under reduced pressure to afford 6-{[ethyl(methyl)sulfamoyl]amino}-3-fluoro-2-({4-oxo-3-[4-(piperazin-1-yl)phenyl]quinazolin-6-yl}oxy)benzonitrile hydrochloride (1.2 g, 98%) as an off-white solid, which was used in the next step without further purification. MS (ESI): m/z 578.50 [M+H]$^+$.

Intermediate 25: (3R)—N-[2,4-difluoro-3-({4-oxo-3-[4-(piperazin-1-yl)phenyl]quinazolin-6-yl}oxy)phenyl]-3-fluoropyrrolidine-1-sulfonamide

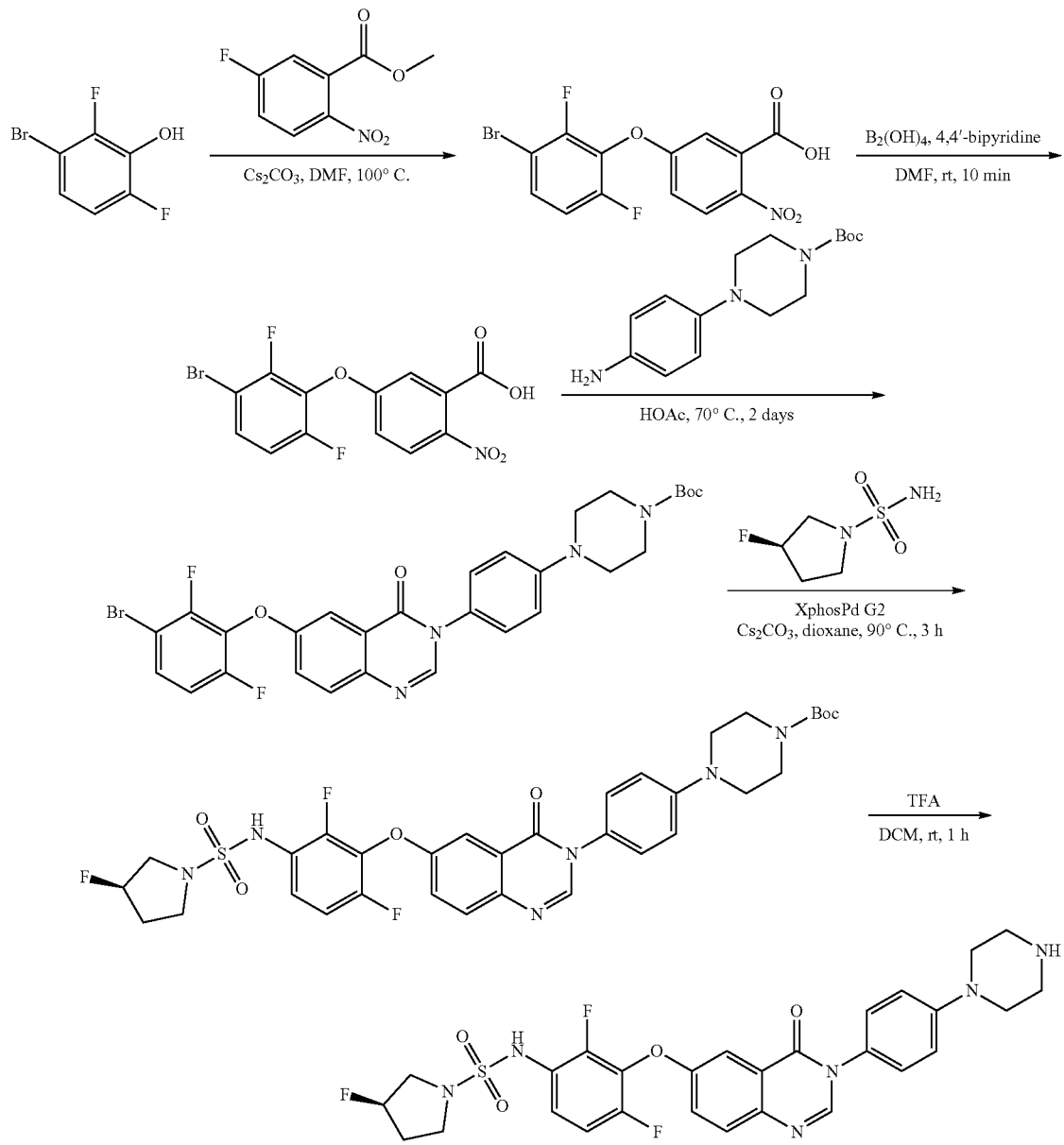

Step 1:
5-(3-bromo-2,6-difluorophenoxy)-2-nitrobenzoic acid

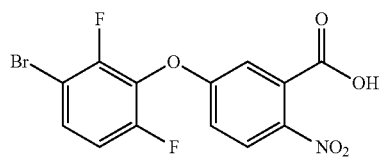 [SMILES: O=C(O)c1cc(Oc2c(F)ccc(Br)c2F)ccc1[N+](=O)[O-]]

To a stirred solution of 3-bromo-2,6-difluorophenol (10 g, 48 mmol) and methyl 5-fluoro-2-nitrobenzoate (9.53 g, 48 mmol) in N, N-dimethylformamide (20 mL) was added cesium carbonate (39.0 g, 120 mmol) at room temperature. The resulting mixture was stirred for 12 h at 100° C., then cooled to room temperature. The mixture was diluted with water (100 mL) and extracted with ethyl acetate (3×100 mL). The combined organic layers were washed with brine (2×50 mL), dried over anhydrous sodium sulfate, filtered, and concentrated. The residue was purified by silica gel column chromatography (petroleum ether/ethyl acetate=1:1) to afford 5-(3-bromo-2,6-difluorophenoxy)-2-nitrobenzoic acid (12.7 g, 71%) as a yellow solid. $^1$H NMR (400 MHz, DMSO-$d_6$) δ 14.03 (s, 1H), 8.22-8.10 (m, 3H), 7.71-7.58 (m, 4H), 3.93 (s, 1H), 3.11 (s, 1H); MS (ESI): m/z 371.92 [M+H]+.

Step 2: 2-amino-5-(3-bromo-2,6-difluorophenoxy)benzoic acid

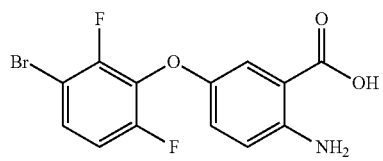

To a stirred solution of 5-(3-bromo-2,6-difluorophenoxy)-2-nitrobenzoic acid (8.0 g, 21 mmol) and tetrahydroxydiboron (3.83 g, 43 mmol) in N, N-dimethylformamide (20 mL) was dropwise added 4,4'-dimethoxy-2,2'-bipyridine (2.31 g, 11 mmol) at room temperature, the resulting mixture was stirred for 10 min at room temperature. The reaction was diluted with water (100 mL) and extracted with ethyl acetate (2×100 mL). The combined organic layers were washed with brine (2×50 mL), dried over anhydrous sodium sulfate, filtered, and concentrated. The residue was purified by silica gel column chromatography (petroleum ether/ethyl acetate=1:1) to afford 2-amino-5-(3-bromo-2,6-difluorophenoxy)benzoic acid (6 g, 82%) as an off-white solid. ¹H NMR (400 MHz, DMSO-$d_6$) δ 7.95 (s, 1H), 7.63 (s, 1H), 7.31 (s, 1H), 7.14 (s, 1H), 6.94 (s, 1H), 3.17 (s, 1H), 1.47 (s, 2H); MS (ESI): m/z 341.90 [M+H]+.

Step 3: tert-butyl 4-{4-[6-(3-bromo-2,6-difluorophenoxy)-4-oxoquinazolin-3-yl]phenyl}piperazine-1-carboxylate

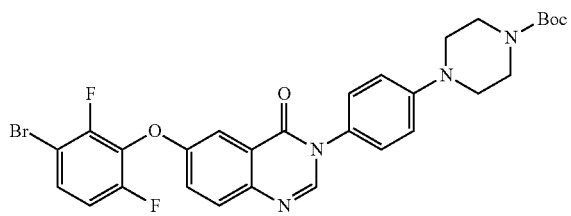 [SMILES: CC(C)(C)OC(=O)N1CCN(c2ccc(-n3cnc4ccc(Oc5c(F)ccc(Br)c5F)cc4c3=O)cc2)CC1]

To a stirred solution of 2-amino-5-(3-bromo-2,6-difluorophenoxy)benzoic acid (2 g, 6 mmol) in acetic acid (20 mL) was slowly added tert-butyl 4-(4-aminophenyl)piperazine-1-carboxylate (1.93 g, 7 mmol) at room temperature. The resulting mixture was stirred for 2 d at 70° C., then cooled to room temperature. The mixture was diluted with water (20 mL) and extracted with dichloromethane (2×100 mL). The combined organic layers were washed with brine (2×20 mL), dried over anhydrous sodium sulfate, filtered, and concentrated. The residue was purified by silica gel column chromatography (petroleum ether/ethyl acetate=1:1) to afford tert-butyl 4-{4-[6-(3-bromo-2,6-difluorophenoxy)-4-oxoquinazolin-3-yl]phenyl}piperazine-1-carboxylate (1.2 g, 34%) as a white solid. MS (ESI): m/z 615.00 [M+H]+.

Step 4: tert-butyl 4-{4-[6-(2,6-difluoro-3-{[(3R)-3-fluoropyrrolidin-1-ylsulfonyl]amino}phenoxy)-4-oxoquinazolin-3-yl]phenyl}piperazine-1-carboxylate

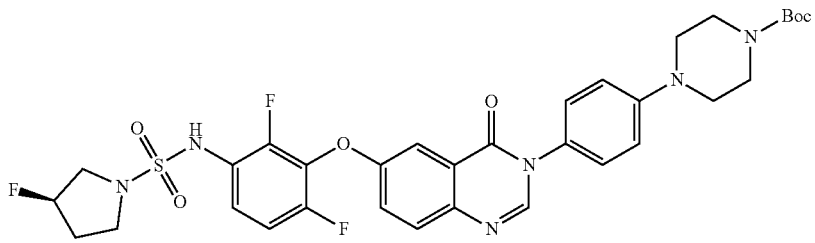 [SMILES: CC(C)(C)OC(=O)N1CCN(c2ccc(-n3cnc4ccc(Oc5c(F)ccc(NS(=O)(=O)N6CC[C@@H](F)C6)c5F)cc4c3=O)cc2)CC1]

To a stirred mixture of tert-butyl 4-{4-[6-(3-bromo-2,6-difluorophenoxy)-4-oxoquinazolin-3-yl]phenyl}piperazine-1-carboxylate (1 g, 2 mmol) and 6-(benzyloxy)-3-(4-bromophenyl)quinazolin-4-one (961.80 mg, 2 mmol) in 1,4-dioxane (15 mL) was added cesium carbonate (1.59 g, 5 mmol) and chloro(2-dicyclohexylphosphino-2',4',6'-triisopropyl-1,1'-biphenyl)[2-(2'-amino-1,1'-biphenyl)]palladium (II) (0.12 g, 0.2 mmol) in portions at room temperature. The resulting mixture was stirred for 12 h at 100° C. under nitrogen atmosphere. The mixture was allowed to cool to room temperature, diluted with water (10 mL) and extracted with ethyl acetate (2×100 mL). The combined organic layers were washed with brine (2×20 mL), dried over anhydrous sodium sulfate, filtered, and concentrated. The residue was purified by silica gel column chromatography (petroleum ether/ethyl acetate=1:1) to afford tert-butyl 4-{4-[6-(2,6-difluoro-3-{[(3R)-3-fluoropyrrolidin-1-ylsulfonyl]amino}phenoxy)-4-oxoquinazolin-3-yl]phenyl}piperazine-1-carboxylate (810 mg, 71%) as a white solid. MS (ESI): m/z 699.15 [M+H]+.

Step 5: (3R)—N-[2,4-difluoro-3-({4-oxo-3-[4-(piperazin-1-yl)phenyl]quinazolin-6-yl}oxy)phenyl]-3-fluoropyrrolidine-1-sulfonamide hydrochloride

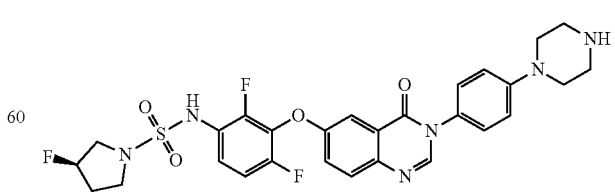

A solution of tert-butyl 4-{4-[6-(2,6-difluoro-3-{[(3R)-3-fluoropyrrolidin-1-ylsulfonyl]amino}phenoxy)-4-oxoquinazolin-3-yl]phenyl}piperazine-1-carboxylate (800 mg, 1 mmol) in 4 M hydrochloric acid in 1,4-dioxane (10 mL) was stirred for 2 h at room temperature. The resulting mixture was concentrated under reduced pressure, the residue was triturated with ethyl acetate (5 mL) and petroleum ether (5 mL) to afford (3R)—N-[2,4-difluoro-3-({4-oxo-3-[4-(piperazin-1-yl)phenyl]quinazolin-6-yl}oxy)phenyl]-3-fluoropyrrolidine-1-sulfonamide hydrochloride (562 mg, 77%) as a white solid. MS (ESI): m/z 601.25 [M+H]⁺.

The following intermediates may be prepared by a procedure analogous to Intermediate 25

| Structure | MS |
| --- | --- |
| | 617.3 [M + H]⁺ |

Intermediate 26

Intermediate 27: (3R)-3-fluoro-N-[4-fluoro-2-methyl-3-({4-oxo-3-[4-(piperazin-1-yl)phenyl]quinazolin-6-yl}oxy)phenyl]pyrrolidine-1-sulfonamide

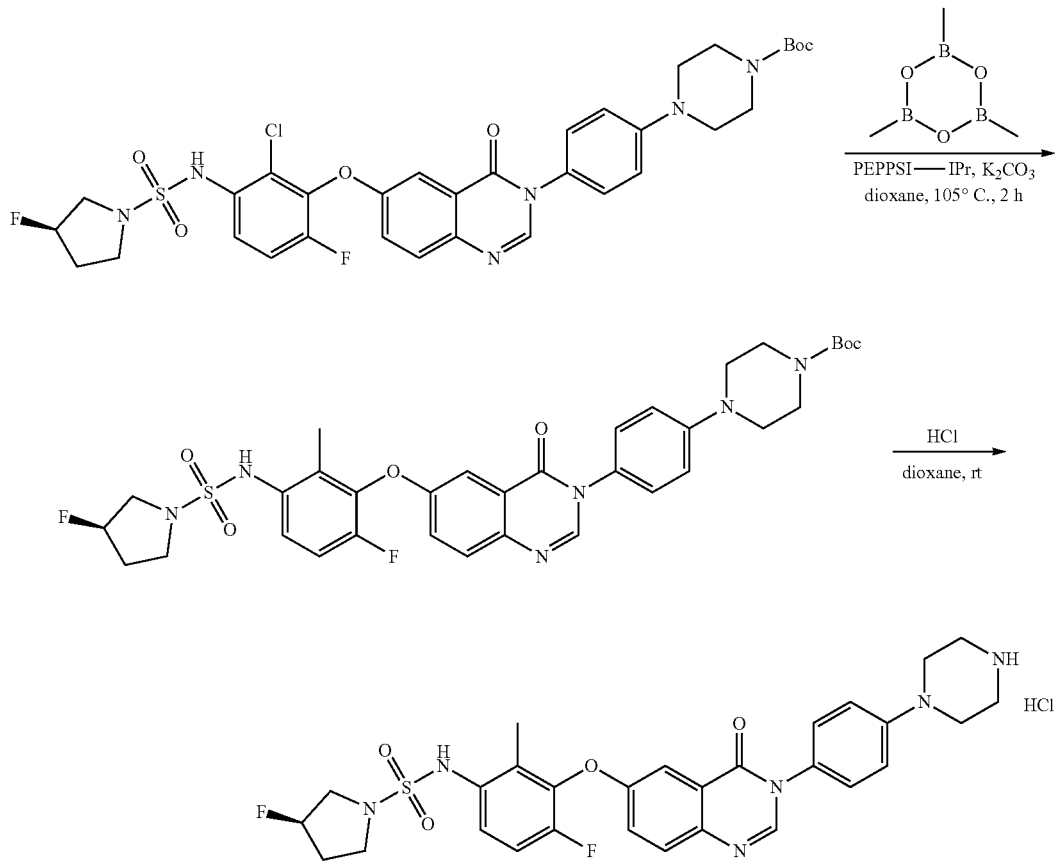

Step 1: tert-butyl 4-{4-[6-(6-fluoro-3-{[(3R)-3-fluoropyrrolidin-1-ylsulfonyl]amino}-2-methylphenoxy)-4-oxoquinazolin-3-yl]phenyl}piperazine-1-carboxylate

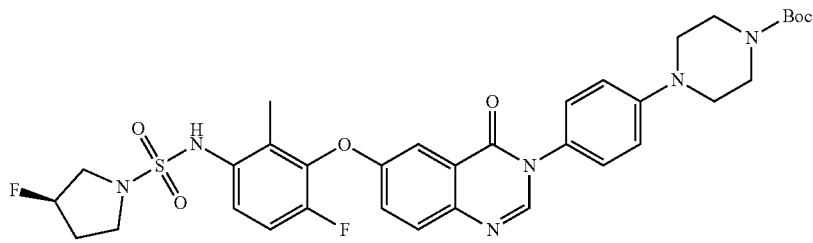 [SMILES: Cc1c(NS(=O)(=O)N2CC[C@@H](F)C2)ccc(F)c1Oc1ccc2ncn(-c3ccc(N4CCN(C(=O)OC(C)(C)C)CC4)cc3)c(=O)c2c1]

To a stirred mixture of tert-butyl 4-{4-[6-(2-chloro-6-fluoro-3-{[(3R)-3-fluoropyrrolidin-1-ylsulfonyl]amino}phenoxy)-4-oxoquinazolin-3-yl]phenyl}piperazine-1-carboxylate (720 mg, 1 mmol) and trimethyl-1,3,5,2,4,6-trioxatriborinane (630 mg, 5 mmol) in 1,4-dioxane (14 mL) was added [1,3-bis(2,6-diisopropylphenyl)imidazol-2-ylidene](3-chloropyridyl)palladium(II) dichloride (68 mg, 0.1 mmol) and potassium carbonate (555 mg, 4 mmol) at room temperature. The resulting mixture was stirred for 2 h at 90° C. under nitrogen atmosphere, then cooled to room temperature. The mixture was quenched with water (40 mL) and extracted with ethyl acetate (3×40 mL). The combined organic layers were washed with brine (3×10 mL), dried over anhydrous sodium sulfate, filtered, and concentrated. The residue was purified by preparative-thin layer chromatography (ethyl acetate) to afford tert-butyl 4-{4-[6-(6-fluoro-3-{1[(3R)-3-fluoropyrrolidin-1-ylsulfonyl]amino}-2-methylphenoxy)-4-oxoquinazolin-3-yl]phenyl}piperazine-1-carboxylate (560 mg, 80%) as a light yellow solid. $^1$H NMR (300 MHz, DMSO-$d_6$) δ 9.39 (s, 1H), 8.29-8.16 (m, 2H), 7.86-7.70 (m, 2H), 7.65 (m, 2H), 7.60-7.40 (m, 1H), 7.49 (s, 2H), 7.44-7.25 (m, 2H), 7.22 (d, J=3.0 Hz, 1H), 7.08 (m, 3H), 5.76 (d, J=0.9 Hz, 1H), 5.37 (d, J=24.1 Hz, 1H), 5.23 (s, OH), 4.23 (m, 1H), 4.10-3.97 (m, 1H), 3.48 (m, 1H), 3.41 (s, 1H), 3.33-3.15 (m, 2H), 2.19 (s, 3H), 2.12 (d, J=16.2 Hz, 1H), 2.00 (d, J=0.9 Hz, 1H), 1.73-1.57 (m, 1H), 1.43 (s, 1H), 1.37-1.08 (m, 3H), 0.89 (m, 2H), 0.87 (s, 3H); MS (ESI): m/z 697.35 [M+H]$^+$.

Step 2: (3R)-3-fluoro-N-[4-fluoro-2-methyl-3-({4-oxo-3-[4-(piperazin-1-yl)phenyl]quinazolin-6-yl}oxy)phenyl]pyrrolidine-1-sulfonamide

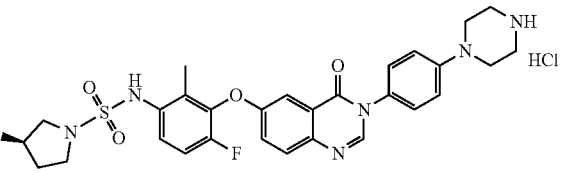

A solution of tert-butyl 4-{4-[6-(6-fluoro-3-{[(3R)-3-fluoropyrrolidin-1-ylsulfonyl]amino}-2-methylphenoxy)-4-oxoquinazolin-3-yl]phenyl}piperazine-1-carboxylate (530 mg, 0.8 mmol) in 4 M hydrochloric acid in 1,4-dioxane (10 mL) was stirred for 2 h at room temperature. The resulting mixture was concentrated under reduced pressure to afford (3R)-3-fluoro-N-[4-fluoro-2-methyl-3-({4-oxo-3-[4-(piperazin-1-yl)phenyl]quinazolin-6-yl}oxy)phenyl]pyrrolidine-1-sulfonamide hydrochloride (450 mg, 99%) as a yellow solid. $^1$H NMR (300 MHz, DMSO-$d_6$) δ 9.39 (s, 1H), 8.27-8.25 (m, 1H), 7.79-7.68 (m, 1H), 7.66-7.10 (m, 4H), 5.90-5.45 (b, 2H), 3.57-3.30 (m, 6H), 3.27-3.11 (m, 2H); MS (ESI): m/z 597.3 [M+H]$^+$.

Intermediate 28: (3R)—N-[2-ethyl-4-fluoro-3-({4-oxo-3-[4-(piperazin-1-yl)phenyl]quinazolin-6-yl}oxy)phenyl]-3-fluoropyrrolidine-1-sulfonamide

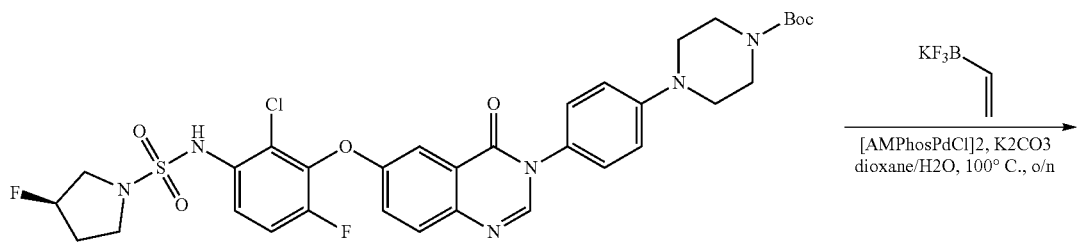

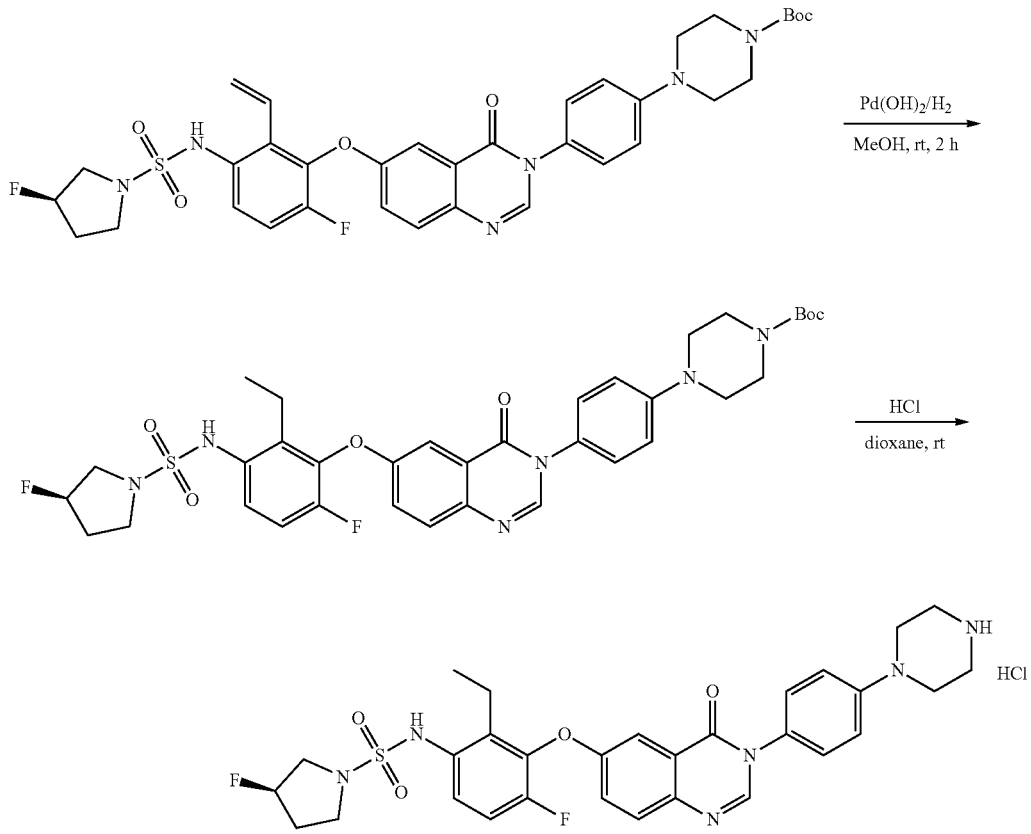

Step 1: tert-butyl 4-{4-[6-(2-ethenyl-6-fluoro-3-{[(3R)-3-fluoropyrrolidin-1-ylsulfonyl]amino}phenoxy)-4-oxoquinazolin-3-yl]phenyl}piperazine-1-carboxylate To a stirred mixture of tert-butyl 4-{4-[6-(2-chloro-6-fluoro-3-{[(3R)-3-fluoropyrrolidin-1-ylsulfonyl]amino}phenoxy)-4-oxoquinazolin-3-yl]phenyl}piperazine-1-carboxylate (300 mg, 0.4 mmol) and bis(di-tert-butyl(4-dimethylaminophenyl)phosphine)dichloropalladium(II) (30 mg, 0.04 mmol) in water (2 mL) and 1,4-dioxane (10 mL) was added potassium carbonate (173 mg, 1.2 mmol) at room temperature. The resulting mixture was stirred for 12 h at 100° C. under nitrogen atmosphere. The mixture was allowed to cool to room temperature, diluted with water (40 mL) and extracted with dichloromethane (3×40 mL). The combined organic layers were washed with brine (3×10 mL), dried over anhydrous sodium sulfate, filtered, and concentrated. The crude product was purified by preparative-high performance liquid chromatography (acetonitrile:ammonium chloride=50:50) to afford tert-butyl 4-{4-[6-(2-ethenyl-6-fluoro-3-{[(3R)-3-fluoropyrrolidin-1-ylsulfonyl]

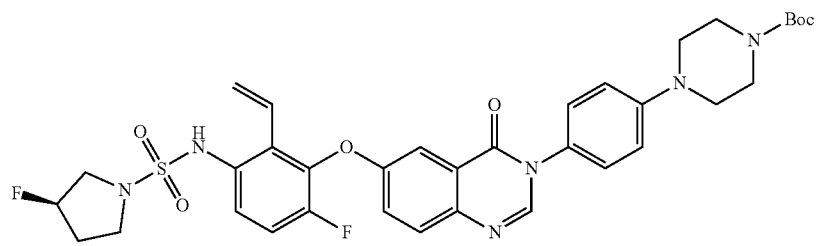 [SMILES: C=Cc1c(NS(=O)(=O)N2CC[C@@H](F)C2)ccc(F)c1Oc1ccc2ncn(-c3ccc(N4CCN(C(=O)OC(C)(C)C)CC4)cc3)c(=O)c2c1]

amino}phenoxy)-4-oxoquinazolin-3-yl]phenyl}piperazine-1-carboxylate (55 mg, 19%) as an off-white solid. MS (ESI): m/z 708.3 [M+H]$^+$; $^1$H NMR (400 MHz, DMSO-d$_6$) δ 9.42 (s, 1H), 8.20 (s, 1H), 7.78 (d, J=8.9 Hz, 1H), 7.58 (dd, J=8.9, 3.0 Hz, 1H), 7.39 (d, J=7.2 Hz, 2H), 7.36-7.29 (m, 2H), 7.23 (d, J=3.0 Hz, 1H), 7.10-7.03 (m, 2H), 6.81 (dd, J=18.0, 12.0 Hz, 1H), 5.85 (dd, J=18.0, 1.8 Hz, 1H), 5.51 (d, J=12.1 Hz, 1H), 5.37 (s, 1H), 5.24 (s, 1H), 4.03 (q, J=7.1 Hz, 1H), 3.46 (d, J=4.9 Hz, 5H), 3.39 (q, J=11.1, 9.7 Hz, 2H), 3.32-3.23 (m, 1H), 3.19 (t, J=5.3 Hz, 4H), 2.15-2.05 (m, 1H), 1.99 (s, 2H), 1.43 (s, 9H), 1.17 (t, J=7.1 Hz, 2H).

Step 2: tert-butyl 4-{4-[6-(2-ethyl-6-fluoro-3-{[(3R)-3-fluoropyrrolidin-1-ylsulfonyl]amino}phenoxy)-4-oxoquinazolin-3-yl]phenyl}piperazine-1-carboxylate

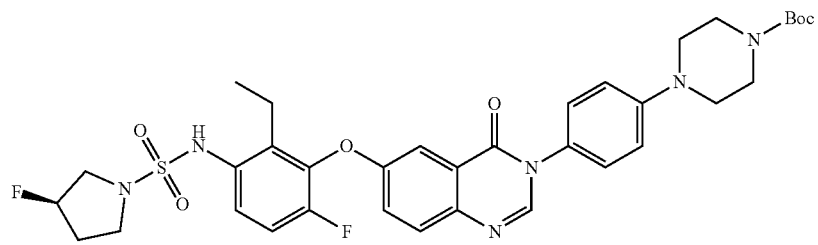 [SMILES: CCc1c(NS(=O)(=O)N2CC[C@@H](F)C2)ccc(F)c1Oc1ccc2ncn(-c3ccc(N4CCN(C(=O)OC(C)(C)C)CC4)cc3)c(=O)c2c1]

To a stirred solution of tert-butyl 4-{4-[6-(2-ethenyl-6-fluoro-3-{[(3R)-3-fluoropyrrolidin-1-ylsulfonyl]amino}phenoxy)-4-oxoquinazolin-3-yl]phenyl}piperazine-1-carboxylate (100 mg, 0.1 mmol) in methanol (10 mL) was added 10% palladium over carbon (15 mg). The mixture was degassed and purged with hydrogen for three times, then stirred for 2 h at room temperature under hydrogen atmosphere. The resulting mixture was filtered through Celite pad, washed with methanol (3×30 mL). The filtrate was concentrated under reduced pressure to afford tert-butyl 4-{4-[6-(2-ethyl-6-fluoro-3-{[(3R)-3-fluoropyrrolidin-1-ylsulfonyl]amino}phenoxy)-4-oxoquinazolin-3-yl]phenyl}piperazine-1-carboxylate (90 mg, 90%) as an off-white solid, which was used in the next step without further purification. MS (ESI): m/z 710.3 [M+H]⁺.

Step 3: (3R)—N-[2-ethyl-4-fluoro-3-({4-oxo-3-[4-(piperazin-1-yl)phenyl]quinazolin-6-yl}oxy)phenyl]-3-fluoropyrrolidine-1-sulfonamide

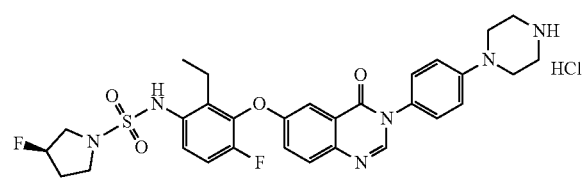 [SMILES: CCc1c(NS(=O)(=O)N2CC[C@@H](F)C2)ccc(F)c1Oc1ccc2ncn(-c3ccc(N4CCNCC4)cc3)c(=O)c2c1 ; Cl]

A solution of tert-butyl 4-{4-[6-(2-ethyl-6-fluoro-3-{[(3R)-3-fluoropyrrolidin-1-ylsulfonyl]amino}phenoxy)-4-oxoquinazolin-3-yl]phenyl}piperazine-1-carboxylate (90 mg, 0.1 mmol) in 4 M hydrochloric acid in 1,4-dioxane (15 mL) was stirred for 2 h at room temperature under nitrogen atmosphere. The resulting mixture was concentrated under reduced pressure to afford (3R)—N-[2-ethyl-4-fluoro-3-({4-oxo-3-[4-(piperazin-1-yl)phenyl]quinazolin-6-yl}oxy)phenyl]-3-fluoropyrrolidine-1-sulfonamide hydrochloride (70 mg, 91%) as an off-white solid, which was used in the next step without further purification. MS (ESI): m/z 610.3 [M+H]⁺.

Intermediate 29: (3R)—N-[2-cyano-4-fluoro-3-[4-oxo-3-[4-(3-piperidyl)phenyl]quinazolin-6-yl]oxyphenyl]-3-fluoro-pyrrolidine-1-sulfonamide

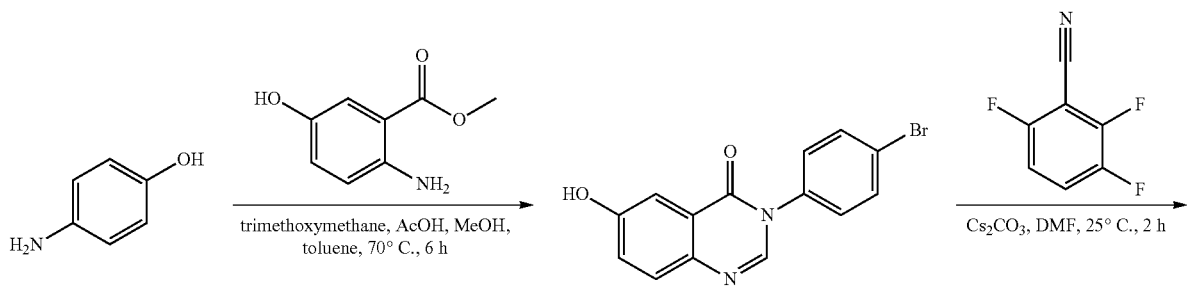

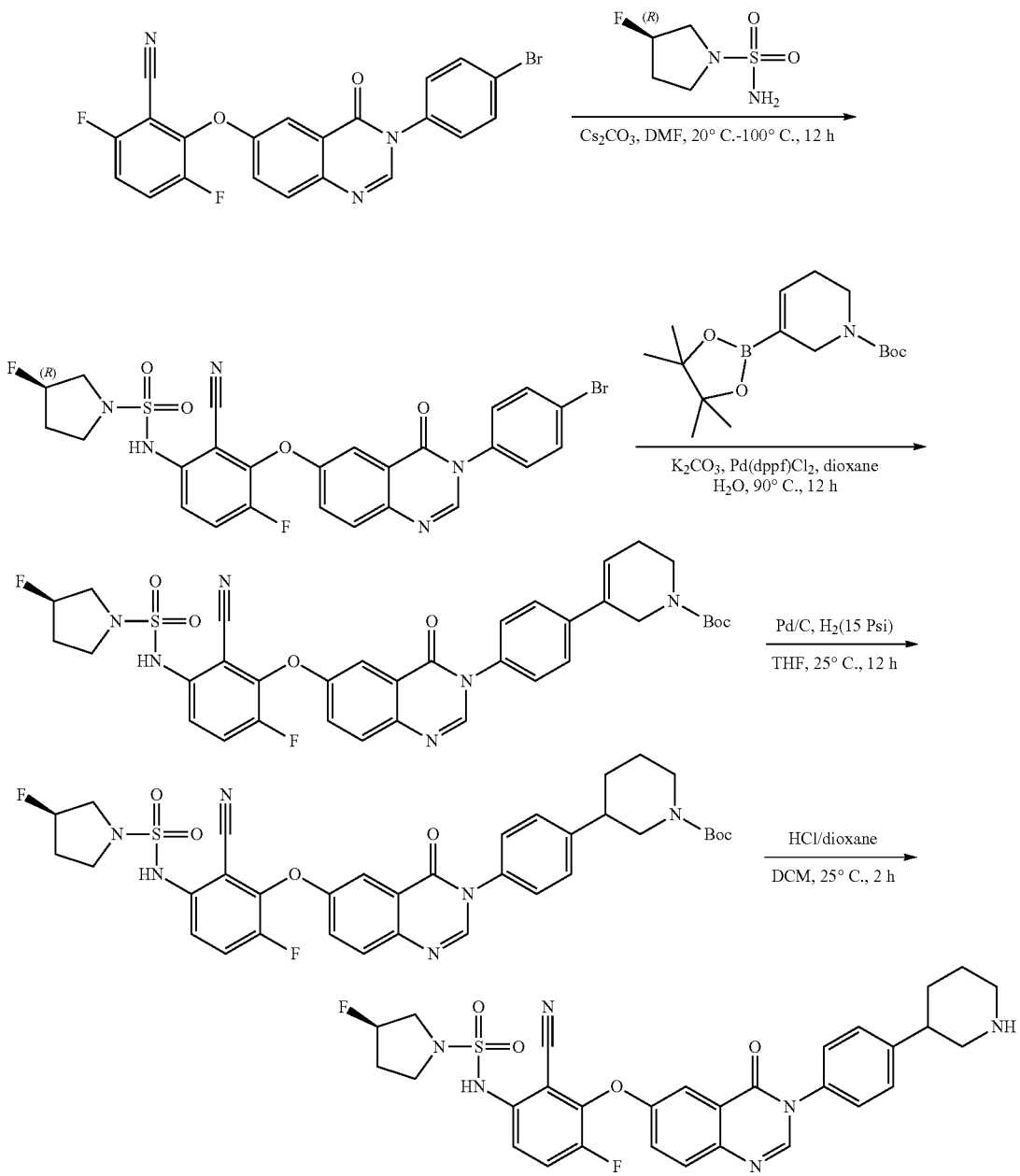

Step 1:
3-(4-bromophenyl)-6-hydroxy-quinazolin-4-one

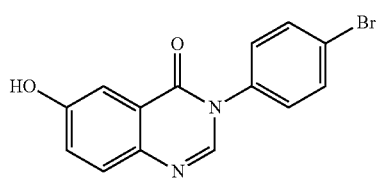 [SMILES: O=c1c2cc(O)ccc2ncn1-c1ccc(Br)cc1]

To a solution of 4-bromoaniline (5.0 g, 29 mmol) in toluene (15 mL) was added trimethoxymethane (4.8 mL, 44 mmol) and acetic acid (1.7 mL, 29 mmol), followed by the addition of methyl 2-amino-5-hydroxy-benzoate (4.86 g, 29 mmol) in methanol (2 mL). The mixture was stirred at 70° C. for 6 h, then cooled to room temperature. The mixture was suspended in methyl tert-butyl ether (15 mL), filtered, and the filter cake was triturated with water (15 mL) to afford 3-(4-bromophenyl)-6-hydroxy-quinazolin-4-one (9.65 g, 83%) as a dark brown solid. MS (ESI) m/z: 318.8 [M+H]$^+$.

Step 2: 2-[3-(4-bromophenyl)-4-oxo-quinazolin-6-yl]oxy-3,6-difluoro-benzonitrile

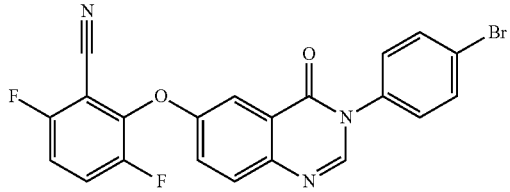 [SMILES: N#Cc1c(F)ccc(F)c1Oc1ccc2ncn(-c3ccc(Br)cc3)c(=O)c2c1]

To a solution of 3-(4-bromophenyl)-6-hydroxy-quinazolin-4-one (5.0 g, 13 mmol) and 2,3,6-trifluorobenzonitrile (2.58 g, 16 mmol) in dimethyl formamide (100 mL) was added cesium carbonate (4.73 g, 14 mmol). The mixture was stirred at 25° C. for 2 h, then diluted with water (20 mL) and extracted with ethyl acetate (3×20 mL). The combined organic layers were washed with brine (3×15 mL), dried over anhydrous sodium sulfate, filtered, and concentrated under reduced pressure. The residue was purified by flash silica gel chromatography (0-36% ethyl acetate/petroleum ether) to afford 2-[3-(4-bromophenyl)-4-oxo-quinazolin-6-yl]oxy-3,6-difluoro-benzonitrile (3.26 g, 56%) as an off-white solid. MS (ESI) m/z: 455.7 [M+H]$^+$; $^1$H NMR (400 MHz, DMSO-d$_6$) δ 8.33 (s, 1H), 7.98 (dt, J=5.2, 10.0 Hz, 1H), 7.86-7.82 (m, 1H), 7.80-7.75 (m, 3H), 7.63-7.51 (m, 4H).

Step 3: (3R)—N-[3-[3-(4-bromophenyl)-4-oxo-quinazolin-6-yl]oxy-2-cyano-4-fluoro-phenyl]-3-fluoro-pyrrolidine-1-sulfonamide

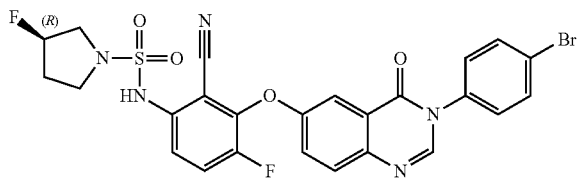

To a solution of 2-[3-(4-bromophenyl)-4-oxo-quinazolin-6-yl]oxy-3,6-difluoro-benzonitrile (4.97 g, 11 mmol) in N,N-dimethylformamide (100 mL) was added cesium carbonate (7.84 g, 24 mmol). The mixture was stirred at 50° C. for 0.5 h. Then the mixture was cooled to 20° C. and (3R)-3-fluoropyrrolidine-1-sulfonamide (1.84 g, 11 mmol) in N,N-dimethylformamide (50 mL) was added, the resulting mixture was stirred at 100° C. for 11.5 h. The reaction was filtered and concentrated under reduced pressure. The crude product was purified by reversed-phase high performance liquid chromatography (40%-70% acetonitrile in water (0.2% formic acid) over 22 min) to afford (3R)—N-[3-[3-(4-bromophenyl)-4-oxo-quinazolin-6-yl]oxy-2-cyano-4-fluoro-phenyl]-3-fluoro-pyrrolidine-1-sulfonamide (5 g, 75%) as a light yellow solid. MS (ESI) m/z: 604.1 [M+H]$^+$; $^1$H NMR (400 MHz, DMSO-d$_6$) δ 10.36 (s, 1H), 8.31 (s, 1H), 8.14 (s, 1H), 7.89-7.83 (m, 2H), 7.78-7.72 (m, 3H), 7.52-7.50 (m, 2H), 7.44 (d, J=2.8 Hz, 1H), 3.53 (s, 1H), 3.50-3.39 (m, 3H), 2.21-1.97 (m, 3H).

Step 4: tert-butyl 5-[4-[6-[2-cyano-6-fluoro-3-[[(3R)-3-fluoropyrrolidin-1-yl]sulfonylamino]phenoxy]-4-oxo-quinazolin-3-yl]phenyl]-3,6-dihydro-2H-pyridine-1-carboxylate

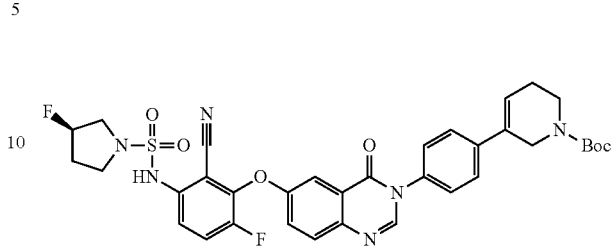

To a solution of (3R)—N-[3-[3-(4-bromophenyl)-4-oxo-quinazolin-6-yl]oxy-2-cyano-4-fluoro-phenyl]-3-fluoro-pyrrolidine-1-sulfonamide (500 mg, 0.8 mmol) and tert-butyl 5-(4,4,5,5-tetramethyl-1,3,2-dioxaborolan-2-yl)-3,6-dihydro-2H-pyridine-1-carboxylate (256 mg, 0.8 mmol) in 1,4-dioxane (10 mL) and water (2 mL) was added potassium carbonate (229 mg, 1.7 mmol) and [1,1'-bis(diphenylphosphino)ferrocene]dichloropalladium(II) (60 mg, 0.08 mmol). The mixture was stirred at 90° C. for 12 h, then cooled to room temperature. The reaction mixture was diluted with water (10 mL) and extracted with ethyl acetate (3×10 mL). The combined organic layers were washed with brine (3×10 mL), dried over anhydrous sodium sulfate, filtered, and concentrated under reduced pressure. The residue was purified by flash silica gel chromatography (0-3% methanol/dichloromethane) to afford tert-butyl 5-[4-[6-[2-cyano-6-fluoro-3-[[(3R)-3-fluoropyrrolidin-1-yl]sulfonylamino]phenoxy]-4-oxo-quinazolin-3-yl]phenyl]-3,6-dihydro-2H-pyridine-1-carboxylate (410 mg, 70%) as a light yellow solid. MS (ESI) m/z: 705.2 [M+H]$^+$.

Step 5: tert-butyl 3-[4-[6-[2-cyano-6-fluoro-3-[[(3R)-3-fluoropyrrolidin-1-yl]sulfonylamino]phenoxy]-4-oxo-quinazolin-3-yl]phenyl]piperidine-1-carboxylate

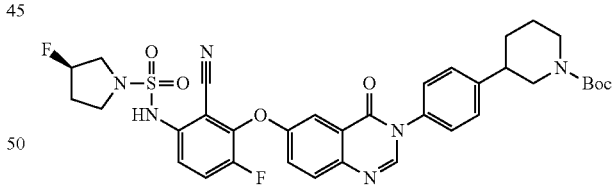

To a solution of tert-butyl 5-[4-[6-[2-cyano-6-fluoro-3-[[(3R)-3-fluoropyrrolidin-1-yl]sulfonylamino]phenoxy]-4-oxo-quinazolin-3-yl]phenyl]-3,6-dihydro-2H-pyridine-1-carboxylate (410 mg, 0.6 mmol) in tetrahydrofuran (5 mL) was added 10% palladium on activated carbon (60 mg). The mixture was degassed and purged with hydrogen three times, then the mixture was allowed to stir under hydrogen atmosphere (15 psi) at 25° C. for 12 h. The reaction mixture was filtered through Celite pad and concentrated under reduced pressure to afford tert-butyl 3-[4-[6-[2-cyano-6-fluoro-3-[[(3R)-3-fluoropyrrolidin-1-yl]sulfonylamino]phenoxy]-4-oxo-quinazolin-3-yl]phenyl]piperidine-1-carboxylate (441 mg, crude) as a light yellow solid. MS (ESI) m/z: 707.1 [M+H]$^+$.

Step 6: (3R)—N-[2-cyano-4-fluoro-3-[4-oxo-3-[4-(3-piperidyl)phenyl]quinazolin-6-yl]oxy-phenyl]-3-fluoro-pyrrolidine-1-sulfonamide

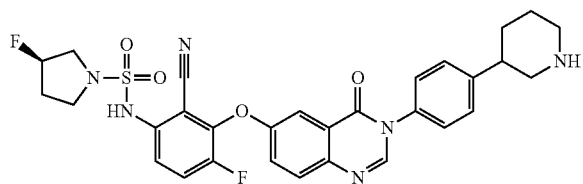 [SMILES: N#Cc1c(NS(=O)(=O)N2CC[C@@H](F)C2)ccc(F)c1Oc1ccc2ncn(-c3ccc(C4CCCNC4)cc3)c(=O)c2c1]

To a solution of tert-butyl 3-[4-[6-[2-cyano-6-fluoro-3-[[(3R)-3-fluoropyrrolidin-1-yl]sulfonylamino]phenoxy]-4-oxo-quinazolin-3-yl]phenyl]piperidine-1-carboxylate (411 mg, 0.6 mmol) in dichloromethane (4 mL) was added 4 M hydrochloric acid in 1,4-dioxane (5.8 mL). The mixture was stirred at 25° C. for 2 h, then concentrated to afford (3R)—N-[2-cyano-4-fluoro-3-[4-oxo-3-[4-(3-piperidyl)phenyl]quinazolin-6-yl]oxy-phenyl]-3-fluoro-pyrrolidine-1-sulfonamide hydrochloride (510 mg, crude) as a yellow solid, which was used in the next step without further purification. MS (ESI) m/z: 607.2 [M+H]⁺.

The following intermediates may be prepared by a procedure analogous to Intermediate 29.

| Structure | MS |
|---|---|
|  | 593.2 [M + H]⁺ |
|  | 593.0 [M + H]⁺ |
|  | 607.2 [M + H]⁺ |

Intermediate 30: (3R)—N-(2-cyano-3-{[3-(4-{2,7-diazaspiro[3.5]nonan-7-yl}phenyl)-4-oxoquinazolin-6-yl]oxy}-4-fluorophenyl)-3-fluoropyrrolidine-1-sulfonamide

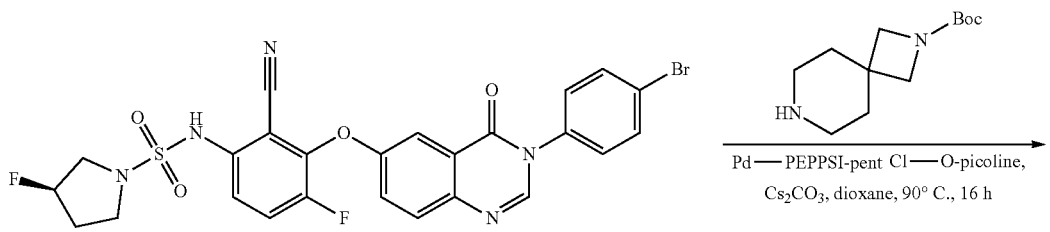

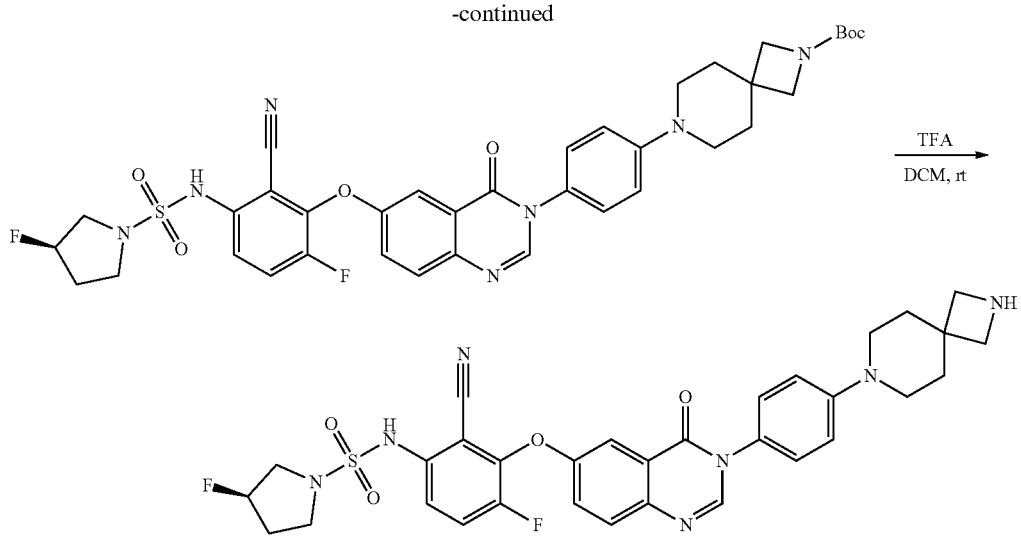

Step 1: tert-butyl 7-{4-[6-(2-cyano-6-fluoro-3-{[(3R)-3-fluoropyrrolidin-1-ylsulfonyl]amino}phenoxy)-4-oxoquinazolin-3-yl]phenyl}-2,7-diazaspiro[3.5]nonane-2-carboxylate

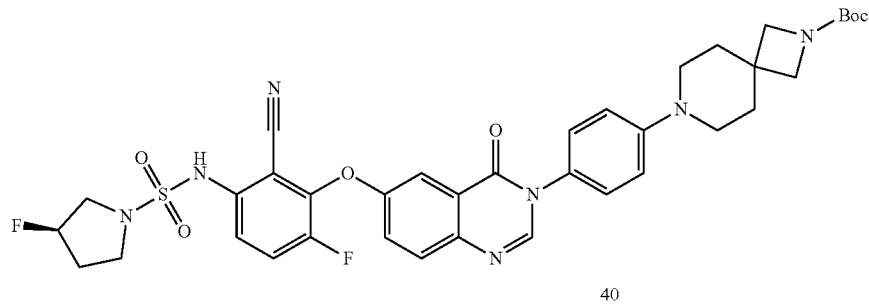

To a solution of (3R)—N-(3-{[3-(4-bromophenyl)-4-oxoquinazolin-6-yl]oxy}-2-cyano-4-fluorophenyl)-3-fluoropyrrolidine-1-sulfonamide (1 g, 2 mmol) in 1,4-dioxane (30 mL) was added tert-butyl 2,7-diazaspiro[3.5]nonane-2-carboxylate (0.75 g, 3 mmol), [1,3-bis(2,6-diisopropylphenyl)imidazol-2-ylidene](3-chloropyridyl)palladium(II) dichloride (0.08 g, 0.08 mmol) and cesium carbonate (1.1 g, 3 mmol), the mixture was stirred for 16 h at 100° C. under nitrogen. The resulting mixture was diluted with water (50 mL) and extracted with ethyl acetate (2×50 mL). The combined organic layers were washed with brine (2×20 mL), dried over anhydrous sodium sulfate, filtered, and concentrated. The residue was purified by silica gel column chromatography (dichloromethane/methanol=10:1) to afford tert-butyl 7-{4-[[6-(2-cyano-6-fluoro-3-{[(3R)-3-fluoropyrrolidin-1-ylsulfonyl]amino}phenoxy)-4-oxoquinazolin-3-yl]phenyl}-2,7-diazaspiro[3.5]nonane-2-carboxylate (680 mg, 55%) as a yellow solid. $^1$H NMR (400 MHz, DMSO-$d_6$) δ 10.34 (s, 1H), 8.26 (s, 1H), 7.89-7.87 (m, 2H), 7.83 (d, J=8.8 Hz, 1H), 7.72 (d, J=2.8 Hz, 1H), 7.69 (s, 1H), 7.31 (d, J=8.8 Hz, 1H), 7.05 (d, J=7.2 Hz, 1H), 5.32 (d, J=32 Hz, 1H), 3.60-3.48 (m, 5H), 3.46-3.44 (m, 3H), 3.21-3.20 (m, 4H), 2.20-2.18 (m, 2H), 1.67-1.60 (m, 4H), 1.40 (s, 9H); MS (ESI): m/z 748.35 [M+H]$^+$.

Step 2: (3R)—N-(2-cyano-3-{[3-(4-{2,7-diazaspiro[3.5]nonan-7-yl}phenyl)-4-oxoquinazolin-6-yl]oxy}-4-fluorophenyl)-3-fluoropyrrolidine-1-sulfonamide

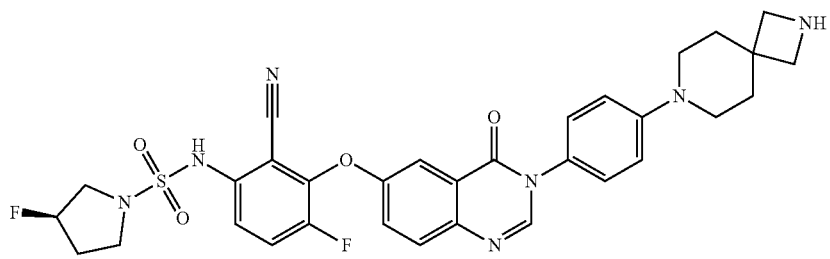 [SMILES: N#Cc1c(NS(=O)(=O)N2CC[C@@H](F)C2)ccc(F)c1Oc1ccc2ncn(-c3ccc(N4CCC5(CC4)CNC5)cc3)c(=O)c2c1]

To a solution of tert-butyl 7-{4-[6-(2-cyano-6-fluoro-3-{1[(3R)-3-fluoropyrrolidin-1-ylsulfonyl]amino}phenoxy)-4-oxoquinazolin-3-yl]phenyl}-2,7-diazaspiro[3.5]nonane-2-carboxylate (690 mg, 0.9 mmol) in dichloromethane (20 mL) was added trifluoroacetic acid (271 mg, 2.8 mmol), the reaction was stirred for 2 h at room temperature, then concentrated to afford (3R)—N-(2-cyano-3-{[3-(4-{2,7-diazaspiro[3.5]nonan-7-yl}phenyl)-4-oxoquinazolin-6-yl]oxy}-4-fluorophenyl)-3-fluoropyrrolidine-1-sulfonamide trifluoroacetate (580 mg, 97%) as a yellow oil. MS (ESI): m/z 648.50 [M+H]$^+$.

The following intermediates may be prepared by a procedure analogous to Intermediate 30.

| Structure | MS |
|---|---|
| 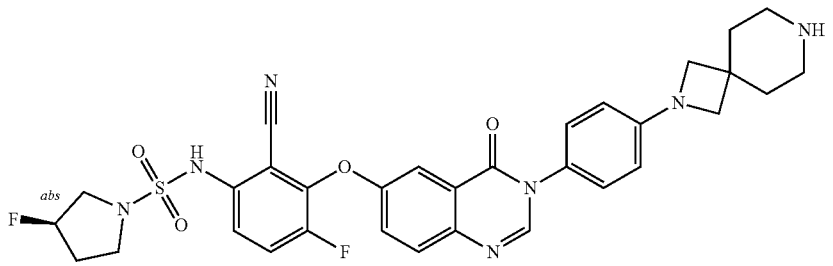 [SMILES: N#Cc1c(NS(=O)(=O)N2CC[C@@H](F)C2)ccc(F)c1Oc1ccc2ncn(-c3ccc(N4CC5(CCNCC5)C4)cc3)c(=O)c2c1]<br>Intermediate 41 | 648.25 [M + H]$^+$ |
| 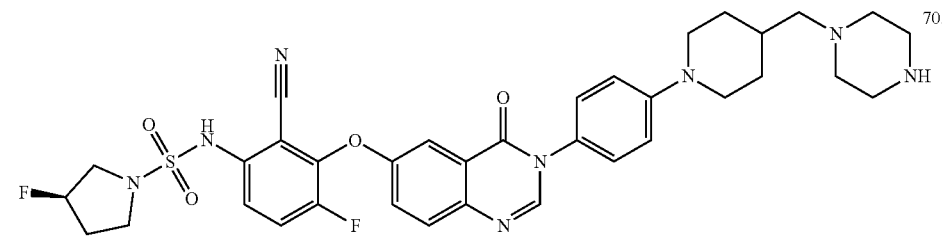<br>Intermediate 42 | 705.40 [M + H]$^+$ |
| 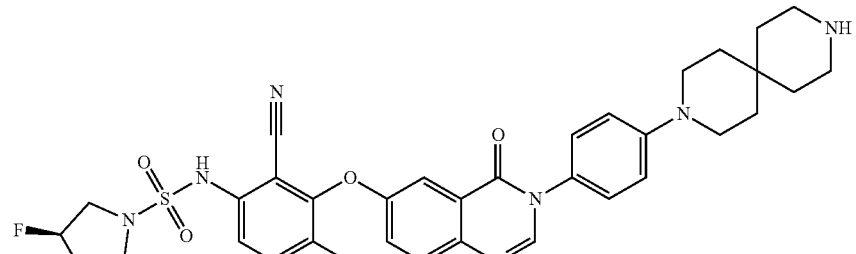<br>Intermediate 43 | 676.25 [M + H]$^+$ |
| 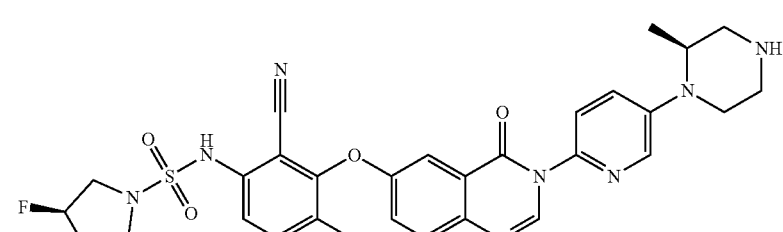<br>Intermediate 44 | 623.45 [M + H]$^+$ |

Example 1: (3R)—N-[2-cyano-3-[3-[4-[4-[[1-[2-(2,6-dioxo-3-piperidyl)-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide Step 1: benzyl 4-(hydroxymethyl) piperidine-1-carboxylate

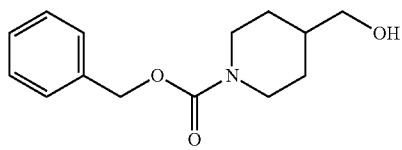 [SMILES: O=C(OCc1ccccc1)N1CCC(CO)CC1]

To a solution of 4-piperidylmethanol (5.0 g, 43 mmol) in dichloromethane (100 mL) was added sodium carbonate (20.7 g, 195 mmol) in water (100 mL) at 0° C., then carbobenzoxy chloride (48 mmol, 6.8 mL) was added dropwise. The mixture was stirred at 20° C. for 16 h, diluted with water (100 mL), extracted with dichloromethane (2×100 mL). The combined organic layers were washed with brine (2×100 mL), dried over sodium sulfate, filtered, and concentrated. The residue was purified by silica gel chromatography (petroleum ether:ethyl acetate=10:1 to 2:1) to afford benzyl 4-(hydroxymethyl) piperidine-1-carboxylate (14.2 g, 66%) as a colorless oil. $^1$H NMR (400 MHz, CDCl$_3$) δ 7.44-7.30 (m, 5H), 5.15 (s, 2H), 4.35-4.16 (m, 2H), 3.53 (t, J=5.7 Hz, 2H), 2.81 (s, 2H), 1.82-1.64 (m, 3H), 1.42 (t, J=5.4 Hz, 1H), 1.19 (d, 2H).

Step 2: benzyl 4-formylpiperidine-1-carboxylate

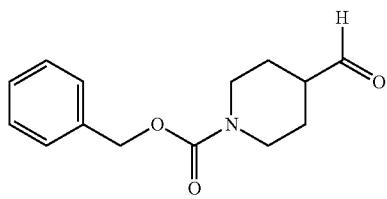 [SMILES: O=CC1CCN(C(=O)OCc2ccccc2)CC1]

To a solution of benzyl 4-(hydroxymethyl) piperidine-1-carboxylate (13.2 g, 53 mmol) in dichloromethane (200 mL) was added Dess-Martin reagent (18 mL, 58 mmol,) at 0° C. The mixture was stirred at 20° C. for 2 h, then diluted with saturated sodium bicarbonate solution (300 mL) and extracted with dichloromethane (2×200 mL). The combined organic layers were washed with brine (2×200 mL), dried over sodium sulfate, filtered, and concentrated. The residue was purified by silica gel chromatography (petroleum ether: ethyl acetate=10:1 to 3:1) to afford benzyl 4-formylpiperidine-1-carboxylate (11.6 g, 88%) as a colorless oil. $^1$H NMR (400 MHz, CDCl$_3$) δ 9.69 (s, 1H), 7.44-7.30 (m, 5H), 5.15 (s, 2H), 4.13-3.99 (m, 2H), 3.05 (t, J=11.0 Hz, 2H), 2.51-2.42 (m, 1H), 1.94 (s, 2H), 1.68-1.58 (t, J=7.2 Hz, 2H).

Step 3: benzyl 4-(dimethoxymethyl) piperidine-1-carboxylate

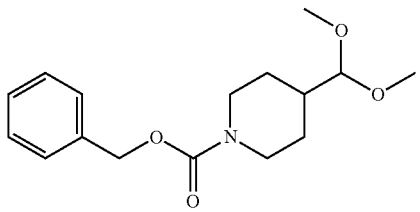 [SMILES: COC(OC)C1CCN(C(=O)OCc2ccccc2)CC1]

To a solution of benzyl 4-formylpiperidine-1-carboxylate (11 g, 45 mmol) in methanol (100 mL) was added trimethoxymethane (24.0 mL, 222 mmol) and 4-methylbenzenesulfonic acid hydrate (423 mg, 2.2 mmol). The mixture was stirred at 20° C. for 12 h, diluted with water (200 mL) and extracted with dichloromethane (2×200 mL). The combined organic layers were washed with brine (2×200 mL), dried over sodium sulfate, filtered, and concentrated to afford benzyl 4-(dimethoxymethyl)piperidine-1-carboxylate (11.2 g, 86%) as a colorless oil. $^1$H NMR (400 MHz, CDCl$_3$) δ 7.42-7.30 (m, 5H), 5.14 (s, 2H), 4.33-4.13 (m, 2H), 4.04 (d, J=6.9 Hz, 1H), 3.37 (s, 6H), 2.76 (s, 2H), 1.86-1.70 (m, 3H), 1.34-1.16 (m, 2H).

Step 4: 4-(dimethoxymethyl)piperidine

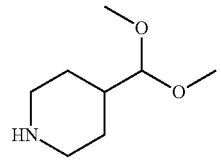

To a solution of benzyl 4-(dimethoxymethyl) piperidine-1-carboxylate (11.2 g, 38 mmol) in methanol (150 mL) was added 10% palladium on carbon (1.25 g, 3.8 mmol) under nitrogen. The suspension was degassed under vacuum and purged with hydrogen several times. The mixture was stirred under hydrogen (15 psi) at 20° C. for 12 h, then filtered, and concentrated to afford 4-(dimethoxymethyl)piperidine (5.92 g, 97%) as a colorless oil. $^1$H NMR (400 MHz, CDCl$_3$) δ 3.95 (d, J=6.8 Hz, 1H), 3.28 (s, 6H), 3.03 (d, J=12.0 Hz, 2H), 2.50 (d, 2H), 1.75-1.64 (m, 4H), 1.24-1.04 (m, 2H).

Step 5: methyl 2-bromo-4-[4-(dimethoxymethyl)-1-piperidyl]benzoate

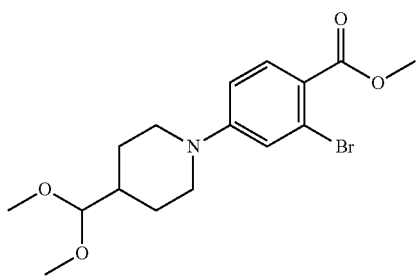

To a solution of 4-(dimethoxymethyl)piperidine (44.4 g, 279 mmol) and methyl 2-bromo-4-fluoro-benzoate (50.0 g, 215 mmol) in dimethyl sulfoxide (500 mL) was added N,N-diisopropylethylamine (55.5 g, 429 mmol). The mixture was stirred at 120° C. for 2 h, diluted with water (1500 mL) and extracted with ethyl acetate (3×500 mL). The combined organic layers were washed with brine (3×1000 mL), dried over anhydrous sodium sulfate, filtered and concentrated. The crude product was triturated with petroleum ether and ethyl acetate (20:1, 200 mL) to give methyl 2-bromo-4-[4-(dimethoxymethyl)-1-piperidyl]benzoate (64 g, 79%) as a light yellow solid.

Step 6: methyl 4-[4-(dimethoxymethyl)-1-piperidyl]-2-formyl-benzoate

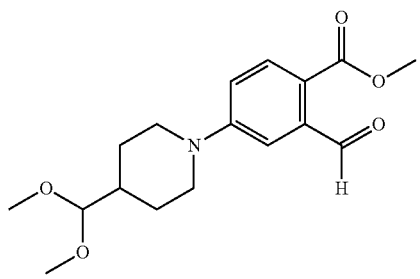

To a solution of methyl 2-bromo-4-[4-(dimethoxymethyl)-1-piperidyl]benzoate (52.0 g, 140 mmol) in N,N-dimethylformamide (500 mL) was added 2-isocyano-2-methyl-propane (23.2 g, 279 mmol), palladium acetate (3.14 g, 14 mmol), tricyclohexylphosphine (3.92 g, 14 mmol), sodium carbonate (14.81 g, 140 mmol) and triethylsilane (48.73 g, 419 mmol). The mixture was stirred at 65° C. for 12 h in an autoclave. The mixture was diluted with water (500 mL) and extracted with ethyl acetate (3×300 mL). The combined organic layers were washed with brine (3×500 mL), dried over anhydrous sodium sulfate, filtered, and concentrated. The residue was purified by flash silica gel chromatography (0-15% ethyl acetate/petroleum ether). Then the crude product was triturated with petroleum ether and ethyl acetate (10:1, 300 mL) to afford methyl 4-[4-(dimethoxymethyl)-1-piperidyl]-2-formyl-benzoate (22 g, 49%) as a light yellow solid. $^1$H NMR (400 MHz, CDCl$_3$) δ 10.74 (s, 1H), 7.90 (d, J=8.8 Hz, 1H), 7.33 (d, J=2.8 Hz, 1H), 7.00 (dd, J=2.8, 8.8 Hz, 1H), 4.06 (d, J=6.4 Hz, 1H), 3.96 (d, J=12.8 Hz, 2H), 3.91 (s, 3H), 3.38 (s, 6H), 2.93-2.82 (m, 2H), 1.86 (d, J=10.0 Hz, 3H), 1.46-1.35 (m, 2H).

Step 7: 3-[5-[4-(dimethoxymethyl)-1-piperidyl]-1-oxo-isoindolin-2-yl]piperidine-2,6-dione

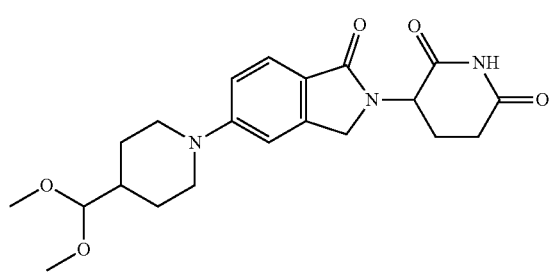

To a solution of 3-aminopiperidine-2,6-dione hydrochloride (12.11 g, 74 mmol) in methanol (400 mL) was added sodium acetate (10.98 g, 134 mmol). The mixture was stirred at 15° C. for 10 min. Then acetic acid (40.18 g, 669 mmol) and methyl 4-[4-(dimethoxymethyl)-1-piperidyl]-2-formyl-benzoate (21.5 g, 67 mmol) were added to the mixture and stirred at 15° C. for 20 min. Then sodium cyanoborohydride (8.41 g, 134 mmol) was added to the mixture. The mixture was stirred at 35° C. for 11.5 h. The crude product was poured into ice water (1000 mL) and adjusted the pH to 8 by saturated sodium bicarbonate. The mixture was stirred at 15° C. for 10 min, filtered, and the filter cake was washed with water (200 mL) and acetonitrile (2×200 mL). The filter cake was dried in vacuum, triturated with ethyl acetate (100 mL) to give 3-[5-[4-(dimethoxymethyl)-1-piperidyl]-1-oxo-isoindolin-2-yl]piperidine-2,6-dione (20 g, 73%) as a light-yellow solid. MS (ESI) m/z: 402.2 [M+H]$^+$; $^1$H NMR (400 MHz, DMSO-d6) δ 10.93 (s, 1H), 7.49 (d, J=8.4 Hz, 1H), 7.07-7.00 (m, 2H), 5.04 (dd, J=5.2, 13.2 Hz, 1H), 4.35-4.25 (m, 1H), 4.24-4.14 (m, 1H), 4.07 (d, J=6.8 Hz, 1H), 3.89 (d, J=12.8 Hz, 2H), 3.27 (s, 6H), 2.94-2.85 (m, 1H), 2.83-2.72 (m, 2H), 2.63-2.54 (m, 1H), 2.36 (dq, J=4.4, 13.2 Hz, 1H), 2.00-1.91 (m, 1H), 1.80 (dtd, J=3.6, 7.6, 15.2 Hz, 1H), 1.70 (d, J=12.8 Hz, 2H), 1.30 (dq, J=3.6, 12.4 Hz, 2H).

Step 8: 1-[2-(2,6-dioxo-3-piperidyl)-1-oxo-isoindolin-5-yl]piperidine-4-carbaldehyde

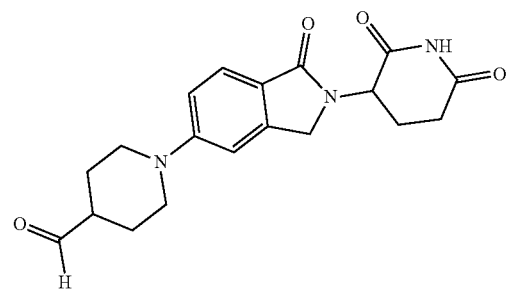 [SMILES: O=CC1CCN(c2ccc3c(c2)CN(C2CCC(=O)NC2=O)C3=O)CC1]

To a solution of 3-[5-[4-(dimethoxymethyl)-1-piperidyl]-1-oxo-isoindolin-2-yl]piperidine-2,6-dione (500 mg, 1.3 mmol) in tetrahydrofuran (50 mL) was added 2 M sulfuric acid (25 mL). The mixture was stirred at 20° C. for 2 h. The reaction was diluted with water (50 mL) and adjusted the pH to 8-9 with saturated aqueous sodium bicarbonate. The mixture was extracted with dichloromethane (3×50 mL). The combined organic layers were washed with brine (3×70 mL), dried over anhydrous sodium sulfate, filtered, and concentrated to afford 1-[2-(2,6-dioxo-3-piperidyl)-1-oxo-isoindolin-5-yl]piperidine-4-carbaldehyde (390 mg, 88%) as a white solid. MS (ESI) m/z: 356.0 [M+H]$^+$.

Step 9: (3R)—N-[2-cyano-3-[3-[4-[4-[[1-[2-(2,6-dioxo-3-piperidyl)-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide

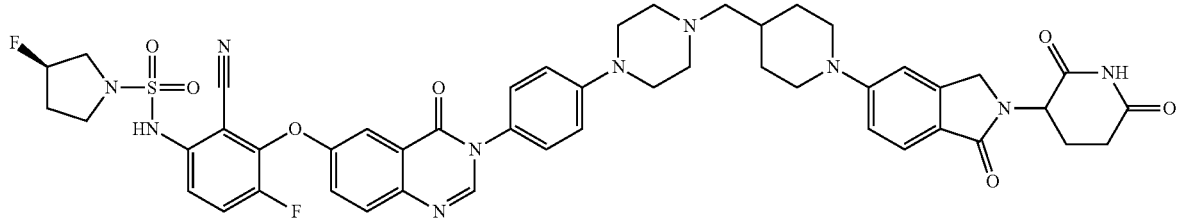 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)cc3)c(=O)c2c1]

To a solution of (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide hydrochloride (100 mg, 0.2 mmol) and 1-[2-(2,6-dioxo-3-piperidyl)-1-oxo-isoindolin-5-yl]piperidine-4-carbaldehyde (66 mg, 0.2 mmol) in isopropanol (5 mL) and dichloromethane (5 mL) was added triethylamine (0.06 mL, 0.5 mmol). The mixture was stirred at 25° C. for 0.5 h, then sodium triacetoxyborohydride (98 mg, 0.5 mmol) was added and stirred at 25° C. for 12 h. The residue was diluted with water (10 mL) and extracted with dichloromethane (3×10 mL). The combined organic layers were washed with brine (3×10 mL), dried over anhydrous sodium sulfate, filtered, and concentrated. The residue was purified by preparative HPLC (mobile phase: [0.2% formic acid in water-acetonitrile]; B %: 17%-47%, 10 min) to afford (3R)—N-[2-cyano-3-[3-[4-[4-[[1-[2-(2,6-dioxo-3-piperidyl)-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide (71.2 mg, 46%) as a white solid. MS (ESI) m/z: 947.3 [M+H]$^+$; $^1$H NMR (400 MHz, DMSO-d$_6$) δ 10.94 (s, 1H), 8.25 (s, 1H), 8.13 (s, 1H), 7.82 (d, J=8.8 Hz, 1H), 7.69 (dd, J=3.0, 8.8 Hz, 1H), 7.51 (d, J=8.8 Hz, 1H), 7.46-7.39 (m, 2H), 7.35 (d, J=8.8 Hz, 2H), 7.12-7.03 (m, 4H), 5.39-5.19 (m, 1H), 5.04 (dd, J=5.2, 13.2 Hz, 1H), 4.35-4.29 (m, 1H), 4.23-4.17 (m, 1H), 3.93-3.86 (m, 2H), 3.48-3.41 (m, 2H), 3.36 (d, J=3.2 Hz, 4H), 3.29-3.22 (m, 3H), 2.97-2.79 (m, 5H), 2.60 (d, J=2.8 Hz, 1H), 2.56 (s, 4H), 2.38 (dd, J=8.8, 13.2 Hz, 1H), 2.16-2.08 (m, 1H), 2.07-2.00 (m, 1H), 1.99-1.79 (m, 4H), 1.30-1.19 (m, 2H).

Example 2: (3R)—N-{2-cyano-3-[(3-{4-[4-({1-[2-(2,6-dioxopiperidin-3-yl)-1-oxo-2,3-dihydro-1H-isoindol-5-yl]azetidin-3-yl}methyl)piperazin-1-yl]phenyl}-4-oxo-3,4-dihydroquinazolin-6-yl)oxy]-4-fluorophenyl}-3-fluoropyrrolidine-1-sulfonamide Step 1: methyl 2-cyano-4-[3-(hydroxymethyl)azetidin-1-yl]benzoate

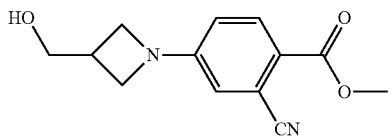

A mixture of azetidin-3-ylmethanol trifluoroacetic acid (2.01 g, 5.0 mmol, 50%), methyl 2-cyano-4-fluorobenzoate (1.08 g, 6.0 mmol), diisopropylethylamine (4.1 mL) and dimethyl sulfoxide (10 mL) was stirred in a sealed tube for 2 h at 110° C., then cooled to room temperature and diluted with water (100 mL). The mixture was extracted with ethyl acetate (2×100 mL). The organic fractions were combined and washed with brine (2×100 mL), dried over anhydrous sodium sulfate, and concentrated. The residue was purified by silica gel column (ethyl acetate/petroleum ether=1:1) to afford methyl 2-cyano-4-[3-(hydroxymethyl)azetidin-1-yl]benzoate (0.45 g, 37%) as a yellow green oil. MS (ESI): m/z 246.95 [M+H]$^+$.

Step 2: methyl 2-cyano-4-(3-formylazetidin-1-yl)benzoate

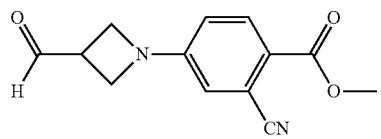 [SMILES: COC(=O)c1ccc(N2CC(C=O)C2)cc1C#N]

A mixture of methyl 2-cyano-4-[3-(hydroxymethyl)azetidin-1-yl]benzoate (7.33 g, 29.8 mmol), and Dess-Martin reagent (13.89 g, 32.7 mmol) in dichloromethane (150 mL) was stirred for 3 h at room temperature, then suspended in water (100 mL) and filtered. The filtrate was extracted with dichloromethane (3×100 mL), combined and concentrated to afford methyl 2-cyano-4-(3-formylazetidin-1-yl)benzoate (7.2 g, 99%) as a solid.

Step 3: methyl 2-cyano-4-[3-(dimethoxymethyl)azetidin-1-yl]benzoate

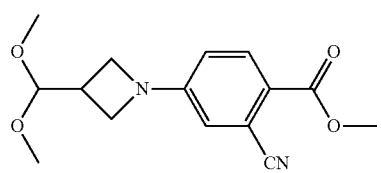 [SMILES: COC(=O)c1ccc(N2CC(C(OC)OC)C2)cc1C#N]

A mixture of methyl 2-cyano-4-(3-formylazetidin-1-yl)benzoate (7.30 g, 30 mmol), p-toluenesulfonic acid (0.26 g, 1.5 mmol), methanol (150 mL) and trimethoxymethane (9.48 g, 89 mmol) was stirred for 2 h at 45° C., then concentrated. The residue was purified by silica gel column (ethyl acetate/petroleum ether=1:5) to afford methyl 2-cyano-4-[3-(dimethoxymethyl)azetidin-1-yl]benzoate (8 g, 92%) as a solid. MS (ESI): m/z 291.00 [M+H]⁺.

Step 4: methyl 4-[3-(dimethoxymethyl)azetidin-1-yl]-2-formylbenzoate

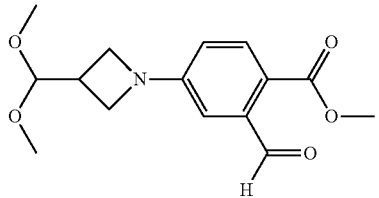 [SMILES: COC(=O)c1ccc(N2CC(C(OC)OC)C2)cc1C=O]

A mixture of methyl 2-cyano-4-[3-(dimethoxymethyl)azetidin-1-yl]benzoate (8.3 g, 29 mmol), pyridine (120 mL), acetic acid (60 mL), water (60 mL), sodium hypophosphite (25.2 g, 286 mmol) and Raney nickel (24.5 g, 286 mmol) was stirred overnight at 70° C., then filtered. The filtrate solution was extracted with ethyl acetate (3×100 mL), dried over anhydrous sodium sulfate and concentrated. The residue was purified by silica gel column (ethyl acetate/petroleum ether=1:5) to afford methyl 4-[3-(dimethoxymethyl)azetidin-1-yl]-2-formylbenzoate (3.11 g, 37%) as a yellow solid. MS (ESI): m/z 294.15 [M+H]⁺.

Step 5: 3-[5-[3-(dimethoxymethyl)azetidin-1-yl]-1-oxo-3H-isoindol-2-yl]piperidine-2,6-dione

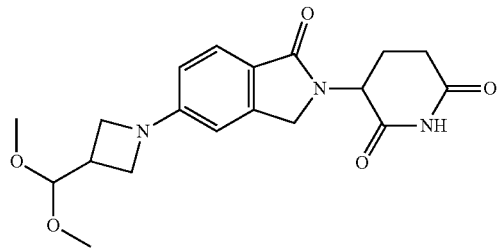 [SMILES: COC(OC)C1CN(c2ccc3c(c2)CN(C2CCC(=O)NC2=O)C3=O)C1]

To a stirred mixture of methyl 4-[3-(dimethoxymethyl)azetidin-1-yl]-2-formylbenzoate (3.10 g, 10.6 mmol), 3-aminopiperidine-2,6-dione hydrochloride (2.09 g, 12.7 mmol) and diisopropylethylamine (2 mL) in dichloromethane (200 mL) and methanol (4 mL) was added acetic acid (2 mL), the mixture was stirred for 4 h at 35° C. Then sodium cyanoborohydride (1.99 g, 31.7 mmol) was added and stirred for another 2 h at 35° C. The reaction was quenched by water (100 mL), extracted with dichloromethane (3×100 mL), dried over anhydrous sodium sulfate and concentrated. The residue was purified by silica gel column (dichloromethane/methanol=95:5) to afford 3-[5-[3-(dimethoxymethyl)azetidin-1-yl]-1-oxo-3H-isoindol-2-yl]piperidine-2,6-dione (3.72 g, 94%) as a light blue solid. MS (ESI): m/z 374.15 [M+H]⁺.

Step 6: 1-[2-(2,6-dioxopiperidin-3-yl)-1-oxo-3H-isoindol-5-yl]azetidine-3-carbaldehyde

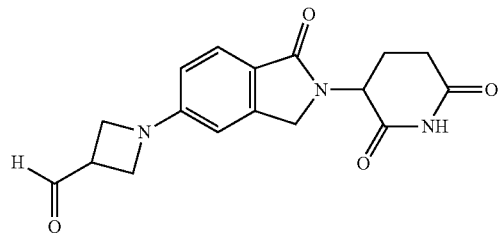 [SMILES: O=CC1CN(c2ccc3c(c2)CN(C2CCC(=O)NC2=O)C3=O)C1]

3-[5-[3-(dimethoxymethyl)azetidin-1-yl]-1-oxo-3H-isoindol-2-yl]piperidine-2,6-dione (1.5 g, 4.0 mmol) was dissolved in trifluoroacetic acid (20 mL), dichloromethane (40 mL) and water (10 mL). The resulting solution was stirred overnight at 40° C., then concentrated to afford 1-[2-(2,6-dioxopiperidin-3-yl)-1-oxo-3H-isoindol-5-yl]azetidine-3-carbaldehyde (1.3 g, 99%) as a yellow solid. MS (ESI): m/z 328.20 [M+H]⁺.

Step 7: (3R)—N-{2-cyano-3-[(3-{4-[4-({1-[2-(2,6-dioxopiperidin-3-yl)-1-oxo-3H-isoindol-5-yl]azetidin-3-yl}methyl)piperazin-1-yl]phenyl}-4-oxoquinazolin-6-yl)oxy]-4-fluorophenyl}-3-fluoropyrrolidine-1-sulfonamide

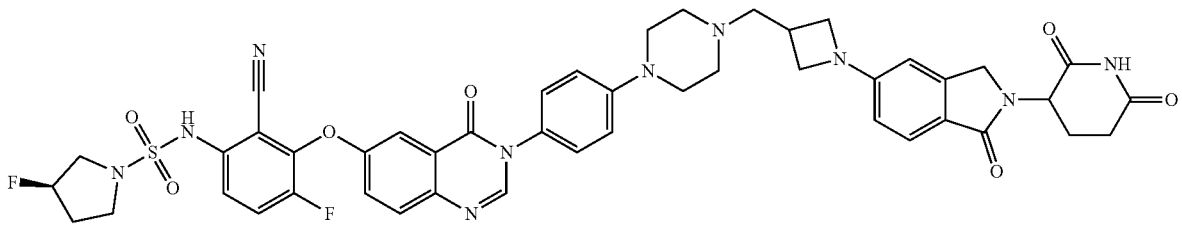 [SMILES: N#Cc1c(NS(=O)(=O)N2CC[C@@H](F)C2)ccc(F)c1Oc1ccc2ncn(-c3ccc(N4CCN(CC5CN(c6ccc7c(c6)CN(C6CCC(=O)NC6=O)C7=O)C5)CC4)cc3)c(=O)c2c1]

A mixture of (3R)—N-[2-cyano-4-fluoro-3-({4-oxo-3-[4-(piperazin-1-yl)phenyl]quinazolin-6-yl}oxy)phenyl]-3-fluoropyrrolidine-1-sulfonamide hydrochloride (350 mg, 0.5 mmol), 1-[2-(2,6-dioxopiperidin-3-yl)-1-oxo-3H-isoindol-5-yl]azetidine-3-carbaldehyde (214 mg, 0.7 mmol), acetic acid (98 mg, 1.6 mmol), diisopropylethylamine (70 mg, 0.5 mmol) and dichloroethane (20 mL) was stirred overnight under nitrogen atmosphere at room temperature. To the above mixture was added sodium triacetoxyborohydride (346 mg, 1.6 mmol), and stirred for another 1 h. The reaction was quenched with water (100 mL), extracted with ethyl acetate (2×100 mL). The combined organic layers were washed with brine (2×100 mL), dried over anhydrous sodium sulfate, filtered, and concentrated. The residue was purified by preparative thin layer chromatography (dichloromethane/methanol=10:1), the crude product was further purified by reversed-phase flash chromatography (mobile phase: acetonitrile in water (10 mM ammonium bicarbonate), 5% to 42% gradient in 30 min) to afford (3R)—N-{2-cyano-3-[(3-{4-[4-({1-[2-(2,6-dioxopiperidin-3-yl)-1-oxo-3H-isoindol-5-yl]azetidin-3-yl}methyl)piperazin-1-yl]phenyl}-4-oxoquinazolin-6-yl)oxy]-4-fluorophenyl}-3-fluoropyrrolidine-1-sulfonamide (130.5 mg, 26%) as a yellow solid. MS (ESI): m/z 917.35 [M+H]$^+$; $^1$H NMR (400 MHz, DMSO-d$_6$) δ 10.94 (s, 1H), 10.15 (s, 1H), 8.25 (s, 1H), 7.82 (d, J=8.9 Hz, 1H), 7.72-7.65 (m, 2H), 7.59-7.39 (m, 3H), 7.35 (d, J=8.5 Hz, 2H), 7.09 (d, J=8.7 Hz, 2H), 6.56-6.44 (m, 2H), 5.42-5.19 (m, 1H), 5.15-4.85 (m, 1H), 4.31 (d, J=17.0 Hz, 1H), 4.18 (d, J=17.0 Hz, 1H), 4.15-4.02 (m, 2H), 3.68-3.55 (m, 3H), 3.49-3.38 (m, 4H), 3.31-3.19 (m, 3H), 3.13-3.05 (m, 1H), 2.95-2.86 (m, 3H), 2.85-2.78 (m, 3H), 2.64-2.55 (m, 2H), 2.42-2.29 (m, 1H), 2.19-2.11 (m, 1H), 2.09-2.01 (m, 1H), 1.99-1.91 (m, 1H), 1.23 (s, 3H).

Example 3: (3R)—N-[2-cyano-3-[3-[6-[4-[[1-[2-(2,6-dioxo-3-piperidyl)-1-oxo-isoindolin-5-yl]-4-piperidyl]methyl]piperazin-1-yl]-3-pyridyl]-4-oxo-quinazolin-6-yl]oxy-4-fluoro-phenyl]-3-fluoro-pyrrolidine-1-sulfonamide Step 1: tert-butyl 4-[[1-[2-(2,6-dioxo-3-piperidyl)-1-oxo-isoindolin-5-yl]-4-piperidyl]methyl]piperazine-1-carboxylate

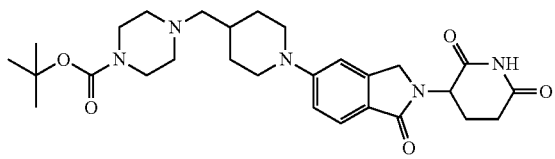 [SMILES: CC(C)(C)OC(=O)N1CCN(CC2CCN(c3ccc4c(c3)CN(C3CCC(=O)NC3=O)C4=O)CC2)CC1]

To a solution of 1-[2-(2,6-dioxo-3-piperidyl)-1-oxo-isoindolin-5-yl]piperidine-4-carbaldehyde (400 mg, 1.1 mmol) and tert-butyl piperazine-1-carboxylate hydrochloride (300 mg, 1.4 mmol) in dichloromethane (4 mL) and isopropanol (4 mL) was added triethylamine (469 μL, 3.4 mmol). The mixture was stirred at 25° C. for 0.5 h. Then sodium triacetoxyborohydride (715 mg, 3.4 mmol) was added to the mixture. The reaction was stirred at 25° C. for 11.5 h. Water (30 mL) was poured into the mixture and stirred for 1 min. The aqueous phase was extracted with ethyl acetate (3×30 mL). The combined organic phase was washed with brine (2×30 mL), dried over anhydrous sodium sulfate, filtered, and concentrated in vacuum. The residue was purified by flash silica gel chromatography (30-50% ethyl acetate/petroleum ether) to afford tert-butyl 4-[[1-[2-(2,6-dioxo-3-piperidyl)-1-oxo-isoindolin-5-yl]-4-piperidyl]methyl]piperazine-1-carboxylate (530 mg, 89%) as a white solid. MS (ESI) m/z: 526.4 [M+H]$^+$.

Step 2: 3-[1-oxo-5-[4-(piperazin-1-ylmethyl)-1-piperidyl]isoindolin-2-yl]piperidine-2,6-dione

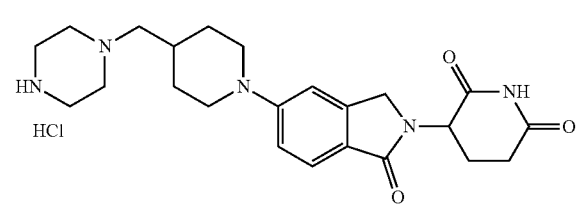 [SMILES: O=C1CCC(N2Cc3cc(N4CCC(CN5CCNCC5)CC4)ccc3C2=O)C(=O)N1 ; Cl]

To a solution of tert-butyl 4-[[1-[2-(2,6-dioxo-3-piperidyl)-1-oxo-isoindolin-5-yl]-4-piperidyl]methyl]piperazine-1-carboxylate (530 mg, 1.0 mmol) in dichloromethane (5 mL) was added 4 N hydrochloric acid in 1,4-dioxane (0.8 mL). The mixture was stirred at 25° C. for 12 h, then filtered to afford 3-[1-oxo-5-[4-(piperazin-1-ylmethyl)-1-piperidyl]isoindolin-2-yl]piperidine-2,6-dione hydrochloride (400 mg, 85%) as a white solid. MS (ESI) m/z: 426.0 [M+H]$^+$.

Step 3: (3R)—N-[2-cyano-3-[3-[6-[4-[[1-[2-(2,6-dioxo-3-piperidyl)-1-oxo-isoindolin-5-yl]-4-piperidyl]methyl]piperazin-1-yl]-3-pyridyl]-4-oxo-quinazolin-6-yl]oxy-4-fluoro-phenyl]-3-fluoro-pyrrolidine-1-sulfonamide

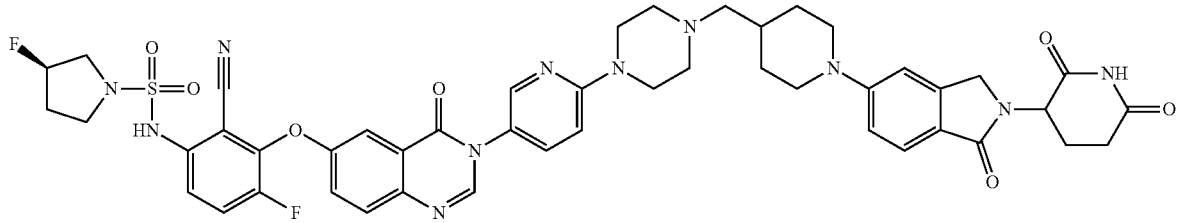 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)nc3)c(=O)c2c1]

To a solution of (3R)—N-[2-cyano-4-fluoro-3-[3-(6-fluoro-3-pyridyl)-4-oxo-quinazolin-6-yl]oxy-phenyl]-3-fluoro-pyrrolidine-1-sulfonamide (120 mg, 0.2 mmol) and 3-[1-oxo-5-[4-(piperazin-1-ylmethyl)-1-piperidyl]isoindolin-2-yl]piperidine-2,6-dione hydrochloride (204 mg, 0.4 mmol) in dimethyl sulfoxide (2 mL) was added diisopropylethylamine (85 mg, 0.7 mmol). The mixture was stirred at 100° C. for 12 h, then cooled and filtered, concentrated under reduced pressure. The residue was purified by preparative HPLC (column: Phenomenex Luna C18 150×25 mm×10 um; mobile phase: [0.2% formic acid in water-acetonitrile]; B %: 15%-45%, 10 min) to afford (3R)—N-[2-cyano-3-[3-[6-[4-[[1-[2-(2,6-dioxo-3-piperidyl)-1-oxo-isoindolin-5-yl]-4-piperidyl]methyl]piperazin-1-yl]-3-pyridyl]-4-oxo-quinazolin-6-yl]oxy-4-fluoro-phenyl]-3-fluoro-pyrrolidine-1-sulfonamide (41.8 mg, 19%) as a yellow solid. MS (ESI) m/z: 948.6 [M+H]$^+$; $^1$H NMR (400 MHz, DMSO-d$_6$) δ 10.95 (s, 1H), 10.36-9.74 (m, 1H), 8.28 (s, 1H), 8.23 (d, J=2.8 Hz, 1H), 7.83 (d, J=8.8 Hz, 1H), 7.78-7.61 (m, 3H), 7.51 (d, J=8.8 Hz, 1H), 7.47-7.39 (m, 2H), 7.10-6.97 (m, 3H), 5.42-5.20 (m, 1H), 5.05 (dd, J=4.8, 13.2 Hz, 1H), 4.39-4.29 (m, 1H), 4.27-4.15 (m, 1H), 3.91 (d, J=13.2 Hz, 2H), 3.77-3.58 (m, 3H), 3.51-3.41 (m, 4H), 3.32-3.21 (m, 4H), 2.97-2.91 (m, 1H), 2.88-2.81 (m, 2H), 2.61 (s, 1H), 2.59-2.55 (m, 2H), 2.44-2.37 (m, 1H), 2.18-1.79 (m, 7H), 1.31-1.21 (m, 2H).

Example 4: (3R)—N-(2-cyano-3-{[3-(4-{4-[2-(1-{2-[(3S)-2,6-dioxopiperidin-3-yl]-1-oxo-2,3-dihydro-1H-isoindol-5-yl}-4-hydroxypiperidin-4-yl)acetyl]piperazin-1-yl}phenyl)-4-oxo-3,4-dihydroquinazolin-6-yl]oxy}-4-fluorophenyl)-3-fluoropyrrolidine-1-sulfonamide Step 1: benzyl 4-(2-tert-butoxy-2-oxo-ethyl)-4-hydroxy-piperidine-1-carboxylate

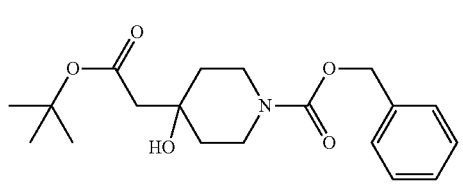 [SMILES: CC(C)(C)OC(=O)CC1(O)CCN(C(=O)OCc2ccccc2)CC1]

To a solution of N-isopropylpropan-2-amine (18.2 mL, 129 mmol) in tetrahydrofuran (120 mL) was added lithium n-butoxide (2.5 M, 51 mL) at 0° C., the mixture was purged with nitrogen for 3 times and stirred at 0° C. for 0.5 h under nitrogen. Then the mixture was cooled to −70° C. and tert-butyl acetate (17.0 mL, 129 mmol) was added. The mixture was stirred at −70° C. for 1 h. Then benzyl 4-oxopiperidine-1-carboxylate (10.3 mL, 51 mmol) in tetrahydrofuran (70 mL) was added and stirred at −70° C. for 1 h. The mixture was poured into ice and saturated aqueous ammonium chloride solution (w/w=1/10, 400 mL) and stirred for 30 min. The aqueous phase was extracted with ethyl acetate (3×500 mL). The combined organic phase was washed with saturated brine (3×500 mL), dried over anhydrous sodium sulfate, filtered, and concentrated. The crude product was purified by flash silica gel chromatography (0-30% ethyl acetate/petroleum ether) to afford benzyl 4-(2-tert-butoxy-2-oxo-ethyl)-4-hydroxy-piperidine-1-carboxylate (15.8 g, 87%) as a yellow oil. $^1$H NMR (400 MHz, DMSO-d$_6$) δ 7.44-7.23 (m, 5H), 5.06 (s, 2H), 4.63 (s, 1H), 3.73 (td, J=3.2, 12.8 Hz, 2H), 3.14 (s, 2H), 2.32 (s, 2H), 1.55 (dd, J=4.0, 7.2 Hz, 4H), 1.39 (s, 9H).

Step 2: tert-butyl 2-(4-hydroxy-4-piperidyl)acetate

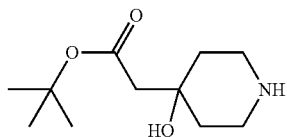

To a solution of benzyl 4-(2-tert-butoxy-2-oxo-ethyl)-4-hydroxy-piperidine-1-carboxylate (8.5 g, 24 mmol) in ethyl acetate (300 mL) was added 10% palladium on carbon (2 g) under nitrogen atmosphere. The suspension was degassed and purged with hydrogen for 3 times, then stirred at 20° C. for 12 h under hydrogen. The reaction mixture was filtered through Celite pad and concentrated to afford tert-butyl 2-(4-hydroxy-4-piperidyl)acetate (4.7 g, 89%) as an off-white oil. $^1$H NMR (400 MHz, DMSO-d$_6$) δ 3.04-2.95 (m, 2H), 2.78 (td, J=4.2, 12.4 Hz, 2H), 2.36 (s, 2H), 1.70-1.56 (m, 2H), 1.53-1.47 (m, 2H), 1.45 (s, 9H).

Step 3: methyl 2-bromo-4-[4-(2-tert-butoxy-2-oxo-ethyl)-4-hydroxy-1-piperidyl]benzoate

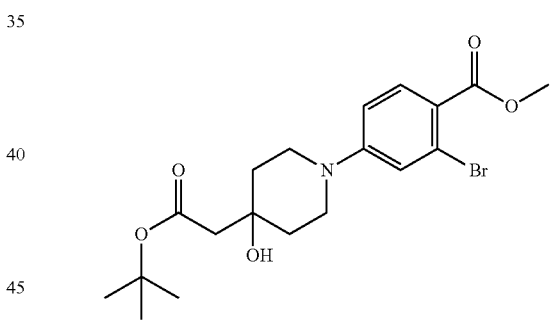

To a solution of tert-butyl 2-(4-hydroxy-4-piperidyl)acetate (1.8 g, 8.4 mmol) in dimethylsulfoxide (30 mL) was added diisopropylethylamine (4.9 mL, 28 mmol) and methyl 2-bromo-4-fluoro-benzoate (1.62 g, 7.0 mmol). The mixture was stirred at 90° C. for 12 h, then diluted with water (150 mL) and extracted with ethyl acetate 300 mL (3×100 mL). The combined organic layers were washed with brine (5×200 mL), dried over anhydrous sodium sulfate, filtered, and concentrated. The crude product was purified by flash silica gel chromatography (0-30% ethyl acetate/petroleum ether) to afford methyl 2-bromo-4-[4-(2-tert-butoxy-2-oxo-ethyl)-4-hydroxy-1-piperidyl]benzoate (2.7 g, 88%) as a yellow oil. MS (ESI) m/z: 430.2 [M+H]$^+$; $^1$H NMR (400 MHz, DMSO-d$_6$) δ 7.71 (d, J=9.0 Hz, 1H), 7.15 (d, J=2.5 Hz, 1H), 6.96 (dd, J=2.8, 9.2 Hz, 1H), 4.67 (s, 1H), 3.76 (s, 3H), 3.64 (br d, J=13.2 Hz, 2H), 3.26-3.16 (m, 2H), 2.33 (s, 2H), 1.74-1.54 (m, 4H), 1.35 (s, 9H).

Step 4: benzyl 4-(2-tert-butoxy-2-oxo-ethyl)-4-hydroxy-piperidine-1-carboxylate

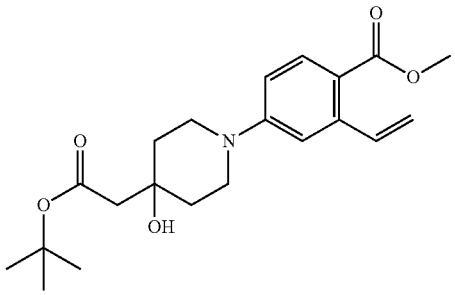 [SMILES: C=Cc1cc(N2CCC(O)(CC(=O)OC(C)(C)C)CC2)ccc1C(=O)OC]

A mixture of methyl 2-bromo-4-[4-(2-tert-butoxy-2-oxo-ethyl)-4-hydroxy-1-piperidyl]benzoate (2.8 g, 6 mmol), potassium vinyltrifluoroborate (3.50 g, 26 mmol), [1,1'-bis(diphenylphosphino)ferrocene]dichloropalladium(II) (478 mg, 0.7 mmol), sodium bicarbonate (1.73 g, 16 mmol) in 1,4-dioxane (30 mL) and water (5 mL) was degassed and purged with nitrogen for 3 times, then the mixture was stirred at 90° C. for 12 h under nitrogen. The mixture was diluted with water (150 mL) and extracted with ethyl acetate (2×100 mL). The combined organic layers were washed with brine (2×200 mL), dried over anhydrous sodium sulfate, filtered, and concentrated. The crude product was purified by flash silica gel chromatography (0-5% ethyl acetate/petroleum ether) to afford methyl 4-[4-(2-tert-butoxy-2-oxo-ethyl)-4-hydroxy-1-piperidyl]-2-vinyl-benzoate (2.4 g, 95%) as a yellow oil. MS (ESI) m/z: 376.2 [M+H]$^+$; $^1$H NMR (400 MHz, DMSO-d$_6$) δ 7.73 (d, J=8.8 Hz, 1H), 7.48 (dd, J=11.2, 17.6 Hz, 1H), 7.02 (d, J=2.4 Hz, 1H), 6.91 (dd, J=2.4, 8.8 Hz, 1H), 5.70 (dd, J=1.6, 17.4 Hz, 1H), 5.32-5.21 (m, 1H), 4.64 (s, 1H), 3.74 (s, 3H), 3.67 (d, J=13.2 Hz, 2H), 3.27-3.17 (m, 2H), 2.34 (s, 2H), 1.78-1.56 (m, 4H), 1.35 (s, 9H).

Step 5: tert-butyl 2-(4-hydroxy-4-piperidyl)acetate

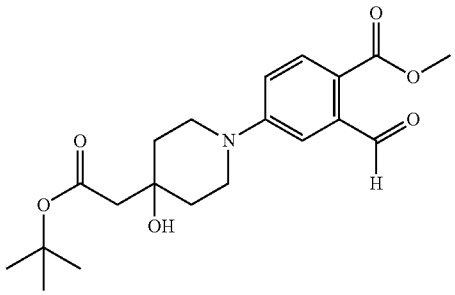 [SMILES: COC(=O)c1ccc(N2CCC(O)(CC(=O)OC(C)(C)C)CC2)cc1C=O]

To a solution of methyl 4-[4-(2-tert-butoxy-2-oxo-ethyl)-4-hydroxy-1-piperidyl]-2-vinyl-benzoate (1.2 g, 3 mmol) in 1,4-dioxane (20 mL) and water (4 mL) was added 2,6-dimethylpyridine (0.70 mL, 6 mmol), potassium osmium (IV) oxide (12.2 mg, 0.06 mmol) and sodium periodate (0.70 mL, 13 mmol). The mixture was stirred at 20° C. for 1 h, then diluted with water (150 mL) and extracted with ethyl acetate (2×100 mL). The combined organic layers were washed with brine (2×200 mL), dried over anhydrous sodium sulfate, filtered, and concentrated. The crude product was purified by flash silica gel chromatography (0-10% methanol/dichloromethane) to afford methyl 4-[4-(2-tert-butoxy-2-oxo-ethyl)-4-hydroxy-1-piperidyl]-2-formyl-benzoate (0.85 g, 68%) as a yellow solid. MS (ESI) m/z: 378.2 [M+H]$^+$; $^1$H NMR (400 MHz, DMSO-d$_6$) δ 10.50 (s, 1H), 7.80 (d, J=8.8 Hz, 1H), 7.24-7.13 (m, 2H), 4.68 (s, 1H), 3.87-3.79 (m, 3H), 3.69 (d, J=13.2 Hz, 2H), 3.30-3.20 (m, 2H), 2.34 (s, 2H), 1.71-1.58 (m, 4H), 1.34 (s, 9H).

Step 6: methyl (4S)-5-amino-4-[5-[4-(2-tert-butoxy-2-oxo-ethyl)-4-hydroxy-1-piperidyl]-1-oxo-isoindolin-2-yl]-5-oxo-pentanoate

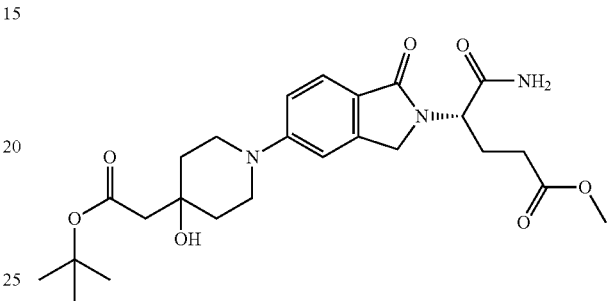

To a solution of methyl (4S)-4,5-diamino-5-oxo-pentanoate hydrochloride (547 mg, 2.8 mmol) in methanol (30 mL) was added sodium cyanoborohydride (233 mg, 3.7 mmol). The mixture was stirred at 15° C. for 10 min. Then sodium acetate (456 mg, 5.6 mmol) and methyl 4-[4-(2-tert-butoxy-2-oxo-ethyl)-4-hydroxy-1-piperidyl]-2-formyl-benzoate (0.7 g, 2 mmol) was added to the mixture. The mixture was stirred at 15° C. for 20 min. Then acetic acid (2.0 mL, 43 mmol) was added to the mixture. The mixture was stirred at 35° C. for 11.5 h. The reaction mixture was basified with sodium bicarbonate solution, extracted with ethyl acetate (2×50 mL). The combined organic layers were washed with brine (2×100 mL), dried over anhydrous sodium sulfate, filtered, and concentrated. The residue was purified by flash silica gel chromatography (0-5% methanol/dichloromethane) to afford methyl (4S)-5-amino-4-[5-[4-(2-tert-butoxy-2-oxo-ethyl)-4-hydroxy-1-piperidyl]-1-oxo-isoindolin-2-yl]-5-oxo-pentanoate (850 mg, 88%) as a white solid. MS (ESI) m/z: 490.2 [M+H]$^+$.

Step 7: methyl (4S)-5-amino-4-[5-[4-(2-tert-butoxy-2-oxo-ethyl)-4-hydroxy-1-piperidyl]-1-oxo-isoindolin-2-yl]-5-oxo-pentanoate

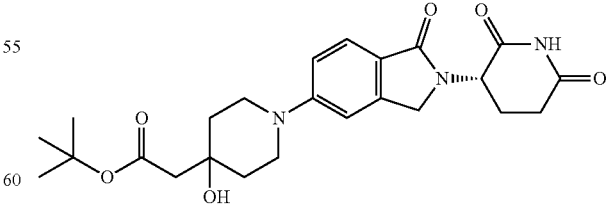

To a solution of methyl (4S)-5-amino-4-[5-[4-(2-tert-butoxy-2-oxo-ethyl)-4-hydroxy-1-piperidyl]-1-oxo-isoindolin-2-yl]-5-oxo-pentanoate (750 mg, 1.5 mmol) in tetrahydrofuran (20 mL) was added lithium tert-butoxide (1 M, 2.8 mL) at −50° C. The mixture was stirred at −20° C. for 1 h.

The reaction mixture was quenched by aqueous 2 M sulfuric acid (2 mL) at 20° C., and then basified with saturated sodium bicarbonate (20 mL) until pH was adjusted to 7-8. The mixture was extracted with ethyl acetate (2×30 mL). The combined organic layers were washed with brine (2×60 mL), dried over anhydrous sodium sulfate, filtered, and concentrated. The residue was purified by preparative HPLC (mobile phase: [0.2% formic acid in water-acetonitrile]; B %: 30%-60%, 2 min) to afford tert-butyl 2-[1-[2-[(3S)-2,6-dioxo-3-piperidyl]-1-oxo-isoindolin-5-yl]-4-hydroxy-4-piperidyl]acetate (450 mg, 53%) as a white solid. MS (ESI) m/z: 458.5 [M+H]$^+$.

Step 8: 2-[1-[2-[(3S)-2,6-dioxo-3-piperidyl]-1-oxo-isoindo lin-5-yl]-4-hydroxy-4-piperidyl]acetic acid

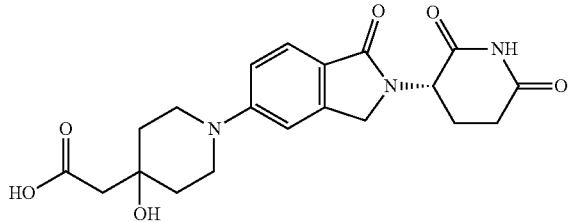 [SMILES: O=C(O)CC1(O)CCN(c2ccc3c(c2)CN([C@H]2CCC(=O)NC2=O)C3=O)CC1]

To a solution of tert-butyl 2-[1-[2-[(3S)-2,6-dioxo-3-piperidyl]-1-oxo-isoindolin-5-yl]-4-hydroxy-4-piperidyl]acetate (300 mg, 0.7 mmol) in dichloromethane (5 mL) was added hydrochloride in 1,4-dioxane (3 mL). The mixture was stirred at 20° C. for 2 h, then concentrated under reduced pressure to afford 2-[1-[2-[(3S)-2,6-dioxo-3-piperidyl]-1-oxo-isoindolin-5-yl]-4-hydroxy-4-piperidyl]acetic acid hydrochloride (260 mg, 72%) as a white solid. MS (ESI) m/z: 402.2 [M+H]$^+$.

Step 9: (3R)—N-[2-cyano-3-[3-[4-[4-[2-[1-[2-[(3S)-2,6-dioxo-3-piperidyl]-1-oxo-isoindolin-5-yl]-4-hydroxy-4-piperidyl]acetyl]piperazin-1-yl]phenyl]-4-oxo-quinazolin-6-yl]oxy-4-fluoro-phenyl]-3-fluoro-pyrrolidine-1-sulfonamide To a solution of 2-[1-[2-[(3S)-2,6-dioxo-3-piperidyl]-1-oxo-isoindolin-5-yl]-4-hydroxy-4-piperidyl]acetic acid (81 mg, 0.2 mmol) and (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide hydrochloride (130 mg, 0.2 mmol) in N,N-dimethylformamide (3 mL) was added 4-methylmorpholine (102 mg, 1.0 mmol). The mixture was stirred at 20° C. for 10 min. Then 1-hydroxybenzotriazole (40 mg, 0.3 mmol) and 1-ethyl-3-(3-dimethylaminopropyl) carbodiimide (58 mg, 0.3 mmol) was added to the mixture. The mixture was stirred at 20° C. for 50 min, then diluted with water (30 mL) and extracted with tetrahydrofuran (3×20 mL). The combined organic layers were washed with brine (3×40 mL), dried over anhydrous sodium sulfate, filtered, and concentrated in vacuum. The residue was purified by flash silica gel chromatography (0-1.5% methanol/dichloromethane) and then by preparative thin layer chromatography (dichloromethane:methanol=10:1) to afford (3R)—N-[2-cyano-3-[3-[4-[4-[2-[1-[2-[(3S)-2,6-dioxo-3-piperidyl]-1-oxo-isoindolin-5-yl]-4-hydroxy-4-piperidyl]acetyl]piperazin-1-yl]phenyl]-4-oxo-quinazolin-6-yl]oxy-4-fluoro-phenyl]-3-fluoro-pyrrolidine-1-sulfonamide (80.1 mg, 38%) as a white solid. MS (ESI) m/z: 991.1 [M+H]$^+$; $^1$H NMR (400 MHz, DMSO-d$_6$) δ 10.93 (s, 1H), 10.33 (s, 1H), 8.26 (s, 1H), 7.91-7.80 (m, 2H), 7.72 (dd, J=3.2, 9.2 Hz, 1H), 7.56-7.46 (m, 2H), 7.42 (d, J=3.2 Hz, 1H), 7.35 (d, J=9.2 Hz, 2H), 7.14-6.99 (m, 4H), 5.46-5.21 (m, 1H), 5.09-4.92 (m, 2H), 4.39-4.27 (m, 1H), 4.24-4.13 (m, 1H), 3.68 (d, J=16.4 Hz, 4H), 3.61 (d, J=13.2 Hz, 2H), 3.53 (s, 1H), 3.47-3.38 (m, 2H), 3.28-3.20 (m, 6H), 2.97-2.81 (m, 1H), 2.62-2.55 (m, 4H), 2.40-2.33 (m, 1H), 2.22-2.08 (m, 2H), 2.00-1.91 (m, 1H), 1.74-1.63 (m, 4H).

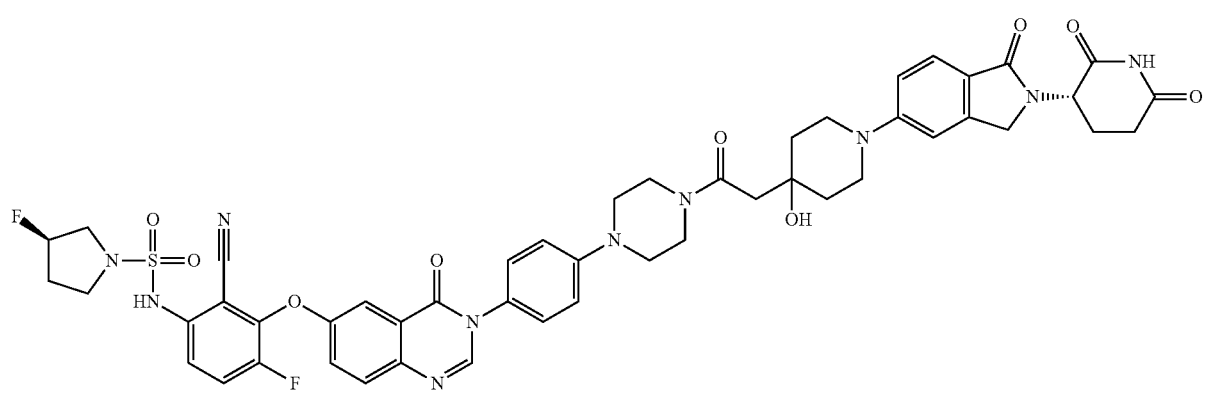 [SMILES: N#Cc1c(NS(=O)(=O)N2CC[C@@H](F)C2)ccc(F)c1Oc1ccc2ncn(-c3ccc(N4CCN(C(=O)CC5(O)CCN(c6ccc7c(c6)CN([C@H]6CCC(=O)NC6=O)C7=O)CC5)CC4)cc3)c(=O)c2c1]

Example 5: (3R)—N-[2-cyano-3-[3-[4-[4-[2-(2,6-dioxo-3-piperidyl)-1-oxo-isoindolin-5-yl]piperazin-1-yl]phenyl]-4-oxo-quinazolin-6-yl]oxy-4-fluoro-phenyl]-3-fluoro-pyrrolidine-1-sulfonamide

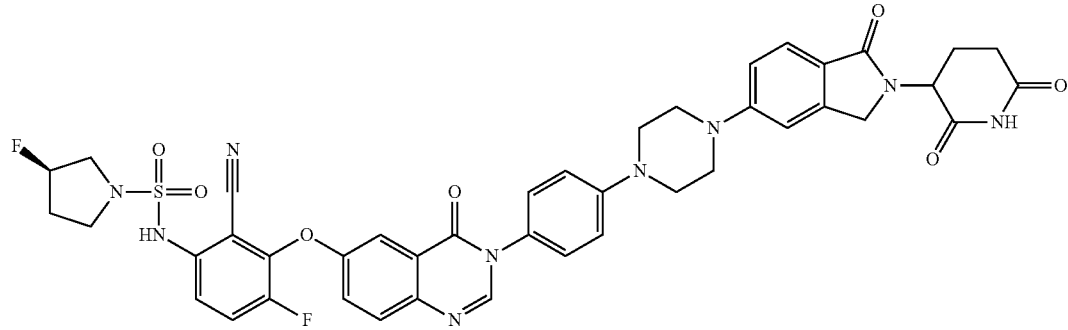 [SMILES: N#Cc1c(NS(=O)(=O)N2CC[C@@H](F)C2)ccc(F)c1Oc1ccc2ncn(-c3ccc(N4CCN(c5ccc6c(c5)CN(C5CCC(=O)NC5=O)C6=O)CC4)cc3)c(=O)c2c1]

A mixture of 3-(5-bromo-1-oxo-isoindolin-2-yl)piperidine-2,6-dione (86 mg, 0.3 mmol), (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide hydrochloride (172 mg, 0.3 mmol), cesium carbonate (261 mg, 0.8 mmol) and [1,3-bis(2,6-di-3-pentylphenyl)imidazol-2-ylidene](3-chloropyridyl)dichloropalladium(II) (10 mg, 0.01 mmol) in N,N-dimethylformamide (5 mL) was degassed and purged with nitrogen for 3 times, and then the mixture was stirred at 100° C. for 12 h under nitrogen. The pH of the reaction solution was adjusted to 8-9 with sodium bicarbonate solution and extracted with ethyl acetate (3×10 mL). The combined organic layers were washed with brine (2×10 mL), dried over anhydrous sodium sulfate, filtered, and concentrated. The crude product was purified by reversed-phase HPLC (column: Phenomenex Luna C18 150×25 mm×10 um; mobile phase: [0.2% formic acid in water-acetonitrile]; B %: 36%-68%, 10 min) to afford (3R)—N-[2-cyano-3-[3-[4-[4-[2-(2,6-dioxo-3-piperidyl)-1-oxo-isoindolin-5-yl]piperazin-1-yl]phenyl]-4-oxo-quinazolin-6-yl]oxy-4-fluoro-phenyl]-3-fluoro-pyrrolidine-1-sulfonamide (34.7 mg, 14%) as an off-white solid. MS (ESI) m/z: 850.5 [M+H]+; 1H NMR (400 MHz, DMSO-$d_6$) δ 10.95 (s, 1H), 10.39-10.29 (m, 1H), 8.27 (s, 1H), 7.90-7.79 (m, 2H), 7.75-7.68 (m, 1H), 7.56 (d, J=8 Hz, 1H), 7.51 (dd, J=3.2, 8.8 Hz, 1H), 7.42 (d, J=2.0 Hz, 1H), 7.37 (d, J=8.4 Hz, 2H), 7.18-7.10 (m, 4H), 5.42-5.20 (m, 1H), 5.06 (dd, J=4.8, 13.2 Hz, 1H), 4.41-4.32 (m, 1H), 4.28-4.19 (m, 1H), 3.55-3.38 (m, 12H), 2.98-2.84 (m, 1H), 2.59 (d, J=16.4 Hz, 1H), 2.41-2.34 (m, 1H), 2.16-1.94 (m, 3H).

Example 73: (3R)—N-(2-cyano-3-{[3-(4-{4-[(1-{2-[(3S)-2,6-dioxopiperidin-3-yl]-4-fluoro-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide Step 1: methyl 2-bromo-3,4-difluorobenzoate

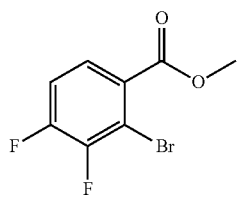

To a stirred solution of 2-bromo-3,4-difluoro-benzoic acid (40.0 g, 169 mmol) in methanol (300 mL) was added sulfuric acid (1.8 mL, 34 mmol) at 0° C. The mixture was stirred at 80° C. for 48 h, then concentrated. The residue was diluted with water (400 mL) and extracted with ethyl acetate (2×200 mL). The combined organic layer was washed with brine (2×200 mL), dried over anhydrous sodium sulfate, filtered, and concentrated to afford methyl 2-bromo-3,4-difluorobenzoate (42 g, 99%) as a yellow oil, which was used in the next step without further purification. 1H NMR (400 MHz, CDCl3) δ 7.68 (ddd, J=2.1, 5.3, 8.8 Hz, 1H), 7.20 (dt, J=7.4, 8.8 Hz, 1H), 3.94 (s, 1H). Step 2: methyl 2-bromo-4-(4-(dimethoxymethyl)piperidin-1-yl)-3-fluorobenzoate

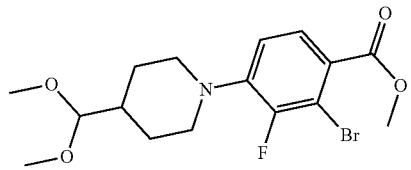 [SMILES: COC(=O)c1ccc(N2CCC(C(OC)OC)CC2)c(F)c1Br]

To a stirred solution of methyl 2-bromo-3,4-difluorobenzoate (8.0 g, 32 mmol) in dimethyl sulfoxide (80 mL) was added diisopropylethylamine (28.0 mL, 159 mmol) and 4-(dimethoxymethyl)piperidine (5.58 g, 35 mmol). The mixture was stirred at 100° C. for 2 h. The reaction was diluted with water (200 mL) and extracted with ethyl acetate (2×150 mL). The combined organic layer was washed with brine (2×150 mL), dried over anhydrous sodium sulfate, filtered, and concentrated. The residue was purified by silica gel chromatography (petroleum ether:ethyl acetate=100:1 to 2:1) to afford methyl 2-bromo-4-[4-(dimethoxymethyl)-1-piperidyl]-3-fluoro-benzoate (6 g, 48%) as a yellow solid. MS (ESI) m/z: 390 [M+H]+; 1H NMR (400 MHz, CDCl3) δ 7.63 (dd, J=1.6, 8.4 Hz, 1H), 6.85 (t, J=8.4 Hz, 1H), 4.10 (d, J=7.2 Hz, 1H), 3.90 (s, 3H), 3.61 (d, J=12.4 Hz, 2H), 3.39 (s, 6H), 2.81-2.55 (m, 2H), 1.86 (d, J=13.6 Hz, 3H), 1.52 (d, J=3.6 Hz, 2H). Step 3: methyl 4-(4-(dimethoxymethyl)piperidin-1-yl)-3-fluoro-2-vinylbenzoate

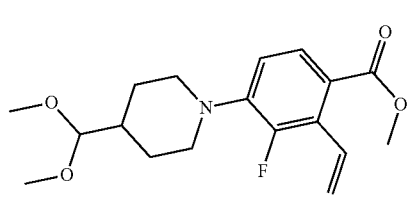 [SMILES: C=Cc1c(C(=O)OC)ccc(N2CCC(C(OC)OC)CC2)c1F]

To a stirred solution of methyl 2-bromo-4-[4-(dimethoxymethyl)-1-piperidyl]-3-fluoro-benzoate (3 g, 8 mmol) in 1,4-dioxane (25 mL) and water (5 mL) was added potassium vinyltrifluoroborate (4.12 g, 31 mmol), [1,1′-bis(diphenylphosphino)ferrocene]dichloropalladium(II) dichloromethane (628 mg, 0.8 mmol) and sodium carbonate (2.04 g, 19 mmol). The reaction mixture was stirred at 90° C. under nitrogen for 12 h. The mixture was filtered and concentrated. The residue was purified by silica gel chromatography (petroleum ether:ethyl acetate=100:1 to 3:1) to afford methyl 4-[4-(dimethoxymethyl)-1-piperidyl]-3-fluoro-2-vinyl-benzoate (2.3 g, 89%) as a light yellow oil. MS (ESI) m/z: 338 [M+H]$^+$; 1H NMR (400 MHz, CDCl3) δ 7.63 (dd, J=1.2, 8.4 Hz, 1H), 7.03 (dd, J=11.6, 17.6 Hz, 1H), 6.83 (t, J=8.4 Hz, 1H), 5.73-5.46 (m, 2H), 4.10 (d, J=7.2 Hz, 1H), 3.85 (s, 3H), 3.63-3.50 (m, 2H), 3.38 (s, 6H), 2.79-2.59 (m, 2H), 1.93-1.72 (m, 3H), 1.53 (dd, J=3.6, 12.0 Hz, 2H). Step 4: methyl 4-(4-(dimethoxymethyl)piperidin-1-yl)-3-fluoro-2-formylbenzoate

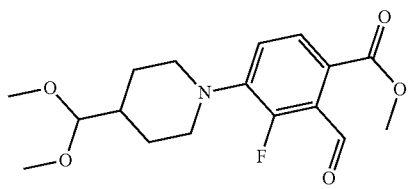 [SMILES: COC(=O)c1ccc(N2CCC(C(OC)OC)CC2)c(F)c1C=O]

To a stirred solution of methyl 4-[4-(dimethoxymethyl)-1-piperidyl]-3-fluoro-2-vinyl-benzoate (1 g, 3 mmol) in 1,4-dioxane (7.5 mL) and water (2.5 mL) was added 2,6-lutidine (0.7 mL, 6 mmol), potassium osmate (VI) dihydrate (22 mg, 0.06 mmol) and sodium periodate (0.07 mL, 12 mmol). The mixture was stirred at 20° C. for 2 h. The reaction was diluted with water (150 mL), extracted with ethyl acetate (3×80 mL). The combined organic phase was washed with brine (80 mL), dried over anhydrous sodium sulfate, filtered, and concentrated. The residue was purified by silica gel chromatography (petroleum ether:ethyl acetate=100:1 to 2:1) to afford methyl 4-[4-(dimethoxymethyl)-1-piperidyl]-3-fluoro-2-formyl-benzoate (900 mg, 89%) as a light yellow solid. 1H NMR (400 MHz, CDCl3) δ 10.42 (s, 1H), 7.66 (d, J=8.6 Hz, 1H), 7.01 (t, J=8.4 Hz, 1H), 4.10 (d, J=7.2 Hz, 1H), 3.90 (s, 3H), 3.64 (d, J=12.0 Hz, 2H), 3.38 (s, 6H), 2.83-2.63 (m, 2H), 1.90-1.73 (m, 3H), 1.50 (dd, J=3.2, 11.8 Hz, 2H). Step 5: methyl (S)-5-amino-4-(5-(4-(dimethoxymethyl)piperidin-1-yl)-4-fluoro-1-oxoisoindolin-2-yl)-5-oxopentanoate

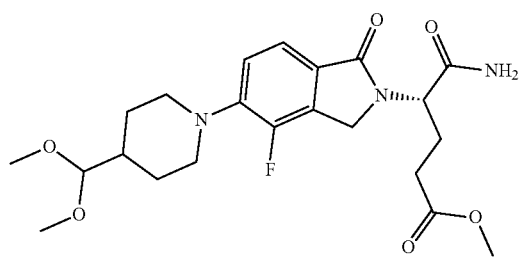

To a stirred solution of methyl 4-[4-(dimethoxymethyl)-1-piperidyl]-3-fluoro-2-formyl-benzoate (600 mg, 1.8 mmol) and methyl (4S)-4,5-diamino-5-oxo-pentanoate hydrochloride (417 mg, 2.1 mmol) in methanol (10 mL) was added sodium acetate (725 mg, 8.8 mmol). The mixture was stirred at 20° C. for 0.5 h, followed by the addition of sodium cyanoborohydride (222 mg, 3.5 mmol). The resulting mixture was stirred at 35° C. for 11 h, then concentrated. The residue was diluted with ethyl acetate (100 mL) and washed with brine (2×60 mL). The combined organic layer was dried over anhydrous sodium sulfate, filtered, and concentrated. The residue was purified by silica gel chromatography (petroleum ether:ethyl acetate=3:1 to 1:100) to afford methyl (4S)-5-amino-4-[5-[4-(dimethoxymethyl)-1-piperidyl]-4-fluoro-1-oxo-isoindolin-2-yl]-5-oxo-pentanoate (500 mg, 59%) as a light yellow solid. MS (ESI) m/z: 452.3 [M+H]$^+$; 1H NMR (400 MHz, CDCl3) δ 7.51 (d, J=8.4 Hz, 1H), 7.02 (t, J=7.8 Hz, 1H), 6.40 (s, 1H), 5.48 (s, 1H), 4.97-4.78 (m, 1H), 4.59-4.36 (m, 2H), 4.11 (d, J=7.2 Hz, 1H), 3.69-3.56 (m, 5H), 3.39 (s, 6H), 2.75 (t, J=11.8 Hz, 2H), 2.52-2.29 (m, 3H), 2.19 (dt, J=5.4, 9.8 Hz, 1H), 1.92-1.80 (m, 3H), 1.61-1.44 (m, 2H). Step 6: (S)-3-(5-(4-(dimethoxymethyl)piperidin-1-yl)-4-fluoro-1-oxoisoindolin-2-yl)piperidine-2,6-dione

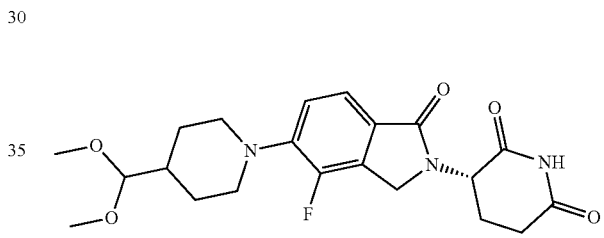

To a stirred solution of methyl (4S)-5-amino-4-[5-[4-(dimethoxymethyl)-1-piperidyl]-4-fluoro-1-oxo-isoindolin-2-yl]-5-oxopentanoate (500 mg, 1.1 mmol) in tetrahydrofuran (10 mL) was dropwise added 2 M sodium tert-butoxide in tetrahydrofuran (1.11 mL) at −70° C. The reaction was stirred at −70° C. for 4 h. The pH of the mixture was adjusted to 5 by addition of 2 M aqueous sulfuric acid solution at −70° C. Then saturated sodium bicarbonate solution was added to adjust the pH to 8. The mixture was extracted with ethyl acetate (2×100 mL). The combined organic layer was dried over anhydrous sodium sulfate, filtered, and concentrated. The residue was purified by silica gel chromatography (petroleum ether:ethyl acetate=3:1 to 1:100) to afford (S)-3-(5-(4-(dimethoxymethyl)piperidin-1-yl)-4-fluoro-1-oxoisoindolin-2-yl)piperidine-2,6-dione (370 mg, 80%) as a light yellow solid. MS (ESI) m/z: 420 [M+H]$^+$; 1H NMR (400 MHz, CDCl3) δ 8.15 (s, 1H), 7.58 (d, J=8.4 Hz, 1H), 7.05 (t, J=7.8 Hz, 1H), 5.19 (dd, J=5.2, 13.2 Hz, 1H), 4.54-4.44 (m, 1H), 4.43-4.27 (m, 1H), 4.11 (d, J=7.2 Hz, 1H), 3.67-3.52 (m, 2H), 3.39 (s, 6H), 3.00-2.70 (m, 4H), 2.35 (s, 1H), 2.23 (s, 1H), 1.87 (d, J=13.6 Hz, 3H), 1.53 (d, J=12.4 Hz, 2H). Step 7:1-[2-[(3S)-2,6-dioxo-3-piperidyl]-4-fluoro-1-oxo-isoindolin-5-yl]piperidine-4-carbaldehyde

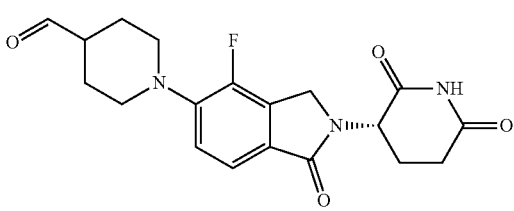 [SMILES: O=CC1CCN(c2ccc3c(c2F)CN([C@H]2CCC(=O)NC2=O)C3=O)CC1]

To a solution of (3S)-3-[5-[4-(dimethoxymethyl)-1-piperidyl]-4-fluoro-1-oxo-isoindolin-2-yl]piperidine-2,6-dione (200 mg, 0.5 mmol) in tetrahydrofuran (2 mL) was added 2 M aqueous sulfuric acid (2.4 mL). The mixture was stirred at 25° C. for 1 h, then diluted with water (5 mL) and extracted with ethyl acetate (3×5 mL). The combined organic phase was washed with brine (2×5 mL), dried over anhydrous sodium sulfate, filtered, and concentrated to afford 1-[2-[(3S)-2,6-dioxo-3-piperidyl]-4-fluoro-1-oxo-isoindolin-5-yl]piperidine-4-carbaldehyde (180 mg, crude) as a white solid, which was used in the next step without further purification. MS (ESI) m/z: 374.1 [M+H]$^+$. Step 8: (3R)—N-[2-cyano-3-[3-[4-[4-[[1-[2-[(3S)-2,6-dioxo-3-piperidyl]-4-fluoro-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide

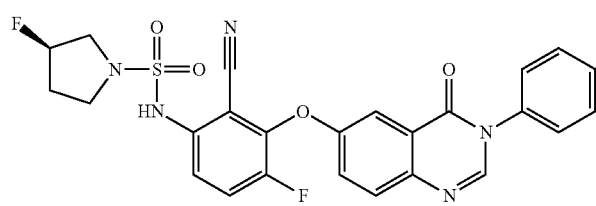

To a solution of 1-[2-[(3S)-2,6-dioxo-3-piperidyl]-4-fluoro-1-oxo-isoindolin-5-yl]piperidine-4-carbaldehyde (92 mg, 0.2 mmol) and (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide hydrochloride (160 mg, 0.2 mmol) in dichloromethane (3 mL) and isopropanol (3 mL) was added triethylamine (0.06 mL, 0.5 mmol). The mixture was stirred at 25° C. for 0.5 h, followed by the addition of sodium triacetoxyborohydride (157 mg, 0.7 mmol). The reaction was stirred at 25° C. for 12 h, then filtered and concentrated. The residue was purified by reverse phase high performance liquid chromatography (mobile phase: 0.2% formic acid in water:acetonitrile; B %: 16%-46%, 10 min) to afford (3R)—N-[2-cyano-3-[3-[4-[4-[[1-[2-[(3S)-2,6-dioxo-3-piperidyl]-4-fluoro-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide formate (112 mg, 43%) as an off-white solid. MS (ESI) m/z: 965.6 [M+H]$^+$; 1H NMR (400 MHz, DMSO-d6) δ 10.98 (s, 1H), 8.25 (s, 1H), 8.13 (s, 1H), 7.82 (d, J=8.8 Hz, 1H), 7.71-7.63 (m, 2H), 7.48 (d, J=8.0 Hz, 1H), 7.45-7.39 (m, 2H), 7.35 (d, J=8.8 Hz, 2H), 7.17 (t, J=8.0 Hz, 1H), 7.08 (d, J=9.2 Hz, 2H), 5.40-5.18 (m, 1H), 5.07 (dd, J=5.2, 13.2 Hz, 1H), 4.48 (d, J=16.8 Hz, 1H), 4.31 (d, J=16.8 Hz, 1H), 3.52 (s, 2H), 3.47-3.42 (m, 2H), 3.41-3.35 (m, 6H), 3.28-3.23 (m, 2H), 2.96-2.72 (m, 8H), 2.61 (s, 1H), 2.42 (dd, J=4.8, 12.8 Hz, 1H), 2.17-2.08 (m, 1H), 2.07-1.95 (m, 2H), 1.86 (d, J=10.8 Hz, 3H), 1.42-1.25 (m, 2H).

Example 74: (3R)—N-{2-cyano-3-[(3-{4-[4-({1-[1-(2,6-dioxopiperidin-3-yl)-1H-indol-4-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide Step 1: 1-[2,6-bis(benzyloxy)pyridin-3-yl]-4-bromoindole

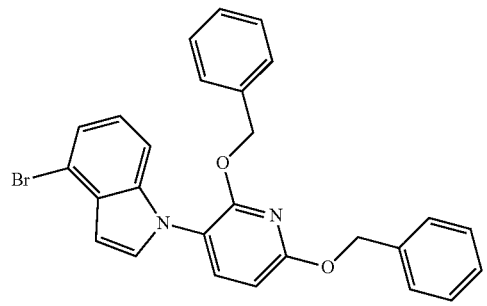 [SMILES: Brc1cccc2c1ccn2-c1ccc(OCc2ccccc2)nc1OCc1ccccc1]

To a stirred solution of 4-bromo-1H-indole (2.0 g, 10 mmol) and 2,6-bis(benzyloxy)pyridin-3-ylboronic acid (3.4 g, 10 mmol) in 1,4-dioxane (40 mL) was added copper (II) acetate (5.6 g, 30 mmol) and potassium tert-butoxide (2.3 g, 20 mmol) in portions at room temperature. The resulting mixture was stirred for 8 h at room temperature under nitrogen atmosphere. The reaction was diluted with water (50 mL) and extracted with ethyl acetate (3×50 mL). The combined organic layers were washed with brine (3×50 mL), dried over anhydrous sodium sulfate, filtered, and concentrated. The residue was purified by silica gel column chromatography (petroleum ether/ethyl acetate=1:1) to afford 1-[2,6-bis(benzyloxy)pyridin-3-yl]-4-bromoindole (900 mg, 18%) as a red solid. MS (ESI): m/z 487.10 [M+H]$^+$. Step 2: 1-[2,6-bis(benzyloxy)pyridin-3-yl]-4-[4-(dimethoxymethyl)piperidin-1-yl]indole

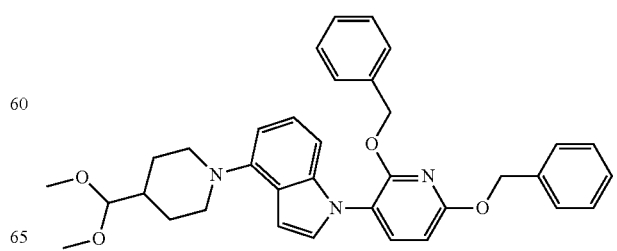

To a stirred mixture of 1-[2,6-bis(benzyloxy)pyridin-3-yl]-4-bromoindole (150 mg, 0.1 mmol) and 4-(dimethoxymethyl)piperidine (19.7 mg, 0.1 mmol) in 1,4-dioxane (20 mL) was added cesium carbonate (101 mg, 0.3 mmol) and dichloro[1,3-bis(2,6-di-3-pentylphenyl)imidazol-2-ylidene](3-chloropyridyl)palladium(II) (134 mg, 0.05 mmol) in portions. The mixture was stirred for 2 h at 90° C. The reaction was cooled to room temperature, diluted with saturated ammonium chloride solution (20 mL) and extracted with ethyl acetate (2×10 mL). The combined organic layers were washed with brine (2×10 mL), dried over anhydrous sodium sulfate, filtered, and concentrated. The residue was purified by preparative thin layer chromatography (petroleum ether/ethyl acetate=5:1) to afford 1-[2,6-bis(benzyloxy)pyridin-3-yl]-4-[4-(dimethoxymethyl)piperidin-1-yl]indole (120 mg, 43%) as a white solid. MS (ESI): m/z 564.35 [M+H]⁺. Step 3: 3-{4-[4-(dimethoxymethyl)piperidin-1-yl]indol-1-yl}piperidine-2,6-dione

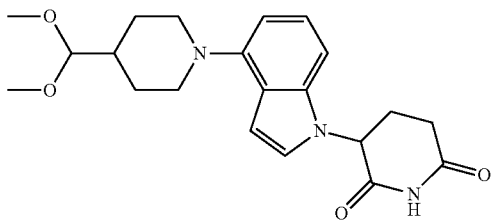 [SMILES: COC(OC)C1CCN(c2cccc3c2ccn3C2CCC(=O)NC2=O)CC1]

To a solution of 1-[2,6-bis(benzyloxy)pyridin-3-yl]-4-[4-(dimethoxymethyl)piperidin-1-yl]indole (200 mg, 0.3 mmol) in ethyl acetate (500 mL) was added 10% palladium on carbon (5 g). The mixture was degassed and purged with hydrogen for three times, then stirred overnight at room temperature under hydrogen atmosphere. The reaction mixture was filtered through Celite pad, the filtrate was concentrated to afford 3-{4-[4-(dimethoxymethyl)piperidin-1-yl]indol-1-yl}piperidine-2,6-dione (80 mg, 59%) as light yellow solid. MS (ESI): m/z 386.10 [M+H]⁺. Step 4: 1-[1-(2,6-dioxopiperidin-3-yl)indol-4-yl]piperidine-4-carbaldehyde

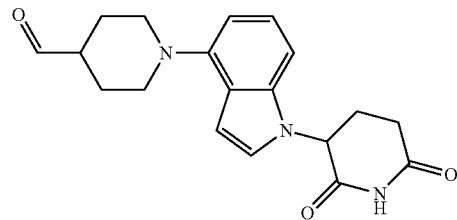 [SMILES: O=CC1CCN(c2cccc3c2ccn3C2CCC(=O)NC2=O)CC1]

To a stirred solution of 3-{4-[4-(dimethoxymethyl)piperidin-1-yl]indol-1-yl}piperidine-2,6-dione (80 mg, 0.2 mmol) and trifluoroacetic acid (2 mL) in dichloromethane (4 mL) was added water (1 mL). The reaction mixture was stirred for 2 h at 40° C. The resulting mixture was concentrated under vacuum to afford 1-[1-(2,6-dioxopiperidin-3-yl)indol-4-yl]piperidine-4-carbaldehyde (60 mg, 85%) as a white oil. Step 5: (3R)—N-(2-cyano-3-[(3-(4-[4-((1-[1-(2,6-dioxopiperidin-3-yl)indol-4-yl]piperidin-4-ylmethyl)piperazin-1-yl]phenyl-4-oxoquinazolin-6-yl)oxy]-4-fluorophenyl-3-fluoropyrrolidine-1-sulfonamide A solution of 1-[1-(2,6-dioxopiperidin-3-yl)indol-4-yl]piperidine-4-carbaldehyde (260 mg, 0.8 mmol) and (3R)—N-[2-cyano-4-fluoro-3-((4-oxo-3-[4-(piperazin-1-yl)phenyl]quinazolin-6-yloxy)phenyl]-3-fluoropyrrolidine-1-sulfonamide (465 mg, 0.8 mmol) in dichloromethane (30 mL) was stirred for 16 h at room temperature under nitrogen atmosphere. To the above mixture was added sodium triacetoxyborohydride (487 mg, 2 mmol). The reaction was stirred for 2 h at room temperature. The mixture was diluted with water (40 mL) and extracted with dichloromethane (3×30 mL). The combined organic layers were washed with brine (30 mL), dried over anhydrous sodium sulfate, filtered, and concentrated under reduced pressure. The residue was purified by preparative thin layer chromatography (dichloromethane/methanol=10:1) to afford (3R)—N-(2-cyano-3-

[(3-(4-[4-((1-[1-(2,6-dioxopiperidin-3-yl)indol-4-yl]piperidin-4-ylmethyl)piperazin-1-yl]phenyl-4-oxoquinazolin-6-yl)oxy]-4-fluorophenyl-3-fluoropyrrolidine-1-sulfonamide (300 mg, 40%) as an off-white solid. 1H NMR (400 MHz, DMSO-d6) δ 11.07 (s, 1H), 8.26 (s, 1H), 7.83 (d, J=8.9 Hz, 1H), 7.70 (m, 1H), 7.44-7.34 (m, 3H), 7.29 (d, J=3.3 Hz, 1H), 7.14-6.98 (m, 3H), 6.56-6.50 (m, 1H), 6.43 (d, J=3.1 Hz, 1H), 5.58 (m, 1H), 5.39-5.26 (d, J=56 Hz, 1H), 3.61 (t, J=12.8 Hz, 2H), 3.54-3.44 (m, 5H), 3.28 (s, 3H), 2.90 (d, J=15.3 Hz, 3H), 2.72 (d, J=13.4 Hz, 4H), 2.65 (s, 1H), 2.41 (s, 1H), 2.13 (m, 2H), 2.08 (s, 1H), 2.04 (s, 1H), 1.91 (d, J=12.1 Hz, 2H), 1.46 (s, 2H), 1.24 (s, 3H); MS (ESI): m/z 931.10 [M+H]$^+$.

Example 75: (3R)—N-{2-cyano-3-[(3-{1-[1-({1-[2-(2,6-dioxopiperidin-3-yl)-1-oxo-2,3-dihydro-1H-isoindol-5-yl]piperidin-4-yl}methyl)piperidin-4-yl]-1H-pyrazol-3-yl}-4-oxo-3,4-dihydroquinazolin-6-yl)oxy]-4-fluorophenyl}-3-fluoropyrrolidine-1-sulfonamide Step 1: tert-butyl 4-{4-[(2,6-dioxopiperidin-3-yl)amino]-2-fluorophenyl}piperidine-1-carboxylate

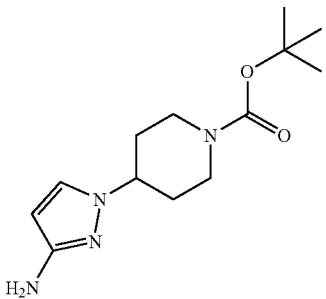 [SMILES: CC(C)(C)OC(=O)N1CCC(n2ccc(N)n2)CC1]

To a solution of tert-butyl 4-(3-nitropyrazol-1-yl)piperidine-1-carboxylate (6.5 g, 22 mmol) in methanol (60 mL) was added 10% palladium on carbon (3.0 g). The mixture was degassed and purged with hydrogen three times. The reaction was stirred at room temperature for 2 h under hydrogen atmosphere, then filtered through Celite pad and concentrated to afford tert-butyl 4-{4-[(2,6-dioxopiperidin-3-yl)amino]-2-fluorophenyl}piperidine-1-carboxylate (6.2 g, 70%) as an off-white solid. MS (ESI): m/z 267.10 [M+H]$^+$. Step 2: tert-butyl 4-[3-(6-hydroxy-4-oxoquinazolin-3-yl)pyrazol-1-yl]piperidine-1-carboxylate

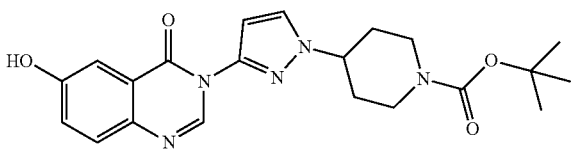 [SMILES: CC(C)(C)OC(=O)N1CCC(n2ccc(-n3cnc4ccc(O)cc4c3=O)n2)CC1]

To a solution of tert-butyl 4-(3-aminopyrazol-1-yl)piperidine-1-carboxylate (6.0 g, 22 mmol) and trimethyl orthoformate (14.3 g, 135 mmol) in pyridine (80 mL) was added 2-amino-5-hydroxybenzoic acid (6.9 g, 45 mmol). The resulting mixture was stirred for 6 h at 120° C. under nitrogen atmosphere. The reaction was cooled to room temperature and concentrated. The residue was purified by silica gel column chromatography (petroleum ether/ethyl acetate=1:1) to afford tert-butyl 4-[3-(6-hydroxy-4-oxoquinazolin-3-yl)pyrazol-1-yl]piperidine-1-carboxylate (3.5 g, 38%) as a brown solid. 1H NMR (400 MHz, DMSO-d6) δ 10.37 (s, 1H), 8.27 (s, 1H), 7.94-7.80 (m, 2H), 7.72-7.62 (m, 1H), 7.61-7.46 (m, 2H), 7.43 (d, J=3.0 Hz, 1H), 7.37-7.29 (m, 2H), 7.04-6.97 (m, 2H), 5.76 (s, 1H), 5.39-5.29 (d, J=40 Hz, 1H), 4.10 (s, 2H), 3.97 (s, 1H), 3.52-3.32 (m, 6H), 2.99 (s, 2H), 2.29-1.99 (m, 3H), 1.99 (s, 1H), 1.43 (s, 9H), 1.29-1.07 (m, 3H); MS (ESI): m/z 412.25 [M+H]$^+$. Step 3: 4-{3-[6-(2-cyano-3,6-difluorophenoxy)-4-oxoquinazolin-3-yl]pyrazol-1-yl}piperidine-1-carboxylate

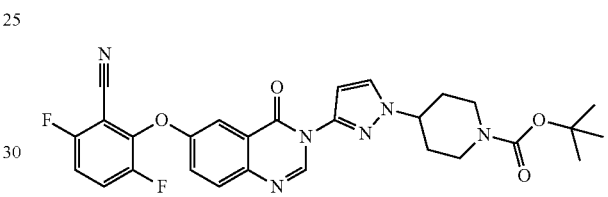

To a stirred solution of tert-butyl 4-[3-(6-hydroxy-4-oxoquinazolin-3-yl)pyrazol-1-yl]piperidine-1-carboxylate (3 g, 7 mmol) and 2,3,6-trifluorobenzonitrile (1.72 g, 11 mmol) in N,N-dimethylformamide (80 mL) was added cesium carbonate (7.13 g, 22 mmol) in portions at room temperature. The resulting mixture was stirred for 3 h at 90° C. under nitrogen atmosphere. The reaction was cooled to room temperature, diluted with water (20 mL) and extracted with ethyl acetate (2×100 mL). The combined organic layers were washed with water (2×100 mL), dried over anhydrous sodium sulfate, filtered, and concentrated. The residue was purified by silica gel column chromatography (petroleum ether/ethyl acetate=1:1) to afford tert-butyl 4-{3-[6-(2-cyano-3,6-difluorophenoxy)-4-oxoquinazolin-3-yl]pyrazol-1-yl}piperidine-1-carboxylate (2.8 g, 70%) as an off-white oil. MS (ESI): m/z 493.25 [M−56+H]$^+$. Step 4: tert-butyl 4-{4-[6-(2-cyano-6-fluoro-3-{[(3R)-3-fluoropyrrolidin-1-ylsulfonyl]amino}phenoxy)-4-oxoquinazolin-3-yl]-3-methoxyphenyl}piperazine-1-carboxylate

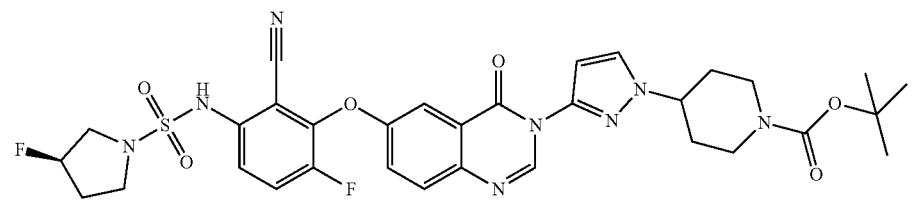 [SMILES: CC(C)(C)OC(=O)N1CCC(n2ccc(-n3cnc4ccc(Oc5c(F)ccc(NS(=O)(=O)N6CC[C@@H](F)C6)c5C#N)cc4c3=O)n2)CC1]

A solution of (3R)-3-fluoropyrrolidine-1-sulfonamide (1.1 g, 7 mmol) in N,N-dimethylformamide (50 mL) was stirred for 0.5 h at 50° C. under nitrogen atmosphere. Then slowly added tert-butyl 4-{4-[6-(2-cyano-3,6-difluorophenoxy)-4-oxoquinazolin-3-yl]-3-methoxyphenyl}piperazine-1-carboxylate (2.5 g, 4 mmol) over 1 min at room temperature. The reaction was stirred for 3 h at 90° C., then cooled to room temperature. The mixture was diluted with water (20 mL) and extracted with ethyl acetate (2×100 mL). The combined organic layers were washed with water (2×30 mL), dried over anhydrous sodium sulfate, filtered, and concentrated. The residue was purified by silica gel column chromatography (petroleum ether/ethyl acetate=1:1) to afford tert-butyl 4-{4-[6-(2-cyano-6-fluoro-3-{[(3R)-3-fluoropyrrolidin-1-ylsulfonyl]amino}phenoxy)-4-oxoquinazolin-3-yl]-3-methoxyphenyl}piperazine-1-carboxylate (3 g, 96%) as a white solid. MS (ESI): m/z 697.30 [M+H]$^+$; 1H NMR (300 MHz, DMSO-d6) δ 10.36 (s, 1H), 8.55 (s, 1H), 8.01-7.81 (m, 5H), 7.73-7.63 (m, 1H), 7.54 (dd, J=9.2, 4.2 Hz, 1H), 7.47 (d, J=3.0 Hz, 1H), 6.64 (d, J=2.5 Hz, 1H), 5.24-5.14 (d, J=30 Hz, 1H), 4.49-4.35 (m, 1H), 4.04 (td, J=10.7, 5.3 Hz, 2H), 3.55 (d, J=2.0 Hz, 3H), 3.53-3.35 (m, 2H), 2.89 (s, 4H), 2.73 (d, J=0.6 Hz, 4H), 2.03 (d, J=23.7 Hz, 5H), 1.82 (qd, J=12.3, 4.3 Hz, 2H), 1.42 (s, 9H). Step 5: (3R)—N-[2-cyano-4-fluoro-3-({4-oxo-3-[1-(piperidin-4-yl)pyrazol-3-yl]quinazolin-6-yl}oxy)phenyl]-3-fluoropyrrolidine-1-sulfonamide hydrochloride

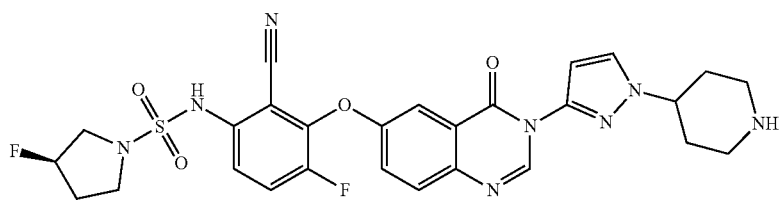 [SMILES: N#Cc1c(NS(=O)(=O)N2CC[C@@H](F)C2)ccc(F)c1Oc1ccc2ncn(-c3ccn(C4CCNCC4)n3)c(=O)c2c1]

A mixture of tert-butyl 4-{3-[6-(2-cyano-6-fluoro-3-{[(3R)-3-fluoropyrrolidin-1-ylsulfonyl]amino}phenoxy)-4-oxoquinazolin-3-yl]pyrazol-1-yl}piperidine-1-carboxylate (500 mg, 0.7 mmol) and 4 M hydrochloric acid in 1,4-dioxane (10 mL) was stirred for 1 h at room temperature. The reaction was concentrated under reduced pressure. The residue was triturated with ethyl acetate (10 mL) to afford (3R)—N-[2-cyano-4-fluoro-3-({4-oxo-3-[1-(piperidin-4-yl)pyrazol-3-yl]quinazolin-6-yl}oxy)phenyl]-3-fluoropyrrolidine-1-sulfonamide hydrochloride (300 mg, 66%) as a white solid. MS (ESI): m/z 597.30 [M+H]$^+$. Step 6: (3R)—N-{2-cyano-3-[(3-{1-[1-({1-[2-(2,6-dioxopiperidin-3-yl)-1-oxo-3H-isoindol-5-yl]piperidin-4-yl}methyl)piperidin-4-yl]pyrazol-3-yl}-4-oxoquinazolin-6-yl)oxy]-4-fluorophenyl}-3-fluoropyrrolidine-1-sulfonamide

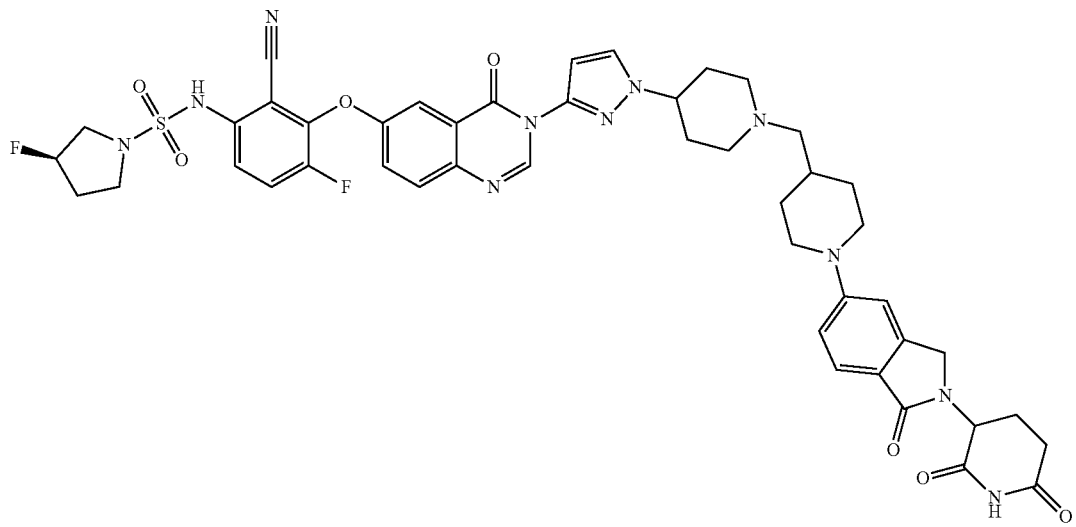 [SMILES: N#Cc1c(NS(=O)(=O)N2CC[C@@H](F)C2)ccc(F)c1Oc1ccc2ncn(-c3ccn(C4CCN(CC5CCN(c6ccc7c(c6)CN(C6CCC(=O)NC6=O)C7=O)CC5)CC4)n3)c(=O)c2c1]

To a stirred solution of (3R)—N-[2-cyano-4-fluoro-3-({4-oxo-3-[1-(piperidin-4-yl)pyrazol-3-yl]quinazolin-6-yl}oxy)phenyl]-3-fluoropyrrolidine-1-sulfonamide hydrochloride (180 mg, 0.3 mmol) in dichloromethane (40 mL) was added 1-[2-(2,6-dioxopiperidin-3-yl)-1-oxo-3H-isoindol-5-yl]piperidine-4-carbaldehyde (101 mg, 0.3 mmol) in portions at room temperature. The pH of the mixture was adjusted to 9 with N,N-diisopropylethylamine (0.1 mL) and stirred for 1 h at room temperature. To the above mixture was added sodium triacetoxyborohydride (181 mg, 0.9 mmol) in portions. The reaction was stirred for 1 h at room temperature, then diluted with water (50 mL) and extracted with dichloromethane (2×100 mL). The combined organic layers were washed with brine (2×20 mL), dried over anhydrous sodium sulfate, filtered, and concentrated. The residue was purified by preparative thin layer chromatography (dichloromethane/methanol=10:1) to afford (3R)—N-{2-cyano-3-[(3-{1-[1-({1-[2-(2,6-dioxopiperidin-3-yl)-1-oxo-3H-isoindol-5-yl]piperidin-4-yl}methyl)piperidin-4-yl]pyrazol-3-yl}-4-oxoquinazolin-6-yl)oxy]-4-fluorophenyl}-3-fluoropyrrolidine-1-sulfonamide (154.3 mg, 57%) as a white solid. 1H NMR (300 MHz, DMSO-d6) δ 10.96 (s, 1H), 8.54 (s, 1H), 7.99 (d, J=2.4 Hz, 1H), 7.84 (d, J=8.9 Hz, 1H), 7.70-7.65 (m, 1H), 7.60 (t, J=9.9 Hz, 2H), 7.52 (d, J=8.8 Hz, 2H), 7.07 (d, J=8.0 Hz, 2H), 6.68 (d, J=2.4 Hz, 1H), 5.39-5.21 (d, J=54 Hz, 1H), 5.05-5.01 (m, 1H), 4.41 (s, 3H), 4.33 (d, J=16.9 Hz, 2H), 4.20 (d, J=16.9 Hz, 1H), 3.91 (d, J=12.4 Hz, 2H), 3.54-3.38 (m, 4H), 3.24 (q, J=8.9 Hz, 2H), 2.88 (q, J=14.8, 12.1 Hz, 1H), 2.62 (s, 1H), 2.55 (s, 1H), 2.40-2.32 (m, 1H), 2.18 (s, 5H), 1.99 (s, 3H), 1.99 (d, J=17.1 Hz, 2H), 1.83 (d, J=12.9 Hz, 4H), 1.24 (s, 1H); MS (ESI): m/z 936.35 [M+H]⁺.

Example 76: (3R)—N-(2-cyano-3-{[3-(4-{4-[(1-{2-[(3S)-2,6-dioxopiperidin-3-yl]-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide Step 1: methyl 2-bromo-4-[3-(hydroxymethyl)azetidin-1-yl]benzoate

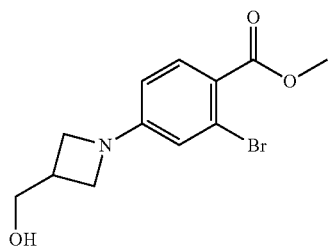 [SMILES: COC(=O)c1ccc(N2CC(CO)C2)cc1Br]

To a solution of azetidin-3-ylmethanol hydrochloride (6.5 g, 53 mmol) in dimethyl sulfoxide (100 mL) was added N,N-diisopropylethylamine (20.4 g, 158 mmol) and methyl 2-bromo-4-fluoro-benzoate (11.03 g, 47 mmol). The mixture was stirred at 110° C. for 12 h, then diluted with water (300 mL) and extracted with ethyl acetate (2×150 mL). The combined organic layers were washed with brine (4×300 mL), dried over sodium sulfate, filtered, and concentrated. The crude product was triturated with petroleum ether/ethyl acetate (93 mL, 30:1) to afford methyl 2-bromo-4-[3-(hydroxymethyl)azetidin-1-yl]benzoate (8.8 g, 56%) as a white solid. MS (ESI) m/z: 302.1 [M+H]⁺; 1H NMR (400 MHz, DMSO-d6) δ 7.71 (d, J=8.8 Hz, 1H), 6.60 (d, J=2.4 Hz, 1H), 6.39 (dd, J=2.4, 8.8 Hz, 1H), 4.81 (t, J=5.2 Hz, 1H), 3.94 (t, J=8.0 Hz, 2H), 3.75 (s, 3H), 3.66 (dd, J=5.6, 8.0 Hz, 2H), 3.56 (t, J=6.0 Hz, 2H), 2.88-2.75 (m, 1H). Step 2: methyl 2-bromo-4-(3-formylazetidin-1-yl)benzoate

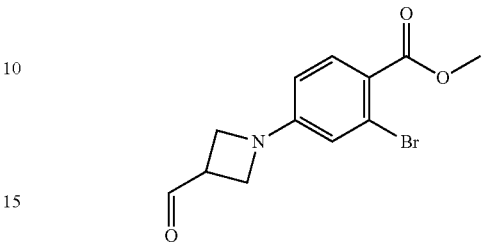

To a solution of oxalyl chloride (5.58 g, 44 mmol) in dichloromethane (30 mL) was dropwise added dimethyl sulfoxide (6.87 g, 88 mmol) in dichloromethane (10 mL) at −70° C. The mixture was stirred at −70° C. for 1 h. Then methyl 2-bromo-4-[3-(hydroxymethyl) azetidin-1-yl]benzoate (8.8 g, 29 mmol) in dichloromethane (30 mL) was dropwise added to the mixture and stirred at −70° C. for 2 h, followed by the addition of triethylamine (14.83 g, 147 mmol). The reaction was stirred at 20° C. for 1 h, then diluted with water (200 mL) and extracted with dichloromethane (2×150 mL). The combined organic layers were washed with brine (3×300 mL), dried over sodium sulfate, filtered, and concentrated to afford methyl 2-bromo-4-(3-formylazetidin-1-yl)benzoate (8 g, 91%) as a white solid, which was used in the next step without further purification. MS (ESI) m/z: 318.0 [M+H2O+H]+. Step 3: methyl 2-bromo-4-[3-(dimethoxymethyl)azetidin-1-yl]benzoate

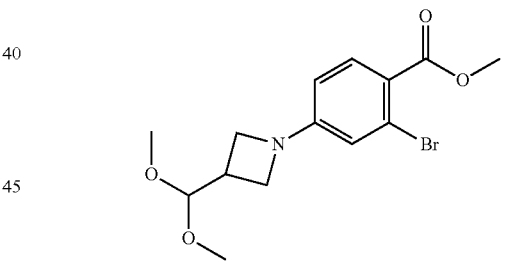

To a solution of methyl 2-bromo-4-(3-formylazetidin-1-yl)benzoate (8.0 g, 27 mmol) in methanol (30 mL) was added pyridinium p-toluenesulfonate (823 mg, 2.7 mmol) and trimethoxymethane (28.5 g, 268 mmol). The mixture was stirred at 25° C. for 12 h, then diluted with water (100 mL) and extracted with ethyl acetate (2×50 mL). The combined organic layers were washed with brine (3×80 mL), dried over sodium sulfate, filtered, and concentrated. The residue was purified by flash silica gel chromatography (0-20% ethyl acetate/petroleum ether) to afford methyl 2-bromo-4-[3-(dimethoxymethyl)azetidin-1-yl]benzoate (6.2 g, 67%) as a white solid. MS (ESI) m/z: 344.0 [M+H]⁺; 1H NMR (400 MHz, DMSO-d6) δ 7.71 (d, J=8.8 Hz, 1H), 6.62 (d, J=2.4 Hz, 1H), 6.40 (dd, J=2.4, 8.8 Hz, 1H), 4.60 (d, J=6.8 Hz, 1H), 3.96 (t, J=8.4 Hz, 2H), 3.77-3.70 (m, 5H), 3.29 (s, 6H), 3.05-2.93 (m, 1H). Step 4: methyl 4-(3-(dimethoxymethyl)azetidin-1-yl)-2-vinylbenzoate

225

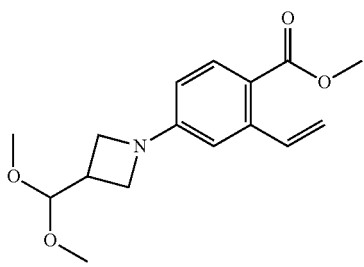

To a solution of methyl 2-bromo-4-[3-(dimethoxymethyl) azetidin-1-yl]benzoate (20 g, 58 mmol) in 1,4-dioxane (200 mL) and water (30 mL) was added [1,1'-bis(diphenylphosphino)ferrocene]dichloropalladium(II) (2.13 g, 3 mmol), potassium vinyltrifluoroborate (31.13 g, 232 mmol) and sodium carbonate (15.4 g, 145 mmol) under nitrogen atmosphere. The mixture was stirred at 90° C. for 12 h, then cooled to room temperature. The mixture was diluted with water (1000 mL) and extracted with ethyl acetate (2×500 mL). The combined organic layers were washed with brine (3×800 mL), dried over anhydrous sodium sulfate, filtered, and concentrated. The residue was purified by flash silica gel chromatography (0 to 5% ethyl acetate/petroleum ether) to give methyl 4-(3-(dimethoxymethyl)azetidin-1-yl)-2-vinyl-benzoate (16 g, 95%) as a colorless oil. 1H NMR (400 MHz, CDCl3) δ 7.86 (d, J=8.4 Hz, 1H), 7.58 (dd, J=10.8, 17.6 Hz, 1H), 6.45 (d, J=2.4 Hz, 1H), 6.30 (dd, J=2.4, 8.8 Hz, 1H), 5.56 (dd, J=1.6, 17.2 Hz, 1H), 5.29 (dd, J=1.6, 10.8 Hz, 1H), 4.63 (d, J=7.2 Hz, 1H), 4.03 (t, J=8.0 Hz, 2H), 3.88-3.79 (m, 5H), 3.39 (s, 6H), 3.10-3.00 (m, 1H). Step 5: methyl 4-[3-(dimethoxymethyl)azetidin-1-yl]-2-formyl-benzoate

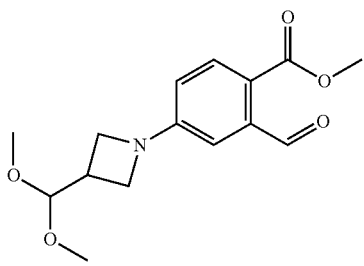 [SMILES: COC(=O)c1ccc(N2CC(C(OC)OC)C2)cc1C=O]

To a solution of methyl 4-[3-(dimethoxymethyl)azetidin-1-yl]-2-vinyl-benzoate (19 g, 65 mmol) in 1,4-dioxane (600 mL) and water (150 mL) was added 2,6-lutidine (13.98 g, 130 mmol), potassium osmate(VI) dihydrate (480 mg, 1.3 mmol) and sodium periodate (55.8 g, 261 mmol). The reaction was stirred at 20° C. for 2 h. The mixture was diluted with water (1000 mL) and extracted with ethyl acetate (3×500 mL). The combined organic phase was washed with brine (200 mL), dried over sodium sulfate, filtered, and concentrated. The residue was purified by flash silica gel chromatography (0 to 15% ethyl acetate/petroleum ether) to afford methyl 4-[3-(dimethoxymethyl)azetidin-1-yl]-2-formyl-benzoate (45 g, 78%) as a yellow oil. 1H NMR (400 MHz, CDCl3) δ 10.72 (s, 1H), 7.90 (d, J=8.8 Hz, 1H), 6.82 (d, J=2.8 Hz, 1H), 6.50 (dd, J=2.8, 8.8 Hz, 1H), 4.61 (d, J=6.8 Hz, 1H), 4.05 (t, J=8.0 Hz, 2H), 3.91 (s, 3H), 3.86 (d, J=5.6, 8.0 Hz, 2H), 3.39 (s, 6H), 3.12-2.99 (m, 1H). Step 6: methyl (4S)-5-amino-4-[5-[3-(dimethoxymethyl)azetidin-1-yl]-1-oxo-isoindolin-2-yl]-5-oxo-pentanoate

226

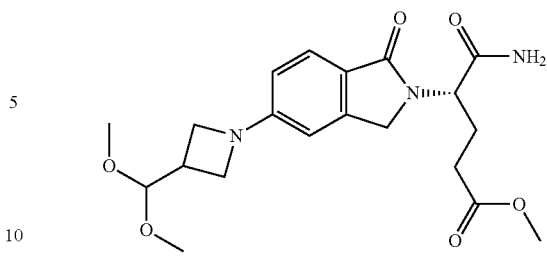

To a solution of methyl (4S)-4,5-diamino-5-oxo-pentanoate hydrochloride (18.5 g, 94 mmol) in methanol (450 mL) was added sodium acetate (12.9 g, 157 mmol) and stirred at 25° C. for 10 min, followed by the addition of methyl 4-[3-(dimethoxymethyl)azetidin-1-yl]-2-formyl-benzoate (23 g, 78 mmol) and acetic acid (22.4 mL, 392 mmol). The mixture was stirred at 25° C. for 20 min. Then sodium cyanoborohydride (9.86 g, 157 mmol) was added and the mixture was stirred at 35° C. for 11.5 h. The reaction was concentrated, the residue was diluted with water (1000 mL) and adjusted the pH to 8 by saturated sodium bicarbonate solution. The mixture was extracted with ethyl acetate (3×1000 mL). The combined organic layers were washed with brine (3×1000 mL), dried over anhydrous sodium sulfate, filtered, and concentrated. The residue was purified by flash silica gel chromatography (0-2% methanol/dichloromethane) to give methyl (4S)-5-amino-4-[5-[3-(dimethoxymethyl)azetidin-1-yl]-1-oxo-isoindolin-2-yl]-5-oxo-pentanoate (25 g, 73%) as an off-white solid. 1H NMR (400 MHz, CDCl3) δ 7.63 (d, J=8.4 Hz, 1H), 6.46-6.35 (m, 3H), 5.39 (s, 1H), 4.85 (dd, J=6.0, 9.2 Hz, 1H), 4.62 (d, J=7.2 Hz, 1H), 4.33 (d, J=2.4 Hz, 2H), 4.01 (t, J=8.0 Hz, 2H), 3.86-3.77 (m, 2H), 3.63 (s, 3H), 3.39 (s, 6H), 3.11-2.99 (m, 1H), 2.47-2.27 (m, 3H), 2.22-2.11 (m, 1H). Step 7: (3S)-3-[5-[3-(dimethoxymethyl)azetidin-1-yl]-1-oxo-isoindolin-2-yl]piperidine-2,6-dione

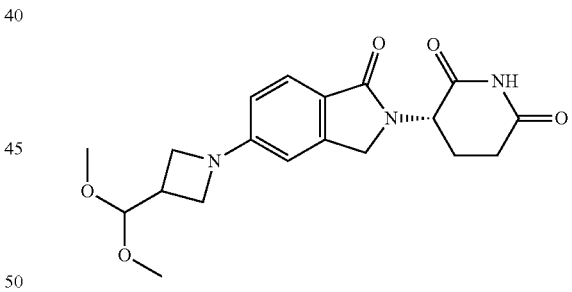

To a solution of methyl (4S)-5-amino-4-[5-[3-(dimethoxymethyl)azetidin-1-yl]-1-oxo-isoindolin-2-yl]-5-oxo-pentanoate (21 g, 52 mmol) in tetrahydrofuran (400 mL) was dropwise added 1 M lithium tert-butoxide in tetrahydrofuran (93 mL) at −30° C. The reaction was stirred at −30° C. for 2 h. The pH of the mixture was adjusted to 5 by 2 M aqueous citric acid solution at −30° C. Then the mixture was diluted with brine (500 mL) and adjusted the pH to 8 by saturated sodium bicarbonate solution. The mixture was extracted with tetrahydrofuran and ethyl acetate (V:V=1:1, 2×300 mL). The combined organic layers were washed with brine (3×500 mL), dried over anhydrous sodium sulfate, filtered, and concentrated. The crude product was triturated with ethyl acetate (200 mL) to afford (3S)-3-[5-[3-(dimethoxymethyl)azetidin-1-yl]-1-oxo-isoindolin-2-yl]piperidine-2,6-dione (37.5 g, 95%) as a light yellow solid. MS (ESI) m/z:

374.1 [M+H]+; 1H NMR (400 MHz, DMSO-d6) δ 10.93 (s, 1H), 7.48 (d, J=8.4 Hz, 1H), 6.55-6.44 (m, 2H), 5.03 (dd, J=5.2, 13.2 Hz, 1H), 4.62 (d, J=6.8 Hz, 1H), 4.35-4.25 (m, 1H), 4.22-4.12 (m, 1H), 3.95 (dt, J=1.6, 8.0 Hz, 2H), 3.76-3.65 (m, 2H), 3.29 (s, 6H), 3.09-2.97 (m, 1H), 2.96-2.84 (m, 1H), 2.61-2.56 (m, 1H), 2.40-2.31 (m, 1H), 1.98-1.91 (m, 1H). Step 8: 1-[2-[(3S)-2,6-dioxo-3-piperidyl]-1-oxo-isoindolin-5-yl]azetidine-3-carbaldehyde

To a solution of (3S)-3-[5-[3-(dimethoxymethyl)azetidin-1-yl]-1-oxo-isoindolin-2-yl]piperidine-2,6-dione (13 g, 35 mmol) in acetone (200 mL) and water (30 mL) was added 4-methylbenzenesulfonic acid (1.2 g, 7 mmol). The mixture was stirred at 70° C. for 4 h, then concentrated under reduced pressure. The residue was triturated with acetone (250 mL) to afford 1-[2-[(3S)-2,6-dioxo-3-piperidyl]-1-oxo-isoindolin-5-yl]azetidine-3-carbaldehyde (10.5 g, 92%) as a yellow solid. MS (ESI) m/z: 328.4 [M+H]+; 1H NMR (400 MHz, DMSO-d6) δ 10.94 (s, 1H), 9.85 (s, 1H), 7.52 (d, J=8.0 Hz, 1H), 6.59 (s, 1H), 6.54 (d, J=8.4 Hz, 1H), 5.04 (dd, J=5.2, 13.2 Hz, 1H), 4.36-4.17 (m, 2H), 4.11-4.01 (m, 4H), 3.64 (d, J=6.8 Hz, 1H), 2.96-2.84 (m, 1H), 2.58 (d, J=17.2 Hz, 1H), 2.42-2.31 (m, 1H), 1.99-1.89 (m, 1H). Step 9: (3R)—N-[2-cyano-3-[3-[4-[4-[[1-[2-[(3S)-2,6-dioxo-3-piperidyl]-1-oxo-isoindolin-5-yl]azetidin-3-yl]methyl]piperazin-1-yl]phenyl]-4-oxo-quinazolin-6-yl]oxy-4-fluoro-phenyl]-3-fluoro-pyrrolidine-1-sulfonamide

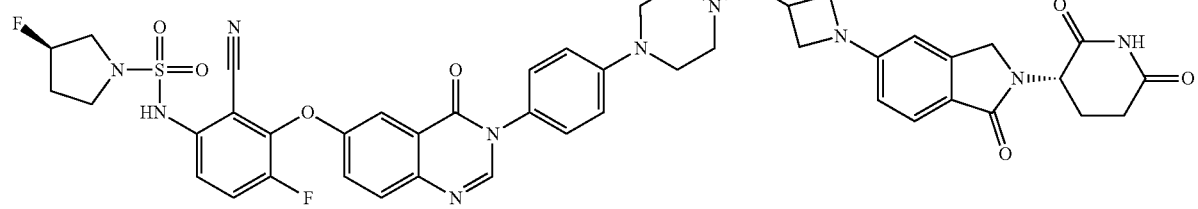

To a solution of (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide (450 mg, 0.7 mmol) in dichloromethane (5 mL) was added 1-[2-[(3S)-2,6-dioxo-3-piperidyl]-1-oxo-isoindolin-5-yl]azetidine-3-carbaldehyde (315 mg, 1 mmol) in isopropanol (5 mL), followed by the addition of acetic acid (88 mg, 1.5 mmol). The mixture was stirred at 25° C. for 10 min. Then sodium triacetoxyborohydride (313 mg, 1.5 mmol) was added and the reaction was stirred at 25° C. for 30 min. The mixture was diluted with water (30 mL) and extracted with tetrahydrofuran (2×15 mL). The combined organic layers were washed with brine (3×20 mL), dried over anhydrous sodium sulfate, filtered, and concentrated. The residue was purified by semi-preparative reverse phase high performance liquid chromatography (mobile phase: 0.2% formic acid in water:acetonitrile; B %: 12%-42%, 15 min) to afford (3R)—N-[2-cyano-3-[3-[4-[4-[[1-[2-[(3S)-2,6-dioxo-3-piperidyl]-1-oxo-isoindolin-5-yl] azetidin-3-yl]methyl]piperazin-1-yl]phenyl]-4-oxo-quinazolin-6-yl]oxy-4-fluoro-phenyl]-3-fluoro-pyrrolidine-1-sulfonamide (257 mg, 37%, 98% de) as an off-white solid. MS (ESI) m/z: 919.3 [M+H]+; 1H NMR (400 MHz, DMSO-d6) δ 11.00-10.84 (m, 1H), 10.23-10.00 (m, 1H), 8.25 (s, 1H), 7.82 (d, J=9.2 Hz, 1H), 7.73 (s, 1H), 7.69 (dd, J=2.8, 9.2 Hz, 1H), 7.50 (d, J=8.4 Hz, 1H), 7.47-7.39 (m, 2H), 7.38-7.29 (m, 2H), 7.13-7.04 (m, 2H), 6.56-6.44 (m, 2H), 5.39-5.20 (m, 1H), 5.08-4.99 (m, 1H), 4.36-4.26 (m, 1H), 4.23-4.14 (m, 1H), 4.12-4.02 (m, 2H), 3.71-3.56 (m, 2H), 3.52-3.34 (m, 4H), 3.29-3.18 (m, 2H), 3.14-3.04 (m, 1H), 2.98-2.72 (m, 6H), 2.69-2.55 (m, 3H), 2.41-2.26 (m, 2H), 2.17-2.09 (m, 1H), 2.09-2.00 (m, 2H), 1.99-1.87 (m, 1H).

Example 77: (3R)—N-(2-cyano-3-{[3-(4-{4-[(1-{2-[(3S)-2,6-dioxopiperidin-3-yl]-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide Step 1: methyl (4S)-5-amino-4-(tert-butoxycarbonylamino)-5-oxo-pentanoate

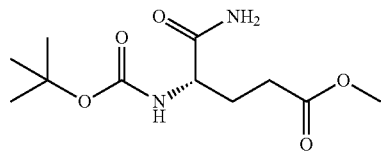 [SMILES: COC(=O)CC[C@H](NC(=O)OC(C)(C)C)C(N)=O]

A mixture of (2S)-2-(tert-butoxycarbonylamino)-5-methoxy-5-oxo-pentanoic acid (25 g, 96 mmol), tert-butyl (2-methylpropan-2-yl)oxycarbonyl carbonate (33.41 g, 153 mmol) and pyridine (1 mL, 191 mmol) in 1,4-dioxane (250 mL) was degassed and purged with nitrogen for three times, then stirred at 0° C. for 0.5 h under nitrogen atmosphere. To the mixture was added ammonium bicarbonate (22.7 g, 287 mmol) at 0° C. and stirred at 25° C. for 16 h. The reaction mixture was diluted with water (500 mL) and extracted with ethyl acetate (2×300 mL). The combined organic layers were washed with brine (3×400 mL), dried over sodium sulfate, filtered, and concentrated. The crude product was triturated with petroleum ether/ethyl acetate (330 mL, 30:1) to afford methyl (4S)-5-amino-4-(tert-butoxycarbonylamino)-5-oxo-pentanoate (39.4 g, 79%) as a white solid. MS (ESI) m/z: 161.2 [M−100+H]+; 1H NMR (400 MHz, DMSO-d6) δ 7.24 (s, 1H), 7.00 (s, 1H), 6.78 (d, J=8.4 Hz, 1H), 3.91-3.82 (m, 1H), 3.58 (s, 3H), 2.30 (t, J=7.6 Hz, 2H), 1.94-1.82 (m, 1H), 1.79-1.66 (m, 1H), 1.37 (s, 9H). Step 2: methyl (4S)-4,5-diamino-5-oxo-pentanoate

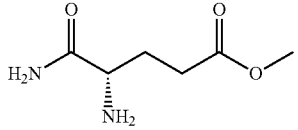

To a solution of methyl (4S)-5-amino-4-(tert-butoxycarbonylamino)-5-oxo-pentanoate (50.0 g, 192 mmol) in dichloromethane (500 mL) was added 4 M hydrochloric acid in 1,4-dioxane (500 mL). The mixture was stirred at 25° C. for 1 h, then concentrated in vacuum. The crude product was triturated with petroleum ether/ethyl acetate (620 mL, 30:1) to afford methyl (4S)-4,5-diamino-5-oxo-pentanoate hydrochloride (35 g, 92%) as a white solid. 1H NMR (400 MHz, DMSO-d6) δ 8.32 (s, 3H), 8.00 (s, 1H), 7.57 (s, 1H), 3.78 (d, J=5.6 Hz, 1H), 3.60 (s, 3H), 2.47-2.40 (m, 2H), 2.07-1.96 (m, 2H). Step 3: methyl (4S)-5-amino-4-[5-[4-(dimethoxymethyl)-1-piperidyl]-1-oxo-isoindolin-2-yl]-5-oxopentanoate

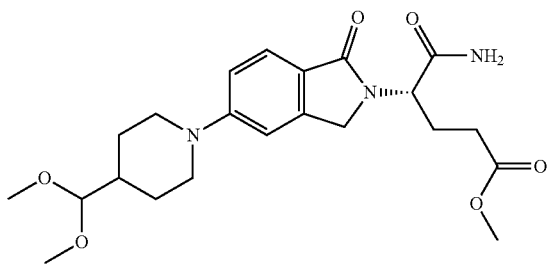 [SMILES: COC(=O)CC[C@@H](C(N)=O)N1Cc2cc(N3CCC(C(OC)OC)CC3)ccc2C1=O]

To a solution of methyl (4S)-4,5-diamino-5-oxo-pentanoate hydrochloride (27.8 g, 142 mmol) in methanol (500 mL) was added sodium acetate (17.9 g, 218 mmol). The mixture was stirred at 25° C. for 30 min, followed by the addition of methyl 4-[4-(dimethoxy methyl)-1-piperidyl]-2-formyl-benzoate (35.0 g, 109 mmol) and acetic acid (31.1 mL, 545 mmol). The mixture was stirred at 25° C. for 30 min, then sodium cyanoborohydride (13.7 g, 218 mmol) was added. The reaction was stirred at 35° C. for 11 h. The mixture was diluted with water (600 mL) and extracted with ethyl acetate (3×500 mL). The combined organic layers were washed with brine (4×600 mL), dried over anhydrous sodium sulfate, filtered, and concentrated. The residue was purified by flash silica gel chromatography (0-10% ethyl acetate/petroleum ether) to afford methyl (4S)-5-amino-4-[5-[4-(dimethoxymethyl)-1-piperidyl]-1-oxo-isoindolin-2-yl]-5-oxopentanoate (40 g, 84%) as a yellow solid. MS (ESI) m/z: 434.3 [M+H]⁺; 1H NMR (400 MHz, DMSO-d6) δ 7.55-7.43 (m, 2H), 7.13 (s, 1H), 7.08-6.97 (m, 2H), 4.67 (dd, J=4.8, 10.4 Hz, 1H), 4.47 (d, J=17.2 Hz, 1H), 4.38-4.27 (m, 1H), 4.07 (d, J=6.8 Hz, 1H), 3.87 (d, J=12.8 Hz, 2H), 3.51 (s, 3H), 3.27 (s, 6H), 2.77 (t, J=11.6 Hz, 2H), 2.27-2.12 (m, 3H), 2.05-1.97 (m, 1H), 1.80 (dtd, J=3.6, 7.6, 11.2 Hz, 1H), 1.70 (d, J=12.8 Hz, 2H), 1.39-1.22 (m, 2H). Step 4: (3S)-3-[5-[4-(dimethoxymethyl)-1-piperidyl]-1-oxo-isoindolin-2-yl]piperidine-2,6-dione

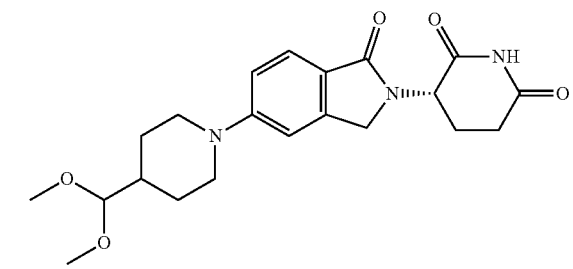 [SMILES: COC(OC)C1CCN(c2ccc3c(c2)CN([C@H]2CCC(=O)NC2=O)C3=O)CC1]

To a solution of methyl (4S)-5-amino-4-[5-[4-(dimethoxymethyl)-1-piperidyl]-1-oxo-isoindolin-2-yl]-5-oxopentanoate (15 g, 35 mmol) in tetrahydrofuran (300 mL) was added 1 M lithium tert-butoxide in tetrahydrofuran (62 mL) at −20° C. The mixture was stirred at −20° C. for 2 h. The reaction was quenched by 0.2 M aqueous sulfuric acid solution to pH 6, then the pH was adjusted to 8 with saturated sodium bicarbonate solution. The mixture was diluted with water (300 mL) and extracted with ethyl acetate (3×200 mL). The combined organic layers were washed with brine (3×200 mL), dried over anhydrous sodium sulfate, filtered, and concentrated. The crude product was triturated with ethyl acetate (100 mL) to afford (3S)-3-[5-[4-(dimethoxymethyl)-1-piperidyl]-1-oxo-isoindolin-2-yl]piperidine-2,6-dione (13 g, 93%) as a yellow solid. Step 5: (3S)-3-[5-[4-(dimethoxymethyl)-1-piperidyl]-1-oxo-isoindolin-2-yl]piperidine-2,6-dione

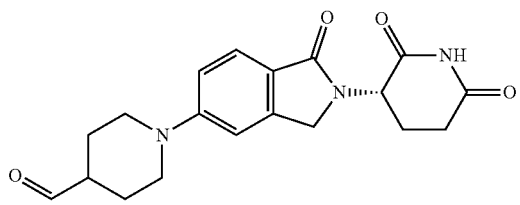 [SMILES: O=CC1CCN(c2ccc3c(c2)CN([C@H]2CCC(=O)NC2=O)C3=O)CC1]

To a solution of (3S)-3-[5-[4-(dimethoxymethyl)-1-piperidyl]-1-oxo-isoindolin-2-yl]piperidine-2,6-dione (2 g, 5 mmol) in acetone (20 mL) and water (2 mL) was added 4-methylbenzenesulfonic acid (171 mg, 1 mmol). The mixture was stirred at 70° C. for 3 h. The crude product was triturated ethyl acetate (20 mL) to afford 1-[2-[(3S)-2,6-dioxo-3-piperidyl]-1-oxo-isoindolin-5-yl]piperidine-4-carbaldehyde (1.5 g, 85%) as a yellow solid. MS (ESI) m/z: 374.2 [M+H2O+H]⁺. Step 6: (3R)—N-[2-cyano-3-[3-[4-[4-[[1-[2-[(3S)-2,6-dioxo-3-piperidyl]-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide

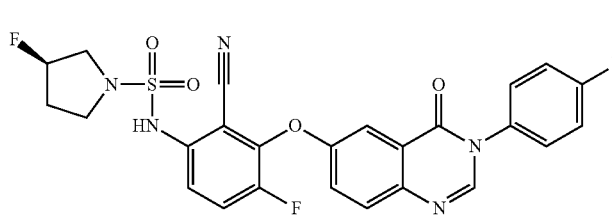

To a solution of 1-[2-[(3S)-2,6-dioxo-3-piperidyl]-1-oxo-isoindolin-5-yl]piperidine-4-carbaldehyde (342 mg, 1 mmol) and (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide (450 mg, 0.7 mmol) in isopropanol (5 mL) and dichloromethane (5 mL) was added acetic acid (88 mg, 1.5 mmol) at 25° C. and stirred for 10 min. Then sodium triacetoxyborohydride (313 mg, 1.5 mmol) was added and the resulting mixture was stirred at 25° C. for 50 min. The reaction mixture was partitioned between tetrahydrofuran (60 mL) and brine (60 mL). The organic phase was washed with brine (3×80 mL), dried over sodium sulfate, filtered, and concentrated. The residue was purified by semi-preparative reverse phase high performance liquid chromatography (mobile phase: [0.2% formic acid in water: acetonitrile]; B %: 12%-42%, 15 min) to afford (3R)—N-[2-cyano-3-[3-[4-[4-[[1-[2-[(3S)-2,6-dioxo-3-piperidyl]-1-oxo-isoindolin-5-yl]-4-piperidyl]methyl]piperazin-1-yl]phenyl]-4-oxo-quinazolin-6-yl]oxy-4-fluoro-phenyl]-3-fluoro-pyrrolidine-1-sulfonamide (250 mg, 35%) as a white solid. MS (ESI) m/z: 948.4 [M+H]⁺; 1H NMR (400 MHz, DMSO-d6) δ 10.95 (s, 1H), 10.26-9.64 (m, 1H), 8.25 (s, 1H), 7.82 (d, J=9.2 Hz, 1H), 7.74-7.63 (m, 2H), 7.51 (d, J=8.4 Hz, 1H), 7.47-7.39 (m, 2H), 7.35 (d, J=8.8 Hz, 2H), 7.13-7.03 (m, 4H), 5.41-5.16 (m, 1H), 5.05 (dd, J=4.8, 13.2 Hz, 1H), 4.39-4.28 (m, 1H), 4.26-4.15 (m, 1H), 3.90 (d, J=12 Hz, 2H), 3.52-3.36 (m, 4H), 3.32-3.20 (m, 4H), 2.91-2.76 (m, 6H), 2.61 (s, 3H), 2.47-2.31 (m, 2H), 2.16-2.02 (m, 2H), 1.96 (dd, J=5.6, 11.2 Hz, 2H), 1.83 (d, J=11.6 Hz, 2H), 1.36-1.09 (m, 2H).

Example 78: (3R)—N-{2-cyano-3-[(3-{4-[4-({1-[1-(2,6-dioxopiperidin-3-yl)-3-methyl-2-oxo-2,3-dihydro-1H-1,3-benzodiazol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide Step 1: N-(4-methoxybenzyl)-5-oxotetrahydrofuran-2-carboxamide

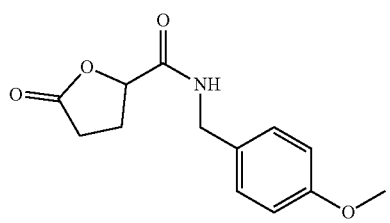 [SMILES: COc1ccc(CNC(=O)C2CCC(=O)O2)cc1]

To 5-oxotetrahydrofuran-2-carboxylic acid (10 g, 77 mmol) was slowly added thionyl chloride (21.0 g, 173 mmol) at 0° C. The mixture was stirred at 85° C. for 3 h, then stirred at 15° C. for 6 h. The mixture was concentrated, the residue was dissolved in anhydrous dichloromethane (1 L) at 0° C. under nitrogen. Then a solution of triethylamine (15.5 g, 153 mmol) and 4-methoxybenzylamine (8.4 g, 62 mmol) in dichloromethane (400 mL) was added, the mixture was stirred at 15° C. for 3 h. The reaction was diluted with water (600 mL) and extracted with dichloromethane (3×300 mL). The combined organic phase was washed with 0.5 M aqueous hydrochloric acid solution (500 mL) and brine (500 mL), dried over anhydrous sodium sulfate, filtered, and concentrated. The residue was purified by flash silica gel chromatography (petroleum ether:ethyl acetate=1:1) to afford N-(4-methoxybenzyl)-5-oxotetrahydrofuran-2-carboxamide (12.4 g, 65%) as a yellow solid. MS (ESI): m/z 250.10 [M+H]+. Step 2: 3-hydroxy-1-(4-methoxybenzyl)piperidine-2,6-dione

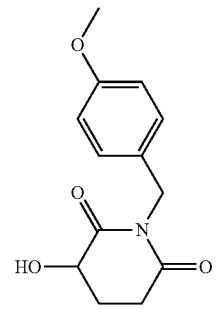

A solution of N-[(4-methoxyphenyl)methyl]-5-oxo-tetrahydrofuran-2-carboxamide (12 g, 48 mmol) in anhydrous tetrahydrofuran (150 mL) was cooled to −78° C. Then potassium tert-butoxide (6.45 g, 58 mmol) in anhydrous tetrahydrofuran (100 mL) was dropwise added to the above solution at −78° C. under nitrogen atmosphere. The reaction was stirred at −40° C. for 1 h. The mixture was diluted with saturated ammonium chloride solution (100 mL), extracted with ethyl acetate (3×150 mL). The combined organic layer was washed with brine (30 mL), dried over anhydrous sodium sulfate, filtered, and concentrated. The residue was purified by silica gel chromatography (petroleum ether:ethyl acetate=1:1) to afford 3-hydroxy-1-(4-methoxybenzyl)piperidine-2,6-dione (11 g, 92%) as a white solid.

Step 3: 1-(4-methoxybenzyl)-2,6-dioxopiperidin-3-yl trifluoromethanesulfonate

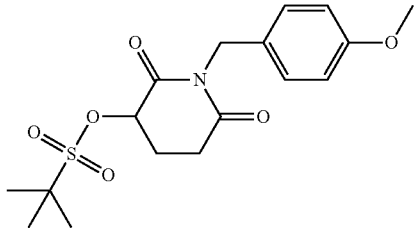 [SMILES: COc1ccc(CN2C(=O)CCC(OS(=O)(=O)C(C)(C)C)C2=O)cc1]

To a stirred solution of 3-hydroxy-1-[(4-methoxyphenyl)methyl]piperidine-2,6-dione (4.0 g, 16 mmol) and pyridine (2.6 mL, 32 mmol) in dichloromethane (40 mL) was dropwise added trifluoromethanesulfonic anhydride (4.1 mL, 24 mmol) at 0° C. under nitrogen atmosphere. The resulting mixture was stirred for 2 h at room temperature under nitrogen atmosphere, then concentrated. The residue was purified by silica gel column chromatography (petroleum ether/ethyl acetate=1:1) to afford 1-[(4-methoxyphenyl)methyl]-2,6-dioxopiperidin-3-yl trifluoromethanesulfonate (4 g, 65%) as a brown solid. MS (ESI): m/z 399.00 [M+H]+. Step 4: 3-(5-bromo-3-methyl-2-oxo-1,3-benzodiazol-1-yl)-1-[(4-methoxyphenyl)methyl]piperidine-2,6-dione

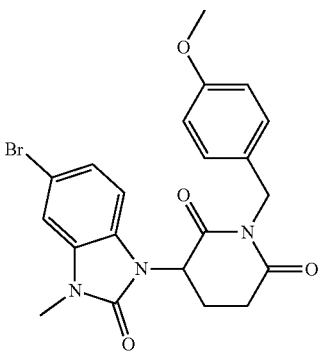 [SMILES: COc1ccc(CN2C(=O)CCC(n3c(=O)n(C)c4cc(Br)ccc43)C2=O)cc1]

To a solution of 6-bromo-1-methyl-3H-1,3-benzodiazol-2-one (0.89 g, 4 mmol) in tetrahydrofuran (30 mL) was added potassium tert-butoxide (0.53 g, 5 mmol) and stirred for 1 h at 50° C. under nitrogen atmosphere. The mixture was cooled to 0° C. and 1-[(4-methoxyphenyl)methyl]-2,6-dioxopiperidin-3-yl trifluoromethanesulfonate (1.5 g, 4 mmol) was added dropwise. The resulting mixture was stirred for 2 h at room temperature under nitrogen atmosphere. The reaction was quenched with saturated ammonium chloride solution at 0° C., the mixture was extracted with ethyl acetate (2×100 mL). The organic layer was concentrated under reduced pressure. The residue was purified by silica gel column chromatography (petroleum ether/ethyl acetate=1:1) to afford 3-(5-bromo-3-methyl-2-oxo-1,3-benzodiazol-1-yl)-1-[(4-methoxyphenyl)methyl] piperidine-2,6-dione (1.2 g, 66%) as a yellow solid. 1H NMR (400 MHz, DMSO-d6) δ 7.48 (d, J=1.9 Hz, 1H), 7.25-7.15 (m, 3H), 7.01 (d, J=8.4 Hz, 1H), 6.90-6.82 (m, 2H), 5.54 (d, 1H), 4.83-4.76 (d, J=14.3 Hz, 2H), 3.73 (s, 3H), 3.35-3.05 (d, 1H), 2.82-2.73 (d, 2H), 2.12-2.02 (m, 1H); MS (ESI): m/z 460.00 [M+H]+. Step 5: 3-(5-bromo-3-methyl-2-oxo-1,3-benzodiazol-1-yl)piperidine-2,6-dione

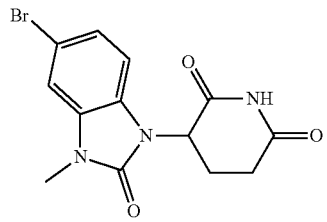

To a solution of 3-(5-bromo-3-methyl-2-oxo-1,3-benzodiazol-1-yl)-1-[(4-methoxyphenyl)methyl]piperidine-2,6-dione (1.2 g, 2.6 mmol) in toluene (5 mL) was added methanesulfonic acid (2.5 mL) in portions at room temperature under nitrogen atmosphere. The resulting mixture was stirred for 2 h at 120° C. under nitrogen atmosphere. The reaction was cooled to room temperature and concentrated. The residue was diluted with water (30 mL), the mixture was filtered and the solid was washed with water (2×5 mL). The residue was purified by reverse phase flash chromatography (mobile phase: acetonitrile in water (10 mmol/L ammonium bicarbonate), 10% to 80% gradient in 40 min) to afford 3-(5-bromo-3-methyl-2-oxo-1,3-benzodiazol-1-yl)piperidine-2,6-dione (430 mg, 48%) as a white solid. 1H NMR (400 MHz, DMSO-d6) δ 11.13 (s, 1H), 7.48 (d, J=1.9 Hz, 1H), 7.30-7.08 (m, 2H), 5.39 (d, 1H), 3.35 (s, 1H), 2.97-2.57 (m, 2H), 2.10-1.98 (m, 1H); MS (ESI): m/z 339.85 [M+H]+. Step 6: 3-{5-[4-(dimethoxymethyl)piperidin-1-yl]-3-methyl-2-oxo-1,3-benzodiazol-1-yl}piperidine-2,6-dione

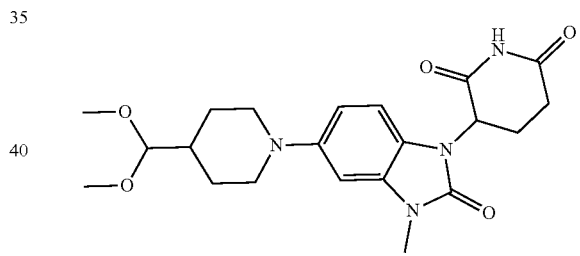

To a stirred solution of 3-(5-bromo-3-methyl-2-oxo-1,3-benzodiazol-1-yl)piperidine-2,6-dione (400 mg, 1.2 mmol) and 4-(dimethoxymethyl)piperidine (283 mg, 1.8 mmol) in N,N-dimethylformamide (10 mL) was added sodium tert-butoxide (341 mg, 3.5 mmol) and dichloro[1,3-bis(2,6-di-3-pentylphenyl)imidazol-2-ylidene](3-chloropyridyl)palladium(II) (49.8 mg, 0.06 mmol) in portions at room temperature. The resulting mixture was stirred for 2 h at 100° C. under nitrogen atmosphere. The mixture was cooled to room temperature, diluted with saturated ammonium chloride (100 mL) and extracted with ethyl acetate (3×200 mL). The combined organic layers were washed with brine (2×50 mL), dried over anhydrous sodium sulfate, filtered, and concentrated. The residue was purified by preparative thin layer chromatography (petroleum ether/ethyl acetate=1:5) to afford 3-{5-[4-(dimethoxymethyl)piperidin-1-yl]-3-methyl-2-oxo-1,3-benzodiazol-1-yl}piperidine-2,6-dione (210 mg, 42%) as a yellow solid. 1H NMR (400 MHz, DMSO-d6) δ 11.08 (s, 1H), 7.96 (s, 1H), 6.93 (d, J=8.5 Hz, 1H), 6.83 (d, J=2.2 Hz, 1H), 6.72-6.59 (m, 1H), 5.29 (d, 1H), 4.21-4.03 (m, 2H), 3.70-3.49 (m, 2H), 3.33-3.21 (m, 10H), 3.03-2.83 (m, 2H), 2.74-2.54 (m, 5H), 2.57-2.48 (m, 1H), 1.99-1.61 (m, 4H), 1.44-1.30 (m, 2H), 1.24 (s, 1H), 1.06 (d, 1H); MS (ESI): m/z 417.15 [M+H]⁺. Step 7: 1-[1-(2,6-dioxopiperidin-3-yl)-3-methyl-2-oxo-1,3-benzodiazol-5-yl]piperidine-4-carbaldehyde

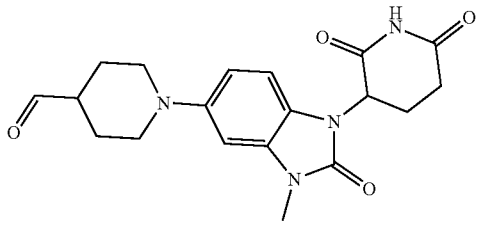 [SMILES: Cn1c(=O)n(C2CCC(=O)NC2=O)c2ccc(N3CCC(C=O)CC3)cc21]

To a stirred solution of 3-{5-[4-(dimethoxymethyl)piperidin-1-yl]-3-methyl-2-oxo-1,3-benzodiazol-1-yl}piperidine-2,6-dione (60 mg, 0.1 mmol) and trifluoroacetic acid (1 mL) in dichloromethane (4 mL) was added water (0.2 mL). The reaction mixture was stirred for 2 h at 40° C. The mixture was cooled to room temperature, adjusted the pH to 8 with saturated ammonium bicarbonate solution. The resulting mixture was extracted with dichloromethane (3×100 mL). The combined organic layers were washed with brine (2×50 mL), dried over anhydrous sodium sulfate, filtered, and concentrated to afford 1-[1-(2,6-dioxopiperidin-3-yl)-3-methyl-2-oxo-1,3-benzodiazol-5-yl]piperidine-4-carbaldehyde (50 mg, 93%) as a yellow oil. 1H NMR (400 MHz, DMSO-d6) δ 11.09 (s, 1H), 7.23-7.01 (m, 1H), 6.97 (t, J=7.9 Hz, 1H), 6.93-6.84 (m, 1H), 5.37 (d, 1H), 4.17-3.62 (s, 2H), 3.35 (s, 2H), 3.30 (s, 2H), 3.12 (d, J=11.2 Hz, 1H), 2.89 (d, 4H), 2.79-2.00 (d, 1H), 1.74-1.49 (d, J=12.3 Hz, 3H), 1.44-1.14 (m, 2H); MS (ESI): m/z 371.10 [M+H]+. Step 8: (3R)—N-(2-cyano-3-[(3-(4-[4-((1-[1-(2,6-dioxopiperidin-3-yl)-3-methyl-2-oxo-1,3-benzodiazol-5-yl]piperidin-4-ylmethyl)piperazin-1-yl]phenyl-4-oxoquinazolin-6-yl)oxy]-4-fluorophenyl-3-fluoropyrrolidine-1-sulfonamide afford (3R)—N-(2-cyano-3-[(3-(4-[4-((1-[1-(2,6-dioxopiperidin-3-yl)-3-methyl-2-oxo-1,3-benzodiazol-5-yl]piperidin-4-ylmethyl)piperazin-1-yl]phenyl-4-oxoquinazolin-6-yl)oxy]-4-fluorophenyl-3-fluoropyrrolidine-1-sulfonamide (262 mg, 43%) as an off-white solid. 1H NMR (400 MHz, DMSO-d6) δ 11.12 (s, 1H), 10.0 (s, 1H), 8.25 (s, 1H), 7.83 (d, J=8.9 Hz, 1H), 7.76 (m, 2H), 7.50-7.30 (m, 4H), 7.10 (d, J=8.7 Hz, 2H), 6.98 (m, 1H), 6.60 (m, 1H), 5.45-5.23 (m, 2H), 3.64 (m, 2H), 3.45 (s, 2H), 3.40 (m, 2H), 3.26 (m, 5H), 2.89 (m, 4H), 2.74-2.58 (m, 6H), 2.52 (m, 6H), 2.21-1.95 (m, 3H), 1.88 (d, J=12.6 Hz, 3H), 1.30 (m, 2H), 1.29-1.21 (m, 1H); MS (ESI): m/z 962.45 [M+H]+.

Example 79: (3R)—N-{2-cyano-3-[(3-{4-[4-({4-[2-(2,6-dioxopiperidin-3-yl)-4-fluoro-1-oxo-2,3-dihydro-1H-isoindol-5-yl]piperidin-1-yl}methyl)piperidin-1-yl]phenyl}-4-oxo-3,4-dihydroquinazolin-6-yl)oxy]-4-fluorophenyl}-3-fluoropyrrolidine-1-sulfonamide Step 1: methyl 4-bromo-2-(bromomethyl)-3-fluorobenzoate

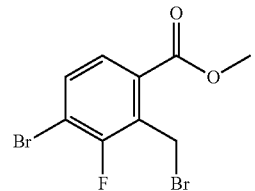

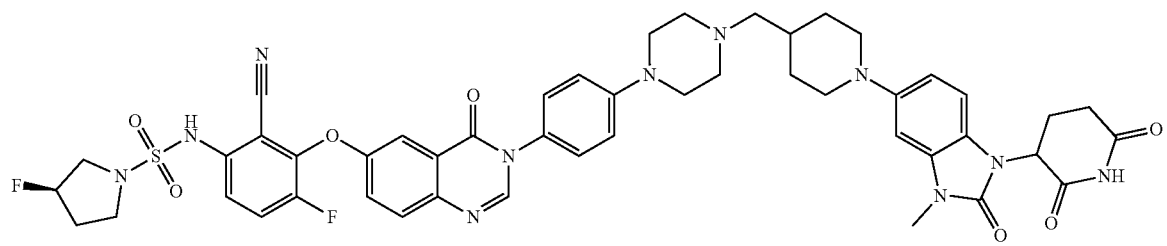 [SMILES: Cn1c(=O)n(C2CCC(=O)NC2=O)c2ccc(N3CCC(CN4CCN(c5ccc(-n6cnc7ccc(Oc8c(F)ccc(NS(=O)(=O)N9CC[C@@H](F)C9)c8C#N)cc7c6=O)cc5)CC4)CC3)cc21]

To a stirred solution of 1-[1-(2,6-dioxopiperidin-3-yl)-3-methyl-2-oxo-1,3-benzodiazol-5-yl]piperidine-4-carbaldehyde (225 mg, 0.6 mmol) and (3R)—N-[2-cyano-4-fluoro-3-((4-oxo-3-[4-(piperazin-1-yl)phenyl]quinazolin-6-yloxy)phenyl]-3-fluoropyrrolidine-1-sulfonamide (369 mg, 0.6 mmol) in dichloromethane (15 mL) was added N,N-diisopropylethylamine until pH 9. The resulting mixture was stirred for 16 h at room temperature under nitrogen atmosphere. To the above mixture was added sodium triacetoxyborohydride (386 mg, 1.8 mmol). The reaction was stirred for another 2 h at room temperature. The mixture was diluted with water (50 mL), extracted with dichloromethane (3×50 mL). The combined organic layers were washed with brine (50 mL), dried over anhydrous sodium sulfate, filtered, and concentrated. The residue was purified by preparative thin layer chromatography (dichloromethane/methanol=10:1) to To a solution of methyl 4-bromo-3-fluoro-2-methylbenzoate (2.5 g, 10 mmol) in dichloroethane (75 mL) was added benzoyl peroxide (0.52 g, 2 mmol) and N-bromosuccinimide (2.16 g, 12 mmol) at room temperature. The resulting mixture was stirred overnight at 90° C. under nitrogen atmosphere. The reaction was cooled to room temperature, diluted with water, and extracted with dichloromethane (3×50 mL). The combined organic layers were washed with brine (3×10 mL), dried over anhydrous sodium sulfate, filtered, and concentrated. The residue was purified by silica gel column chromatography (petroleum ether/ethyl acetate=5:1) to afford methyl 4-bromo-2-(bromomethyl)-3-fluorobenzoate (2 g, 61%) as an off-white solid. Step 2: 3-(5-bromo-4-fluoro-1-oxo-3H-isoindol-2-yl)piperidine-2,6-dione

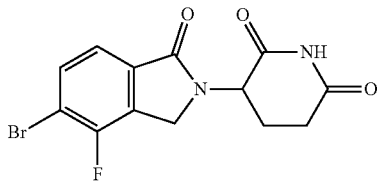 [SMILES: O=C1CCC(N2Cc3c(ccc(Br)c3F)C2=O)C(=O)N1]

To a mixture of methyl 4-bromo-2-(bromomethyl)-3-fluorobenzoate (1.5 g, 4.6 mmol) and 3-aminopiperidine-2,6-dione (1.77 g, 14 mmol) in acetonitrile (50 mL) was added N,N-diisopropylethylamine (10 mL, 57 mmol) at room temperature. The resulting mixture was stirred overnight at 80° C. under nitrogen atmosphere. The mixture was cooled to room temperature, diluted with water (20 mL) and extracted with ethyl acetate (3×25 mL). The combined organic layers were washed with brine (3×10 mL), dried over anhydrous sodium sulfate, filtered, and concentrated. The residue was purified by silica gel column chromatography (petroleum ether/ethyl acetate=1:1) to afford 3-(5-bromo-4-fluoro-1-oxo-3H-isoindol-2-yl)piperidine-2,6-dione (1.23 g, 78%) as a light yellow solid. MS (ESI): m/z 341.1 [M+H]+. Step 3: tert-butyl 4-[2-(2,6-dioxopiperidin-3-yl)-4-fluoro-1-oxo-3H-isoindol-5-yl]-3,6-dihydro-2H-pyridine-1-carboxylate

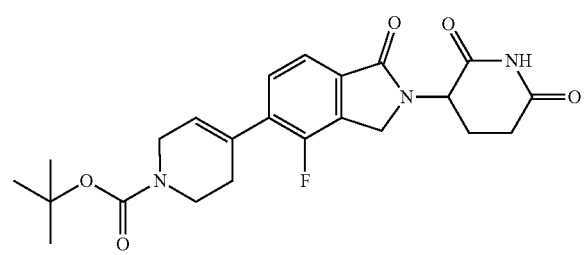 [SMILES: CC(C)(C)OC(=O)N1CC=C(c2ccc3c(c2F)CN(C2CCC(=O)NC2=O)C3=O)CC1]

To a mixture of 3-(5-bromo-4-fluoro-1-oxo-3H-isoindol-2-yl)piperidine-2,6-dione (450 mg, 1.3 mmol) in water (3 mL) and 1,4-dioxane (12 mL) was added tert-butyl 4-(4,4,5,5-tetramethyl-1,3,2-dioxaborolan-2-yl)-3,6-dihydro-2H-pyridine-1-carboxylate (530 mg, 1.7 mmol), [1,1'-bis(diphenylphosphino)ferrocene]dichloropalladium(II) (72.9 mg, 0.1 mmol) and cesium fluoride (601 mg, 4 mmol). The resulting mixture was stirred for 3 h at 90° C. under nitrogen atmosphere. The reaction was cooled to room temperature, diluted with water (20 mL), and extracted with ethyl acetate (3×25 mL). The combined organic layers were washed with brine (3×10 mL), dried over anhydrous sodium sulfate, filtered, and concentrated. The residue was purified by silica gel column chromatography (petroleum ether/ethyl acetate=1:1) to afford tert-butyl 4-[2-(2,6-dioxopiperidin-3-yl)-4-fluoro-1-oxo-3H-isoindol-5-yl]-3,6-dihydro-2H-pyridine-1-carboxylate (230 mg, 39%) as a light yellow solid. MS (ESI): m/z 443.4 [M+H]+; 1H NMR (300 MHz, CDCl3) δ 7.99 (s, 1H), 7.65 (d, J=7.8 Hz, 1H), 7.40 (t, J=7.1 Hz, 1H), 7.00 (s, 1H), 6.02 (s, 1H), 5.21 (dd, J=13.2, 5.1 Hz, 1H), 4.54 (d, J=16.3 Hz, 1H), 4.39 (d, J=16.3 Hz, 1H), 4.10 (d, J=3.2 Hz, 2H), 3.64 (t, J=5.6 Hz, 2H), 2.95-2.75 (m, 2H), 2.53 (s, 2H), 2.39 (qd, J=12.9, 5.0 Hz, 1H), 2.23 (d, J=11.8 Hz, 1H), 1.26 (s, 7H), 0.87 (q, J=7.0 Hz, 4H). Step 4: tert-butyl 4-[2-(2,6-dioxopiperidin-3-yl)-4-fluoro-1-oxo-3H-isoindol-5-yl]piperidine-1-carboxylate

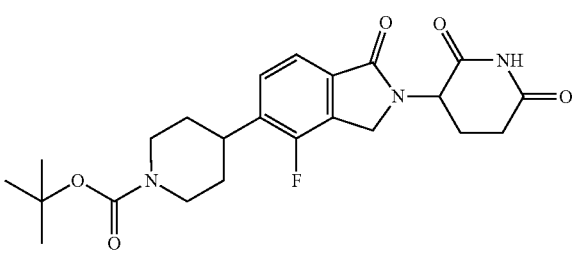 [SMILES: CC(C)(C)OC(=O)N1CCC(c2ccc3c(c2F)CN(C2CCC(=O)NC2=O)C3=O)CC1]

To a solution of tert-butyl 4-[2-(2,6-dioxopiperidin-3-yl)-4-fluoro-1-oxo-3H-isoindol-5-yl]-3,6-dihydro-2H-pyridine-1-carboxylate (200 mg, 0.5 mmol) in tetrahydrofuran (15 mL) was added 10% palladium on carbon (100 mg) at room temperature. The resulting mixture was degassed and purged with hydrogen for three times, then stirred for 3 h at room temperature under hydrogen atmosphere. The reaction mixture was filtered through Celite pad, washed with ethyl acetate (3×50 mL). The filtrate was concentrated to afford tert-butyl 4-[2-(2,6-dioxopiperidin-3-yl)-4-fluoro-1-oxo-3H-isoindol-5-yl]piperidine-1-carboxylate (185 mg, 92%) as a light yellow solid. MS (ESI): m/z 445.4 [M+H]+. Step 5: 3-[4-fluoro-1-oxo-5-(piperidin-4-yl)-3H-isoindol-2-yl]piperidine-2,6-dione

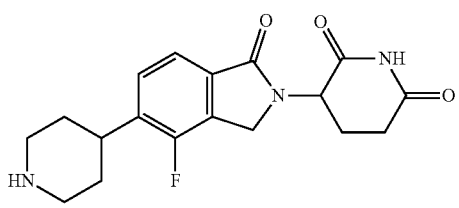 [SMILES: O=C1CCC(N2Cc3c(ccc(C4CCNCC4)c3F)C2=O)C(=O)N1]

A solution of tert-butyl 4-[2-(2,6-dioxopiperidin-3-yl)-4-fluoro-1-oxo-3H-isoindol-5-yl]piperidine-1-carboxylate (500 mg, 1 mmol) and 4 M hydrochloric acid in 1,4-dioxane (15 mL) was stirred for 3 h at room temperature. The reaction was concentrated to afford 3-[4-fluoro-1-oxo-5-(piperidin-4-yl)-3H-isoindol-2-yl]piperidine-2,6-dione hydrochloride (350 mg, 90%) as a light yellow solid, which was used in the next step without further purification. MS (ESI): m/z 345.3 [M+H]+. Step 6: (3R)—N-{2-cyano-3-[(3-{4-[4-({4-[2-(2,6-dioxopiperidin-3-yl)-4-fluoro-1-oxo-3H-isoindol-5-yl]piperidin-1-yl}methyl)piperidin-1-yl]phenyl}-4-oxoquinazolin-6-yl)oxy]-4-fluorophenyl}-3-fluoropyrrolidine-1-sulfonamide

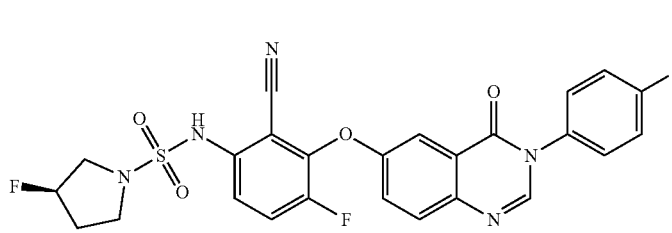 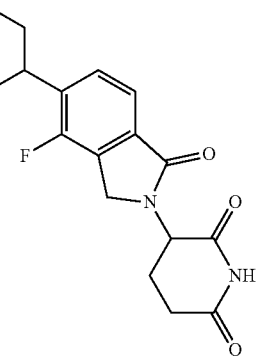

A mixture of 3-[4-fluoro-1-oxo-5-(piperidin-4-yl)-3H-isoindol-2-yl]piperidine-2,6-dione (136 mg, 0.4 mmol), (3R)—N-[2-cyano-4-fluoro-3-({3-[4-(4-formylpiperidin-1-yl)phenyl]-4-oxoquinazolin-6-yl}oxy)phenyl]-3-fluoropyrrolidine-1-sulfonamide (250 mg, 0.4 mmol), dichloromethane (15 mL) and N,N-diisopropylethylamine (3 mL) was stirred overnight at room temperature under nitrogen atmosphere. To the above mixture was added sodium triacetoxyborohydride (250.5 mg, 1.2 mmol) over 1 min. The reaction was stirred for 2 h at room temperature. The mixture was diluted with water (10 mL), extracted with dichloromethane (3×15 mL). The combined organic layers were washed with brine (3×10 mL), dried over anhydrous sodium sulfate, filtered, and concentrated. The residue was purified by preparative thin layer chromatography (dichloromethane/methanol=10:1) to afford (3R)—N-{2-cyano-3-[(3-{4-[4-({4-[2-(2,6-dioxopiperidin-3-yl)-4-fluoro-1-oxo-3H-isoindol-5-yl]piperidin-1-yl}methyl)piperidin-1-yl]phenyl}-4-oxoquinazolin-6-yl)oxy]-4-fluorophenyl}-3-fluoropyrrolidine-1-sulfonamide (96.3 mg, 23%) as an off-white solid. MS (ESI): m/z 964.3 [M+H]+; 1H NMR (400 MHz, DMSO-d6) δ 11.02 (s, 1H), 8.24 (s, 1H), 7.81 (d, J=8.9 Hz, 1H), 7.67 (dd, J=9.0, 3.0 Hz, 1H), 7.61 (d, J=7.7 Hz, 1H), 7.51 (s, 2H), 7.39-7.33 (d, J=8.7 Hz, 4H), 7.08 (d, J=8.7 Hz, 2H), 5.35 (s, 1H), 5.21 (s, 1H), 4.57 (d, J=17.4 Hz, 1H), 4.39 (d, J=17.3 Hz, 1H), 3.92-3.80 (m, 2H), 3.61 (m, 1H), 3.25 (d, 2H), 3.00-2.86 (d, 2H), 2.80 (t, J=12.1 Hz, 2H), 2.61 (d, J=16.6 Hz, 1H), 2.55 (s, 5H), 2.45 (d, J=13.0 Hz, 2H), 2.01-1.86 (d, J=12.9 Hz, 11H), 1.32 (d, J=13.4 Hz, 2H), 1.24 (s, 2H).

Example 80: (3R)—N-(2-cyano-3-{[3-(4-{4-[(1-{4-[(3R*)-2,6-dioxopiperidin-3-yl]-2-fluorophenyl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide Step 1: 4-(dimethoxymethyl)-1-(2-fluoro-4-nitrophenyl) piperidine

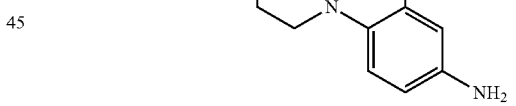

To a solution of 4-(dimethoxymethyl)piperidine (10 g, 63 mmol) in dimethyl sulfoxide (120 mL) was added N,N-diisopropylethylamine (16.23 g, 125 mmol) and 1,2-difluoro-4-nitro-benzene (7.0 mL, 63 mmol). The reaction was stirred at 110° C. for 1 h. The mixture was diluted with water (300 mL) and extracted with ethyl acetate (2×300 mL). The combined organic layers were washed with brine (4×500 mL), dried over anhydrous sodium sulfate, filtered, and concentrated. The crude product was triturated with petroleum ether/ethyl acetate (63 mL, 20:1) to afford 4-(dimethoxymethyl)-1-(2-fluoro-4-nitro-phenyl)piperidine (15.8 g, 84%) as a yellow solid. MS (ESI) m/z: 299.2 [M+H]+; 1H NMR (400 MHz, DMSO-d6) δ 8.03-7.93 (m, 2H), 7.21-7.07 (m, 1H), 4.10 (d, J=6.8 Hz, 1H), 3.70 (d, J=12.8 Hz, 2H), 3.27 (s, 6H), 2.89 (d, J=2.0, 12.4 Hz, 2H), 1.88-1.68 (m, 3H), 1.36 (d, J=4.0, 12.4 Hz, 2H). Step 2: 4-[4-(dimethoxymethyl)-1-piperidyl]-3-fluoro-aniline

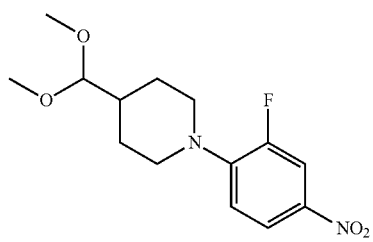 [SMILES: COC(OC)C1CCN(c2ccc([N+](=O)[O-])cc2F)CC1]

To a solution of 4-(dimethoxymethyl)-1-(2-fluoro-4-nitro-phenyl)piperidine (15.8 g, 53 mmol) in ethanol (100 mL) and water (100 mL) was added ammonium chloride (14.2 g, 264 mmol) and iron (14.8 g, 264 mmol). The mixture was stirred at 70° C. for 2 h, then diluted with water (500 mL) and extracted with ethyl acetate (2×600 mL). The combined organic layers were washed with brine (3×800 mL), dried over anhydrous sodium sulfate, filtered, and concentrated. The crude product was triturated with petroleum ether/ethyl acetate (84 mL, 20:1) to afford 4-[4-(dimethoxymethyl)-1-piperidyl]-3-fluoro-aniline (14 g, 99%) as a yellow solid. MS (ESI) m/z: 269.0 [M+H]+; 1H NMR (400 MHz, DMSO-d6) δ 6.75 (dd, J=8.8, 10.0 Hz, 1H), 6.39-6.25 (m, 2H), 4.93 (s, 2H), 4.09 (d, J=7.2 Hz, 1H), 3.27 (s, 6H), 3.13-3.04 (m, 2H), 2.49-2.42 (m, 2H), 1.71-1.54 (m, 3H), 1.41-1.26 (m, 2H). Step 3: 4-(dimethoxymethyl)-1-(2-fluoro-4-iodo-phenyl) piperidine

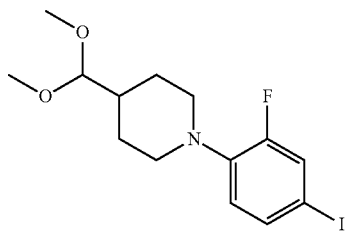 [SMILES: COC(OC)C1CCN(c2ccc(I)cc2F)CC1]

To a solution of 4-[4-(dimethoxymethyl)-1-piperidyl]-3-fluoro-aniline (12 g, 45 mmol) and p-toluensulfonic acid (25.5 g, 134 mmol) in acetonitrile (120 mL) was dropwise added sodium nitrite (6.17 g, 89 mmol) and potassium iodide (18.6 g, 112 mmol) in water (30 mL) at 0° C. The mixture was stirred at 40° C. for 1 h. The reaction was poured into water (500 mL) and extracted with ethyl acetate (3×400 mL). The combined organic layers were washed with brine (3×800 mL), dried over anhydrous sodium sulfate, filtered, and concentrated. The residue was purified by flash silica gel chromatography (0-20% ethyl acetate/petroleum ether) to afford 4-(dimethoxymethyl)-1-(2-fluoro-4-iodo-phenyl) piperidine (9 g, 53%) as a yellow solid. MS (ESI) m/z: 380.0 [M+H]+; 1H NMR (400 MHz, DMSO-d6) δ 7.47 (dd, J=2.0, 12.0 Hz, 1H), 7.41 (dd, J=1.6, 8.4 Hz, 1H), 6.85-6.78 (m, 1H), 4.10 (d, J=6.4 Hz, 1H), 3.41-3.29 (m, 4H), 3.27 (s, 6H), 1.74-1.63 (m, 3H), 1.42-1.30 (m, 2H). Step 4: 2, 6-dibenzyloxy-3-[4-[4-(dimethoxymethyl)-1-piperidyl]-3-fluoro-phenyl]pyridine

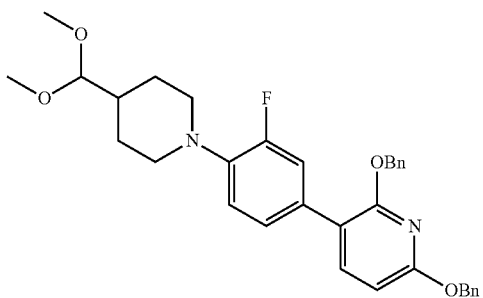 [SMILES: COC(OC)C1CCN(c2ccc(-c3ccc(OCc4ccccc4)nc3OCc3ccccc3)cc2F)CC1]

To a solution of 4-(dimethoxymethyl)-1-(2-fluoro-4-iodo-phenyl)piperidine (7.8 g, 21 mmol) and 2,6-dibenzyloxy-3-(4,4,5,5-tetramethyl-1,3,2-dioxaborolan-2-yl)pyridine (8.58 g, 21 mmol) in 1,4-dioxane (80 mL) and water (16 mL) was added sodium carbonate (6.54 g, 62 mmol) and [1,1'-bis(diphenylphosphino)ferrocene]dichloropalladium(II) (1.51 g, 2.1 mmol) under nitrogen atmosphere. The mixture was stirred at 90° C. for 3 h. The reaction was diluted with water (200 mL) and extracted with ethyl acetate (3×200 mL). The combined organic layers were washed with brine (3×600 mL), dried over anhydrous sodium sulfate, filtered, and concentrated. The residue was purified by flash silica gel chromatography (0-10% ethyl acetate/petroleum ether) to afford 2, 6-dibenzyloxy-3-[4-[4-(dimethoxymethyl)-1-piperidyl]-3-fluoro-phenyl]pyridine (9.3 g, 83%) as a yellow solid. MS (ESI) m/z: 543.4 [M+H]+; 1H NMR (400 MHz, DMSO-d6) δ 7.74 (d, J=8.4 Hz, 1H), 7.45-7.26 (m, 12H), 7.01 (t, J=9.2 Hz, 1H), 6.52 (d, J=8.0 Hz, 1H), 5.40 (s, 2H), 5.36 (s, 2H), 4.10 (d, J=6.4 Hz, 1H), 3.37 (d, J=11.6 Hz, 2H), 3.27 (s, 6H), 2.67-2.56 (m, 2H), 1.76-1.63 (m, 3H), 1.44-1.30 (m, 2H). Step 5: 3-[4-[4-(dimethoxymethyl)-1-piperidyl]-3-fluoro-phenyl]piperidine-2,6-dione

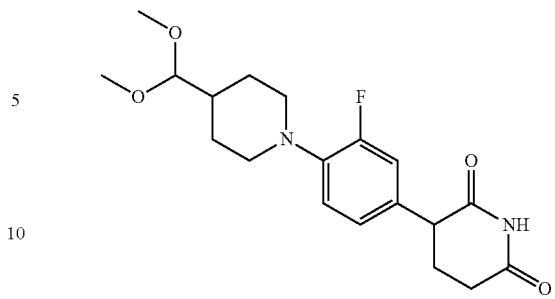

To a solution of 2, 6-dibenzyloxy-3-[4-[4-(dimethoxymethyl)-1-piperidyl]-3-fluoro-phenyl]pyridine (8.3 g, 15 mmol) in 2,2,2-trifluoroethanol (150 mL) was added 10% palladium on carbon (0.8 g) under nitrogen. The suspension was degassed and purged with hydrogen for three times. The mixture was stirred under hydrogen (50 psi) at 30° C. for 12 h, then filtered through Celite pad, and concentrated. The crude product was triturated with petroleum ether/ethyl acetate (50 mL, 1:1) to afford 3-[4-[4-(dimethoxymethyl)-1-piperidyl]-3-fluoro-phenyl]piperidine-2,6-dione (5.2 g, 93%) as a white solid. MS (ESI) m/z: 365.2 [M+H]+; 1H NMR (400 MHz, DMSO-d6) δ 10.81 (s, 1H), 7.02 (d, J=1.6 Hz, 1H), 6.98 (d, J=4.4 Hz, 1H), 6.96-6.93 (m, 1H), 4.11 (d, J=6.4 Hz, 1H), 3.79 (dd, J=4.8, 12.0 Hz, 1H), 3.27 (s, 6H), 2.71-2.54 (m, 5H), 2.18 (dd, J=4.4, 12.4 Hz, 1H), 2.04-1.94 (m, 1H), 1.77-1.61 (m, 4H), 1.45-1.32 (m, 2H). Step 6: (3R)-3-[4-[4-(dimethoxymethyl)-1-piperidyl]-3-fluoro-phenyl]piperidine-2, 6-dione and (3S)-3-[4-[4-(dimethoxymethyl)-1-piperidyl]-3-fluoro-phenyl]piperidine-2, 6-dione

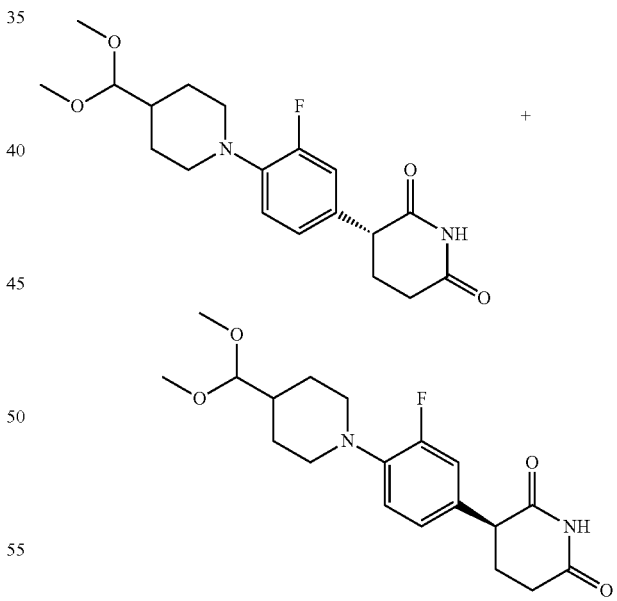

3-[4-[4-(dimethoxymethyl)-1-piperidyl]-3-fluoro-phenyl]piperidine-2, 6-dione (4.5 g) was purified by preparative supercritical fluid chromatography (mobile phase: carbon dioxide:isopropanol; 50% B isocratic elution). Peak 1 was isolated as (3R)-3-[4-[4-(dimethoxymethyl)-1-piperidyl]-3-fluoro-phenyl]piperidine-2,6-dione (2.2 g, 98%) as a white solid. MS (ESI) m/z: 365.2 [M+H]+. Peak 2 was isolated as (3S)-3-[4-[4-(dimethoxymethyl)-1-piperidyl]-3-fluoro-phenyl]piperidine-2, 6-dione (2.2 g, 98%) as a white solid. MS (ESI) m/z: 365.2 [M+H]+. Step 7: 1-[4-[(3R)-2, 6-dioxo-3-piperidyl]-2-fluoro-phenyl]piperidine-4-carbaldehyde

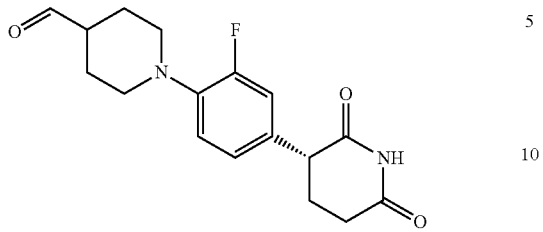

To a solution of (3R)-3-[4-[4-(dimethoxymethyl)-1-piperidyl]-3-fluoro-phenyl]piperidine-2, 6-dione (2 g, 5 mmol) in acetone (20 mL) and water (2 mL) was added p-toluensulfonic acid (189 mg, 1.1 mmol). The mixture was stirred at 70° C. for 3 h, then concentrated to afford 1-[4-[(3R)-2, 6-dioxo-3-piperidyl]-2-fluoro-phenyl]piperidine-4-carbaldehyde (1.7 g, 97%) as a yellow solid, which was used in the next step without further purification. MS (ESI) m/z: 319.1 [M+H]+. Step 8: (3R)—N-[2-cyano-3-[3-[4-[4-[[1-[4-[(3R)-2,6-dioxo-3-piperidyl]-2-fluoro-phenyl]-4-piperidyl]methyl]piperazin-1-yl]phenyl]-4-oxo-quinazolin-6-yl]oxy-4-fluoro-phenyl]-3-fluoro-pyrrolidine-1-sulfonamide

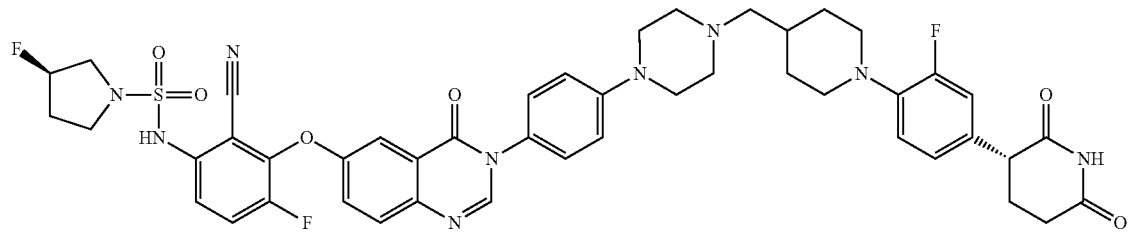 [SMILES: N#Cc1c(NS(=O)(=O)N2CC[C@@H](F)C2)ccc(F)c1Oc1ccc2ncn(-c3ccc(N4CCN(CC5CCN(c6ccc([C@H]7CCC(=O)NC7=O)cc6F)CC5)CC4)cc3)c(=O)c2c1]

To a solution of (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide (2.5 g, 4 mmol) in dichloromethane (20 mL) was added 1-[4-[(3R)-2,6-dioxo-3-piperidyl]-2-fluoro-phenyl]piperidine-4-carbaldehyde (1.7 g, 5 mmol) in dimethyl sulfoxide (20 mL) and acetic acid (494 mg, 8 mmol). The mixture was stirred at 25° C. for 15 min. Then sodium triacetoxyborohydride (1.74 g, 8 mmol) was added and the mixture was stirred at 25° C. for 30 min. The reaction was diluted with water (100 mL) and extracted with tetrahydrofuran (2×60 mL). The combined organic layers were washed with brine (3×200 mL), dried over sodium sulfate, filtered, and concentrated. The residue was purified by preparative high-performance liquid chromatography (mobile phase: 0.2% formic acid in water:acetonitrile; gradient: 30%-60% B over 20 min). The crude product was further purified by preparative supercritical fluid chromatography (mobile phase: carbon dioxide:acetonitrile/isopropanol (0.1% ammonia); B %: 57.5% isocratic elution) to afford (3R)—N-[2-cyano-3-[3-[4-[4-[[1-[4-[(3R)-2,6-dioxo-3-piperidyl]-2-fluoro-phenyl]-4-piperidyl]methyl]piperazin-1-yl]phenyl]-4-oxo-quinazolin-6-yl]oxy-4-fluoro-phenyl]-3-fluoro-pyrrolidine-1-sulfonamide (1.85 g, 64%) as a white solid. MS (ESI) m/z: 910.5 [M+H]$^+$; 1H NMR (400 MHz, DMSO-d6) δ 10.83 (s, 1H), 10.30-9.74 (m, 1H), 8.25 (s, 1H), 7.82 (d, J=9.2 Hz, 1H), 7.74-7.62 (m, 2H), 7.46-7.39 (m, 2H), 7.36 (d, J=8.8 Hz, 2H), 7.09 (d, J=9.2 Hz, 2H), 7.05-6.98 (m, 2H), 6.97-6.93 (m, 1H), 5.41-5.19 (m, 1H), 3.80 (dd, J=4.8, 11.8 Hz, 1H), 3.50-3.40 (m, 2H), 3.36 (s, 4H), 3.31-3.30 (m, 2H), 3.29-3.22 (m, 2H), 3.06-2.74 (m, 4H), 2.73-2.60 (m, 5H), 2.47-2.44 (m, 1H), 2.27-2.17 (m, 1H), 2.16-2.09 (m, 1H), 2.07-1.95 (m, 2H), 1.90-1.76 (m, 3H), 1.42-1.27 (m, 2H).

Example 81: (3R)—N-(2-cyano-3-{[3-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-4-oxo-3,4-dihydroquinazolin-6-yl]oxy}-4-fluorophenyl)-3-fluoropyrrolidine-1-sulfonamide Step 1: 4-(dimethoxymethyl)-1-(4-nitrophenyl)piperidine

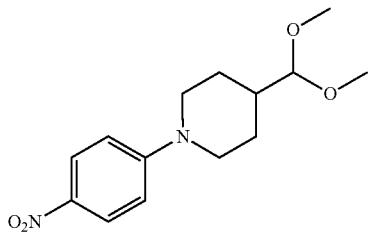 [SMILES: COC(OC)C1CCN(c2ccc([N+](=O)[O-])cc2)CC1]

To a solution of 1-fluoro-4-nitrobenzene (11.3 mL, 106 mmol) and 4-(dimethoxymethyl)piperidine (17.8 g, 112 mmol) in dimethyl sulfoxide (150 mL) was added N-ethyl-N,N-diisopropylamine (74.1 mL, 425 mmol). The reaction was stirred at 90° C. for 3 h. The mixture was filtered, the filter cake was washed with acetonitrile (50 mL), dried in vacuum to afford 4-(dimethoxymethyl)-1-(4-nitrophenyl)piperidine (29 g, 95%) as a yellow solid, which was used in the next step without further purification. MS (ESI) m/z: 281.0 [M+H]+. Step 2: 4-(4-(dimethoxymethyl)piperidin-1-yl)aniline

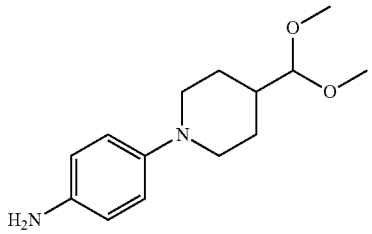

To a solution of 4-(dimethoxymethyl)-1-(4-nitrophenyl)piperidine (29.0 g, 103 mmol) in ethanol (300 mL) and water (60 mL) was added iron (28.9 g, 517 mmol) and ammonium chloride (16.6 g, 310 mmol). The reaction was stirred at 75° C. for 3 h. The mixture was diluted with brine (50 mL) and extracted with ethyl acetate (3×50 mL). The combined organic layers were washed with brine (3×50 mL), dried over sodium sulfate, filtered, and concentrated. The residue was purified by column chromatography (petroleum ether/ethyl acetate=100:1 to 1:1) to afford 4-(4-(dimethoxymethyl)piperidin-1-yl)aniline (21 g, 77%) as a brown solid. MS (ESI) m/z: 251.1 [M+H]+. Step 3: 3-(4-(4-(dimethoxymethyl)piperidin-1-yl)phenyl)-6-hydroxyquinazolin-4(3H)-one

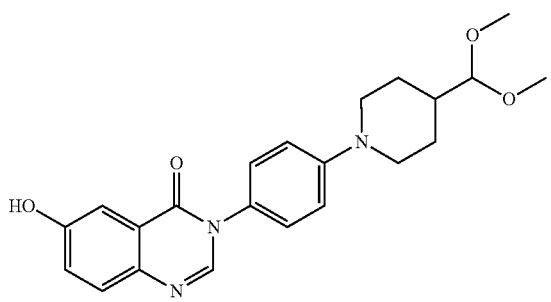 [SMILES: COC(OC)C1CCN(c2ccc(-n3cnc4ccc(O)cc4c3=O)cc2)CC1]

To a solution of methyl 2-amino-5-hydroxybenzoate (3.67 g, 22 mmol) and 4-(4-(dimethoxymethyl)piperidin-1-yl)aniline (5.5 g, 22 mmol) in toluene (10 mL) and methanol (2 mL) was added trimethoxymethane (3.6 mL, 33 mmol) and acetic acid (1.3 mL, 22 mmol). The mixture was stirred at 70° C. for 6 h, then cooled to room temperature. The mixture was suspended in tert-butyl methyl ether (35 mL), filtered and washed with tert-butyl methyl ether (35 mL) to afford 3-(4-(4-(dimethoxymethyl)piperidin-1-yl)phenyl)-6-hydroxyquinazolin-4(3H)-one (7.7 g, 87%) as a brown solid. MS (ESI) m/z: 396.3 [M+H]+; 1H NMR (400 MHz, DMSO-d6) δ 10.14 (s, 1H), 8.09 (s, 1H), 7.59 (d, J=8.8 Hz, 1H), 7.47 (d, J=2.8 Hz, 1H), 7.24-7.34 (m, 3H), 7.03 (d, J=8.8 Hz, 2H), 4.10 (d, J=6.8 Hz, 1H), 3.80 (d, J=12.4 Hz, 2H), 3.28 (s, 6H), 2.64-2.79 (m, 2H), 1.72 (d, J=12.0 Hz, 3H), 1.25-1.42 (m, 2H). Step 4: 2-((3-(4-(4-(dimethoxymethyl)piperidin-1-yl)phenyl)-4-oxo-3,4-dihydroquinazolin-6-yl)oxy)-3,6-difluorobenzonitrile

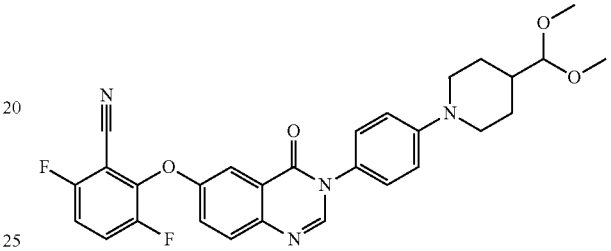

To a solution of 3-(4-(4-(dimethoxymethyl)piperidin-1-yl)phenyl)-6-hydroxyquinazolin-4(3H)-one (7.7 g, 19 mmol) and 2,3,6-trifluorobenzonitrile (3.98 g, 25 mmol) in N,N-dimethylformamide (80 mL) was added cesium carbonate (8.25 g, 25 mmol). The mixture was stirred at 25° C. for 5 h, then diluted with brine (80 mL) and extracted with tetrahydrofuran (3×80 mL) and ethyl acetate (3×80 mL). The combined organic layers were washed with brine (3×50 mL), dried over sodium sulfate, filtered, and concentrated. The crude product was triturated with petroleum ether/ethyl acetate (3:1) to afford 2-((3-(4-(4-(dimethoxymethyl)piperidin-1-yl)phenyl)-4-oxo-3,4-dihydroquinazolin-6-yl)oxy)-3,6-difluorobenzonitrile (14.4 g, crude) as a yellow solid. MS (ESI) m/z: 533.3 [M+H]+; 1H NMR (400 MHz, DMSO-d6) δ 8.28 (s, 1H), 7.98 (td, J=10.8, 5.2 Hz, 1H), 7.80-7.86 (m, 1H), 7.73-7.79 (m, 1H), 7.53-7.66 (m, 2H), 7.31 (d, J=8.8 Hz, 2H), 7.04 (d, J=9.2 Hz, 2H), 4.04-4.16 (m, 1H), 3.82 (d, J=12.4 Hz, 2H), 3.29 (s, 6H), 2.67-2.77 (m, 2H), 1.69-1.85 (m, 3H), 1.27-1.43 (m, 2H). Step 5: (R)—N-(2-cyano-3-((3-(4-(4-(dimethoxymethyl)piperidin-1-yl)phenyl)-4-oxo-3,4-dihydroquinazolin-6-yl)oxy)-4-fluorophenyl)-3-fluoropyrrolidine-1-sulfonamide

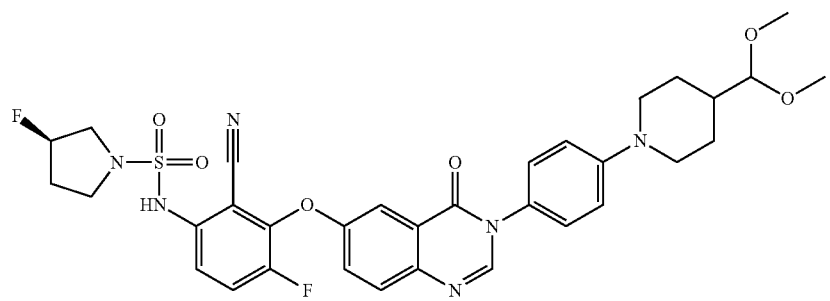 [SMILES: COC(OC)C1CCN(c2ccc(-n3cnc4ccc(Oc5c(F)ccc(NS(=O)(=O)N6CC[C@@H](F)C6)c5C#N)cc4c3=O)cc2)CC1]

To a solution of 2-((3-(4-(4-(dimethoxymethyl)piperidin-1-yl)phenyl)-4-oxo-3,4-dihydroquinazolin-6-yl)oxy)-3,6-difluorobenzonitrile (10.4 g, 19 mmol) and (3R)-3-fluoropyrrolidine-1-sulfonamide (5.91 g, 35 mmol) in N,N-dimethylformamide (100 mL) was added cesium carbonate (19.1 g, 59 mmol). The mixture was stirred at 80° C. for 5 h, then diluted with water (100 mL), extracted with tetrahydrofuran (3×100 mL) and ethyl acetate (3×100 mL). The combined organic layers were washed with brine (3×80 mL), dried over sodium sulfate, filtered, and concentrated. The residue was purified by preparative high-performance liquid chromatography (mobile phase: [0.2% formic acid in water-acetonitrile]; B %: 46%-76%, 20 min) to afford (R)—N-(2-cyano-3-((3-(4-(4-(dimethoxymethyl)piperidin-1-yl) phenyl)-4-oxo-3,4-dihydroquinazolin-6-yl)oxy)-4-fluorophenyl)-3-fluoropyrrolidine-1-sulfonamide (7.8 g, 57%) as a yellow solid. MS (ESI) m/z: 681.3 [M+H]⁺; 1H NMR (400 MHz, DMSO-d6) δ 10.12-10.47 (m, 1H), 8.26 (s, 1H), 8.13 (s, 1H), 7.95 (s, 1H), 7.79-7.89 (m, 2H), 7.71 (dd, J=8.8, 3.2 Hz, 1H), 7.52 (dd, J=9.2, 4.0 Hz, 1H), 7.42 (d, J=3.2 Hz, 1H), 7.29 (d, J=8.8 Hz, 2H), 7.03 (d, J=9.2 Hz, 2H), 5.21-5.43 (m, 1H), 4.09 (d, J=6.8 Hz, 1H), 3.80 (d, J=12.4 Hz, 2H), 3.52 (s, 1H), 3.41-3.49 (m, 2H), 3.27 (s, 6H), 2.65-2.72 (m, 2H), 1.97-2.20 (m, 2H), 1.64-1.84 (m, 3H), 1.26-1.43 (m, 2H). Step 6: (R)—N-(2-cyano-4-fluoro-3-(3-(4-(4-formylpiperidin-1-yl)phenyl)-4-oxo-3,4-dihydroquinazolin-6-yl)oxy)phenyl)-3-fluoropyrrolidine-1-sulfonamide

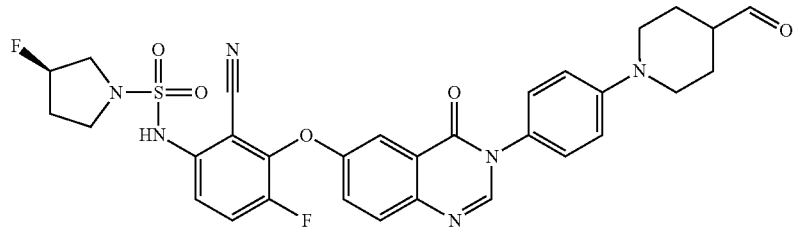 [SMILES: N#Cc1c(NS(=O)(=O)N2CC[C@@H](F)C2)ccc(F)c1Oc1ccc2ncn(-c3ccc(N4CCC(C=O)CC4)cc3)c(=O)c2c1]

To a solution of (R)—N-(2-cyano-3-((3-(4-(4-(dimethoxymethyl)piperidin-1-yl)phenyl)-4-oxo-3,4-dihydroquinazolin-6-yl)oxy)-4-fluorophenyl)-3-fluoropyrrolidine-1-sulfonamide (3 g, 4 mmol) in acetone (30 mL) and water (3 mL) was added p-toluenesulfonic acid (303 mg, 1.8 mmol). The mixture was stirred at 70° C. for 3 h, then concentrated to afford (R)—N-(2-cyano-4-fluoro-3-((3-(4-(4-formylpiperidin-1-yl)phenyl)-4-oxo-3,4-dihydroquinazolin-6-yl)oxy) phenyl)-3-fluoropyrrolidine-1-sulfonamide (2.8 g, crude) as a yellow solid. MS (ESI) m/z: 635.2 [M+H]+. Step 7: (R)—N-(2-cyano-3-((3-(4-(4-((4-(2-((S)-2,6-dioxopiperidin-3-yl)-1-oxoisoindolin-5-yl)piperidin-1-yl)methyl)piperidin-1-yl)phenyl)-4-oxo-3,4-dihydroquinazolin-6-yl)oxy)-4-fluorophenyl)-3-fluoropyrrolidine-1-sulfonamide

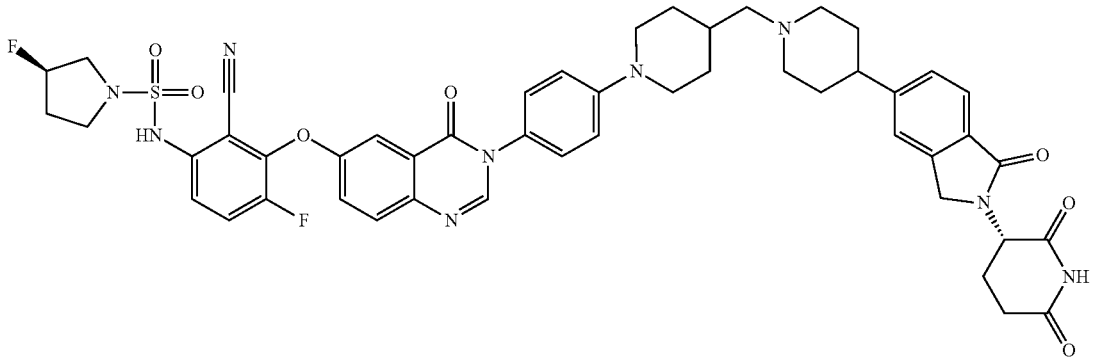 [SMILES: N#Cc1c(NS(=O)(=O)N2CC[C@@H](F)C2)ccc(F)c1Oc1ccc2ncn(-c3ccc(N4CCC(CN5CCC(c6ccc7c(c6)CN([C@H]6CCC(=O)NC6=O)C7=O)CC5)CC4)cc3)c(=O)c2c1]

To a solution of (R)-3-((R)-1-oxo-5-(piperidin-4-yl)-2,3-dihydro-1H-inden-2-yl)piperidine-2,6-dione (2.47 g, 4.4 mmol) in dichloromethane (30 mL) and isopropanol (30 mL) was added sodium acetate (253 mg, 3 mmol). The mixture was stirred at 25° C. for 10 min, followed by the addition of (R)—N-(2-cyano-4-fluoro-3-((3-(4-(4-formylpiperidin-1-yl)phenyl)-4-oxo-3,4-dihydroquinazolin-6-yl)oxy)phenyl)-3-fluoropyrrolidine-1-sulfonamide (2.8 g, 4.4 mmol), the mixture was stirred at 25° C. for 10 min. Then sodium triacetoxyborohydride (1.87 g, 8.8 mmol) was added, the mixture was stirred at 25° C. for 40 min. The reaction was diluted with brine (80 mL) and sodium bicarbonate (80 mL), extracted with tetrahydrofuran (3×100 mL). The combined organic layers were washed with brine (3×80 mL), dried over sodium sulfate, filtered, and concentrated. The residue was purified by preparative high-performance liquid chromatography (mobile phase: 0.2% formic acid in water:acetonitrile; gradient: 20%-50% B over 14 min). The crude product was further purified by supercritical fluid chromatography (mobile phase: carbon dioxide:acetonitrile/isopropanol (0.1% ammonia solution); B %: 70%) to afford (R)—N-(2-cyano-3-((3-(4-(4-((4-(2-((S)-2,6-dioxopiperidin-3-yl)-1-oxoisoindolin-5-yl)piperidin-1-yl)methyl)piperidin-1-yl)phenyl)-4-oxo-3,4-dihydroquinazolin-6-yl)oxy)-4-fluorophenyl)-3-fluoropyrrolidine-1-sulfonamide (1.28 g, 30%) as an off-white solid. MS (ESI) m/z: 946.3 [M+H]+; 1H NMR (400 MHz, DMSO-d6) δ 10.99 (s, 1H), 9.05-9.67 (m, 1H), 8.23 (s, 1H), 7.80 (d, J=8.8 Hz, 1H), 7.64-7.73 (m, 2H), 7.50 (s, 2H), 7.38-7.44 (m, 2H), 7.29-7.37 (m, 3H), 7.07 (d, J=9.2 Hz, 2H), 5.17-5.39 (m, 1H), 5.11 (dd, J=13.2, 5.6 Hz, 1H), 4.39-4.51 (m, 1H), 4.26-4.37 (m, 1H), 3.85 (d, J=12.0 Hz, 2H), 3.41 (dd, J=12.4, 3.8 Hz, 3H), 3.28 (s, 2H), 3.13-3.23 (m, 1H), 2.85-3.09 (m, 4H), 2.80 (br t, J=12.0 Hz, 3H), 2.53-2.69 (m, 2H), 2.30-2.47 (m, 1H), 2.08-2.18 (m, 1H), 1.91-2.05 (m, 7H), 1.87 (d, J=12.4 Hz, 2H), 1.26-1.40 (m, 2H).

Example 82: (3R)—N-{2-cyano-3-[(3-{4-[4-({1-[2-(2,6-dioxopiperidin-3-yl)-1-oxo-2,3-dihydro-1H-isoindol-5-yl]piperidin-4-yl}oxy)piperidin-1-yl]phenyl}-4-oxo-3,4-dihydroquinazolin-6-yl)oxy]-4-fluorophenyl}-3-fluoropyrrolidine-1-sulfonamide Step 1:
6-(benzyloxy)-3-(4-bromophenyl)quinazolin-4-one

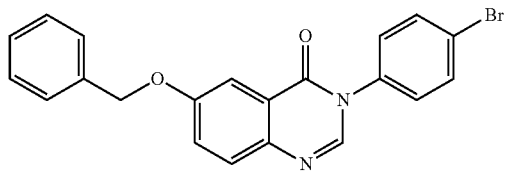 [SMILES: O=c1c2cc(OCc3ccccc3)ccc2ncn1-c1ccc(Br)cc1]

To a stirred solution of 3-(4-bromophenyl)-6-hydroxyquinazolin-4-one (8.3 g, 26 mmol) and benzyl bromide (5.37 g, 31 mmol) in N,N-dimethylformamide (100 mL) was added cesium carbonate (17.91 g, 55 mmol) in portions at room temperature. The resulting mixture was stirred for 2 h at room temperature, then suspended in water (100 mL). The precipitate was collected by filtration and washed with water (2×100 mL). The crude product was purified by trituration with ethyl acetate (20 mL) and petroleum ether (20 mL) to afford 6-(benzyloxy)-3-(4-bromophenyl)quinazolin-4-one (10 g, 94%) as a white solid. MS (ESI): m/z 409.05 [M+H]+.

Step 2: tert-butyl 4-[(1-{4-[6-(benzyloxy)-4-oxoquinazolin-3-yl]phenyl}piperidin-4-yl)oxy]piperidine-1-carboxylate

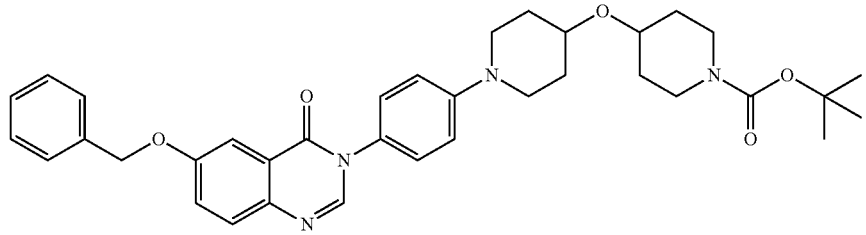 [SMILES: CC(C)(C)OC(=O)N1CCC(OC2CCN(c3ccc(-n4cnc5ccc(OCc6ccccc6)cc5c4=O)cc3)CC2)CC1]

To a stirred mixture of 6-(benzyloxy)-3-(4-bromophenyl)quinazolin-4-one (700 mg, 1.7 mmol) and tert-butyl 4-(piperidin-4-yloxy)piperidine-1-carboxylate (587 mg, 2 mmol) in 1,4-dioxane (20 mL) was added cesium carbonate (1.68 g, 5 mmol) and (2-dicyclohexylphosphino-2',6'-diisopropoxy-1,1'-biphenyl)[2-(2'-amino-1,1'-biphenyl)]palladium(II) methanesulfonate (144 mg, 0.2 mmol) in portions at room temperature. The resulting mixture was stirred overnight at 90° C., then cooled to room temperature. The mixture was diluted with water (10 mL), extracted with ethyl acetate (2×100 mL). The combined organic layers were washed with brine (2×20 mL), dried over anhydrous sodium sulfate, filtered, and concentrated. The residue was purified by silica gel column chromatography (petroleum ether/ethyl acetate=1:1) to afford tert-butyl 4-[(1-{4-[6-(benzyloxy)-4-oxoquinazolin-3-yl]phenyl}piperidin-4-yl)oxy]piperidine-1-carboxylate (980 mg, 93%) as a white solid. 1H NMR (300 MHz, DMSO-d6) δ 7.73-7.62 (m, 1H), 7.59-7.45 (m, 2H), 7.51-7.31 (m, 3H), 7.34-7.24 (m, 5H), 7.09-7.00 (m, 2H), 5.26 (s, 2H), 3.67 (t, J=4.3 Hz, 6H), 3.34 (s, 4H), 3.05-2.91 (m, 4H), 1.90 (d, J=11.7 Hz, 4H), 1.77 (d, J=11.5 Hz, 2H), 1.40 (s, 9H); MS (ESI): m/z 611.45 [M+H]+. Step 3: 6-(benzyloxy)-3-{4-[4-(piperidin-4-yloxy)piperidin-1-yl]phenyl}quinazolin-4-one

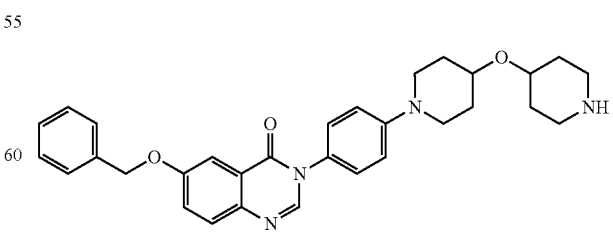

A solution of tert-butyl 4-[(1-{4-[6-(benzyloxy)-4-oxoquinazolin-3-yl]phenyl}piperidin-4-yl)oxy]piperidine-1-carboxylate (980 mg, 1.6 mmol) and 4 M hydrogen chloride in 1,4-dioxane (20 mL) was stirred for 2 h at room temperature, then concentrated. The residue was triturated with ethyl acetate (10 mL), filtered to afford 6-(benzyloxy)-3-{4-[4-(piperidin-4-yloxy)piperidin-1-yl]phenyl}quinazolin-4-one hydrochloride (800 mg, 91%) as a white solid. MS (ESI): m/z 511.40 [M+H]+. Step 4: 3-(5-{4-[(1-{4-[6-(benzyloxy)-4-oxoquinazolin-3-yl]phenyl}piperidin-4-yl)oxy]piperidin-1-yl}-1-oxo-3H-isoindol-2-yl)piperidine-2,6-dione

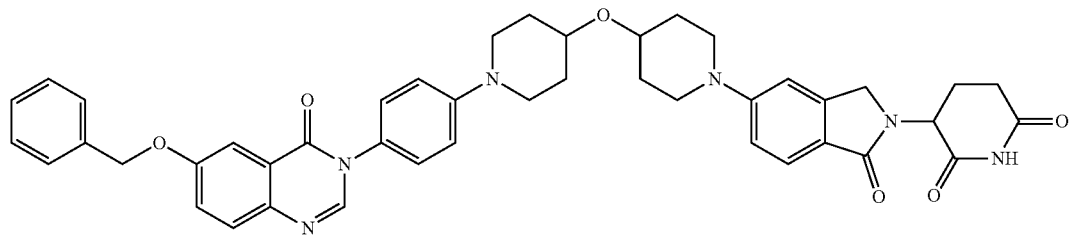 [SMILES: O=C1CCC(N2Cc3cc(N4CCC(OC5CCN(c6ccc(-n7cnc8ccc(OCc9ccccc9)cc8c7=O)cc6)CC5)CC4)ccc3C2=O)C(=O)N1]

To a stirred mixture of 6-(benzyloxy)-3-{4-[4-(piperidin-4-yloxy)piperidin-1-yl]phenyl}quinazolin-4-one hydrochloride (700 mg, 1.3 mmol) and 3-(5-bromo-1-oxo-3H-isoindol-2-yl)piperidine-2,6-dione (496 mg, 1.5 mmol) in N,N-dimethylformamide (15 mL) was added cesium carbonate (1.67 g, 5 mmol) and dichloro[1,3-bis(2,6-di-3-pentylphenyl)imidazol-2-ylidene](3-chloropyridyl)palladium(II) (53.8 mg, 0.06 mmol) at room temperature. The resulting mixture was stirred for 5 h at 90° C., then cooled to room temperature. The mixture was diluted with water (10 mL), extracted with ethyl acetate (2×100 mL). The combined organic layers were washed with water (2×20 mL), dried over anhydrous sodium sulfate, filtered, and concentrated. The residue was purified by silica gel column chromatography (petroleum ether/ethyl acetate=1:1) to afford 3-(5-{4-[(1-{4-[6-(benzyloxy)-4-oxoquinazolin-3-yl]phenyl}piperidin-4-yl)oxy]piperidin-1-yl}-1-oxo-3H-isoindol-2-yl)piperidine-2,6-dione (900 mg, 93%) as an off-white solid. 1H NMR (400 MHz, DMSO-d6) δ 10.96 (s, 1H), 8.19 (s, 1H), 7.73-7.64 (m, 2H), 7.56-7.55 (m, 4H), 7.54-7.47 (m, 2H), 7.42-7.41 (m, 3H), 7.11-7.04 (m, 4H), 5.77 (s, 3H), 5.27 (s, 2H), 5.05-4.98 (m, 1H), 4.33 (d, J=16.9 Hz, 1H), 4.21 (d, J=16.9 Hz, 1H), 4.04 (q, J=7.1 Hz, 1H), 3.69 (q, J=15.1, 12.2 Hz, 6H), 3.61 (s, 4H), 3.10 (t, J=10.5 Hz, 1H), 3.04 (s, 2H), 3.01 (d, J=10.9 Hz, 1H), 2.91-2.86 (m, 1H), 2.63-2.54 (m, 2H), 2.00 (s, 1H), 1.96-1.91 (m, 2H), 1.59-1.47 (m, 4H), 1.24 (s, 1H), 1.22 (s, 1H), 1.18 (t, J=7.1 Hz, 1H); MS (ESI): m/z 753.35 [M+H]+. Step 5: 3-{5-[4-({1-[4-(6-hydroxy-4-oxoquinazolin-3-yl)phenyl]piperidin-4-yl}oxy)piperidin-1-yl]-1-oxo-3H-isoindol-2-yl}piperidine-2,6-dione

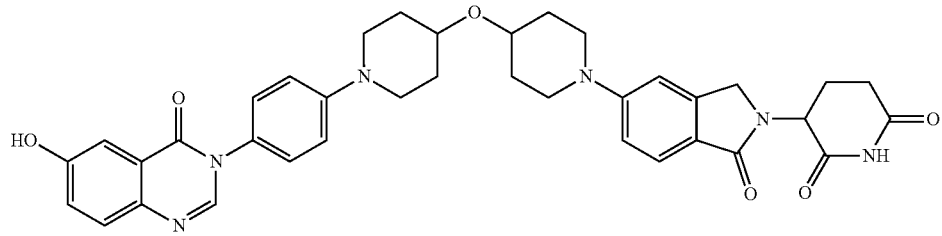 [SMILES: O=C1CCC(N2Cc3cc(N4CCC(OC5CCN(c6ccc(-n7cnc8ccc(O)cc8c7=O)cc6)CC5)CC4)ccc3C2=O)C(=O)N1]

To a solution of 3-(5-{4-[(1-{4-[6-(benzyloxy)-4-oxoquinazolin-3-yl]phenyl}piperidin-4-yl)oxy]piperidin-1-yl}-1-oxo-3H-isoindol-2-yl)piperidine-2,6-dione (600 mg, 0.8 mmol) in tetrahydrofuran (50 mL) and N,N-dimethylformamide (10 mL) was added 10% palladium on carbon (300 mg). The mixture was degassed and purged with hydrogen three times before stirring at room temperature for 2 h under hydrogen atmosphere. The mixture was filtered through Celite pad, concentrated under reduced pressure to afford 3-{5-[4-({1-[4-(6-hydroxy-4-oxoquinazolin-3-yl)phenyl]piperidin-4-yl}oxy)piperidin-1-yl]-1-oxo-3H-isoindol-2-yl}piperidine-2,6-dione (400 mg, 76%) as an off-white solid. MS (ESI): m/z 663.45 [M−56+H]+. Step 6: 2-[(3-{4-[4-({1-[2-(2,6-dioxopiperidin-3-yl)-1-oxo-3H-isoindol-5-yl]piperidin-4-yl}oxy)piperidin-1-yl]phenyl}-4-oxoquinazolin-6-yl)oxy]-3,6-difluorobenzonitrile

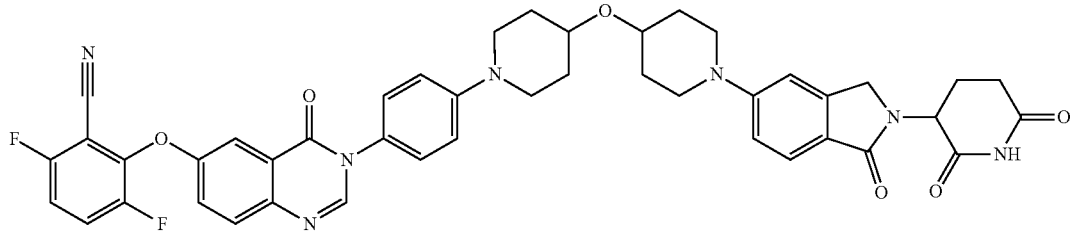 [SMILES: N#Cc1c(F)ccc(F)c1Oc1ccc2ncn(-c3ccc(N4CCC(OC5CCN(c6ccc7c(c6)CN(C6CCC(=O)NC6=O)C7=O)CC5)CC4)cc3)c(=O)c2c1]

To a stirred solution of 3-{5-[4-({1-[4-(6-hydroxy-4-oxoquinazolin-3-yl)phenyl]piperidin-4-yl}oxy)piperidin-1-yl]-1-oxo-3H-isoindol-2-yl}piperidine-2,6-dione (500 mg, 0.8 mmol) and 2,3,6-trifluorobenzonitrile (178 mg, 1.1 mmol) in N,N-dimethylformamide (15 mL) was added cesium carbonate (614 mg, 1.9 mmol) at room temperature. The resulting mixture was stirred overnight at 90° C. under nitrogen atmosphere. The reaction was cooled to room temperature, diluted with water (20 mL) and extracted with ethyl acetate (3×100 mL). The combined organic layers were washed with brine (2×100 mL), dried over anhydrous sodium sulfate, filtered, and concentrated. The residue was purified by silica gel column chromatography (petroleum ether/ethyl acetate=1:1) to afford 2-[(3-{4-[4-({1-[2-(2,6-dioxopiperidin-3-yl)-1-oxo-3H-isoindol-5-yl]piperidin-4-yl}oxy)piperidin-1-yl]phenyl}-4-oxoquinazolin-6-yl)oxy]-3,6-difluorobenzonitrile (510 mg, 85%) as an off-white solid. MS (ESI): m/z 800.55 [M+H]+. Step 7: (3R)—N-{2-cyano-3-[(3-{4-[4-({1-[2-(2,6-dioxopiperidin-3-yl)-1-oxo-3H-isoindol-5-yl]piperidin-4-yl}oxy)piperidin-1-yl]phenyl}-4-oxoquinazolin-6-yl)oxy]-4-fluorophenyl}-3-fluoropyrrolidine-1-sulfonamide resulting mixture was stirred for 0.5 h at 50° C. under nitrogen atmosphere. Then 2-[(3-{4-[4-({1-[2-(2,6-dioxopiperidin-3-yl)-1-oxo-3H-isoindol-5-yl]piperidin-4-yl}oxy)piperidin-1-yl]phenyl}-4-oxoquinazolin-6-yl)oxy]-3,6-difluorobenzonitrile (320 mg, 0.4 mmol) was added to the above mixture in portions, the reaction was stirred for 3 h at 90° C., then cooled to room temperature. The mixture was diluted with water (80 mL) and extracted with ethyl acetate (2×100 mL). The combined organic layers were washed with brine (3×10 mL), dried over anhydrous sodium sulfate, filtered, and concentrated. The residue was purified by preparative thin layer chromatography (dichloromethane/methanol=10:1) to afford (3R)—N-{2-cyano-3-[(3-{4-[4-({1-[2-(2,6-dioxopiperidin-3-yl)-1-oxo-3H-isoindol-5-yl]piperidin-4-yl}oxy)piperidin-1-yl]phenyl}-4-oxoquinazolin-6-yl)oxy]-4-fluorophenyl}-3-fluoropyrrolidine-1-sulfonamide (53.4 mg, 14%) as a white solid. 1H NMR (300 MHz, DMSO-d6) δ 10.96 (s, 1H), 10.36 (s, 1H), 8.27 (s, 1H), 7.93-7.79 (m, 2H), 7.72-7.62 (m, 1H), 7.58-7.39 (m, 2H), 7.31 (d, J=8.8 Hz, 1H), 7.11-6.99 (m, 6H), 5.41-5.15 (d, J=78 Hz, 1H), 5.05-5.01 (m, 2H), 4.28-4.14 (m, 2H), 3.75-3.66 (m, 6H), 3.64 (t, J=11.2 Hz,

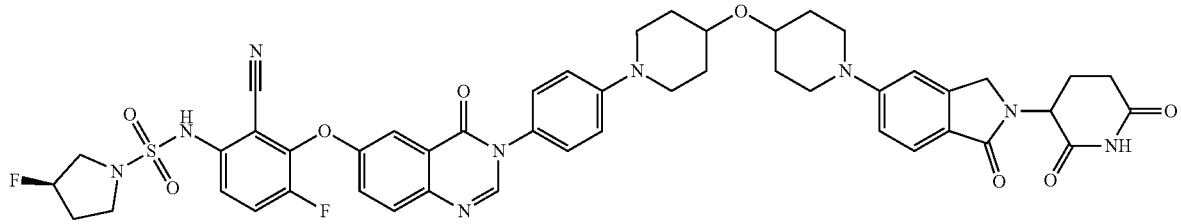 [SMILES: N#Cc1c(NS(=O)(=O)N2CC[C@@H](F)C2)ccc(F)c1Oc1ccc2ncn(-c3ccc(N4CCC(OC5CCN(c6ccc7c(c6)CN(C6CCC(=O)NC6=O)C7=O)CC5)CC4)cc3)c(=O)c2c1]

To a stirred solution of (3R)-3-fluoropyrrolidine-1-sulfonamide (101 mg, 0.6 mmol) in N,N-dimethylformamide (10 mL) was added cesium carbonate (326 mg, 1 mmol). The 1H), 3.55 (s, 2H), 3.53-3.40 (m, 5H), 2.59 (d, J=16.4 Hz, 1H), 2.46-2.29 (m, 3H), 1.92 (d, J=12.5 Hz, 5H), 1.59-1.50 (m, 5H), 1.24 (s, 2H); MS (ESI): m/z 948.62 [M+H]+.

Example 176: Exemplary synthesis of (3R)—N-{2-cyano-3-[(3-{4-[4-(2-{4-[2-(2,6-dioxopiperidin-3-yl)-1-oxo-2,3-dihydro-1H-isoindol-5-yl]piperidin-1-yl}ethyl)piperazin-1-yl]phenyl}-4-oxo-3,4-dihydroquinazolin-6-yl)oxy]-4-fluorophenyl}-3-fluoropyrrolidine-1-sulfonamide
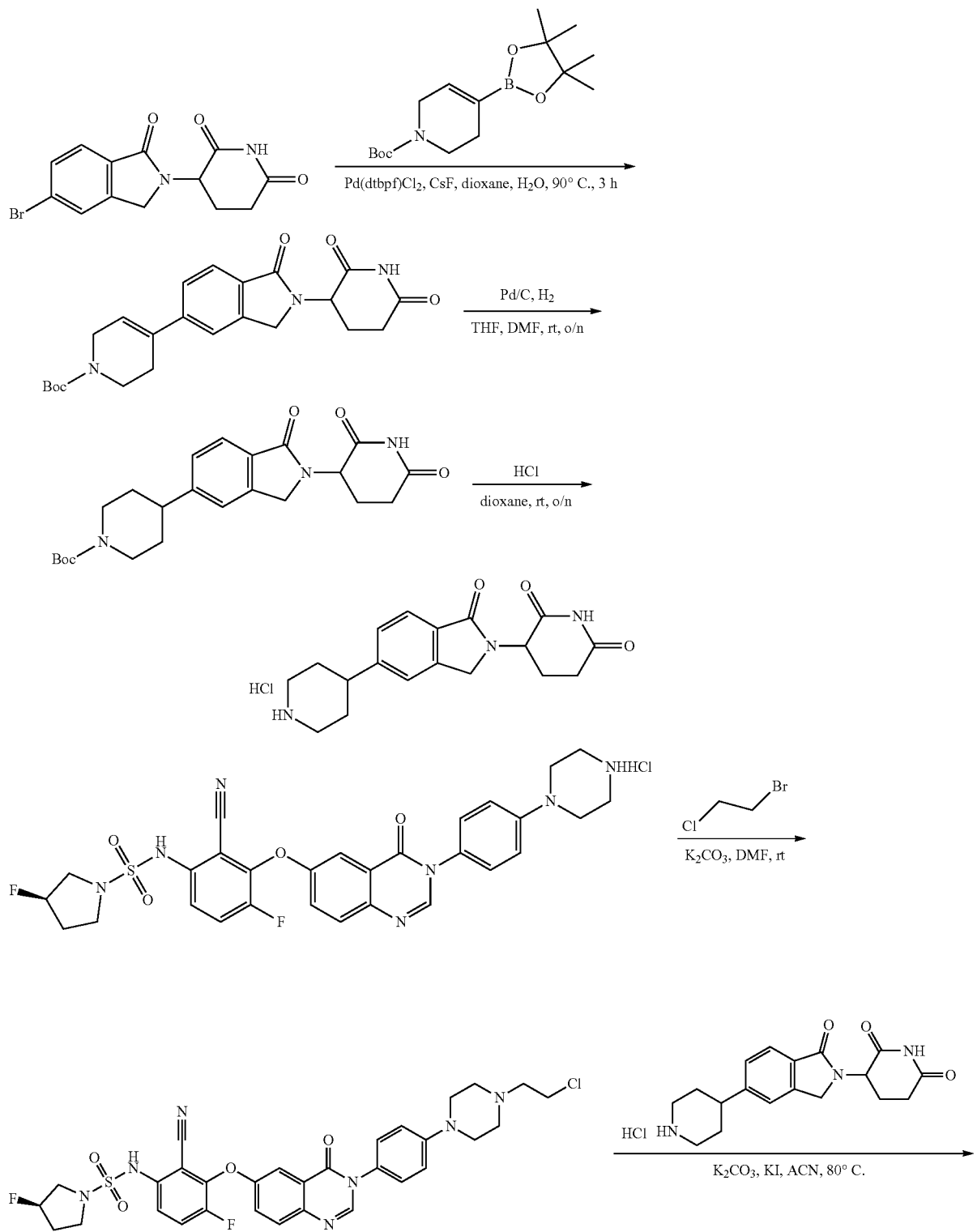

-continued

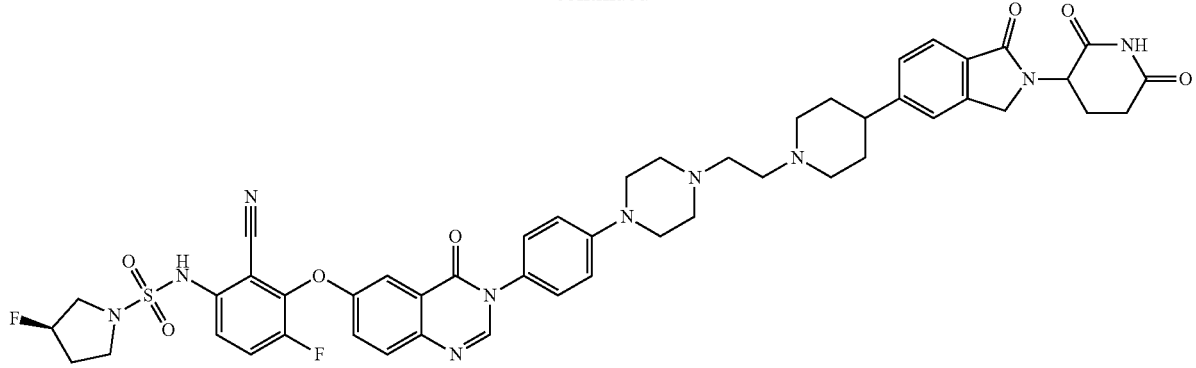

Step 1: tert-butyl 4-[2-(2,6-dioxopiperidin-3-yl)-1-oxo-3H-isoindol-5-yl]-3,6-dihydro-2H-pyridine-1-carboxylate

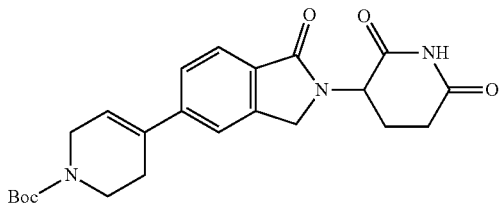 [SMILES: CC(C)(C)OC(=O)N1CC=C(c2ccc3c(c2)CN(C2CCC(=O)NC2=O)C3=O)CC1]

To a solution of 3-(5-bromo-1-oxo-3H-isoindol-2-yl)piperidine-2,6-dione (1.0 g, 3 mmol) and tert-butyl 4-(4,4,5,5-tetramethyl-1,3,2-dioxaborolan-2-yl)-3,6-dihydro-2H-pyridine-1-carboxylate (0.96 g, 3 mmol) in 1,4-dioxane (10 mL) and water (2 mL) was added cesium fluoride (1.4 g, 9 mmol) and [1,1'-bis(diphenylphosphino)ferrocene]dichloropalladium(II) (0.23 g, 0.3 mmol). The mixture was stirred for 3 h at 90° C. under a nitrogen atmosphere, then concentrated under reduced pressure. The residue was purified by preparative-thin layer chromatography (petroleum ether/ethyl acetate=1:1) to afford tert-butyl 4-[2-(2,6-dioxopiperidin-3-yl)-1-oxo-3H-isoindol-5-yl]-3,6-dihydro-2H-pyridine-1-carboxylate (1.0 g, 76%) as a white solid. $^1$H NMR (400 MHz, CDCl$_3$) δ 8.34 (s, 1H), 7.86 (d, J=8.0 Hz, 1H), 7.51 (d, J=8.1 Hz, 1H), 7.45 (s, 1H), 6.15 (s, 1H), 5.34-5.21 (m, 1H), 4.51 (d, J=16.0 Hz, 1H), 4.40-4.28 (m, 1H), 4.15-4.10 (m, 2H), 3.78-3.55 (m, 2H), 2.98-2.79 (m, 2H), 2.71-2.49 (m, 2H), 2.48-2.31 (m, 1H), 2.29-2.19 (m, 1H), 1.65-1.41 (m, 10H), 1.27 (s, 2H), 0.95-0.79 (m, 1H); MS (ESI): m/z 426.20 [M+H]$^+$.

Step 2: tert-butyl 4-[2-(2,6-dioxopiperidin-3-yl)-1-oxo-3H-isoindol-5-yl]piperidine-1-carboxylate

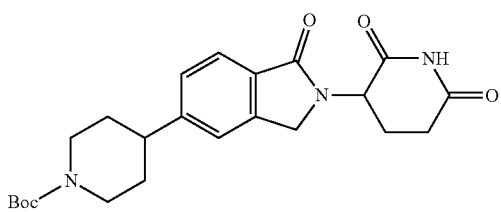 [SMILES: CC(C)(C)OC(=O)N1CCC(c2ccc3c(c2)CN(C2CCC(=O)NC2=O)C3=O)CC1]

To solution of tert-butyl 4-[2-(2,6-dioxopiperidin-3-yl)-1-oxo-3H-isoindol-5-yl]-3,6-dihydro-2H-pyridine-1-carboxylate (5.0 g, 12 mmol) in N,N-dimethylformamide (100 mL) and tetrahydrofuran (200 mL) was added 10% palladium over carbon (2 g). The mixture was degassed and purged with hydrogen for three time before stirring at room temperature for 12 h under hydrogen atmosphere. The mixture was filtered through Celite pad and concentrated under reduced pressure to afford tert-butyl 4-[2-(2,6-dioxopiperidin-3-yl)-1-oxo-3H-isoindol-5-yl]piperidine-1-carboxylate (4.0 g, 80%) as a white solid. MS (ESI): m/z 426.25 [M+H]$^+$.

Step 3: 3-[1-oxo-5-(piperidin-4-yl)-3H-isoindol-2-yl]piperidine-2,6-dione hydrochloride

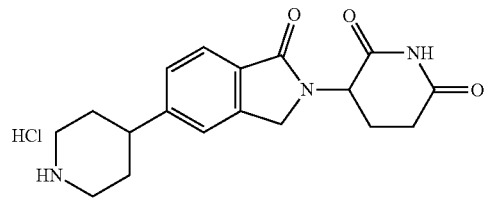 [SMILES: Cl ; O=C1CCC(N2Cc3cc(C4CCNCC4)ccc3C2=O)C(=O)N1]

A solution of tert-butyl 4-[2-(2,6-dioxopiperidin-3-yl)-1-oxo-3H-isoindol-5-yl]piperidine-1-carboxylate (4.7 g, 11 mmol) and 4 M hydrochloric acid in 1,4-dioxane (80 mL) was stirred for 12 h at room temperature, then concentrated. The residue was triturated with petroleum ether (20 mL) and washed with petroleum ether (20 mL) to afford 3-[1-oxo-5-(piperidin-4-yl)-3H-isoindol-2-yl]piperidine-2,6-dione hydrochloride (3.8 g, 95%) as a white solid. $^1$H NMR (400 MHz, DMSO-d$_6$): δ 11.01 (s, 1H), 9.15-8.75 (m, 2H), 7.71 (d, J=7.8 Hz, 1H), 7.46 (s, 1H), 7.41-7.31 (m, 1H), 5.21-5.01 (m, 1H), 4.45 (d, J=17.3 Hz, 1H), 4.32 (d, J=17.3 Hz, 1H), 3.71-3.61 (m, 1H), 3.56-3.49 (m, 2H), 3.37 (d, J=12.3 Hz, 2H), 3.11-2.88 (m, 4H), 2.60 (d, J=17.4 Hz, 1H), 2.48-2.31 (m, 1H), 2.04-1.83 (m, 5H); MS (ESI): m/z 328.15 [M+H]$^+$.

Step 4: (3R)—N-{3-[(3-{4-[4-(2-chloroethyl)piper-azin-1-yl]phenyl}-4-oxoquinazolin-6-yl)oxy]-2-cyano-4-fluorophenyl}-3-fluoropyrrolidine-1-sulfonamide

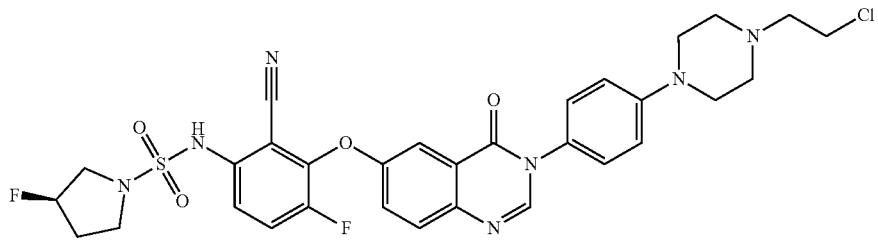 [SMILES: N#Cc1c(NS(=O)(=O)N2CC[C@@H](F)C2)ccc(F)c1Oc1ccc2ncn(-c3ccc(N4CCN(CCCl)CC4)cc3)c(=O)c2c1]

To a stirred solution of (3R)—N-[2-cyano-4-fluoro-3-({4-oxo-3-[4-(piperazin-1-yl)phenyl]quinazolin-6-yl}oxy)phenyl]-3-fluoropyrrolidine-1-sulfonamide hydrochloride (1 g, 1 mmol) in N,N-diisopropylethylamine (2 mL) and dimethyl sulfoxide (15 mL) was added 1-bromo-2-chloroethane (6.68 g, 46 mmol), the resulting mixture was stirred for 2 h at 50° C. The reaction was diluted with water (10 mL) and extracted with ethyl acetate (2×100 mL). The combined organic layers were washed with brine (2×20 mL), dried over anhydrous sodium sulfate, filtered, and concentrated. The residue was purified by silica gel column chromatography (dichloromethane/methanol=10:1) to afford (3R)—N-{3-[(3-{4-[4-(2-chloroethyl)piperazin-1-yl]phenyl}-4-oxoquinazolin-6-yl)oxy]-2-cyano-4-fluorophenyl}-3-fluoropyrrolidine-1-sulfonamide (280 mg, 27%) as a white solid. $^1$H NMR (400 MHz, DMSO-$d_6$) δ 10.28 (s, 1H), 8.26 (s, 1H), 7.87-7.78 (m, 2H), 7.71-7.62 (m, 1H), 7.51-7.45 (m, 1H), 7.42 (d, J=3.1 Hz, 1H), 7.38-7.29 (m, 2H), 7.11-7.04 (m, 2H), 5.41-5.35 (d, J=20 Hz, 1H), 3.79 (t, J=6.7 Hz, 2H), 3.51 (d, J=2.2 Hz, 1H), 3.48-3.39 (m, 4H), 2.85 (s, 3H), 2.75 (s, 4H), 2.14 (s, 1H), 2.13-1.97 (m, 2H); MS (ESI): m/z 669.17 [M+H]$^+$.

Step 5: (3R)—N-{2-cyano-3-[(3-{4-[4-(2-{4-[2-(2,6-dioxopiperidin-3-yl)-1-oxo-3H-isoindol-5-yl]piperidin-1-yl}ethyl)piperazin-1-yl]phenyl}-4-oxoquinazolin-6-yl)oxy]-4-fluorophenyl}-3-fluoropyrrolidine-1-sulfonamide To a stirred solution of (3R)—N-{3-[(3-{4-[4-(2-chloroethyl)piperazin-1-yl]phenyl}-4-oxoquinazolin-6-yl)oxy]-2-cyano-4-fluorophenyl}-3-fluoropyrrolidine-1-sulfonamide (160 mg, 0.2 mmol) and 3-[1-oxo-5-(piperidin-4-yl)-3H-isoindol-2-yl]piperidine-2,6-dione hydrochloride (104 mg, 0.3 mmol) in dimethyl sulfoxide (5 mL) was dropwise added N,N-diisopropylethylamine (1 mL) at room temperature, the resulting mixture was stirred for 5 h at 80° C. The reaction was diluted with water (20 mL) and extracted with ethyl acetate (3×60 mL). The combined organic layers were washed with brine (20 mL), dried over anhydrous sodium sulfate, filtered, and concentrated. The product was purified by preparative-high performance liquid chromatography (25%-55% acetonitrile in water (10 mmol/L ammonium bicarbonate) over 9 min) to afford (3R)—N-{2-cyano-3-[(3-{4-[4-(2-{4-[2-(2,6-dioxopiperidin-3-yl)-1-oxo-3H-isoindol-5-yl]piperidin-1-yl}ethyl)piperazin-1-yl]phenyl}-4-oxoquinazolin-6-yl)oxy]-4-fluorophenyl}-3-fluoropyrrolidine-1-sulfonamide (71.6 mg, 30%) as a white solid. $^1$H NMR (400 MHz, DMSO-$d_6$) δ 10.28 (s, 1H), 8.26 (s, 1H), 7.87-7.78 (m, 1H), 7.71-62 (m, 2H), 7.51-7.47 (m, 1H), 7.42 (d, J=3.1 Hz, 4H), 7.38-7.29 (m, 2H), 7.11-7.04 (m, 2H), 5.41-5.35 (d, J=3.1, 24 Hz, 1H), 5.24 (d, J=3.9 Hz, 1H), 3.79 (t, J=6.7 Hz, 1H), 3.51 (d, J=2.2 Hz, 10H), 3.48-3.39 (m, 2H), 2.85 (s, 4H), 2.75 (s, 6H), 2.14 (s, 3H), 2.13-1.97 (m, 7H), 0.96-0.87 (m, 1H); MS (ESI): m/z 962.60 [M+H]$^+$.

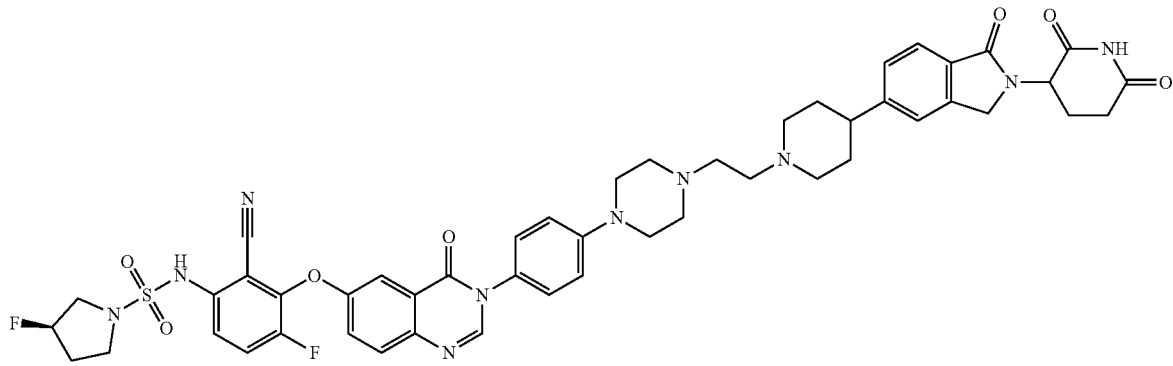 [SMILES: N#Cc1c(NS(=O)(=O)N2CC[C@@H](F)C2)ccc(F)c1Oc1ccc2ncn(-c3ccc(N4CCN(CCN5CCC(c6ccc7c(c6)CN(C6CCC(=O)NC6=O)C7=O)CC5)CC4)cc3)c(=O)c2c1]

Example 177: Exemplary synthesis of (3R)—N-{3-[(3-{4-[4-({1-[2-(2,6-dioxopiperidin-3-yl)-1-oxo-2,3-dihydro-1H-isoindol-5-yl]piperidin-4-yl}methyl)piperazin-1-yl]phenyl}-4-oxo-3,4-dihydroquinazolin-6-yl)oxy]-2,4-difluorophenyl}-3-fluoropyrrolidine-1-sulfonamide

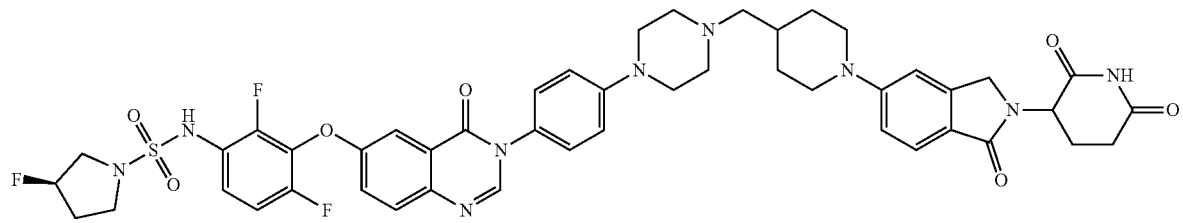 [SMILES: O=C1CCC(N2Cc3cc(N4CCC(CN5CCN(c6ccc(-n7cnc8ccc(Oc9c(F)ccc(NS(=O)(=O)N%10CC[C@@H](F)C%10)c9F)cc8c7=O)cc6)CC5)CC4)ccc3C2=O)C(=O)N1]

To a stirred solution of (3R)—N-[2,4-difluoro-3-({4-oxo-3-[4-(piperazin-1-yl)phenyl]quinazolin-6-yl}oxy)phenyl]-3-fluoropyrrolidine-1-sulfonamide hydrochloride (120 mg, 0.2 mmol) in dichloromethane (40 mL) was added 1-[2-(2,6-dioxopiperidin-3-yl)-1-oxo-3H-isoindol-5-yl]piperidine-4-carbaldehyde (66.9 mg, 0.2 mmol) in portions at room temperature, followed by the addition of N,N-diisopropylethylamine (1 mL). The mixture was stirred for 1 h at room temperature, then sodium triacetoxyborohydride (119.8 mg, 0.6 mmol) was added in portions. The resulting mixture was stirred for 1 h at room temperature. The reaction was diluted with water (50 mL) and extracted with dichloromethane (2×100 mL). The combined organic layers were washed with brine (2×20 mL), dried over anhydrous sodium sulfate, filtered, and concentrated. The residue was purified by preparative-thin layer chromatography (dichloromethane/methanol=10:1) to afford (3R)—N-{3-[(3-{4-[4-({1-[2-(2,6-dioxopiperidin-3-yl)-1-oxo-3H-isoindol-5-yl]piperidin-4-yl}methyl)piperazin-1-yl]phenyl}-4-oxoquinazolin-6-yl)oxy]-2,4-difluorophenyl}-3-fluoropyrrolidine-1-sulfonamide (107.1 mg, 60%) as a white solid. $^1$H NMR (300 MHz, DMSO-$d_6$) δ 10.93 (s, 1H), 9.90 (s, 1H), 8.25 (s, 2H), 7.81 (d, J=8.9 Hz, 1H), 7.55-7.27 (m, 6H), 7.10-7.00 (m, 4H), 5.36-5.18 (d, J=54 Hz, 1H), 5.04 (s, 1H), 4.32 (d, J=16.9 Hz, 2H), 3.89 (d, J=12.5 Hz, 2H), 3.47 (d, J=2.1 Hz, 3H), 3.44-3.32 (m, 5H), 3.31-3.22 (m, 3H), 2.89 (s, 5H), 2.61 (s, 1H), 2.24 (s, 1H), 2.14-2.01 (m, 2H), 2.00-1.91 (m, 2H), 1.82 (d, J=11.8 Hz, 3H), 1.21 (d, J=13.0 Hz, 2H); MS (ESI): m/z 940.50 [M+H]$^+$.

Example 178: Exemplary synthesis of (3R)—N-{2-cyano-3-[(3-{4-[4-({2-[2-(2,6-dioxopiperidin-3-yl)-1-oxo-2,3-dihydro-1H-isoindol-5-yl]-2-azaspiro[3.3]heptan-6-yl}oxy)piperidin-1-yl]phenyl}-4-oxo-3,4-dihydroquinazolin-6-yl)oxy]-4-fluorophenyl}-3-fluoropyrrolidine-1-sulfonamide

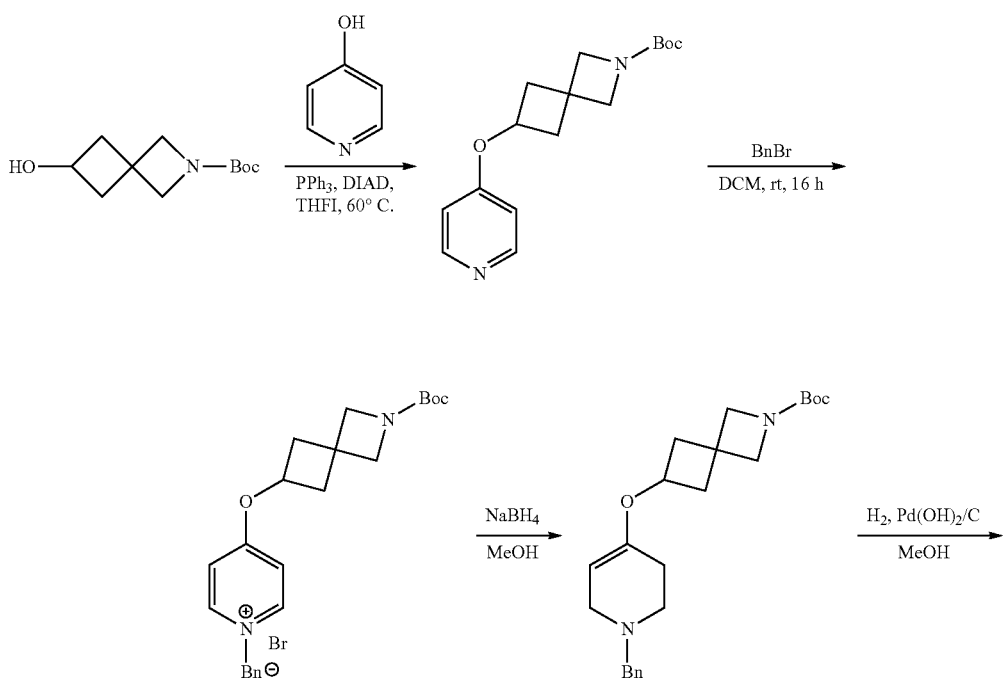

-continued
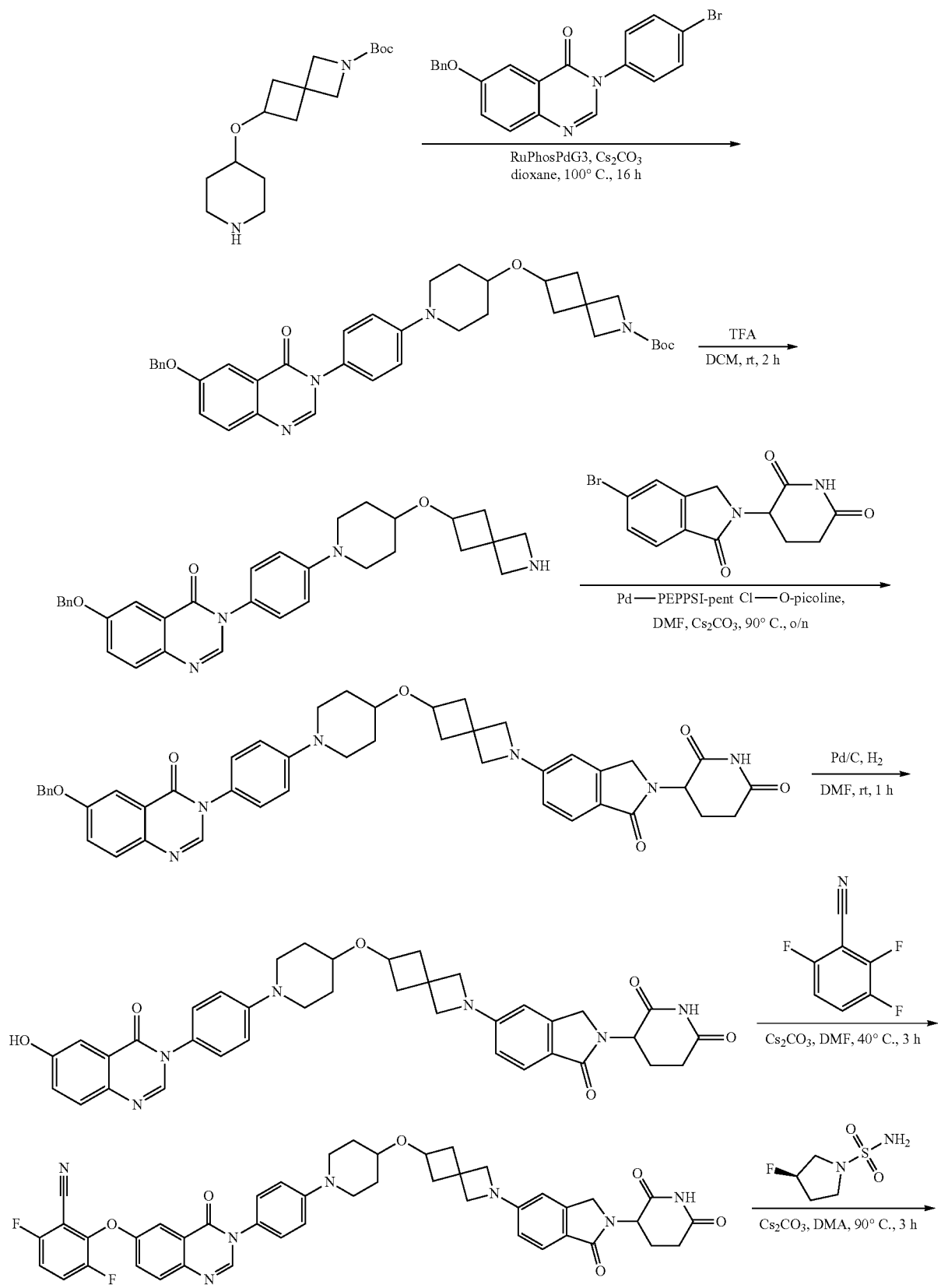

-continued

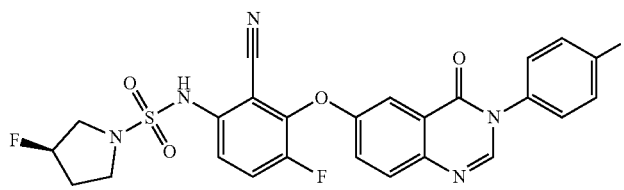

Step 1: tert-butyl 6-(pyridin-4-yloxy)-2-azaspiro[3.3]heptane-2-carboxylate

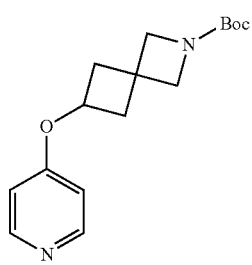 [SMILES: CC(C)(C)OC(=O)N1CC2(CC(Oc3ccncc3)C2)C1]

To a stirred mixture of triphenylphosphine (8.85 g, 34 mmol) in tetrahydrofuran (200.00 mL) was added diethyl azodicarboxylate (5.88 g, 34 mmol), 4-hydroxypyridine (2.14 g, 22 mmol) and tert-butyl 6-hydroxy-2-azaspiro[3.3]heptane-2-carboxylate (4.80 g, 22 mmol). The resulting solution was stirred for 16 h at 60° C., then diluted with water (200 mL) and extracted with ethyl acetate (3×120 mL). The combined organic layers were washed with brine (2×60 mL), dried over anhydrous sodium sulfate, filtered, and concentrated. The residue was purified by silica gel column (ethyl acetate/petroleum ether=7/3) to afford tert-butyl 6-(pyridin-4-yloxy)-2-azaspiro[3.3]heptane-2-carboxylate (6.53 g, crude) as light yellow oil. MS (ESI): m/z 291.20 [M+H]$^+$.

Step 2: 1-benzyl-4-[[2-(tert-butoxycarbonyl)-2-azaspiro[3.3]heptan-6-yl]oxy]pyridin-1-ium bromide

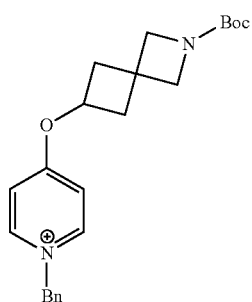 [SMILES: CC(C)(C)OC(=O)N1CC2(CC(Oc3cc[n+](Cc4ccccc4)cc3)C2)C1]

To a stirred solution of tert-butyl 6-(pyridin-4-yloxy)-2-azaspiro[3.3]heptane-2-carboxylate (6.53 g, 22 mmol) in dichloromethane (100 mL) was added benzyl bromide (4.62 g, 27 mmol). The resulting solution was stirred for 16 h at room temperature, then concentrated. The residue was triturated with petroleum ether to afford 1-benzyl-4-[[2-(tert-butoxycarbonyl)-2-azaspiro[3.3]heptan-6-yl]oxy]pyridin-1-ium bromide (8.54 g, 82%) as a white solid. MS (ESI): m/z 381.25 [M+H]$^+$.

Step 3: tert-butyl 6-[(1-benzyl-3,6-dihydro-2H-pyridin-4-yl)oxy]-2-azaspiro[3.3]heptane-2-carboxylate

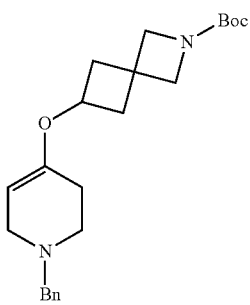 [SMILES: CC(C)(C)OC(=O)N1CC2(CC(OC3=CCN(Cc4ccccc4)CC3)C2)C1]

To a stirred solution of 1-benzyl-4-[[2-(tert-butoxycarbonyl)-2-azaspiro[3.3]heptan-6-yl]oxy]pyridin-1-ium bromide (8.54 g, 18 mmol) in methanol (100 mL) was added sodium borohydride (2.04 g, 55 mmol). The resulting mixture was stirred for 16 h at room temperature, then diluted with ice water (100 mL) and extracted with ethyl acetate (100 mL). The organic layer was dried over anhydrous sodium sulfate, filtered, and concentrated. The residue was purified by flash-preparative-high performance liquid chromatography (10%-70% acetonitrile in water (10 mmol/L ammonium bicarbonate) over 30 min) to afford tert-butyl 6-[(1-benzyl-3,6-dihydro-2H-pyridin-4-yl)oxy]-2-azaspiro[3.3]heptane-2-carboxylate (3.6 g, 51%) as yellow oil. MS (ESI): m/z 385.10 [M+H]$^+$.

Step 4: tert-butyl 6-(piperidin-4-yloxy)-2-azaspiro[3.3]heptane-2-carboxylate

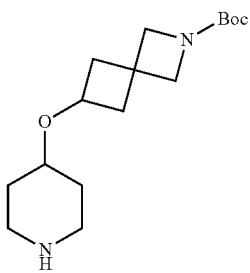 [SMILES: CC(C)(C)OC(=O)N1CC2(CC(OC3CCNCC3)C2)C1]

To a stirred solution of tert-butyl 6-[(1-benzyl-3,6-dihydro-2H-pyridin-4-yl)oxy]-2-azaspiro[3.3]heptane-2-carboxylate (3.6 g, 9 mmol) in methanol (100 mL) was added 20% palladium hydroxide on carbon (1.50 g, 0.01 mmol), the mixture was degassed and purged with hydrogen three times before stirring at 30° C. for 5 h under hydrogen atmosphere. The mixture was filtered through Celite pad, the filtrate solution was concentrated to afford tert-butyl 6-(piperidin-4-yloxy)-2-azaspiro[3.3]heptane-2-carboxylate (2.81 g, 98%) as a yellow solid.

Step 5: tert-butyl 6-[(1-{4-[6-(benzyloxy)-4-oxoquinazolin-3-yl]phenyl}piperidin-4-yl)oxy]-2-azaspiro[3.3]heptane-2-carboxylate

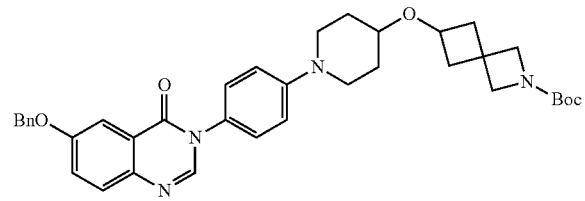 [SMILES: CC(C)(C)OC(=O)N1CC2(CC(OC3CCN(c4ccc(-n5cnc6ccc(OCc7ccccc7)cc6c5=O)cc4)CC3)C2)C1]

To a stirred mixture of tert-butyl 6-(piperidin-4-yloxy)-2-azaspiro[3.3]heptane-2-carboxylate (700 mg, 2 mmol) and 6-(benzyloxy)-3-(4-bromophenyl)quinazolin-4-one (962 mg, 2 mmol) in 1,4-dioxane (20 mL) was added cesium carbonate (2.3 g, 7 mmol) and chloro(2-dicyclohexylphosphino-2',4',6'-triisopropyl-1,1'-biphenyl)[2-(2'-amino-1,1'-biphenyl)]palladium(II) (200 mg, 0.2 mmol) in portions at room temperature. The resulting mixture was stirred for 12 h at 100° C. under nitrogen atmosphere. The mixture was allowed to cool to room temperature, quenched by water (10 mL) and extracted with ethyl acetate (2×100 mL). The combined organic layers were washed with brine (2×20 mL), dried over anhydrous sodium sulfate, filtered, and concentrated. The residue was purified by silica gel chromatography (petroleum ether/ethyl acetate=1:1) to afford tert-butyl 6-[(1-{4-[6-(benzyloxy)-4-oxoquinazolin-3-yl]phenyl}piperidin-4-yl)oxy]-2-azaspiro[3.3]heptane-2-carboxylate (902 mg, 61%) as a white solid. $^1$H NMR (400 MHz, DMSO-$d_6$) δ 8.17 (s, 1H), 7.73-7.63 (m, 2H), 7.50 (d, J=7.0 Hz, 8H), 7.05 (d, J=8.7 Hz, 2H), 5.26 (s, 2H), 3.97 (p, J=7.0 Hz, 5H), 3.59 (s, 2H), 3.47 (s, 1H), 3.34 (s, 2H), 2.95-2.85 (m, 2H), 2.46-2.36 (m, 2H), 2.02-1.89 (m, 2H), 1.36 (s, 9H); MS (ESI): m/z 623.50 [M+H]$^+$.

Step 6: 3-[4-(4-{2-azaspiro[3.3]heptan-6-yloxy}piperidin-1-yl)phenyl]-6-(benzyloxy)quinazolin-4-one

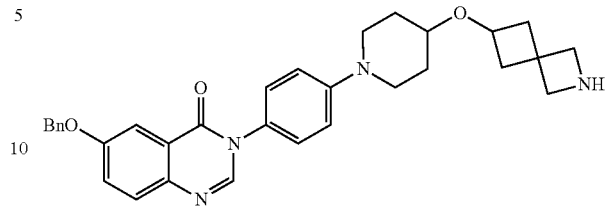

To a stirred solution of tert-butyl 6-[(1-{4-[6-(benzyloxy)-4-oxoquinazolin-3-yl]phenyl}piperidin-4-yl)oxy]-2-azaspiro[3.3]heptane-2-carboxylate (900 mg, 1 mmol) in dichloromethane (10 mL) was dropwise added trifluoroacetic acid (2 mL). The resulting mixture was stirred for 2 h at room temperature, then concentrated under reduced pressure. The residue was diluted with dichloromethane (20 mL), the pH of the solution was adjusted to 8 with N,N-diisopropylethylamine and concentrated under reduced pressure. The residue was purified by reversed-phase flash chromatography (10%-50% acetonitrile in water (10 mmol/L ammonium bicarbonate) over 10 min) to afford 3-[4-(4-{2-azaspiro[3.3]heptan-6-yloxy}piperidin-1-yl)phenyl]-6-(benzyloxy)quinazolin-4-one (720 mg, 95%) as a white solid. MS (ESI): m/z 523.40 [M+H]$^+$.

Step 7: 3-(5-{6-[(1-{4-[6-(benzyloxy)-4-oxoquinazolin-3-yl]phenyl}piperidin-4-yl)oxy]-2-azaspiro[3.3]heptan-2-yl}-1-oxo-3H-isoindol-2-yl)piperidine-2,6-dione

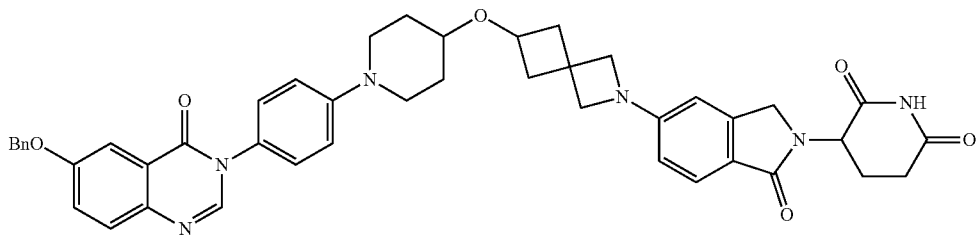 [SMILES: O=C1CCC(N2Cc3cc(N4CC5(CC(OC6CCN(c7ccc(-n8cnc9ccc(OCc%10ccccc%10)cc9c8=O)cc7)CC6)C5)C4)ccc3C2=O)C(=O)N1]

To a stirred solution of 3-[4-(4-{2-azaspiro[3.3]heptan-6-yloxy}piperidin-1-yl)phenyl]-6-(benzyloxy)quinazolin-4-one (700 mg, 1.3 mmol) and 3-(5-bromo-1-oxo-3H-isoindol-2-yl)piperidine-2,6-dione (433 mg, 1 mmol) in N,N-dimethylformamide (20 mL) was added cesium carbonate (1.75 g, 5 mmol) and dichloro[1,3-bis(2,6-di-3-pentylphenyl)imidazol-2-ylidene](3-chloropyridyl)palladium(II) (56.3 mg, 0.07 mmol) in portions at room temperature under nitrogen atmosphere. The resulting mixture was stirred for 12 h at 90° C. under nitrogen atmosphere, then cooled to room temperature. The mixture was diluted with water (10 mL) and extracted with ethyl acetate (2×100 mL). The combined organic layers were washed with brine (2×20 mL), dried over anhydrous sodium sulfate, filtered, and concentrated. The residue was purified by silica gel column chromatography (dichloromethane/methanol=10:1) to afford 3-(5-{6-[(1-{4-[6-(benzyloxy)-4-oxoquinazolin-3-yl]phenyl}piperidin-4-yl)oxy]-2-azaspiro[3.3]heptan-2-yl}-1-oxo-3H-isoindol-2-yl)piperidine-2,6-dione (451 mg, 44%) as a white solid. $^1$H NMR (400 MHz, DMSO-$d_6$) δ 10.94 (s, 1H), 8.18 (s, 1H), 7.73-7.63 (m, 2H), 7.59-7.27 (m, 4H), 7.10-7.02 (m, 5H), 6.49 (d, J=1.9 Hz, 2H), 6.45 (s, 2H), 5.26 (s, 2H), 5.03-5.01 (d, J=13.3, 5.1 Hz, 1H), 4.30 (d, J=17.0 Hz, 2H), 4.17 (d, J=16.9 Hz, 1H), 3.92 (s, 4H), 3.86 (s, 2H), 3.65-3.57 (m, 1H), 3.55-3.47 (m, 3H), 2.93-2.83 (m, 2H), 2.62-2.52 (m, 2H), 2.18-2.02 (m, 2H), 2.01-1.86 (m, 3H); MS (ESI): m/z 765.60 [M+H]$^+$.

Step 8: 3-(5-{6-[(1-{4-[6-(benzyloxy)-4-oxoquinazolin-3-yl]phenyl}piperidin-4-yl)oxy]-2-azaspiro[3.3]heptan-2-yl}-1-oxo-3H-isoindol-2-yl)piperidine-2,6-dione

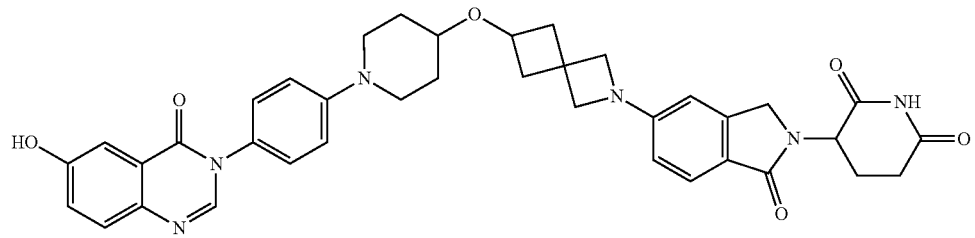 [SMILES: O=C1CCC(N2Cc3cc(N4CC5(CC(OC6CCN(c7ccc(-n8cnc9ccc(O)cc9c8=O)cc7)CC6)C5)C4)ccc3C2=O)C(=O)N1]

To a solution of 3-(5-{6-[(1-{4-[6-(benzyloxy)-4-oxoquinazolin-3-yl]phenyl}piperidin-4-yl)oxy]-2-azaspiro[3.3]heptan-2-yl}-1-oxo-3H-isoindol-2-yl)piperidine-2,6-dione (450 mg, 0.6 mmol) in tetrahydrofuran (5 mL) and N,N-dimethylformamide (15 mL) was added 10% palladium over carbon (0.9 g). The mixture was degassed and purged with hydrogen for three times, then stirred for 1 h at room temperature under hydrogen atmosphere. The mixture was filtered through a Celite pad and concentrated under reduced pressure to afford 3-{5-[6-({1-[4-(6-hydroxy-4-oxoquinazolin-3-yl)phenyl]piperidin-4-yl}oxy)-2-azaspiro[3.3]heptan-2-yl]-1-oxo-3H-isoindol-2-yl}piperidine-2,6-dione (389 mg, 98%) as an off-white solid. MS (ESI): m/z 673.50 [M+H]$^+$.

Step 9: 2-[(3-{4-[4-(2-{4-[2-(2,6-dioxopiperidin-3-yl)-1-oxo-3H-isoindol-5-yl]piperazin-1-yl}ethyl)piperazin-1-yl]phenyl}-4-oxoquinazolin-6-yl)oxy]-3,6-difluorobenzonitrile

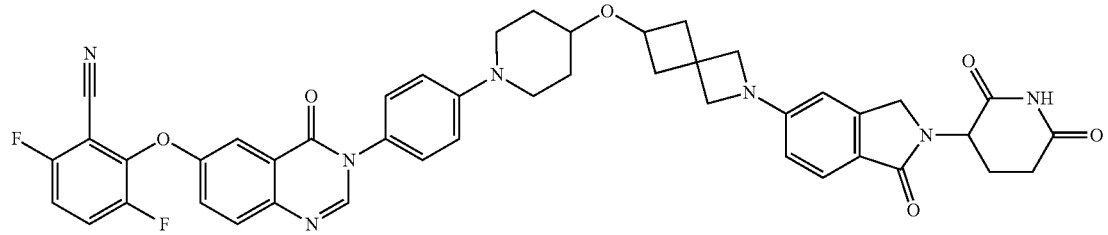 [SMILES: N#Cc1c(F)ccc(F)c1Oc1ccc2ncn(-c3ccc(N4CCC(OC5CC6(C5)CN(c5ccc7c(c5)CN(C5CCC(=O)NC5=O)C7=O)C6)CC4)cc3)c(=O)c2c1]

To a stirred solution of 3-{5-[4-(2-{4-[4-(6-hydroxy-4-oxoquinazolin-3-yl)phenyl]piperazin-1-yl}ethyl)piperazin-1-yl]-1-oxo-3H-isoindol-2-yl}piperidine-2,6-dione (210 mg, 0.3 mmol) and 2,3,6-trifluorobenzonitrile (24.4 mg, 0.2 mmol) in dimethylacetamide (15 mL) was added cesium carbonate (303.3 mg, 0.9 mmol) in portions at room temperature. The resulting mixture was stirred for 3 h at 90° C. under nitrogen atmosphere. The mixture was allowed to cool to room temperature, diluted with water (20 mL) and extracted with ethyl acetate (2×100 mL). The combined organic layers were washed with water (2×100 mL), dried over anhydrous sodium sulfate, filtered, and concentrated. The residue was purified by silica gel column chromatography (petroleum ether/ethyl acetate=1:1) to afford 2-[(3-{4-[4-(2-{4-[2-(2,6-dioxopiperidin-3-yl)-1-oxo-3H-isoindol-5-yl]piperazin-1-yl}ethyl)piperazin-1-yl]phenyl}-4-oxoquinazolin-6-yl)oxy]-3,6-difluorobenzonitrile (200 mg, 80%) as an off-white solid. MS (ESI): m/z 812.45 [M+H]$^+$.

Step 10: (3R)—N-{2-cyano-3-[(3-{4-[4-({1-[1-(2,6-dioxopiperidin-3-yl)-3-methyl-2-oxo-1,3-benzodiazol-4-yl]azetidin-3-yl}methyl)piperazin-1-yl]phenyl}-4-oxoquinazolin-6-yl)oxy]-4-fluorophenyl}-3-fluoropyrrolidine-1-sulfonamide

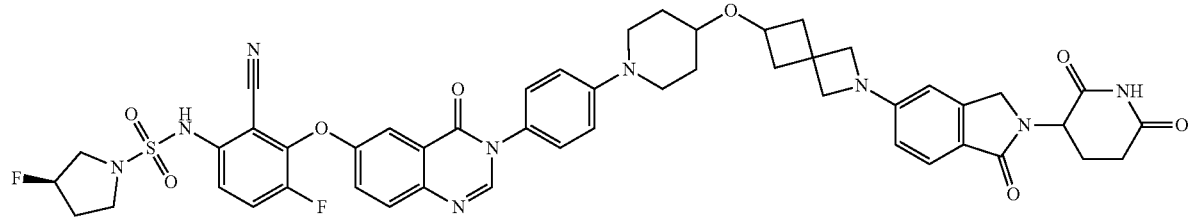 [SMILES: N#Cc1c(NS(=O)(=O)N2CC[C@@H](F)C2)ccc(F)c1Oc1ccc2ncn(-c3ccc(N4CCC(OC5CC6(C5)CN(c5ccc7c(c5)CN(C5CCC(=O)NC5=O)C7=O)C6)CC4)cc3)c(=O)c2c1]

To a stirred solution of (3R)-3-fluoropyrrolidine-1-sulfonamide (62.2 mg, 0.4 mmol) in N, N-dimethylformamide (20 mL) was added cesium carbonate (240.8 mg, 0.7 mmol), the mixture was stirred for 0.5 h at 50° C. under nitrogen atmosphere. To the above mixture was added 2-[(3-{4-[4-({2-[2-(2,6-dioxopiperidin-3-yl)-1-oxo-3H-isoindol-5-yl]-2-azaspiro[3.3]heptan-6-yl}oxy)piperidin-1-yl]phenyl}-4-oxoquinazolin-6-yl)oxy]-3,6-difluorobenzonitrile (200 mg, 0.2 mmol) in portions at room temperature. The resulting mixture was stirred for 3 h at 90° C., then cooled to room temperature, diluted with water (10 mL) and extracted with ethyl acetate (2×100 mL). The combined organic layers were washed with brine (2×20 mL), dried over anhydrous sodium sulfate, filtered, and concentrated. The crude product was purified by chiral preparative-high performance liquid chromatography (20%-80% methanol/dichloromethane (1:1) in methyl tert-butyl ether (0.1% diethylamine)) to afford (3R)—N-{2-cyano-3-[(3-{4-[4-({2-[2-(2,6-dioxopiperidin-3-yl)-1-oxo-3H-isoindol-5-yl]-2-azaspiro[3.3]heptan-6-yl}oxy)piperidin-1-yl]phenyl}-4-oxoquinazolin-6-yl)oxy]-4-fluorophenyl}-3-fluoropyrrolidine-1-sulfonamide (42.3 mg, 17%) as a white solid. $^1$H NMR (400 MHz, DMSO-$d_6$) δ 10.93 (s, 1H), 10.34 (s, 1H), 8.26 (s, 1H), 7.83 (s, 3H), 7.71-7.61 (m, 2H), 7.34-7.27 (m, 3H), 7.08-7.02 (m, 2H), 6.52-6.41 (m, 2H), 5.38 (s, 1H), 5.25-5.03 (d, J=88 Hz, 1H), 4.30 (d, J=17.0 Hz, 3H), 4.17 (d, J=17.0 Hz, 2H), 4.06 (p, J=7.1 Hz, 2H), 3.92 (s, 2H), 3.86 (s, 2H), 3.61 (d, J=12.0 Hz, 2H), 3.53-3.46 (m, 2H), 3.46-3.39 (m, 2H), 3.01-2.88 (m, 3H), 2.62-2.51 (m, 3H), 2.42-2.27 (m, 1H), 2.13-21.93 (m, 7H), 1.51 (d, J=9.6 Hz, 2H); MS (ESI): m/z 934.70 [M+H]$^+$.

Example 179: Exemplary synthesis of (3R)—N-(2-cyano-3-{[3-(4-{4-[(2-{2-[(3S)-2,6-dioxopiperidin-3-yl]-1-oxo-2,3-dihydro-1H-isoindol-5-yl}-2-azaspiro[3.3]heptan-6-yl)methyl]piperazin-1-yl}phenyl)-4-oxo-3,4-dihydroquinazolin-6-yl]oxy}-4-fluorophenyl)-3-fluoropyrrolidine-1-sulfonamide

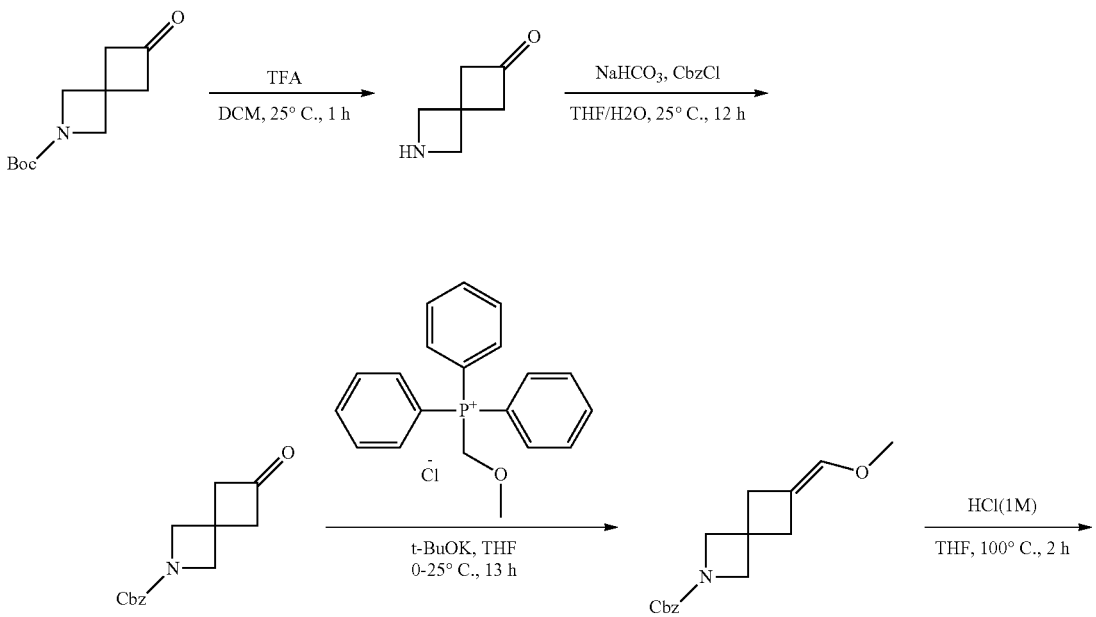

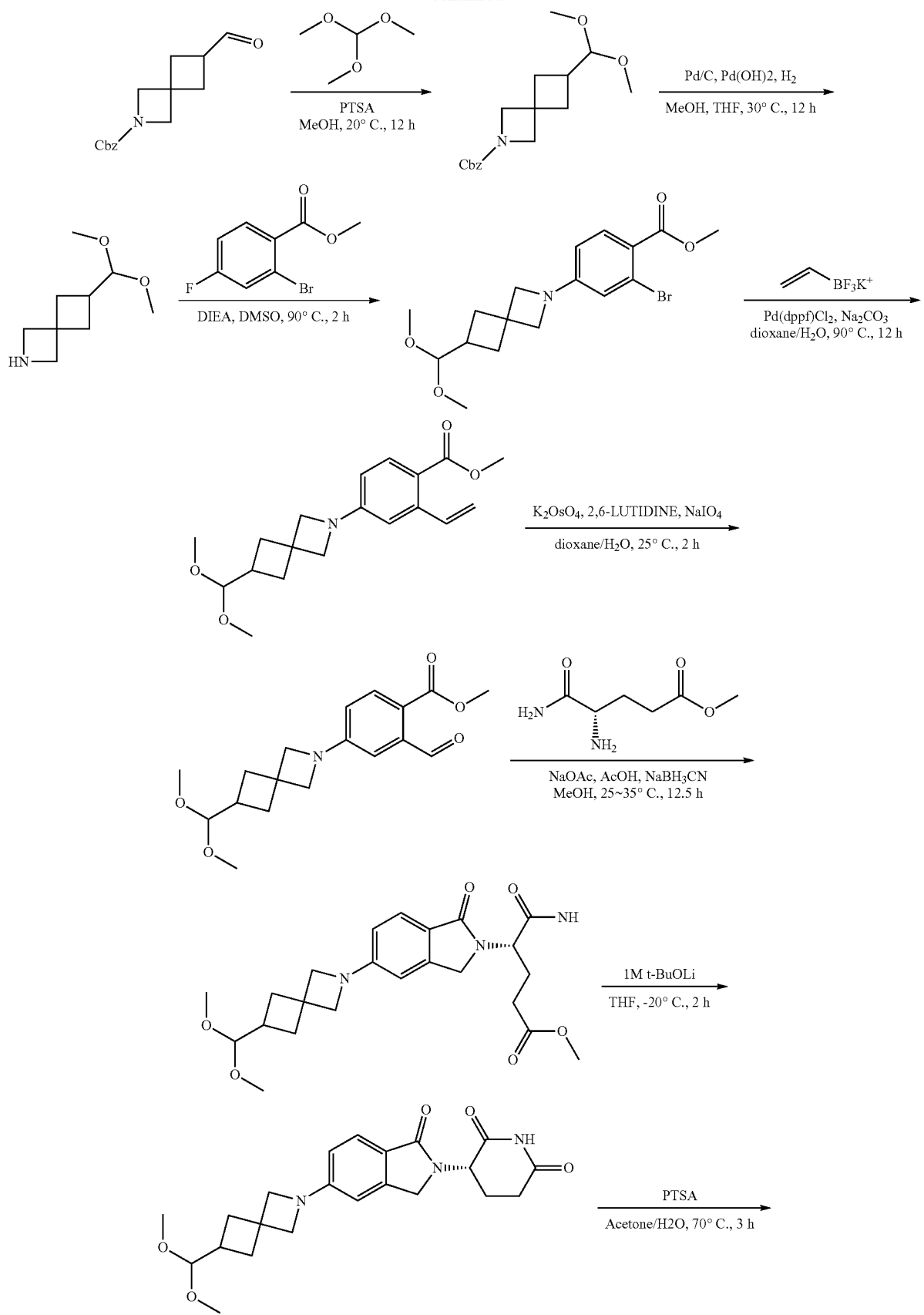

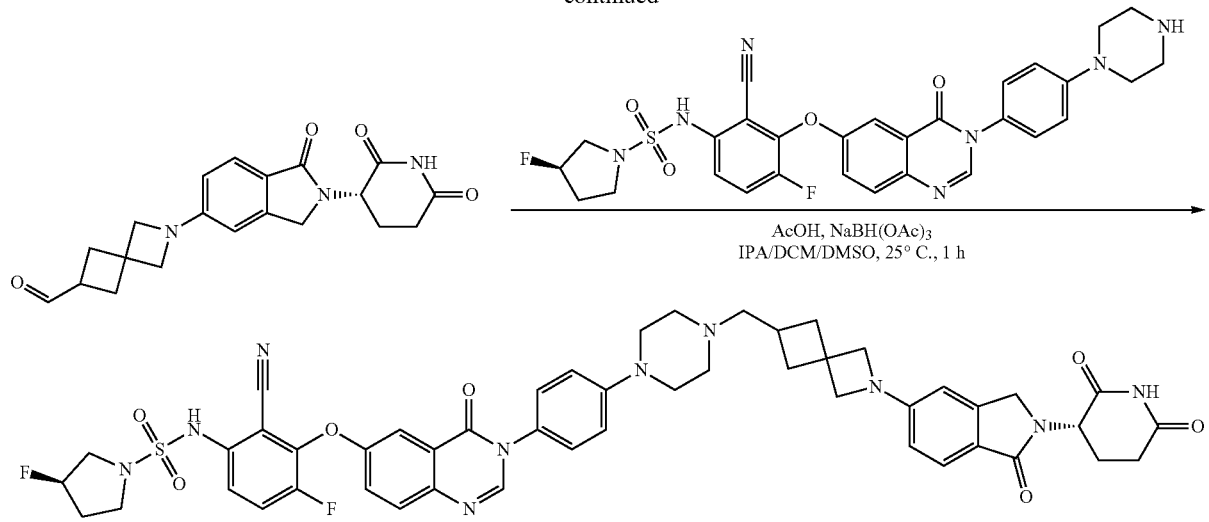

Step 1: 2-azaspiro[3.3]heptan-6-one

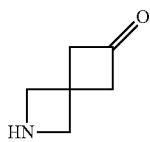

To a solution of tert-butyl 6-oxo-2-azaspiro[3.3]heptane-2-carboxylate (23.0 g, 109 mmol) in dichloromethane (230 mL) was added trifluoroacetic acid (88.3 g, 774 mmol). The reaction was stirred at 25° C. for 1 h, then concentrated to afford 2-azaspiro[3.3]heptan-6-one trifluoroacetate (24.51 g) as a yellow oil, which was used in the next step without further purification.

Step 2: benzyl 6-oxo-2-azaspiro[3.3]heptane-2-carboxylate

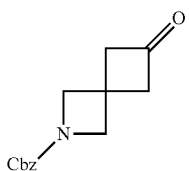 [SMILES: O=C1CC2(C1)CN(C(=O)OCc1ccccc1)C2]

To a solution of 2-azaspiro[3.3]heptan-6-one trifluoroacetate (24.51 g, 109 mmol) in tetrahydrofuran (240 mL) was dropwise added sodium bicarbonate (45.72 g, 544 mmol) in water (120 mL), followed by the addition of benzyl chloroformate (22.28 g, 131 mmol). The resulting mixture was stirred at 25° C. for 12 h. The reaction was diluted with water (100 mL) and extracted with ethyl acetate (3×200 mL). The combined organic layers were washed with brine (3×200 mL), dried over sodium sulfate, filtered, and concentrated under reduced pressure. The residue was purified by column chromatography (petroleum ether/ethyl acetate=100/1 to 3/2) to afford benzyl 6-oxo-2-azaspiro[3.3]heptane-2-carboxylate (26 g, 97%) as a white solid. MS (ESI) m/z: 268.0 [M+Na]$^+$.

Step 3: benzyl 6-(methoxymethylene)-2-azaspiro[3.3]heptane-2-carboxylate

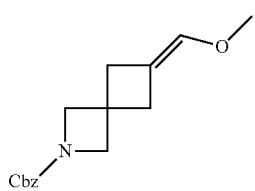 [SMILES: COC=C1CC2(C1)CN(C(=O)OCc1ccccc1)C2]

To a solution of methoxymethyl-triphenylphosphonium chloride (52.41 g, 153 mmol) in tetrahydrofuran (400 mL) was dropwise added 1M potassium tert-butoxide (163 mL) at 0° C. The mixture was stirred at 0° C. for 1 h, followed by the addition of benzyl 6-oxo-2-azaspiro[3.3]heptane-2-carboxylate (25.0 g, 102 mmol) in tetrahydrofuran (100 mL) at 0° C. The resulting mixture was stirred at 25° C. for 12 h. The reaction was diluted with water (200 mL) and extracted with ethyl acetate (3×200 mL). The combined organic layers were washed with brine (3×200 mL), dried over sodium sulfate, filtered, and concentrated under reduced pressure. The residue was purified by flash silica gel chromatography (0-30% ethyl acetate/petroleum ether) to afford benzyl 6-(methoxymethylene)-2-azaspiro[3.3]heptane-2-carboxylate (6 g, 20%) as a yellow oil. MS (ESI) m/z: 274.1 [M+H]$^+$; $^1$H NMR (400 MHz, CDCl$_3$) δ 7.30-7.41 (m, 5H), 5.77-5.88 (m, 1H), 5.09 (s, 2H), 4.01 (s, 4H), 3.55 (s, 3H), 2.88 (s, 2H), 2.80 (s, 2H).

Step 4: benzyl 6-formyl-2-azaspiro[3.3]heptane-2-carboxylate

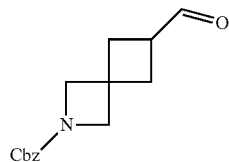 [SMILES: O=CC1CC2(C1)CN(C(=O)OCc1ccccc1)C2]

To a solution of benzyl 6-(methoxymethylene)-2-azaspiro[3.3]heptane-2-carboxylate (6.0 g, 22 mmol) in tetrahydrofuran (120 mL) was added 1 M aqueous hydrochloric acid solution (120 mL). The mixture was stirred at 100° C. for 2 h, then diluted with saturated sodium bicarbonate solution (100 mL) and extracted with ethyl acetate (3×100 mL). The combined organic layers were washed with brine (3×100 mL), dried over sodium sulfate, filtered, and concentrated to afford benzyl 6-formyl-2-azaspiro[3.3]heptane-2-carboxylate (5.69 g, crude) as a yellow oil, which was used in the next step directly. MS (ESI) m/z: 260.1 [M+H]$^+$.

Step 5: benzyl 6-(dimethoxymethyl)-2-azaspiro[3.3]heptane-2-carboxylate

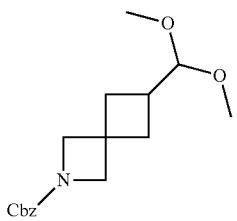 [SMILES: COC(OC)C1CC2(C1)CN(C(=O)OCc1ccccc1)C2]

To a solution of benzyl 6-formyl-2-azaspiro[3.3]heptane-2-carboxylate (5.69 g, 22 mmol) and trimethoxymethane (23.29 g, 219 mmol) in methanol (4 mL) was added p-toluenesulfonic acid (377 mg, 2 mmol). The mixture was stirred at 20° C. for 12 h, then diluted with water (120 mL) and extracted with ethyl acetate (3×100 mL). The combined organic layers were washed with brine (3×100 mL), dried over sodium sulfate, filtered, and concentrated under reduced pressure. The residue was purified by flash silica gel chromatography (0-20% ethyl acetate/petroleum ether) to afford benzyl 6-(dimethoxymethyl)-2-azaspiro[3.3]heptane-2-carboxylate (4.15 g, 43%, 70% purity) as a colorless oil. MS (ESI) m/z: 306.1 [M+H]$^+$; $^1$H NMR (400 MHz, CDCl$_3$) δ 7.30-7.39 (m, 5H), 5.08 (s, 2H), 4.22 (d, J=6.0 Hz, 1H), 4.00 (s, 2H), 3.91 (s, 2H), 3.32 (s, 6H), 2.40-2.51 (m, 1H), 2.17-2.27 (m, 2H), 2.06-2.12 (m, 2H).

Step 6: 6-(dimethoxymethyl)-2-azaspiro[3.3]heptane

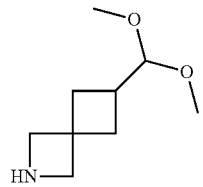

To a solution of benzyl 6-(dimethoxymethyl)-2-azaspiro[3.3]heptane-2-carboxylate (4.15 g, 13 mmol) in methanol (20 mL) and tetrahydrofuran (20 mL) was added 10% palladium on carbon (0.2 g) and 10% palladium hydroxide (0.2 g). The suspension was degassed and purged with hydrogen three times. The mixture was stirred under hydrogen (50 psi) at 30° C. for 12 h, then filtered through Celite pad and concentrated to afford 6-(dimethoxymethyl)-2-azaspiro[3.3]heptane (2.2 g, 94%) as a black solid. MS (ESI) m/z: 172.1 [M+H]$^+$; $^1$H NMR (400 MHz, CDCl$_3$) δ 4.20 (d, J=6.0 Hz, 1H), 3.72 (s, 2H), 3.63 (s, 2H), 3.30 (s, 6H), 2.37-2.52 (m, 1H), 2.16-2.32 (m, 2H), 2.00-2.10 (m, 2H).

Step 7: methyl 2-bromo-4-[6-(dimethoxymethyl)-2-azaspiro[3.3]heptan-2-yl]benzoate

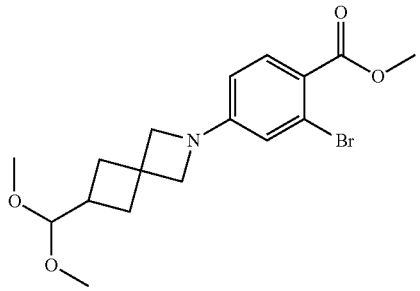 [SMILES: COC(=O)c1ccc(N2CC3(CC(C(OC)OC)C3)C2)cc1Br]

To a solution of 6-(dimethoxymethyl)-2-azaspiro[3.3]heptane (720 mg, 4.2 mmol) and methyl 2-bromo-4-fluorobenzoate (817 mg, 3.5 mmol) in dimethyl sulfoxide (15 mL) was added N-ethyl-N,N-diisopropylamine (1.8 mL, 10 mmol). The mixture was stirred at 90° C. for 2 h, then diluted with water (50 mL) and extracted with ethyl acetate (3×50 mL). The combined organic layers were washed with brine (3×50 mL), dried over sodium sulfate, filtered, and concentrated under reduced pressure. The residue was purified by flash silica gel chromatography (0-10% ethyl acetate/petroleum ether) to afford methyl 2-bromo-4-[6-(dimethoxymethyl)-2-azaspiro[3.3]heptan-2-yl]benzoate (870 mg, 58%) as a colorless oil. MS (ESI) m/z: 384.1 [M+H]$^+$.

Step 8: methyl 4-[6-(dimethoxymethyl)-2-azaspiro[3.3]heptan-2-yl]-2-vinyl-benzoate

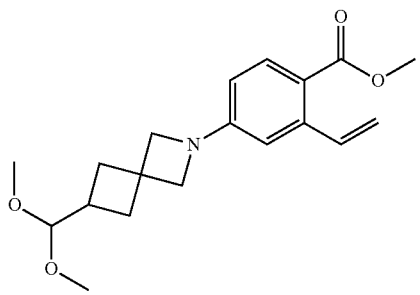

A mixture of methyl 2-bromo-4-[6-(dimethoxymethyl)-2-azaspiro[3.3]heptan-2-yl]benzoate (870 mg, 2.3 mmol), sodium carbonate (480 mg, 4.5 mmol), 1,1-bis(diphenylphosphino)ferrocene-palladium (II) chloride (166 mg, 0.2 mmol) and potassium vinyltrifluoroborate (1.21 g, 9 mmol) in 1,4-dioxane (10 mL) and water (2 mL) was degassed and purged with nitrogen three times, then the mixture was stirred at 90° C. for 12 h under nitrogen atmosphere. The reaction was diluted with water (30 mL) and extracted with ethyl acetate (3×30 mL). The combined organic layers were washed with brine (3×30 mL), dried over sodium sulfate, filtered, and concentrated under reduced pressure. The residue was purified by flash silica gel chromatography (0-10% ethyl acetate/petroleum ether) to afford methyl 4-[6-(dimethoxymethyl)-2-azaspiro[3.3]heptan-2-yl]-2-vinyl-benzoate (580 mg, 73%) as a yellow oil. MS (ESI) m/z: 332.1 [M+H]$^+$.

Step 9: methyl 4-[6-(dimethoxymethyl)-2-azaspiro[3.3]heptan-2-yl]-2-formyl-benzoate

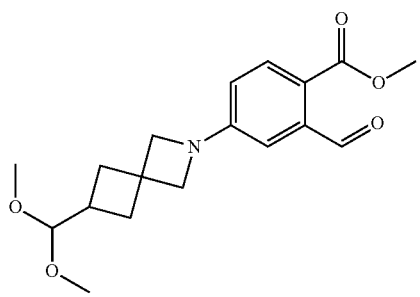 [SMILES: COC(=O)c1ccc(N2CC3(CC(C(OC)OC)C3)C2)cc1C=O]

To a solution of methyl 4-[6-(dimethoxymethyl)-2-azaspiro[3.3]heptan-2-yl]-2-vinyl-benzoate (580 mg, 1.8 mmol) in 1,4-dioxane (6 mL) and water (1.5 mL) was added 2,6-dimethylpyridine (375 mg, 3.5 mmol), sodium periodate (1.50 g, 7 mmol) and potassium osmate(VI) dihydrate (13 mg, 0.04 mmol). The mixture was stirred at 25° C. for 2 h, then filtered and washed with ethyl acetate (10 mL). The filtrate solution was diluted with water (30 mL) and extracted with ethyl acetate (3×30 mL). The combined organic layers were washed with brine (3×30 mL), dried over sodium sulfate, filtered, and concentrated. The residue was purified by flash silica gel chromatography (0-20% ethyl acetate/petroleum ether) to afford methyl 4-[6-(dimethoxymethyl)-2-azaspiro[3.3]heptan-2-yl]-2-formyl-benzoate (340 mg, 55%) as a yellow oil. MS (ESI) m/z: 334.1 [M+H]$^+$.

Step 10: methyl (4S)-5-amino-4-[5-[6-(dimethoxymethyl)-2-azaspiro[3.3]heptan-2-yl]-1-oxo-isoindolin-2-yl]-5-oxo-pentanoate

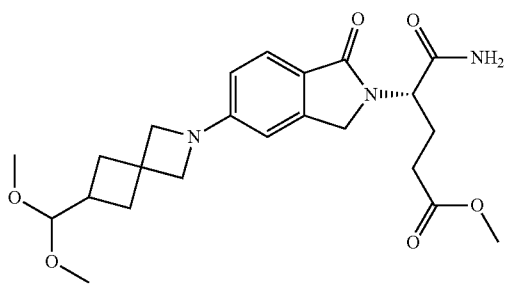 [SMILES: COC(=O)CC[C@@H](C(N)=O)N1Cc2cc(N3CC4(CC(C(OC)OC)C4)C3)ccc2C1=O]

To a solution of methyl (4S)-4,5-diamino-5-oxo-pentanoate hydrochloride (200 mg, 1 mmol) in methanol (10 mL) was slowly added sodium acetate (83 mg, 1 mmol) at 25° C., followed by the addition of methyl 4-[6-(dimethoxymethyl)-2-azaspiro[3.3]heptan-2-yl]-2-formyl-benzoate (340 mg, 1 mmol) and acetic acid (612 mg, 10 mmol). The mixture was stirred at 25° C. for 15 min. Then sodium cyanoborohydride (128 mg, 2 mmol) was added and the resulting mixture was stirred at 35° C. for 12 h. The mixture was diluted saturated sodium bicarbonate solution to adjust the pH to 8 and extracted with ethyl acetate and tetrahydrofuran (1:1, 3×20 mL). The combined organic layers were washed with brine (3×20 mL), dried over sodium sulfate, filtered, and concentrated under reduced pressure. The residue was purified by flash silica gel chromatography (0-5% methanol/dichloromethane) to afford methyl (4S)-5-amino-4-[5-[6-(dimethoxymethyl)-2-azaspiro[3.3]heptan-2-yl]-1-oxo-isoindolin-2-yl]-5-oxo-pentanoate (315 mg, 69%) as a colorless oil. MS (ESI) m/z: 446.3 [M+H]$^+$.

Step 11: (3S)-3-[5-[6-(dimethoxymethyl)-2-azaspiro[3.3]heptan-2-yl]-1-oxo-isoindolin-2-yl]piperidine-2,6-dione

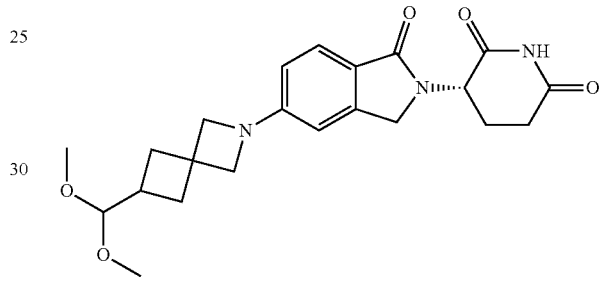

To a solution of methyl (4S)-5-amino-4-[5-[6-(dimethoxymethyl)-2-azaspiro[3.3]heptan-2-yl]-1-oxo-isoindolin-2-yl]-5-oxo-pentanoate (315 mg, 0.7 mmol) in tetrahydrofuran (6 mL) was added 1 M lithium tert-butanol (1.3 mL). The mixture was stirred at −20° C. for 2 h, then 2 M aqueous sulfuric acid solution was added to adjust the pH to 5 at −20° C., followed by the addition of saturated sodium bicarbonate solution to adjust the pH to 8. The mixture was extracted with ethyl acetate (3×20 mL). The combined organic layers were washed with brine (3×20 mL), dried over anhydrous sodium sulfate, filtered, and concentrated. The crude product was triturated with ethyl acetate to afford (3S)-3-[5-[6-(dimethoxymethyl)-2-azaspiro[3.3]heptan-2-yl]-1-oxo-isoindolin-2-yl]piperidine-2,6-dione (170 mg, 58%) as a white solid. MS (ESI) m/z: 414.2 [M+H]$^+$.

Step 12: 2-[2-[(3S)-2,6-dioxo-3-piperidyl]-1-oxo-isoindolin-5-yl]-2-azaspiro[3.3]heptane-6-carbaldehyde

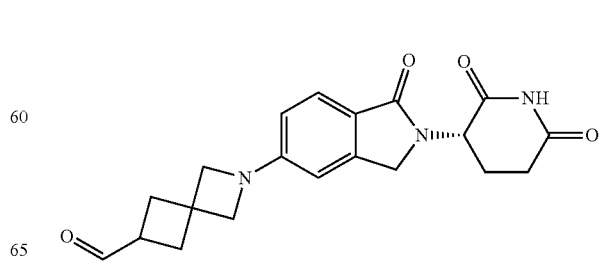

To a solution of (3S)-3-[5-[6-(dimethoxymethyl)-2-azaspiro[3.3]heptan-2-yl]-1-oxo-isoindolin-2-yl]piperidine-2,6-dione (170 mg, 0.4 mmol) in acetone (2 mL) and water (0.2 mL) was added p-toluenesulfonic acid (14 mg, 0.8 mmol). The mixture was stirred at 70° C. for 3 h, then concentrated to afford 2-[2-[(3S)-2,6-dioxo-3-piperidyl]-1-oxo-isoindolin-5-yl]-2-azaspiro[3.3]heptane-6-carbaldehyde (151 mg) as a yellow solid, which was used in the next step without further purification. MS (ESI) m/z: 368.1 [M+H]+.

Step 13: (3R)—N-[2-cyano-3-[3-[4-[4-[[2-[2-[(3S)-2,6-dioxo-3-piperidyl]-1-oxo-isoindolin-5-yl]-2-azaspiro[3.3]heptan-6-yl]methyl]piperazin-1-yl]phenyl]-4-oxo-quinazolin-6-yl]oxy-4-fluoro-phenyl]-3-fluoro-pyrrolidine-1-sulfonamide were washed with brine (3×20 mL), dried over anhydrous sodium sulfate, filtered, and concentrated. The residue was purified by preparative high performance liquid chromatography 915%-45% acetonitrile in water (0.2% formic acid) over 15 min) to afford (3R)—N-[2-cyano-3-[3-[4-[4-[[2-[2-[(3S)-2,6-dioxo-3-piperidyl]-1-oxo-isoindolin-5-yl]-2-azaspiro[3.3]heptan-6-yl]methyl]piperazin-1-yl]phenyl]-4-oxo-quinazolin-6-yl]oxy-4-fluoro-phenyl]-3-fluoro-pyrrolidine-1-sulfonamide formate (193.4 mg, 62%) as an off-white solid. MS (ESI) m/z: 959.5 [M+H]+; $^1$H NMR (400 MHz, DMSO-$d_6$) δ 10.92 (s, 1H), 9.69-10.52 (m, 1H), 8.23 (s, 1H), 8.13 (s, 1H), 7.81 (d, J=9.2 Hz, 1H), 7.67 (dd, J=8.8, 3.0 Hz, 1H), 7.53-7.64 (m, 1H), 7.48 (d, J=8.4 Hz, 1H), 7.32-7.43 (m, 4H), 7.09 (d, J=8.8 Hz, 2H), 6.42-6.54 (m, 2H), 5.18-5.39 (m, 1H), 5.03 (dd, J=13.2, 5.2 Hz, 1H), 4.13-4.35 (m, 2H), 3.97 (s, 2H), 3.78-3.87 (m, 2H), 3.35-

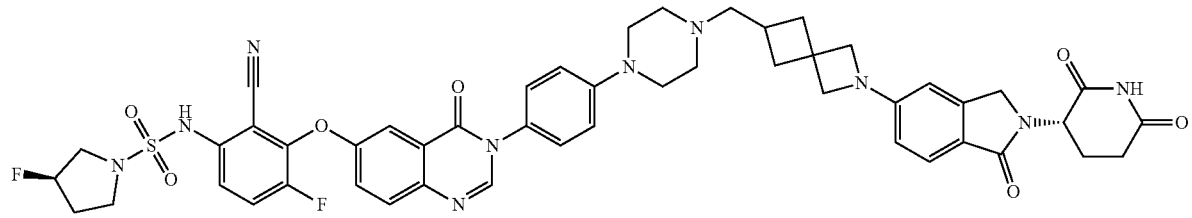 [SMILES: N#Cc1c(NS(=O)(=O)N2CC[C@@H](F)C2)ccc(F)c1Oc1ccc2ncn(-c3ccc(N4CCN(CC5CC6(C5)CN(c5ccc7c(c5)CN([C@H]5CCC(=O)NC5=O)C7=O)C6)CC4)cc3)c(=O)c2c1]

To a solution of (3R)—N-[2-cyano-4-fluoro-3-[4-oxo-3-(4-piperazin-1-ylphenyl)quinazolin-6-yl]oxy-phenyl]-3-fluoro-pyrrolidine-1-sulfonamide (178 mg, 0.3 mmol) in dimethyl sulfoxide (4 mL) and dichloromethane (2 mL) was added 2-[2-[(3S)-2,6-dioxo-3-piperidyl]-1-oxo-isoindolin-5-yl]-2-azaspiro[3.3]heptane-6-carbaldehyde (151 mg, 0.4 mmol) in dichloromethane (4 mL) and isopropanol (4 mL), followed by the addition of acetic acid (35 mg, 0.6 mmol). The mixture was stirred at 25° C. for 10 min, then sodium triacetoxyborohydride (124 mg, 0.6 mmol) was added and the resulting mixture was stirred at 25° C. for 50 min. The mixture was poured into brine (30 mL), saturated sodium bicarbonate solution (10 mL) and tetrahydrofuran (20 mL) and stirred for 10 min. Then the mixture was extracted with tetrahydrofuran (3×10 mL). The combined organic layers 3.52 (m, 4H), 3.33-3.34 (m, 2H), 3.17-3.27 (m, 2H), 2.65-2.98 (m, 7H), 2.54-2.63 (m, 2H), 2.31-2.44 (m, 3H), 1.91-2.15 (m, 5H).

Example 180: Exemplary synthesis of (3R)—N-{2-cyano-3-[(3-{8-[2-(1-{2-[(3S)-2,6-dioxopiperidin-3-yl]-1-oxo-2,3-dihydro-1H-isoindol-5-yl}-4-hydroxypiperidin-4-yl)acetyl]-1-oxa-8-azaspiro[4.5]decan-3-yl}-4-oxo-3,4-dihydroquinazolin-6-yl)oxy]-4-fluorophenyl}-3-fluoropyrrolidine-1-sulfonamide

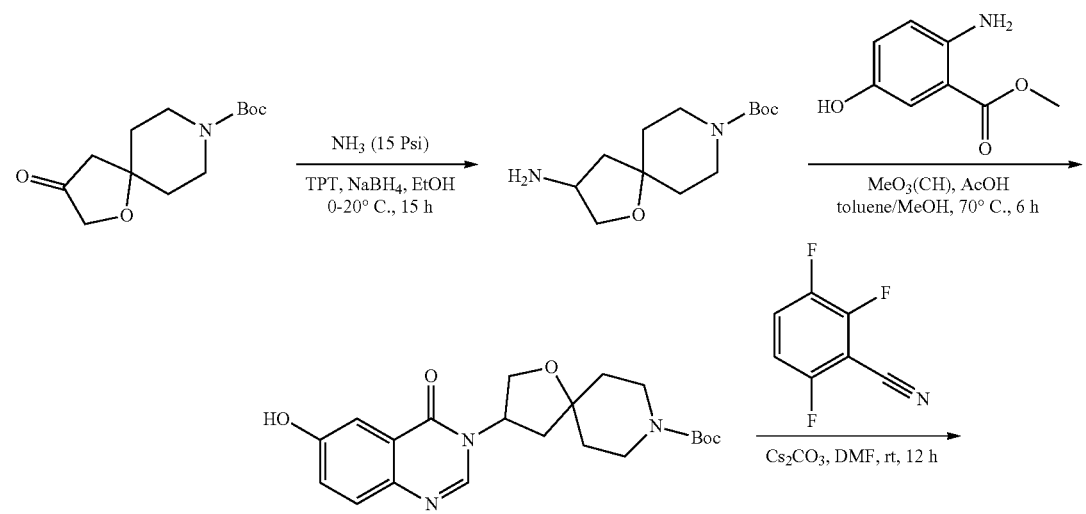

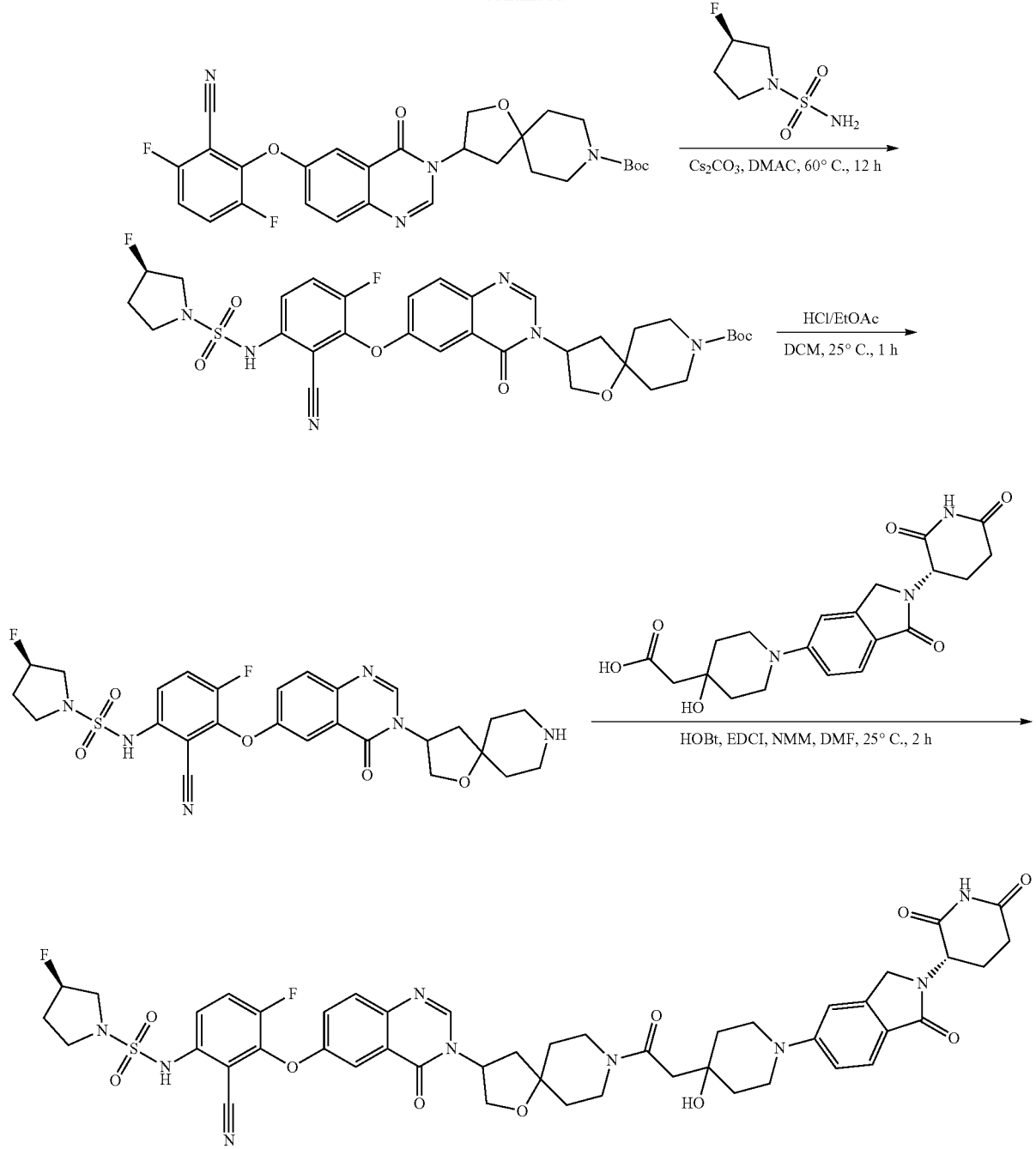

Step 1: tert-butyl 3-(6-hydroxy-4-oxoquinazolin-3(4H)-yl)-1-oxa-8-azaspiro[4.5]decane-8-carboxylate

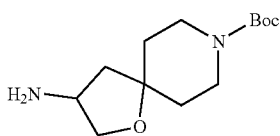 [SMILES: CC(C)(C)OC(=O)N1CCC2(CC1)CC(N)CO2]

To a solution of tert-butyl 3-amino-1-oxa-8-azaspiro[4.5]decane-8-carboxylate (1.8 g, 7 mmol) and methyl 2-amino-5-hydroxybenzoate (1.17 g, 7 mmol) in toluene (18 mL) and methanol (3.6 mL) was added trimethoxymethane (1.2 mL 10 mmol) and acetic acid (0.4 mL, 7 mmol). The mixture was stirred at 70° C. for 6 h, then cooled to room temperature. The reaction was suspended in tert-butyl methyl ether (35 mL), the mixture was filtered and washed with tert-butyl methyl ether (35 mL). The filter cake was purified by preparative high performance liquid chromatography (28-58% acetonitrile in water (0.2% formic acid) over 15 min) to afford tert-butyl 3-(6-hydroxy-4-oxoquinazolin-3(4H)-yl)-1-oxa-8-azaspiro[4.5]decane-8-carboxylate (1.7 g, 59%) as a brown solid. MS (ESI) m/z: 402.2 [M+H]+.

Step 2: tert-butyl 3-(6-(2-cyano-3,6-difluorophenoxy)-4-oxoquinazolin-3(4H)-yl)-1-oxa-8-azaspiro[4.5]decane-8-carboxylate

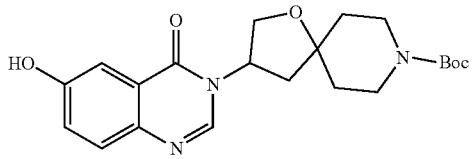 [SMILES: CC(C)(C)OC(=O)N1CCC2(CC1)CC(n1cnc3ccc(O)cc3c1=O)CO2]

To a solution of tert-butyl 3-(6-hydroxy-4-oxoquinazolin-3(4H)-yl)-1-oxa-8-azaspiro[4.5]decane-8-carboxylate (1.4 g, 3 mmol) and 2,3,6-trifluorobenzonitrile (548 mg, 3.5 mmol) in N,N-dimethylformamide (20 mL) was added cesium carbonate (1.31 g, 4 mmol). The mixture was stirred at 15° C. for 1 h, then diluted with water (15 mL) and extracted with ethyl acetate (3×15 mL). The combined organic layers were washed with brine (3×15 mL), dried over anhydrous sodium sulfate, filtered, and concentrated under reduced pressure. The residue was purified by flash silica gel chromatography (0-50% ethyl acetate/petroleum ether) to afford tert-butyl 3-(6-(2-cyano-3,6-difluorophenoxy)-4-oxoquinazolin-3(4H)-yl)-1-oxa-8-azaspiro[4.5]decane-8-carboxylate (1.8 g, 90%) as a brown solid. MS (ESI) m/z: 539.4 [M+H]$^+$.

Step 3: tert-butyl 3-[6-[2-cyano-6-fluoro-3-[[(3R)-3-fluoropyrrolidin-1-yl]sulfonylamino]phenoxy]-4-oxo-quinazolin-3-yl]-1-oxa-8-azaspiro[4.5]decane-8-carboxylate

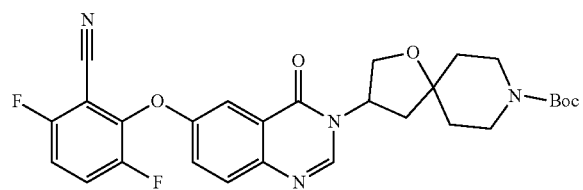 [SMILES: CC(C)(C)OC(=O)N1CCC2(CC1)CC(n1cnc3ccc(Oc4c(F)ccc(F)c4C#N)cc3c1=O)CO2]

To a solution of (3R)-3-fluoropyrrolidine-1-sulfonamide (406 mg, 2 mmol) and tert-butyl 3-[6-(2-cyano-3,6-difluoro-phenoxy)-4-oxo-quinazolin-3-yl]-1-oxa-8-azaspiro[4.5]decane-8-carboxylate (650 mg, 1 mmol) in N,N-dimethylacetamide (10 mL) was added cesium carbonate (1.18 g, 3.6 mmol). The mixture was stirred at room temperature for 12 h, then diluted with water (10 mL) and extracted with ethyl acetate (3×10 mL). The combined organic layers were washed with brine (3×10 mL), dried over anhydrous sodium sulfate, filtered, and concentrated under reduced pressure. The residue was purified by preparative high performance liquid chromatography (42%-72% acetonitrile in water (0.2% formic acid) over 15 min) to afford tert-butyl 3-[6-[2-cyano-6-fluoro-3-[[(3R)-3-fluoropyrrolidin-1-yl]sulfonylamino]phenoxy]-4-oxo-quinazolin-3-yl]-1-oxa-8-azaspiro[4.5]decane-8-carboxylate (400 mg, 48%) as a white solid. MS (ESI) m/z: 687.2 [M+H]$^+$.

Step 4: tert-butyl 3-[6-[2-cyano-6-fluoro-3-[[(3R)-3-fluoropyrrolidin-1-yl]sulfonylamino]phenoxy]-4-oxo-quinazolin-3-yl]-1-oxa-8-azaspiro[4.5]decane-8-carboxylate

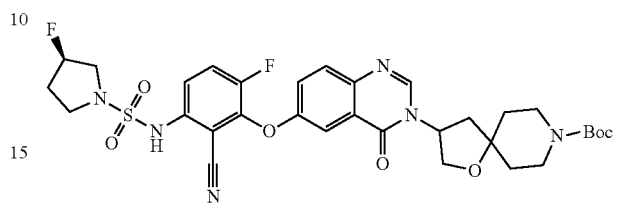

To a solution of (3R)-3-fluoropyrrolidine-1-sulfonamide (406 mg, 2.4 mmol) and tert-butyl 3-[6-(2-cyano-3,6-difluoro-phenoxy)-4-oxo-quinazolin-3-yl]-1-oxa-8-azaspiro[4.5]decane-8-carboxylate (650 mg, 1.2 mmol) in N,N-dimethylacetamide (10 mL) was added cesium carbonate (1.18 g, 3.6 mmol). The mixture was stirred at 60° C. for 12 h, then diluted with water (10 mL) and extracted with ethyl acetate (3×10 mL). The combined organic layers were washed with brine (3×10 mL), dried over anhydrous sodium sulfate, filtered, and concentrated under reduced pressure. The residue was purified by preparative high performance liquid chromatography (42%-72% acetonitrile in water (0.2% formic acid) over 15 min) to afford tert-butyl 3-[6-[2-cyano-6-fluoro-3-[[(3R)-3-fluoropyrrolidin-1-yl]sulfonylamino]phenoxy]-4-oxo-quinazolin-3-yl]-1-oxa-8-azaspiro[4.5]decane-8-carboxylate (400 mg, 48%) as a white solid. MS (ESI) m/z: 687.2 [M+H]$^+$.

Step 5: (3R)—N-[2-cyano-4-fluoro-3-[3-(1-oxa-8-azaspiro[4.5]decan-3-yl)-4-oxo-quinazolin-6-yl]oxyphenyl]-3-fluoro-pyrrolidine-1-sulfonamide

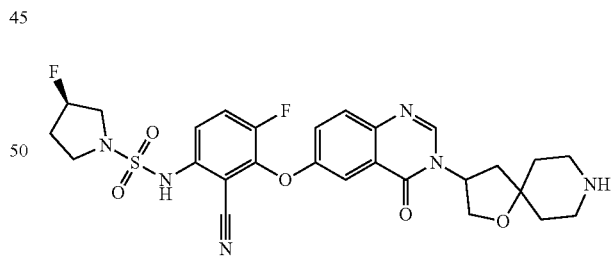

To a solution of tert-butyl 3-[6-[2-cyano-6-fluoro-3-[[(3R)-3-fluoropyrrolidin-1-yl]sulfonylamino]phenoxy]-4-oxo-quinazolin-3-yl]-1-oxa-8-azaspiro[4.5]decane-8-carboxylate (400 mg, 0.6 mmol) in dichloromethane (4 mL) was added 4 M hydrochloric acid in ethyl acetate (2 mL). The mixture was stirred at 25° C. for 1 h, then concentrated to afford (3R)—N-[2-cyano-4-fluoro-3-[3-(1-oxa-8-azaspiro[4.5]decan-3-yl)-4-oxo-quinazolin-6-yl]oxy-phenyl]-3-fluoro-pyrrolidine-1-sulfonamide (340 mg) as a yellow solid, which was used in the next step without further purification. MS (ESI) m/z: 587.2 [M+H]$^+$.

Step 6: (3R)—N-[2-cyano-3-[3-[8-[2-[1-[2-[(3S)-2, 6-dioxo-3-piperidyl]-1-oxo-isoindolin-5-yl]-4-hydroxy-4-piperidyl]acetyl]-1-oxa-8-azaspiro[4.5]decan-3-yl]-4-oxo-quinazolin-6-yl]oxy-4-fluorophenyl]-3-fluoro-pyrrolidine-1-sulfonamide

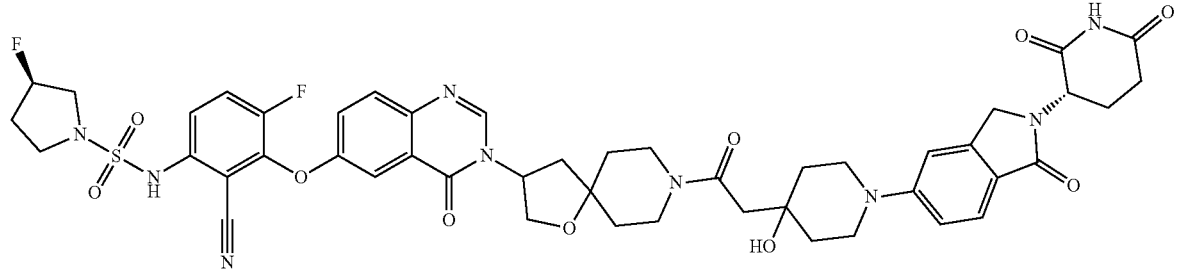 [SMILES: N#Cc1c(NS(=O)(=O)N2CC[C@@H](F)C2)ccc(F)c1Oc1ccc2ncn(C3COC4(CCN(C(=O)CC5(O)CCN(c6ccc7c(c6)CN([C@H]6CCC(=O)NC6=O)C7=O)CC5)CC4)C3)c(=O)c2c1]

To a solution of (3R)—N-[2-cyano-4-fluoro-3-[3-(1-oxa-8-azaspiro[4.5]decan-3-yl)-4-oxo-quinazolin-6-yl]oxy-phenyl]-3-fluoro-pyrrolidine-1-sulfonamide (150 mg, 0.3 mmol) and 2-[1-[2-[(3S)-2,6-dioxo-3-piperidyl]-1-oxo-isoindolin-5-yl]-4-hydroxy-4-piperidyl]acetic acid (123 mg, 0.3 mmol) in dimethyl formamide (5 mL) was added N-methylmorpholine (0.1 mL, 1 mmol) The mixture was stirred at 25° C. for 10 min, followed by the addition of N-(3-dimethylaminopropyl)-N-ethylcarbodiimide hydrochloride (64 mg, 0.3 mmol) and 1-hydroxybenzotriazole (45 mg, 0.3 mmol). The mixture was stirred at 25° C. for 2 h. The reaction was diluted with brine (10 mL) and extracted with tetrahydrofuran (3×10 mL). The combined organic layers were washed with brine (3×10 mL), dried over anhydrous sodium sulfate, filtered, and concentrated under reduced pressure. The residue was purified by preparative high performance liquid chromatography (35%-65% acetonitrile in water (0.2% formic acid) over 7 min) to afford (3R)—N-[2-cyano-3-[3-[8-[2-[1-[2-[(3S)-2,6-dioxo-3-piperidyl]-1-oxo-isoindolin-5-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-fluoro-pyrrolidine-1-sulfonamide (128.5 mg, 50%) as a white solid. MS (ESI) m/z: 970.6 [M+H]$^+$; $^1$H NMR (400 MHz, DMSO-$d_6$) δ 10.94 (s, 1H), 10.44-10.25 (m, 1H), 8.35 (s, 1H), 7.89-7.74 (m, 2H), 7.68 (dd, J=3.2, 8.8 Hz, 1H), 7.56-7.45 (m, 2H), 7.38 (d, J=2.8 Hz, 1H), 7.11-6.97 (m, 2H), 5.44-5.17 (m, 2H), 5.07-5.01 (m, 2H), 4.35-4.27 (m, 1H), 4.23-4.06 (m, 3H), 3.80-3.71 (m, 1H), 3.60 (d, J=12.0 Hz, 3H), 3.54-3.38 (m, 5H), 3.27-3.16 (m, 2H), 2.95-2.83 (m, 1H), 2.60 (d, J=3.2 Hz, 1H), 2.44-2.29 (m, 3H), 2.20-1.88 (m, 5H), 1.77-1.42 (m, 8H).

Example 247: Exemplary synthesis of (3R)—N-{2-cyano-3-[(3-{4-[4-({1-[2-(2,6-dioxopiperidin-3-yl)-7-fluoro-1-oxo-2,3-dihydro-1H-isoindol-5-yl]azetidin-3-yl}methyl)piperazin-1-yl]phenyl}-4-oxo-3,4-dihydroquinazolin-6-yl)oxy]-4-fluorophenyl}-3-fluoropyrrolidine-1-sulfonamide Step 1: methyl 4-bromo-2-(bromomethyl)-6-fluorobenzoate

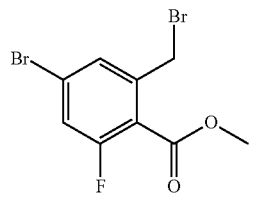

To a mixture of methyl 4-bromo-2-fluoro-6-methylbenzoate (6.0 g, 24 mmol) and azobisisobutyronitrile (0.8 g, 5 mmol) in dichloroethane (20 mL) was added N-bromosuccinimide (4.32 g, 24 mmol), and the resulting mixture was stirred at 80° C. for 12 h under nitrogen atmosphere. The reaction was diluted with saturated aqueous ammonium chloride solution (100 mL) and extracted with dichloromethane (2×100 mL). The combined organic layers were washed with brine (2×20 mL), dried over anhydrous sodium sulfate, filtered, and concentrated to afford methyl 4-bromo-2-(bromomethyl)-6-fluorobenzoate (7.2 g, 91%) as an off-white solid, which was used in the next step without further purification.

Step 2: tert-butyl (4S)-4-(5-bromo-7-fluoro-1-oxo-3H-isoindol-2-yl)-4-carbamoylbutanoate

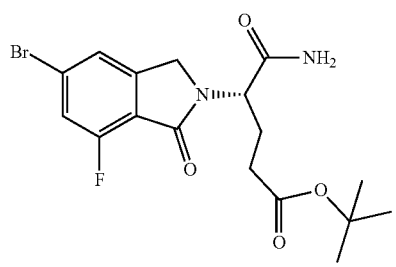 [SMILES: CC(C)(C)OC(=O)CC[C@@H](C(N)=O)N1Cc2cc(Br)cc(F)c2C1=O]

To a mixture of methyl 4-bromo-2-(bromomethyl)-6-fluorobenzoate (1 g, 3 mmol) and tert-butyl (4S)-4-amino-4-carbamoylbutanoate (620.5 mg, 3 mmol) in N,N-dimethylformamide (20 mL) was added N,N-diisopropylethylamine (5 mL). The resulting mixture was stirred for 3 h at 50° C., then 5 h at 100° C. The reaction mixture was cooled to room temperature, diluted with water (60 mL) and extracted with ethyl acetate (3×100 mL). The combined organic layers were washed with brine (2×20 mL), dried over anhydrous sodium sulfate, filtered, and concentrated. The residue was purified by silica gel column chromatography (petroleum ether/ethyl acetate=1:1) to afford tert-butyl (4S)-4-(5-bromo-7-fluoro-1-oxo-3H-isoindol-2-yl)-4-carbamoylbutanoate (1.1 g, 86%) as a yellow solid. MS (ESI): m/z 417.05 [M+H]$^+$.

Step 3: (4S)-4-carbamoyl-4-{5-[3-(dimethoxymethyl)azetidin-1-yl]-7-fluoro-1-oxo-3H-isoindol-2-yl}butanoate

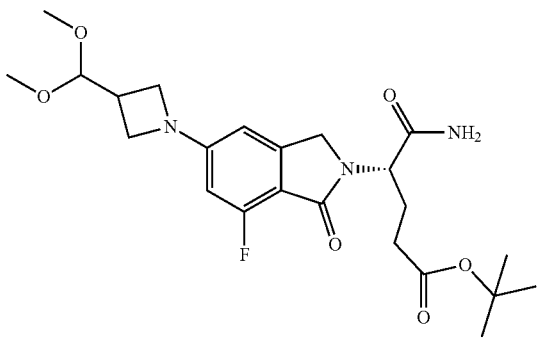 [SMILES: COC(OC)C1CN(c2cc(F)c3c(c2)CN([C@@H](CCC(=O)OC(C)(C)C)C(N)=O)C3=O)C1]

To a mixture of tert-butyl (4S)-4-(5-bromo-7-fluoro-1-oxo-3H-isoindol-2-yl)-4-carbamoylbutanoate (500 mg, 1 mmol), 3-(dimethoxymethyl)azetidine (158 mg, 1 mmol) and cesium fluoride (549 mg, 3.6 mmol) in 1,4-dioxane (20 mL) was added dichloro[1,3-bis(2,6-di-3-pentylphenyl)imidazol-2-ylidene](2-methylpyridyl)palladium(II) (50.6 mg, 0.06 mmol) in portions, the resulting mixture was stirred for 3 h at 70° C. under nitrogen atmosphere. The mixture was cooled to room temperature, diluted with water (80 mL) and extracted with ethyl acetate (2×100 mL). The combined organic layers were washed with brine (2×20 mL), dried over anhydrous sodium sulfate, filtered, and concentrated. The crude product was purified by silica gel chromatography (petroleum ether/ethyl acetate=3:1 to 1:100) to afford tert-butyl (4S)-4-carbamoyl-4-{5-[3-(dimethoxymethyl)azetidin-1-yl]-7-fluoro-1-oxo-3H-isoindol-2-yl}butanoate (260 mg, 46%) as a white solid. $^{1}$H NMR (400 MHz, CDCl$_{3}$) δ 6.33 (s, 1H), 6.12 (s, 1H), 6.03-5.98 m, 1H), 5.23 (s, 1H), 4.82-4.74 (m, 1H), 4.60 (d, J=6.8 Hz, 1H), 4.34 (d, J=3.0 Hz, 2H), 3.99 (t, J=8.0 Hz, 2H), 3.80-3.72 (m, 2H), 3.39 (s, 5H), 3.05 (q, J=5.9 Hz, 1H), 2.39-2.05 (m, 3H), 1.42 (s, 9H), 1.26 (s, 3H); MS (ESI): m/z 466.15 [M+H]$^{+}$.

Step 4: 3-{5-[3-(dimethoxymethyl)azetidin-1-yl]-7-fluoro-1-oxo-3H-isoindol-2-yl}piperidine-2,6-dione

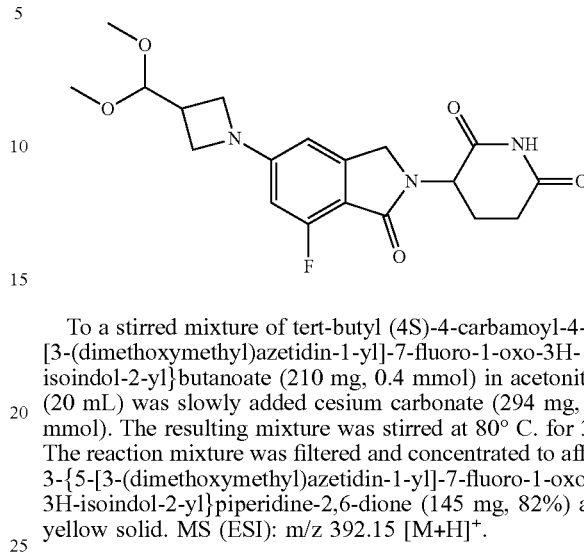

To a stirred mixture of tert-butyl (4S)-4-carbamoyl-4-{5-[3-(dimethoxymethyl)azetidin-1-yl]-7-fluoro-1-oxo-3H-isoindol-2-yl}butanoate (210 mg, 0.4 mmol) in acetonitrile (20 mL) was slowly added cesium carbonate (294 mg, 0.9 mmol). The resulting mixture was stirred at 80° C. for 3 h. The reaction mixture was filtered and concentrated to afford 3-{5-[3-(dimethoxymethyl)azetidin-1-yl]-7-fluoro-1-oxo-3H-isoindol-2-yl}piperidine-2,6-dione (145 mg, 82%) as a yellow solid. MS (ESI): m/z 392.15 [M+H]$^{+}$.

Step 5: 1-{2-[(3S)-2,6-dioxopiperidin-3-yl]-7-fluoro-1-oxo-3H-isoindol-5-yl}azetidine-3-carbaldehyde

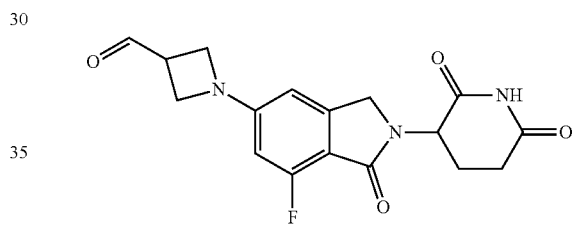

To a solution of (3S)-3-{5-[3-(dimethoxymethyl)cyclobutyl]-7-fluoro-1-oxo-3H-isoindol-2-yl}piperidine-2,6-dione (140 mg, 0.4 mmol) in dichloromethane (8 mL) was added water (2 mL) and trifluoroacetic acid (4 mL). The resulting mixture was stirred for 2 h at 40° C., then concentrated to afford 1-{2-[(3S)-2,6-dioxopiperidin-3-yl]-7-fluoro-1-oxo-3H-isoindol-5-yl}azetidine-3-carbaldehyde trifluoroacetate (95 mg, 77%) as a white solid. MS (ESI): m/z 364.10 [M+H+H$_{2}$O]$^{+}$.

Step 6: (3R)—N-(2-cyano-3-{[3-(4-{4-[(1-{2-[(3S)-2,6-dioxopiperidin-3-yl]-7-fluoro-1-oxo-3H-isoindol-5-yl}azetidin-3-yl)methyl]piperazin-1-yl}phenyl)-4-oxoquinazolin-6-yl]oxy}-4-fluorophenyl)-3-fluoropyrrolidine-1-sulfonamide

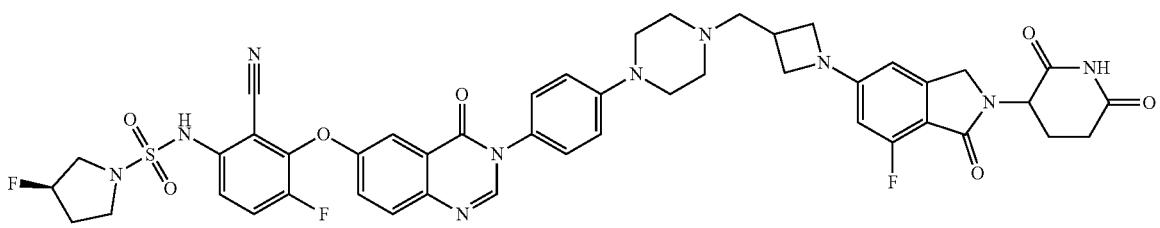 [SMILES: N#Cc1c(NS(=O)(=O)N2CC[C@@H](F)C2)ccc(F)c1Oc1ccc2ncn(-c3ccc(N4CCN(CC5CN(c6cc(F)c7c(c6)CN(C6CCC(=O)NC6=O)C7=O)C5)CC4)cc3)c(=O)c2c1]

To a mixture of 1-[2-(2,6-dioxopiperidin-3-yl)-7-fluoro-1-oxo-3H-isoindol-5-yl]azetidine-3-carbaldehyde trifluoroacetate (90 mg, 0.3 mmol) and (3R)—N-[2-cyano-4-fluoro-3-({4-oxo-3-[4-(piperazin-1-yl)phenyl]quinazolin-6-yl}oxy)phenyl]-3-fluoropyrrolidine-1-sulfonamide hydrochloride (201.4 mg, 0.3 mmol) in dichloromethane (20 mL) was added N,N-diisopropylethylamine (0.1 mL, 0.5 mmol) and acetic acid (0.1 mL, 1 mmol). The mixture was stirred for 3 h at room temperature, followed by the addition of sodium triacetoxyborohydride (166 mg, 0.8 mmol) in portions and stirred for 2 h at room temperature. The reaction mixture was diluted with water (20 mL) and extracted with dichloromethane (3×100 mL). The combined organic layers were washed with brine (2×20 mL), dried over anhydrous sodium sulfate, filtered, and concentrated. The residue was purified by preparative thin layer chromatography (dichloromethane/methanol=10:1) to afford (3R)—N-(2-cyano-3-{[3-(4-{4-[(1-{2-[(3S)-2,6-dioxopiperidin-3-yl]-7-fluoro-1-oxo-3H-isoindol-5-yl}azetidin-3-yl)methyl]piperazin-1-yl}phenyl)-4-oxoquinazolin-6-yl]oxy}-4-fluorophenyl)-3-fluoropyrrolidine-1-sulfonamide (10.5 mg, 4.3%) as a white solid. $^{1}$H NMR (400 MHz, DMSO-$d_6$) δ 10.95 (s, 1H), 8.25 (s, 1H), 7.82 (d, J=8.9 Hz, 1H), 7.69 (dd, J=8.9, 3.1 Hz, 2H), 7.64 (s, 2H), 7.41 (d, J=3.0 Hz, 2H), 7.35 (d, J=8.6 Hz, 2H), 6.24 (d, J=11.9 Hz, 1H), 5.7 (s, 1H), 5.23 (s, 1H), 5.00 (dd, J=13.3, 5.0 Hz, 1H), 4.19 (d, J=17.2 Hz, 1H), 4.08 (t, J=7.8 Hz, 2H), 3.65 (s, 2H), 3.07 (s, 6H), 2.88 (d, J=12.9 Hz, 1H), 2.70 (s, 4H), 2.61 (s, 1H), 2.31 (s, 3H), 2.13 (d, J=15.4 Hz, 2H), 2.04 (s, 3H), 1.95 (s, 1H), 1.24 (s, 2H); MS (ESI): m/z 935.50 [M−H]−.

Example 248: Exemplary synthesis of (3R)—N-(2-cyano-3-{[3-(1-{1-[(1-{2-[(3S)-2,6-dioxopiperidin-3-yl]-1-oxo-2,3-dihydro-1H-isoindol-5-yl}piperidin-4-yl)methyl]piperidin-4-yl}-1H-pyrazol-3-yl)-4-oxo-3,4-dihydroquinazolin-6-yl]oxy}-4-fluorophenyl)-3-fluoropyrrolidine-1-sulfonamide To a solution of (3R)—N-[2-cyano-4-fluoro-3-[4-oxo-3-[1-(4-piperidyl)pyrazol-3-yl]quinazolin-6-yl]oxy-phenyl]-3-fluoro-pyrrolidine-1-sulfonamide (3.35 g, 6 mmol) in dimethyl sulfoxide (40 mL) was added 1-[2-[(3S)-2,6-dioxo-3-piperidyl]-1-oxo-isoindolin-5-yl]piperidine-4-carbaldehyde (2.59 g, 7 mmol) in isopropanol (10 mL) and dichloromethane (10 mL), followed by the addition of acetic acid (0.64 mL, 11 mmol). The mixture was stirred at 25° C. for 10 min, then sodium triacetoxyborohydride (2.38 g, 11 mmol) was added and the mixture was stirred at 25° C. for 50 min. The reaction mixture was diluted with saturated aqueous sodium bicarbonate solution (1000 mL) and extracted with tetrahydrofuran (3×300 mL). The combined organic layers were washed with brine (3×300 mL), dried over sodium sulfate, filtered, and concentrated. The residue was purified by preparative HPLC (20%-50% acetonitrile in water (0.2% formic acid) over 10 min), then further purified by flash column chromatography (dichloromethane/methanol=1:0 to 10:1) to afford (3R)—N-[2-cyano-3-[3-[1-[1-[[1-[2-[(3S)-2,6-dioxo-3-piperidyl]-1-oxo-isoindolin-5-yl]-4-piperidyl]methyl]-4-piperidyl]pyrazol-3-yl]-4-oxo-quinazolin-6-yl]oxy-4-fluoro-phenyl]-3-fluoro-pyrrolidine-1-sulfonamide (2.51 g, 47%) as a white solid. MS (ESI) m/z: 936.2 [M+H]$^+$; $^{1}$H NMR (400 MHz, DMSO-$d_6$) δ 10.94 (s, 1H), 8.53 (s, 1H), 7.97 (s, 1H), 7.83 (d, J=8.8 Hz, 1H), 7.68 (dd, J=2.4, 8.8 Hz, 1H), 7.58 (t, J=10 Hz, 1H), 7.51 (d, J=8.4 Hz, 1H), 7.47-7.37 (m, 2H), 7.10-7.02 (m, 2H), 6.66 (s, 1H), 5.40-5.18 (m, 1H), 5.04 (dd, J=4.8, 13.2 Hz, 1H), 4.46-4.27 (m, 2H), 4.24-4.15 (m, 1H), 3.90 (d, J=12.0 Hz, 2H), 3.48-3.43 (m, 2H), 3.28-3.20 (m, 4H), 2.92-2.80 (m, 3H), 2.75-2.54 (m, 5H), 2.42-2.30 (m, 1H), 2.17 (s, 4H), 2.08 (d, J=8.0 Hz, 2H), 1.98-1.88 (m, 2H), 1.82 (d, J=12.0 Hz, 2H), 1.32-1.17 (m, 2H).

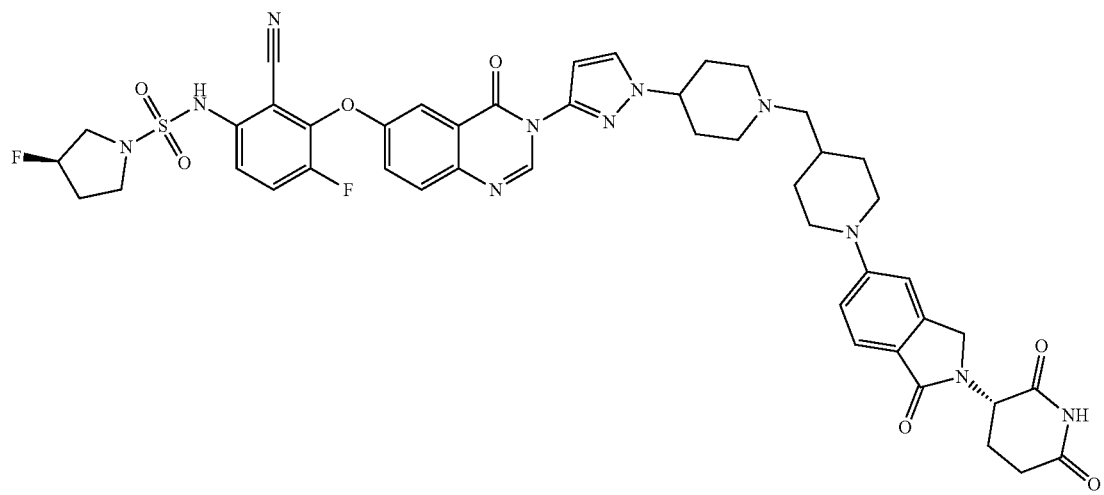 [SMILES: N#Cc1c(NS(=O)(=O)N2CC[C@@H](F)C2)ccc(F)c1Oc1ccc2ncn(-c3ccn(C4CCN(CC5CCN(c6ccc7c(c6)CN([C@H]6CCC(=O)NC6=O)C7=O)CC5)CC4)n3)c(=O)c2c1]

Example 249: Exemplary synthesis of (3R)—N-(2-cyano-4-fluoro-3-{[4-oxo-3-(4-{1-[(1r,3r)-3-({1-[2-(2,6-dioxopiperidin-3-yl)-1-oxo-2,3-dihydro-1H-isoindol-5-yl]piperidin-4-yl}oxy)cyclobutyl]piperidin-4-yl}phenyl)-3,4-dihydroquinazolin-6-yl]oxy}phenyl)-3-fluoropyrrolidine-1-sulfonamide Step 1: tert-butyl 4-[4-(6-hydroxy-4-oxoquinazolin-3-yl)phenyl]piperidine-1-carboxylate

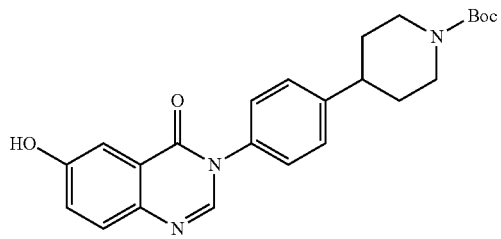 [SMILES: CC(C)(C)OC(=O)N1CCC(c2ccc(-n3cnc4ccc(O)cc4c3=O)cc2)CC1]

To a mixture of 2-amino-5-hydroxybenzoic acid (6.0 g, 39 mmol) and trimethyl orthoformate (12.47 g, 117 mmol) in pyridine (75 mL) was added tert-butyl 4-(4-aminophenyl)piperidine-1-carboxylate (14.08 g, 51 mmol), and the resulting mixture was stirred for 12 h at 120° C. under nitrogen atmosphere. The reaction mixture was cooled to room temperature, diluted with water (500 mL) and extracted with ethyl acetate (3×200 mL). The combined organic layers were washed with brine (3×10 mL), dried over anhydrous sodium sulfate, filtered, and concentrated. The residue was purified by silica gel column chromatography (petroleum ether/ethyl acetate=1:8) to afford tert-butyl 4-[4-(6-hydroxy-4-oxoquinazolin-3-yl)phenyl]piperidine-1-carboxylate (11 g, 67%) as a light brown solid. MS (ESI): m/z 422.1 [M+H]$^+$; $^1$H NMR (300 MHz, DMSO-d$_6$) δ 10.15 (s, 1H), 8.14 (d, J=1.9 Hz, 1H), 7.61 (dd, J=8.7, 1.8 Hz, 1H), 7.53-7.40 (m, 5H), 7.36 (s, 1H), 4.11-3.96 (m, 2H), 2.79 (t, J=12.8 Hz, 3H), 1.81 (d, J=12.9 Hz, 2H), 1.57 (td, J=12.5, 4.1 Hz, 2H), 1.43 (d, J=1.9 Hz, 9H).

Step 2: tert-butyl 4-{4-[6-(benzyloxy)-4-oxoquinazolin-3-yl]phenyl}piperidine-1-carboxylate

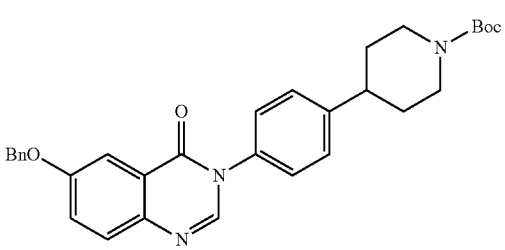 [SMILES: CC(C)(C)OC(=O)N1CCC(c2ccc(-n3cnc4ccc(OCc5ccccc5)cc4c3=O)cc2)CC1]

To a solution of tert-butyl 4-[4-(6-hydroxy-4-oxoquinazolin-3-yl)phenyl]piperidine-1-carboxylate (6.0 g, 14 mmol) in N,N-dimethylformamide (75 mL) was added benzyl bromide (3.65 g, 21 mmol) and cesium carbonate (13.91 g, 43 mmol), and the resulting mixture was stirred for 2 h at room temperature under nitrogen atmosphere. The reaction mixture was diluted with water (200 mL) and extracted with ethyl acetate (3×150 mL). The combined organic layers were washed with brine (3×10 mL), dried over anhydrous sodium sulfate, filtered, and concentrated. The residue was purified by silica gel column chromatography (petroleum ether/ethyl acetate=1:1) to afford tert-butyl 4-{4-[6-(benzyloxy)-4-oxoquinazolin-3-yl]phenyl}piperidine-1-carboxylate (6.1 g, 84%) as a light brown solid. MS (ESI): m/z 511.1 [M+H]$^+$.

Step 3: 6-(benzyloxy)-3-[4-(piperidin-4-yl)phenyl]quinazolin-4-one hydrochloride

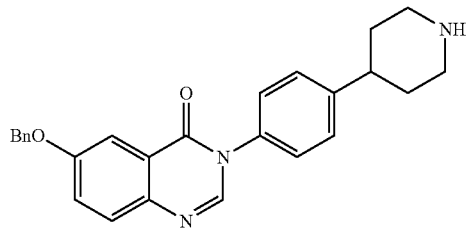 [SMILES: O=c1c2cc(OCc3ccccc3)ccc2ncn1-c1ccc(C2CCNCC2)cc1]

A mixture of tert-butyl 4-{4-[6-(benzyloxy)-4-oxoquinazolin-3-yl]phenyl}piperidine-1-carboxylate (3 g, 6 mmol) and 4 M hydrochloric acid in 1,4-dioxane (25 mL) was stirred for 3 h at room temperature, then concentrated to afford 6-(benzyloxy)-3-[4-(piperidin-4-yl)phenyl]quinazolin-4-one hydrochloride (2.5 g, crude) as a white solid, which was used in the next step without further purification. MS (ESI): m/z 411.1 [M+H]$^+$.

Step 4: tert-butyl 4-[(1r,3r)-3-(4-{4-[6-(benzyloxy)-4-oxoquinazolin-3-yl]phenyl}piperidin-1-yl)cyclobutoxy]piperidine-1-carboxylate

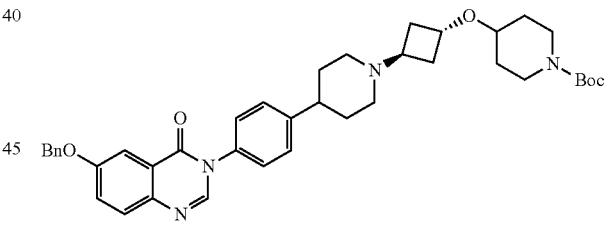

To a mixture of 6-(benzyloxy)-3-[4-(piperidin-4-yl)phenyl]quinazolin-4-one hydrochloride (3 g, 7 mmol) and tert-butyl 4-[(1s,3s)-3-(trifluoromethanesulfonyloxy)cyclobutoxy]piperidine-1-carboxylate (2.7 g, 7 mmol) in acetonitrile (70 mL) was added N,N-diisopropylethylamine (5.8 mL, 33 mmol), and the resulting mixture was stirred for 5 h at room temperature under nitrogen atmosphere. The reaction was diluted with water (100 mL) and extracted with ethyl acetate (3×50 mL). The combined organic layers were washed with brine (3×10 mL), dried over anhydrous sodium sulfate, filtered, and concentrated. The residue was purified by reversed-phase flash chromatography (10% to 90% acetonitrile in water (10 mM ammonium bicarbonate) over 45 min) to afford tert-butyl 4-[(1r,3r)-3-(4-{4-[6-(benzyloxy)-4-oxoquinazolin-3-yl]phenyl}piperidin-1-yl)cyclobutoxy]piperidine-1-carboxylate (3.9 g, 88%) as a light yellow solid. MS (ESI): m/z 664.8 [M+H]$^+$.

Step 5: 6-(benzyloxy)-3-(4-{1-[(1r,3r)-3-(piperidin-4-yloxy)cyclobutyl]piperidin-4-yl}phenyl)quinazolin-4-one

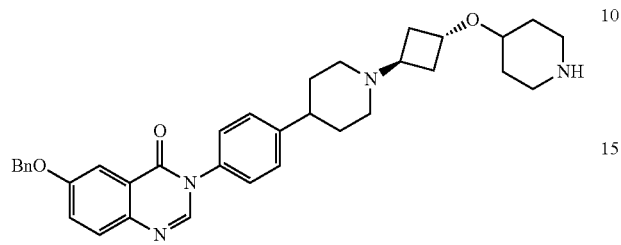

To a solution of tert-butyl 4-[(1r,3r)-3-(4-{4-[6-(benzyloxy)-4-oxoquinazolin-3-yl]phenyl}piperidin-1-yl)cyclobutoxy]piperidine-1-carboxylate (3.5 g, 5 mmol) in tetrahydrofuran (40 mL) was added 4 M hydrochloric acid in 1,4-dioxane (25 mL). The resulting mixture was stirred for 2 h at room temperature, then concentrated. The residue was purified by reversed-phase flash chromatography (10% to 90% acetonitrile in water (10 mM ammonium bicarbonate) over 45 min) to afford 6-(benzyloxy)-3-(4-{1-[(1r,3r)-3-(piperidin-4-yloxy)cyclobutyl]piperidin-4-yl}phenyl)quinazolin-4-one (2.5 g, 84%) as an off-white solid. MS (ESI): m/z 564.8 [M+H]$^+$.

Step 6: 6-(benzyloxy)-3-(4-{1-[(1r,3r)-3-(piperidin-4-yloxy)cyclobutyl]piperidin-4-yl}phenyl)quinazolin-4-one

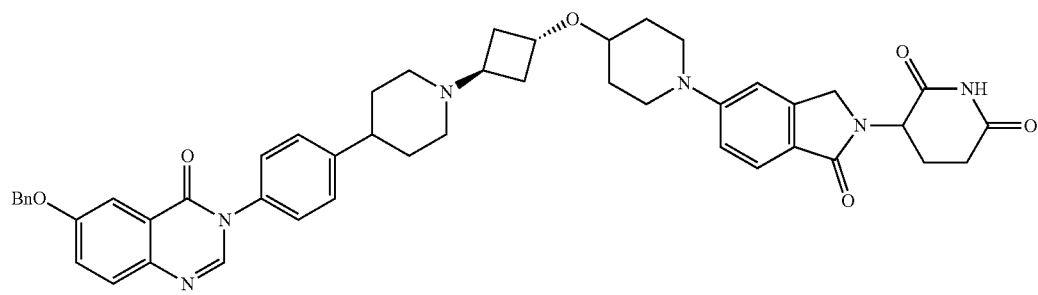 [SMILES: O=C1CCC(N2Cc3cc(N4CCC(O[C@H]5C[C@H](N6CCC(c7ccc(-n8cnc9ccc(OCc%10ccccc%10)cc9c8=O)cc7)CC6)C5)CC4)ccc3C2=O)C(=O)N1]

To a mixture of 6-(benzyloxy)-3-(4-{1-[(1r,3r)-3-(piperidin-4-yloxy)cyclobutyl]piperidin-4-yl}phenyl)quinazolin-4-one (500 mg, 0.9 mmol), 3-(5-bromo-1-oxo-3H-isoindol-2-yl)piperidine-2,6-dione (343 mg, 1 mmol) and cesium carbonate (865 mg, 2.7 mmol) in N,N-dimethylacetamide (15 mL) was added dichloro[1,3-bis(2,6-di-3-pentylphenyl)imidazol-2-ylidene](2-methylpyridyl)palladium(II) (1.5 mg, 0.002 mmol). The resulting mixture was stirred for 3 h at 100° C. under nitrogen atmosphere, then cooled to room temperature. The mixture was diluted with water (100 mL) and extracted with ethyl acetate (3×60 mL). The combined organic layers were dried over anhydrous sodium sulfate, filtered, and concentrated to afford 3-(1-oxo-5-{4-[(1r,3r)-3-(4-{4-[6-(benzyloxy)-4-oxoquinazolin-3-yl]phenyl}piperidin-1-yl)cyclobutoxy]piperidin-1-yl}-3H-isoindol-2-yl)piperidine-2,6-dione (510 mg, 71%) as a purple solid. MS (ESI): m/z 806.9 [M+H]$^+$; $^1$H NMR (400 MHz, DMSO-d$_6$) δ 10.95 (s, 1H), 8.23 (s, 1H), 7.74-7.61 (m, 2H), 7.57 (dd, J=8.9, 3.0 Hz, 1H), 7.54-7.46 (m, 2H), 7.50 (s, 2H), 7.46-7.34 (m, 7H), 7.38-7.31 (m, 1H), 7.06 (d, J=10.0 Hz, 2H), 5.27 (s, 2H), 5.04 (dd, J=13.3, 5.1 Hz, 1H), 4.71 (s, 2H), 4.33 (d, J=17.0 Hz, 1H), 4.19 (s, 2H), 3.71 (s, 1H), 3.02 (s, 6H), 2.95 (s, 1H), 2.79 (s, 1H), 2.59 (d, J=15.4 Hz, 3H), 2.22-2.14 (m, 2H), 2.05-1.95 (m, OH), 1.96 (s, 1H), 1.89 (d, J=10.6 Hz, 1H), 1.80 (t, J=11.4 Hz, 3H), 1.70 (t, J=12.1 Hz, 2H), 0.90-0.79 (m, 1H), 0.57 (s, 2H), 0.51 (s, 1H).

Step 7: 6-(benzyloxy)-3-(4-{1-[(1r,3r)-3-(piperidin-4-yloxy)cyclobutyl]piperidin-4-yl}phenyl)quinazolin-4-one

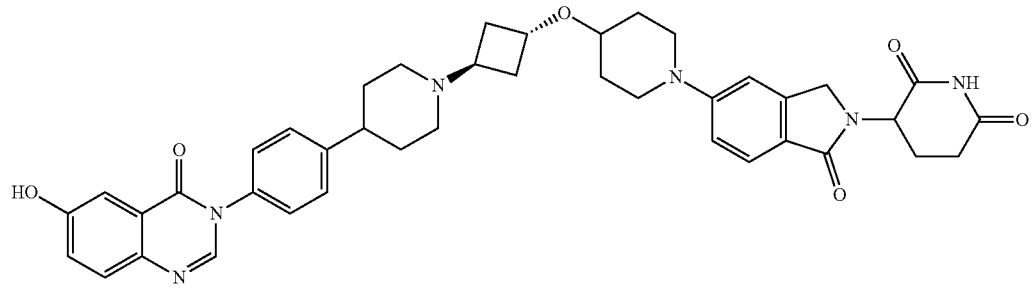 [SMILES: O=C1CCC(N2Cc3cc(N4CCC(O[C@H]5C[C@H](N6CCC(c7ccc(-n8cnc9ccc(O)cc9c8=O)cc7)CC6)C5)CC4)ccc3C2=O)C(=O)N1]

To a solution of 3-(1-oxo-5-{4-[(1r,3r)-3-(4-{4-[6-(benzyloxy)-4-oxoquinazolin-3-yl]phenyl}piperidin-1-yl)cyclobutoxy]piperidin-1-yl}-3H-isoindol-2-yl)piperidine-2,6-dione (450 mg, 0.6 mmol) in tetrahydrofuran (25 mL) was added 10% palladium on carbon (178 mg). The suspension was degassed under vacuum and purged with hydrogen several times. The resulting mixture was stirred under hydrogen atmosphere for 2 h at room temperature, then filtered and washed with N,N-dimethylformamide (3×10 mL). The filtrate was concentrated to afford 3-(1-oxo-5-{4-[(1r,3r)-3-{4-[4-(6-hydroxy-4-oxoquinazolin-3-yl)phenyl]piperidin-1-yl}cyclobutoxy]piperidin-1-yl}-3H-isoindol-2-yl)piperidine-2,6-dione (290 mg, 72%) as an off-white solid. MS (ESI): m/z 716.8 [M+H]$^+$; $^1$H NMR (300 MHz, DMSO-$d_6$) δ 10.99 (d, J=6.8 Hz, 1H), 8.14 (s, 1H), 7.95 (s, 2H), 7.91-7.68 (m, 2H), 7.73-7.59 (m, 2H), 7.04 (m, 1H), 6.90-6.76 (m, 1H), 5.18-5.00 (m, 1H), 4.79 (m, 1H), 4.66-4.09 (m, 3H), 3.79 (d, 1H), 3.52 (m, J=4.0 Hz, 1H), 3.11-2.92 (m, 3H), 2.89 (s, 4H), 2.85 (d, 3H), 2.73 (d, 1H), 2.61 (m, 1H), 2.18 (m, 2H), 1.91-1.58 (m, 12H), 1.48 (m, 2H), 1.37-1.25 (m, 1H), 0.83 (m, 3H).

Step 8: 3,6-difluoro-2-{[4-oxo-3-(4-{1-[(1r,3r)-3-({1-[2-(2,6-dioxopiperidin-3-yl)-1-oxo-3H-isoindol-5-yl]piperidin-4-yl}oxy)cyclobutyl]piperidin-4-yl}phenyl)quinazolin-6-yl]oxy}benzonitrile To a solution of 3-(1-oxo-5-{4-[(1r,3r)-3-{4-[4-(6-hydroxy-4-oxoquinazolin-3-yl)phenyl]piperidin-1-yl}cyclobutoxy]piperidin-1-yl}-3H-isoindol-2-yl)piperidine-2,6-dione (200 mg, 0.3 mmol) in N,N-dimethylformamide (25 mL) was added cesium carbonate (272.7 mg, 0.8 mmol) and 2,3,6-trifluorobenzonitrile (65.7 mg, 0.4 mmol). The resulting mixture was stirred for 4 h at room temperature under nitrogen atmosphere. The reaction mixture was diluted with water (100 mL) and extracted with dichloromethane (3×35 mL). The combined organic layers were washed with brine (3×10 mL), dried over anhydrous sodium sulfate, filtered, and concentrated. The residue was purified by reversed-phase flash chromatography (10% to 90% acetonitrile in water (10 mmol/L ammonium bicarbonate) over 30 min) to afford 3,6-difluoro-2-{[4-oxo-3-(4-{1-[(1r,3r)-3-({1-[2-(2,6-dioxopiperidin-3-yl)-1-oxo-3H-isoindol-5-yl]piperidin-4-yl}oxy)cyclobutyl]piperidin-4-yl}phenyl)quinazolin-6-yl]oxy}benzonitrile (130 mg, 55%) as an off-white solid. MS (ESI): m/z 716.8 [M+H]$^+$.

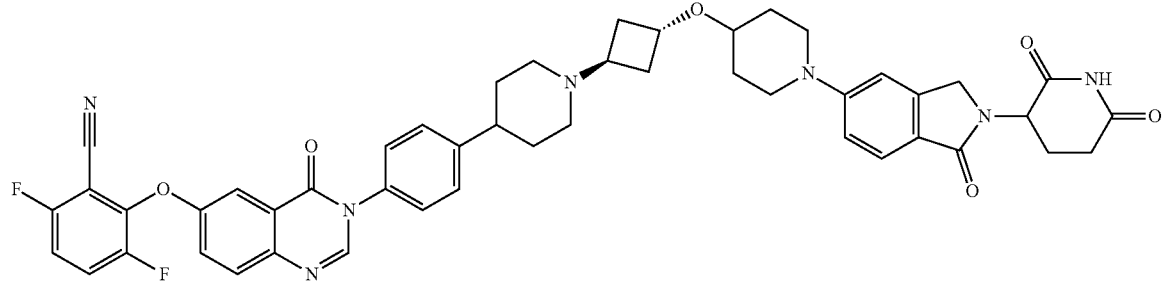 [SMILES: N#Cc1c(F)ccc(F)c1Oc1ccc2ncn(-c3ccc(C4CCN([C@H]5C[C@H](OC6CCN(c7ccc8c(c7)CN(C7CCC(=O)NC7=O)C8=O)CC6)C5)CC4)cc3)c(=O)c2c1]

Step 9: (3R)—N-(2-cyano-4-fluoro-3-{[4-oxo-3-(4-{1-[(1r,3r)-3-({1-[2-(2,6-dioxopiperidin-3-yl)-1-oxo-3H-isoindol-5-yl]piperidin-4-yl}oxy)cyclobutyl]piperidin-4-yl}phenyl)quinazolin-6-yl]oxy}phenyl)-3-fluoropyrrolidine-1-sulfonamide

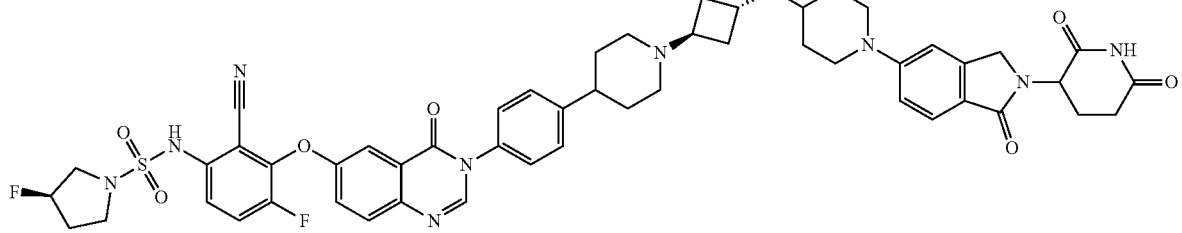

To a solution of 3,6-difluoro-2-{[4-oxo-3-(4-{1-[(1r,3r)-3-({1-[2-(2,6-dioxopiperidin-3-yl)-1-oxo-3H-isoindol-5-yl]piperidin-4-yl}oxy)cyclobutyl]piperidin-4-yl}phenyl)quinazolin-6-yl]oxy}benzonitrile (100 mg, 0.1 mmol) and (3R)-3-fluoropyrrolidine-1-sulfonamide (19.7 mg, 0.1 mmol) in N,N-dimethylformamide (20 mL) was added cesium carbonate (114.5 mg, 0.3 mmol). The resulting mixture was stirred for 12 h at 50° C. under nitrogen atmosphere. The reaction mixture was cooled to room temperature, diluted with water (100 mL) and extracted with dichloromethane (3×20 mL). The combined organic layers were washed with brine (10 mL), dried over anhydrous sodium sulfate, filtered, and concentrated. The residue was purified by preparative thin layer chromatography (dichloromethane/methanol=10:1) to afford (3R)—N-(2-cyano-4-fluoro-3-{[4-oxo-3-(4-{1-[(1r,3r)-3-({1-[2-(2,6-dioxopiperidin-3-yl)-1-oxo-3H-isoindol-5-yl]piperidin-4-yl}oxy)cyclobutyl]piperidin-4-yl}phenyl)quinazolin-6-yl]oxy}phenyl)-3-fluoropyrrolidine-1-sulfonamide (9.6 mg, 7.4%) as an off-white solid. MS (ESI): m/z 1001.4 [M+H]$^+$; $^1$H NMR (400 MHz, DMSO-d$_6$) δ 10.95 (s, 2H), 8.27 (s, 1H), 8.14 (s, 1H), 7.79 (s, 1H), 7.55 (d, 1H), 7.40 (m, 9H), 7.16 (m, 2H), 7.06 (m, 2H), 4.31 (m, 7H), 3.70 (d, 10H), 3.01 (d, 11H), 2.31 (s, 9H), 1.89 (m, 17H), 1.56 (s, 5H), 1.36 (s, 15H), 1.24 (s, 2H).

Example 250: Exemplary synthesis of (3R)—N-(2-cyano-3-{[3-(4-{2-[(1-{2-[(3S)-2,6-dioxopiperidin-3-yl]-1-oxo-2,3-dihydro-1H-isoindol-5-yl}piperidin-4-yl)oxy]-7-azaspiro[3.5]nonan-7-yl}phenyl)-4-oxo-3,4-dihydroquinazolin-6-yl]oxy}-4-fluorophenyl)-3-fluoropyrrolidine-1-sulfonamide Step 1: tert-butyl 2-(pyridin-4-yloxy)-7-azaspiro[3.5]nonane-7-carboxylate

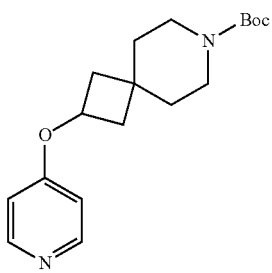 [SMILES: CC(C)(C)OC(=O)N1CCC2(CC1)CC(Oc1ccncc1)C2]

To a mixture of sodium hydride (2.49 g, 104 mmol) in dimethyl sulfoxide (167 mL) was dropwise added tert-butyl 2-hydroxy-7-azaspiro[3.5]nonane-7-carboxylate (10 g, 41 mmol). The mixture was stirred at 30° C. for 1 h, then 4-chloropyridine (4.70 g, 41 mmol) was slowly added, the mixture was stirred at room temperature for 1 h and at 80° C. for 12 h under nitrogen atmosphere. The reaction was diluted with saturated ammonium chloride solution (100 mL) at 0° C. and extracted with dichloromethane (3×200 mL). The combined organic layers were washed with brine (3×150 mL), dried over anhydrous sodium sulfate, filtered, and concentrated. The residue was purified by silica gel column chromatography (dichloromethane/methanol=12:1) to afford tert-butyl 2-(pyridin-4-yloxy)-7-azaspiro[3.5]nonane-7-carboxylate (10.62 g, 80%) as a white solid. MS (ESI): m/z 319.15 [M+H]$^+$.

Step 2: 1-benzyl-4-[[7-(tert-butoxycarbonyl)-7-azaspiro[3.5]nonan-2-yl]oxy]pyridin-1-ium

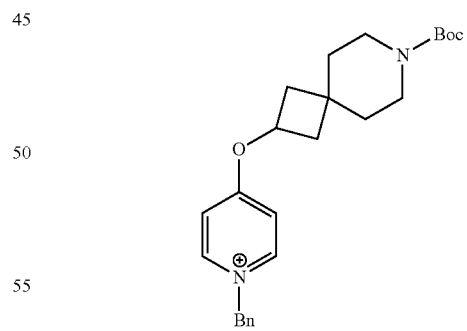

To a solution of tert-butyl 2-(pyridin-4-yloxy)-7-azaspiro[3.5]nonane-7-carboxylate (10 g, 31 mmol) in dichloromethane (200 mL) was added benzyl bromide (26.86 g, 157 mmol). The reaction was stirred for 2 h at room temperature, then concentrated. The residue was purified by silica gel column chromatography (dichloromethane/methanol=10:1) to afford 1-benzyl-4-[[7-(tert-butoxycarbonyl)-7-azaspiro[3.5]nonan-2-yl]oxy]pyridin-1-ium (12 g, 93%) as a yellow oil. MS (ESI): m/z 409.35 [M+H]$^+$.

Step 3: tert-butyl 2-[(1-benzyl-3,6-dihydro-2H-pyridin-4-yl)oxy]-7-azaspiro[3.5]nonane-7-carboxylate

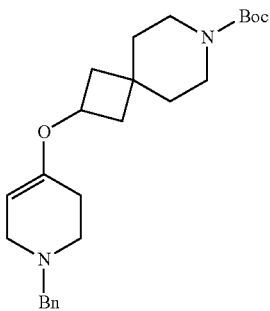 [SMILES: CC(C)(C)OC(=O)N1CCC2(CC1)CC(OC1=CCN(Cc3ccccc3)CC1)C2]

To a solution of 1-benzyl-4-[[7-(tert-butoxycarbonyl)-7-azaspiro[3.5]nonan-2-yl]oxy]pyridin-1-ium (10 g, 24 mmol) in methanol (200 mL) was added sodium borane (2.70 g, 73 mmol). The reaction was stirred for 2 h at room temperature, then diluted with saturated ammonium chloride solution (100 mL) and extracted with ethyl acetate (2×100 mL). The combined organic layers were washed with brine (2×150 mL), dried over anhydrous sodium sulfate, filtered, and concentrated. The residue was purified by silica gel column chromatography (petroleum ether/ethyl acetate=2:1) to afford tert-butyl 2-[(1-benzyl-3,6-dihydro-2H-pyridin-4-yl)oxy]-7-azaspiro[3.5]nonane-7-carboxylate (6.3 g, 63%) as a light yellow oil. MS (ESI): m/z 413.25 [M+H]$^+$.

Step 4: tert-butyl 2-(piperidin-4-yloxy)-7-azaspiro[3.5]nonane-7-carboxylate

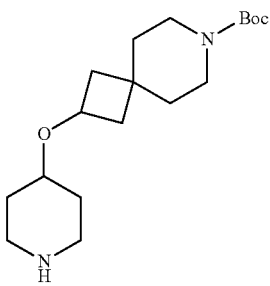 [SMILES: CC(C)(C)OC(=O)N1CCC2(CC1)CC(OC1CCNCC1)C2]

To a solution of tert-butyl 2-[(1-benzyl-3,6-dihydro-2H-pyridin-4-yl)oxy]-7-azaspiro[3.5]nonane-7-carboxylate (6.3 g, 15 mmol) in methanol (100 mL) was added 10% palladium on carbon (5.0 g) under nitrogen atmosphere. The suspension was degassed under vacuum and purged with hydrogen several times. The resulting mixture was stirred under hydrogen atmosphere for 12 h. The reaction mixture was filtered through a Celite pad and concentrated to afford tert-butyl 2-(piperidin-4-yloxy)-7-azaspiro[3.5]nonane-7-carboxylate (5 g, crude) as an off-white oil, which was used in the next step without further purification.

Step 5: tert-butyl 2-({1-[2-(2,6-dioxopiperidin-3-yl)-1-oxo-3H-isoindol-5-yl]piperidin-4-yl}oxy)-7-azaspiro[3.5]nonane-7-carboxylate

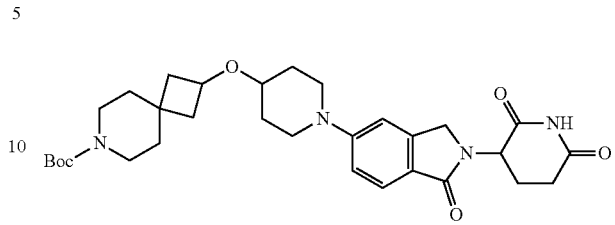

To a solution of tert-butyl 2-(piperidin-4-yloxy)-7-azaspiro[3.5]nonane-7-carboxylate (700 mg, 2 mmol) and 3-(5-bromo-1-oxo-3H-isoindol-2-yl)piperidine-2,6-dione (697 mg, 2 mmol) in N,N-dimethylformamide (20 mL) was added cesium carbonate (2812 mg, 9 mmol) and dichloro[1,3-bis(2,6-di-3-pentylphenyl)imidazol-2-ylidene](2-methylpyridyl)palladium(II) (91 mg, 0.1 mmol). The resulting mixture was stirred at 90° C. for 12 h under nitrogen atmosphere. The mixture was cooled to room temperature, diluted with water (10 mL) and extracted with ethyl acetate (2×100 mL). The combined organic layers were washed with brine (2×20 mL), dried over anhydrous sodium sulfate, filtered, and concentrated. The residue was purified by silica gel column chromatography (dichloromethane/methanol=10:1) to afford tert-butyl 2-({1-[2-(2,6-dioxopiperidin-3-yl)-1-oxo-3H-isoindol-5-yl]piperidin-4-yl}oxy)-7-azaspiro[3.5]nonane-7-carboxylate (612 mg, 67%) as a white solid. $^1$H NMR (400 MHz, DMSO-d$_6$) δ 10.95 (s, 1H), 7.60 (d, J=8.8 Hz, 1H), 7.09-7.01 (m, 2H), 5.52-5.42 (m, 2H), 5.03 (s, 1H), 4.30 (d, J=17.0 Hz, 1H), 4.17 (d, J=17.0 Hz, 1H), 4.07 (p, J=7.1 Hz, 1H), 3.92 (s, 2H), 3.86 (s, 2H), 3.62 (s, 2H), 3.50-3.45 (m, 1H), 3.03-2.83 (m, 4H), 2.73 (s, 1H), 2.62-2.52 (m, 3H), 2.42-2.27 (m, 1H), 2.18-2.08 (m, 2H), 1.99-1.87 (m, 3H), 1.59-1.46 (m, 9H); MS (ESI): m/z 566.55 [M+H]$^+$.

Step 6: 3-[5-(4-{7-azaspiro[3.5]nonan-2-yloxy}piperidin-1-yl)-1-oxo-3H-isoindol-2-yl]piperidine-2,6-dione hydrochloride

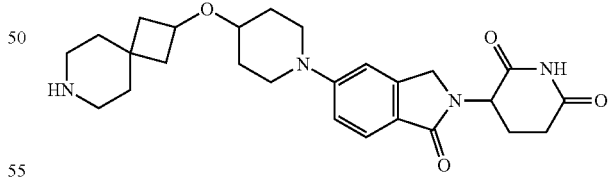

A solution of tert-butyl 2-({1-[2-(2,6-dioxopiperidin-3-yl)-1-oxo-3H-isoindol-5-yl]piperidin-4-yl}oxy)-7-azaspiro[3.5]nonane-7-carboxylate (612 mg, 1 mmol) and 4 M hydrochloride in 1,4-dioxane (20 mL) was stirred for 2 h at room temperature. The reaction was concentrated to afford 3-[5-(4-{7-azaspiro[3.5]nonan-2-yloxy}piperidin-1-yl)-1-oxo-3H-isoindol-2-yl]piperidine-2,6-dione hydrochloride (541 mg, crude) as a white solid, which was used in the next step without further purification. MS (ESI): m/z 467.35 [M+H]$^+$.

Step 7: 3-(5-{4-[(7-{4-[6-(benzyloxy)-4-oxoquinazolin-3-yl]phenyl}-7-azaspiro[3.5]nonan-2-yl)oxy]piperidin-1-yl}-1-oxo-3H-isoindol-2-yl)piperidine-2,6-dione

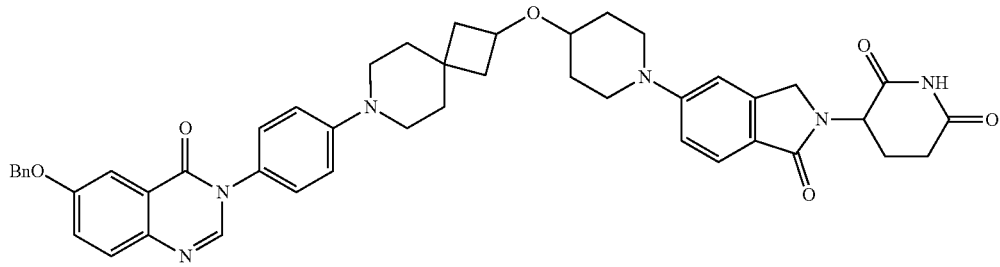 [SMILES: O=C1CCC(N2Cc3cc(N4CCC(OC5CC6(CCN(c7ccc(-n8cnc9ccc(OCc%10ccccc%10)cc9c8=O)cc7)CC6)C5)CC4)ccc3C2=O)C(=O)N1]

To a mixture of 3-[5-(4-{7-azaspiro[3.5]nonan-2-yloxy}piperidin-1-yl)-1-oxo-3H-isoindol-2-yl]piperidine-2,6-dione hydrochloride (300 mg, 0.6 mmol) and 6-(benzyloxy)-3-(4-bromophenyl)quinazolin-4-one (243 mg, 0.6 mmol) in N,N-dimethylformamide (5 mL) was added dichloro[1,3-bis(2,6-di-3-pentylphenyl)imidazol-2-ylidene](2-methylpyridyl)palladium(II) (0.84 mg, 0.001 mmol) and cesium carbonate (971.6 mg, 3 mmol). The resulting mixture was stirred at 90° C. for 5 h, then cooled to room temperature. The mixture was diluted with water (20 mL) and extracted with ethyl acetate (2×100 mL). The combined organic layers were washed with brine (2×20 mL), dried over anhydrous sodium sulfate, filtered, and concentrated. The residue was purified by silica gel column chromatography (dichloromethane/methanol=10:1) to afford 3-(5-{4-[(7-{4-[6-(benzyloxy)-4-oxoquinazolin-3-yl]phenyl}-7-azaspiro[3.5]nonan-2-yl)oxy]piperidin-1-yl}-1-oxo-3H-isoindol-2-yl)piperidine-2,6-dione (325 mg, 69%) as a brown solid. $^1$H NMR (300 MHz, DMSO-$d_6$) δ 10.93 (s, 1H), 8.16 (d, J=1.6 Hz, 1H), 7.73-7.62 (m, 3H), 7.59-7.25 (m, 6H), 7.10-7.00 (m, 5H), 6.66 (t, J=9.5 Hz, 1H), 5.75 (d, J=1.5 Hz, 1H), 5.26 (s, 1H), 4.45-4.26 (m, 3H), 3.68 (d, J=12.9 Hz, 2H), 3.28 (d, J=4.7 Hz, 2H), 3.15 (s, 2H), 2.92-2.83 (m, 2H), 2.60 (s, 2H), 2.21 (d, J=9.3 Hz, 1H), 1.49 (d, J=9.7 Hz, 1H), 1.23 (s, 9H), 1.10 (d, J=5.9 Hz, 2H); MS (ESI): m/z 793.40 [M+H]$^+$.

Step 8: 3-{5-[4-({7-[4-(6-hydroxy-4-oxoquinazolin-3-yl)phenyl]-7-azaspiro[3.5]nonan-2-yl}oxy)piperidin-1-yl]-1-oxo-3H-isoindol-2-yl}piperidine-2,6-dione

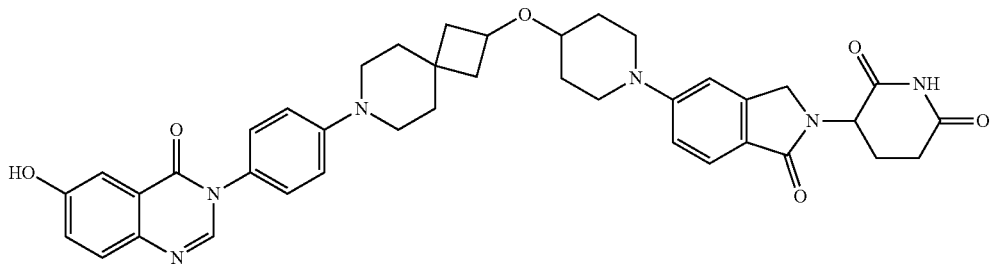 [SMILES: O=C1CCC(N2Cc3cc(N4CCC(OC5CC6(CCN(c7ccc(-n8cnc9ccc(O)cc9c8=O)cc7)CC6)C5)CC4)ccc3C2=O)C(=O)N1]

To a solution of 3-(5-{4-[(7-{4-[6-(benzyloxy)-4-oxoquinazolin-3-yl]phenyl}-7-azaspiro[3.5]nonan-2-yl)oxy]piperidin-1-yl}-1-oxo-3H-isoindol-2-yl)piperidine-2,6-dione (379 mg, 0.5 mmol) in tetrahydrofuran (20 mL) and N,N-dimethylformamide (20 mL) was added 10% palladium on carbon (200 mg) under nitrogen atmosphere. The suspension was degassed under vacuum and purged with hydrogen several times. The resulting mixture was stirred under hydrogen atmosphere for 2 h, then filtered through a Celite pad and concentrated to afford 3-{5-[4-({7-[4-(6-hydroxy-4-oxoquinazolin-3-yl)phenyl]-7-azaspiro[3.5]nonan-2-yl}oxy)piperidin-1-yl]-1-oxo-3H-isoindol-2-yl}piperidine-2,6-dione (310 mg, 92%) as an off-white solid. $^1$H NMR (400 MHz, DMSO-$d_6$) δ 10.95 (s, 1H), 10.15 (s, 1H), 8.09 (s, 1H), 7.95 (s, 1H), 7.53-7.44 (m, 2H), 7.36-7.26 (m, 3H), 7.05-6.89 (m, 4H), 5.04-5.01 (d, J=12 Hz, 1H), 4.32 (d, J=16.8 Hz, 3H), 4.24-4.13 (m, 2H), 3.69 (d, J=12.7 Hz, 1H), 3.21 (s, 1H), 3.15 (t, J=5.6 Hz, 2H), 3.04 (t, J=10.3 Hz, 2H), 2.94 (s, 3H), 2.89 (s, 2H), 2.78 (s, 2H), 2.41-2.33 (m, 1H), 2.22 (t, J=9.0 Hz, 2H), 1.96 (s, 3H), 1.89 (d, J=12.2 Hz, 2H), 1.72-1.61 (m, 5H), 1.48 (t, J=11.1 Hz, 1H); MS (ESI): m/z 703.45 [M+H]$^+$.

Step 9: 2-[(3-{4-[2-({1-[2-(2,6-dioxopiperidin-3-yl)-1-oxo-3H-isoindol-5-yl]piperidin-4-yl}oxy)-7-azaspiro[3.5]nonan-7-yl]phenyl}-4-oxoquinazolin-6-yl)oxy]-3,6-difluorobenzonitrile

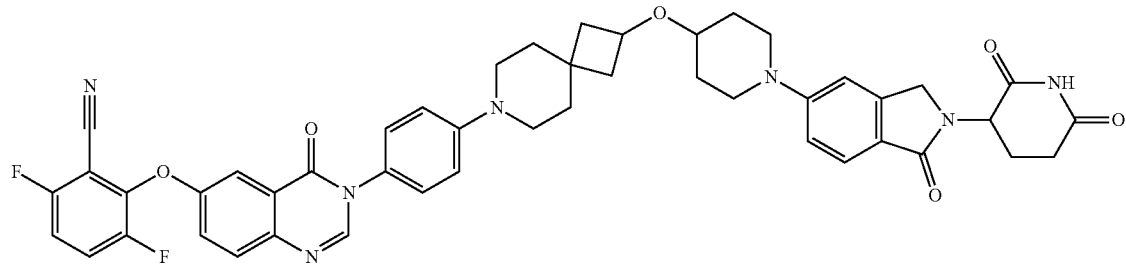 [SMILES: N#Cc1c(F)ccc(F)c1Oc1ccc2ncn(-c3ccc(N4CCC5(CC4)CC(OC4CCN(c6ccc7c(c6)CN(C6CCC(=O)NC6=O)C7=O)CC4)C5)cc3)c(=O)c2c1]

To a mixture of 3-{5-[4-({7-[4-(6-hydroxy-4-oxoquinazolin-3-yl)phenyl]-7-azaspiro[3.5]nonan-2-yl}oxy)piperidin-1-yl]-1-oxo-3H-isoindol-2-yl}piperidine-2,6-dione (300 mg, 0.4 mmol) in N,N-dimethylacetamide (15 mL) was added 2,3,6-trifluorobenzonitrile (101 mg, 0.6 mmol) in portions. The resulting mixture was stirred at 40° C. for 3 h, then filtered and washed with N,N-dimethylacetamide (20 mL). The filtrate solution was concentrated to afford 2-[(3-{4-[2-({1-[2-(2,6-dioxopiperidin-3-yl)-1-oxo-3H-isoindol-5-yl]piperidin-4-yl}oxy)-7-azaspiro[3.5]nonan-7-yl]phenyl}-4-oxoquinazolin-6-yl)oxy]-3,6-difluorobenzonitrile (218 mg, 61%) as an off-white solid. MS (ESI): m/z 840.65 [M+H]$^+$.

Step 10: (R)—N-(2-cyano-3-((3-(4-(2-((1-(2-((S)-2,6-dioxopiperidin-3-yl)-1-oxoisoindolin-5-yl)piperidin-4-yl)oxy)-7-azaspiro[3.5]nonan-7-yl)phenyl)-4-oxo-3,4-dihydroquinazolin-6-yl)oxy)-4-fluorophenyl)-3-fluoropyrrolidine-1-sulfonamide

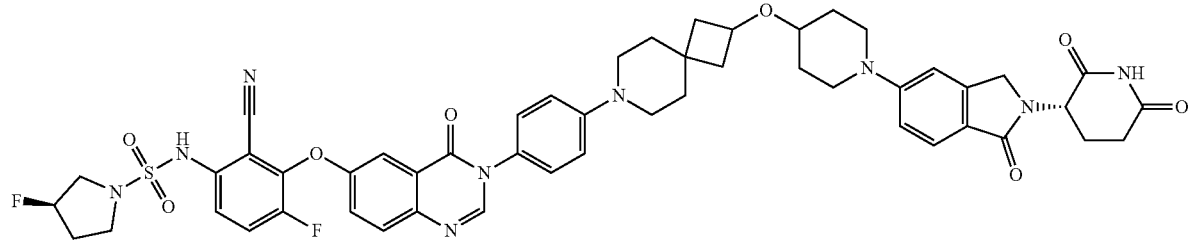 [SMILES: N#Cc1c(NS(=O)(=O)N2CC[C@@H](F)C2)ccc(F)c1Oc1ccc2ncn(-c3ccc(N4CCC5(CC4)CC(OC4CCN(c6ccc7c(c6)CN([C@H]6CCC(=O)NC6=O)C7=O)CC4)C5)cc3)c(=O)c2c1]

To a solution of (3R)-3-fluoropyrrolidine-1-sulfonamide (45 mg, 0.3 mmol) in N,N-dimethylacetamide (20 mL) was added cesium carbonate (146 mg, 0.4 mmol), and the mixture was stirred for 0.5 h at 50° C. under nitrogen atmosphere. Then 2-[(3-{4-[2-({1-[2-(2,6-dioxopiperidin-3-yl)-1-oxo-3H-isoindol-5-yl]piperidin-4-yl}oxy)-7-azaspiro[3.5]nonan-7-yl]phenyl}-4-oxoquinazolin-6-yl)oxy]-3,6-difluorobenzonitrile (150 mg, 0.2 mmol) was added over 1 min, and the resulting mixture was stirred for 3 h at 90° C. The reaction mixture was cooled to room temperature, diluted with water (10 mL) and extracted with ethyl acetate (2×100 mL). The combined organic layers were washed with brine (2×20 mL), dried over anhydrous sodium sulfate, filtered, and concentrated. The residue was purified by preparative thin layer chromatography (methanol/dichloromethane=1:12), then further purified by chiral SFC (methyl tert-butyl ether (0.1% formic acid):(methanol/dichloromethane=1:1)=20:80) to afford (R)—N-(2-cyano-3-((3-(4-(2-((1-(2-((S)-2,6-dioxopiperidin-3-yl)-1-oxoisoindolin-5-yl)piperidin-4-yl)oxy)-7-azaspiro[3.5]nonan-7-yl)phenyl)-4-oxo-3,4-dihydroquinazolin-6-yl)oxy)-4-fluorophenyl)-3-fluoropyrrolidine-1-sulfonamide (45.6 mg, 25%) as a white solid.

$^1$H NMR (400 MHz, DMSO-d$_6$) δ 10.95 (s, 1H), 10.35 (s, 1H), 8.25 (s, 1H), 7.87-7.78 (m, 2H), 7.71 (s, 1H), 7.51-7.49 (m, J=8.9, 3.9 Hz, 2H), 7.42 (d, J=3.0 Hz, 1H), 7.29 (d, J=8.7 Hz, 2H), 7.09-7.00 (m, 4H), 5.41-5.35 (d, J=24 Hz, 1H), 5.25 (s, 1H), 5.05 (s, 1H), 4.32 (d, J=16.8 Hz, 2H), 4.24-4.10 (m, 2H), 3.68 (d, J=12.8 Hz, 2H), 3.57-3.49 (m, 2H), 3.52-3.39 (m, 2H), 3.25-3.18 (m, 2H), 3.09-2.99 (m, 2H), 2.90-2.80 (d, J=40 Hz, 1H), 2.58 (d, J=17.5 Hz, 1H), 2.44-2.30 (m, 3H), 2.26-2.15 (m, 2H), 2.18-2.01 (m, 3H), 2.01-1.92 (m, 6H), 1.92-1.85 (m, 2H); MS (ESI): m/z 986.40 [M+H]$^+$.

The following compounds in Table 1 were prepared according to the procedures described above using the appropriate starting materials and intermediates. For example, Compounds 6-29, 181-240, and 254-268 can be prepared according to the procedures outlined in General Scheme 1 or 1' and Examples 1 and 2. Examples 83-138 can similarly be prepared according to the procedures outlined in General Scheme 1 or 1' and Examples 1 and 73-81. Examples 139-178 can be prepared according to the procedures outlined in General Scheme 1 or 1' and Example 2. Compounds 30-64 can be prepared according to the procedures outlined in General Scheme 2 or 2' and Example 3. Compounds 65-70 and 241-243 can be prepared according to the procedures outlined in General Scheme 3 or 3' and Example 4. Compounds 71, 72, and 269 can be prepared according to the procedures outlined in General Scheme 4 or 4' and Example 5. Compounds 244-246 can be prepared according to the procedures outlined in Example 176. Compound 251 can be can be prepared according to the procedures outlined in Example 247. Compounds 252 and 253 can be prepared according to the procedures outlined in Example 248.

TABLE 1

| Cmp. No. | Structure | IUPAC Name | 1H NMR |
|---|---|---|---|
| 6 | 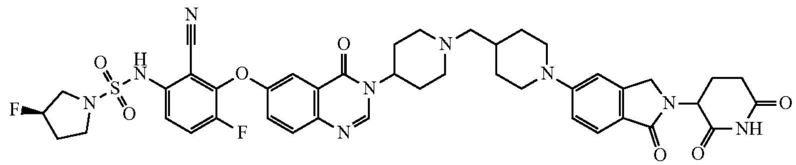 [SMILES: N#Cc1c(NS(=O)(=O)N2CC[C@@H](F)C2)ccc(F)c1Oc1ccc2ncn(C3CCN(CC4CCN(c5ccc6c(c5)CN(C5CCC(=O)NC5=O)C6=O)CC4)CC3)c(=O)c2c1] | (3R)-N-[2-cyano-3-({3-[1-({1-[2-(2,6-dioxopiperidin-3-yl)-1-oxo-2,3-dihydro-1H-isoindol-5-yl]methyl}piperidin-4-yl)methyl]piperidin-4-yl]-4-oxo-3,4-dihydroquinazolin-6-yl}oxy)-4-fluorophenyl]-3-fluoropyrrolidine-1-sulfonamide | 1H NMR (400 MHz, DMSO-d6) δ 10.94 (s, 1H), 8.31-8.41 (m, 1H), 8.13 (s, 1H), 7.76 (d, J = 8.8 Hz, 1H), 7.55-7.69 (m, 2H), 7.51 (d, J = 8.8 Hz, 1H), 7.36-7.43 (m, 2H), 7.04-7.09 (m, 2H), 5.18-5.41 (m, 1H), 5.01-5.07 (m, 1H), 4.59-4.72 (m, 1H), 4.29-4.37 (m, 1H), 4.17-4.23 (m, 1H), 3.87-3.95 (m, 2H), 3.39-3.47 (m, 2H), 3.19-3.27 (m, 3H), 2.81-2.95 (m, 4H), 2.60 (d, J = 1.8 Hz, 1H), 2.56 (s, 2H), 2.35-2.40 (m, 1H), 2.17-2.27 (m, 2H), 2.08-2.15 (m, 1H), 1.79-2.06 (m, 9H), 1.19-1.30 ppm (m, 2H) |
| 7 | 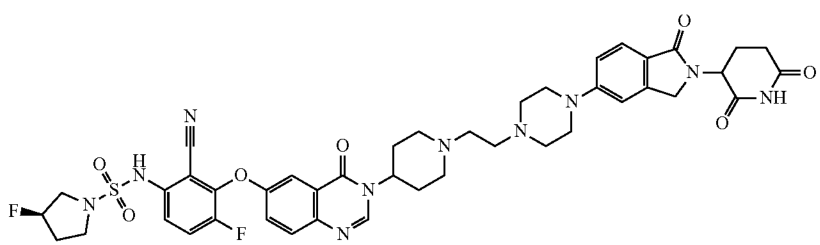 [SMILES: N#Cc1c(NS(=O)(=O)N2CC[C@@H](F)C2)ccc(F)c1Oc1ccc2ncn(C3CCN(CCN4CCN(c5ccc6c(c5)CN(C5CCC(=O)NC5=O)C6=O)CC4)CC3)c(=O)c2c1] | (3R)-N-[2-cyano-3-({3-[1-(2-{4-[2-(2,6-dioxopiperidin-3-yl)-1-oxo-2,3-dihydro-1H-isoindol-5-yl]piperazin-1-yl}ethyl)piperidin-4-yl]-4-oxo-3,4-dihydroquinazolin-6-yl}oxy)-4-fluorophenyl]-3-fluoropyrrolidine-1-sulfonamide | 1H NMR (400 MHz, DMSO-d6) δ 10.95 (s, 1H), 8.37 (s, 1H), 8.14 (s, 1H), 7.76 (d, J = 8.8 Hz, 1H), 7.64 (dd, J = 8.8, 2.8 Hz, 1H), 7.54 (d, J = 8.4 Hz, 1H), 7.48 (t, J = 9.6 Hz, 1H), 7.32-7.39 (m, 2H), 7.07-7.14 (m, 2H), 5.19-5.37 (m, 1H), 5.05 (dd, J = 13.2, 5.2 Hz, 1H), 4.65-4.72 (m, 1H), 4.31-4.37 (m, 1H), 4.19-4.25 (m, 1H), 3.41 (s, 4H), 3.25-3.32 (m, 4H), 3.21 (dd, J = 9.2, 7.2 Hz, 2H), 2.95-3.01 (m, 2H), 2.86-2.93 (m, 1H), 2.74 (s, 7H), 2.57-2.61 (m, 1H), 2.35-2.43 (m, 1H), 2.21-2.30 (m, 2H), 2.07-2.19 (m, 1H), 2.04 ppm (d, J = 4.4 Hz, 5H) |

| Cmp. No. | Structure | IUPAC Name | ¹H NMR |
|---|---|---|---|
| 8 | 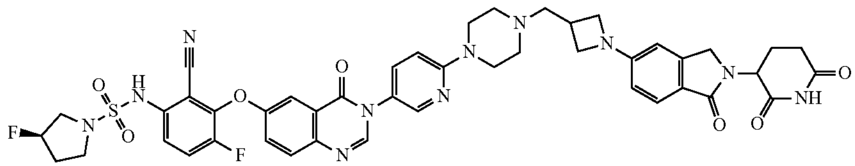 | (3R)-N-{2-cyano-3-[(3-{6-[4-({1-[2-(2,6-dioxopiperidin-3-yl)-1-oxo-2,3-dihydro-1H-isoindol-5-yl]azetidin-3-yl}methyl)piperazin-1-yl]pyridin-3-yl}-4-oxo-3,4-dihydroquinazolin-6-yl)oxy]-4-fluorophenyl}-3-fluoropyrrolidine-1-sulfonamide | ¹H NMR (400 MHz, DMSO-$d_6$) δ 10.94 (s, 1H), 8.28 (s, 1H), 8.23 (s, 1H), 7.83 (d, J = 9.0 Hz, 1H), 7.76-7.58 (m, 3H), 7.55-7.45 (m, 2H), 7.44-7.39 (m, 2H), 7.01 (d, J = 9.2 Hz, 1H), 6.55-6.42 (m, 3H), 5.13-4.98 (m, 1H), 4.35-4.26 (m, 1H), 4.22-4.13 (m, 1H), 4.09-4.01 (m, 2H), 3.98-3.89 (m, 1H), 3.68-3.59 (m, 5H), 3.45-3.39 (m, 2H), 3.31-3.19 (m, 2H), 3.15-3.05 (m, 1H), 2.95-2.83 (m, 3H), 2.60 (s, 1H), 2.58-2.53 (m, 1H), 2.19-2.01 (m, 2H), 1.99-1.89 (m, 2H), 1.31-1.25 (m, 4H) |
| 9 | 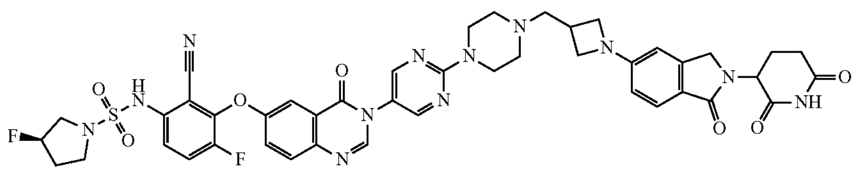 [SMILES: N#Cc1c(NS(=O)(=O)N2CC[C@@H](F)C2)ccc(F)c1Oc1ccc2ncn(-c3cnc(N4CCN(CC5CN(c6ccc7c(c6)CN(C6CCC(=O)NC6=O)C7=O)C5)CC4)nc3)c(=O)c2c1] | (3R)-N-{2-cyano-3-[(3-{2-[4-({1-[2-(2,6-dioxopiperidin-3-yl)-1-oxo-2,3-dihydro-1H-isoindol-5-yl]azetidin-3-yl}methyl)piperazin-1-yl]pyrimidin-5-yl}-4-oxo-3,4-dihydroquinazolin-6-yl)oxy]-4-fluorophenyl}-3-fluoropyrrolidine-1-sulfonamide | ¹H NMR (400 MHz, DMSO-$d_6$) δ 10.96 (s, 1H), 10.23 (s, 1H), 8.55 (s, 2H), 8.33 (s, 1H), 7.85 (d, J = 8.9 Hz, 1H), 7.73 (d, 2H), 7.53-7.41 (d, J = 3.0 Hz, 3H), 6.56-6.46 (m, 2H), 5.38 (d, J = 3.4 Hz, 1H), 5.24 (s, 1H), 5.05-4.31 (d, J = 16.9 Hz, 1H), 4.18 (d, J = 16.9 Hz, 1H), 4.07 (t, J = 7.8 Hz, 2H), 3.88 (s, 4H), 3.63-3.54 (m, 3H), 3.29 (t, J = 8.8 Hz, 1H), 3.13-3.04 (m, 1H), 2.98-2.84 (m, 3H), 2.70 (s, 3H), 2.59 (d, J = 17.3 Hz, 1H), 2.50-2.36 (d, 1H), 2.11 (d, J = 20.0 Hz, 3H), 1.96 (d, J = 12.7 Hz, 1H), 1.24 (s, 2H) |

| Cmp. No. | Structure | IUPAC Name | 1H NMR |
|---|---|---|---|
| 10 | 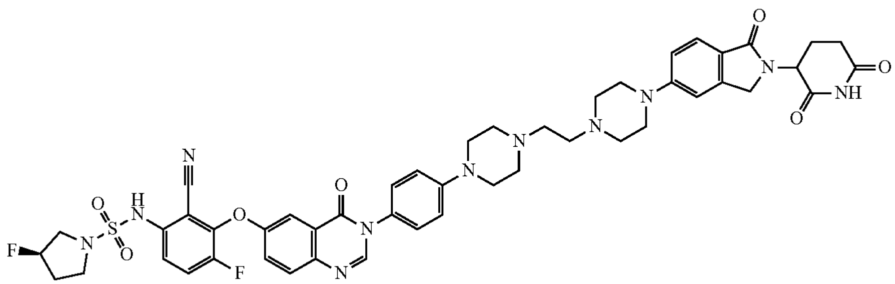 [SMILES: N#Cc1c(NS(=O)(=O)N2CC[C@@H](F)C2)ccc(F)c1Oc1ccc2ncn(-c3ccc(N4CCN(CCN5CCN(c6ccc7c(c6)CN(C6CCC(=O)NC6=O)C7=O)CC5)CC4)cc3)c(=O)c2c1] | (3R)-N-{2-cyano-3-[(4-{4-(2-{4-[2-(2,6-dioxopiperidin-3-yl)-1-oxo-2,3-dihydro-1H-isoindol-5-yl]piperazin-1-yl}ethyl)piperazin-1-yl]phenyl}-4-oxo-3,4-dihydroquinazolin-6-yl)oxy]-4-fluorophenyl}-3-fluoropyrrolidine-1-sulfonamide | 1H NMR (400 MHz, DMSO-d6) δ 10.95 (s, 1H), 8.23 (s, 1H), 8.13 (s, 1H), 7.80 (d, J = 8.8 Hz, 1H), 7.67 (dd, J = 2.8, 8.8 Hz, 1H), 7.54 (d, J = 8.4 Hz, 1H), 7.40-7.32 (m, 4H), 7.12-7.05 (m, 4H), 5.40-5.17 (m, 1H), 5.05 (dd, J = 4.8, 13.2 Hz, 1H), 4.37-4.31 (m, 1H), 4.24-4.18 (m, 1H), 3.48 (d, J = 2.8 Hz, 8H), 3.23-3.17 (m, 3H), 2.91-2.76 (m, 11H), 2.60 (d, J = 2.4 Hz, 1H), 2.58-2.53 (m, 2H), 2.45-2.41 (m, 2H), 2.39, 2.35 (m, 1H), 2.16-2.06 (m, 1H), 2.05-1.95 (m, 2H) |
| 11 | 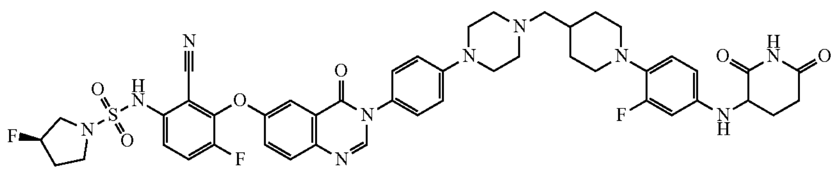 [SMILES: N#Cc1c(NS(=O)(=O)N2CC[C@@H](F)C2)ccc(F)c1Oc1ccc2ncn(-c3ccc(N4CCN(CC5CCN(c6ccc(NC7CCC(=O)NC7=O)cc6F)CC5)CC4)cc3)c(=O)c2c1] | (3R)-N-(2-cyano-3-{[3-(4-{4-[(1-{4-[(2,6-dioxopiperidin-3-yl)amino]-2-fluorophenyl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO-d6) δ 10.78 (s, 1H), 8.24 (s, 1H), 7.81 (d, J = 8.9 Hz, 1H), 7.68 (dd, J = 9.0, 3.0 Hz, 1H), 7.60 (s, 1H), 7.40-7.35 (d, J = 8.6 Hz, 4H), 7.08 (d, J = 8.6 Hz, 2H), 6.84 (t, J = 9.3 Hz, 1H), 6.50 (dd, J = 15.0, 2.5 Hz, 1H), 6.42 (dd, J = 8.8, 2.5 Hz, 1H), 5.80 (d, J = 7.7 Hz, 1H), 5.35 (s, 1H), 4.31-4.18 (m, 1H), 3.13 (d, J = 11.0 Hz, 6H), 2.73 (ddd, J = 17.6, 12.2, 5.5 Hz, 3H), 2.58 (dd, J = 13.7, 8.2 Hz, 4H), 2.08-2.02 (s, 4H), 1.82 (t, J = 13.6 Hz, 5H), 1.71 (s, 1H), 1.29 (s, 3H), 1.23 (s, 1H), 0.95-0.76 (m, 1H) |
| 12 | 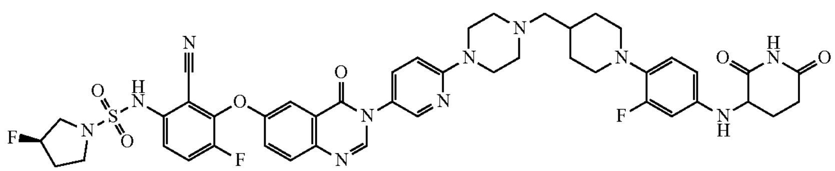 [SMILES: N#Cc1c(NS(=O)(=O)N2CC[C@@H](F)C2)ccc(F)c1Oc1ccc2ncn(-c3ccc(N4CCN(CC5CCN(c6ccc(NC7CCC(=O)NC7=O)cc6F)CC5)CC4)nc3)c(=O)c2c1] | (3R)-N-(2-cyano-3-{[3-(6-{4-[(1-{4-[(2,6-dioxopiperidin-3-yl)amino]-2-fluorophenyl}piperidin-4-yl)methyl]piperazin-1-yl}pyridin-3-yl)-4-oxo-3,4-dihydroquinazolin-6-yl]oxy}-4-fluorophenyl)-3-fluoropyrrolidine-1-sulfonamide | 1H NMR (400 MHz, DMSO-d6) δ 10.79 (s, 1H), 8.28 (s, 1H), 8.22 (d, J = 2.6 Hz, 1H), 7.82 (d, J = 8.9 Hz, 1H), 7.75-7.65 (m, 3H), 7.56-7.40 (d, J = 3.0 Hz, 2H), 7.00 (d, J = 9.2 Hz, 1H), 6.85 (t, J = 9.3 Hz, 1H), 6.51 (dd, J = 14.9, 2.5 Hz, 1H), 6.43 (d, J = 8.6 Hz, 1H), 5.80 (d, J = 7.6 Hz, 1H), 5.36 (s, 1H), 4.26 (dt, J = 12.5, 6.3 Hz, 1H), 3.61 (s, 4H), 3.42 (s, 1H), 3.13 (d, J = 10.9 Hz, 2H), |

TABLE 1-continued

| Cmp. No. | Structure | IUPAC Name | ¹H NMR |
|---|---|---|---|
| 13 | 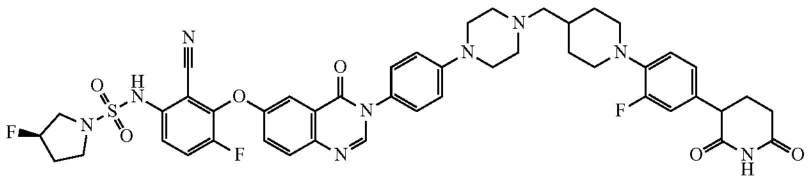 [SMILES: N#Cc1c(NS(=O)(=O)N2CC[C@@H](F)C2)ccc(F)c1Oc1ccc2ncn(-c3ccc(N4CCN(CC5CCN(c6ccc(C7CCC(=O)NC7=O)cc6F)CC5)CC4)cc3)c(=O)c2c1] | (3R)-N-{2-cyano-3-[(3-{4-[4-({1-[4-(2,6-dioxopiperidin-3-yl)-2-fluorophenyl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | 2.90-2.74 (dt, J = 23.0, 5.3 Hz, 2H), 2.74 (s, 1H), 2.62-2.53 (m, 4H), 2.08 (s, 2H), 2.02 (s, 1H), 1.94-1.78 (m, 3H), 1.70 (s, 2H), 1.50 (s, 1H), 1.31 (s, 4H), 1.24 (s, 9 H), 0.99-0.77 (m, 3H) ¹H NMR (400 MHz, DMSO-d₆) δ 10.83 (s, 1H), 10.04 (s, 1H), 8.26 (s, 1H), 7.82 (d, J = 8.9 Hz, 1H), 7.76-7.64 (m, 2H), 7.55-7.49(m, 2H), 7.46-7.39 (m, 2H), 7.36 (d, J = 8.6 Hz, 2H), 7.13-6.92 (m, 3H), 5.37 (s, 1H), 3.81 (dd, J = 11.9, 4.9 Hz, 1H), 3.27 (s, 3H), 3.15 (s, 2H), 2.76-2.59 (m, 7H), 2.33-2.06 (m, 1H), 2.06-1.96 (m, 3H), 1.85 (d, J = 12.6 Hz, 2H), 1.50 (s, 3H), 1.43-1.30 (m, 3H), 1.24 (s, 3H), 0.96-0.78 (m, 1H) |
| 14 | 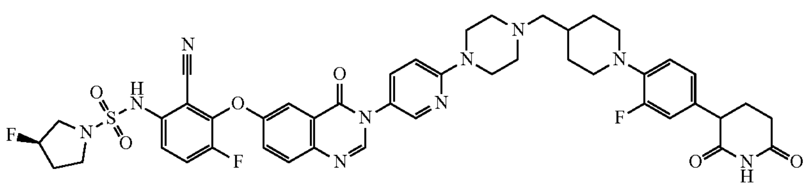 [SMILES: N#Cc1c(NS(=O)(=O)N2CC[C@@H](F)C2)ccc(F)c1Oc1ccc2ncn(-c3ccc(N4CCN(CC5CCN(c6ccc(C7CCC(=O)NC7=O)cc6F)CC5)CC4)nc3)c(=O)c2c1] | (3R)-N-{2-cyano-3-[(3-{6-[4-({1-[4-(2,6-dioxopiperidin-3-yl)-2-fluorophenyl]piperidin-4-yl}methyl)piperazin-1-yl]pyridin-3-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.83 (s, 1H), 10.05 (b, 1H), 8.28 (s, 1H), 8.11 (s, 1H), 7.83 (d, 1H), 7.71 (s, 3H), 7.45-7.38 (m, 1H), 7.06-6.86 (m, 5H), 5.46-5.32 (d, J = 56.0 Hz, 1H), 3.80 (s, 1H), 3.64-3.61 (m, 4H), 3.55-3.53 (m, 1H), 3.46-3.31 (m, 3H), 2.72-2.59 (m, 7H), 2.41-2.36 (m, 1H), 2.21-2.09 (m, 2H), 2.11-2.10 (m, 1H), 2.01-2.00 (m, 1H), 1.85-1.80 (m, 2H), 1.78-1.76 (m, 4H), 1.40-1.29 (m, 3H), 1.24 (s, 3H) |

| Cmp. No. | Structure | IUPAC Name | ¹H NMR |
|---|---|---|---|
| 15 | 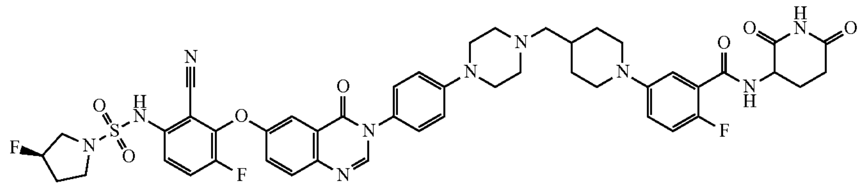 [SMILES: N#Cc1c(NS(=O)(=O)N2CC[C@@H](F)C2)ccc(F)c1Oc1ccc2ncn(-c3ccc(N4CCN(CC5CCN(c6ccc(F)c(C(=O)NC7CCC(=O)NC7=O)c6)CC5)CC4)cc3)c(=O)c2c1] | 5-(4-{[4-(4-{6-[2-cyano-6-fluoro-3-{[(3R)-3-fluoropyrrolidin-1-yl]sulfonyl}aminophenoxy]-4-oxo-3,4-dihydroquinazolin-3-yl}phenyl)piperazin-1-yl]methyl}piperidin-1-yl)-N-(2,6-dioxopiperidin-3-yl)-2-fluorobenzamide | ¹H NMR (400 MHz, DMSO-d₆) δ 10.86 (s, 1H), 9.74-10.32 (m, 1H), 8.41-8.52 (m, 1H), 8.25 (s, 1H), 8.13 (s, 1H), 7.82 (d, J = 8.8 Hz, 1H), 7.61-7.75 (m, 2H), 7.39-7.49 (m, 2H), 7.35 (d, J = 8.8 Hz, 2H), 7.06-7.19 (m, 5H), 5.18-5.39 (m, 1H), 4.70-4.80 (m, 1H), 3.65 (d, J = 11.2 Hz, 2H), 3.40-3.50 (m, 2H), 3.36 (s, 4H), 3.27 (d, J = 9.2 Hz, 4H), 2.68-2.89 (m, 6H), 2.55 (d, J = 3.6 Hz, 2H), 2.08-2.16 (m, 2H), 1.97-2.07 (m, 2H), 1.84 (d, J = 11.2 Hz, 3H), 1.19-1.37 ppm (m, 2H) |
| 16 | 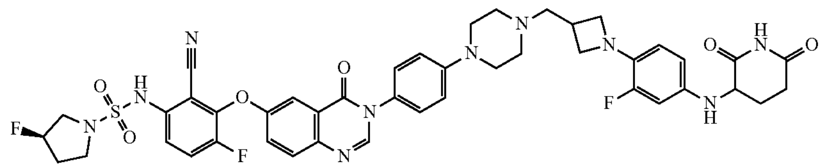 [SMILES: N#Cc1c(NS(=O)(=O)N2CC[C@@H](F)C2)ccc(F)c1Oc1ccc2ncn(-c3ccc(N4CCN(CC5CN(c6ccc(NC7CCC(=O)NC7=O)cc6F)C5)CC4)cc3)c(=O)c2c1] | (3R)-N-(2-cyano-3-{[3-(4-{[4-((1-{4-(2,6-dioxopiperidin-3-yl)amino]-2-fluorophenyl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.78 (s, 1H), 8.25 (s, 1H), 7.82 (d, J = 9.0 Hz, 1H), 7.69-7.67 (m, 4H), 7.08 (d, J = 8.8 Hz, 2H), 6.51-6.41 (m, 3H), 5.57 (s, 1H), 5.36-5.22 (d, J = 56.0 Hz, 1H), 4.21-4.00 (m, 1H), 3.99 (s, 2H), 3.70-3.68 (m, 3H), 3.53-3.45 (m, 2H), 2.96 (s, 2H), 2.79-2.59 (m, 4H), 2.55-2.53 (m, 7H), 2.23-2.05 (m, 3H), 1.82-1.80 (m, 1H), 1.25-1.24 (m, 5H) |
| 17 | 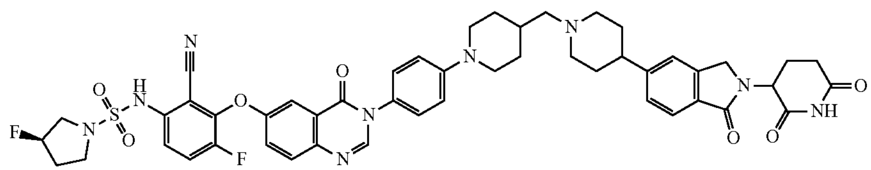 [SMILES: N#Cc1c(NS(=O)(=O)N2CC[C@@H](F)C2)ccc(F)c1Oc1ccc2ncn(-c3ccc(N4CCC(CN5CCC(c6ccc7c(c6)CN(C6CCC(=O)NC6=O)C7=O)CC5)CC4)cc3)c(=O)c2c1] | (3R)-N-{2-cyano-3-[(3-(4-{[4-[2-(2,6-dioxopiperidin-3-yl)-1-oxo-2,3-dihydro-1H-isoindol-5-yl]piperidin-1-yl]methyl}piperidin-1-yl]phenyl}-4-oxo-3,4-dihydroquinazolin-6-yl]oxy]-4-fluorophenyl}-3-fluoropyrrolidine-1-sulfonamide | ¹H NMR (400 MHz, DMSO-d₆) δ 11.01 (s, 1H), 9.43 (s, 1H), 8.24 (s, 1H), 7.81 (d, J = 8.9 Hz, 1H), 7.74-7.63 (m, 2H), 7.50 (s, 2H), 7.46-7.28 (m, 5H), 7.11-7.04 (m, 2H), 5.32-5.18 (d, J = 56.0 Hz, 1H), 5.02 (m, 1H), 4.45 (d, J = 17.3 Hz, 1H), 4.32 (d, J=12.1 Hz, 2H), 3.85 (d, J = 17.3 Hz, 1H), 3.68-3.41 (m, 3H), 3.31-3.11 (m, 3H), 3.05- |

TABLE 1-continued

| Cmp. No. | Structure | IUPAC Name | ¹H NMR |
|---|---|---|---|
| 18 | 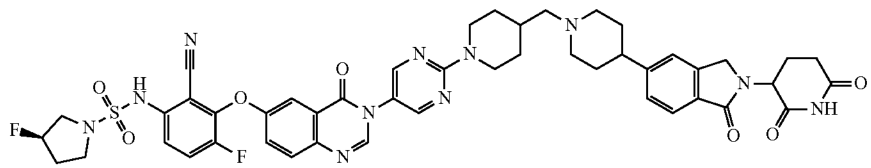 [SMILES: N#Cc1c(NS(=O)(=O)N2CC[C@@H](F)C2)ccc(F)c1Oc1ccc2ncn(-c3cnc(N4CCC(CN5CCC(c6ccc7c(c6)CN(C6CCC(=O)NC6=O)C7=O)CC5)CC4)nc3)c(=O)c2c1] | (3R)-N-{2-cyano-3-[(3-{2-[4-({4-[2-(2,6-dioxopiperidin-3-yl)-1-oxo-2,3-dihydro-1H-isoindol-5-yl]piperidin-1-yl}methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 11.01 (s, 1H), 8.52 (s, 2H), 8.30 (s, 1H), 7.82 (d, J = 8.9 Hz, 1H), 7.69 (m, 2H), 7.50 (s, 2H), 7.43 (s, 1H), 7.38 (d, J = 3.0 Hz, 1H), 7.34 (s, 1H), 5.35-5.21 (d, J = 56.0 Hz, 1H), 5.12 (m, 1H), 4.74 (d, J = 12.8 Hz, 2H), 4.46 (d, J = 17.5 Hz, 1H), 4.32 (d, J = 17.2 Hz, 1H), 3.50 (m, 3H), 3.27-3.07 (m, 4H), 3.07-2.80 (m, 6H), 2.65-2.52 (m, 2H), 2.41 (d, J = 13.2 Hz, 1H), 2.00 (d, J = 14.5 Hz, 2H), 1.87 (m, 6H), 1.25 (d, J = 9.2 Hz, 4H) |
| | | | 2.72 (m, 7H), 2.65-2.56 (m, 1H), 2.48-2.28 (m, 1H), 2.25-1.82 (m, 10H), 1.45-1.19 (m, 6H) |
| 19 | 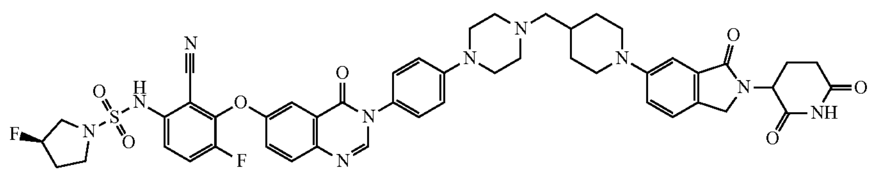 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)C(=O)N(C6CCC(=O)NC6=O)C7)CC5)CC4)cc3)c(=O)c2c1] | (3R)-N-{2-cyano-3-[(3-(4-[4-({1-[2-(2,6-dioxopiperidin-3-yl)-3-oxo-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.98 (s, 1H), 9.96 (b, 1H), 8.26 (s, 1H), 7.89-7.82 (m, 1H), 7.70-7.66 (m, 2H), 7.46-7.33 (m, 5H), 7.30-7.28 (m, 1H), 7.21-7.18 (m, 1H), 7.14-7.10 (m, 1H), 5.37-5.23 (m, 1H), 5.14-5.10 (m, 1H), 4.39-4.34 (m, 1H), 4.28-4.21 (m, 1H), 3.85-3.79 (m, 2H), 3.45 (s, 2H), 3.25 (s, 2H),2.99-2.85 (m, 2H), 2.81-2.76 (m, 3H), 2.64-2.52 (m, 2H), 2.45-2.34 (m, 2H), 2.04 (s, 4H), 1.90-1.85 (m, 3H), 1.32-1.27 (m, 5H) |

TABLE 1-continued

| Cmp. No. | Structure | IUPAC Name | ¹H NMR |
|---|---|---|---|
| 20 | 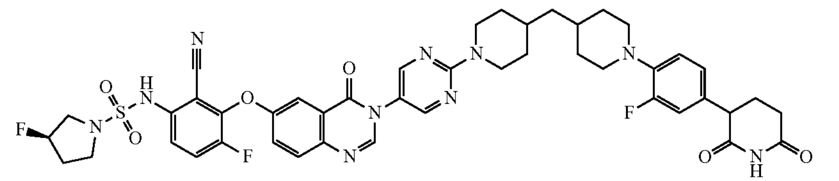 [SMILES: N#Cc1c(NS(=O)(=O)N2CC[C@@H](F)C2)ccc(F)c1Oc1ccc2ncn(-c3cnc(N4CCC(CC5CCN(c6ccc(C7CCC(=O)NC7=O)cc6F)CC5)CC4)nc3)c(=O)c2c1] | (3R)-N-{2-cyano-3-[(3-{2-[4-{[4-(2,6-dioxopiperidin-3-yl)-2-fluorophenyl]piperidin-1-yl}methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.87 (s, 1H), 8.51 (s, 3H), 8.29 (s, 1H), 7.82 (d, J = 8.9 Hz, 2H), 7.69-7.41 (m, 2H), 7.39-7.25 (m, 2H), 7.14-7.02 (m, 2H), 5.36 (s, 1H), 5.18 (s, 1H), 4.73 (d, J = 13.0 Hz, 1H), 4.10-3.88 (m, 1H), 3.26 (d, J = 7.4 Hz, 2H), 3.16 (t, J = 8.8 Hz, 3H), 3.01 (t, J = 12.0 Hz, 3H), 2.67 (td, J = 12.3, 6.1 Hz, 2H), 2.54 (s, 2H), 2.29-2.07 (m, 2H), 2.01 (dt, J = 13.2, 4.6 Hz, 1H), 1.86 (d, J = 13.8 Hz, 3H), 1.23 (s, 1H) |
| 21 | 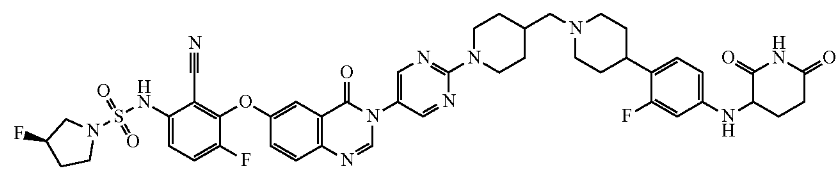 [SMILES: N#Cc1c(NS(=O)(=O)N2CC[C@@H](F)C2)ccc(F)c1Oc1ccc2ncn(-c3cnc(N4CCC(CN5CCC(c6ccc(NC7CCC(=O)NC7=O)cc6F)CC5)CC4)nc3)c(=O)c2c1] | (3R)-N-{2-cyano-3-[(3-{2-[4-{[4-(2,6-dioxopiperidin-3-yl)amino]-2-fluorophenyl}piperidin-1-yl]methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.87 (s, 1H), 8.51 (s, 3H), 8.29 (s, 1H), 7.82 (d, J = 8.9 Hz, 2H), 7.69-7.41 (m, 2H), 7.39-7.25 (m, 2H), 7.14-7.02 (m, 2H), 5.36 (s, 1H), 5.18 (s, 1H), 4.73 (d, J = 13.0 Hz, 1H), 4.10-3.88 (m, 1H), 3.26 (d, J = 7.4 Hz, 2H), 3.16 (t, J = 8.8 Hz, 3H), 3.01 (t, J = 12.0 Hz, 3H), 2.67 (td, J = 12.3, 6.1 Hz, 2H), 2.54 (s, 2H), 2.29-2.07 (m, 2H), 2.01 (dt, J = 13.2, 4.6 Hz, 1H), 1.86 (d, J = 13.8 Hz, 3H), 1.23 (s, 1H) |
| 22 | 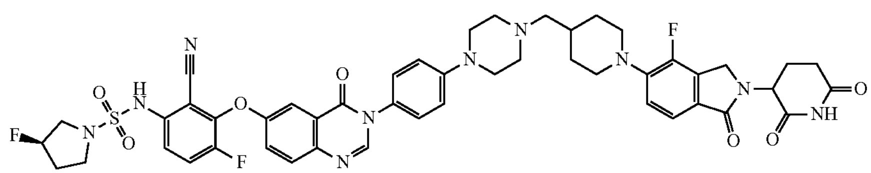 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6F)CN(C6CCC(=O)NC6=O)C7=O)CC5)CC4)cc3)c(=O)c2c1] | (3R)-N-{2-cyano-3-[(3-{4-[4-({1-[2-(2,6-dioxopiperidin-3-yl)-4-fluoro-1-oxo-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 11.00 (s, 1H), 8.26 (s, 1H), 7.83-7.79 (m, 1H), 7.75-7.69 (m, 1H), 7.49-7.36 (m, 5H), 7.19-7.15 (m, 1H), 7.10-7.05 (m, 2H), 5.23-5.17 (m, 1H), 5.08-5.04 (m, 1H), 4.49-4.39 (m, 1H), 4.32-4.22 (m, 1H), 3.52-3.43 (m, 4H), 3.34 (s, 3H), 2.92-2.83 (m, 4H), 2.68-2.60 (m, 2H), 2.55 (s, 1H), 2.04 (s, 3H), 1.98-1.89 (m, 3H), 1.87-1.82 (m, 2H), 1.35-1.31 (m, 1H) |

| Cmp. No. | Structure | IUPAC Name | 1H NMR |
|---|---|---|---|
| 23 | 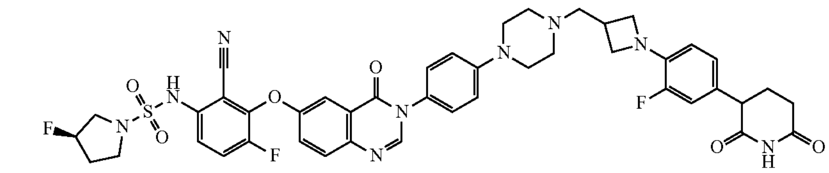 [SMILES: N#Cc1c(NS(=O)(=O)N2CC[C@@H](F)C2)ccc(F)c1Oc1ccc2ncn(-c3ccc(N4CCN(CC5CN(c6ccc(C7CCC(=O)NC7=O)cc6F)C5)CC4)cc3)c(=O)c2c1] | (3R)-N-{2-cyano-3-[(3-(4-[4-({1-[4-(2,6-dioxopiperidin-3-yl)-2-fluorophenyl]azetidin-3-yl}methyl)piperazin-1-yl]phenyl}-4-oxo-3,4-dihydroquinazolin-6-yl)oxy]-4-fluorophenyl}-3-fluoropyrrolidine-1-sulfonamide | 1H NMR (400 MHz, DMSO-d6) δ 10.80 (s, 1H), 10.09 (s, 1H), 8.25 (s, 1H), 7.82 (d, J = 8.9 Hz, 1H), 7.79-7.55 (m, 2H), 7.51-7.26 (m, 4H), 7.25-7.01 (m, 2H), 6.99-6.76 (m, 2H), 6.61-6.42 (m, 1H), 5.43-5.15 (m, 1H), 4.11-4.01 (m, 2H), 3.81-3.69 (m, 1H), 3.68-3.58 (m, 2H), 3.55-3.39 (m, 3H), 3.28-3.24 (m, 2H), 3.11-2.72 (m, 7H), 2.69-2.58 (m, 1H), 2.49-2.44 (m, 1H), 2.23-2.08 (m, 2H), 2.07-1.98 (m, 2H), 1.29-1.19 (m, 3H) |
| 24 | 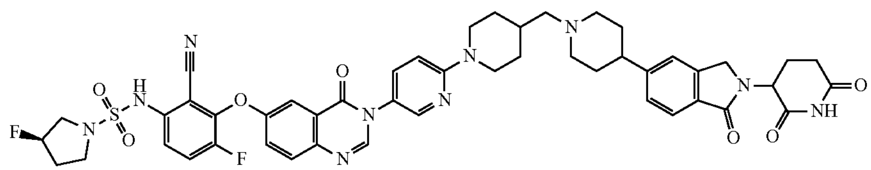 | (3R)-N-{2-cyano-3-[(3-{6-[4-(2-{4-[2-(2,6-dioxopiperidin-3-yl)-1-oxo-2,3-dihydro-1H-isoindol-5-yl]piperidin-1-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | 1H NMR (400 MHz, DMSO-d6) δ 11.01 (s, 1H), 8.27 (s, 1H), 8.20 (d, J = 2.8 Hz, 1H), 7.82 (d, J = 9.0 Hz, 1H), 7.74-7.65 (m, 4H), 7.50 (s, 2H), 7.45-7.37 (m, 2H), 7.00 (d, J = 9.2 Hz, 1H), 5.35-5.21 (d, J=56.0 Hz, 1H), 5.12 (m, 1H), 4.44 (t, J = 16.7 Hz, 4H), 4.32 (d, J = 17.5 Hz, 1H), 3.43 (m,2H), 3.23(m, 2H), 3.14 (d, J = 7.3 Hz, 3H), 3.00-2.92 (m, 7H), 2.63 (s, 2H), 2.57 (d, J = 16.9 Hz, 1H), 2.45-2.37 (m, 1H), 2.01 (s, 9H), 1.99 (s, 2H), 1.87 (d, J=12.6 Hz, 2H), 1.48 (s, 1H) |
| 25 | 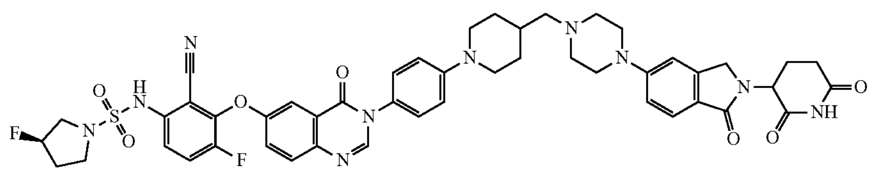 [SMILES: N#Cc1c(NS(=O)(=O)N2CC[C@@H](F)C2)ccc(F)c1Oc1ccc2ncn(-c3ccc(N4CCC(CN5CCN(c6ccc7c(c6)CN(C6CCC(=O)NC6=O)C7=O)CC5)CC4)cc3)c(=O)c2c1] | (3R)-N-{2-cyano-3-[(3-(4-[4-(2-{4-[2-(2,6-dioxopiperidin-3-yl)-1-oxo-2,3-dihydro-1H-isoindol-5-yl]piperazin-1-yl}methyl)piperidin-1-yl]phenyl}-4-oxo-3,4-dihydroquinazolin-6-yl)oxy]-4-fluorophenyl}-4- | 1H NMR (400 MHz, DMSO-d6) δ 10.97 (s, 1H), 8.25 (s, 1H), 7.82 (d, J = 8.9 Hz, 1H), 7.72-7.69 (m, 2H), 7.69 (s, 1H), 7.55 (d, J = 8.3 Hz, 2H), 7.43-7.40 (m, 2H), 7.31 (d, J = 8.8 Hz, 4H), 5.36-5.23 (d, J = 52.0 Hz, 4H), 4.34 (d, J = 17.1 Hz, 2H), 4.22 (d, J = 17.1 Hz, 2H), 3.82 |

TABLE 1-continued

| Cmp. No. | Structure | IUPAC Name | ¹H NMR |
|---|---|---|---|
| 26 | 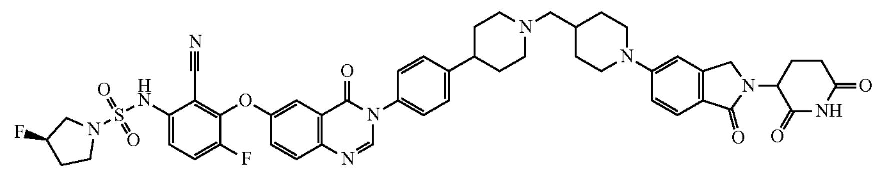 [SMILES: N#Cc1c(NS(=O)(=O)N2CC[C@@H](F)C2)ccc(F)c1Oc1ccc2ncn(-c3ccc(C4CCN(CC5CCN(c6ccc7c(c6)CN(C6CCC(=O)NC6=O)C7=O)CC5)CC4)cc3)c(=O)c2c1] | (3R)-N-{2-cyano-3-[(3-{4-[1-({1-[2-(2,6-dioxopiperidin-3-yl)-1-oxo-2,3-dihydro-1H-isoindol-5-yl]piperidin-4-yl}methyl)piperidin-4-yl]phenyl}-4-oxo-3,4-dihydroquinazolin-6-yl)oxy]-4-fluorophenyl}-3-fluoropyrrolidine-1-sulfonamide | (d, J = 12.3 Hz, 5H), 2.98-2.84 (m, 2H), 2.77 (t, J = 11.9 Hz, 4H), 2.59 (d, J = 16.5 Hz, 2H), 2.54-2.34 (m, 8H), 2.12-2.04 (m, 4H), 2.00-1.93 (m, 3H), 1.23-1.20 (m, 3H) <br><br> ¹H NMR (400 MHz, DMSO-d₆) δ 10.96 (s, 1H), 8.28 (s, 1H), 7.82 (d, J = 8.9 Hz, 1H), 7.68-7.58 (m, 1H), 7.57-7.37 (m, 8H), 7.08 (d, J = 7.8 Hz, 2H), 5.36-5.22 (d, J = 56.0 Hz, 1H), 5.08-5.02 (m, 1H), 4.34 (d, J = 17.0 Hz, 1H), 4.21 (d, J = 16.9 Hz, 1H), 3.93 (d, J = 12.6 Hz, 2H), 3.21-3.02 (m, 8H), 2.96-2.87 (m, 6H), 2.62 (s, 2H), 2.43-2.31 (m, 1H), 2.30-1.83 (m, 10H), 1.30-1.27 (m, 2H) |
| 27 | 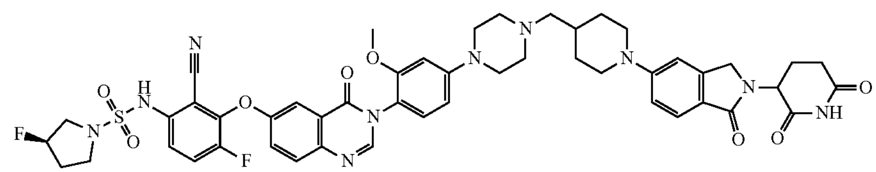 [SMILES: COc1cc(N2CCN(CC3CCN(c4ccc5c(c4)CN(C4CCC(=O)NC4=O)C5=O)CC3)CC2)ccc1-n1cnc2ccc(Oc3c(F)ccc(NS(=O)(=O)N4CC[C@@H](F)C4)c3C#N)cc2c1=O] | (3R)-N-{2-cyano-3-[(3-{4-[4-({1-[2-(2,6-dioxopiperidin-3-yl)-1-oxo-2,3-dihydro-1H-isoindol-5-yl]piperidin-4-yl}methyl)piperazin-1-yl]-2-methoxyphenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.96 (s, 1H), 10.03 (b, 1H), 8.11 (s, 1H), 7.82 (d, J = 4.6 Hz, 1H), 7.52-7.50 (m, 2H), 7.43-4.42 (m, 1H), 7.41-7.35 (m, 2H), 7.25-7.23 (m, 1H), 7.08 (s, 2H), 6.73 (s, 1H), 6.63 (s, 1H), 5.37-5.22 (d, J = 56.0 Hz, 1H), 5.05-4.98 (m, 1H), 4.33-4.21 (m, 2H), 3.95-3.86 (m, 2H), 3.75 (s, 1H), 3.45 -3.42 (m, 1H), 2.89-2.73 (m, 7H), 2.59-2.32 (m, 4H), 2.11-2.03 (m, 6H), 1.99-1.94 (m, 2H), 1.24 (s, 2H) |
| 28 | 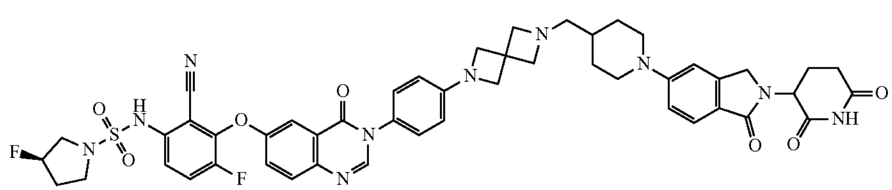 [SMILES: N#Cc1c(NS(=O)(=O)N2CC[C@@H](F)C2)ccc(F)c1Oc1ccc2ncn(-c3ccc(N4CC5(CN(CC6CCN(c7ccc8c(c7)CN(C7CCC(=O)NC7=O)C8=O)CC6)C5)C4)cc3)c(=O)c2c1] | (3R)-N-{2-cyano-3-[(3-{4-[6-({1-[2-(2,6-dioxopiperidin-3-yl)-1-oxo-2,3-dihydro-1H-isoindol-5-yl]piperidin-4-yl}methyl)-2,6-diazaspiro[3.3]heptan-2-yl]phenyl}-4-oxo-3,4-dihydroquinazolin-6- | ¹H NMR (400 MHz, DMSO-d₆) δ 10.96 (s, 1H), 8.20 (s, 1H), 7.80 (d, J = 8.9 Hz, 1H), 7.72-7.69 (m, 1H), 7.52 (d, J = 8.4 Hz, 1H), 7.36 (d, J = 3.0 Hz, 1H), 7.34-7.27 (m, 5H), 7.06 (d, J = 8.6 Hz, 2H), 6.58 (d, J = 8.2 Hz, 2H), 5.34-5.20 (d, J = 56.0 Hz, 1H), 4.33 (d, J = 16.9 Hz, 2H), 4.20 (d, |

TABLE 1-continued

| Cmp. No. | Structure | IUPAC Name | ¹H NMR |
|---|---|---|---|
| 29 | 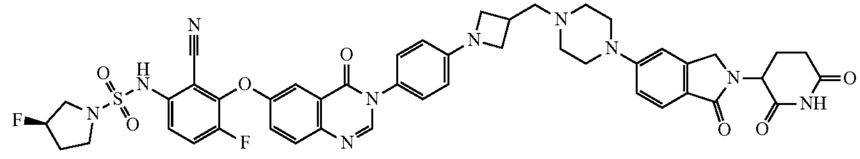 [SMILES: N#Cc1c(NS(=O)(=O)N2CC[C@@H](F)C2)ccc(F)c1Oc1ccc2ncn(-c3ccc(N4CC(CN5CCN(c6ccc7c(c6)CN(C6CCC(=O)NC6=O)C7=O)CC5)C4)cc3)c(=O)c2c1] | (3R)-N-{2-cyano-3-[(3-{4-[3-({4-[2-(2,6-dioxopiperidin-3-yl)-1-oxo-2,3-dihydro-1H-isoindol-5-yl]piperazin-1-yl}methyl)azetidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.95 (s, 1H), 8.23 (s, 1H), 7.82 (d, J = 8.9 Hz, 1H), 7.78-7.65 (m, 2H), 7.55 (d, J = 8.4 Hz, 1H), 7.46-7.43 (m, 1H), 7.41 (d, J = 3.1 Hz, 1H), 7.29 (d, J = 8.6 Hz, 2H), 7.10 (d, J = 8.6 Hz, 2H), 6.54 (d, J = 8.7 Hz, 2H), 5.40-5.22 (d, J = 54.0 Hz, 1H), 4.35-4.15 (m, 2H), 4.05 (t, J = 7.5 Hz, 2H), 3.60 (t, J = 6.5 Hz, 2H), 3.50 (d, J = 8.4 Hz, 2H), 2.94-2.86 (m, 7H), 2.81-2.75 (m, 7H), 2.62-2.60 (m, 1H), 2.25-2.15 (m, 5H), 1.48-1.46 (m, 1H) |
| 30 | 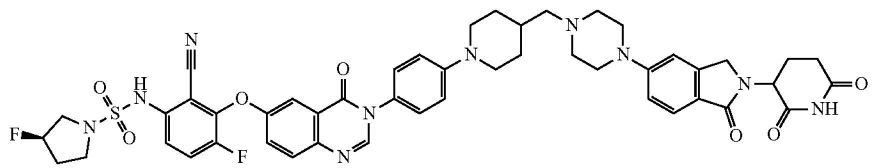 [SMILES: N#Cc1c(NS(=O)(=O)N2CC[C@@H](F)C2)ccc(F)c1Oc1ccc2ncn(-c3ccc(N4CCC(CN5CCN(c6ccc7c(c6)CN(C6CCC(=O)NC6=O)C7=O)CC5)CC4)cc3)c(=O)c2c1] | (3R)-N-{2-cyano-3-[(3-(4-{4-[2-(2,6-dioxopiperidin-3-yl)-1,3-dioxo-2,3-dihydro-1H-isoindol-5-yl]piperazin-1-yl}methyl)piperidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 11.09 (s, 1H), 8.24 (s, 1H), 8.13 (s, 1H), 7.85-7.79 (m, 1H), 7.74-7.66 (m, 3H), 7.47-7.36 (m, 3H), 7.33-7.26 (m, 3H), 7.05 (d, J = 8.8 Hz, 2H), 5.39-5.20 (m, 1H), 5.07 (dd, J = 5.2, 13.2 Hz, 1H), 3.84-3.76 (m, 2H), 3.54-3.49 (m, 4H), 3.35 (s, 4H), 2.89-2.80 (m, 2H), 2.78-2.71 (m, 3H), 2.65-2.57 (m, 3H), 2.46-2.40 (m, 3H), 2.16-2.09 (m, 1H), 2.07-2.00 (m, 2H), 1.83 (d, J = 10.0 Hz, 3H), 1.36-1.16 (m, 3H) |

TABLE 1-continued

| Cmp. No. | Structure | IUPAC Name | $^1$H NMR |
|---|---|---|---|
| 31 | 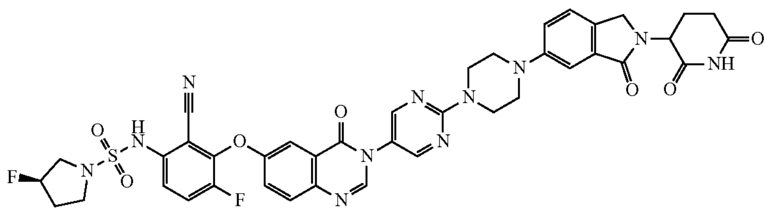 | (3R)-N-(2-cyano-3-[[3-(2-{4-[2-(2,6-dioxopiperidin-3-yl)-1,3-dioxo-2,3-dihydro-1H-isoindol-5-yl]piperazin-1-yl}pyrimidin-5-yl)-4-oxo-3,4-dihydroquinazolin-6-yl]oxy]-4-fluorophenyl)-3-fluoropyrrolidine-1-sulfonamide | $^1$H NMR (400 MHz, DMSO-d$_6$) δ 11.10 (s, 1H), 10.36 (s, 1H), 8.58 (s, 2H), 8.34 (s, 1H), 7.84 (t, J = 10.4 Hz, 2H), 7.78-7.69 (m, 2H), 7.52 (m, 1H), 7.42 (m, 2H), 7.31 (d, J = 8.7 Hz, 1 H), 5.39-5.25 (dd, 1H), 5.09 (m, 1H), 3.98 (t, J = 5.3 Hz, 4H), 3.64 (s, 4 H), 3.54-3.44 (m, 4H), 2.96-2.83 (m, 1H), 2.64-2.52 (m, 2H), 2.16-2.02 (m, 3H) |
| 32 | 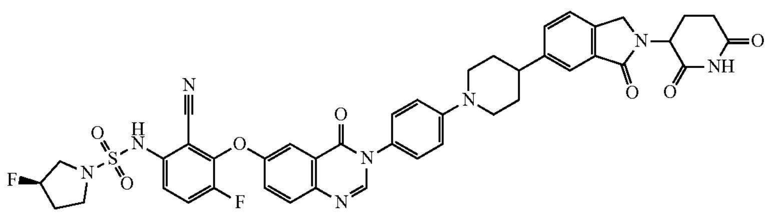 [SMILES: N#Cc1c(NS(=O)(=O)N2CC[C@@H](F)C2)ccc(F)c1Oc1ccc2ncn(-c3ccc(N4CCC(c5ccc6c(c5)C(=O)N(C5CCC(=O)NC5=O)C6)CC4)cc3)c(=O)c2c1] | (3R)-N-(2-cyano-3-{[3-(4-{4-[2-(2,6-dioxopiperidin-3-yl)-1,3-dioxo-2,3-dihydro-1H-isoindol-5-yl]piperidin-1-yl}phenyl)-4-oxo-3,4-dihydroquinazolin-6-yl]oxy}-4-fluorophenyl)-3-fluoropyrrolidine-1-sulfonamide | $^1$H NMR (400 MHz, DMSO-d$_6$) δ 11.00 (s, 1H), 10.36 (s, 1H), 8.28 (s, 1H), 7.83 (d, J = 9.2 Hz, 1H), 7.71 (dd, J = 3.2, 9.2 Hz, 1H), 7.60 (s, 1H), 7.59-7.54 (m, 2H), 7.53-7.48 (m, 1H), 7.42 (d, J = 3.2 H z, 1H), 7.33 (d, J = 8.8 Hz, 2H), 7.11 (d, J = 8.8 Hz, 2H), 5.44-5.22 (m, 1H), 5.18-5.06 (m, 1H), 4.48-4.38 (m, 1H), 4.34-4.22 (m, 1H), 4.02-3.89 (m, 2H), 3.54-3.48 (m, 1H), 3.46-3.42 (m, 2H), 2.92-2.85 (m, 3H), 2.65-2.59 (m, 2H), 2.45-2.38 (m, 2H), 2.20-2.08 (m, 2H), 2.06-1.89 (m, 4H), 1.87-1.73 (m, 2H) |
| 33 | 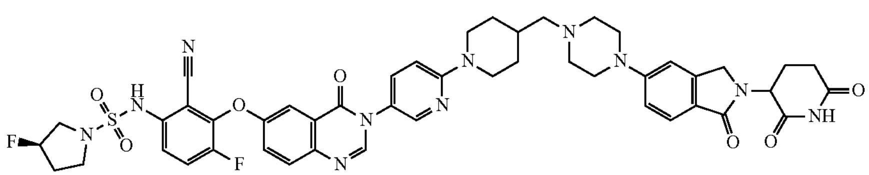 [SMILES: N#Cc1c(NS(=O)(=O)N2CC[C@@H](F)C2)ccc(F)c1Oc1ccc2ncn(-c3ccc(N4CCC(CN5CCN(c6ccc7c(c6)CN(C6CCC(=O)NC6=O)C7=O)CC5)CC4)nc3)c(=O)c2c1] | (3R)-N-{2-cyano-3-[(3-{6-[4-({4-[2-(2,6-dioxopiperidin-3-yl)-1,3-dioxo-2,3-dihydro-1H-isoindol-5-yl]piperazin-1-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | $^1$H NMR (400 MHz, DMSO-d$_6$) δ 11.11-11.05 (m, 1H), 8.27 (s, 1H), 8.17 (d, J = 2.4 Hz, 1H), 8.13 (s, 1 H), 7.82 (d, J = 8.8 Hz, 1H), 7.74-7.61 (m, 4H), 7.49-7.35 (m, 3H), 7.28 (br d, J = 8.8 Hz, 1H), 6.95 (d, J = 8.8 Hz, 1 H), 5.41-5.18 (m, 1H), 5.08 (dd, J = 5.2, 12.8 Hz, 1H), 4.37 (dd, J = 1.6, 11.2 Hz, 2H), 3.57-3.41 (m, 8H), 2.95-2.83 (m, 4H), 2.63- |

TABLE 1-continued

| Cmp. No. | Structure | IUPAC Name | ¹H NMR |
|---|---|---|---|
| 34 | 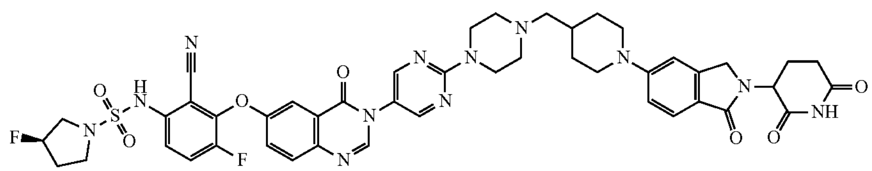 [SMILES: N#Cc1c(NS(=O)(=O)N2CC[C@@H](F)C2)ccc(F)c1Oc1ccc2ncn(-c3cnc(N4CCN(CC5CCN(c6ccc7c(c6)CN(C6CCC(=O)NC6=O)C7=O)CC5)CC4)nc3)c(=O)c2c1] | (3R)-N-{2-cyano-3-[(3-{2-[4-({1-[2-(2,6-dioxopiperidin-3-yl)-1-oxo-2,3-dihydro-1H-isoindol-5-yl]piperidin-4-yl}methyl)piperazin-1-yl]pyrimidin-5-yl}-4-oxo-3,4-dihydroquinazolin-6-yl)oxy]-4-fluorophenyl}-3-fluoropyrrolidine-1-sulfonamide | 2.58 (m, 2H), 2.44-2.35 (m, 4H), 2.20-1.88 (m, 6H), 1.82 (d, J = 11.2 Hz, 2H), 1.21-1.08 (m, 2H) ¹H NMR (400 MHz, DMSO-d₆) δ 10.94 (s, 1H), 10.38-9.94 (m, 1H), 8.54 (s, 2H), 8.31 (s, 1H), 7.83 (d, J = 8.8 Hz, 1H), 7.76-7.62 (m, 2H), 7.53-7.48 (m, 1H), 7.47-7.42 (m, 1H), 7.40 (d, J = 2.8 Hz, 1H), 7.08-7.04 (m, 2H), 5.39-5.21 (m, 1H), 5.04 (dd, J = 5.2, 13.2 Hz, 1H), 4.35-4.29 (m, 1H), 4.23-4.17 (m, 1H), 3.94-3.84 (m, 4H), 3.48-3.42 (m, 2H), 3.30-3.26 (m, 2H), 2.95-2.81 (m, 5H), 2.61-2.60 (m, 1H), 2.40-2.36 (m, 1H), 2.14-2.10 (m, 1H), 2.08-2.00 (m, 2H), 2.00-1.92 (m, 2H), 1.83 (d, J = 12.8 Hz, 3H), 1.27-1.19 (m, 6H) |
| 35 | 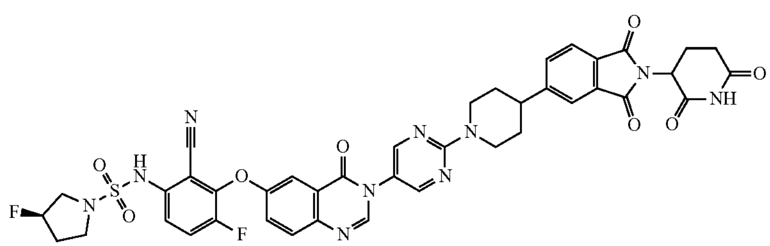 [SMILES: N#Cc1c(NS(=O)(=O)N2CC[C@@H](F)C2)ccc(F)c1Oc1ccc2ncn(-c3cnc(N4CCC(c5ccc6c(c5)C(=O)N(C5CCC(=O)NC5=O)C6=O)CC4)nc3)c(=O)c2c1] | (3R)-N-(2-cyano-3-[[3-(2-{4-[2-(2,6-dioxopiperidin-3-yl)-1,3-dioxo-2,3-dihydro-1H-isoindol-5-yl]piperidin-1-yl}pyrimidin-5-yl)-4-oxo-3,4-dihydroquinazolin-6-yl]oxy]-4-fluorophenyl)-3-fluoropyrrolidine-1-sulfonamide | N/A |

TABLE 1-continued

| Cmp. No. | Structure | IUPAC Name | ¹H NMR |
|---|---|---|---|
| 36 | 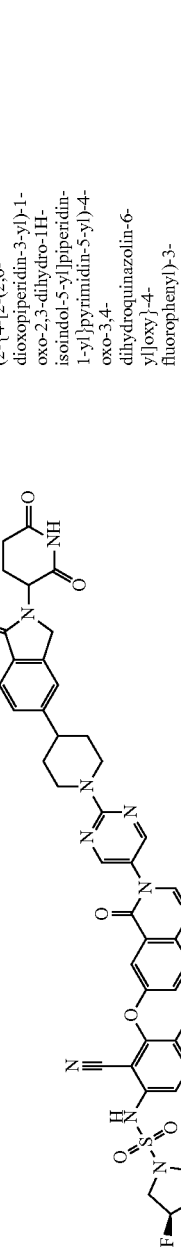 | (3R)-N-(2-cyano-3-{[3-(2-{4-[2-(2,6-dioxopiperidin-3-yl)-1-oxo-2,3-dihydro-1H-isoindol-5-yl]piperidin-1-yl}pyrimidin-5-yl)-4-oxo-3,4-dihydroquinazolin-6-yl]oxy}-4-fluorophenyl)-3-fluoropyrrolidine-1-sulfonamide | N/A |
| 37 | 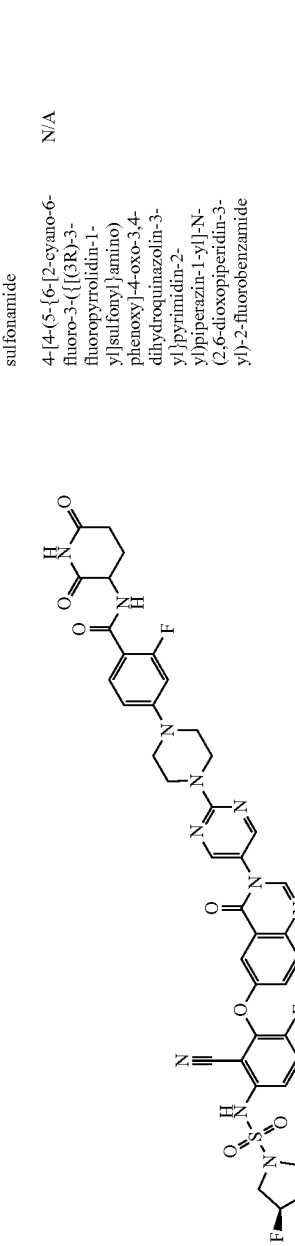 | 4-[4-(5-{6-[2-cyano-6-fluoro-3-{[(3R)-3-fluoropyrrolidin-1-yl]sulfonyl}amino)phenoxy]-4-oxo-3,4-dihydroquinazolin-3-yl}pyrimidin-2-yl)piperazin-1-yl]-N-(2,6-dioxopiperidin-3-yl)-2-fluorobenzamide | N/A |
| 38 | 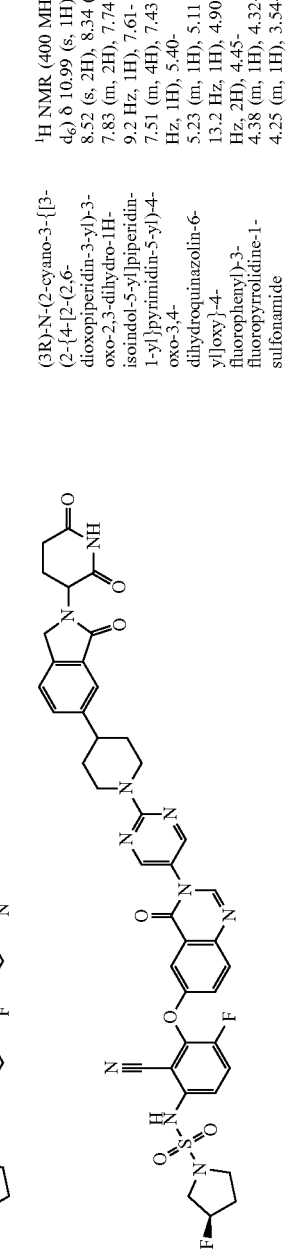 | (3R)-N-(2-cyano-3-{[3-(2-{4-[2-(2,6-dioxopiperidin-3-yl)-3-oxo-2,3-dihydro-1H-isoindol-5-yl]piperidin-1-yl}pyrimidin-5-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.99 (s, 1H), 10.35 (s, 1H), 8.52 (s, 2H), 8.34 (s, 1H), 7.90-7.83 (m, 2H), 7.74 (dd, J = 3.2, 9.2 Hz, 1H), 7.61-7.51 (m, 4H), 7.43 (d, J = 2.8 Hz, 1H), 5.40-5.23 (m, 1H), 5.11 (dd, J = 5.2, 13.2 Hz, 1H), 4.90 (d, J = 12.8 Hz, 2H), 4.45-4.38 (m, 1H), 4.32-4.25 (m, 1H), 3.54-3.43 (m, 3H), 3.12-3.02 (m, 3H), 2.96-2.87 (m, 1H), 2.60 (d, J = 15.6 Hz, 1H), 2.39 (dd, J = 4.4, 13.2 Hz, 1H), 2.18-1.88 (m, 6H), 1.72-1.60 (m, 2H) |

TABLE 1-continued

| Cmp. No. | Structure | IUPAC Name | ¹H NMR |
|---|---|---|---|
| 39 | 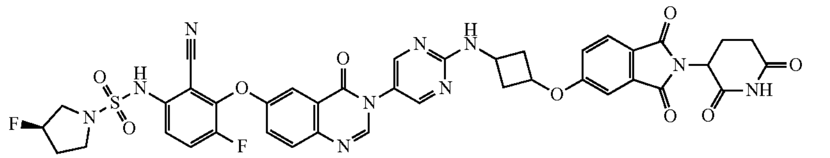 [SMILES: N#Cc1c(NS(=O)(=O)N2CC[C@@H](F)C2)ccc(F)c1Oc1ccc2ncn(-c3cnc(NC4CC(Oc5ccc6c(c5)C(=O)N(C5CCC(=O)NC5=O)C6=O)C4)nc3)c(=O)c2c1] | (3R)-N-{2-cyano-3-[(3-{2-[(3-{2-[(2,6-dioxopiperidin-3-yl)-1,3-dioxo-2,3-dihydro-1H-isoindol-5-yl]oxy}cyclobutyl)amino]pyrimidin-5-yl]-4-oxo-3,4-dihydroquinazolin-6-yl}oxy]-4-fluorophenyl}-3-fluoropyrrolidine-1-sulfonamide | ¹H NMR (400 MHz, DMSO-d₆) δ 11.12 (s, 1H), 10.34 (s, 1H), 8.45 (s, 2H), 8.32 (s, 1H), 8.13 (s, 1H), 7.85 (dd, J = 3.6, 8.4 Hz, 3H), 7.73 (m, 1H), 7.52 (dd, J = 4.0, 8.8 Hz, 1H), 7.42 (d, J = 2.4 Hz, 1H), 7.34-7.28 (m, 2H), 5.41-5.23 (m, 1H), 5.16-5.09 (m, 2H), 4.56-4.46 (m, 1H), 4.19-4.04 (m, 3H), 3.52 (s, 1H), 3.17 (s, 6H), 2.94-2.82 (m, 1H), 2.83-2.82 (m, 1H), 2.16-2.02 (m, 3H) |
| 40 | 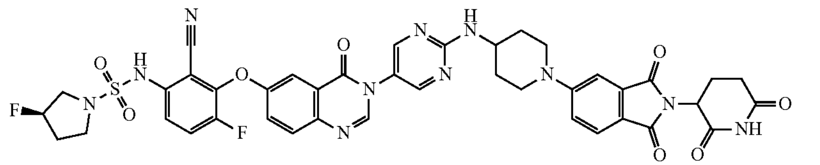 [SMILES: N#Cc1c(NS(=O)(=O)N2CC[C@@H](F)C2)ccc(F)c1Oc1ccc2ncn(-c3cnc(NC4CCN(c5ccc6c(c5)C(=O)N(C5CCC(=O)NC5=O)C6=O)CC4)nc3)c(=O)c2c1] | (3R)-N-[2-cyano-3-({3-[2-{[2-(2,6-dioxopiperidin-3-yl)-1,3-dioxo-2,3-dihydro-1H-isoindol-5-yl]piperidin-4-yl}amino)pyrimidin-5-yl]-4-oxo-3,4-dihydroquinazolin-6-yl}oxy)-4-fluorophenyl]-3-fluoropyrrolidine-1-sulfonamide | N/A |
| 41 | 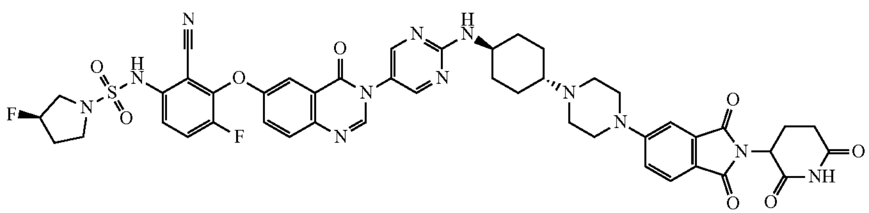 [SMILES: N#Cc1c(NS(=O)(=O)N2CC[C@@H](F)C2)ccc(F)c1Oc1ccc2ncn(-c3cnc(N[C@H]4CC[C@H](N5CCN(c6ccc7c(c6)C(=O)N(C6CCC(=O)NC6=O)C7=O)CC5)CC4)nc3)c(=O)c2c1] | (3R)-N-(2-cyano-4-fluoro-3-{[4-oxo-3-(2-{[(1r,4r)-4-{4-[2-(2,6-dioxopiperidin-3-yl)-1,3-dioxo-2,3-dihydro-1H-isoindol-5-yl]piperazin-1-yl}cyclohexyl]amino}pyrimidin-5-yl)-3,4-dihydroquinazolin-6-yl]oxy}phenyl)-3-fluoropyrrolidine-1-sulfonamide | N/A |

TABLE 1-continued

| Cmp. No. | Structure | IUPAC Name | ¹H NMR |
|---|---|---|---|
| 42 | 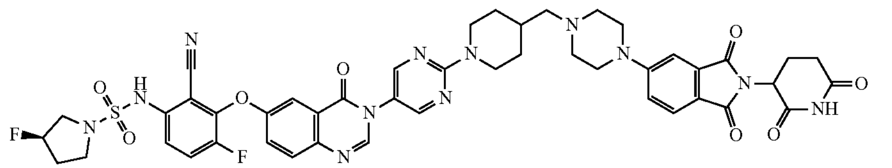 [SMILES: N#Cc1c(NS(=O)(=O)N2CC[C@@H](F)C2)ccc(F)c1Oc1ccc2ncn(-c3cnc(N4CCC(CN5CCN(c6ccc7c(c6)C(=O)N(C6CCC(=O)NC6=O)C7=O)CC5)CC4)nc3)c(=O)c2c1] | (3R)-N-{2-cyano-3-[(3-(2-{4-[(4-[2-(2,6-dioxopiperidin-3-yl)-1,3-dioxo-2,3-dihydro-1H-isoindol-5-yl]piperazin-1-yl}methyl)piperidin-1-yl]pyrimidin-5-yl]-4-oxo-3,4-dihydroquinazolin-6-yl)oxy]-4-fluorophenyl}-3-fluoropyrrolidine-1-sulfonamide | N/A |
| 43 | 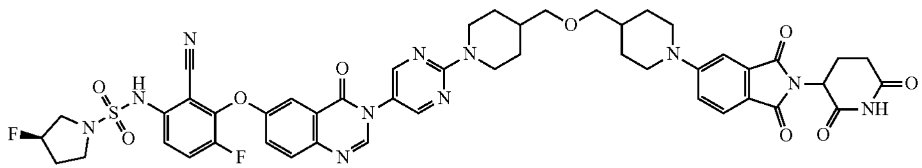 [SMILES: N#Cc1c(NS(=O)(=O)N2CC[C@@H](F)C2)ccc(F)c1Oc1ccc2ncn(-c3cnc(N4CCC(COCC5CCN(c6ccc7c(c6)C(=O)N(C6CCC(=O)NC6=O)C7=O)CC5)CC4)nc3)c(=O)c2c1] | (3R)-N-(2-cyano-3-{[3-(2-{4-[({1-[2-(2,6-dioxopiperidin-3-yl)-1,3-dioxo-2,3-dihydro-1H-isoindol-5-yl]piperidin-4-yl}methoxy)methyl]piperidin-1-yl}pyrimidin-5-yl)-4-oxo-3,4-dihydroquinazolin-6-yl]oxy}-4-fluorophenyl)-3-fluoropyrrolidine-1-sulfonamide | N/A |
| 44 | 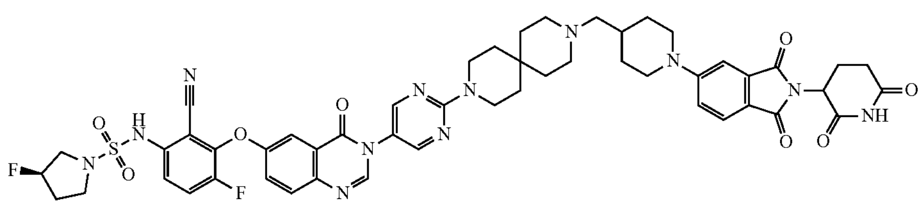 [SMILES: N#Cc1c(NS(=O)(=O)N2CC[C@@H](F)C2)ccc(F)c1Oc1ccc2ncn(-c3cnc(N4CCC5(CCN(CC6CCN(c7ccc8c(c7)C(=O)N(C7CCC(=O)NC7=O)C8=O)CC6)CC5)CC4)nc3)c(=O)c2c1] | (3R)-N-{2-cyano-3-[(2-{9-({1-[2-(2,6-dioxopiperidin-3-yl)-1,3-dioxo-2,3-dihydro-1H-isoindol-5-yl]piperidin-4-yl}methyl)-3,9-diazaspiro[5.5]undecan-3-yl]pyrimidin-5-yl)-4-oxo-3,4-dihydroquinazolin-6-yl]oxy}-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 45 | 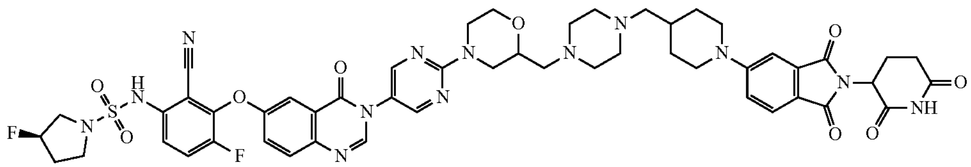 [SMILES: N#Cc1c(NS(=O)(=O)N2CC[C@@H](F)C2)ccc(F)c1Oc1ccc2ncn(-c3cnc(N4CCOC(CN5CCN(CC6CCN(c7ccc8c(c7)C(=O)N(C7CCC(=O)NC7=O)C8=O)CC6)CC5)C4)nc3)c(=O)c2c1] | (3R)-N-[2-cyano-3-({3-[2-(2-{[4-({1-[2-(2,6-dioxopiperidin-3-yl)-1,3-dioxo-2,3-dihydro-1H-isoindol-5-yl]piperidin-4-yl}methyl)piperazin-1-yl]methyl}morpholin-4-yl)pyrimidin-5-yl]-4-oxo-3,4-dihydroquinazolin-6-yl}oxy)-4-fluorophenyl]-3-fluoropyrrolidine-1-sulfonamide | N/A |
| 46 | 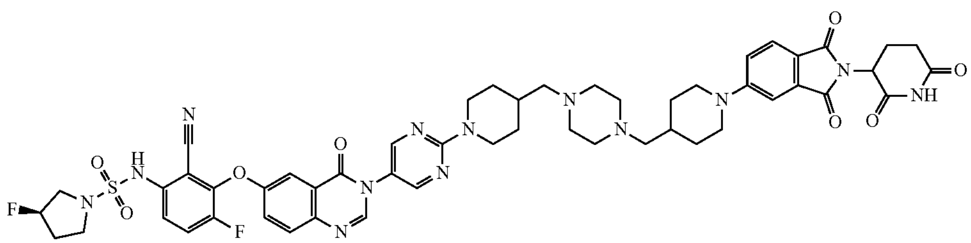 [SMILES: N#Cc1c(NS(=O)(=O)N2CC[C@@H](F)C2)ccc(F)c1Oc1ccc2ncn(-c3cnc(N4CCC(CN5CCN(CC6CCN(c7ccc8c(c7)C(=O)N(C7CCC(=O)NC7=O)C8=O)CC6)CC5)CC4)nc3)c(=O)c2c1] | (3R)-N-[2-cyano-3-({3-[2-(4-{[4-({1-[2-(2,6-dioxopiperidin-3-yl)-1,3-dioxo-2,3-dihydro-1H-isoindol-5-yl]piperidin-4-yl}methyl)piperazin-1-yl]methyl}piperidin-1-yl)pyrimidin-5-yl]-4-oxo-3,4-dihydroquinazolin-6-yl}oxy)-4-fluorophenyl]-3-fluoropyrrolidine-1-sulfonamide | N/A |
| 47 | 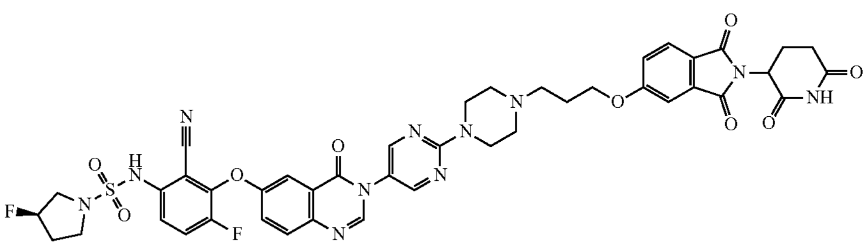 [SMILES: N#Cc1c(NS(=O)(=O)N2CC[C@@H](F)C2)ccc(F)c1Oc1ccc2ncn(-c3cnc(N4CCN(CCCOc5ccc6c(c5)C(=O)N(C5CCC(=O)NC5=O)C6=O)CC4)nc3)c(=O)c2c1] | (3R)-N-{2-cyano-3-[(3-{2-[4-(3-{[2-(2,6-dioxopiperidin-3-yl)-1,3-dioxo-2,3-dihydro-1H-isoindol-5-yl]oxy}propyl)piperazin-1-yl]pyrimidin-5-yl]-4-oxo-3,4-dihydroquinazolin-6-yl}oxy)-4-fluorophenyl]-3-fluoropyrrolidine-1-sulfonamide | N/A |

TABLE 1-continued

| Cmp. No. | Structure | IUPAC Name | ¹H NMR |
|---|---|---|---|
| 48 | 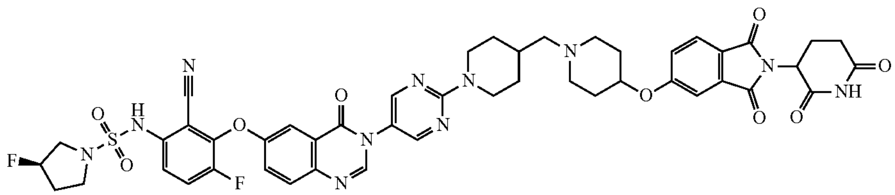 [SMILES: N#Cc1c(NS(=O)(=O)N2CC[C@@H](F)C2)ccc(F)c1Oc1ccc2ncn(-c3cnc(N4CCC(CN5CCC(Oc6ccc7c(c6)C(=O)N(C6CCC(=O)NC6=O)C7=O)CC5)CC4)nc3)c(=O)c2c1] | (3R)-N-(2-cyano-3-{[2-(4-{[(4-{[2-(2,6-dioxopiperidin-3-yl)-1,3-dioxo-2,3-dihydro-1H-isoindol-5-yl]oxy}piperidin-1-yl)methyl]piperidin-1-yl}pyrimidin-5-yl)-4-oxo-3,4-dihydroquinazolin-6-yl]oxy}-4-fluorophenyl)-3-fluoropyrrolidine-1-sulfonamide | N/A |
| 49 | 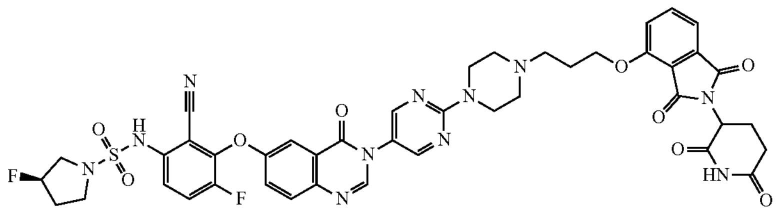 [SMILES: N#Cc1c(NS(=O)(=O)N2CC[C@@H](F)C2)ccc(F)c1Oc1ccc2ncn(-c3cnc(N4CCN(CCCOc5cccc6c5C(=O)N(C5CCC(=O)NC5=O)C6=O)CC4)nc3)c(=O)c2c1] | (3R)-N-{2-cyano-3-[(3-{2-[4-(3-{[2-(2,6-dioxopiperidin-3-yl)-1,3-dioxo-2,3-dihydro-1H-isoindol-4-yl]oxy}propyl)piperazin-1-yl]pyrimidin-5-yl}-4-oxo-3,4-dihydroquinazolin-6-yl)oxy]-4-fluorophenyl}-3-fluoropyrrolidine-1-sulfonamide | N/A |
| 50 | 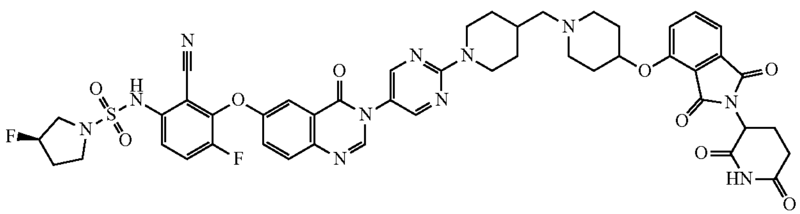 [SMILES: N#Cc1c(NS(=O)(=O)N2CC[C@@H](F)C2)ccc(F)c1Oc1ccc2ncn(-c3cnc(N4CCC(CN5CCC(Oc6cccc7c6C(=O)N(C6CCC(=O)NC6=O)C7=O)CC5)CC4)nc3)c(=O)c2c1] | (3R)-N-(2-cyano-3-{[2-(4-{[(4-{[2-(2,6-dioxopiperidin-3-yl)-1,3-dioxo-2,3-dihydro-1H-isoindol-4-yl]oxy}piperidin-1-yl)methyl]piperidin-1-yl}pyrimidin-5-yl)-4-oxo-3,4-dihydroquinazolin-6-yl]oxy}-4-fluorophenyl)-3-fluoropyrrolidine-1-sulfonamide | N/A |

TABLE 1-continued

| Cmp. No. | Structure | IUPAC Name | ¹H NMR |
|---|---|---|---|
| 51 | 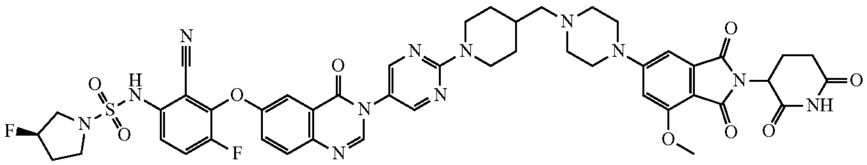 [SMILES: COc1cc(N2CCN(CC3CCN(c4ncc(-n5cnc6ccc(Oc7c(F)ccc(NS(=O)(=O)N8CC[C@@H](F)C8)c7C#N)cc6c5=O)cn4)CC3)CC2)cc2c1C(=O)N(C1CCC(=O)NC1=O)C2=O] | (3R)-N-{2-cyano-3-[(3-{2-[4-[(4-[2-(2,6-dioxopiperidin-3-yl)-7-methoxy-1,3-dioxo-2,3-dihydro-1H-isoindol-5-yl]piperazin-1-yl}methyl)piperidin-1-yl]pyrimidin-5-yl]-4-oxo-3,4-dihydroquinazolin-6-yl]oxy]-4-fluorophenyl}-3-fluoropyrrolidine-1-sulfonamide | N/A |
| 52 | 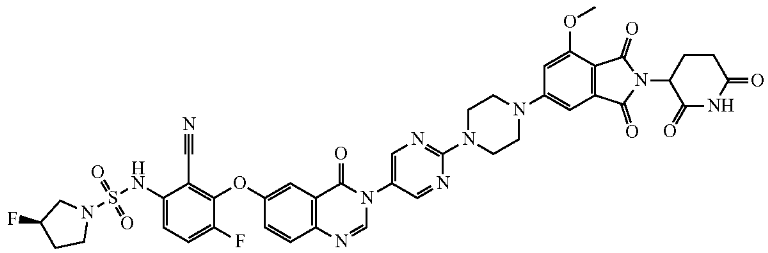 [SMILES: COc1cc(N2CCN(c3ncc(-n4cnc5ccc(Oc6c(F)ccc(NS(=O)(=O)N7CC[C@@H](F)C7)c6C#N)cc5c4=O)cn3)CC2)cc2c1C(=O)N(C1CCC(=O)NC1=O)C2=O] | (3R)-N-(2-cyano-3-{[3-(2-{4-[2-(2,6-dioxopiperidin-3-yl)-7-methoxy-1,3-dioxo-2,3-dihydro-1H-isoindol-5-yl]piperazin-1-yl}pyrimidin-5-yl)-4-oxo-3,4-dihydroquinazolin-6-yl]oxy}-4-fluorophenyl)-3-fluoropyrrolidine-1-sulfonamide | N/A |
| 53 | 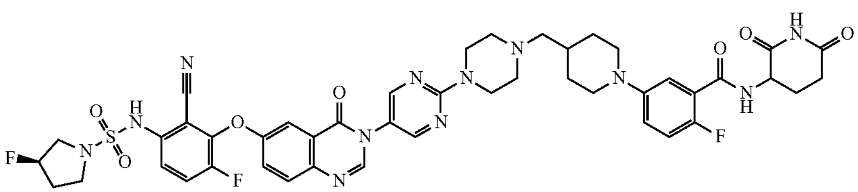 [SMILES: N#Cc1c(NS(=O)(=O)N2CC[C@@H](F)C2)ccc(F)c1Oc1ccc2ncn(-c3cnc(N4CCN(CC5CCN(c6ccc(F)c(C(=O)NC7CCC(=O)NC7=O)c6)CC5)CC4)nc3)c(=O)c2c1] | 5-(4-{[4-(5-{6-[2-cyano-6-fluoro-3-({[(3R)-3-fluoropyrrolidin-1-yl]sulfonyl}amino)phenoxy]-4-oxo-3,4-dihydroquinazolin-3-yl}pyrimidin-2-yl)piperazin-1-yl]methyl}piperidin-1-yl)-N-(2,6-dioxopiperidin-3-yl)-2-fluorobenzamide | N/A |

TABLE 1-continued

| Cmp. No. | Structure | IUPAC Name | ¹H NMR |
|---|---|---|---|
| 54 | 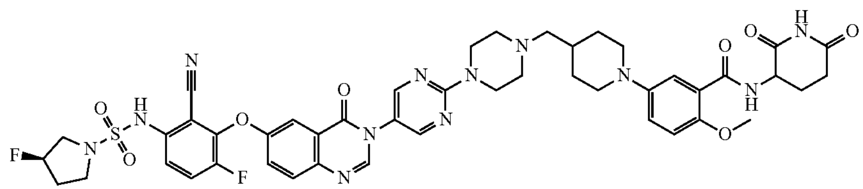 | 5-(4-{[4-(5-{6-[2-cyano-6-fluoro-3-({[(3R)-3-fluoropyrrolidin-1-yl]sulfonyl}amino)phenoxy]-4-oxo-3,4-dihydroquinazolin-3-yl}pyrimidin-2-yl)piperazin-1-yl]methyl}piperidin-1-yl)-N-(2,6-dioxopiperidin-3-yl)-2-methoxybenzamide | N/A |
| 55 | 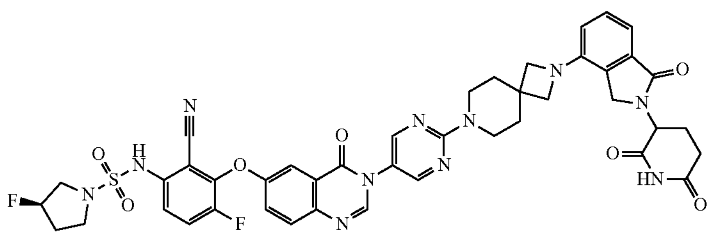 [SMILES: N#Cc1c(NS(=O)(=O)N2CC[C@@H](F)C2)ccc(F)c1Oc1ccc2ncn(-c3cnc(N4CCC5(CC4)CN(c4cccc6c4CN(C4CCC(=O)NC4=O)C6=O)C5)nc3)c(=O)c2c1] | (3R)-N-(2-cyano-3-{[3-(2-{2-[2-(2,6-dioxopiperidin-3-yl)-1-oxo-2,3-dihydro-1H-isoindol-4-yl]-2,7-diazaspiro[3.5]nonan-7-yl}pyrimidin-5-yl)-4-oxo-3,4-dihydroquinazolin-6-yl]oxy}-4-fluorophenyl)-3-fluoropyrrolidine-1-sulfonamide | N/A |
| 56 | 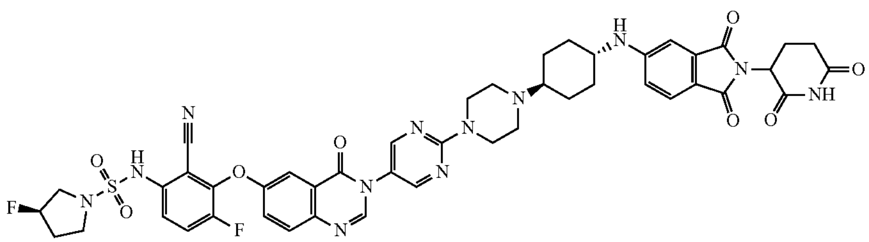 [SMILES: N#Cc1c(NS(=O)(=O)N2CC[C@@H](F)C2)ccc(F)c1Oc1ccc2ncn(-c3cnc(N4CCN([C@H]5CC[C@H](Nc6ccc7c(c6)C(=O)N(C6CCC(=O)NC6=O)C7=O)CC5)CC4)nc3)c(=O)c2c1] | (3R)-N-(2-cyano-4-fluoro-3-{[4-oxo-3-(2-(4-[(1r,4r)-4-{[2-(2,6-dioxopiperidin-3-yl)-1,3-dioxo-2,3-dihydro-1H-isoindol-5-yl]amino}cyclohexyl]piperazin-1-yl]pyrimidin-5-yl)-3,4-dihydroquinazolin-6-yl]oxy}phenyl)-3-fluoropyrrolidine-1-sulfonamide | N/A |

TABLE 1-continued

| Cmp. No. | Structure | IUPAC Name | ¹H NMR |
|---|---|---|---|
| 57 | 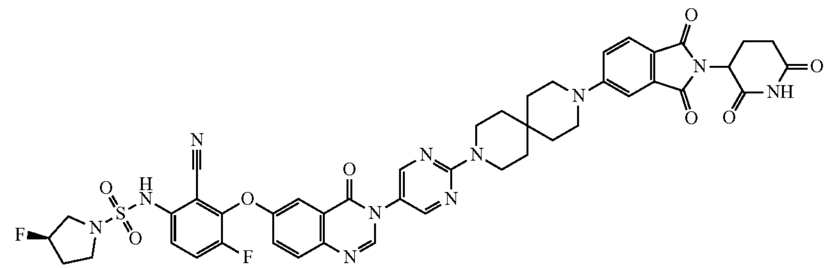 [SMILES: N#Cc1c(NS(=O)(=O)N2CC[C@@H](F)C2)ccc(F)c1Oc1ccc2ncn(-c3cnc(N4CCC5(CCN(c6ccc7c(c6)C(=O)N(C6CCC(=O)NC6=O)C7=O)CC5)CC4)nc3)c(=O)c2c1] | (3R)-N-(2-cyano-3-{[3-(2-{9-[2-(2,6-dioxopiperidin-3-yl)-1,3-dioxo-2,3-dihydro-1H-isoindol-5-yl]-3,9-diazaspiro[5.5]undecan-3-yl}pyrimidin-5-yl)-4-oxo-3,4-dihydroquinazolin-6-yl]oxy}-4-fluorophenyl)-3-fluoropyrrolidine-1-sulfonamide | N/A |
| 58 | 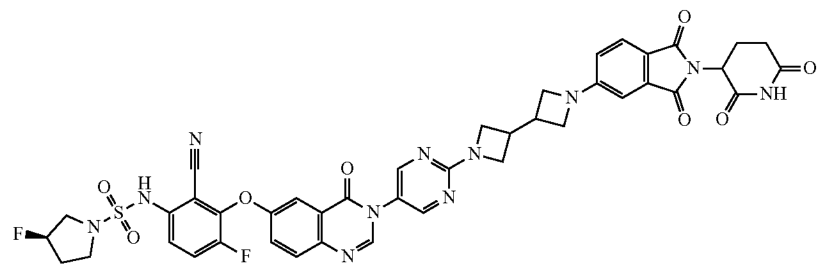 [SMILES: N#Cc1c(NS(=O)(=O)N2CC[C@@H](F)C2)ccc(F)c1Oc1ccc2ncn(-c3cnc(N4CC(C5CN(c6ccc7c(c6)C(=O)N(C6CCC(=O)NC6=O)C7=O)C5)C4)nc3)c(=O)c2c1] | (3R)-N-(2-cyano-3-{[3-(2-{1'-[2-(2,6-dioxopiperidin-3-yl)-1,3-dioxo-2,3-dihydro-1H-isoindol-5-yl]-[3,3'-biazetidin]-1-yl}pyrimidin-5-yl)-4-oxo-3,4-dihydroquinazolin-6-yl]oxy}-4-fluorophenyl)-3-fluoropyrrolidine-1-sulfonamide | N/A |
| 59 | 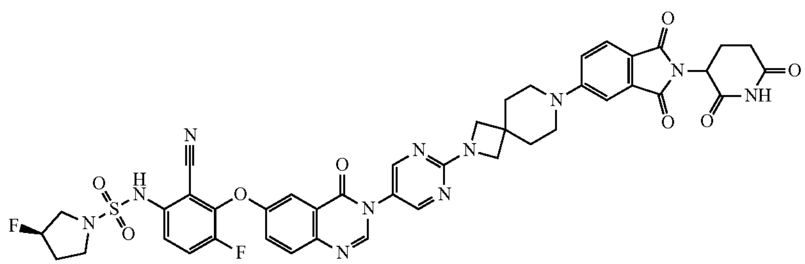 [SMILES: N#Cc1c(NS(=O)(=O)N2CC[C@@H](F)C2)ccc(F)c1Oc1ccc2ncn(-c3cnc(N4CC5(CCN(c6ccc7c(c6)C(=O)N(C6CCC(=O)NC6=O)C7=O)CC5)C4)nc3)c(=O)c2c1] | (3R)-N-(2-cyano-3-{[3-(2-{7-[2-(2,6-dioxopiperidin-3-yl)-1,3-dioxo-2,3-dihydro-1H-isoindol-5-yl]-2,7-diazaspiro[3.5]nonan-2-yl}pyrimidin-5-yl)-4-oxo-3,4-dihydroquinazolin-6-yl]oxy}-4-fluorophenyl)-3-fluoropyrrolidine-1-sulfonamide | N/A |
| 60 | 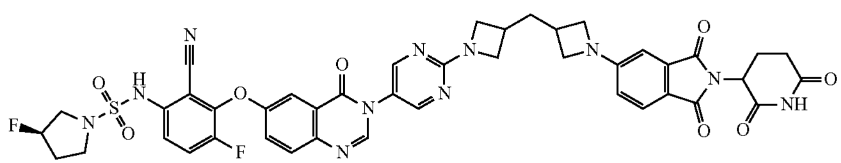 [SMILES: N#Cc1c(NS(=O)(=O)N2CC[C@@H](F)C2)ccc(F)c1Oc1ccc2ncn(-c3cnc(N4CC(CC5CN(c6ccc7c(c6)C(=O)N(C6CCC(=O)NC6=O)C7=O)C5)C4)nc3)c(=O)c2c1] | (3R)-N-{2-cyano-3-[(3-{2-[3-({1-[2-(2,6-dioxopiperidin-3-yl)-1,3-dioxo-2,3-dihydro-1H-isoindol-5-yl]azetidin-3-yl}methyl)azetidin-1-yl]pyrimidin-5-yl]-4- | ¹H NMR (400 MHz, DMSO-d₆) δ 11.08 (s, 1H), 10.35 (s, 1H), 8.48 (s, 2H), 8.30 (s, 1H), 7.9-2-7.69 (m, 3H), 7.64 (d, J = 8.4 Hz, 1H), 7.54-7.47 (m, 1H), 7.40 (d, J = 2.4 Hz, 1H), 6.78 (s, 1H), 6.70-6.55 (m, 1H), 5.49- |

TABLE 1-continued

| Cmp. No. | Structure | IUPAC Name | ¹H NMR |
|---|---|---|---|
| 61 | 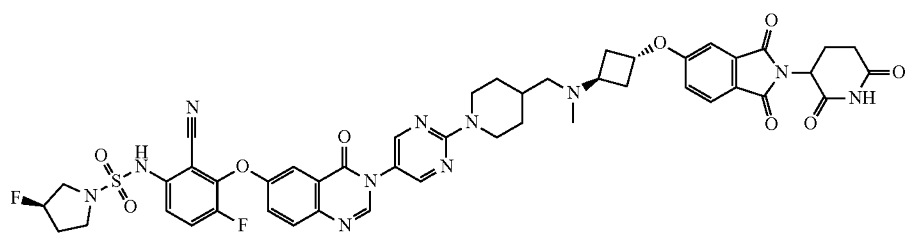 [SMILES: CN(CC1CCN(c2ncc(-n3cnc4ccc(Oc5c(F)ccc(NS(=O)(=O)N6CC[C@@H](F)C6)c5C#N)cc4c3=O)cn2)CC1)[C@H]1C[C@H](Oc2ccc3c(c2)C(=O)N(C2CCC(=O)NC2=O)C3=O)C1] | (3R)-N-{2-cyano-4-fluoro-3-[(3-{2-[4-({methyl[(1r,3r)-3-{[2-(2,6-dioxopiperidin-3-yl)-1,3-dioxo-2,3-dihydro-1H-isoindol-5-yl]oxy}cyclobutyl]amino}methyl)piperidin-1-yl]pyrimidin-5-yl}-4-oxo-3,4-dihydroquinazolin-6-yl)oxy]phenyl}-3-fluoropyrrolidine-1-sulfonamide | 5.18 (m, 1H), 5.10-4.98 (m, 1H), 4.23-4.12 (m, 4H), 3.81-3.68 (m, 4H), 3.51 (s, 1H), 3.43 (s, 2H), 2.90-2.73 (m, 3H), 2.61-2.52 (m, 3H), 2.16-1.98 (m, 5H) |
| 62 | 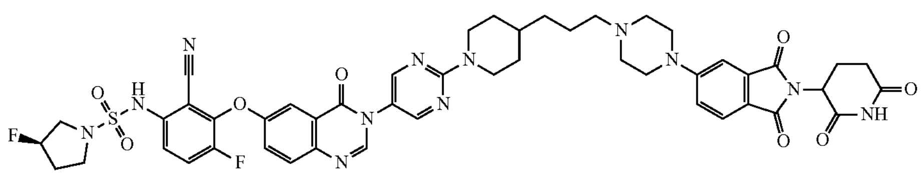 [SMILES: N#Cc1c(NS(=O)(=O)N2CC[C@@H](F)C2)ccc(F)c1Oc1ccc2ncn(-c3cnc(N4CCC(CCCN5CCN(c6ccc7c(c6)C(=O)N(C6CCC(=O)NC6=O)C7=O)CC5)CC4)nc3)c(=O)c2c1] | (3R)-N-{2-cyano-3-[(3-{2-[4-(3-{4-[2-(2,6-dioxopiperidin-3-yl)-1,3-dioxo-2,3-dihydro-1H-isoindol-5-yl]piperazin-1-yl}propyl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | $^1$H NMR |
|---|---|---|---|
| 63 | 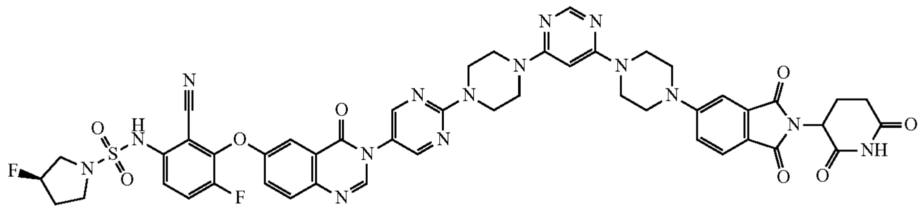 [SMILES: N#Cc1c(NS(=O)(=O)N2CC[C@@H](F)C2)ccc(F)c1Oc1ccc2ncn(-c3cnc(N4CCN(c5cc(N6CCN(c7ccc8c(c7)C(=O)N(C7CCC(=O)NC7=O)C8=O)CC6)ncn5)CC4)nc3)c(=O)c2c1] | (3R)-N-{2-cyano-3-[(3-{2-[4-(6-{4-[2-(2,6-dioxopiperidin-3-yl)-1,3-dioxo-2,3-dihydro-1H-isoindol-5-yl]piperazin-1-yl}pyrimidin-4-yl)piperazin-1-yl]pyrimidin-5-yl}]-4-oxo-3,4-dihydroquinazolin-6-yl)oxy]-4-fluorophenyl}-3-fluoropyrrolidine-1-sulfonamide | N/A |
| 64 | 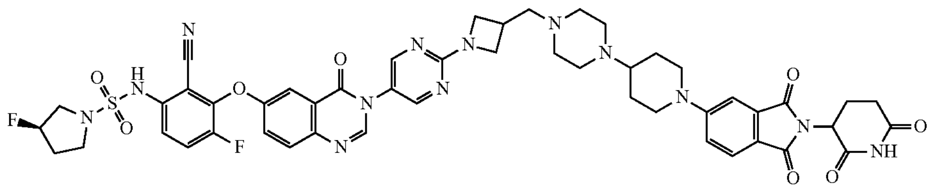 [SMILES: N#Cc1c(NS(=O)(=O)N2CC[C@@H](F)C2)ccc(F)c1Oc1ccc2ncn(-c3cnc(N4CC(CN5CCN(C6CCN(c7ccc8c(c7)C(=O)N(C7CCC(=O)NC7=O)C8=O)CC6)CC5)C4)nc3)c(=O)c2c1] | (3R)-N-(2-cyano-3-{[3-(2-{3-[(4-{1-[2-(2,6-dioxopiperidin-3-yl)-1,3-dioxo-2,3-dihydro-1H-isoindol-5-yl]piperidin-4-yl}piperazin-1-yl)methyl]azetidin-1-yl}pyrimidin-5-yl)-4-oxo-3,4-dihydroquinazolin-6-yl]oxy}-4-fluorophenyl)-3-fluoropyrrolidine-1-sulfonamide | N/A |
| 65 | 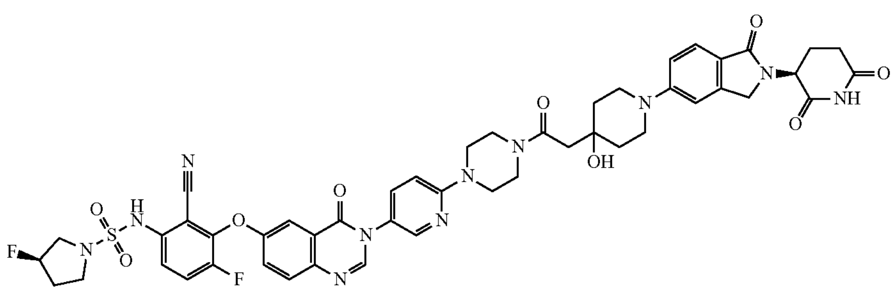 [SMILES: N#Cc1c(NS(=O)(=O)N2CC[C@@H](F)C2)ccc(F)c1Oc1ccc2ncn(-c3ccc(N4CCN(C(=O)CC5(O)CCN(c6ccc7c(c6)CN([C@H]6CCC(=O)NC6=O)C7=O)CC5)CC4)nc3)c(=O)c2c1] | (3R)-N-(2-cyano-3-{[3-(6-{4-[2-(1-{2-[(3S)-2,6-dioxopiperidin-3-yl]-1-oxo-2,3-dihydro-1H-isoindol-5-yl}-4-hydroxypiperidin-4-yl)acetyl]piperazin-1-yl}pyridin-3-yl)-4-oxo-3,4-dihydroquinazolin-6-yl]oxy}-4-fluorophenyl)-3-fluoropyrrolidine-1-sulfonamide | $^1$H NMR (400 MHz, DMSO-$d_6$) δ 10.96 (s, 1H), 10.38 (s, 1H), 8.30 (s, 1H), 8.24 (d, J = 2.6 Hz, 1H), 7.85 (d, J = 8.9 Hz, 2H), 7.73 (m, 2H), 7.56-7.47 (m, 2H), 7.42 (d, J = 3.0 Hz, 1H), 7.08 (s, 2H), 7.05-6.90 (m, 1H), 5.39-5.26 (d, J = 56.0 Hz, 1H), 5.05-4.90 (m, 1H), 4.32 (d, J= 16.9 Hz, 1H), 4.20 (d, J = 16.8 Hz, 1H), 3.80-3.57 (m, 11H), 3.52-3.41 (m, 4H), 3.25 (t, J = 10.7 Hz, 2H), 2.91 (m, 1H), 2.61 (m, 3 H), 2.37 (m, 2H), 2.19-2.01 (m, 2H), 1.98 (s, 1H), 1.71 (d, J = 13.8 Hz, 4H) |

TABLE 1-continued

| Cmp. No. | Structure | IUPAC Name | ¹H NMR |
|---|---|---|---|
| 66 | 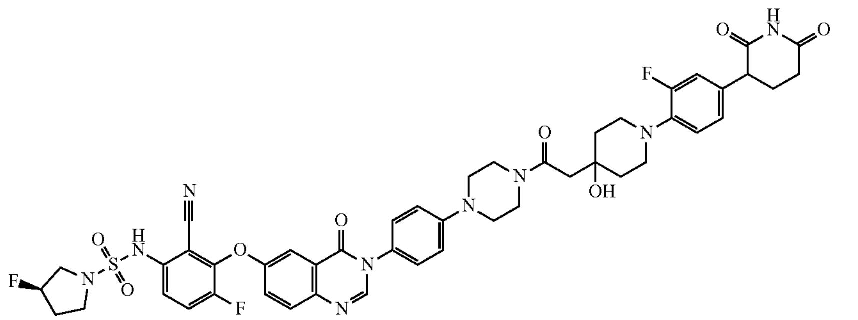 [SMILES: N#Cc1c(NS(=O)(=O)N2CC[C@@H](F)C2)ccc(F)c1Oc1ccc2ncn(-c3ccc(N4CCN(C(=O)CC5(O)CCN(c6ccc(C7CCC(=O)NC7=O)cc6F)CC5)CC4)cc3)c(=O)c2c1] | (3R)-N-{2-cyano-3-[(3-(4-(2-{1-[4-(2,6-dioxopiperidin-3-yl)-2-fluorophenyl]-4-hydroxypiperidin-4-yl}acetyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.83 (s, 1H), 8.25 (s, 1H), 7.90 (s, 1H), 7.82 (d, J = 8.9 Hz, 1H), 7.75-7.65 (m, 1H), 7.64-7.58 (m, 1H), 7.45-7.33 (m, 3H), 7.23 (s, 1H), 7.12-6.94 (m, 6H), 5.42-5.19 (m, 1H), 5.11-4.75 (m, 1H), 3.82-3.62 (m, 10H), 3.49-3.35 (m, 1H), 3.29-3.19 (m, 4H), 3.12-2.97 (m, 3H), 2.71-2.58 (m, 3H), 2.46 (s, 1H), 2.29-2.07 (m, 2H), 2.06-1.95 (m, 2H), 1.88-1.75 (m, 2H), 1.74-1.61 (m, 2H), 1.23 (s, 1H) |
| 67 | 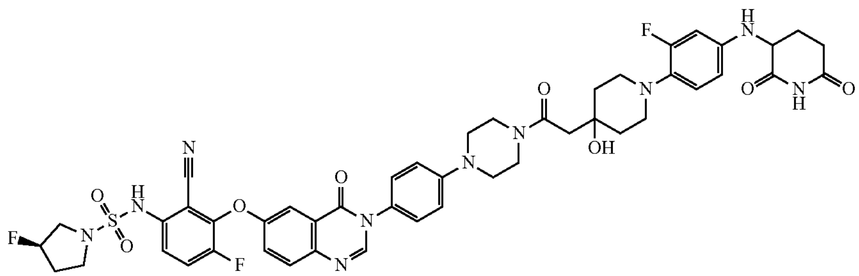 [SMILES: N#Cc1c(NS(=O)(=O)N2CC[C@@H](F)C2)ccc(F)c1Oc1ccc2ncn(-c3ccc(N4CCN(C(=O)CC5(O)CCN(c6ccc(NC7CCC(=O)NC7=O)cc6F)CC5)CC4)cc3)c(=O)c2c1] | (3R)-N-{2-cyano-3-[(4-{4-[2-(1-{4-[2-(2,6-dioxopiperidin-3-yl)amino]-2-fluorophenyl}-4-hydroxypiperidin-4-yl}acetyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.79 (s, 2H), 8.27 (s, 1H), 7.87-7.75 (m, 2H), 7.71 (d, 1H), 7.49 (d, 1H), 7.13-7.28 (m, 4H), 7.13-7.06 (m, 2H), 6.86 (t, J = 9.3 Hz, 1H), 6.50 (m, 1H), 6.42 (m, 1H), 5.78 (d, J = 7.6 Hz, 1H), 5.38-5.24 (d, J = 3.7 Hz, 1H), 4.86 (s, 1H), 4.25 (d, 1H), 3.77 (s, 1H), 3.75-3.64 (m, 4H), 3.42 (d, J = 4.9 Hz, 3H), 3.28-3.23 (t, J = 5.3 Hz, 6H), 2.89 (d, 4H), 2.74 (m, 1H), 2.63-2.53 (m, 3H), 2.09 (d, 3H), 1.86-1.71 (m, 3H), 1.67 (d, J = 12.6 Hz, 2H), 1.24 (s, 1H) |
| 68 | 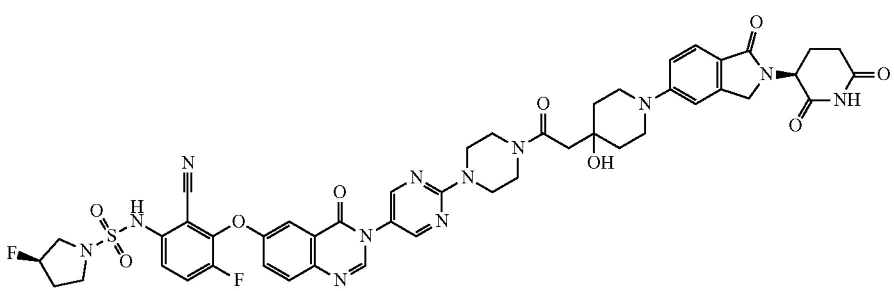 [SMILES: N#Cc1c(NS(=O)(=O)N2CC[C@@H](F)C2)ccc(F)c1Oc1ccc2ncn(-c3cnc(N4CCN(C(=O)CC5(O)CCN(c6ccc7c(c6)CN([C@H]6CCC(=O)NC6=O)C7=O)CC5)CC4)nc3)c(=O)c2c1] | (3R)-N-{2-cyano-3-[{2-(4-[2-(1-{2-[(3S)-2,6-dioxopiperidin-3-yl]-1-oxo-2,3-dihydro-1H-isoindol-5-yl}-4-hydroxypiperidin-4-yl}acetyl)piperazin-1-yl]pyrimidin-5-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.96 (s, 1H), 10.36 (s, 1H), 8.56 (s, 2H), 8.33 (s, 1H), 7.85 (d, J = 8.9 Hz, 1H), 7.74 (m, 1H), 7.51 (t, J = 8.1 Hz, 2H), 7.42 (d, J = 3.0 Hz, 1H), 7.07 (d, J = 9.0 Hz, 2H), 5.39-5.25 (d, J = 56.0 Hz, 1H), 5.05-5.00 (m, 2H), 4.32 (d, J = 16.8 Hz, 1H), 4.20 (d, J = 16.9 Hz, 1H), 3.87-3.79 (m, 4H), 3.67-3.62 (m, 6H), 3.45 (m, 3H), 3.25 (t, J = 10.7 Hz, 2H), 2.97-2.84 (m, 1H), 2.59 (s, 3H), 2.44- |

| Cmp. No. | Structure | IUPAC Name | ¹H NMR |
|---|---|---|---|
| 69 | 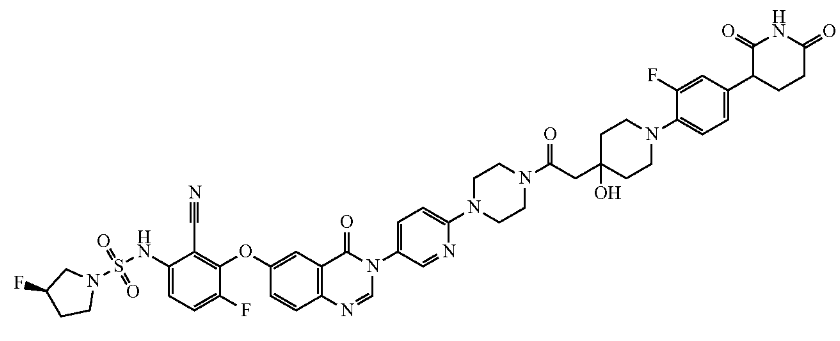 [SMILES: N#Cc1c(NS(=O)(=O)N2CC[C@@H](F)C2)ccc(F)c1Oc1ccc2ncn(-c3ccc(N4CCN(C(=O)CC5(O)CCN(c6ccc(C7CCC(=O)NC7=O)cc6F)CC5)CC4)nc3)c(=O)c2c1] | (3R)-N-{2-cyano-3-[(3-{6-[4-(2-{1-[4-(2,6-dioxopiperidin-3-yl)-2-fluorophenyl]-4-hydroxypiperidin-4-yl}acetyl)piperazin-1-yl]pyridin-3-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.83 (s, 1H), 8.35-8.17 (m, 1H), 7.82 (d, J = 8.5 Hz, 3H), 7.78-7.65 (m, 1H), 7.64-7.55 (m, 1H), 7.45-7.35 (m, 1H), 7.20 (s, 2H), 7.05-6.93 (m, 5H), 5.42-5.12 (m, 1H), 4.93 (s, 1H), 3.83-3.79 (m, 1H), 3.75-3.69 (m, 3H), 3.68-3.59 (m, 6H), 3.57-3.46 (m, 1H), 3.45-3.18 (m, 4H), 3.12-2.95 (m, 3H), 2.72-2.59 (m, 2H), 2.48-2.42 (m, 1H), 2.28-1.95 (m, 3H), 1.89-1.65 (m, 3H), 1.23 (s, 1H) |
| 70 | 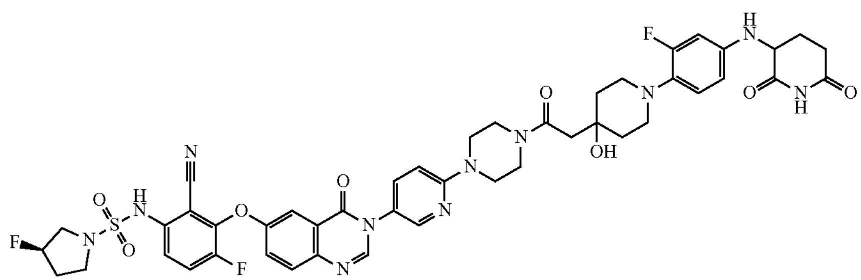 [SMILES: N#Cc1c(NS(=O)(=O)N2CC[C@@H](F)C2)ccc(F)c1Oc1ccc2ncn(-c3ccc(N4CCN(C(=O)CC5(O)CCN(c6ccc(NC7CCC(=O)NC7=O)cc6F)CC5)CC4)nc3)c(=O)c2c1] | (3R)-N-(2-cyano-3-{[3-(6-{4-[2-(1-{4-[(2,6-dioxopiperidin-3-yl)amino]-2-fluorophenyl}-4-hydroxypiperidin-4-yl)acetyl]piperazin-1-yl}pyridin-3-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.79 (s, 2H), 8.30 (s, 1H), 8.24 (d, J = 2.7 Hz, 1H), 7.88-7.76 (m, 2H), 7.73 (d, 2H), 7.49 (m, 1H), 7.41 (d, J = 3.0 Hz, 2H), 7.00 (d, J = 9.1 Hz, 1H), 6.86 (t, J = 9.3 Hz, 1H), 6.50 (m, 1H), 6.42 (m, 1H), 5.79 (s, 1H), 5.38-5.25 (s, 1H), 4.86 (s, 1H), 4.26 (d, 1H), 3.76 (d, J= 1.4 Hz, 1H), 3.72-3.58 (m, 9H), 3.42 (d, J = 4.9 Hz, 3H), 2.93 (d, J = 10.5 Hz, 4H), 2.89-2.82 (m, 1H), 2.74 (d, 3H), 2.63-2.02 (m, 3H), 1.92-1.72 (m, 1H), 1.68 (d, J = 12.6 Hz, 2H), 1.45 (d, J = 12.6 Hz, 2H), 1.24 (s, 1H) |

TABLE 1-continued

| Cmp. No. | Structure | IUPAC Name | 1H NMR |
|---|---|---|---|
| 71 | 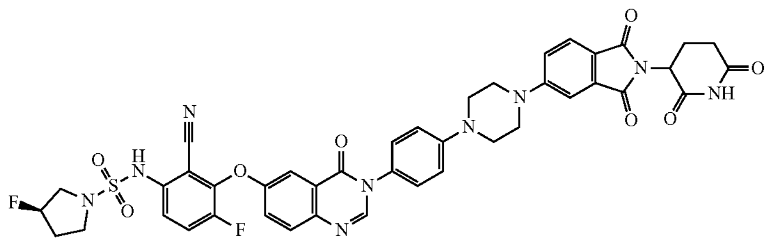 [SMILES: N#Cc1c(NS(=O)(=O)N2CC[C@@H](F)C2)ccc(F)c1Oc1ccc2ncn(-c3ccc(N4CCN(c5ccc6c(c5)C(=O)N(C5CCC(=O)NC5=O)C6=O)CC4)cc3)c(=O)c2c1] | (3R)-N-(2-cyano-3-{[3-(4-{4-[2-(2,6-dioxopiperidin-3-yl)-1,3-dioxo-2,3-dihydro-1H-isoindol-5-yl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO-d6) δ 11.08 (s, 1H), 10.39-10.22 (m, 1H), 8.27 (s, 1H), 7.88-7.78 (m, 2H), 7.74-7.69 (m, 2H), 7.51 (dd, J = 4.0, 9.2 Hz, 1H), 7.42 (d, J = 2.8 Hz, 2H), 7.38-7.30 (m, 3H), 7.12 (d, J = 9.2 Hz, 2H), 5.41-5.21 (m, 1H), 5.08 (dd, J = 5.2, 12.8 Hz, 1H), 3.65 (d, J = 5.6 Hz, 4H), 3.53-3.35 (m, 8H), 2.95-2.83 (m, 1H), 2.64-2.54 (m, 2H), 2.19-1.97 (m, 3H) |
| 72 | 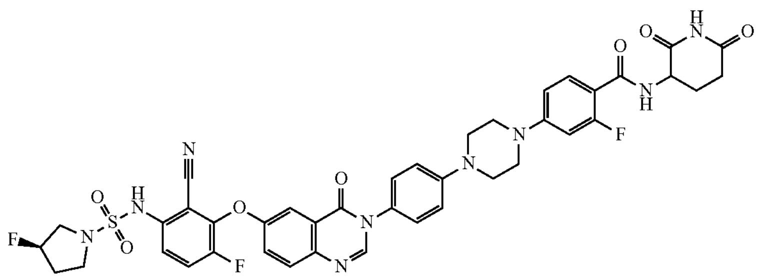 [SMILES: N#Cc1c(NS(=O)(=O)N2CC[C@@H](F)C2)ccc(F)c1Oc1ccc2ncn(-c3ccc(N4CCN(c5ccc(C(=O)NC6CCC(=O)NC6=O)c(F)c5)CC4)cc3)c(=O)c2c1] | 4-[4-(4-{6-[2-cyano-6-fluoro-3-{[(3R)-3-fluoropyrrolidin-1-yl]sulfonyl}amino)phenoxy]-4-oxo-3,4-dihydroquinazolin-3-yl}phenyl)piperazin-1-yl]-N-(2,6-dioxopiperidin-3-yl)-2-fluorobenzamide | 1H NMR (400 MHz, DMSO-d6) δ 10.85 (s, 1H), 10.34 (s, 1H), 8.27 (s, 1H), 8.11-8.05 (m, 1H), 7.91-7.80 (m, 1H), 7.75-7.63 (m, 2H), 7.52 (dd, J = 4.4, 9.2 Hz, 1H), 7.42 (d, J = 3.2 Hz, 1H), 7.36 (d, J = 8.8 Hz, 2H), 7.13 (d, J = 8.8 Hz, 2H), 6.94-6.83 (m, 2H), 5.42-5.22 (m, 1H), 4.80-4.69 (m, 1H), 3.54-3.42 (m, 7H), 3.41-3.36 (m, 5H), 2.83-2.71 (m, 1H), 2.45-2.37 (m, 1H), 2.20-2.01 (m, 4H) |
| 83 | 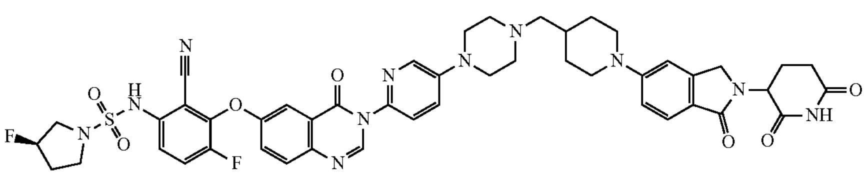 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)cn3)c(=O)c2c1] | (3R)-N-{2-cyano-3-{[5-[4-({1-[2-(2,6-dioxopiperidin-3-yl)-1-oxo-2,3-dihydro-1H-isoindol-5-yl]piperidin-4-yl}methyl)piperazin-1-yl]pyridin-2-yl}-4-oxo-3,4-dihydroquinazolin-6-yl]oxy]-4-fluorophenyl}-3-fluoropyrrolidine-1-sulfonamide | 1H NMR (400 MHz, DMSO-d6) δ 10.96 (s, 1H), 8.45 (s, 1H), 8.31 (d, J = 2.5 Hz, 1H), 7.85 (d, J = 9.0 Hz, 1H), 7.76 (m, 2H), 7.61 (d, J = 3.5 Hz, 2H), 7.55 (m, 1H), 7.50 (m, 2H), 7.05 (d, J = 2.2 Hz, 1H), 5.38-5.24 (d, J = 56 Hz, 1H), 5.05 (m, 1H), 4.33 (d, J = 16.9 Hz, 1H), 4.20 (d, J = 16.9 Hz, 1H), 3.91 (d, J = 12.5 Hz, 2H), 3.50-3.37 (m, 7H), 3.25(m, 2H), 2.88 (m, 6H), 2.78 (s, 1H), 2.64 (m, 1H), 2.37(m, 1H), 2.13 (m, 2H), 2.06 (d, J = 7.5 Hz, 2H), 1.98 (m, 1H), 1.24 (m, 4H) |

TABLE 1-continued

| Cmp. No. | Structure | IUPAC Name | ¹H NMR |
|---|---|---|---|
| 84 | 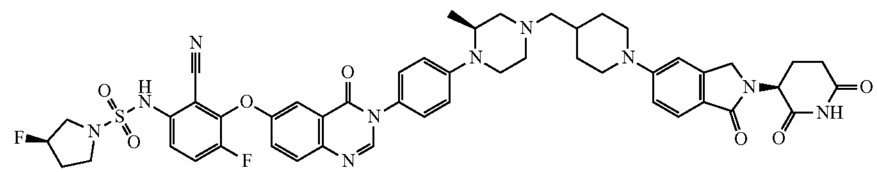 [SMILES: C[C@H]1CN(CC2CCN(c3ccc4c(c3)CN([C@H]3CCC(=O)NC3=O)C4=O)CC2)CCN1c1ccc(-n2cnc3ccc(Oc4c(F)ccc(NS(=O)(=O)N5CC[C@@H](F)C5)c4C#N)cc3c2=O)cc1] | (3R)-N-{2-cyano-3-[(3-(4-[(2S)-4-[(1-{2-[(3S)-2,6-dioxopiperidin-3-yl]-1-oxo-2,3-dihydro-1H-isoindol-5-yl}piperidin-4-yl)methyl]-2-methylpiperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.96 (s, 1H), 10.21 (s, 1H), 8.27 (s, 1H), 7.88-7.75 (m, 2H), 7.70-7.60 (m, 1H), 7.59 (s, 2H), 7.42 (d, J = 3.0 Hz, 1H), 7.33 (d, J = 8.4 Hz, 2H), 7.09-6.98 (m, 4H), 5.37-5.27 (d, J = 13.1, 40 Hz, 1H), 5.24 (s, 1H), 4.32 (d, J = 16.9 Hz, 1H), 4.20 (d, J = 16.8 Hz, 2H), 4.12 (s, 3H), 3.49 (s, 2H), 3.41 (s, 2H), 3.06 (s, 1H), 2.86 (t, J = 12.9 Hz, 8H), 2.58 (d, J = 17.0 Hz, 2H), 2.13 (s, 4H), 2.00-1.92 (m, 3H), 1.83 (s, 2H), 1.23 (s, 3H), 1.10 (d, J = 6.2 Hz, 3H) |
| 85 | 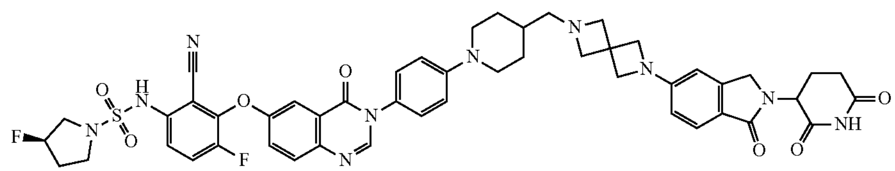 [SMILES: N#Cc1c(NS(=O)(=O)N2CC[C@@H](F)C2)ccc(F)c1Oc1ccc2ncn(-c3ccc(N4CCC(CN5CC6(C5)CN(c5ccc7c(c5)CN(C5CCC(=O)NC5=O)C7=O)C6)CC4)cc3)c(=O)c2c1] | (3R)-N-{2-cyano-3-[(3-{4-[4-({6-[2-(2,6-dioxopiperidin-3-yl)-1-oxo-2,3-dihydro-1H-isoindol-5-yl}-2,6-diazaspiro[3.3]heptan-2-yl}methyl)piperidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.95 (s, 1H), 10.35 (s, 1H), 10.25 (s, 1H), 8.63 (s, 2H), 8.26 (s, 1H), 7.84 (s, 1H), 7.84 (d, J = 8.9 Hz, 1H), 7.72-7.56 (m, 1H), 7.52 (d, J = 8.3 Hz, 2H), 7.43 (d, J = 2.9 Hz, 1H), 7.32 (d, J = 8.9 Hz, 2H), 7.07 (d, J = 8.9 Hz, 2H), 6.59 (s, 1H), 6.53-6.40 (m, 1H), 5.39 (s, OH), 5.26 (s, OH), 5.04-4.85 (m, 1H), 4.41 (s, 2H), 4.32 (d, J = 16.8 Hz, 2H), 4.20 (d, J = 17.5 Hz, 2H), 4.05 (s, 2H), 3.83 (d, J = 12.4 Hz, 2H), 3.68-3.56 (m, 3H), 3.52 (s, 1H), 3.45 (s, 2H), 3.14-3.05 (m, 5H), 2.93-2.84 (m, 1H), 2.76-2.60 (m, 2H), 2.58 (d, J = 25.7 Hz, 1H), 2.19-2.07 (m, 1H), 1.79 (d, J = 11.6 Hz, 3H), 1.27-1.05 (m, 1H) |
| 86 | 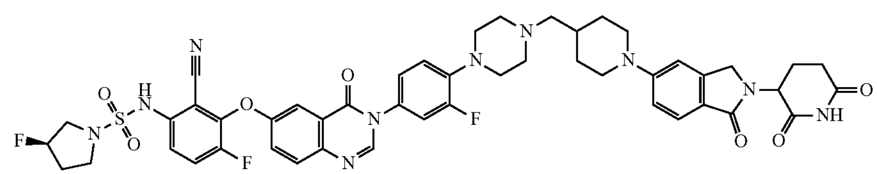 | (3R)-N-{2-cyano-3-[(3-(4-[1-[2-(2,6-dioxopiperidin-3-yl)-1-oxo-2,3-dihydro-1H-isoindol-5-yl]piperidin-4-yl}methyl)piperazin-1-yl]-3-fluorophenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.95 (s, 1H), 8.29 (s, 1H), 7.83 (d, J = 8.9 Hz, 1H), 7.70 (dd, J = 8.9, 2.9 Hz, 2H), 7.55-7.39 (m, 4H), 7.31 (d, J = 8.7 Hz, 1H), 7.21 (d, J = 8.9 Hz, 2H), 7.06 (d, J = 8.4 Hz, 2H), 5.37-5.23 (s, 1H), 5.05 (dd, J = 13.2, 5.1 Hz, 1H), 4.33 (d, J = 16.9 Hz, 1H), 4.20 (d, J = 16.8 Hz, 1H), 3.91 (d, J = 12.2 Hz, 1H) |

TABLE 1-continued

| Cmp. No. | Structure | IUPAC Name | ¹H NMR |
|---|---|---|---|
| 87 | 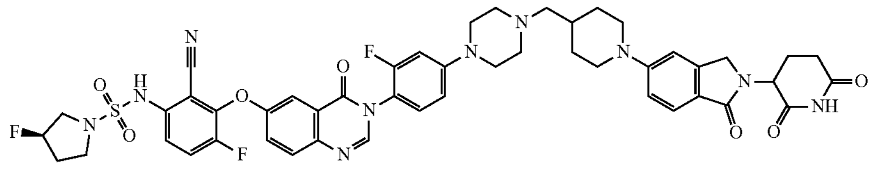 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)cc3F)c(=O)c2c1] | fluoropyrrolidine-1-sulfonamide | 2H), 3.15 (s, 4H), 2.98-2.80 (m, 4H), 2.59 (d, J = 16.6 Hz, 2H), 2.42-2.34 (m, 2H), 2.12 (s, 1H), 2.04-1.93 (m, 4H), 1.83 (d, J = 12.8 Hz, 3H), 1.24 (s, 7H) |
| 88 | 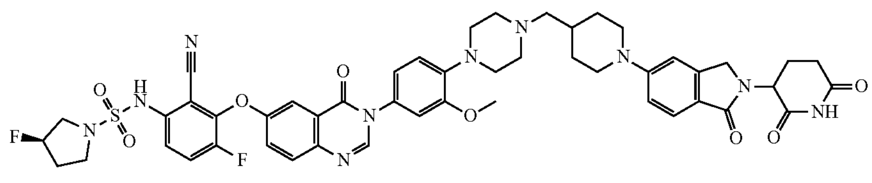 [SMILES: COc1cc(-n2cnc3ccc(Oc4c(F)ccc(NS(=O)(=O)N5CC[C@@H](F)C5)c4C#N)cc3c2=O)ccc1N1CCN(CC2CCN(c3ccc4c(c3)CN(C3CCC(=O)NC3=O)C4=O)CC2)CC1] | (3R)-N-{2-cyano-3-[(3-{4-[4-({1-[2-(2,6-dioxopiperidin-3-yl)-1-oxo-2,3-dihydro-1H-isoindol-5-yl]piperidin-4-yl}methyl)piperazin-1-yl]-2-fluorophenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 9.62 (s, 1H), 8.14 (s, 2H), 7.87 (s, 1H), 7.78-7.61 (m, 2H), 7.51 (t, J = 7.8 Hz, 3H), 7.42 (d, J = 3.0 Hz, 1H), 7.28-6.97 (m, 1H), 7.04-6.95 (m, 4H), 5.30-5.20(d, J = 30 Hz, 1H), 5.01 (d, J = 12.9 Hz, 2H), 4.25-3.85 (m, 6H), 3.83 (d, J = 1.9 Hz, 3H), 3.66-3.48 (m, 10H), 3.34 (s, 1H), 2.91-2.75 (m, 3H), 2.61 (t, J = 6.0 Hz, 4H), 2.40 (s, 5H), 2.01-1.87 (m, 7H), 1.23 (s, 1H) |
| 89 | 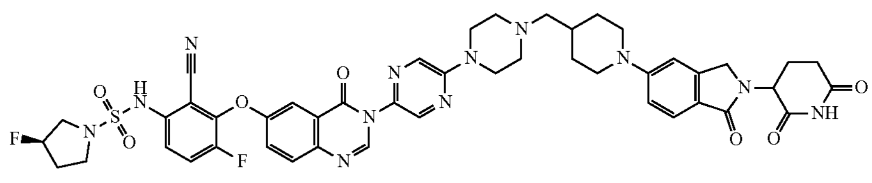 [SMILES: N#Cc1c(NS(=O)(=O)N2CC[C@@H](F)C2)ccc(F)c1Oc1ccc2ncn(-c3cnc(N4CCN(CC5CCN(c6ccc7c(c6)CN(C6CCC(=O)NC6=O)C7=O)CC5)CC4)cn3)c(=O)c2c1] | (3R)-N-{2-cyano-3-[(3-{4-[4-({1-[2-(2,6-dioxopiperidin-3-yl)-1-oxo-2,3-dihydro-1H-isoindol-5-yl]piperidin-4-yl}methyl)piperazin-1-yl]-3-methoxyphenyl}-4-oxo-3,4-dihydroquinazolin-6-yl)oxy]-4-fluorophenyl}-3-fluoropyrrolidine-1-sulfonamide | 1H NMR (400 MHz, DMSO-d₆) δ 10.97 (s, 1H), 10.24-9.50 (s, 1H), 8.30 (s, 1H), 7.80(s,1H), 7.70(m, 1H),7.61(s, 1H), 7.45 (m, 1H), 7.30(m, 1H), 7.07 (d, J = 7.7 Hz, 4H), 5.40-5.35 (d, J = 56 Hz, 1H), 5.05 (m, 1H), 4.33 (d, J = 16.9 Hz, 1H), 3.91 (d, J = 12.3 Hz, 4H), 3.43 (s, 1H), 3.24 (d, J = 7.3 Hz, 1H), 3.13 (m, 2H), 3.02 (t, J = 11.6 Hz, 1H), 2.88 (s, 4H), 2.63 (m, 4H), 2.44-2.33 (m, 2H), 2.09-1.84 (m, 6H) 1.58 (d, J = 10.8 Hz, 1H), 1.24 (s, 4H), 0.85 (d, J = 7.5 Hz, 1H) |
| | | (3R)-N-{2-cyano-3-[(5-{4-[2-(2,6-dioxopiperidin-3-yl)-1-oxo-2,3-dihydro-1H-isoindol-5-yl]piperidin-4-yl}methyl)piperazin-1-yl]pyrazin-2-yl}-4-oxo-3,4-dihydroquinazolin-6-yl)oxy]-4-fluorophenyl}-3- | ¹H NMR (400 MHz, DMSO-d₆) δ 10.96 (s, 1H), 8.27 (s, 1H), 7.83 (s, 3H), 7.88-7.66 (m, 2H), 7.56-7.39 (m, 1H), 7.34 (d, J = 8.4 Hz, 2H), 7.11-6.98 (m, 4H), 5.40-5.30 (d, J = 30 Hz 1H), 5.05-5.03 (m, 1H), 4.33 (d, J = 16.9 Hz, 3H), 4.20 (d, J = 16.9 Hz, 2H), 4.13 (s, 1H), 3.91 (d, J = 12.4 Hz, 2H), 3.51 (s, 1H), 2.87 (t, J = 12.3 |

| Cmp. No. | Structure | IUPAC Name | 1H NMR |
|---|---|---|---|
| 90 | 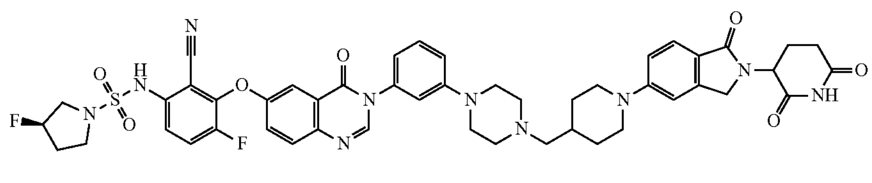 [SMILES: N#Cc1c(NS(=O)(=O)N2CC[C@@H](F)C2)ccc(F)c1Oc1ccc2ncn(-c3cccc(N4CCN(CC5CCN(c6ccc7c(c6)CN(C6CCC(=O)NC6=O)C7=O)CC5)CC4)c3)c(=O)c2c1] | (3R)-N-{2-cyano-3-[(3-{3-[4-({1-[2-(2,6-dioxopiperidin-3-yl)-1-oxo-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | Hz, 1H), 2.62 (s, 3H), 2.55 (s,3H), 2.42-2.40 (m, 3H), 2.39-2.28 (m, 1H), 2.16 (s, 1H), 2.02-1.91 (m, 1H), 1.84 (d, J = 12.5 Hz, 2H), 1.48 (s, 1H), 1.27 (s, 7H), 1.11 (d, J = 6.2 Hz, 3H), 0.85 (q, J = 7.4, 6.7 Hz, 1H) |
| 91 | 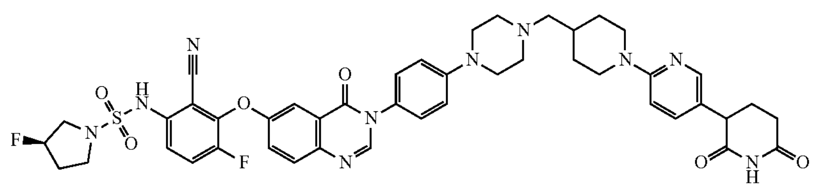 [SMILES: N#Cc1c(NS(=O)(=O)N2CC[C@@H](F)C2)ccc(F)c1Oc1ccc2ncn(-c3ccc(N4CCN(CC5CCN(c6ccc(C7CCC(=O)NC7=O)cn6)CC5)CC4)cc3)c(=O)c2c1] | (3R)-N-{2-cyano-3-[(3-{4-[4-({1-[5-(2,6-dioxopiperidin-3-yl)pyridin-2-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | 1H NMR (400 MHz, DMSO-d6) δ 10.95 (s, 1H), 8.28 (d, J = 1.4 Hz, 1H), 7.87-7.80 (m, 1H), 7.71 (dd, J = 8.9, 3.1 Hz, 2H), 7.51 (d, J = 8.6 Hz, 1H), 7.44-7.34 (m, 3H), 7.12-7.06 (d, J = 8.9 Hz, 4H), 6.91 (d, J = 8.0 Hz, 1H), 5.37 (s, 1H), 5.05 (dd, J = 13.6, 4.9 Hz, 1H), 4.33-4.20 (d, J = 17.0 Hz, 2H), 3.90 (d, J = 12.4 Hz, 2H), 3.45 (s, 1H), 3.35 (s, 2H), 2.87 (q, J = 12.4, 10.8 Hz, 4H), 2.59 (d, J = 15.6 Hz, 2H), 2.52 (s, 2H), 2.37-2.04 (m, 5H), 1.82 (d, J = 13.1 Hz, 2H), 1.24 (s, 3H) |
| | | | 1H NMR (400 MHz, DMSO-d6) δ 10.83 (s, 1H), 9.96 (s, 1H), 8.26 (s, 1H), 7.96 (d, J = 2.5 Hz, 1H), 7.86 - 7.82 (m, 1H), 7.81-7.75 (m, 1H), 7.74-7.68 (m, 1H), 7.55 - 7.48 (m, 1H), 7.45-7.35 (m, 4H), 7.13 (d, J = 9.0 Hz, 2H), 6.84 (d, J = 8.9 Hz, 1H), 5.45-5.22 (m, 1H), 4.30 (d, J = 12.7 Hz, 2H), 3.81-3.71 (m, 1H), 3.55-3.39 (m, 5H), 3.35-3.25 (m, 4H), 3.10 (m, 3H), 2.93-2.76 (m, 4H), 2.75-2.65 (m, 1H), 2.59-2.52 (m, 1H), 2.26-2.15 (m, 2H), 2.13-1.92 (m, 3H), 1.82 (d, J = 12.6 Hz, 2H), 1.26-1.12 (m, 2H) |

TABLE 1-continued

| Cmp. No. | Structure | IUPAC Name | ¹H NMR |
|---|---|---|---|
| 92 | 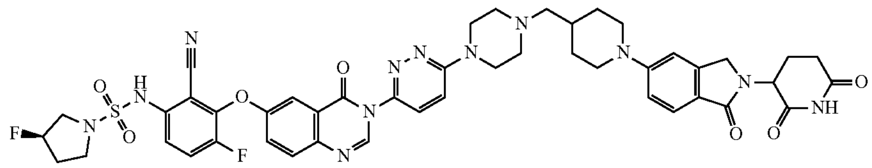 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)nn3)c(=O)c2c1] | (3R)-N-{2-cyano-3-[(3-{6-[4-({1-[2-(2,6-dioxopiperidin-3-yl)-1-oxo-2,3-dihydro-1H-isoindol-5-yl]piperidin-4-yl}methyl)piperazin-1-yl]pyridazin-3-yl]-4-oxo-3,4-dihydroquinazolin-6-yl)oxy]-4-fluorophenyl}-3-fluoropyrrolidine-1-sulfonamide | ¹H NMR (400 MHz, DMSO-$d_6$) δ 10.97 (s, 1H), 10.34 (s, 1H), 8.77 (s, 1H), 8.49 (s, 1H), 7.92-7.66 (m, 3H), 7.61-7.45 (m, 4H), 7.07 (d, J = 7.7 Hz, 2H), 5.40-5.35 (d, J = 15 Hz, 1H), 5.22 (s, 1H), 4.33 (d, J = 17.1 Hz, 2H), 4.20 (d, J = 16.8 Hz, 5H), 3.91 (d, J = 12.4 Hz, 1H), 3.68 - 3.56 (m, 1H), 3.38 (s, 2H), 3.13 (q, J = 7.6 Hz, 1H), 2.89 (q, J = 14.0, 12.8 Hz, 6H), , 2.62 (s, 1H), 2.55 (s, 1H), 2.13 (d, J = 8.1 Hz, 1H), 2.01 - 1.86 (m, 6H), 1.27 (td, J = 7.8, Hz, 9H) |
| 93 | 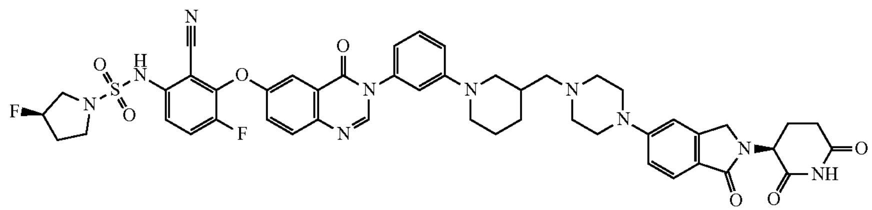 [SMILES: N#Cc1c(NS(=O)(=O)N2CC[C@@H](F)C2)ccc(F)c1Oc1ccc2ncn(-c3cccc(N4CCCC(CN5CCN(c6ccc7c(c6)CN([C@H]6CCC(=O)NC6=O)C7=O)CC5)C4)c3)c(=O)c2c1] | (3R)-N-{2-cyano-3-[(3-(3-{[(4-{2-[(3S)-2,6-dioxopiperidin-3-yl]-1-oxo-2,3-dihydro-1H-isoindol-5-yl]piperidin-1-yl]methyl}phenyl)-4-oxo-3,4-dihydroquinazolin-6-yl)oxy]-4-fluorophenyl}-3-fluoropyrrolidine-1-sulfonamide | ¹H NMR (400 MHz, DMSO-$d_6$) δ 10.96 (s, 1H), 8.26 (s, 1H), 7.83 (d, J = 8.9 Hz, 1H), 7.70 (dd, J = 8.9, 3.0 Hz, 1H), 7.55 (d, J = 8.4 Hz, 1H), 7.46 (s, 1H), 7.41 (d, J = 2.9 Hz, 1H), 7.33 (d, J = 8.6 Hz, 2H), 7.08 (dd, J = 20.0, 9.4 Hz, 4H), 5.37 (s, 1H), 5.24 (s, 1H), 5.06 (dd, J = 13.3, 5.0 Hz, 1H), 4.34 (d, J = 17.0 Hz, 1H), 4.22 (d, J = 17.0 Hz, 1H), 3.77 (d, J = 12.3 Hz, 1H), 3.67 (d, J = 12.2 Hz, 1H), 3.47 (s, 2H), 3.39 (s, 4H), 2.98-2.79 (m, 2H), 2.63 (d, J = 11.3 Hz, 2H), 2.13 (s, 1H), 2.05 (s, 2H), 2.00-1.93 (m, 1H), 1.83 (s, 2H), 1.74 (s, 1H), 1.61 (d, J = 11.8 Hz, 1H), 1.26-1.16 (m, 2H) |
| 94 | 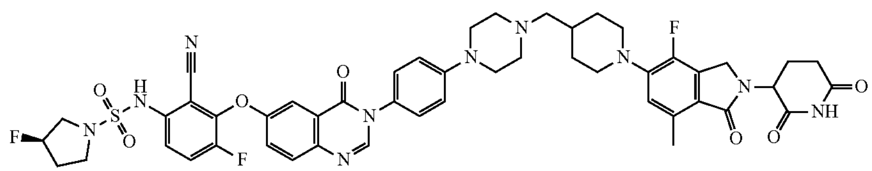 | (3R)-N-{2-cyano-3-[(3-(4-{1-[2-(2,6-dioxopiperidin-3-yl)-4-fluoro-7-methyl-1-oxo-2,3-dihydro-1H-isoindol-5-yl]piperidin-4-yl}methyl)piperazin-1-yl]phenyl)-4-oxo-3,4-dihydroquinazolin-6-yl)oxy]-4-fluorophenyl}-3-fluoropyrrolidine-1-sulfonamide | ¹H NMR (400 MHz, DMSO-$d_6$) δ 10.98 (s, 1H), 10.04 (s, 1H), 8.25 (s, 1H), 7.82 (d, J = 8.9 Hz, 1H), 7.69 (dd, J = 8.9, 3.0 Hz, 2H), 7.42 (dd, J = 13.2, 3.6 Hz, 2H), 7.35 (d, J = 8.5 Hz, 2H), 7.09 (d, J = 8.7 Hz, 2H), 6.91 (d, J = 7.4 Hz, 1H), 5.36 (d, J = 4.8 Hz, 1H), 5.26-5.19 (m, 1H), 4.40 (d, J = 16.9 Hz, 1H), 4.24 (d, J = 17.0 Hz, 1H), 3.55-3.42 (m, 2H), 3.37 (d, J = 7.6 Hz, 1H), 3.29-3.21 (m, |

| Cmp. No. | Structure | IUPAC Name | ¹H NMR |
|---|---|---|---|
| 95 | 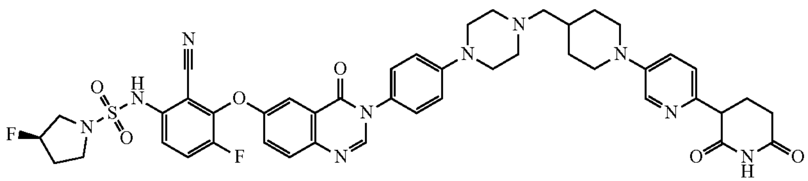 [SMILES: N#Cc1c(NS(=O)(=O)N2CC[C@@H](F)C2)ccc(F)c1Oc1ccc2ncn(-c3ccc(N4CCN(CC5CCN(c6ccc(C7CCC(=O)NC7=O)nc6)CC5)CC4)cc3)c(=O)c2c1] | (3R)-N-{2-cyano-3-[(3-{4-[4-({1-[6-(2,6-dioxopiperidin-3-yl)pyridin-3-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | 4H), 3.11 (m, 3H), 2.97-2.71 (m, 7H), 2.63-2.55 (m,1H), 2.54 (s, 4H), 2.47-2.34 (m, 2H), 2.17-2.03 (m, 2H), 2.04 (s, 1H), 1.96 (dq, J = 10.7, 5.2, 4.2 Hz, 3H), 1.33 (d, J = 12.1 Hz, 2H) |
|  |  |  | ¹H NMR (400 MHz, DMSO-d₆) δ 10.80 (s, 1H), 9.97 (s, 1H), 8.28-8.20 (m, 2H), 7.87-7.64 (m, 3H), 7.52-7.45 (m, 1H), 7.44-7.29 (m, 4H), 7.22-7.05 (m, 3H), 5.37 (d, J = 3.0 Hz, 1H), 3.96-3.85 (m, 1H), 3.77 (d, J = 12.5 Hz, 2H), 3.49 (s, 1H), 3.47-3.37 (m, 3H), 3.31-3.28 (m, 1H), 3.22-2.96 (m, 4H), 2.89-2.69 (m, 4H), 2.65-2.55 (m, 2H), 2.25-1.74 (m, 8H), 1.42-1.21 (m, 4H), 0.96-0.76 (m, 1H) |
| 96 | 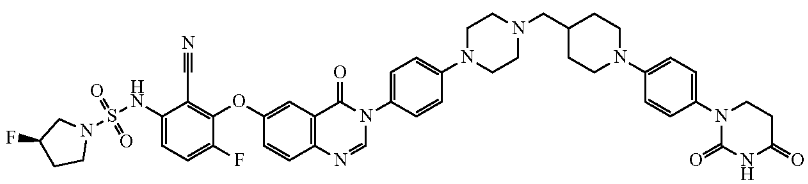 | (3R)-N-{2-cyano-3-[(3-(4-[4-({1-[4-(2,4-dioxo-1,3-diazinan-1-yl)phenyl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.27 (s, 1H), 10.03 (s, 1H), 8.25 (s, 1H), 7.82 (d, J = 8.9 Hz, 1H), 7.79-7.55 (m, 2H), 7.51-7.29 (m, 4H), 7.21-7.07 (m, 4H), 6.98-6.91 (m, 2H), 5.45-5.15 (m, 1H), 3.78-3.65 (m, 4H), 3.52-3.38 (m, 3H), 3.36-3.21 (m, 7H), 2.81 (s, 4H), 2.75-2.65 (m, 4H), 2.25-1.99 (m, 2H), 1.95-1.75 (m, 3H), 1.33-1.19 (m, 2H) |

| Cmp. No. | Structure | IUPAC Name | $^1$H NMR |
|---|---|---|---|
| 97 | 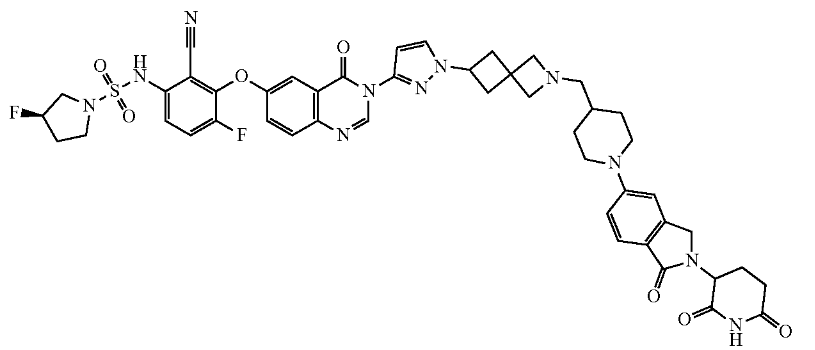 [SMILES: N#Cc1c(NS(=O)(=O)N2CC[C@@H](F)C2)ccc(F)c1Oc1ccc2ncn(-c3ccn(C4CC5(C4)CN(CC4CCN(c6ccc7c(c6)CN(C6CCC(=O)NC6=O)C7=O)CC4)C5)n3)c(=O)c2c1] | (3R)-N-{2-cyano-3-[(3-{1-[2-({1-[2-(2,6-dioxopiperidin-3-yl)-1-oxo-2,3-dihydro-1H-isoindol-5-yl]piperidin-4-yl}methyl)-2-azaspiro[3.3]heptan-6-yl]-1H-pyrazol-3-yl}-4-oxo-3,4-dihydroquinazolin-6-yl)oxy]-4-fluorophenyl}-3-fluoropyrrolidine-1-sulfonamide | $^1$H NMR (400 MHz, DMSO-d$_6$) δ 10.96 (s, 1H), 8.54 (s, 1H), 7.99 (d, J = 2.4 Hz, 1H), 7.84 (d, J = 8.9 Hz, 1H), 7.70-7.65 (m, 1H), 7.60 (t, J = 9.9 Hz, 2H), 7.52 (d, J = 8.8 Hz, 2H), 7.07 (d, J = 8.0 Hz, 2H), 6.68 (d, J = 2.4 Hz, 1H), 5.39-5.21 (d, J =54 Hz, 1H), 5.05-5.01 (m, 1H), 4.41 (s, 3H), 4.33 (d, J = 16.9 Hz, 2H), 4.20 (d, J = 16.9 Hz, 1H), 3.91 (d, J = 12.4 Hz, 2H), 3.54-3.38 (m, 4H), 3.24 (q, J = 8.9 Hz, 2H), 2.88 (q, J = 14.8, 12.1 Hz, 1H), 2.62 (s, 1H), 2.55 (s, 1H), 2.40-2.32 (m, 1H), 2.18 (s, 5H), 1.99 (s, 3H), 1.99 (d, J = 17.1 Hz, 2H), 1.83 (d, J = 12.9 Hz, 4H), 1.24 (s, 1H) |
| 98 | 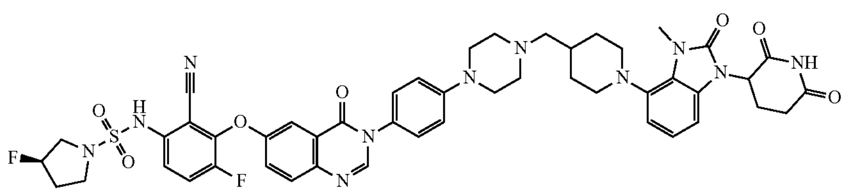 [SMILES: Cn1c(=O)n(C2CCC(=O)NC2=O)c2cccc(N3CCC(CN4CCN(c5ccc(-n6cnc7ccc(Oc8c(F)ccc(NS(=O)(=O)N9CC[C@@H](F)C9)c8C#N)cc7c6=O)cc5)CC4)CC3)c21] | (3R)-N-{2-cyano-3-[(3-{4-[4-({1-[2-(2,6-dioxopiperidin-3-yl)-3-methyl-2-oxo-2,3-dihydro-1H-1,3-benzodiazol-4-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | $^1$H NMR (400 MHz, DMSO-d$_6$) δ 11.12 (s, 1H), 8.25 (s, 1H), 7.83 (d, J = 8.9 Hz, 1H), 7.76 (m, 1H), 7.65 (m, 1H), 7.48 (m, 1H), 7.42 (m, 1H), 7.36 (d, J = 8.6 Hz, 2H), 7.10 (d, J = 8.7 Hz, 2H), 6.98 (m, 2H),5.36-5.23 (m,2H), 3.64 (s, 4H), 3.36 (s, 9H), 3.26 (m,3H), 3.19 (m, 4H), 2.89 (m, 5H), 2.74-2.62 (m, 7H), 2.66 (s, 1H), 2.21-1.95 (m, 2H), 1.88 (d, J=12.6 Hz, 3H), 1.50 (m, 3H), 1.29-1.21 (m, 5H), 0.83 (m, 1H) |

TABLE 1-continued

| Cmp. No. | Structure | IUPAC Name | ¹H NMR |
|---|---|---|---|
| 99 | 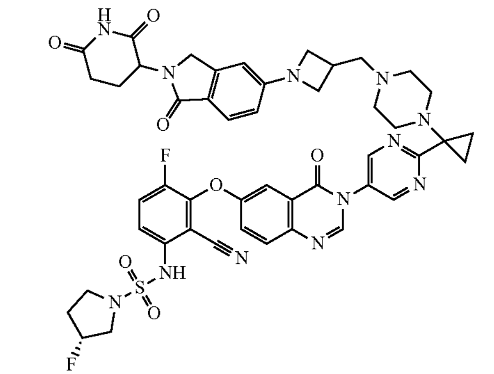 [SMILES: N#Cc1c(NS(=O)(=O)N2CC[C@@H](F)C2)ccc(F)c1Oc1ccc2ncn(-c3cnc(C4(N5CCN(CC6CN(c7ccc8c(c7)CN(C7CCC(=O)NC7=O)C8=O)C6)CC5)CC4)nc3)c(=O)c2c1] | (3R)-N-(2-cyano-3-[[3-(2-{1-[4-({1-[2-(2,6-dioxopiperidin-3-yl)-1-oxo-2,3-dihydro-1H-isoindol-5-yl]azetidin-3-yl}methyl)piperazin-1-yl]cyclopropyl}pyrimidin-5-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.95 (s, 1H), 8.93 (s, 2H), 8.40 (s, 1H), 7.85 (d, J = 8.9 Hz, 1H), 7.72-7.62 (m, 1H), 7.49-7.42 (m, 2H), 7.41 (d, J = 3.0 Hz, 1H), 7.34-7.24 (m, 1H), 6.56-6.44 (m, 2H), 5.19-5.15 (, J = 12 Hz, 1H), 5.04-5.03 (m, 1H), 4.32 (d, J = 17.0 Hz, 1H), 4.18 (d, J = 16.9 Hz, 1H), 4.09 (s, 2H), 3.65 (s, 2H), 2.93-2.81 (m, 16H), 2.59 (d, J = 16.5 Hz, 1H), 2.36-2.21 (m, 1H), 2.02-1.90 (m, 3H), 1.48-1.41 (m, 2H), 1.23 (d, J = 5.9 Hz, 3H) |
| 100 | 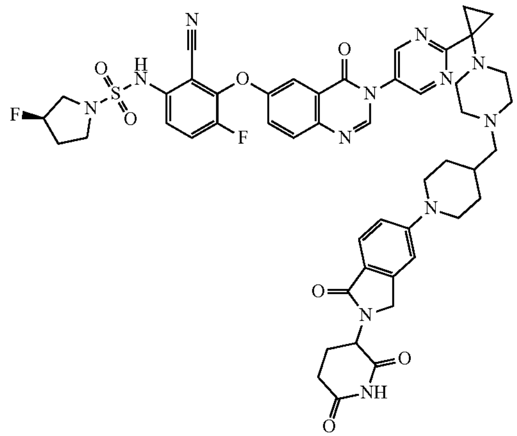 [SMILES: N#Cc1c(NS(=O)(=O)N2CC[C@@H](F)C2)ccc(F)c1Oc1ccc2ncn(-c3cnc(C4(N5CCN(CC6CCN(c7ccc8c(c7)CN(C7CCC(=O)NC7=O)C8=O)CC6)CC5)CC4)nc3)c(=O)c2c1] | (3R)-N-(2-cyano-3-[[3-(2-{1-[4-({1-[2-(2,6-dioxopiperidin-3-yl)-1-oxo-2,3-dihydro-1H-isoindol-5-yl]piperidin-4-yl}methyl)piperazin-1-yl]cyclopropyl}pyrimidin-5-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.97 (s, 1H), 9.24 (s, 2H), 8.94 (s, 1H), 8.40 (s, 1H), 7.85 (d, J = 8.9 Hz, 1H), 7.73-7.71 (m, 2H), 7.52 (d, J = 8.7 Hz, 1H), 7.41 (d, J = 3.0 Hz, 1H), 7.38-7.27 (m, 2H), 7.07 (d, J = 7.9 Hz, 2H), 5.37-5.19(m, J = 54 Hz, 1H), 5.05-5.01 (m, 1H), 4.33 (d, J = 16.9 Hz, 1H), 4.20 (d, J = 16.9 Hz, 1H), 3.91 (d, J = 12.4 Hz, 6H), 3.13 (s, 5H), 2.90-2.85 (m, 1H), 2.62 (s, 1H), 2.37-2.21 (m, 1H), 2.00 (s, 1H), 1.83 (d, J = 12.3 Hz, 3H), 1.45 (s, 2H), 1.24 (s, 9H) |

TABLE 1-continued

| Cmp. No. | Structure | IUPAC Name | ¹H NMR |
|---|---|---|---|
| 101 | 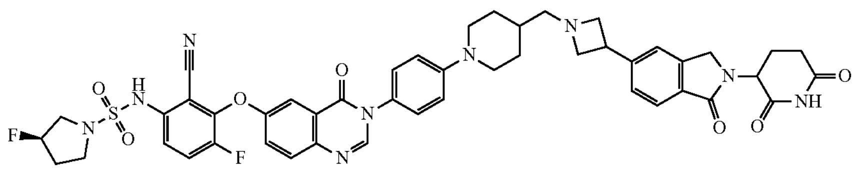 [SMILES: N#Cc1c(NS(=O)(=O)N2CC[C@@H](F)C2)ccc(F)c1Oc1ccc2ncn(-c3ccc(N4CCC(CN5CC(c6ccc7c(c6)CN(C6CCC(=O)NC6=O)C7=O)C5)CC4)cc3)c(=O)c2c1] | (3R)-N-{2-cyano-3-[(3-{4-[4-({3-[2-(2,6-dioxopiperidin-3-yl)-1-oxo-2,3-dihydro-1H-isoindol-5-yl]azetidin-1-yl}methyl)piperidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 11.01 (s, 1H), 10.33 (s, 1H), 8.49 (s, 1H), 8.23 (s, 1H), 7.81 (d, J = 8.9 Hz, 1H), 7.75 (s, 3H), 7.68 (dd, J = 13.1, 4.6 Hz, 1H), 7.59-7.32 (d, J = 8.7 Hz, 4H), 7.07 (d, J = 8.7 Hz, 2H), 5.34 (s, 1H), 5.21 (s, 1H), 4.16 (s, 6H), 3.84 (d, J = 12.2 Hz, 2H), 3.62 (s, 4H), 3.60-3.14 (dd, J = 7.4, 4.2 Hz, 5H), 2.93 (s, 2H), 2.77 (t, J = 11.9 Hz, 3H), 2.63 (s, 4H), 2.51 (s, 2H), 2.34 (s, 3H), 1.81 (d, J = 12.6 Hz, 3H), 1.31-1.22 (m, 32H), 0.84 (s, 1H) |
| 102 | 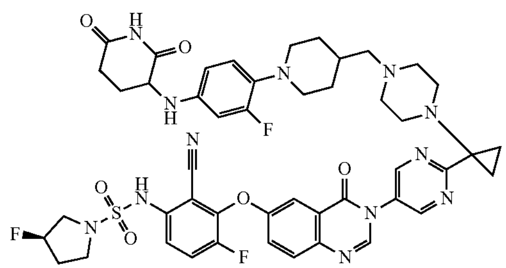 [SMILES: N#Cc1c(NS(=O)(=O)N2CC[C@@H](F)C2)ccc(F)c1Oc1ccc2ncn(-c3cnc(C4(N5CCN(CC6CCN(c7ccc(NC8CCC(=O)NC8=O)cc7F)CC6)CC5)CC4)nc3)c(=O)c2c1] | (3R)-N-[2-cyano-3-({3-[2-(1-{4-[(1-{4-[(2,6-dioxopiperidin-3-yl)amino]-2-fluorophenyl}piperidin-4-yl)methyl]piperazin-1-yl}cyclopropyl)pyrimidin-5-yl]-4-oxo-3,4-dihydroquinazolin-6-yl}oxy)-4-fluorophenyl]-3-fluoropyrrolidine-1-sulfonamide | ¹H NMR (400 MHz, DMSO-d₆) δ 10.79 (s, 1H), 9.18 (s, 1H), 8.94 (s, 2H), 8.40 (s, 1H), 7.85 (m, 1H), 7.72 (m, 1H), 7.41 (s, 3H), 6.84 (m, 1H), 6.57-6.46 (m, 2H), 5.82 (s, 1H), 5.21 (s, 1H), 4.26 (s, 2H), 3.83 (s, 5H), 3.12 (s, 10H), 2.74 (s, 4H), 2.08 (s, 2H), 1.83 (s, 7H), 1.47 (s, 4H), 1.37 (s, 3H) |
| 103 | 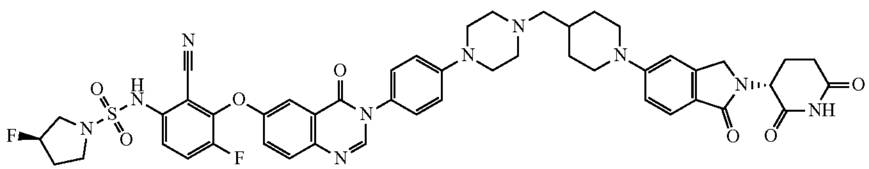 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN([C@@H]6CCC(=O)NC6=O)C7=O)CC5)CC4)cc3)c(=O)c2c1] | (3R)-N-(2-cyano-3-[{3-(4-{4-[((1-{2-[(3R)-2,6-dioxopiperidin-3-yl]-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.94 (s, 1H), 10.15-9.86 (m, 1H), 8.25 (s, 1H), 7.83 (d, J = 8.8 Hz, 1H), 7.70 (dd, J = 2.8, 8.9 Hz, 2H), 7.52 (d, J = 8.8 Hz, 1H), 7.48-7.40 (m, 2H), 7.36 (d, J = 8.8 Hz, 2H), 7.15-7.04 (m, 4H), 5.41-5.19 (m, 1H), 5.05 (dd, J = 5.2, 13.2 Hz, 1H), 4.39-4.27 (m, 1H), 4.25-4.16 (m, 1H), 3.91 (d, J = 12.0 Hz, 2H), 3.51-3.43 (m, 1H), 3.37 (d, J = 11.2 Hz, 4H), 3.31-3.24 (m, 3H), 2.99-2.72 (m, 7H), 2.62 (s, 1H), 2.57 (s, 2H), 2.45-2.37 (m, 1H), 2.15-2.01 (m, 2H), 2.01-1.89 (m, 2H), 1.84 (d, J = 13.2 Hz, 2H), 1.31-1.22 (m, 2H) |

TABLE 1-continued

| Cmp. No. | Structure | IUPAC Name | ¹H NMR |
|---|---|---|---|
| 104 | 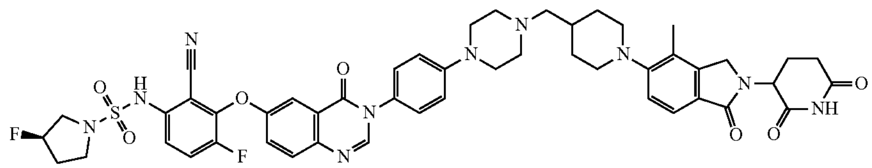 [SMILES: Cc1c(N2CCC(CN3CCN(c4ccc(-n5cnc6ccc(Oc7c(F)ccc(NS(=O)(=O)N8CC[C@@H](F)C8)c7C#N)cc6c5=O)cc4)CC3)CC2)ccc2c1CN(C1CCC(=O)NC1=O)C2=O] | (3R)-N-{2-cyano-3-[(3-{4-[4-({1-[2-(2,6-dioxopiperidin-3-yl)-4-methyl-1-oxo-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.98 (s, 1H), 8.23 (s, 2H), 7.79 (d, J = 8.8 Hz, 1H), 7.65 (d, J = 2.8 Hz, 1H), 7.63 (d, J = 3.2 Hz, 1H), 7.39-7.30 (m, 5H), 7.14 (d, J = 8.4 Hz, 1H), 7.06 (d, J = 9.2 Hz, 2H), 5.20 (d, J = 32 Hz, 1H), 5.09-5.08 (m, 1H), 4.33-4.17 (m, 2H), 4.02 (s, 2H), 3.36-3.25 (m, 9H), 2.95-2.83 (m, 1H), 2.81-2.43 (m, 10H), 2.23 (s, 3H), 2.11-1.73 (m, 6H), 1.36-1.33 (m, 2H) |
| 105 | 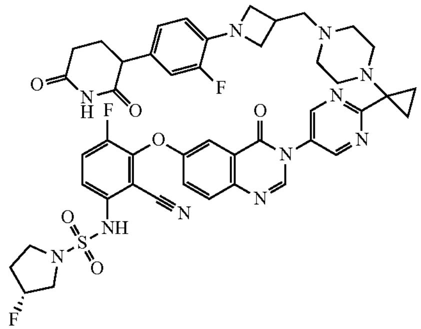 [SMILES: N#Cc1c(NS(=O)(=O)N2CC[C@@H](F)C2)ccc(F)c1Oc1ccc2ncn(-c3cnc(C4(N5CCN(CC6CN(c7ccc(C8CCC(=O)NC8=O)cc7F)C6)CC5)CC4)nc3)c(=O)c2c1] | (3R)-N-(2-cyano-3-[[3-(2-{1-[4-({1-[4-(2,6-dioxopiperidin-3-yl)-2-fluorophenyl]azetidin-3-yl}methyl)piperazin-1-yl]pyrimidin-5-yl}-4-oxo-3,4-dihydroquinazolin-6-yl]oxy]-4-fluorophenyl)-3-fluoropyrrolidine-1-sulfonamide | ¹H NMR (400 MHz, DMSO-d₆) δ 10.78 (s, 1H), 8.92 (s, 2H), 8.39 (s, 1H), 7.84 (d, J = 8.9 Hz, 1H), 7.73-7.72 (m, 1H), 7.71-7.40 (m, 3H), 6.96-6.87 (m, 2H), 6.48 (m, 1H), 5.38-5.19 (m, 1H), 4.45-4.25 (m, 6H), 4.02 (s, 2H), 3.76-3.55 (m, 6H), 3.24-3.02 (m, 9H), 2.55-2.53 (m, 3H), 2.28-1.97 (m, 5H), 1.55 (s, 2H), 1.25 (s, 2H), 1.02 (s, 1H) |
| 106 | 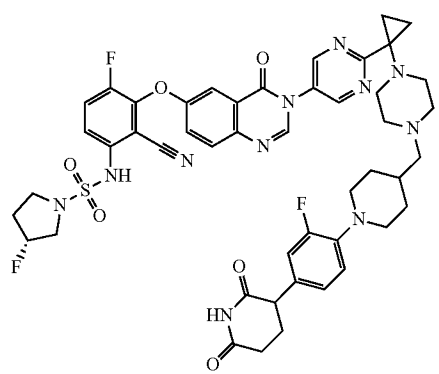 [SMILES: N#Cc1c(NS(=O)(=O)N2CC[C@@H](F)C2)ccc(F)c1Oc1ccc2ncn(-c3cnc(C4(N5CCN(CC6CCN(c7ccc(C8CCC(=O)NC8=O)cc7F)CC6)CC5)CC4)nc3)c(=O)c2c1] | (3R)-N-(2-cyano-3-[[3-(2-{1-[4-(2,6-dioxopiperidin-3-yl)-2-fluorophenyl]piperidin-4-yl}methyl)piperazin-1-yl]pyrimidin-5-yl}-4-oxo-3,4-dihydroquinazolin-6-yl]oxy]-4-fluorophenyl)-3-fluoropyrrolidine-1-sulfonamide | ¹H NMR (400 MHz, DMSO-d₆) δ 10.83 (s, 1H), 8.93 (s, 2H), 8.40 (s, 1H), 7.85 (d, J = 8.9 Hz, 1H), 7.78-7.66 (m, 1H), 7.62-7.45 (m, 1H), 7.41 (d, J = 2.9 Hz, 1H), 7.38-7.31 (m, 1H), 7.07-6.92 (m, 3H), 5.38-5.19 (m, 1H), 3.99-3.65 (m, 2H), 3.58-3.38 (m, 3H), 3.35-3.25 (m, 4H), 3.24-2.82 (m, 6H), 2.75-2.59 (m, 4H), 2.48-2.46 (m, 1H), 2.28-2.09 (m, 2H), 2.07-1.94 (m, 3H), 1.85 (d, J = 12.4 Hz, 3H), 1.45 (s, 2H), 1.36 (s, 2H), 1.24 (s, 2H) |

| Cmp. No. | Structure | IUPAC Name | 1H NMR |
|---|---|---|---|
| 107 | 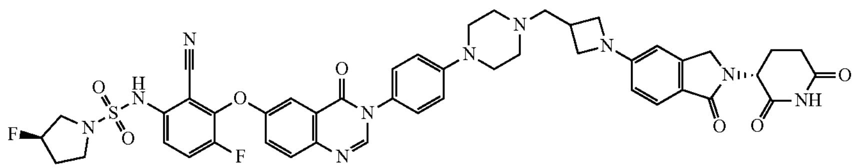 | (3R)-N-(2-cyano-3-{[3-(4-{4-[(1-{2-[(3R)-2,6-dioxopiperidin-3-yl]-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO-d6) δ 10.94 (s, 1H), 10.57-9.68 (m, 1H), 8.25 (s, 1H), 7.82 (d, J = 9.2 Hz, 1H), 7.75-7.62 (m, 2H), 7.50 (d, J = 8.4 Hz, 1H), 7.47-7.39 (m, 2H), 7.35 (d, J = 8.8 Hz, 2H), 7.09 (d, J = 8.8 Hz, 2H), 6.64-6.41 (m, 2H), 5.43-5.17 (m, 1H), 5.04 (dd, J = 4.8, 13.2 Hz, 1H), 4.39-4.25 (m, 1H), 4.23-4.13 (m, 1H), 4.08 (t, J = 7.6 Hz, 2H), 3.63 (s, 2H), 3.52-3.37 (m, 4H), 3.29-3.24 (m, 2H), 3.14-3.05 (m, 1H), 3.00-2.86 (m, 3H), 2.85-2.71 (m, 4H), 2.58 (d, J = 16.8 Hz, 1H), 2.39-2.29 (m, 1H), 2.18-2.09 (m, 1H), 2.07 (s, 2H), 2.05-2.00 (m, 1H), 1.99-1.89 (m, 1H) |
| 108 | 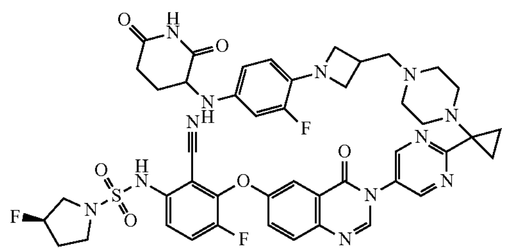 [SMILES: N#Cc1c(NS(=O)(=O)N2CC[C@@H](F)C2)ccc(F)c1Oc1ccc2ncn(-c3cnc(C4(N5CCN(CC6CN(c7ccc(NC8CCC(=O)NC8=O)cc7F)C6)CC5)CC4)nc3)c(=O)c2c1] | (3R)-N-[2-cyano-3-({3-[2-(1-{4-[(1-{4-[(2,6-dioxopiperidin-3-yl)amino]-2-fluorophenyl}azetidin-3-yl)methyl]piperazin-1-yl}cyclopropyl)pyrimidin-5-yl]-4-oxo-3,4-dihydroquinazolin-6-yl}oxy)-4-fluorophenyl]-3-fluoropyrrolidine-1-sulfonamide | 1H NMR (400 MHz, DMSO-d6) δ 10.76 (s, 1H), 9.51 (s, 1H), 8.92 (s, 2H), 8.39 (s, 1H), 7.84 (d, J = 8.9 Hz, 1H), 7.71-7.52 (m, 1H), 7.47 (s, 1H), 7.40 (d, J = 3.0 Hz, 1H), 7.34-7.24 (m, 1H), 6.49-6.46 (m,1H), 6.45-6.32 (m, 2H), 5.58-5.45 (d, J = 52 Hz, 1H), 5.34 (t, J = 4.5 Hz, 1H), 4.20-3.89 (m, 2H), 3.96-3.87 (m, 3H), 3.53-3.45 (m, 3H), 3.30 (d, J = 3.9 Hz, 3H), 3.18 (d, J = 8.2 Hz, 2H), 3.03 (s, 2H), 2.73 (td, J = 11.9, 6.0 Hz, 1H), 2.62-2.52 (m, 2H), 2.15-1.96 (m, 4H), 2.05 (s, 2H), 1.83-1.45 (m, 1H), 1.45 (d, J = 3.3 Hz, 2H), 1.23 (d, J = 5.6 Hz, 3H) |

| Cmp. No. | Structure | IUPAC Name | ¹H NMR |
|---|---|---|---|
| 109 | 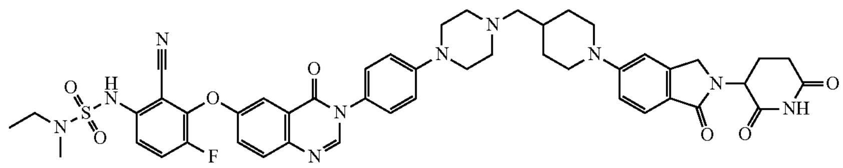 [SMILES: CCN(C)S(=O)(=O)Nc1ccc(F)c(Oc2ccc3ncn(-c4ccc(N5CCN(CC6CCN(c7ccc8c(c7)CN(C7CCC(=O)NC7=O)C8=O)CC6)CC5)cc4)c(=O)c3c2)c1C#N] | 2-[(3-{4-[4-({1-[2-(2,6-dioxopiperidin-3-yl)-1-oxo-2,3-dihydro-1H-isoindol-5-yl]piperidin-4-yl}methyl)piperazin-1-yl]phenyl}-4-oxo-3,4-dihydroquinazolin-6-yl)oxy]-6-{[(ethyl(methyl)sulfamoyl]amino}-3-fluorobenzonitrile | ¹H NMR (400 MHz, DMSO-d₆) δ 10.95 (s, 1H), 9.99 (s, 1H), 8.26 (s, 1H), 7.83 (d, J = 8.9 Hz, 1H), 7.76 (d, J = 10.0 Hz, 2H), 7.51 (d, J = 8.3 Hz, 1H), 7.49-7.38 (m, 2H), 7.35 (d, J = 8.6 Hz, 2H), 7.09-7.05 (m, 4H), 5.05 (m, 1H), 4.33 (d, J = 16.8 Hz, 1H), 4.20 (d, J = 16.9 Hz, 1H), 3.90 (d, J = 12.5 Hz, 2H), 3.20 (m, 3H),3.12 (m, 2H), 2.96-2.81 (m, 3H), 2.70-2.60 (m,6H), 2.59 (d, J = 17.6 Hz, 2H), 2.55 (s, 3H), 2.37 (m, 2H), 1.96 (m, 1H), 1.88 (s, 3H), 1.29-1.22 (m, 3H), 1.04 (t, J = 7.1 Hz, 3H) |
| 110 | 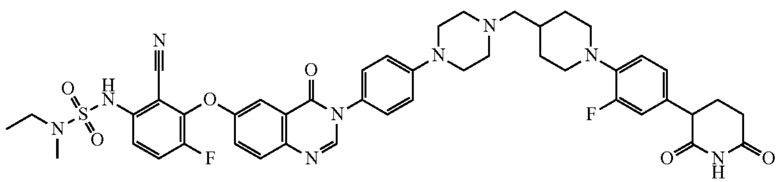 [SMILES: CCN(C)S(=O)(=O)Nc1ccc(F)c(Oc2ccc3ncn(-c4ccc(N5CCN(CC6CCN(c7ccc(C8CCC(=O)NC8=O)cc7F)CC6)CC5)cc4)c(=O)c3c2)c1C#N] | 2-[(3-{4-[4-({1-[4-(2,6-dioxopiperidin-3-yl)-2-fluorophenyl]piperidin-4-yl}methyl)piperazin-1-yl]phenyl}-4-oxo-3,4-dihydroquinazolin-6-yl)oxy]-6-{[ethyl(methyl)sulfamoyl]amino}-3-fluorobenzonitrile | ¹H NMR (400 MHz, DMSO-d₆) δ 10.83 (s, 1H), 10.00 (s, 1H), 8.26 (s, 1H), 7.83 (d, J = 8.9 Hz, 1H), 7.76-7.61 (m, 2H), 7.47-7.38 (m, 2H), 7.37-7.28 (m, 2H), 7.13-7.06 (m, 2H), 7.04-6.91 (m, 3H), 3.95-3.72 (m, 1H), 3.45-3.35 (m, 1H), 3.29-3.19 (m, 3H), 3.15-3.05 (m, 2H), 2.81-2.73 (m, 4H), 2.71-2.59 (m, 5H), 2.58-2.52 (m, 1H), 2.48-2.41 (m, 2H), 2.31-2.15 (m, 2H), 2.09-1.95 (m, 2H), 1.85 (d, J = 12.9 Hz, 2H), 1.83-1.73 (m, 1H), 1.48-1.29 (m, 3H), 1.28-1.25 (m, 1H), 1.09-0.99 (m, 3H), 0.95-0.85 (m, 1H) |
| 111 | 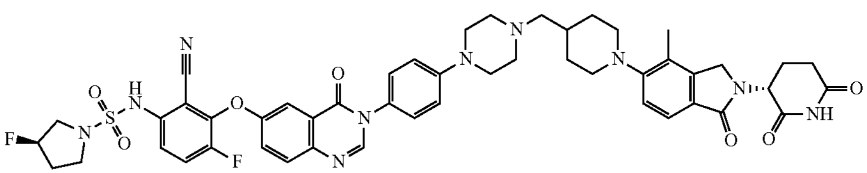 [SMILES: Cc1c(N2CCC(CN3CCN(c4ccc(-n5cnc6ccc(Oc7c(F)ccc(NS(=O)(=O)N8CC[C@@H](F)C8)c7C#N)cc6c5=O)cc4)CC3)CC2)ccc2c1CN([C@@H]1CCC(=O)NC1=O)C2=O] | (3R)-N-(2-cyano-3-{[3-(4-{4-[(1-{2-[(3R*)-2,6-dioxopiperidin-3-yl]-4-methyl-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | δ 1.20-1.28 (m, 3 H), 1.33-1.42 (m, 2 H), 1.82-1.93 (m, 3 H), 1.94-2.06 (m, 3 H), 2.16-2.22 (m, 4 H), 2.53-2.56 (m, 3 H), 2.57 (s, 2 H), 2.67 (td, J = 4.0, 2.0 Hz, 2 H), 2.70 (d, J = 4.4 Hz, 1 H), 2.82-2.99 (m, 2 H), 3.13-3.21 (m, 3 H), 3.29 (s, 2 H), 3.35-3.37 (m, 2 H), 4.19 (d, J = 16.4 Hz, 1 H), 4.30-4.39 (m, 1 H), 5.06-5.13 (m, 1 H), 5.18 - 5.40 (m, 1 H), 7.09 (d, J = 8.8 Hz, 2 H), 7.15 (d, J = 8.0 Hz, 1 H), 7.35 (d, J = 8.8 |

TABLE 1-continued

| Cmp. No. | Structure | IUPAC Name | ¹H NMR |
|---|---|---|---|
| | | | Hz, 2 H), 7.40 (d, J = 2.8 Hz, 2 H), 7.52 (d, J = 8.0 Hz, 1 H), 7.68 (dd, J = 8.8, 2.8 Hz, 2 H), 7.78-7.85 (m, 1 H), 8.25 (s, 1 H), 10.98 (s, 1 H) |
| 112 | 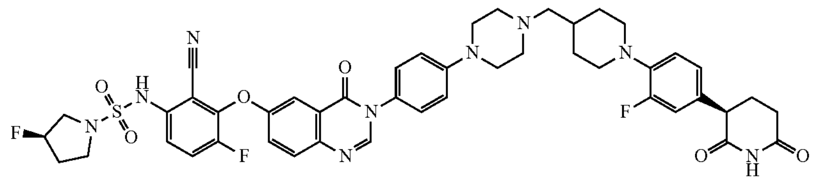 [SMILES: N#Cc1c(NS(=O)(=O)N2CC[C@@H](F)C2)ccc(F)c1Oc1ccc2ncn(-c3ccc(N4CCN(CC5CCN(c6ccc([C@H]7CCC(=O)NC7=O)cc6F)CC5)CC4)cc3)c(=O)c2c1] | (3R)-N-(2-cyano-3-{[3-(4-{4-[(1-{4-[(3R*)-2,6-dioxopiperidin-3-yl]-2-fluorophenyl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.83 (s, 1H), 10.30-9.74 (m, 1H), 8.25 (s, 1H), 7.82 (d, J = 9.2 Hz, 1H), 7.74-7.62 (m, 2H), 7.46-7.39 (m, 2H), 7.36 (d, J = 8.8 Hz, 2H), 7.09 (d, J = 9.2 Hz, 2H), 7.05-6.98 (m, 2H), 6.97-6.93 (m, 1H), 5.41-5.19 (m, 1H), 3.80 (dd, J = 4.8, 11.8 Hz, 1H), 3.50-3.40 (m, 2H), 3.36 (s, 4H), 3.31-3.30 (m, 2H), 3.29-3.22 (m, 2H), 3.06-2.74 (m, 4H), 2.73-2.60 (m, 5H), 2.47-2.44 (m, 1H), 2.27-2.17 (m, 1H), 2.16-2.09 (m, 1H), 2.07-1.95 (m, 2H), 1.90-1.76 (m, 3H), 1.42-1.27 (m, 2H) |
| 113 | 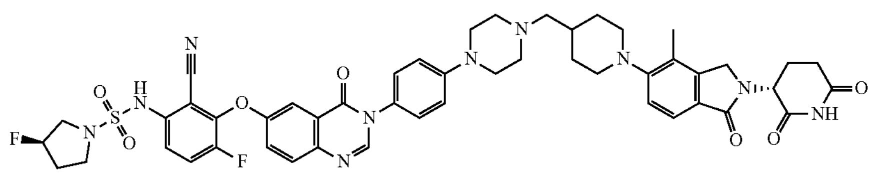 [SMILES: Cc1c(N2CCC(CN3CCN(c4ccc(-n5cnc6ccc(Oc7c(F)ccc(NS(=O)(=O)N8CC[C@@H](F)C8)c7C#N)cc6c5=O)cc4)CC3)CC2)ccc2c1CN([C@@H]1CCC(=O)NC1=O)C2=O] | (3R)-N-(2-cyano-3-{[3-(4-{4-[(1-{2-[(3R*)-2,6-dioxopiperidin-3-yl]-4-methyl-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 1.23 (s, 3 H), 1.31-1.42 (m, 2 H), 1.82-1.93 (m, 3 H), 1.93-2.07 (m, 3 H), 2.21 (s, 4 H), 2.53-2.60 (m, 2 H), 2.64-2.69 (m, 2 H), 2.69-2.75 (m, 2 H), 2.86-2.98 (m, 2 H), 3.11-3.21 (m, 3 H), 3.35-3.51 (m, 6 H), 4.19 (d, J = 16.4 Hz, 1 H), 4.28-4.43 (m, 1 H), 5.04-5.15 (m, 1 H), 5.18-5.40 (m, 1 H), 7.06-7.12 (m, 2 H), 7.15 (d, J = 8.4 Hz, 1 H), 7.35 (d, J = 9.2 Hz, 2 H), 7.39-7.46 (m, 2 H), 7.49-7.54 (m, 1 H), 7.69 (dd, J = 9.2, 3.2 Hz, 2 H), 7.79-7.86 (m, 1 H), 8.25 (s, 1 H), 10.98 (s, 1 H) |

| Cmp. No. | Structure | IUPAC Name | ¹H NMR |
|---|---|---|---|
| 114 | 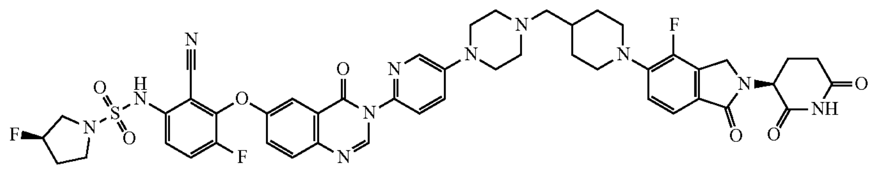 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6F)CN([C@H]6CCC(=O)NC6=O)C7=O)CC5)CC4)cn3)c(=O)c2c1] | (3R)-N-(2-cyano-3-{[3-(5-{4-[(1-{2-[(3S)-2,6-dioxopiperidin-3-yl]-4-fluoro-1-oxo-2,3-dihydro-1H-isoindol-5-yl}piperidin-4-yl)methyl]piperazin-1-yl}pyridin-2-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.98 (s, 1H), 10.11 (s, 1H), 8.45 (s, 1H), 8.31 (s, 1H), 7.84 (d, J = 8.9 Hz, 1H), 7.71 (dd, J = 9.0, 3.1 Hz, 2H), 7.60 (d, J = 3.6 Hz, 2H), 7.51-7.42 (m, 3H), 7.18 (t, J = 7.9 Hz, 1H), 5.37 (s, 1H), 5.07 (dd, J = 13.3, 5.1 Hz, 1H), 4.48 (d, J = 17.0 Hz, 1H), 4.31 (d, J = 16.9 Hz, 1H), 3.58 (d, J = 17.1 Hz, 3H), 3.49 (d, J = 17.1 Hz, 2H), 2.81 (t, J = 11.9 Hz, 6H), 2.59 (d, J = 16.3 Hz, 2H), 2.13 (s, 1H), 2.05 (s, 2H), 2.01 - 1.94 (m, 1H), 1.87 (d, J = 12.6 Hz, 3H), 1.34 (d, J = 11.8 Hz, 2H), 1.24 (s, 1H) |
| 115 | 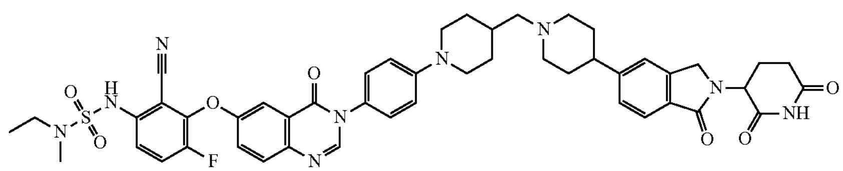 [SMILES: CCN(C)S(=O)(=O)Nc1ccc(F)c(Oc2ccc3ncn(-c4ccc(N5CCC(CN6CCC(c7ccc8c(c7)CN(C7CCC(=O)NC7=O)C8=O)CC6)CC5)cc4)c(=O)c3c2)c1C#N] | 2-[(3-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-4-oxo-3,4-dihydroquinazolin-6-yl)oxy]-6-{[ethyl(methyl)sulfamoyl]amino}-3-fluorobenzonitrile | ¹H NMR (400 MHz, DMSO-d₆) δ 11.00 (s, 1H), 8.24 (s, 1H), 7.8 (d, J = 9.0 Hz, 1H), 7.13-7.10 (m, 2H), 7.69-7.58 (m, 2H), 7.41-7.33 (m, 5H), 7.06-7.03 (m, 2H), 5.13-5.09 (m, 1H), 4.49-4.29 (m, 2H), 3.87-3.83 (m, 2H), 3.04-3.02 (m, 2H), 2.84-2.73 (m, 10H), 2.38-2.31 (m, 2H), 2.10-1.82 (m, 10H), 1.25 (s, 2H), 1.32-1.12 (m, 2H), 1.03-1.01 (m, 3H) |
| 116 | 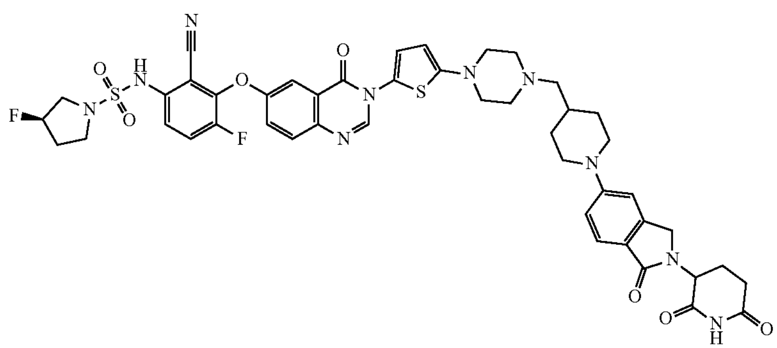 [SMILES: N#Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)s3)c(=O)c2c1] | (3R)-N-{2-cyano-3-[(3-{5-[4-({1-[2-(2,6-dioxopiperidin-3-yl)-1-oxo-2,3-dihydro-1H-isoindol-5-yl]piperidin-4-yl}methyl)piperazin-1-yl]thiophen-2-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.98 (d, J = 16.6 Hz, 1H), 8.43 (s, 1H), 8.15-7.35 (m, 7H), 7.06 (s, 3H), 6.14 (s, 1H), 5.51-5.19 (m, 1H), 5.05 (s, 1H), 4.45-4.15 (m, 3H), 3.90 (s, 3H), 3.18 (s, 6H), 2.86 (s, 5H), 2.68 (s, 5H), 2.38 (s, 4H), 2.19-1.99 (m, 4H), 1.82 (d, J = 13.2 Hz, 3H), 1.23 (s, 3H) |

| Cmp. No. | Structure | IUPAC Name | ¹H NMR |
|---|---|---|---|
| 117 | 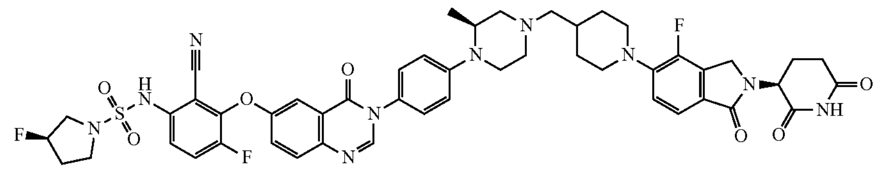 | (3R)-N-{2-cyano-3-[(3-(4-[(2S)-4-[(1-{2-[(3S)-2,6-dioxopiperidin-3-yl]-4-fluoro-1-oxo-2,3-dihydro-1H-isoindol-5-yl}piperidin-4-yl)methyl]-2-methylpiperazin-1-yl]phenyl]-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.98 (s, 1H), 8.24 (s, 2H), 7.80 (d, J = 8.9 Hz, 2H), 7.65 (dd, J = 8.9, 3.0 Hz, 1H), 7.52-7.37 (m, 1H), 7.32 (d, J = 8.5 Hz, 1H), 7.18 (t, J = 7.9 Hz, 1H), 7.00 (d, J = 8.7 Hz, 1H), 6.81 (d, J = 8.7 Hz, 2H), 5.36 (s, 1H), 5.18 (s, 1H), 4.49 (d, J = 17.0 Hz, 1H), 4.32 (d, J = 16.9 Hz, 1H), 4.12 (s, 1H), 3.52 (s, 2H), 3.43 (d, J = 12.1 Hz, 1H), 3.32 (m, 3H), 3.13 (m, 1H), 2.95 (d, J = 7.2 Hz, 8H), 2.79 (d, J = 12.0 Hz, 1H), 2.62 (s, 1H), 2.27-2.14 (d, J = 8.5 Hz, 5H), 2.01 (s, 2H), 1.88 (d, J = 12.4 Hz, 2H), 1.76 (s, 1H), 1.33 (d, J = 12.3 Hz, 3H), 1.15 (dt, J = 13.6, 6.7 Hz, 8H) |
| 118 | 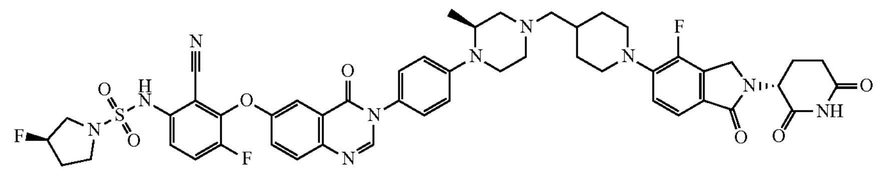 [SMILES: C[C@H]1CN(CC2CCN(c3ccc4c(c3F)CN([C@@H]3CCC(=O)NC3=O)C4=O)CC2)CCN1c1ccc(-n2cnc3ccc(Oc4c(F)ccc(NS(=O)(=O)N5CC[C@@H](F)C5)c4C#N)cc3c2=O)cc1] | (3R)-N-{2-cyano-3-[(3-(4-[(2S)-4-[(1-{2-[(3R)-2,6-dioxopiperidin-3-yl]-4-fluoro-1-oxo-2,3-dihydro-1H-isoindol-5-yl}piperidin-4-yl)methyl]-2-methylpiperazin-1-yl]phenyl]-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.98 (s, 1H), 8.35 (s, 2H), 7.81 (d, J = 8.9 Hz, 2H), 7.52-7.37 (m, 4H), 7.32 (d, J = 8.7 Hz, 1H), 7.18 (t, J = 7.8 Hz, 1H), 5.37 (s, 1H), 5.19 (s, 1H), 4.49 (d, J = 17.0 Hz, 1H), 4.32 (d, J = 16.9 Hz, 1H), 4.12 (s, 1H), 3.58 (d, J = 12.3 Hz, 3H), 3.37 (s, 1H), 2.92 (d, J = 7.1 Hz, 8H), 2.84-2.78 (s, 3H), 2.62 (s, 2H), 1.99 (d, J = 8.5 Hz, 3H), 1.31 (s, 3H), 1.27-1.07 (m, 7H) |
| 119 | 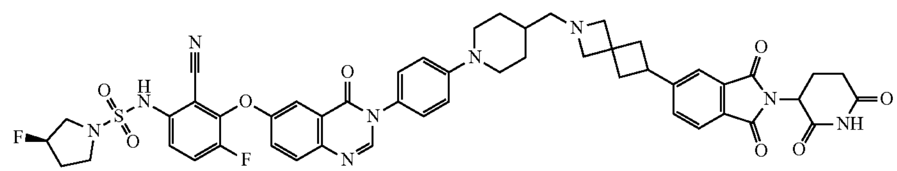 [SMILES: N#Cc1c(NS(=O)(=O)N2CC[C@@H](F)C2)ccc(F)c1Oc1ccc2ncn(-c3ccc(N4CCC(CN5CC6(CC(c7ccc8c(c7)C(=O)N(C7CCC(=O)NC7=O)C8=O)C6)C5)CC4)cc3)c(=O)c2c1] | (3R)-N-{2-cyano-3-[(3-{4-[4-(6-[2-[(3-(2,6-dioxopiperidin-3-yl))-1,3-dioxo-2,3-dihydro-1H-isoindol-5-yl]-2-azaspiro[3.3]heptan-2-yl}methyl)piperidin-1-yl]phenyl]-4-oxo-3,4-dihydroquinazolin-6-yl)oxy]-4-fluorophenyl}-3-fluoropyrrolidine-1-sulfonamide | 1H NMR (400 MHz, DMSO-d₆) δ 8.22 (s, 1H), 7.89-7.81 (m, 3H), 7.81 (d, J = 8.9 Hz, 2H), 7.72-7.67 (m, 1H), 7.47 (s, 1H), 7.39 (d, J = 3.0 Hz, 3H), 7.10-7.02 (m, 2H), 5.34-5.24 (d, J = 40 Hz, 1H), 5.24-5.10 (m, 1H), 4.08 (s, 4H), 3.81 (d, J = 12.5 Hz, 2H), 3.66-3.57 (m, 2H), 3.40 (s, 6H), 3.22-3.08 (m, 1H), 2.90-2.81 (m, 3H), 2.76 (t, J = 11.9 Hz, 2H), 2.67-2.53 (m, 2H), 2.17-1.96 (m, 1H), 1.76 (d, J = 11.7 Hz, 5H), 1.31 (s, 1H), 1.29-1.21 (m, 6H) |

TABLE 1-continued

| Cmp. No. | Structure | IUPAC Name | ¹H NMR |
|---|---|---|---|
| 120 | 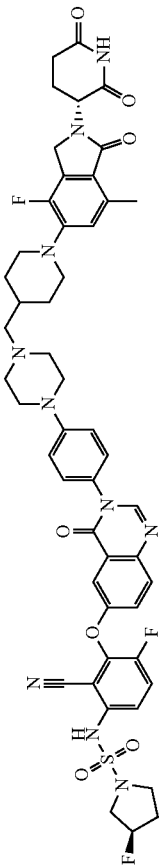 | (3R)-N-(2-cyano-3-{[3-(4-{4-[(1-{2-[(3R*)-2,6-dioxopiperidin-3-yl]-4-fluoro-7-methyl-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.97 (s, 1H), 8.25 (s, 1H), 7.82 (d, J = 8.8 Hz, 1H), 7.60-7.71 (m, 2H), 7.39-7.45 (m, 2H), 7.35 (d, J = 8.8 Hz, 2H), 7.08 (d, J = 9.2 Hz, 2H), 6.90 (d, J = 7.2 Hz, 1H), 5.21-5.37 (m, 1H), 5.03 (dd, J = 13.2, 5.1 Hz, 1H), 4.40 (d, J = 17.0 Hz, 1H), 4.20-4.27 (m, 1H), 3.40-3.56 (m, 8H), 3.21-3.29 (m, 4H), 2.86-2.93 (m, 2H), 2.79 (t, J = 12.0 Hz, 4H), 2.60 (d, J = 1.2 Hz, 1H), 2.54 (s, 3H), 2.40-2.43 (m, 1H), 2.08-2.14 (m, 1H), 1.92-2.07 (m, 3H), 1.85 (d, J = 11.6 Hz, 3H), 1.28-1.38 (m, 2H) |
| 121 | 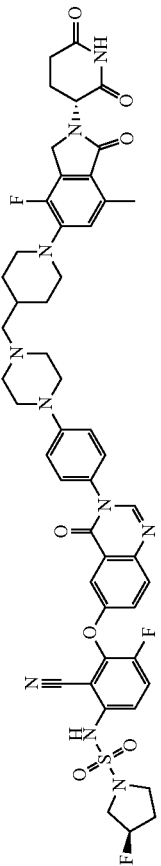 | (3R)-N-(2-cyano-3-{[3-(4-{4-[(1-{2-[(3R*)-2,6-dioxopiperidin-3-yl]-4-fluoro-7-methyl-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.97 (s, 1H), 8.25 (s, 1H), 7.82 (d, J = 9.2 Hz, 1H), 7.63-7.73 (m, 2H), 7.39-7.46 (m, 2H), 7.35 (d, J = 8.8 Hz, 2H), 7.09 (d, J = 8.8 Hz, 2H), 6.90 (d, J = 7.2 Hz, 1H), 5.20-5.40 (m, 1H), 5.03 (dd, J = 13.2, 5.0 Hz, 1H), 4.24 (d, J = 16.8 Hz, 1H), 3.44-3.53 (m, 5H), 3.36 (s, 5H), 3.27 (d, J = 8.4 Hz, 2H), 2.86-2.93 (m, 2H), 2.79 (t, J = 11.2 Hz, 4H), 2.60 (s, 1H), 2.54 (s, 3H), 2.40 (dd, J = 13.2, 4.9 Hz, 1H), 2.09-2.14 (m, 1H), 1.91-2.07 (m, 3H), 1.85 (d, J = 10.0 Hz, 3H), 1.29-1.39 (m, 2H) |
| 122 | 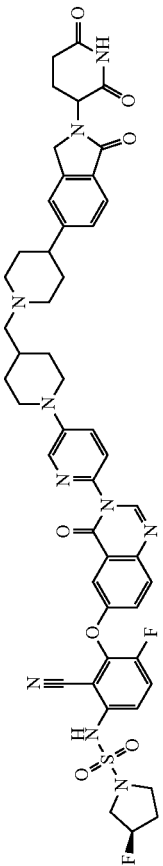 | (3R)-N-{2-cyano-3-[(3-{5-[4-({4-[2-(2,6-dioxopiperidin-3-yl)-1H-isoindol-5-yl]piperidin-1-yl}methyl)piperidin-1-yl]pyridin-2-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 1.27-1.48 (m, 2 H), 1.91-2.07 (m, 6 H), 2.09-2.20 (m, 2 H), 2.30-2.44 (m, 3 H), 2.56-2.64 (m, 1 H), 2.80-2.92 (m, 3 H), 2.93-3.09 (m, 5 H), 3.24-3.30 (m, 1 H), 3.41 (s, 2 H), 3.43-3.51 (m, 1 H), 3.53-3.74 (m, 2 H), 3.91 (d, J=12.8 Hz, 2 H), 4.27-4.37 (m, 1 H), 4.39-4.54 (m, 1 H), 5.11 (dd, J = 13.2, 5.2 Hz, 1 H), 5.19-5.42 (m, 1 |

| Cmp. No. | Structure | IUPAC Name | ¹H NMR |
|---|---|---|---|
| | | | H), 7.38-7.47 (m, 3 H), 7.49 (s, 1 H), 7.58 (d, J = 1.2 Hz, 2 H), 7.62-7.75 (m, 3 H), 7.83 (d, J = 8.8 Hz, 1 H), 8.29 (s, 1 H), 8.44 (s, 1 H), 10.69-10.89 (m, 1 H), 10.99 (s, 1 H) |
| 123 | 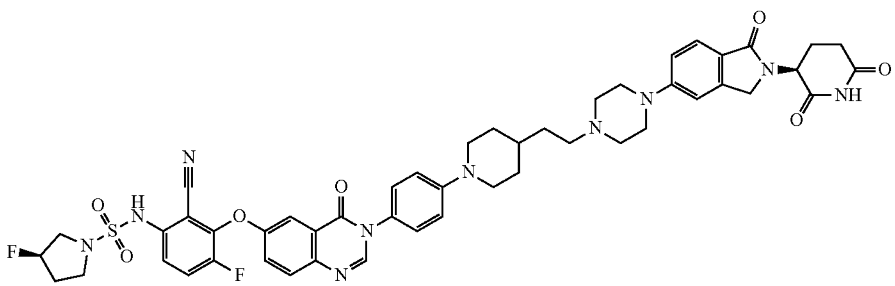 [SMILES: N#Cc1c(NS(=O)(=O)N2CC[C@@H](F)C2)ccc(F)c1Oc1ccc2ncn(-c3ccc(N4CCC(CCN5CCN(c6ccc7c(c6)CN([C@H]6CCC(=O)NC6=O)C7=O)CC5)CC4)cc3)c(=O)c2c1] | (3R)-N-{2-cyano-3-[(3-(4-{4-[2-(4-{2-[(3S)-2,6-dioxopiperidin-3-yl]-1-oxo-2,3-dihydro-1H-isoindol-5-yl}piperidin-1-yl)ethyl]piperidin-1-yl}phenyl)-4-oxo-3,4-dihydroquinazolin-6-yl]oxy]-4-fluorophenyl}-3-fluoropyrrolidine-1-sulfonamide | ¹H NMR (400 MHz, DMSO-d₆) δ 10.94 (s, 1H), 8.23 (s, 1H), 8.13 (s, 1H), 7.81 (d, J = 8.8 Hz, 1H), 7.67 (dd, J = 3.2, 9.2 Hz, 1H), 7.56 (d, J = 8.4 Hz, 2H), 7.44-7.35 (m, 2H), 7.30 (d, J = 9.2 Hz, 2H), 7.14-7.00 (m, 4H), 5.39-5.18 (m, 1H), 5.05 (dd, J = 5.2, 13.2 Hz, 1H), 4.37-4.17 (m, 2H), 3.80 (d, J = 12.0 Hz, 2H), 3.53-3.36 (m, 6H), 3.27-3.18 (m, 2H), 3.05-2.85 (m, 5H), 2.83-2.68 (m, 4H), 2.64-2.53 (m, 2H), 2.42 (s, 1H), 2.14-1.92 (m, 3H), 1.85-1.73 (m, 2H), 1.62-1.46 (m, 3H), 1.36-1.21 (m, 2H) |
| 124 | 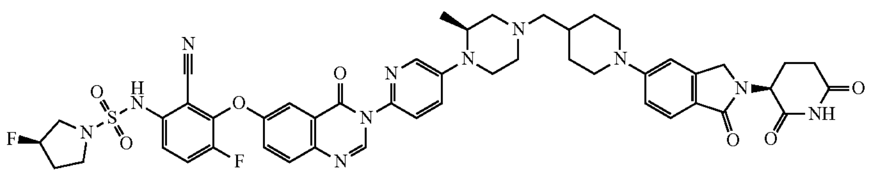 | (3R)-N-{2-cyano-3-[(3-{5-[(2S)-4-[(1-{2-[(3S)-2,6-dioxopiperidin-3-yl]-1-oxo-2,3-dihydro-1H-isoindol-5-yl}piperidin-4-yl)methyl]-2-methylpiperazin-1-yl]pyridin-2-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.94 (s, 1H), 8.45 (s, 1H), 8.22 (s, 1H), 7.84 (d, J = 8.9 Hz,1H), 7.71-7.67 (m, 1H), 7.63-7.42 (m, 5H), 7.05 (d, J = 7.6 Hz, 2H), 5.40-5.21 (m, 1H), 5.04-5.01 (m, 1H), 4.33 (d, J = 17.1 Hz, 7H), 4.20 (d, J = 16.8 Hz, 2H), 3.92 (s, 3H), 3.76 (s, 3H), 3.51 (s, 1H), 3.40 (s, 3H), 3.31 (s, 3H), 2.88 (d, J = 12.6 Hz, 7H), 2.60 (s, 2H), 2.30 (s, 5H), 2.15 (s, 4H), 1.98 (s, 4H), 1.24 (s, 1H) |
| 125 | 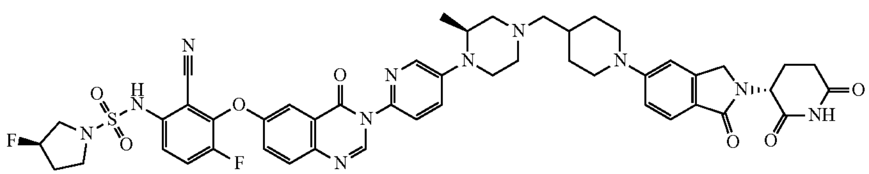 [SMILES: C[C@H]1CN(CC2CCN(c3ccc4c(c3)CN([C@@H]3CCC(=O)NC3=O)C4=O)CC2)CCN1c1ccc(-n2cnc3ccc(Oc4c(F)ccc(NS(=O)(=O)N5CC[C@@H](F)C5)c4C#N)cc3c2=O)nc1] | (3R)-N-{2-cyano-3-[(3-{5-[(2S)-4-[(1-{2-[(3R)-2,6-dioxopiperidin-3-yl]-1-oxo-2,3-dihydro-1H-isoindol-5-yl}piperidin-4-yl)methyl]-2-methylpiperazin-1-yl]pyridin-2-yl]-4-oxo-3,4-dihydroquinazolin-6-yl)oxy]-4-fluorophenyl}- | ¹H NMR (400 MHz, DMSO-d₆) δ 10.94 (s, 1H), 8.45 (s, 1H), 8.22 (s, 1H), 7.84 (d, J = 8.9 Hz,1H), 7.71-7.67 (m, 1H), 7.63-7.42 (m, 5H), 7.05 (d, J = 7.6 Hz, 2H), 5.40-5.21 (m, 1H), 5.04-5.01(m, 1H), 4.33 (d, J = 17.1 Hz, 7H), 4.20 (d, J = 16.8 Hz, 2H), 3.92 (s, 3H), 3.76 (s, 3H), 3.51 (s, 1H), 3.40 (s, 3H), 3.31 (s, 3H), 2.88 |

TABLE 1-continued

| Cmp. No. | Structure | IUPAC Name | ¹H NMR |
|---|---|---|---|
| 126 | 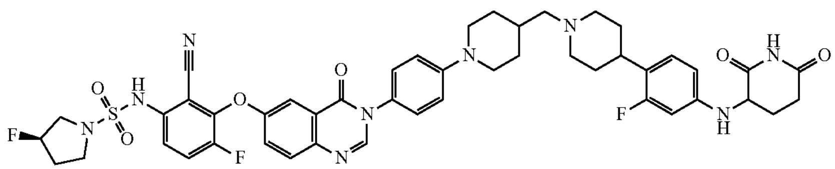 [SMILES: N#Cc1c(NS(=O)(=O)N2CC[C@@H](F)C2)ccc(F)c1Oc1ccc2ncn(-c3ccc(N4CCC(CN5CCC(c6ccc(NC7CCC(=O)NC7=O)cc6F)CC5)CC4)cc3)c(=O)c2c1] | fluorophenyl}-3-fluoropyrrolidine-1-sulfonamide | (d, J = 12.6 Hz, 7H), 2.60 (s, 2H), 2.30 (s, 5H), 2.15 (s, 4H), 1.98 (s, 4H), 1.24 (s, 1H) |
| 127 | 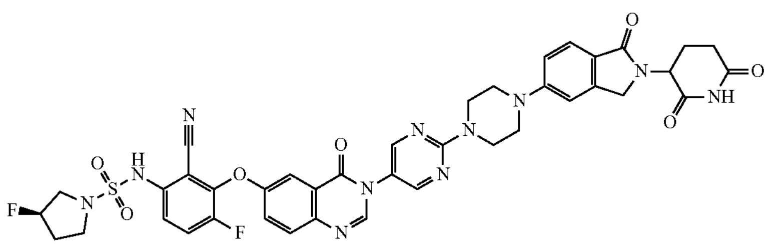 [SMILES: N#Cc1c(NS(=O)(=O)N2CC[C@@H](F)C2)ccc(F)c1Oc1ccc2ncn(-c3cnc(N4CCN(c5ccc6c(c5)CN(C5CCC(=O)NC5=O)C6=O)CC4)nc3)c(=O)c2c1] | (3R)-N-(2-cyano-3-{[3-(4-{4-[(4-{[(2,6-dioxopiperidin-3-yl)amino]-2-fluorophenyl}piperidin-1-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 10.80 (s, 1H), 8.22 (s, 1H), 7.79 (d, J = 9.2 Hz, 1H), 7.65 (dd, J = 2.8, 9.2 Hz, 1H), 7.38 (d, J = 2.8 Hz, 1H), 7.32 (d, J = 8.4 Hz, 3H), 7.06 (d, J = 8.8 Hz, 2H), 7.02-6.89 (m, 2H), 6.50-6.44 (m, 2H), 6.08 (d, J = 7.2 Hz, 1H), 5.33 (d, J = 4.4 Hz, 1H), 4.37-4.26 (m, 1H), 3.84 (d, J = 11.6 Hz, 2H), 3.42-3.37 (m, 2H), 3.27-3.21 (m, 4H), 2.83-2.75 (m, 5H), 2.59 (s, 2H), 2.13-2.07 (m, 4H), 1.84 (d, J = 12.4 Hz, 8H), 1.41-1.20 (m, 4H) |
| 128 | 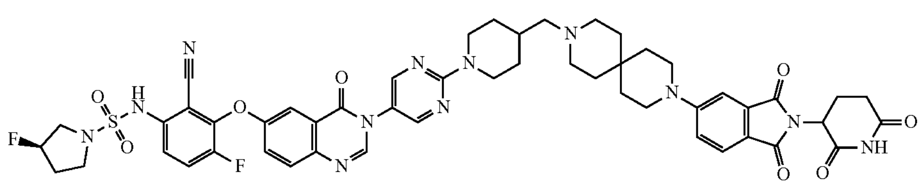 [SMILES: N#Cc1c(NS(=O)(=O)N2CC[C@@H](F)C2)ccc(F)c1Oc1ccc2ncn(-c3cnc(N4CCC(CN5CCC6(CC5)CCN(c5ccc7c(c5)C(=O)N(C5CCC(=O)NC5=O)C7=O)CC6)CC4)nc3)c(=O)c2c1] | (3R)-N-(2-cyano-3-{[3-(2-{4-[2-(2,6-dioxopiperidin-3-yl)-1-oxo-2,3-dihydro-1H-isoindol-5-yl]piperazin-1-yl}pyrimidin-5-yl)-4-oxo-3,4-dihydroquinazolin-6-yl]oxy}-4-fluorophenyl)-3-fluoropyrrolidine-1-sulfonamide | N/A |
| | | (3R)-N-{2-cyano-3-[(3-{2-[4-(2-{4-[2-(2,6-dioxopiperidin-3-yl)-1,3-dioxo-2,3-dihydro-1H-isoindol-5-yl]piperazin-1-yl}ethyl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | 1H NMR |
|---|---|---|---|
| 129 | 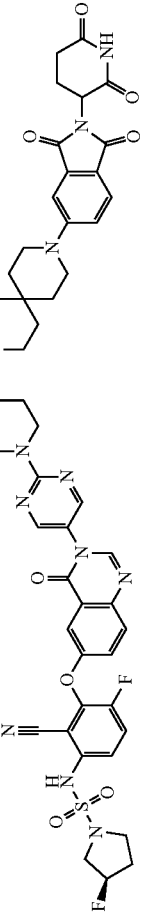 | (3R)-N-{2-cyano-3-[(3-{2-[4-({9-[2-(2,6-dioxopiperidin-3-yl)-1,3-dioxo-2,3-dihydro-1H-isoindol-5-yl]-3,9-diazaspiro[5.5]undecan-3-yl}methyl)piperidin-1-yl]pyrimidin-5-yl}]-4-oxo-3,4-dihydroquinazolin-6-yl)oxy]-4-fluorophenyl}-3-fluoropyrrolidine-1-sulfonamide | N/A |
| 130 | 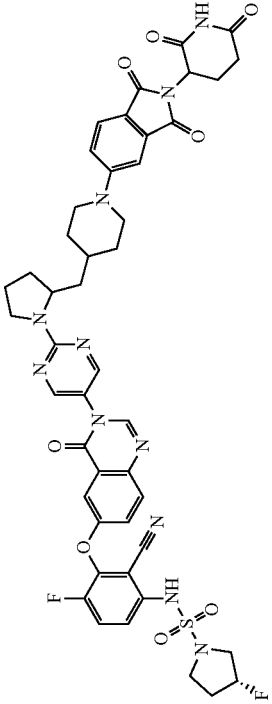 | (3R)-N-{2-cyano-3-[(3-{2-[2-({1-[2-(2,6-dioxopiperidin-3-yl)-1,3-dioxo-2,3-dihydro-1H-isoindol-5-yl]piperidin-4-yl}methyl)pyrrolidin-1-yl]pyrimidin-5-yl}]-4-oxo-3,4-dihydroquinazolin-6-yl)oxy]-4-fluorophenyl}-3-fluoropyrrolidine-1-sulfonamide | N/A |
| 131 | 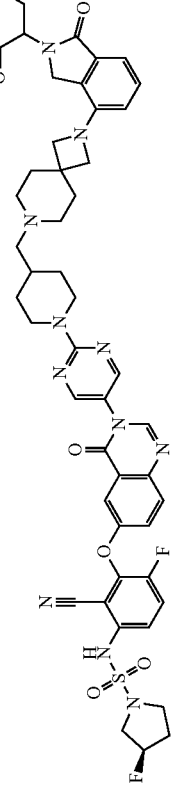 | (3R)-N-{2-cyano-3-[(3-{2-[4-({2-[2-(2,6-dioxopiperidin-3-yl)-1-oxo-2,3-dihydro-1H-isoindol-4-yl]-2,7-diazaspiro[3.5]nonan-7-yl}methyl)piperidin-1-yl]pyrimidin-5-yl}]-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 132 | 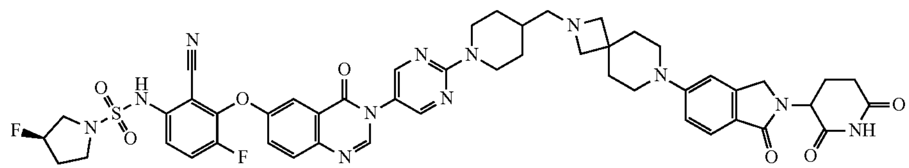 [SMILES: N#Cc1c(NS(=O)(=O)N2CC[C@@H](F)C2)ccc(F)c1Oc1ccc2ncn(-c3cnc(N4CCC(CN5CC6(CCN(c7ccc8c(c7)CN(C7CCC(=O)NC7=O)C8=O)CC6)C5)CC4)nc3)c(=O)c2c1] | (3R)-N-{2-cyano-3-[(3-{2-[4-({7-[2-(2,6-dioxopiperidin-3-yl)-1-oxo-2,3-dihydro-1H-isoindol-5-yl]-2,7-diazaspiro[3.5]nonan-2-yl}methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |
| 133 | 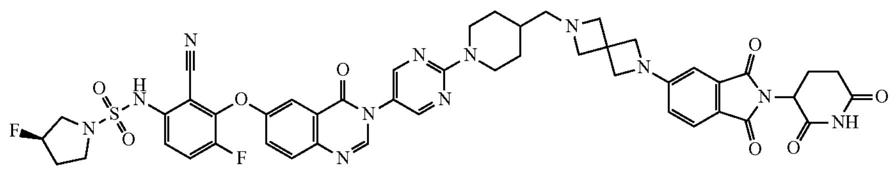 [SMILES: N#Cc1c(NS(=O)(=O)N2CC[C@@H](F)C2)ccc(F)c1Oc1ccc2ncn(-c3cnc(N4CCC(CN5CC6(C5)CN(c5ccc7c(c5)C(=O)N(C5CCC(=O)NC5=O)C7=O)C6)CC4)nc3)c(=O)c2c1] | (3R)-N-{2-cyano-3-[(3-{2-[4-({6-[2-(2,6-dioxopiperidin-3-yl)-1,3-dioxo-2,3-dihydro-1H-isoindol-5-yl]-2,6-diazaspiro[3.3]heptan-2-yl}methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |
| 134 | 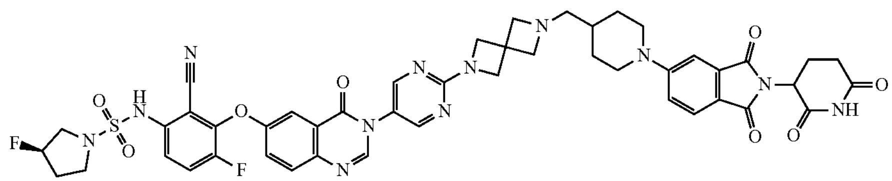 [SMILES: N#Cc1c(NS(=O)(=O)N2CC[C@@H](F)C2)ccc(F)c1Oc1ccc2ncn(-c3cnc(N4CC5(CN(CC6CCN(c7ccc8c(c7)C(=O)N(C7CCC(=O)NC7=O)C8=O)CC6)C5)C4)nc3)c(=O)c2c1] | (3R)-N-{2-cyano-3-[(3-{2-[6-({1-[2-(2,6-dioxopiperidin-3-yl)-1,3-dioxo-2,3-dihydro-1H-isoindol-5-yl]piperidin-4-yl}methyl)-2,6-diazaspiro[3.3]heptan-2-yl]pyrimidin-5-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 135 | 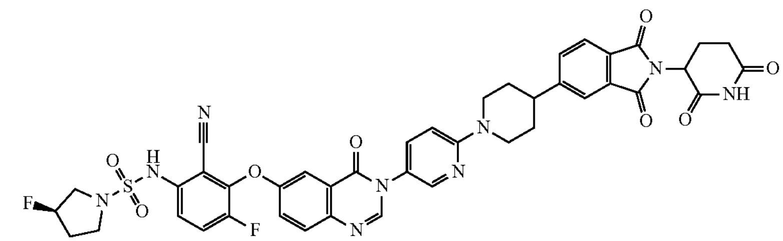 [SMILES: N#Cc1c(NS(=O)(=O)N2CC[C@@H](F)C2)ccc(F)c1Oc1ccc2ncn(-c3ccc(N4CCC(c5ccc6c(c5)C(=O)N(C5CCC(=O)NC5=O)C6=O)CC4)nc3)c(=O)c2c1] | (3R)-N-(2-cyano-3-{[3-(6-{4-[2-(2,6-dioxopiperidin-3-yl)-1,3-dioxo-2,3-dihydro-1H-isoindol-5-yl]piperidin-1-yl}pyridin-3-yl)-4-oxo-3,4-dihydroquinazolin-6-yl]oxy}-4-fluorophenyl)-3-fluoropyrrolidine-1-sulfonamide | N/A |
| 136 | 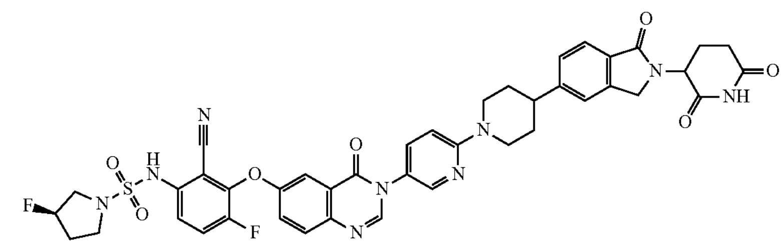 [SMILES: N#Cc1c(NS(=O)(=O)N2CC[C@@H](F)C2)ccc(F)c1Oc1ccc2ncn(-c3ccc(N4CCC(c5ccc6c(c5)CN(C5CCC(=O)NC5=O)C6=O)CC4)nc3)c(=O)c2c1] | (3R)-N-(2-cyano-3-{[3-(6-{4-[2-(2,6-dioxopiperidin-3-yl)-1-oxo-2,3-dihydro-1H-isoindol-5-yl]piperidin-1-yl}pyridin-3-yl)-4-oxo-3,4-dihydroquinazolin-6-yl]oxy}-4-fluorophenyl)-3-fluoropyrrolidine-1-sulfonamide | N/A |
| 137 | 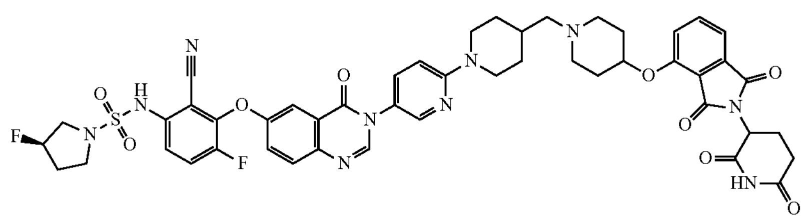 [SMILES: N#Cc1c(NS(=O)(=O)N2CC[C@@H](F)C2)ccc(F)c1Oc1ccc2ncn(-c3ccc(N4CCC(CN5CCC(Oc6cccc7c6C(=O)N(C6CCC(=O)NC6=O)C7=O)CC5)CC4)nc3)c(=O)c2c1] | (3R)-N-(2-cyano-3-{[3-(6-{4-[({2-(2,6-dioxopiperidin-3-yl)-1,3-dioxo-2,3-dihydro-1H-isoindol-4-yl}oxy)piperidin-1-yl]methyl]piperidin-1-yl}pyridin-3-yl)-4-oxo-3,4-dihydroquinazolin-6-yl]oxy}-4-fluorophenyl)-3-fluoropyrrolidine-1-sulfonamide | ¹H NMR (400 MHz, DMSO-$d_6$) δ 11.13 (s, 1H), 8.25 (s, 1H), 8.18 (d, J = 2.8 Hz, 1H), 8.14 (s, 1H), 7.87-7.78 (m, 2H), 7.71-7.65 (m, 2H), 7.64-7.60 (m, 1H), 7.57-7.47 (m, 2H), 7.41-7.33 (m, 2H), 6.97 (d, J = 9.2 Hz, 1H), 5.35-5.21 (m, 1H), 5.10 (dd, J = 5.6, 12.8 Hz, 1H), 4.90 (s, 1H), 4.39 (d, J = 12.8 Hz, 2H), 3.18-3.21 (m, 4H), 3.00-2.83 (m, 6H), 2.73 (s, 2H), 2.65-2.54 (m, 2H), 2.12-1.99 (m, 7H), 1.97-1.88 (m, 2H), 1.87-1.79 (m, 2H), 1.25-1.13 (m, 2H) |

TABLE 1-continued

| Cmp. No. | Structure | IUPAC Name | ¹H NMR |
|---|---|---|---|
| 138 | 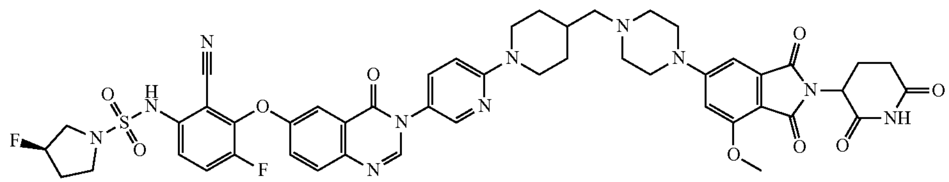 [SMILES: COc1cc(N2CCN(CC3CCN(c4ccc(-n5cnc6ccc(Oc7c(F)ccc(NS(=O)(=O)N8CC[C@@H](F)C8)c7C#N)cc6c5=O)cn4)CC3)CC2)cc2c1C(=O)N(C1CCC(=O)NC1=O)C2=O] | (3R)-N-{2-cyano-3-[(3-{6-[4-({4-[2-(2,6-dioxopiperidin-3-yl)-7-methoxy-1,3-dioxo-2,3-dihydro-1H-isoindol-5-yl]piperazin-1-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | N/A |
| 139 | 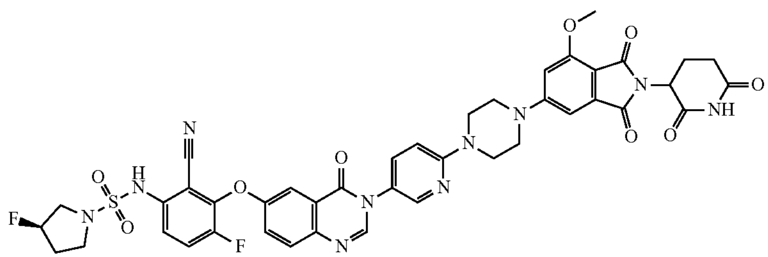 [SMILES: COc1cc(N2CCN(c3ccc(-n4cnc5ccc(Oc6c(F)ccc(NS(=O)(=O)N7CC[C@@H](F)C7)c6C#N)cc5c4=O)cn3)CC2)cc2c1C(=O)N(C1CCC(=O)NC1=O)C2=O] | (3R)-N-(2-cyano-3-{[3-(6-{4-[2-(2,6-dioxopiperidin-3-yl)-7-methoxy-1,3-dioxo-2,3-dihydro-1H-isoindol-5-yl]piperazin-1-yl}pyridin-3-yl)-4-oxo-3,4-dihydroquinazolin-6-yl]oxy}-4-fluorophenyl)-3-fluoropyrrolidine-1-sulfonamide | N/A |
| 140 | 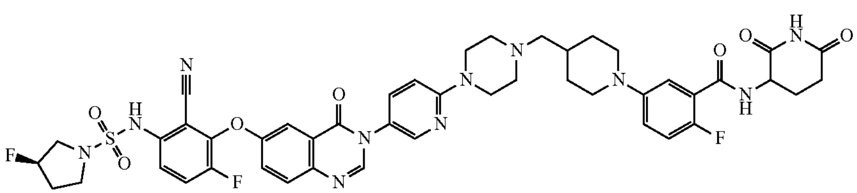 [SMILES: N#Cc1c(NS(=O)(=O)N2CC[C@@H](F)C2)ccc(F)c1Oc1ccc2ncn(-c3ccc(N4CCN(CC5CCN(c6ccc(F)c(C(=O)NC7CCC(=O)NC7=O)c6)CC5)CC4)nc3)c(=O)c2c1] | 5-(4-{[4-(5-{6-[2-cyano-6-fluoro-3-({[(3R)-3-fluoropyrrolidin-1-yl]sulfonyl}amino)phenoxy]-4-oxo-3,4-dihydroquinazolin-3-yl}pyridin-2-yl)piperazin-1-yl]methyl}piperidin-1-yl)-N-(2,6-dioxopiperidin-3-yl)-2-fluorobenzamide | N/A |

TABLE 1-continued

| Cmp. No. | Structure | IUPAC Name | $^1$H NMR |
|---|---|---|---|
| 141 | 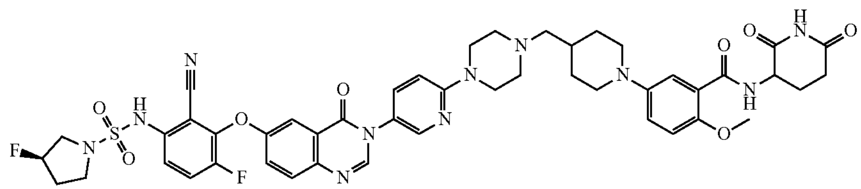 [SMILES: COc1ccc(N2CCC(CN3CCN(c4ccc(-n5cnc6ccc(Oc7c(F)ccc(NS(=O)(=O)N8CC[C@@H](F)C8)c7C#N)cc6c5=O)cn4)CC3)CC2)cc1C(=O)NC1CCC(=O)NC1=O] | 5-(4-{[4-(5-{6-[2-cyano-6-fluoro-3-({[(3R)-3-fluoropyrrolidin-1-yl]sulfonyl}amino)phenoxy]-4-oxo-3,4-dihydroquinazolin-3-yl}pyridin-2-yl)piperazin-1-yl]methyl}piperidin-1-yl)-N-(2,6-dioxopiperidin-3-yl)-2-methoxybenzamide | N/A |
| 142 | 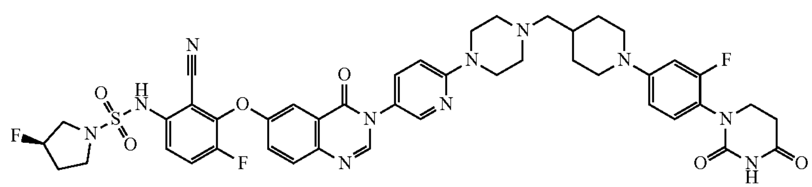 [SMILES: N#Cc1c(NS(=O)(=O)N2CC[C@@H](F)C2)ccc(F)c1Oc1ccc2ncn(-c3ccc(N4CCN(CC5CCN(c6ccc(N7CCC(=O)NC7=O)c(F)c6)CC5)CC4)nc3)c(=O)c2c1] | (3R)-N-{2-cyano-3-[(3-{6-[4-({1-[4-(2,4-dioxo-1,3-diazinan-1-yl)-3-fluorophenyl]piperidin-4-yl}methyl)piperazin-1-yl]pyridin-3-yl}-4-oxo-3,4-dihydroquinazolin-6-yl)oxy]-4-fluorophenyl}-3-fluoropyrrolidine-1-sulfonamide | N/A |
| 143 | 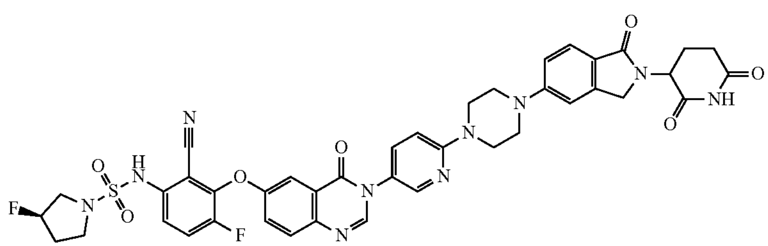 | (3R)-N-(2-cyano-3-{[3-(6-{4-[2-(2,6-dioxopiperidin-3-yl)-1-oxo-2,3-dihydro-1H-isoindol-5-yl]piperazin-1-yl}pyridin-3-yl)-4-oxo-3,4-dihydroquinazolin-6-yl]oxy}-4-fluorophenyl)-3-fluoropyrrolidine-1-sulfonamide | N/A |

TABLE 1-continued

| Cmp. No. | Structure | IUPAC Name | ¹H NMR |
|---|---|---|---|
| 144 | 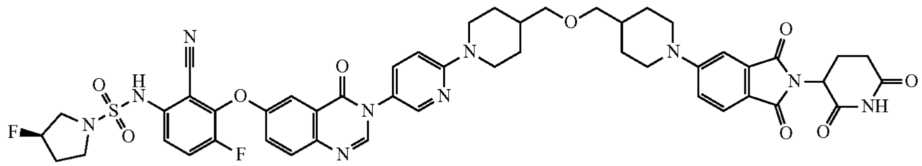 [SMILES: N#Cc1c(NS(=O)(=O)N2CC[C@@H](F)C2)ccc(F)c1Oc1ccc2ncn(-c3ccc(N4CCC(COCC5CCN(c6ccc7c(c6)C(=O)N(C6CCC(=O)NC6=O)C7=O)CC5)CC4)nc3)c(=O)c2c1] | (3R)-N-(2-cyano-3-{[3-(6-{4-[({1-[2-(2,6-dioxopiperidin-3-yl)-1,3-dioxo-2,3-dihydro-1H-isoindol-5-yl]piperidin-4-yl}methoxy)methyl]piperidin-1-yl}pyridin-3-yl)-4-oxo-3,4-dihydroquinazolin-6-yl]oxy}-4-fluorophenyl)-3-fluoropyrrolidine-1-sulfonamide | N/A |
| 145 | 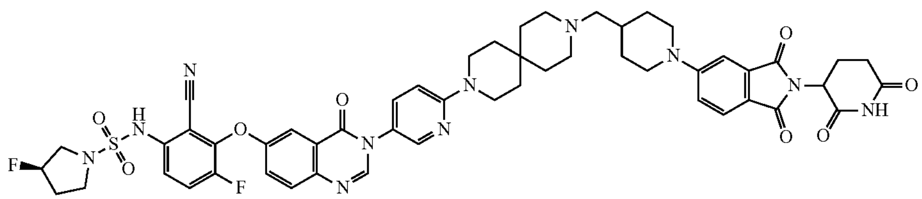 [SMILES: N#Cc1c(NS(=O)(=O)N2CC[C@@H](F)C2)ccc(F)c1Oc1ccc2ncn(-c3ccc(N4CCC5(CCN(CC6CCN(c7ccc8c(c7)C(=O)N(C7CCC(=O)NC7=O)C8=O)CC6)CC5)CC4)nc3)c(=O)c2c1] | (3R)-N-{2-cyano-3-[(3-{6-[9-({1-[2-(2,6-dioxopiperidin-3-yl)-1,3-dioxo-2,3-dihydro-1H-isoindol-5-yl]piperidin-4-yl}methyl)-3,9-diazaspiro[5.5]undecan-3-yl]pyridin-3-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 11.08 (s, 1H), 8.24 (s, 1H), 8.18 (d, J = 2.6 Hz, 1H), 8.14 (s, 1H), 7.80 (d, J = 8.9 Hz, 1H), 7.70-7.63 (m, 3H), 7.45-7.24 (m, 5H), 6.96 (d, J = 9.3 Hz, 1H), 5.35-5.17 (m, 1H), 5.07 (dd, J = 5.4, 12.9 Hz, 1H), 4.08 (d, J = 12.5 Hz, 2H), 3.59 (s, 6H), 3.24-3.14 (m, 4H), 3.10-2.99 (m, 6H), 2.91-2.84 (m, 3H), 2.17-1.93 (m, 5H), 1.81 (d, J = 11.0 Hz, 2H), 1.71 (s, 4H), 1.55 (s, 4H), 1.31-1.18 (m, 2H) |
| 146 | 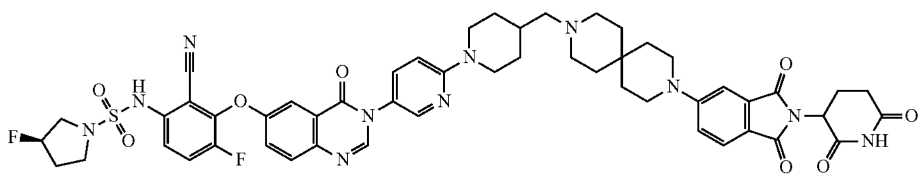 [SMILES: N#Cc1c(NS(=O)(=O)N2CC[C@@H](F)C2)ccc(F)c1Oc1ccc2ncn(-c3ccc(N4CCC(CN5CCC6(CC5)CCN(c5ccc7c(c5)C(=O)N(C5CCC(=O)NC5=O)C7=O)CC6)CC4)nc3)c(=O)c2c1] | (3R)-N-{2-cyano-3-[(3-{6-[4-({9-[2-(2,6-dioxopiperidin-3-yl)-1,3-dioxo-2,3-dihydro-1H-isoindol-5-yl]-3,9-diazaspiro[5.5]undecan-3-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 147 | 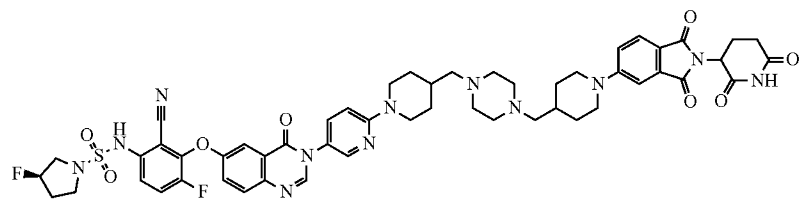 [SMILES: N#Cc1c(NS(=O)(=O)N2CC[C@@H](F)C2)ccc(F)c1Oc1ccc2ncn(-c3ccc(N4CCC(CN5CCN(CC6CCN(c7ccc8c(c7)C(=O)N(C7CCC(=O)NC7=O)C8=O)CC6)CC5)CC4)nc3)c(=O)c2c1] | (3R)-N-[2-cyano-3-({6-(4-{[4-({1-[2-(2,6-dioxopiperidin-3-yl)-1,3-dioxo-2,3-dihydro-1H-isoindol-5-yl]piperidin-4-yl}methyl)piperazin-1-yl]methyl}piperidin-1-yl)pyridin-3-yl]-4-oxo-3,4-dihydroquinazolin-6-yl}oxy)-4-fluorophenyl]-3-fluoropyrrolidine-1-sulfonamide | N/A |
| 148 | 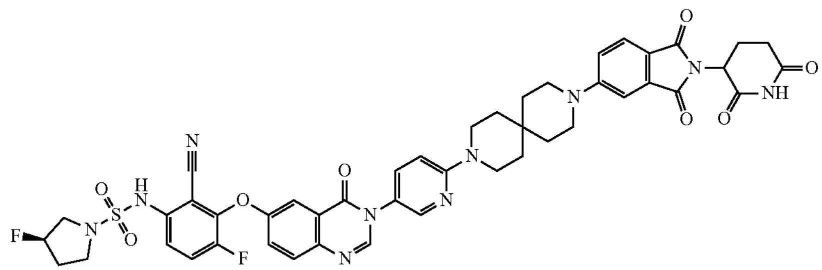 [SMILES: N#Cc1c(NS(=O)(=O)N2CC[C@@H](F)C2)ccc(F)c1Oc1ccc2ncn(-c3ccc(N4CCC5(CCN(c6ccc7c(c6)C(=O)N(C6CCC(=O)NC6=O)C7=O)CC5)CC4)nc3)c(=O)c2c1] | (3R)-N-(2-cyano-3-{[3-(6-{9-[2-(2,6-dioxopiperidin-3-yl)-1,3-dioxo-2,3-dihydro-1H-isoindol-5-yl]-3,9-diazaspiro[5.5]undecan-3-yl}pyridin-3-yl)-4-oxo-3,4-dihydroquinazolin-6-yl]oxy}-4-fluorophenyl)-3-fluoropyrrolidine-1-sulfonamide | N/A |
| 149 | 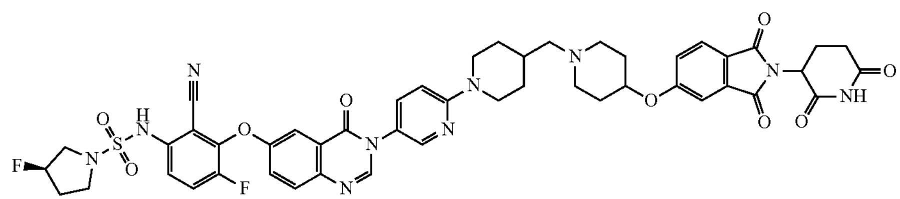 [SMILES: N#Cc1c(NS(=O)(=O)N2CC[C@@H](F)C2)ccc(F)c1Oc1ccc2ncn(-c3ccc(N4CCC(CN5CCC(Oc6ccc7c(c6)C(=O)N(C6CCC(=O)NC6=O)C7=O)CC5)CC4)nc3)c(=O)c2c1] | (3R)-N-(2-cyano-3-{[3-(6-{4-[({4-[(2-(2,6-dioxopiperidin-3-yl)-1,3-dioxo-2,3-dihydro-1H-isoindol-5-yl]oxy}piperidin-1-yl)methyl]piperidin-1-yl}pyridin-3-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 11.08 (s, 1 H), 10.34 (s, 1 H), 8.29 (s, 1 H), 8.18 (d, J = 2.8 Hz, 1 H), 7.77-7.90 (m, 2 H), 7.69-7.75 (m, 1 H), 7.62-7.68 (m, 2 H), 7.47-7.53 (m, 1 H), 7.41 (d, J = 2.8 Hz, 1 H), 7.32 (s, 1 H), 7.25 (d, J = 8.8 Hz, 1 H), 6.96 (d, J = 9.2 Hz, 1 H), 5.21-5.42 (m, 1 H), 5.06 (dd, J = 12.8, 5.2 Hz, 1 H), 3.62 (s, 4 H), 3.35-3.55 (m, 10 H), 2.82-2.93 (m, 1 H), 2.51-2.63 (m, 4 H), 1.98-2.17 (m, 3 H), 1.52-1.65 (m, 8 H) |

TABLE 1-continued

| Cmp. No. | Structure | IUPAC Name | ¹H NMR |
|---|---|---|---|
| 150 | 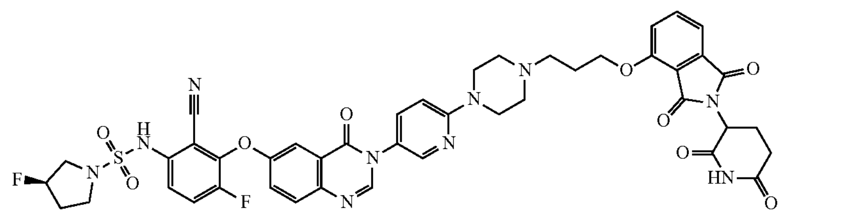 [SMILES: N#Cc1c(NS(=O)(=O)N2CC[C@@H](F)C2)ccc(F)c1Oc1ccc2ncn(-c3ccc(N4CCN(CCCOc5cccc6c5C(=O)N(C5CCC(=O)NC5=O)C6=O)CC4)nc3)c(=O)c2c1] | (3R)-N-{2-cyano-3-[(3-{6-[4-(3-{[2-(2,6-dioxopiperidin-3-yl)-1,3-dioxo-2,3-dihydro-1H-isoindol-4-yl]oxy}propyl)piperazin-1-yl]pyridin-3-yl}-4-oxo-3,4-dihydroquinazolin-6-yl)oxy]-4-fluorophenyl}-3-fluoropyrrolidine-1-sulfonamide | N/A |
| 151 | 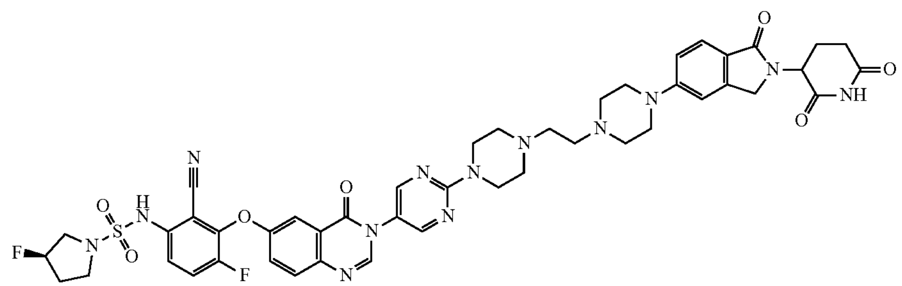 [SMILES: N#Cc1c(NS(=O)(=O)N2CC[C@@H](F)C2)ccc(F)c1Oc1ccc2ncn(-c3cnc(N4CCN(CCN5CCN(c6ccc7c(c6)CN(C6CCC(=O)NC6=O)C7=O)CC5)CC4)nc3)c(=O)c2c1] | (3R)-N-{2-cyano-3-[(3-{2-[4-(2-{4-[2-(2,6-dioxopiperidin-3-yl)-1-oxo-2,3-dihydro-1H-isoindol-5-yl]piperazin-1-yl}ethyl)piperazin-1-yl]pyrimidin-5-yl}-4-oxo-3,4-dihydroquinazolin-6-yl)oxy]-4-fluorophenyl}-3-fluoropyrrolidine-1-sulfonamide | N/A |
| 152 | 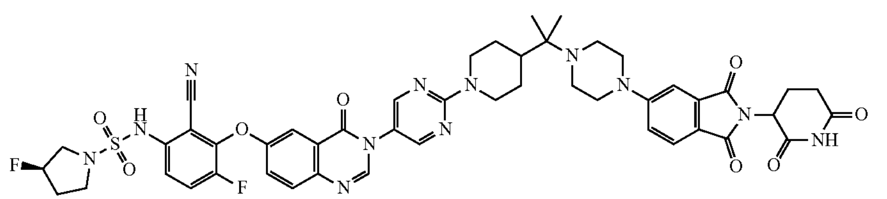 [SMILES: CC(C)(C1CCN(c2ncc(-n3cnc4ccc(Oc5c(F)ccc(NS(=O)(=O)N6CC[C@@H](F)C6)c5C#N)cc4c3=O)cn2)CC1)N1CCN(c2ccc3c(c2)C(=O)N(C2CCC(=O)NC2=O)C3=O)CC1] | (3R)-N-{2-cyano-3-[(3-{2-[4-(2-{4-[2-(2,6-dioxopiperidin-3-yl)-1,3-dioxo-2,3-dihydro-1H-isoindol-5-yl]piperazin-1-yl}propan-2-yl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |

| Cmp. No. | Structure | IUPAC Name | ¹H NMR |
|---|---|---|---|
| 153 | 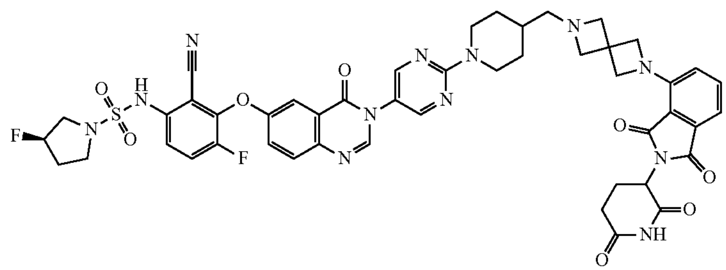 [SMILES: N#Cc1c(NS(=O)(=O)N2CC[C@@H](F)C2)ccc(F)c1Oc1ccc2ncn(-c3cnc(N4CCC(CN5CC6(C5)CN(c5cccc7c5C(=O)N(C5CCC(=O)NC5=O)C7=O)C6)CC4)nc3)c(=O)c2c1] | (3R)-N-{2-cyano-3-[(3-{2-[4-({6-[2-(2,6-dioxopiperidin-3-yl)-1,3-dioxo-2,3-dihydro-1H-isoindol-4-yl]-2,6-diazaspiro[3.3]heptan-2-yl}methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |
| 154 | 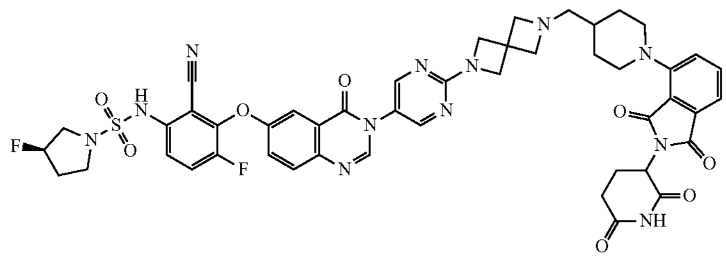 | (3R)-N-{2-cyano-3-[(3-{2-[6-({1-[2-(2,6-dioxopiperidin-3-yl)-1,3-dioxo-2,3-dihydro-1H-isoindol-4-yl]piperidin-4-yl}methyl)-2,6-diazaspiro[3.3]heptan-2-yl]pyrimidin-5-yl}-4-oxo-3,4-dihydroquinazolin-6-yl)oxy]-4-fluorophenyl}-3-fluoropyrrolidine-1-sulfonamide | N/A |
| 155 | 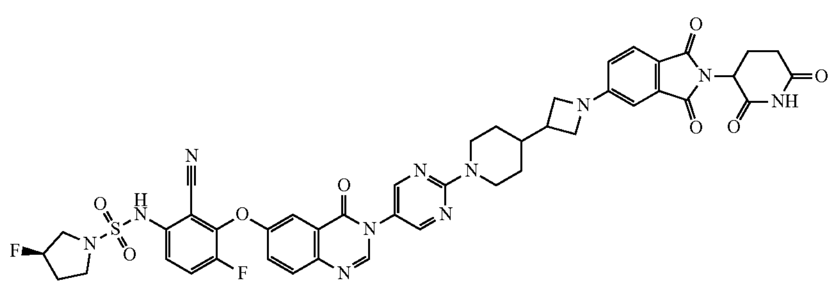 [SMILES: N#Cc1c(NS(=O)(=O)N2CC[C@@H](F)C2)ccc(F)c1Oc1ccc2ncn(-c3cnc(N4CCC(C5CN(c6ccc7c(c6)C(=O)N(C6CCC(=O)NC6=O)C7=O)C5)CC4)nc3)c(=O)c2c1] | (3R)-N-[2-cyano-3-({3-[2-(4-{1-[2-(2,6-dioxopiperidin-3-yl)-1,3-dioxo-2,3-dihydro-1H-isoindol-5-yl]azetidin-3-yl}piperidin-1-yl)pyrimidin-5-yl]-4-oxo-3,4-dihydroquinazolin-6-yl}oxy)-4-fluorophenyl]-3-fluoropyrrolidine-1-sulfonamide | N/A |

TABLE 1-continued

| Cmp. No. | Structure | IUPAC Name | ¹H NMR |
|---|---|---|---|
| 156 | 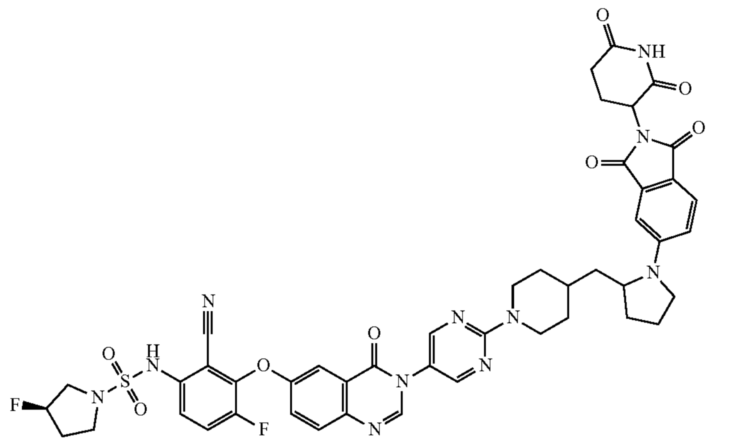 | (3R)-N-{2-cyano-3-[(3-{2-[4-({1-[2-(2,6-dioxopiperidin-3-yl)-1,3-dioxo-2,3-dihydro-1H-isoindol-5-yl]pyrrolidin-2-yl}methyl)piperidin-1-yl]pyrimidin-5-yl}-4-oxo-3,4-dihydroquinazolin-6-yl)oxy]-4-fluorophenyl}-3-fluoropyrrolidine-1-sulfonamide | N/A |
| 157 | 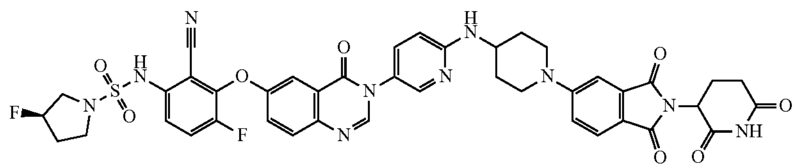 [SMILES: N#Cc1c(NS(=O)(=O)N2CC[C@@H](F)C2)ccc(F)c1Oc1ccc2ncn(-c3ccc(NC4CCN(c5ccc6c(c5)C(=O)N(C5CCC(=O)NC5=O)C6=O)CC4)nc3)c(=O)c2c1] | (3R)-N-[2-cyano-3-({3-[6-({1-[2-(2,6-dioxopiperidin-3-yl)-1,3-dioxo-2,3-dihydro-1H-isoindol-5-yl]piperidin-4-yl}amino)pyridin-3-yl]-4-oxo-3,4-dihydroquinazolin-6-yl}oxy)-4-fluorophenyl]-3-fluoropyrrolidine-1-sulfonamide | N/A |
| 158 | 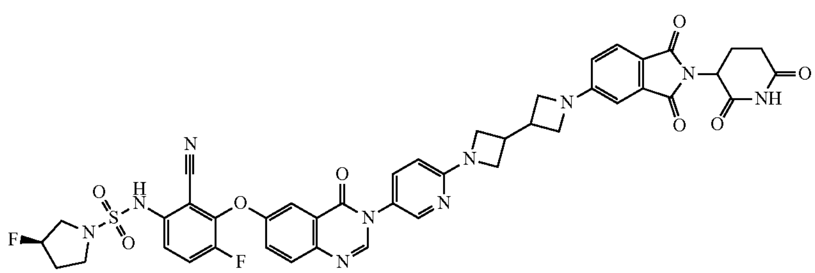 [SMILES: N#Cc1c(NS(=O)(=O)N2CC[C@@H](F)C2)ccc(F)c1Oc1ccc2ncn(-c3ccc(N4CC(C5CN(c6ccc7c(c6)C(=O)N(C6CCC(=O)NC6=O)C7=O)C5)C4)nc3)c(=O)c2c1] | (3R)-N-(2-cyano-3-{[3-(6-{1'-[2-(2,6-dioxopiperidin-3-yl)-1,3-dioxo-2,3-dihydro-1H-isoindol-5-yl]-[3,3'-biazetidin]-1-yl}pyridin-3-yl)-4-oxo-3,4-dihydroquinazolin-6-yl]oxy}-4-fluorophenyl)-3-fluoropyrrolidine-1-sulfonamide | N/A |

TABLE 1-continued

| Cmp. No. | Structure | IUPAC Name | ¹H NMR |
|---|---|---|---|
| 159 | 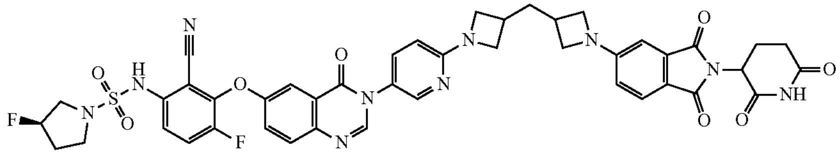 | (3R)-N-{2-cyano-3-[(3-{6-[3-({1-[2-(2,6-dioxopiperidin-3-yl)-1,3-dioxo-2,3-dihydro-1H-isoindol-5-yl]azetidin-3-yl}methyl)azetidin-1-yl]pyridin-3-yl}-4-oxo-3,4-dihydroquinazolin-6-yl)oxy]-4-fluorophenyl}-3-fluoropyrrolidine-1-sulfonamide | N/A |
| 160 | 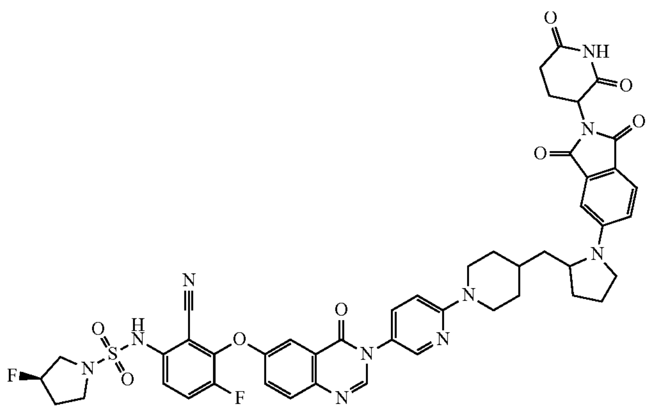 [SMILES: N#Cc1c(NS(=O)(=O)N2CC[C@@H](F)C2)ccc(F)c1Oc1ccc2ncn(-c3ccc(N4CCC(CC5CCCN5c5ccc6c(c5)C(=O)N(C5CCC(=O)NC5=O)C6=O)CC4)nc3)c(=O)c2c1] | (3R)-N-{2-cyano-3-[(3-{6-[4-({1-[2-(2,6-dioxopiperidin-3-yl)-1,3-dioxo-2,3-dihydro-1H-isoindol-5-yl]pyrrolidin-2-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | N/A |
| 161 | 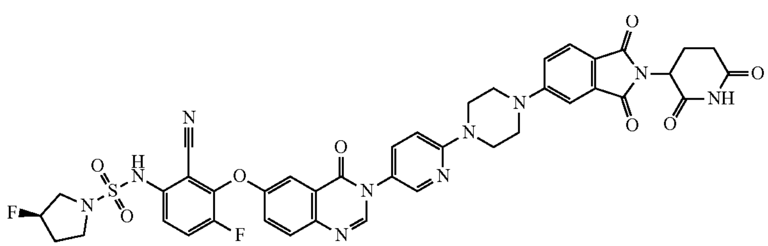 | (3R)-N-{2-cyano-3-[{3-(6-[4-[2-(2,6-dioxopiperidin-3-yl)-1,3-dioxo-2,3-dihydro-1H-isoindol-5-yl]piperazin-1-yl]pyridin-3-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 162 | 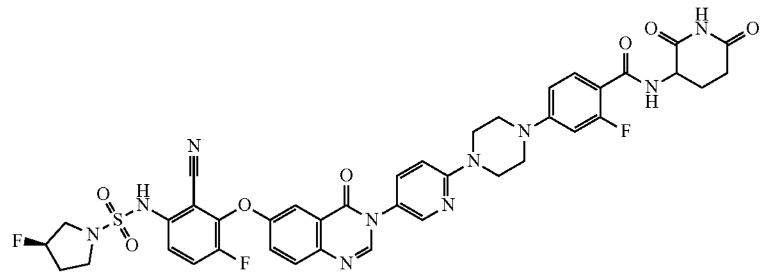 [SMILES: N#Cc1c(NS(=O)(=O)N2CC[C@@H](F)C2)ccc(F)c1Oc1ccc2ncn(-c3ccc(N4CCN(c5ccc(C(=O)NC6CCC(=O)NC6=O)c(F)c5)CC4)nc3)c(=O)c2c1] | 4-[4-(5-{6-[2-cyano-6-fluoro-3-{[(3R)-3-fluoropyrrolidin-1-yl]sulfonyl}amino]phenoxy]-4-oxo-3,4-dihydroquinazolin-3-yl}pyridin-2-yl)piperazin-1-yl]-N-(2,6-dioxopiperidin-3-yl)-2-fluorobenzamide | N/A |
| 163 | 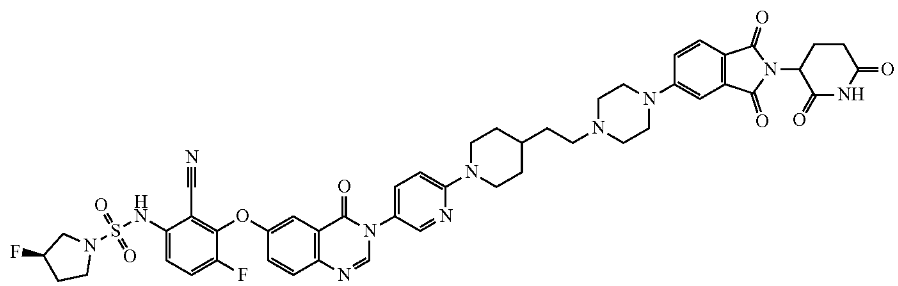 [SMILES: N#Cc1c(NS(=O)(=O)N2CC[C@@H](F)C2)ccc(F)c1Oc1ccc2ncn(-c3ccc(N4CCC(CCN5CCN(c6ccc7c(c6)C(=O)N(C6CCC(=O)NC6=O)C7=O)CC5)CC4)nc3)c(=O)c2c1] | (3R)-N-{2-cyano-3-[(3-{6-[4-(2-{4-[2-(2,6-dioxopiperidin-3-yl)-1,3-dioxo-2,3-dihydro-1H-isoindol-5-yl]piperazin-1-yl}ethyl)piperidin-1-yl]pyridin-3-yl}-4-oxo-3,4-dihydroquinazolin-6-yl)oxy]-4-fluorophenyl}-3-fluoropyrrolidine-1-sulfonamide | N/A |
| 164 | 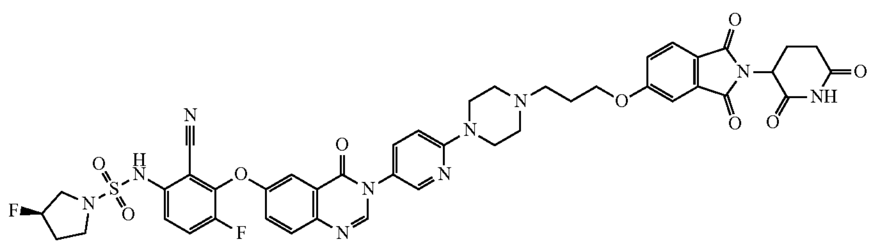 [SMILES: N#Cc1c(NS(=O)(=O)N2CC[C@@H](F)C2)ccc(F)c1Oc1ccc2ncn(-c3ccc(N4CCN(CCCOc5ccc6c(c5)C(=O)N(C5CCC(=O)NC5=O)C6=O)CC4)nc3)c(=O)c2c1] | (3R)-N-{2-cyano-3-[(3-{6-[4-(3-{[2-(2,6-dioxopiperidin-3-yl)-1,3-dioxo-2,3-dihydro-1H-isoindol-5-yl]oxy}propyl)piperazin-1-yl]pyridin-3-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 165 | 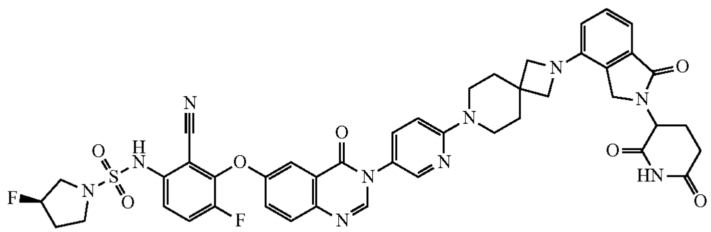 [SMILES: N#Cc1c(NS(=O)(=O)N2CC[C@@H](F)C2)ccc(F)c1Oc1ccc2ncn(-c3ccc(N4CCC5(CC4)CN(c4cccc6c4CN(C4CCC(=O)NC4=O)C6=O)C5)nc3)c(=O)c2c1] | (3R)-N-(2-cyano-3-{[3-(6-{2-[2-(2,6-dioxopiperidin-3-yl)-1-oxo-2,3-dihydro-1H-isoindol-4-yl]-2,7-diazaspiro[3.5]nonan-7-yl}pyridin-3-yl)-4-oxo-3,4-dihydroquinazolin-6-yl]oxy}-4-fluorophenyl)-3-fluoropyrrolidine-1-sulfonamide | N/A |
| 166 | 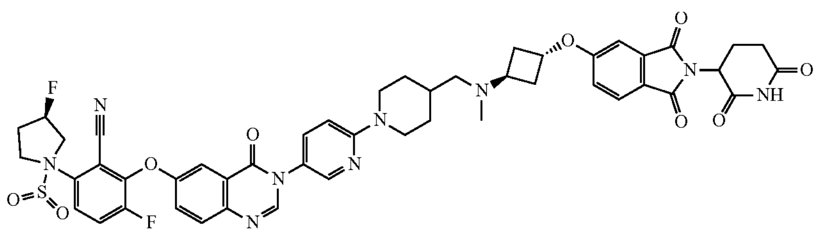 | (3R)-N-{2-cyano-4-fluoro-3-[(3-{6-[4-({methyl[(1r,3r)-3-{[2-(2,6-dioxopiperidin-3-yl)-1,3-dioxo-2,3-dihydro-1H-isoindol-5-yl]oxy}cyclobutyl]amino}methyl)piperidin-1-yl]pyridin-3-yl}-4-oxo-3,4-dihydroquinazolin-6-yl)oxy]phenyl}-3-fluoropyrrolidine-1-sulfonamide | N/A |
| 167 | 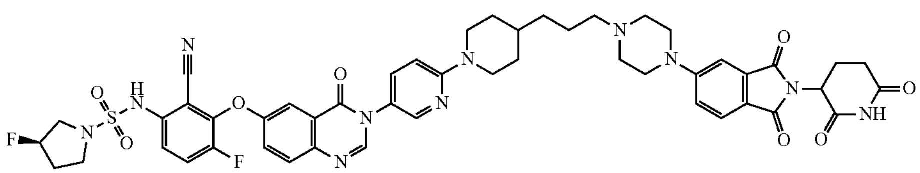 | (3R)-N-{2-cyano-3-[(3-{6-[4-(3-{4-[2-(2,6-dioxopiperidin-3-yl)-1,3-dioxo-2,3-dihydro-1H-isoindol-5-yl]piperazin-1-yl}propyl)piperidin-1-yl]pyridin-3-yl}-4-oxo-3,4-dihydroquinazolin-6-yl)oxy]-4-fluorophenyl}-3-fluoropyrrolidine-1-sulfonamide | N/A |

TABLE 1-continued

| Cmp. No. | Structure | IUPAC Name | ¹H NMR |
|---|---|---|---|
| 168 | 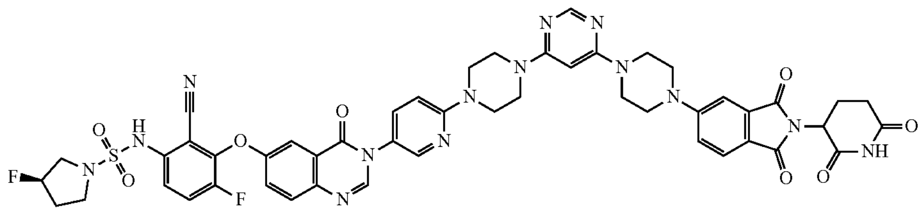 [SMILES: N#Cc1c(NS(=O)(=O)N2CC[C@@H](F)C2)ccc(F)c1Oc1ccc2ncn(-c3ccc(N4CCN(c5cc(N6CCN(c7ccc8c(c7)C(=O)N(C7CCC(=O)NC7=O)C8=O)CC6)ncn5)CC4)nc3)c(=O)c2c1] | (3R)-N-{2-cyano-3-[(3-{6-[4-(6-{4-[2-(2,6-dioxopiperidin-3-yl)-1,3-dioxo-2,3-dihydro-1H-isoindol-5-yl]piperazin-1-yl}pyrimidin-4-yl)piperazin-1-yl]pyridin-3-yl}-4-oxo-3,4-dihydroquinazolin-6-yl)oxy]-4-fluorophenyl}-3-fluoropyrrolidine-1-sulfonamide | N/A |
| 169 | 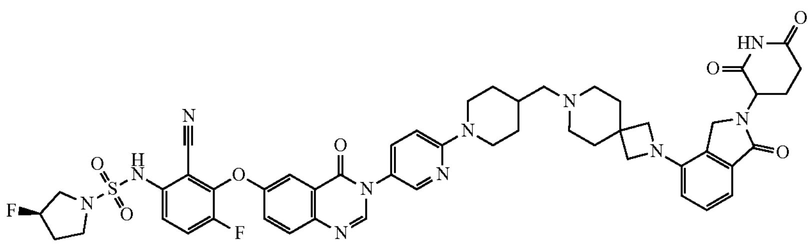 [SMILES: N#Cc1c(NS(=O)(=O)N2CC[C@@H](F)C2)ccc(F)c1Oc1ccc2ncn(-c3ccc(N4CCC(CN5CCC6(CC5)CN(c5cccc7c5CN(C5CCC(=O)NC5=O)C7=O)C6)CC4)nc3)c(=O)c2c1] | (3R)-N-{2-cyano-3-[(3-{6-[4-({2-[2-(2,6-dioxopiperidin-3-yl)-1-oxo-2,3-dihydro-1H-isoindol-4-yl]-2,7-diazaspiro[3.5]nonan-7-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | N/A |
| 170 | 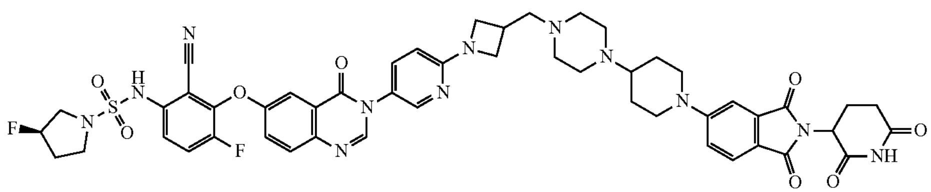 [SMILES: N#Cc1c(NS(=O)(=O)N2CC[C@@H](F)C2)ccc(F)c1Oc1ccc2ncn(-c3ccc(N4CC(CN5CCN(C6CCN(c7ccc8c(c7)C(=O)N(C7CCC(=O)NC7=O)C8=O)CC6)CC5)C4)nc3)c(=O)c2c1] | (3R)-N-(2-cyano-3-{[3-(6-{3-[(4-{1-[2-(2,6-dioxopiperidin-3-yl)-1,3-dioxo-2,3-dihydro-1H-isoindol-5-yl]piperidin-4-yl}piperazin-1-yl)methyl]azetidin-1-yl}pyridin-3-yl)-4-oxo-3,4-dihydroquinazolin-6-yl]oxy}-4-fluorophenyl)-3-fluoropyrrolidine-1-sulfonamide | ¹H NMR (400 MHz, DMSO-d₆) δ 11.09 (s, 1H), 8.23 (s, 1H), 8.15 (d, J = 2.8 Hz, 1H), 8.13 (s, 1H), 7.80 (m, 1H), 7.70-7.62 (m, 3H), 7.52-7.43 (m, 1H), 7.39-7.31 (m, 3H), 7.27 (dd, J = 1.6, 8.4 Hz, 1H), 6.48 (d, J = 8.8 Hz, 1H), 5.36-5.18 (m, 1H), 5.07 (dd, J = 5.2, 12.8 Hz, 1H), 4.17-4.07 (m, 4H), 3.69 (m, 3H), 3.30 (m, 2H), 3.27 (m, 2H), 3.25-3.23 (m, 2H), 3.21-3.15 (m, 3H), 3.01-2.93 (m, 4H), 2.91 (m, 1H), 2.90-2.84 (m, 4H), 2.61-2.53 (m, 2H), 2.16-2.05 (m, 1H), 2.04-1.93 (m, 4H), 1.52 (m, 2H) |

TABLE 1-continued

| Cmp. No. | Structure | IUPAC Name | $^1$H NMR |
|---|---|---|---|
| 171 | 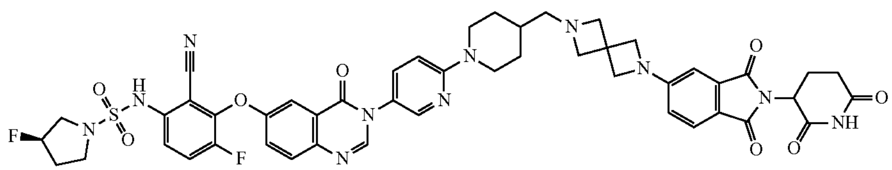 | (3R)-N-{2-cyano-3-[(3-{6-[4-({6-[2-(2,6-dioxopiperidin-3-yl)-1,3-dioxo-2,3-dihydro-1H-isoindol-5-yl]-2,6-diazaspiro[3.3]heptan-2-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | $^1$H NMR (400 MHz, DMSO-d$_6$) δ 11.08 (s, 1H), 8.25 (s, 1H), 8.18 (d, J = 2.4 Hz, 1H), 8.14 (s, 1H), 7.80 (m, 1H), 7.71-7.62 (m, 3H), 7.48-7.35 (m, 2H), 7.31 (m, 1H), 6.97 (d, J = 9.2 Hz, 1H), 6.85 (d, J = 1.6 Hz, 1H), 6.70 (dd, J = 1.6, 8.4 Hz, 1H), 5.36-5.16 (m, 1H), 5.06 (dd, J = 5.6, 12.8 Hz, 2H), 4.38 (d, J = 12.8 Hz, 2H), 4.20 (s, 4H), 4.13 (s, 2H), 3.25 (m, 2H), 3.16 (m, 2H), 2.99-2.93 (m, 2H), 2.93-2.82 (m, 4H), 2.70-2.53 (m, 2H), 2.23-1.87 (m, 4H), 1.86-1.77 (m, 1H), 1.72 (d, J = 13.2 Hz, 2H), 1.17 (m, 2H) |
| 172 | 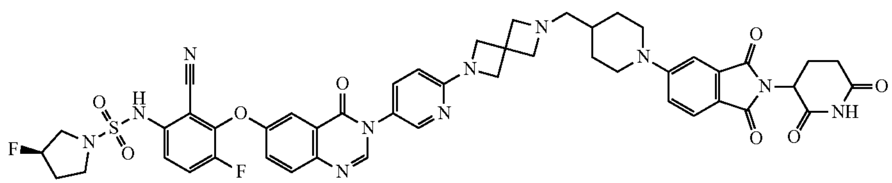 [SMILES: N#Cc1c(NS(=O)(=O)N2CC[C@@H](F)C2)ccc(F)c1Oc1ccc2ncn(-c3ccc(N4CC5(CN(CC6CCN(c7ccc8c(c7)C(=O)N(C7CCC(=O)NC7=O)C8=O)CC6)C5)C4)nc3)c(=O)c2c1] | (3R)-N-{2-cyano-3-[(3-{6-[6-({1-[2-(2,6-dioxopiperidin-3-yl)-1,3-dioxo-2,3-dihydro-1H-isoindol-5-yl]piperidin-4-yl}methyl)-2,6-diazaspiro[3.3]heptan-2-yl]pyridin-3-yl}-4-oxo-3,4-dihydroquinazolin-6-yl)oxy]-4-fluorophenyl}-3-fluoropyrrolidine-1-sulfonamide | N/A |
| 173 | 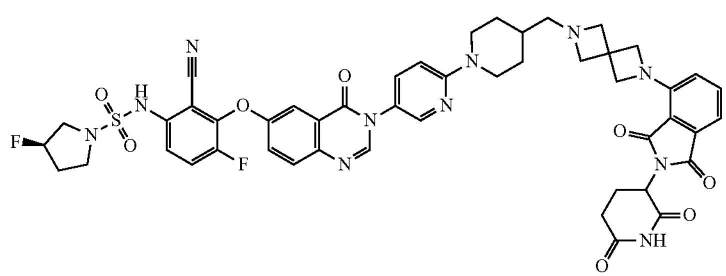 [SMILES: N#Cc1c(NS(=O)(=O)N2CC[C@@H](F)C2)ccc(F)c1Oc1ccc2ncn(-c3ccc(N4CCC(CN5CC6(C5)CN(c5cccc7c5C(=O)N(C5CCC(=O)NC5=O)C7=O)C6)CC4)nc3)c(=O)c2c1] | (3R)-N-{2-cyano-3-[(3-{6-[4-({6-[2-(2,6-dioxopiperidin-3-yl)-1,3-dioxo-2,3-dihydro-1H-isoindol-4-yl]-2,6-diazaspiro[3.3]heptan-2-yl}methyl)piperidin-1-yl]pyridin-3-yl}-4-oxo-3,4-dihydroquinazolin-6-yl)oxy]-4-fluorophenyl}-3-fluoropyrrolidine-1-sulfonamide | $^1$H NMR (400 MHz, DMSO-d$_6$) δ 11.08 (s, 1H), 8.24 (s, 1H), 8.18 (d, J = 2.8 Hz, 1H), 7.82-7.78 (m, 1H), 7.70-7.64 (m, 2H), 7.62-7.56 (m, 1H), 7.37 (s, 2H), 7.33-7.27 (m, 1H), 7.15 (d, J = 7.2 Hz, 1H), 6.96 (d, J = 8.8 Hz, 1H), 6.82 (d, J = 8.4 Hz, 1H), 5.37-5.16 (m, 1H), 5.05 (dd, J = 5.2, 12.4 Hz, 1H), 4.43-4.31 (m, 6H), 4.26-4.07 (m, 3H), 3.28-3.09 (m, 6H), 3.02-2.82 (m, 5H), 2.65-2.53 (m, 2H), 2.18-2.03 (m, 1H), 2.03-1.95 (m, 2H), 1.86-1.75 (m, 1H), 1.74-1.67 (m, 2H), 1.24-1.13 (m, 2H) |

TABLE 1-continued

| Cmp. No. | Structure | IUPAC Name | ¹H NMR |
|---|---|---|---|
| 174 | 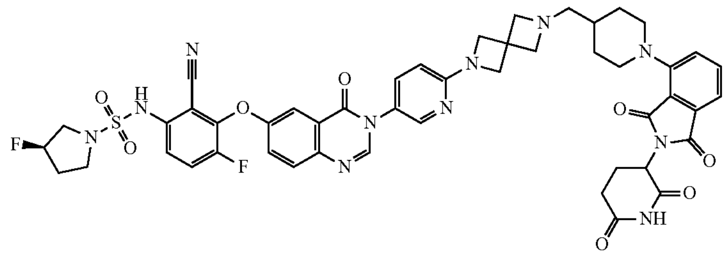 [SMILES: N#Cc1c(NS(=O)(=O)N2CC[C@@H](F)C2)ccc(F)c1Oc1ccc2ncn(-c3ccc(N4CC5(CN(CC6CCN(c7cccc8c7C(=O)N(C7CCC(=O)NC7=O)C8=O)CC6)C5)C4)nc3)c(=O)c2c1] | (3R)-N-{2-cyano-3-[(3-{6-[6-({1-[2-(2,6-dioxopiperidin-3-yl)-1,3-dioxo-2,3-dihydro-1H-isoindol-4-yl]piperidin-4-yl}methyl)-2,6-diazaspiro[3.3]heptan-2-yl]pyridin-3-yl}-4-oxo-3,4-dihydroquinazolin-6-yl)oxy]-4-fluorophenyl}-3-fluoropyrrolidine-1-sulfonamide | N/A |
| 175 | 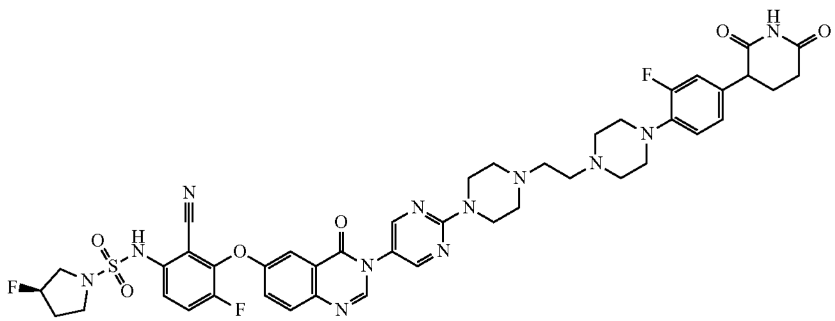 [SMILES: N#Cc1c(NS(=O)(=O)N2CC[C@@H](F)C2)ccc(F)c1Oc1ccc2ncn(-c3cnc(N4CCN(CCN5CCN(c6ccc(C7CCC(=O)NC7=O)cc6F)CC5)CC4)nc3)c(=O)c2c1] | (3R)-N-{2-cyano-3-{(3-{2-[4-(2-{4-[4-(2,6-dioxopiperidin-3-yl)-2-fluorophenyl]piperazin-1-yl}ethyl)piperazin-1-yl]pyrimidin-5-yl}-4-oxo-3,4-dihydroquinazolin-6-yl)oxy]-4-fluorophenyl}-3-fluoropyrrolidine-1-sulfonamide | ¹H NMR (400 MHz, DMSO-d₆) δ 10.84 (s, 1H), 8.55 (s, 2H), 8.31 (s, 1H), 7.83 (d, J = 8.9 Hz, 1H), 7.78-7.67 (m, 1H), 7.53 (s, 1H), 7.42-7.32 (m, 2H), 7.11-6.95 (m, 3H), 5.35 (s, 1H), 5.22 (s, 1H), 3.89 (s, 4H), 3.82-3.28 (m, 1H), 3.14 (s, 4H), 2.96 (s, 7H), 2.73 (s, 7H), 2.64-2.58 (m, 1H), 2.55 (s, 1H), 2.27-2.10 (m, 1H), 2.13-1.96 (m, 2H), 1.57 (s, 1H), 1.24 (s, 3H), 0.84-0.78 (m, 1H) |
| 181 | 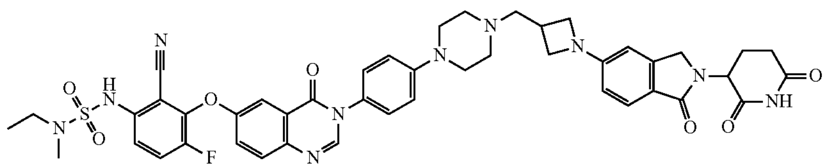 [SMILES: CCN(C)S(=O)(=O)Nc1ccc(F)c(Oc2ccc3ncn(-c4ccc(N5CCN(CC6CN(c7ccc8c(c7)CN(C7CCC(=O)NC7=O)C8=O)C6)CC5)cc4)c(=O)c3c2)c1C#N] | 2-[(3-{4-[4-({1-[2-(2,6-dioxopiperidin-3-yl)-1-oxo-2,3-dihydro-1H-isoindol-5-yl]azetidin-3-yl}methyl)piperazin-1-yl]phenyl}-4-oxo-3,4-dihydroquinazolin-6-yl)oxy]-6-{[ethyl(methyl)sulfamoyl]amino}-3-fluorobenzonitrile | ¹H NMR (300 MHz, DMSO) δ 10.94 (s, 1H), 10.20 (b, 1H), 8.26 (s, 1H), 7.85-7.69 (m, 3H), 7.51-7.32 (m, 5H), 7.08 (d, J = 9.0Hz, 1H), 6.53-6.48 (m, 2H), 5.07-5.01 (m, 1H), 4.39-4.15 (m, 2H), 4.09-4.07 (m, 2H), 3.64 (s, 2H), 3.34-3.32 (m, 4H), 3.14-3.12 (m, 3H), 2.65-2.51 (m, 10H), 2.35-2.31 (m, 3H), 1.95 -1.91 (m, 1H), 1.06-1.02 (m, 3H) |

TABLE 1-continued

| Cmp. No. | Structure | IUPAC Name | $^1$H NMR |
|---|---|---|---|
| 182 | 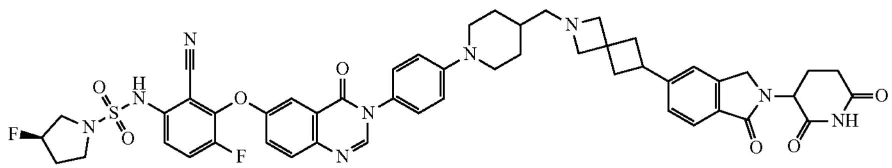 [SMILES: N#Cc1c(NS(=O)(=O)N2CC[C@@H](F)C2)ccc(F)c1Oc1ccc2ncn(-c3ccc(N4CCC(CN5CC6(CC(c7ccc8c(c7)CN(C7CCC(=O)NC7=O)C8=O)C6)C5)CC4)cc3)c(=O)c2c1] | (3R)-N-{2-cyano-3-[(3-(4-[4-((6-[2-(2,6-dioxopiperidin-3-yl)-1-oxo-2,3-dihydro-1H-isoindol-5-yl]-2-azaspiro[3.3]heptan-2-yl}methyl)piperidin-1-yl]phenyl}-4-oxo-3,4-dihydroquinazolin-6-yl)oxy]-4-fluorophenyl}-3-fluoropyrrolidine-1-sulfonamide | $^1$H NMR (300 MHz, DMSO) δ 10.99 (s, 1 H), 10.35 (dd, J = 6.8, 3.6 Hz, 1 H), 9.72-9.91 (m, 1 H), 8.24 (s, 1 H), 7.82 (d, J = 9.2 Hz, 1 H), 7.67 (d, J = 8.0 Hz, 2 H), 7.45-7.49 (m, 2 H), 7.41 (d, J = 3.6 Hz, 1 H), 7.37 (d, J = 7.6 Hz, 1 H), 7.32 (d, J = 8.8 Hz, 2 H), 7.06 (d, J = 9.2 Hz, 2 H), 5.20 - 5.42 (m, 1 H), 5.06-5.16 (m, 1 H), 4.37-4.47 (m, 2 H), 4.24-4.35 (m, 2 H), 4.11-4.23 (m, 2 H), 4.01-4.09 (m, 1 H), 3.79-3.86 (m, 2 H), 3.13 (dd, J = 6.0, 3.2 Hz, 2 H), 2.86-2.97 (m, 2 H), 2.70-2.81 (m, 5 H), 2.60-2.65 (m, 3 H), 2.09 - 2.19 (m, 1 H), 1.94 (s, 2 H), 1.74-1.82 (m, 3 H) 1.19-1.37 (m, 5 H) |
| 183 | 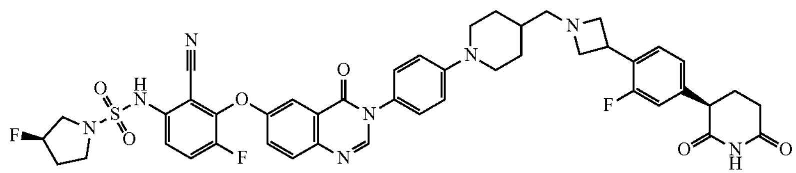 [SMILES: N#Cc1c(NS(=O)(=O)N2CC[C@@H](F)C2)ccc(F)c1Oc1ccc2ncn(-c3ccc(N4CCC(CN5CC(c6ccc([C@H]7CCC(=O)NC7=O)cc6F)C5)CC4)cc3)c(=O)c2c1] | (3R)-N-(2-cyano-3-{[3-(4-{4-[(3R)-2,6-dioxopiperidin-3-yl]-2-fluorophenyl}azetidin-1-yl)methyl]piperidin-1-yl]phenyl}-4-oxo-3,4-dihydroquinazolin-6-yl]oxy}-4-fluorophenyl)-3-fluoropyrrolidine-1-sulfonamide | $^1$H NMR (400 MHz, DMSO) δ 10.89 (s, 1H), 10.59 (s, 1H), 8.25 (s, 1H), 7.83 (d, J = 8.9 Hz, 1H), 7.75 (t, J = 9.8 Hz, 2H), 7.70 (m, 2H), 7.40 (m, 1H), 7.32 (d, J = 8.6 Hz, 2H), 7.19-7.11 (m, 2H), 7.06 (d, J = 8.7 Hz, 2H), 5.25 (d, J = 56 Hz, 1H), 4.46-4.05 (m, 5H), 3.93 (m, 1H), 3.82 (d, J = 12.2 Hz, 2H), 3.52-3.43 (m, 1H), 3.31 (m, 3H), 3.21 (s, 2H), 2.90-2.73 (m, 3H), 2.63 (m, 1H), 2.55 (t, J = 4.1 Hz, 1H), 2.27 (m, 1H), 2.07 (m, 2H), 1.83 (d, J = 11.8 Hz, 3H), 1.36-1.14 (m, 2H) |
| 184 | 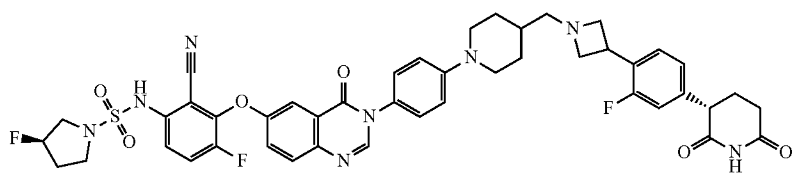 [SMILES: N#Cc1c(NS(=O)(=O)N2CC[C@@H](F)C2)ccc(F)c1Oc1ccc2ncn(-c3ccc(N4CCC(CN5CC(c6ccc([C@@H]7CCC(=O)NC7=O)cc6F)C5)CC4)cc3)c(=O)c2c1] | (3R)-N-(2-cyano-3-{[3-(4-{4-[(3S)-2,6-dioxopiperidin-3-yl]-2-fluorophenyl}azetidin-1-yl)methyl]piperidin-1-yl]phenyl}-4-oxo-3,4-dihydroquinazolin-6-yl]oxy}-4-fluorophenyl)-3-fluoropyrrolidine-1-sulfonamide | $^1$H NMR (400 MHz, DMSO) δ 10.89 (s, 1H), 10.59 (s, 1H), 8.25 (s, 1H), 7.83 (d, J = 8.9 Hz, 2H), 7.75 (t, J = 9.8 Hz, 2H), 7.70 (m, 2H), 7.40 (m, 1H), 7.32 (d, J = 8.6 Hz, 2H), 7.19-7.11 (m, 2H), 7.06 (d, J = 8.7 Hz, 2H), 5.25 (d, J = 56 Hz, 1H), 4.46-4.05 (m, 5H), 3.93 (m, 1H), 3.82 (d, J = 12.2 Hz, 2H), 3.52-3.43 (m, 1H), 3.31 (m, 3H), 3.21 (s, 2H), 2.90-2.73 (m, 3H), 2.63 (m, 1H), 2.55 (t, |

TABLE 1-continued

| Cmp. No. | Structure | IUPAC Name | ¹H NMR |
|---|---|---|---|
| 185 | 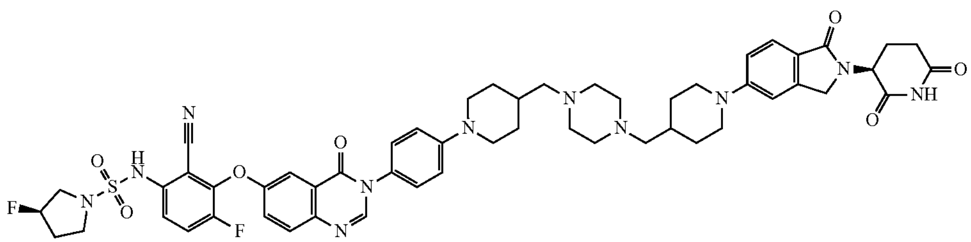 [SMILES: N#Cc1c(NS(=O)(=O)N2CC[C@@H](F)C2)ccc(F)c1Oc1ccc2ncn(-c3ccc(N4CCC(CN5CCN(CC6CCN(c7ccc8c(c7)CN([C@H]7CCC(=O)NC7=O)C8=O)CC6)CC5)CC4)cc3)c(=O)c2c1] | (3R)-N-{2-cyano-3-[(3-{4-[4-({4-[(1-{2-[(3S)-2,6-dioxopiperidin-3-yl]-1-oxo-2,3-dihydro-1H-isoindol-5-yl}piperidin-4-yl)methyl]piperazin-1-yl}methyl)piperidin-1-yl]phenyl}-4-oxo-3,4-dihydroquinazolin-6-yl)oxy]-4-fluorophenyl}-3-fluoropyrrolidine-1-sulfonamide | J = 4.1 Hz, 1H), 2.27 (m, 1H), 2.07 (m, 2H), 1.83 (d, J = 11.8 Hz, 3H), 1.36-1.14 (m, 2H) |
| 186 | 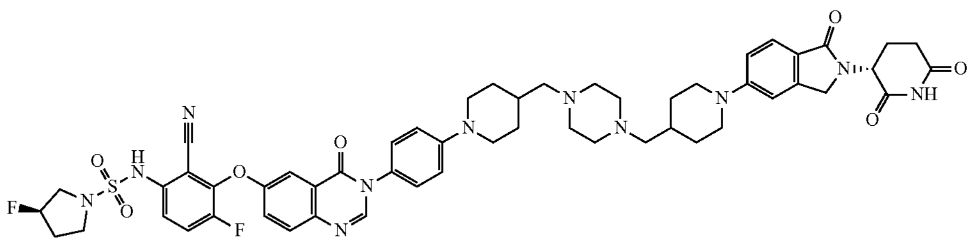 [SMILES: N#Cc1c(NS(=O)(=O)N2CC[C@@H](F)C2)ccc(F)c1Oc1ccc2ncn(-c3ccc(N4CCC(CN5CCN(CC6CCN(c7ccc8c(c7)CN([C@@H]7CCC(=O)NC7=O)C8=O)CC6)CC5)CC4)cc3)c(=O)c2c1] | (3R)-N-{2-cyano-3-[(3-{4-[4-({4-[(1-{2-[(3R)-2,6-dioxopiperidin-3-yl]-1-oxo-2,3-dihydro-1H-isoindol-5-yl}piperidin-4-yl)methyl]piperazin-1-yl}methyl)piperidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.94 (s, 1H), 9.45 (b, 1H), 8.23 (s, 1H), 7.80 (d, J = 8.4 Hz, 1H), 7.67 (d, J = 3.2 Hz, 1H), 7.50 (d, J = 8.4 Hz, 2H), 7.40-7.30 (m, 4H), 7.06 (s, 4H), 5.17 (d, J = 32 Hz, 1H), 5.02-5.00 (m, 1H), 4.30-4.22 (m, 2H), 3.90-3.79 (m, 4H), 3.15-3.13 (m, 2H), 2.92-2.55 (m, 15H), 2.35-2.22 (m, 3H), 2.12-1.93 (m, 4H), 1.80-1.78 (m, 6H), 1.30-1.20 (m, 6H) |
| 187 | 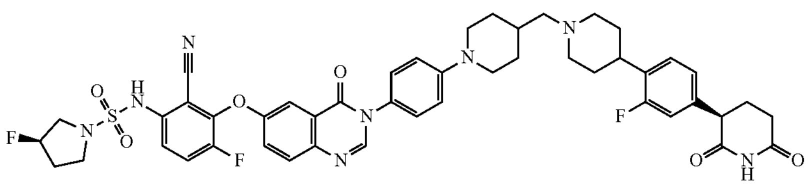 [SMILES: N#Cc1c(NS(=O)(=O)N2CC[C@@H](F)C2)ccc(F)c1Oc1ccc2ncn(-c3ccc(N4CCC(CN5CCC(c6ccc([C@H]7CCC(=O)NC7=O)cc6F)CC5)CC4)cc3)c(=O)c2c1] | (3R)-N-(2-cyano-3-{[3-(4-{4-[(3R)-2,6-dioxopiperidin-3-yl]-2-fluorophenyl}piperidin-1-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.87 (s, 1H), 8.23 (s, 1H), 7.81 (d, J = 8.9 Hz, 1H), 7.67 (m, 1H), 7.47 (t, J = 9.9 Hz, 1H), 7.40 (d, J = 3.0 Hz, 1H), 7.35-7.32 (m, 4H), 7.13-7.03 (m, 4H), 5.34-5.21 (d, J = 56 Hz, 1H), 4.11 (s, 1H), 3.93-3.81 (m, 3H), 3.45-3.38 (m, 3H), 3.28 (m, 4H), 3.23-3.13 (m, 3H), 3.02 (s, 1H), 2.83-2.78 (m, 5H), 2.75-2.66 (m, 2H), 2.69-2.62 (m, 1H), 2.31-2.17 (m, 2H), 1.98 (s, 10H), 1.45 (d, J = 14.7 Hz, 2H), 1.39-1.22 (m, 1H) |

TABLE 1-continued

| Cmp. No. | Structure | IUPAC Name | ¹H NMR |
|---|---|---|---|
| 188 | 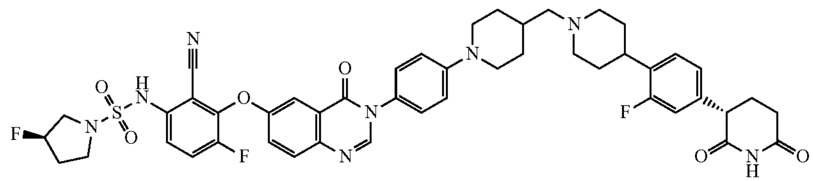 [SMILES: N#Cc1c(NS(=O)(=O)N2CC[C@@H](F)C2)ccc(F)c1Oc1ccc2ncn(-c3ccc(N4CCC(CN5CCC(c6ccc([C@@H]7CCC(=O)NC7=O)cc6F)CC5)CC4)cc3)c(=O)c2c1] | (3R)-N-(2-cyano-3-{[3-(4-{4-[(4-{[(3S)-2,6-dioxopiperidin-3-yl]-2-fluorophenyl}piperidin-1-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.87 (s, 1H), 8.23 (s, 1H), 7.81 (d, J = 8.9 Hz, 1H), 7.67 (m, 1H), 7.47 (t, J = 9.9 Hz, 1H), 7.40 (d, J = 3.0 Hz, 1H), 7.35-7.32 (m, 4H), 7.13-7.03 (m, 4H), 5.34-5.21 (d, J = 56 Hz, 1H), 3.98-3.80 (m, 3H), 3.45-3.38 (m, 3H), 3.28 (m, 3H), 3.23-3.13 (m, 2H), 3.02 (s, 1H), 2.83-2.78 (m, 5H), 2.75-2.66 (m, 1H), 2.69-2.62 (m, 1H), 2.31-2.17 (m, 1H), 2.15 (m, 1H), 2.10-1.98(m,5H),1.98-1.80 (m, 4H), 1.45 (d, J = 14.7 Hz, 2H) |
| 189 | 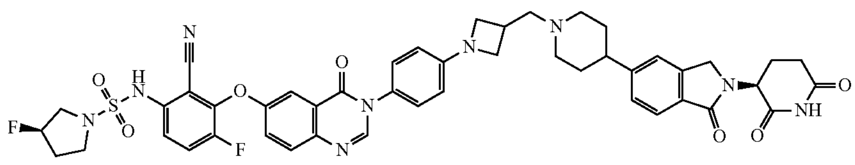 [SMILES: N#Cc1c(NS(=O)(=O)N2CC[C@@H](F)C2)ccc(F)c1Oc1ccc2ncn(-c3ccc(N4CC(CN5CCC(c6ccc7c(c6)CN([C@H]6CCC(=O)NC6=O)C7=O)CC5)C4)cc3)c(=O)c2c1] | (3R)-N-(2-cyano-3-{[3-(4-{3-[(4-{2-[(3S)-2,6-dioxopiperidin-3-yl]-1-oxo-2,3-dihydro-1H-isoindol-5-yl}piperidin-1-yl)methyl]azetidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.99 (s, 1H), 10.05 (s, 1H), 8.50 (s, 1H), 8.22 (s, 1H), 7.81 (d, J = 8.9 Hz, 1H), 7.74-7.65 (m, 2H), 7.61 (s, 1H), 7.49 (s, 1H), 7.39 (d, J = 3.1 Hz, 3H), 7.35-7.26 (m, 2H), 6.59-6.52 (m, 2H), 5.36 (s, 1H), 5.22 (s, 1H), 4.45 (d, J = 17.4 Hz, 1H), 4.32 (d, J = 17.4 Hz, 1H), 4.10 (t, J = 7.5 Hz, 2H), 3.68 (s, 4H), 3.69-3.57 (m, 3H), 3.25 (s, 3H), 3.14 (dd, J = 7.4, 3.7 Hz, 2H), 2.99-2.81 (m, 4H), 2.60 (d, J = 17.1 Hz, 3H), 2.03-1.96 (m, 10H), 1.91 (s, 1H), 1.26 (td, J = 7.3, 4.9 Hz, 13H) |

TABLE 1-continued

| Cmp. No. | Structure | IUPAC Name | ¹H NMR |
|---|---|---|---|
| 190 | 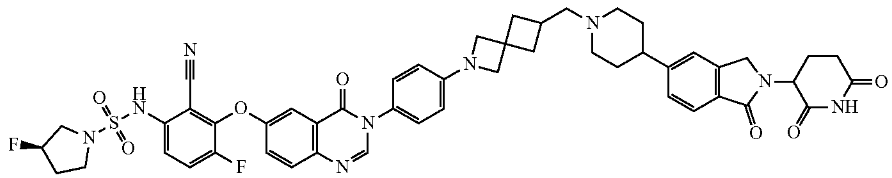 [SMILES: N#Cc1c(NS(=O)(=O)N2CC[C@@H](F)C2)ccc(F)c1Oc1ccc2ncn(-c3ccc(N4CC5(CC(CN6CCC(c7ccc8c(c7)CN(C7CCC(=O)NC7=O)C8=O)CC6)C5)C4)cc3)c(=O)c2c1] | (3R)-N-{2-cyano-3-[(3-(4-[6-({4-[2-(2,6-dioxopiperidin-3-yl)-1-oxo-2,3-dihydro-1H-isoindol-5-yl]piperidin-1-yl}methyl)-2-azaspiro[3.3]heptan-2-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 11.00 (s, 1 H), 9.14-9.91 (m, 1 H), 8.19 (s, 1 H), 7.79 (d, J = 8.8 Hz, 1 H), 7.60-7.74 (m, 2 H), 7.48 (s, 1 H), 7.33-7.44 (m, 3 H), 7.23-7.32 (m, 3 H), 6.51 (d, J = 8.8 Hz, 2 H), 5.16-5.36 (m, 1 H), 5.11 (dd, J = 13.2, 4.8 Hz, 1 H), 4.40-4.49 (m, 1 H), 4.27-4.35 (m, 1 H), 3.94 (s, 2 H), 3.80 (s, 2 H), 3.36-3.40 (m, 2 H), 3.25 (dd, J = 17.2, 5.2 Hz, 3 H), 3.09-3.20 (m, 2 H), 2.99-3.08 (m, 1 H), 2.84-2.97 (m, 3 H), 2.54-2.65 (m, 3 H), 2.38-2.46 (m, 3 H), 1.85-2.13 (m, 9 H) |
| 191 | 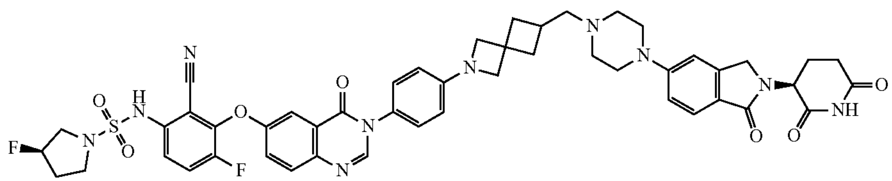 [SMILES: N#Cc1c(NS(=O)(=O)N2CC[C@@H](F)C2)ccc(F)c1Oc1ccc2ncn(-c3ccc(N4CC5(CC(CN6CCN(c7ccc8c(c7)CN([C@H]7CCC(=O)NC7=O)C8=O)CC6)C5)C4)cc3)c(=O)c2c1] | (3R)-N-(2-cyano-3-{[3-(4-{6-[(4-{2-[(3S)-2,6-dioxopiperidin-3-yl]-1-oxo-2,3-dihydro-1H-isoindol-5-yl]piperazin-1-yl}methyl)-2-azaspiro[3.3]heptan-2-yl]phenyl}-4-oxo-3,4-dihydroquinazolin-6-yl]oxy}-4-fluorophenyl)-3-fluoropyrrolidine-1-sulfonamide | ¹H NMR (400 MHz, DMSO) δ 10.95 (s, 1H), 8.21 (s, 1H), 7.80 (d, J = 8.8 Hz, 1H), 7.67 (dd, J = 2.8, 8.8 Hz, 1H), 7.64-7.52 (m, 2H), 7.43-7.36 (m, 2H), 7.26 (d, J = 8.8 Hz, 2H), 7.13-7.05 (m, 2H), 6.50 (d, J = 8.8 Hz, 2H), 5.38-5.19 (m, 1H), 5.05 (dd, J = 5.6, 13.2 Hz, 1H), 4.39-4.29 (m, 1H), 4.25-4.17 (m, 1H), 3.92 (s, 2H), 3.78 (s, 2H), 3.51-3.39 (m, 4H), 3.26-3.20 (m, 3H), 2.93-2.69 (m, 6H), 2.68-2.53 (m, 4H), 2.42-2.33 (m, 4H), 2.19-2.06 (m, 1H), 2.04-1.90 (m, 4H) |
| 192 | 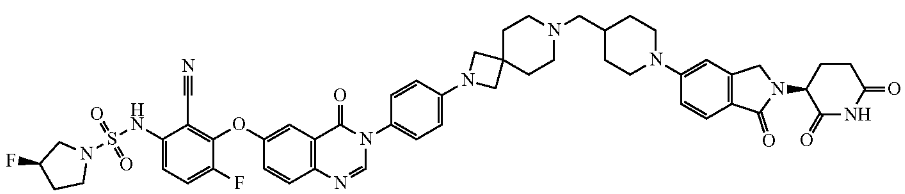 [SMILES: N#Cc1c(NS(=O)(=O)N2CC[C@@H](F)C2)ccc(F)c1Oc1ccc2ncn(-c3ccc(N4CC5(CCN(CC6CCN(c7ccc8c(c7)CN([C@H]7CCC(=O)NC7=O)C8=O)CC6)CC5)C4)cc3)c(=O)c2c1] | (3R)-N-(2-cyano-3-{[3-(4-{7-[(1-{2-[(3S)-2,6-dioxopiperidin-3-yl]-1-oxo-2,3-dihydro-1H-isoindol-5-yl]piperidin-4-yl}methyl)-2,7-diazaspiro[3.5]nonan-2-yl]phenyl}-4-oxo-3,4-dihydroquinazolin-6-yl]oxy}-4-fluorophenyl)-3-fluoropyrrolidine-1-sulfonamide | ¹H NMR (400 MHz, DMSO) δ 8.89 (s, 10H), 8.19 (s, 1H), 7.77 (d, J = 8.8 Hz, 1H), 7.63 (d, J = 3.2Hz, 1H), 7.60 (d, J = 3.2 Hz, 1H), 7.31-7.25 (m, 5H), 7.03 (d, J = 8.0 Hz, 1H), 6.50 (d, J = 8.8 Hz, 1H), 5.32 (d, J = 32 Hz, 1H), 5.02-5.00 (m, 2H), 4.34-4.17 (m, 2H), 3.89-3.86 (m, 2H), 3.60-3.18 (m, 4H), 2.89-2.81 (m, 3H), 2.62-2.31 (m, 5H), 2.12-1.86 (m, 5H), 1.77-1.74 (m, 7H) |

TABLE 1-continued

| Cmp. No. | Structure | IUPAC Name | ¹H NMR |
|---|---|---|---|
| 193 | 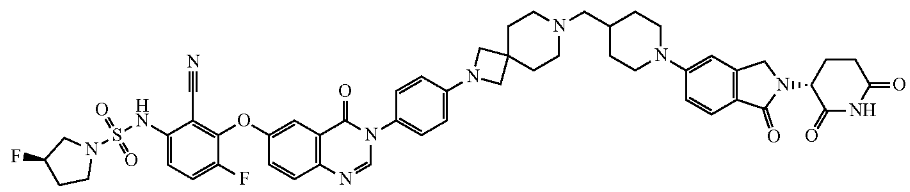 [SMILES: N#Cc1c(NS(=O)(=O)N2CC[C@@H](F)C2)ccc(F)c1Oc1ccc2ncn(-c3ccc(N4CC5(CCN(CC6CCN(c7ccc8c(c7)CN([C@@H]7CCC(=O)NC7=O)C8=O)CC6)CC5)C4)cc3)c(=O)c2c1] | (3R)-N-(2-cyano-3-{[3-(4-{7-[(1-{2-[(3R)-2,6-dioxopiperidin-3-yl]-1-oxo-2,3-dihydro-1H-isoindol-5-yl}piperidin-4-yl)methyl]-2,7-diazaspiro[3.5]nonan-2-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.92 (s, 1H), 8.18 (s, 4H), 8.19 (s, 1H), 7.77 (d, J = 8.8 Hz, 1H), 7.63 (d, J = 3.2Hz, 1H), 7.60 (d, J = 3.2 Hz, 1H), 7.31-7.25 (m, 5H), 7.03 (d, J = 8.0 Hz, 1H), 6.50 (d, J = 8.8 Hz, 1H), 5.32 (d, J = 32 Hz, 1H), 5.02-5.00 (m, 2H), 4.34-4.17 (m, 2H), 3.89-3.86 (m, 2H), 3.60-3.18 (m, 5H), 2.89-2.81 (m, 9H), 2.62-2.31 (m, 6H), 2.12-1.86 (m, 6H), 1.77-1.74 (m, 7H) |
| 194 | 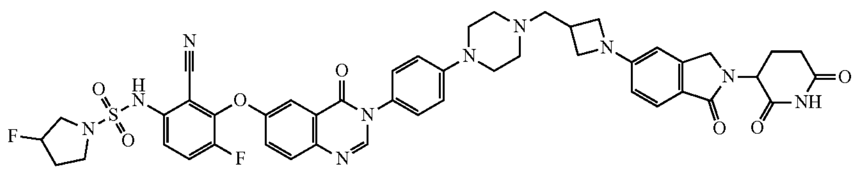 [SMILES: N#Cc1c(NS(=O)(=O)N2CCC(F)C2)ccc(F)c1Oc1ccc2ncn(-c3ccc(N4CCN(CC5CN(c6ccc7c(c6)CN(C6CCC(=O)NC6=O)C7=O)C5)CC4)cc3)c(=O)c2c1] | N-{2-cyano-3-[(3-{4-[4-({1-[2-(2,6-dioxopiperidin-3-yl)-1-oxo-2,3-dihydro-1H-isoindol-5-yl]azetidin-3-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.94 (s, 1H), 10.35-10.01 (m, 1H), 8.25 (s, 1H), 7.82 (d, J = 8.8 Hz, 1H), 7.75-7.62 (m, 2H), 7.52-7.47 (m, 1H), 7.46-7.38 (m, 2H), 7.37-7.31 (m, 2H), 7.08 (d, J = 8.8 Hz, 2H), 6.55-6.46 (m, 2H), 5.40-5.18 (m, 1H), 5.10-4.99 (m, 1H), 4.37-4.27 (m, 1H), 4.24-4.13 (m, 1H), 4.11-3.98 (m, 2H), 3.69-3.56 (m, 2H), 3.51 (s, 1H), 3.47-3.43 (m, 2H), 3.15-3.03 (m, 2H), 2.95-2.82 (m, 3H), 2.81-2.68 (m, 3H), 2.68-2.65 (m, 1H), 2.63-2.54 (m, 4H), 2.24 (s, 1H), 2.17-1.83 (m, 4H) |

TABLE 1-continued

| Cmp. No. | Structure | IUPAC Name | 1H NMR |
|---|---|---|---|
| 195 | (structure) | (3S)-N-(2-cyano-3-{[3-(4-{4-[(1-{2-[(3S)-2,6-dioxopiperidin-3-yl]-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.94 (s, 1 H), 9.89-10.55 (m, 1 H), 8.25 (s, 1 H), 8.13 (s, 1 H), 7.82 (d, J = 9.2 Hz, 1 H), 7.64-7.76 (m, 2 H), 7.47-7.53 (m, 1 H), 7.38-7.47 (m, 2 H), 7.35 (d, J = 8.4 Hz, 2 H), 7.04-7.13 (m, 2 H), 6.46-6.56 (m, 2 H), 5.20-5.39 (m, 1 H), 5.03 (dd, J = 13.2, 5.2 Hz, 1 H), 4.27-4.35 (m, 1 H), 4.14-4.22 (m, 1 H), 4.07 (t, J = 7.2 Hz, 2 H), 3.63 (s, 2 H), 3.45 (s, 2 H), 3.29-3.31 (m, 2 H), 3.27 (s, 2 H), 3.07-3.12 (m, 1 H), 2.73-2.99 (m, 7 H), 2.54-2.63 (m, 2 H), 2.31-2.47 (m, 2 H), 1.99-2.15 (m, 2 H), 1.90-1.99 (m, 1 H) |
| 196 | (structure) | (3S)-N-(2-cyano-3-{[3-(4-{4-[(1-{2-[(3R)-2,6-dioxopiperidin-3-yl]-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.95 (s, 1 H), 9.82-10.52 (m, 1 H), 8.25 (s, 1 H), 8.13 (s, 1 H), 7.82 (d, J = 9.2 Hz, 1 H), 7.69 (dd, J = 8.8, 3.2 Hz, 2 H), 7.49 (d, J = 8.4 Hz, 1 H), 7.42-7.47 (m, 1 H), 7.40 (d, J = 2.8 Hz, 1 H), 7.35 (d, J = 8.8 Hz, 2 H), 7.09 (d, J = 8.8 Hz, 2 H), 6.53 (s, 1 H), 6.49 (dd, J = 8.4, 1.6 Hz, 1 H), 5.19-5.41 (m, 1 H), 5.04 (dd, J = 13.2, 4.8 Hz, 1 H), 4.26-4.35 (m, 1 H), 4.14-4.22 (m, 1 H), 4.04-4.12 (m, 2 H), 3.60-3.68 (m, 2 H), 3.40-3.48 (m, 2 H), 3.37 (s, 2 H), 3.25-3.29 (m, 2 H), 3.05-3.13 (m, 1 H), 2.69-3.01 (m, 7 H), 2.60 (d, J = 2.4 Hz, 1 H), 2.56 (d, J = 1.2 Hz, 1 H), 2.33-2.48 (m, 2 H), 2.08-2.17 (m, 1 H), 2.00-2.07 (m, 1 H), 1.90-1.99 (m, 1 H) |

TABLE 1-continued

| Cmp. No. | Structure | IUPAC Name | ¹H NMR |
|---|---|---|---|
| 197 | 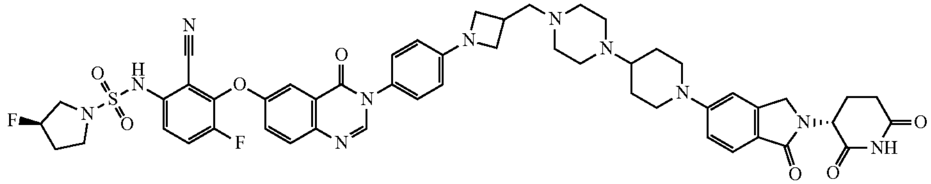 [SMILES: N#Cc1c(NS(=O)(=O)N2CC[C@@H](F)C2)ccc(F)c1Oc1ccc2ncn(-c3ccc(N4CC(CN5CCN(C6CCN(c7ccc8c(c7)CN([C@@H]7CCC(=O)NC7=O)C8=O)CC6)CC5)C4)cc3)c(=O)c2c1] | (3R)-N-[2-cyano-3-({3-[4-(3-{[4-(1-{2-[(3R*)-2,6-dioxopiperidin-3-yl]-1-oxo-2,3-dihydro-1H-isoindol-5-yl}piperidin-4-yl)piperazin-1-yl]methyl}azetidin-1-yl)phenyl]-4-oxo-3,4-dihydroquinazolin-6-yl}oxy)-4-fluorophenyl]-3-fluoropyrrolidine-1-sulfonamide | ¹H NMR (400 MHz, DMSO) δ 10.95 (s, 1H), 8.19 (s, 1H), 7.79 (d, J = 8.8 Hz, 1H), 7.65 (dd, J = 2.4, 8.8 Hz, 1H), 7.52 (d, J = 8.4 Hz, 1H), 7.47-7.38 (m, 1H), 7.38-7.35 (m, 1H), 7.34-7.23 (m, 3H), 7.10-7.05 (m, 2H), 6.51 (d, J = 8.4 Hz, 2H), 5.35-5.17 (m, 1H), 5.04 (dd, J = 4.8, 13.2 Hz, 1H), 4.35-4.17 (m, 2H), 4.03-3.91 (m, 4H), 3.57-3.50 (m, 2H), 3.25-3.22 (m, 2H), 3.17-3.08 (m, 2H), 3.02-2.97 (m, 1H), 2.92-2.75 (m, 7H), 2.68-2.58 (m, 3H), 2.41-2.33 (m, 2H), 2.20-2.08 (m, 1H), 2.03-1.87 (m, 5H), 1.64-1.42 (m, 3H), 1.24-1.14 (m, 3H) |
| 198 | 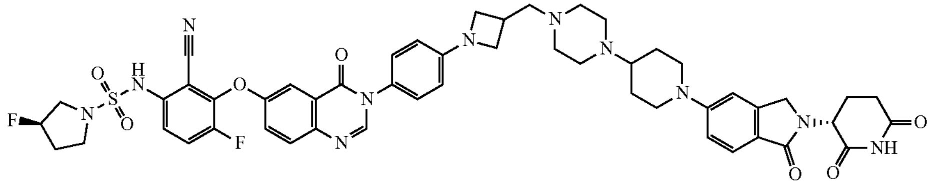 [SMILES: N#Cc1c(NS(=O)(=O)N2CC[C@@H](F)C2)ccc(F)c1Oc1ccc2ncn(-c3ccc(N4CC(CN5CCN(C6CCN(c7ccc8c(c7)CN([C@@H]7CCC(=O)NC7=O)C8=O)CC6)CC5)C4)cc3)c(=O)c2c1] | (3R)-N-[2-cyano-3-({3-[4-(3-{[4-(1-{2-[(3R*)-2,6-dioxopiperidin-3-yl]-1-oxo-2,3-dihydro-1H-isoindol-5-yl}piperidin-4-yl)piperazin-1-yl]methyl}azetidin-1-yl)phenyl]-4-oxo-3,4-dihydroquinazolin-6-yl}oxy)-4-fluorophenyl]-3-fluoropyrrolidine-1-sulfonamide | ¹H NMR (400 MHz, DMSO) δ 10.95 (s, 1H), 8.20 (s, 1H), 7.79 (d, J = 9.2 Hz, 1H), 7.65 (dd, J = 3.2, 9.2 Hz, 1H), 7.52 (d, J = 8.4 Hz, 1H), 7.43 (s, 1H), 7.37 (d, J = 2.4 Hz, 1H), 7.34-7.23 (m, 3H), 7.12-7.02 (m, 2H), 6.51 (d, J = 8.8 Hz, 2H), 5.36-5.17 (m, 1H), 5.04 (dd, J = 4.8, 12.8 Hz, 1H), 4.35-4.16 (m, 2H), 4.05-3.89 (m, 4H), 3.58-3.49 (m, 2H), 3.26-3.24 (m, 2H), 3.19-3.14 (m, 2H), 2.99 (dd, J = 2.4, 6.4 Hz, 1H), 2.92-2.77 (m, 7H), 2.69-2.58 (m, 3H), 2.37-2.31 (m, 2H), 2.15-2.07 (m, 1H), 2.05-1.88 (m, 5H), 1.67-1.42 (m, 3H), 1.36-1.06 (m, 3H) |

TABLE 1-continued

| Cmp. No. | Structure | IUPAC Name | ¹H NMR |
|---|---|---|---|
| 199 | 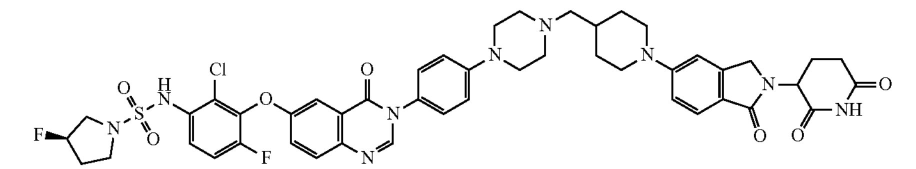 [SMILES: O=C1CCC(N2Cc3cc(N4CCC(CN5CCN(c6ccc(-n7cnc8ccc(Oc9c(F)ccc(NS(=O)(=O)N%10CC[C@@H](F)C%10)c9Cl)cc8c7=O)cc6)CC5)CC4)ccc3C2=O)C(=O)N1] | (3R)-N-{2-chloro-3-[(3-{4-[4-({1-[2-(2,6-dioxopiperidin-3-yl)-1-oxo-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.96 (s, 1H), 9.69 (s, 1H), 8.24 (s, 1H), 7.81 (d, J = 8.9 Hz, 1H), 7.68-7.62 (m, 1H), 7.60-7.47 (m, 3H), 7.36-7.23 (m, 3H), 7.05 (d, J = 8.5 Hz, 4H), 5.45-5.19 (m, 1H), 5.15-4.95 (m, 1H), 4.32 (d, J = 16.8 Hz, 1H), 4.19 (d, J = 16.9 Hz, 1H), 3.89 (d, J = 12.4 Hz, 2H), 3.52-3.39 (m, 3H), 3.36-3.34 (m, 1H), 3.31-3.19 (m, 5H), 2.97-2.79 (m, 3H), 2.65-2.52 (m, 4H), 2.59 (d, J = 16.1 Hz, 1H), 2.23 (d, J = 6.5 Hz, 2H), 2.18-1.95 (m, 3H), 1.81 (d, J = 11.9 Hz, 3H), 1.26-1.14 (m, 2H) |
| 200 | 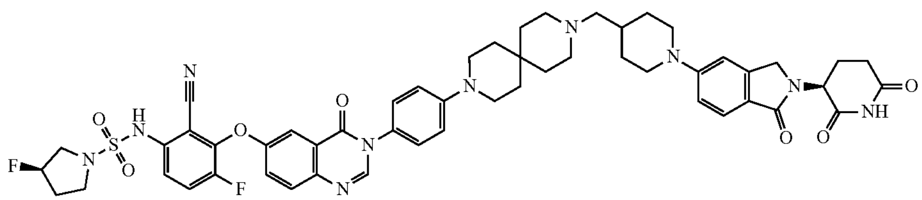 | (3R)-N-(2-cyano-3-{[3-(4-{9-[(1-{[2-[(3S)-2,6-dioxopiperidin-3-yl)-1-oxo-2,3-dihydro-1H-isoindol-5-yl]piperidin-4-yl}methyl)-3,9-diazaspiro[5.5]undecan-3-yl]phenyl}-4-oxo-3,4-dihydroquinazolin-6-yl]oxy}-4-fluorophenyl)-3-fluoropyrrolidine-1-sulfonamide | ¹H NMR (300 MHz, DMSO) δ 10.94 (s, 1H), 8.18 (d, J = 16.0 Hz, 1H), 7.78 (d, J = 8.9 Hz,1H),7.63-7.55 (m, 2H), 7.50 (d, J = 9.0 Hz, 1H), 7.44-7.21 (m, 4H), 7.10-6.99 (m, 5H), 5.3-5.24(d, J = 18 Hz, 1H), 5.21-5.01 (m, 1H), 4.32-4.19 (m, 6H), 3.88-3.87 (m, 6H), 3.42-3.18 (m, 9H), 2.98-2.87 (m, 2H), 2.91-2.76 (m, 1H), 2.62 (s, 4H), 2.47-2.29 (m, 3H), 1.58 (s, 4H), 1.21 (s, 2H), 1.27-1.11 (m, 4H), 1.05 (t, J = 7.1 Hz, 2H) |
| 201 | 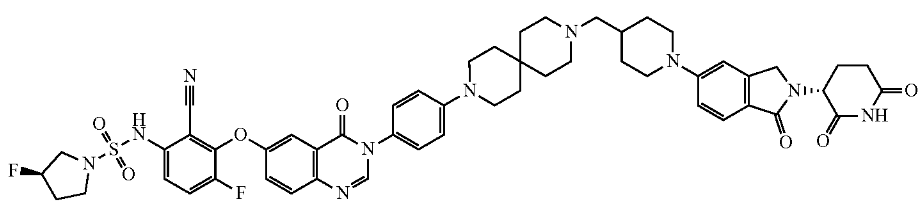 [SMILES: N#Cc1c(NS(=O)(=O)N2CC[C@@H](F)C2)ccc(F)c1Oc1ccc2ncn(-c3ccc(N4CCC5(CCN(CC6CCN(c7ccc8c(c7)CN([C@@H]7CCC(=O)NC7=O)C8=O)CC6)CC5)CC4)cc3)c(=O)c2c1] | (3R)-N-(2-cyano-3-{[3-(4-{9-[(1-{2-[(3R)-2,6-dioxopiperidin-3-yl)-1-oxo-2,3-dihydro-1H-isoindol-5-yl]piperidin-4-yl}methyl)-3,9-diazaspiro[5.5]undecan-3-yl]phenyl}-4-oxo-3,4-dihydroquinazolin-6-yl]oxy}-4-fluorophenyl)-3-fluoropyrrolidine-1-sulfonamide | ¹H NMR (300 MHz, DMSO) δ 10.94 (s, 1H), 8.47 (s, 2H),8.15 (s, 1H), 7.79 (d, J = 8.9 Hz, 1H), 7.51 (d, J = 9.0 Hz, 1H), 7.41-7.22 (m, 4H), 7.05-7.01 (m, 4H), 5.35 (s, 1H), 5.16-5.04 (d, J = 36 Hz, 1H), 4.32 (d, J = 16.9 Hz, 1H), 4.20 (d, J = 16.8 Hz, 1H), 3.89 (d, J = 12.5 Hz, 2H), 3.38-3.18 (m, 3H), 2.98-2.78 (m, 11H), 2.62 (s, 2H), 2.42-2.29 (m, 1H), 1.94 (s, 3H), 1.82 (s, 2H), 1.62 (s, 8H), 1.17 (s, 7H) |

TABLE 1-continued

| Cmp. No. | Structure | IUPAC Name | 1H NMR |
|---|---|---|---|
| 202 | 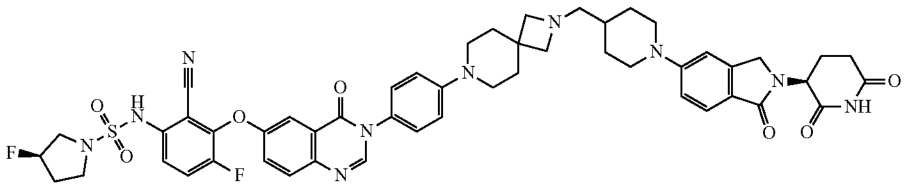 [SMILES: N#Cc1c(NS(=O)(=O)N2CC[C@@H](F)C2)ccc(F)c1Oc1ccc2ncn(-c3ccc(N4CCC5(CC4)CN(CC4CCN(c6ccc7c(c6)CN([C@H]6CCC(=O)NC6=O)C7=O)CC4)C5)cc3)c(=O)c2c1] | (3R)-N-(2-cyano-3-{[3-(4-{2-[(1-{2-[(3R)-2,6-dioxopiperidin-3-yl]-1-oxo-2,3-dihydro-1H-isoindol-5-yl}piperidin-4-yl)methyl]-2,7-diazaspiro[3.5]nonan-7-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.94 (s, 1H), 8.21 (s, 1H), 7.89-7.87 (m, 2H), 7.80 (d, J = 8.8 Hz, 1H), 7.62 (d, J = 3.2 Hz, 1H), 7.49 (d, J = 4.4 Hz, 1H), 7.38-7.22 (m, 5H), 7.03-7.22 (m, 4H), 5.32 (d, J = 32 Hz, 1H), 5.02-5.01 (m, 1H), 4.32-4.22 (m, 2H), 3.87-3.84 (m, 2H), 3.48-3.34 (m, 12H), 2.93-2.79 (m, 9H), 2.51-2.45 (m, 5H), 2.12-1.89 (m, 4H), 1.79-1.78 (m, 6H) |
| 203 | 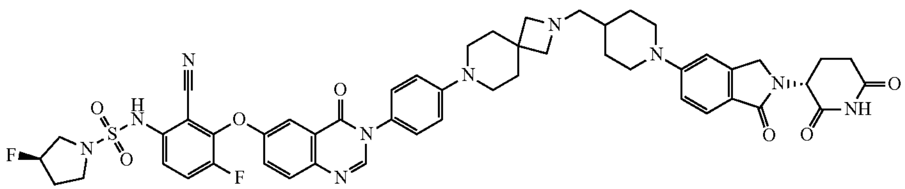 [SMILES: N#Cc1c(NS(=O)(=O)N2CC[C@@H](F)C2)ccc(F)c1Oc1ccc2ncn(-c3ccc(N4CCC5(CC4)CN(CC4CCN(c6ccc7c(c6)CN([C@@H]6CCC(=O)NC6=O)C7=O)CC4)C5)cc3)c(=O)c2c1] | (3R)-N-(2-cyano-3-{[3-(4-{2-[(1-{2-[(3S)-2,6-dioxopiperidin-3-yl]-1-oxo-2,3-dihydro-1H-isoindol-5-yl}piperidin-4-yl)methyl]-2,7-diazaspiro[3.5]nonan-7-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.94 (s, 1H), 8.21 (s, 1H), 7.89-7.87 (m, 2H), 7.80 (d, J = 3.2 Hz, 1H), 7.62 (d, J = 3.2 Hz, 1H), 7.49 (d, J = 4.4 Hz, 1H), 7.38-7.22 (m, 5H), 7.03-7.22 (m, 4H), 5.32 (d, J = 32 Hz, 1H), 5.02-5.01 (m, 1H), 4.32-4.22 (m, 2H), 3.87-3.84 (m, 2H), 3.18-3.14 (m, 8H), 2.93-2.79 (m, 5H), 2.51-2.45 (m, 2H), 2.02-1.69 (m, 10H), 1.32-1.18 (m, 3H) |
| 204 | 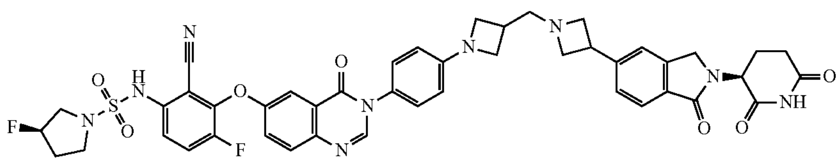 [SMILES: N#Cc1c(NS(=O)(=O)N2CC[C@@H](F)C2)ccc(F)c1Oc1ccc2ncn(-c3ccc(N4CC(CN5CC(c6ccc7c(c6)CN([C@H]6CCC(=O)NC6=O)C7=O)C5)C4)cc3)c(=O)c2c1] | (3R)-N-(2-cyano-3-{[3-(4-{3-[(2-{[(3S)-2,6-dioxopiperidin-3-yl]-1-oxo-2,3-dihydro-1H-isoindol-5-yl}azetidin-1-yl)methyl]azetidin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 11.00 (s, 1H), 8.20 (s, 1H), 8.11 (s, 1H), 7.81 (d,1H), 7.79 (d, J = 8.9 Hz, 1H), 7.70 (d, J = 7.8 Hz, 2H), 7.70-7.61 (m,1H), 7.51 (d, J = 8.0 Hz, 2H), 7.40-7.24 (m, 3H), 6.53 (d, J = 8.7 Hz, 2H), 5.33 (s, 1H), 5.19 (s, 1H), 4.97 (dd, J = 13.3, 5.11 Hz, 1H), 4.46 (d, J = 17.2 Hz, 1H), 4.33 (d, J = 17.3 Hz, 2H), 3.98 (t, J = 7.5 Hz, 3H), 3.86 (s, 1H), 3.59 (t, J = 6.2 Hz, 2H), 3.30-3.08 (m, 2H), 3.02 (t, J = 6.2 Hz, 2H), 2.92 (dq, J = 12.4, 6.3, 5.4 Hz, 5H), 2.81 (s, 2H), 2.61 (d, J = 17.3 Hz, 1H), 2.17-1.98 (m, 1H), 2.02 (s, 1H), 1.96 (s, 3H), 1.24 (s, 1H), 1.16 (t, J = 7.3 Hz, 5H) |

| Cmp. No. | Structure | IUPAC Name | ¹H NMR |
|---|---|---|---|
| 205 | 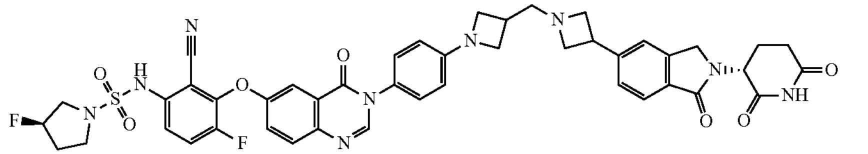 [SMILES: N#Cc1c(NS(=O)(=O)N2CC[C@@H](F)C2)ccc(F)c1Oc1ccc2ncn(-c3ccc(N4CC(CN5CC(c6ccc7c(c6)CN([C@@H]6CCC(=O)NC6=O)C7=O)C5)C4)cc3)c(=O)c2c1] | (3R)-N-(2-cyano-3-{[3-(4-{3-[(3-{2-[(3R)-2,6-dioxopiperidin-3-yl]-1-oxo-2,3-dihydro-1H-isoindol-5-yl}azetidin-1-yl]methyl]azetidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 11.00 (s, 1H), 8.21 (s, 1H), 8.15-7.80 (d, J = 8.9 Hz, 1H), 7.74 (m, 1H), 7.69-7.63 (m, 2H), 7.54 (d, J = 7.2 Hz, 1H), 7.38 (d, J = 3.0 Hz, 1H), 7.30 (d, J = 8.4 Hz, 3H), 6.54 (d, J = 8.3 Hz, 2H), 5.34 (s, 1H), 5.21 (s, 1H), 4.46 (d, J = 17.3 Hz, 1H), 4.34 (d, J = 17.2 Hz, 1H), 4.00 (t, J = 7.5 Hz, 3H), 3.63 (s, 2H), 3.51 (s, 1H), 3.31 (s, 3H), 3.19 (s, 1H), 2.93 (s, 3H), 2.71 (s, 3H), 2.00 (s, 3H), 1.38 (dd, J = 14.9, 6.7 Hz, 1H), 1.24 (s, 3H), 1.17 (t, J = 7.3 Hz, 2H), 0.85 (d, J = 7.0 Hz, 1H) |
| 206 | 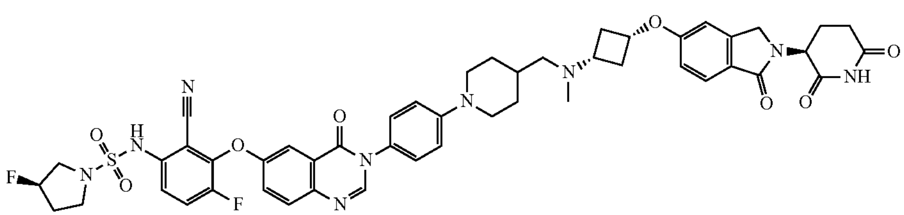 [SMILES: CN(CC1CCN(c2ccc(-n3cnc4ccc(Oc5c(F)ccc(NS(=O)(=O)N6CC[C@@H](F)C6)c5C#N)cc4c3=O)cc2)CC1)[C@H]1C[C@@H](Oc2ccc3c(c2)CN([C@H]2CCC(=O)NC2=O)C3=O)C1] | (3R)-N-{2-cyano-4-fluoro-3-[(3-{4-[4-({methyl[(1r,3r)-3-({2-[(3S)-2,6-dioxopiperidin-3-yl]-1-oxo-2,3-dihydro-1H-isoindol-5-yl}oxy)cyclobutyl]amino}methyl)piperidin-1-yl]phenyl}-4-oxo-3,4-dihydroquinazolin-6-yl)oxy]phenyl}-3-fluoropyrrolidine-1-sulfonamide | ¹H NMR (400 MHz, DMSO) δ 10.98 (s, 1H), 8.24 (s, 1H), 7.81 (d, J = 8.9 Hz, 1H), 7.72-7.55 (m, 2H), 7.56 (s, 2H), 7.41 (d, J = 3.1 Hz, 2H), 7.32 (d, J = 8.8 Hz, 2H), 7.09-7.03 (m, 3H), 7.02-6.91 (m, 1H), 5.36 (s, 1H), 5.22 (s, 1H), 5.08 (dd, J = 13.3, 5.1 Hz, 1H), 4.89 (s, 1H), 4.39 (d, J = 17.2 Hz, 1H), 4.27 (d, J = 17.3 Hz, 2H), 3.91 (d, 2H), 3.83 (d, 3H), 3.66 (d, 1H), 3.43 (d, J = 12.0 Hz, 3H), 2.97-2.85 (m, 2H), 2.79 (t, J = 12.0 Hz, 3H), 2.62 (s, 2H), 2.55 (s, 10H), 2.43-2.34 (m, 3H), 2.17-2.07 (m, 2H), 2.04-1.95 (m, 3H), 1.83 (d, J = 11.8 Hz, 2H), 1.34 (d, J = 3.4 Hz, 2H), 1.29-1.14 (m, 2H), 0.98 (s, 1H), 0.85 (s, 1H), 0.61 (s, 1H) |

TABLE 1-continued

| Cmp. No. | Structure | IUPAC Name | ¹H NMR |
|---|---|---|---|
| 207 | 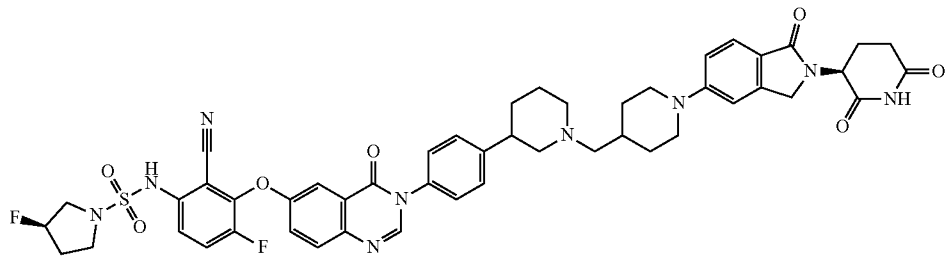 [SMILES: N#Cc1c(NS(=O)(=O)N2CC[C@@H](F)C2)ccc(F)c1Oc1ccc2ncn(-c3ccc(C4CCCN(CC5CCN(c6ccc7c(c6)CN([C@H]6CCC(=O)NC6=O)C7=O)CC5)C4)cc3)c(=O)c2c1] | (3R)-N-(2-cyano-3-{[3-(4-{1-[(1-{2-[(3S)-2,6-dioxopiperidin-3-yl]-1-oxo-2,3-dihydro-1H-isoindol-5-yl}piperidin-4-yl)methyl]piperidin-3-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.95 (s, 1H), 8.27 (s, 1H), 8.13 (s, 1H), 7.82 (d, J = 8.8 Hz, 1H), 7.68 (dd, J = 2.9, 8.8 Hz, 1H), 7.53-7.46 (m, 6H), 7.39 (d, J = 2.8 Hz, 1H), 7.34 (dd, J = 3.9, 9.2 Hz, 1H), 7.09-7.03 (m, 2H), 5.37-5.17 (m, 1H), 5.04 (dd, J = 5.1, 13.2 Hz, 1H), 4.36-4.28 (m, 1H), 4.23-4.16 (m, 1H), 3.90 (d, J = 12.4 Hz, 2H), 3.43-3.38 (m, 2H), 3.28 (d, J = 4.0 Hz, 2H), 3.22-3.17 (m, 1H), 3.12 - 3.03 (m, 1H), 2.93-2.78 (m, 5H), 2.58 (d, J = 16.4 Hz, 2H), 2.43 - 2.33 (m, 1H), 2.13 - 1.76 (m, 11H), 1.71-1.56 (m, 1H), 1.31-1.18 (m, 2H) |
| 208 | 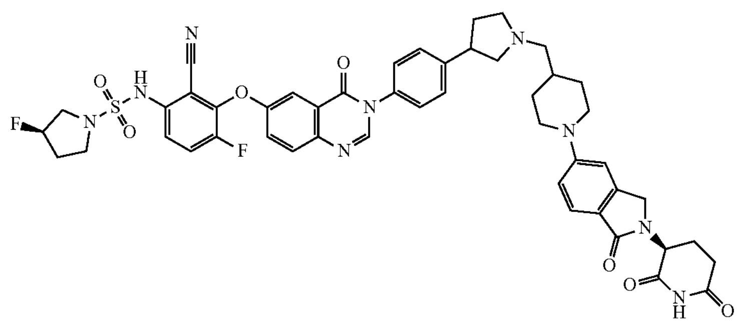 [SMILES: N#Cc1c(NS(=O)(=O)N2CC[C@@H](F)C2)ccc(F)c1Oc1ccc2ncn(-c3ccc(C4CCN(CC5CCN(c6ccc7c(c6)CN([C@H]6CCC(=O)NC6=O)C7=O)CC5)C4)cc3)c(=O)c2c1] | (3R)-N-(2-cyano-3-{[3-(4-{1-[(1-{2-[(3S)-2,6-dioxopiperidin-3-yl]-1-oxo-2,3-dihydro-1H-isoindol-5-yl}piperidin-4-yl)methyl]pyrrolidin-3-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.94 (s, 1H), 8.27 (s, 1H), 8.13 (s, 1H), 7.82 (d, J = 8.8 Hz, 1H), 7.68 (dd, J = 3.2, 8.8 Hz, 1H), 7.57-7.44 (m, 6H), 7.39 (d, J = 2.8 Hz, 1H), 7.33 (dd, J = 3.6, 9.2 Hz, 1H), 7.10-7.05 (m, 2H), 5.35-5.18 (m, 1H), 5.04 (dd, J = 5.2, 13.2 Hz, 1H), 4.37-4.27 (m, 1H), 4.24-4.15 (m, 1H), 3.92 (d, J = 11.6 Hz, 2H), 3.73-3.53 (m, 2H), 3.43-3.37 (m, 2H), 3.28-3.24 (m, 2H), 3.21-3.12 (m, 2H), 3.09-2.96 (m, 2H), 2.95-2.90 (m, 1H), 2.90-2.81 (m, 3H), 2.62-2.55 (m, 1H), 2.46-2.40 (m, 1H), 2.37 (dd, J = 4.4, 13.2 Hz, 1H), 2.09-1.93 (m, 5H), 1.90-1.82 (m, 2H), 1.36-1.26 (m, 2H) |

TABLE 1-continued

| Cmp. No. | Structure | IUPAC Name | ¹H NMR |
|---|---|---|---|
| 209 | 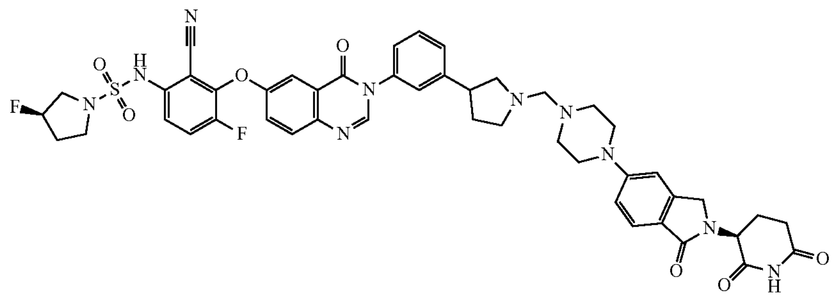 [SMILES: N#Cc1c(NS(=O)(=O)N2CC[C@@H](F)C2)ccc(F)c1Oc1ccc2ncn(-c3cccc(C4CCN(CN5CCN(c6ccc7c(c6)CN([C@H]6CCC(=O)NC6=O)C7=O)CC5)C4)c3)c(=O)c2c1] | (3R)-N-(2-cyano-3-{[3-(3-{[4-{2-[(3S)-2,6-dioxopiperidin-3-yl]-1-oxo-2,3-dihydro-1H-isoindol-5-yl]piperazin-1-yl}methyl)pyrrolidin-1-yl]phenyl}-4-oxo-3,4-dihydroquinazolin-6-yl]oxy}-4-fluorophenyl)-3-fluoropyrrolidine-1-sulfonamide | ¹H NMR (400 MHz, DMSO) δ 10.94 (s, 1H), 10.54-9.82 (m, 1H), 8.25 (s, 1H), 8.13 (s, 1H), 7.82 (d, J = 8.8 Hz, 1H), 7.70 (dd, J = 3.2, 8.8 Hz, 2H), 7.53 (d, J = 8.4 Hz, 1H), 7.47-7.42 (m, 1H), 7.41 (d, J = 2.8 Hz, 1H), 7.30 (t, J = 8.4 Hz, 1H), 7.12-7.05 (m, 2H), 6.70-6.61 (m, 3H), 5.40-5.19 (m, 1H), 5.05 (dd, J = 5.0, 13.2 Hz, 1H), 4.33 (d, J = 16.8 Hz, 1H), 4.26-4.15 (m, 1H), 3.44 (s, 2H), 3.38 (s, 4H), 3.28-3.23 (m, 2H), 3.06-2.98 (m, 1H), 2.96-2.84 (m, 2H), 2.80-2.71 (m, 2H), 2.69-2.64 (m, 2H), 2.58 (d, J = 17.6 Hz, 4H), 2.41-2.30 (m, 1H), 2.22-1.90 (m, 5H), 1.82-1.68 (m, 1H) |
| 210 | 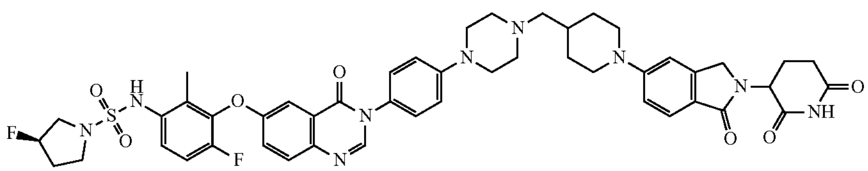 [SMILES: Cc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)cc3)c(=O)c2c1] | (3R)-N-{3-[(3-{4-[4-({1-[2-(2,6-dioxopiperidin-3-yl)-1-oxo-2,3-dihydro-1H-isoindol-5-yl]piperidin-4-yl}methyl)piperazin-1-yl]phenyl}-4-oxo-3,4-dihydroquinazolin-6-yl)oxy]-4-fluoro-2-methylphenyl}-3-fluoropyrrolidine-1-sulfonamide | ¹H NMR (300 MHz, DMSO) δ 10.94 (s, 2H), 8.22 (s, 2H), 7.80 (d, J = 8.9 Hz, 2H), 7.67-7.57 (m, 1H), 7.51 (d, J = 8.4 Hz, 2H), 7.31 (d, J = 9.2 Hz, 6H), 7.23 (s, 2H), 7.05 (d, J = 8.5 Hz, 5H), 5.41 (s, 1H), 5.23 (s, 1H), 4.33 (d, J = 16.9 Hz, 2H), 4.20 (d, J = 16.9 Hz, 2H), 3.89 (d, J = 12.7 Hz, 3H), 3.50 (s, 2H), 2.85 - 2.65 (m, 5H), 2.61 (s, 1H), 2.20-216 (m, 5H), 2.08 (s, 1H), 1.98 (s, 2H), 1.83-1.80 (m, 4H), 1.22-1020 (m, 4H) |

| Cmp. No. | Structure | IUPAC Name | ¹H NMR |
|---|---|---|---|
| 211 | 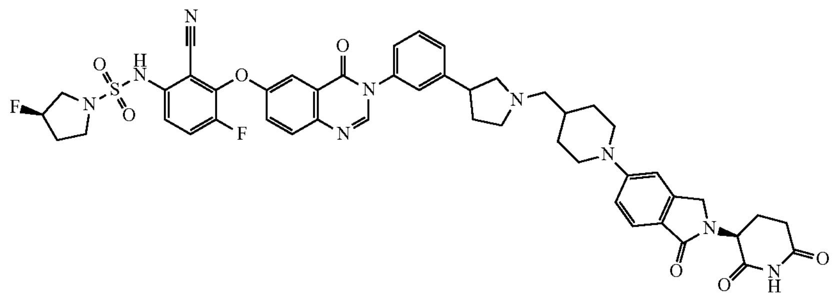 [SMILES: N#Cc1c(NS(=O)(=O)N2CC[C@@H](F)C2)ccc(F)c1Oc1ccc2ncn(-c3cccc(C4CCN(CC5CCN(c6ccc7c(c6)CN([C@H]6CCC(=O)NC6=O)C7=O)CC5)C4)c3)c(=O)c2c1] | (3R)-N-(2-cyano-3-{[3-(3-{1-[(1-{[2-[(3S)-2,6-dioxopiperidin-3-yl]-1-oxo-2,3-dihydro-1H-isoindol-5-yl]piperidin-4-yl}methyl)pyrrolidin-3-yl]phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.94 (s, 1H), 8.30 (s, 1H), 8.13 (s, 1H), 7.83 (d, J = 9.2 Hz, 1H), 7.69 (dd, J = 3.0, 8.8 Hz, 1H), 7.55 (d, J = 7.6 Hz, 2H), 7.52 (s, 1H), 7.50-7.43 (m, 3H), 7.39 (d, J = 3.2 Hz, 1H), 7.33-7.27 (m, 1H), 7.08-7.04 (m, 2H), 5.35-5.16 (m, 1H), 5.07-5.01 (m, 1H), 4.34-4.29 (m, 1H), 4.23-4.16 (m, 1H), 3.90 (d, J = 11.2 Hz, 3H), 3.68-3.48 (m, 3H), 3.23 (d, J = 4.4 Hz, 2H), 3.18-3.12 (m, 2H), 2.97-2.93 (m, 1H), 2.92-2.80 (m, 4H), 2.60 (s, 1H), 2.35 (s, 1H), 2.17-1.90 (m, 7H), 1.85-1.78 (m, 2H), 1.31-1.22 (m, 2H) |
| 212 | 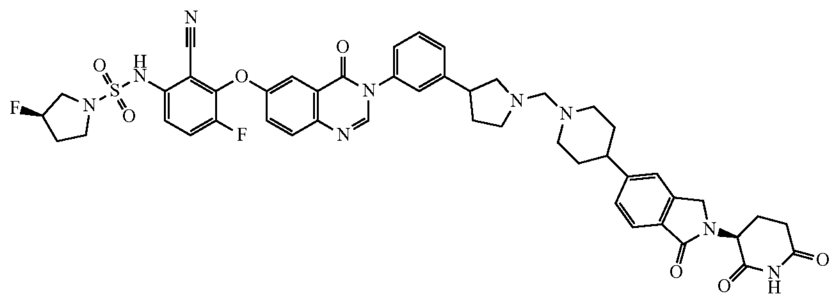 [SMILES: N#Cc1c(NS(=O)(=O)N2CC[C@@H](F)C2)ccc(F)c1Oc1ccc2ncn(-c3cccc(C4CCN(CN5CCC(c6ccc7c(c6)CN([C@H]6CCC(=O)NC6=O)C7=O)CC5)C4)c3)c(=O)c2c1] | (3R)-N-(2-cyano-3-{[3-(3-{[4-{2-[(3S)-2,6-dioxopiperidin-3-yl]-1-oxo-2,3-dihydro-1H-isoindol-5-yl]piperidin-1-yl}methyl)pyrrolidin-3-yl]phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.99 (s, 1H), 8.25 (s, 1H), 8.13 (s, 1H), 7.82 (d, J = 8.8 Hz, 1H), 7.71-7.66 (m, 2H), 7.49 (s, 2H), 7.46-7.23 (m, 5H), 6.70 (d, J = 8.0 Hz, 1H), 6.66 (d, J = 2.0 Hz, 2H), 5.38-5.16 (m, 1H), 5.11 (dd, J = 5.0, 13.2 Hz, 1H), 4.50-4.40 (m, 1H), 4.36-4.26 (m, 1H), 3.58-3.45 (m, 3H), 3.25-3.15 (m, 4H), 3.10-3.02 (m, 2H), 2.97-2.84 (m, 3H), 2.81-2.70 (m, 2H), 2.64-2.56 (m, 1H), 2.45-2.32 (m, 2H), 2.25-2.08 (m, 2H), 2.05-1.71 (m, 9H) |
| 213 | 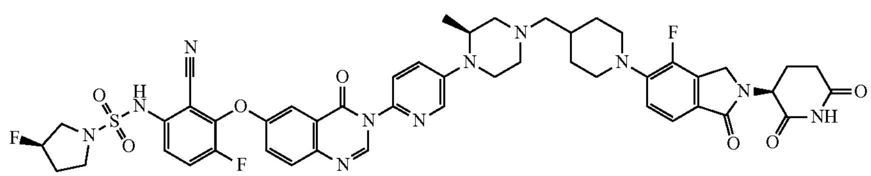 [SMILES: C[C@H]1CN(CC2CCN(c3ccc4c(c3F)CN([C@H]3CCC(=O)NC3=O)C4=O)CC2)CCN1c1ccc(-n2cnc3ccc(Oc4c(F)ccc(NS(=O)(=O)N5CC[C@@H](F)C5)c4C#N)cc3c2=O)nc1] | (3R)-N-{2-cyano-3-[(3-{5-[(2S)-4-[(1-{2-[(3S)-2,6-dioxopiperidin-3-yl]-4-fluoro-1-oxo-2,3-dihydro-1H-isoindol-5-yl]piperidin-4-yl}methyl)-2-methylpiperazin-1-yl]pyridin-2-yl}methyl)-4-oxo-3,4-dihydroquinazolin-6-yl]oxy}-4-fluorophenyl}-3-fluoropyrrolidine-1-sulfonamide | ¹H NMR (400 MHz, DMSO) δ 10.98 (s, 1H), 10.31 (s, 1H), 8.46 (s, 1H), 8.23 (s, 1H), 7.85 (d, 3H), 7.59 (d, J = 8.9 Hz, 1H), 7.54-7.44 (m, 4H), 7.19 (t, J = 7.9 Hz, 1H), 5.38-5.25 (s, 1H), 5.08 (dd, J = 5.1 Hz, 1H), 4.49 (d, J = 16.9 Hz, 1H), 4.32 (d, J = 16.9 Hz, 1H), 4.20 (s, 1H), 3.65 (d, 4H), 3.31 (s, 2H), 3.10 (m, 1H), 2.99-2.60 (d, 5H), 2.43 (dd, J = 13.1, 4.7 Hz, 1H), 2.28 (s, 2H), 2.15 (s, 2H), 2.00 (s, 4H), 1.88 (d, J = 12.7 |

| Cmp. No. | Structure | IUPAC Name | $^1$H NMR |
|---|---|---|---|
| 214 | 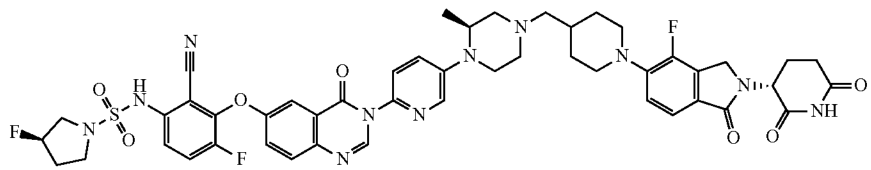 [SMILES: C[C@H]1CN(CC2CCN(c3ccc4c(c3F)CN([C@@H]3CCC(=O)NC3=O)C4=O)CC2)CCN1c1ccc(-n2cnc3ccc(Oc4c(F)ccc(NS(=O)(=O)N5CC[C@@H](F)C5)c4C#N)cc3c2=O)nc1] | (3R)-N-{2-cyano-3-[(3-{5-[(2S)-4-[(1-{2-[(3R)-2,6-dioxopiperidin-3-yl]-4-fluoro-1-oxo-2,3-dihydro-1H-isoindol-5-yl}piperidin-4-yl)methyl]-2-methylpiperazin-1-yl]pyridin-2-yl}-4-oxo-3,4-dihydroquinazolin-6-yl)oxy]-4-fluorophenyl}-3-fluoropyrrolidine-1-sulfonamide | $^1$H NMR (400 MHz, DMSO) δ 10.98 (s, 1H), 10.32 (s, 1H), 8.46 (s, 1H), 8.23 (s, 1H), 7.85-7.72 (s, 3.0 Hz, 3H), 7.59 (d, J = 8.8 Hz, 1H), 7.54-7.44 (m, 4H), 7.19 (t, J = 7.9 Hz, 1H), 5.38-5.25 (s, 1H), 5.08 (dd, J = 13.2, 5.1 Hz, 1H), 4.49 (d, J = 17.0 Hz, 1H), 4.32 (d, J = 16.9 Hz, 1H), 4.20 (s, 1H), 3.52 (s, 4H), 3.42 (s, 2H), 3.09 (s, 1H), 2.93-2.82 (t, 5H), 2.62 (s, 1H), 2.28 (s, 3H), 2.14 (s, 2H), 2.00 (s, 8H), 1.88 (d, J = 12.5 Hz, 4H), 11.24 (s, 5H), 1.15 (d, J = 6.3 Hz, 3H) |
| 215 | 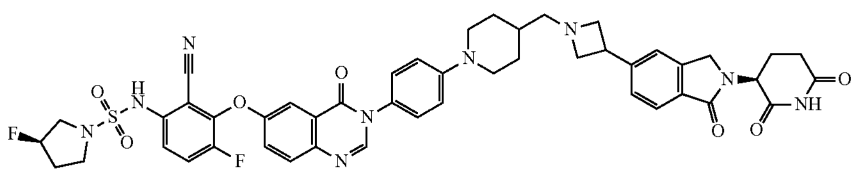 [SMILES: N#Cc1c(NS(=O)(=O)N2CC[C@@H](F)C2)ccc(F)c1Oc1ccc2ncn(-c3ccc(N4CCC(CN5CC(c6ccc7c(c6)CN([C@H]6CCC(=O)NC6=O)C7=O)C5)CC4)cc3)c(=O)c2c1] | (3R)-N-(2-cyano-3-[{3-(4-{[(3-{2-[(3S)-2,6-dioxopiperidin-3-yl]-1-oxo-2,3-dihydro-1H-isoindol-5-yl}azetidin-1-yl]methyl]piperidin-1-yl}phenyl)-4-oxo-3,4-dihydroquinazolin-6-yl]oxy}-3-fluorophenyl)-3-fluoropyrrolidine-1-sulfonamide | $^1$H NMR (300 MHz, DMSO) δ 10.99 (s, 1H), 8.22 (s, 1H), 8.21 (s, 1H), 7.80 (d, J = 8.9 Hz, 1H), 7.73 (d, J = 7.9 Hz, 2H), 7.65 (dd, J = 9.0, 2.8 Hz, 1H), 7.55 (d, J = 8.0 Hz, 1H), 7.42-7.30 (m, 2H), 7.35-7.24 (m, 3H), 7.06 (d, J = 9.0 Hz, 2H), 5.36 (s, 1H), 5.10 (d, J = 5.0 Hz, 1H), 4.47 (d, J = 17.4 Hz, 2H), 4.34 (d, J = 17.4 Hz, 3H), 3.82 (d, J = 12.2 Hz, 3H), 3.40 (dd, J = 12.3, 4.3 Hz, 1H), 3.32 (s, 3H), 3.29-3.07 (m, 3H), 3.00-2.84 (m, 3H), 2.76 (t, J = 11.3 Hz, 2H), 2.61 (d, J = 16.6 Hz, 1H), 2.47-2.34 (m, 1H), 2.12 (ddd, J = 13.2, 8.9, 4.4 Hz, 3H), 2.06-1.96 (m, 2H), 1.80 (d, J = 12.7 Hz, 1H), 1.68 (s, 3H), 1.39-1.11 (m, 2H) |

TABLE 1-continued

| Cmp. No. | Structure | IUPAC Name | ¹H NMR |
|---|---|---|---|
| 216 | 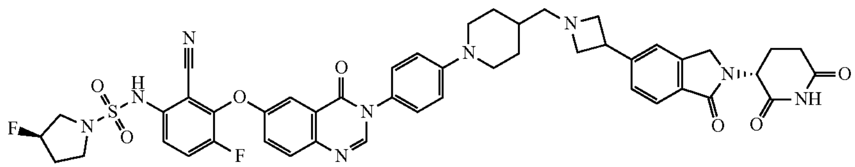 [SMILES: N#Cc1c(NS(=O)(=O)N2CC[C@@H](F)C2)ccc(F)c1Oc1ccc2ncn(-c3ccc(N4CCC(CN5CC(c6ccc7c(c6)CN([C@@H]6CCC(=O)NC6=O)C7=O)C5)CC4)cc3)c(=O)c2c1] | (3R)-N-(2-cyano-3-{[3-(4-{4-[(3-{2-[(3R)-2,6-dioxopiperidin-3-yl]-1-oxo-2,3-dihydro-1H-isoindol-5-yl}azetidin-1-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.99 (s, 1H), 10.05 (s, 1H), 8.50 (s, 1H), 8.22 (s, 1H), 7.81 (d, J = 8.9 Hz, 1H), 7.74-7.65 (m, 2H), 7.61 (s, 1H), 7.49 (s, 2H), 7.39 (d, J = 3.1 Hz, 3H), 7.35-7.26 (m, 2H), 5.36 (s, 1H), 5.22 (s, 1H), 4.45 (d, J = 17.4 Hz, 2H), 4.10 (t, J = 7.5 Hz, 3H), 3.68 (s, 3H), 3.69-3.57 (m, 1H), 3.25 (s, 3H), 3.14 (dd, J = 7.4, 3.7 Hz, 3H), 2.99-2.81 (m, 2H), 2.60 (d, J = 17.1 Hz, 1H), 2.46 (d, 1H), 2.03-1.96 (m, 1H), 1.91 (s, 2H), 1.88 (s, 3H), 1.54 (s, 2H), 1.26 (td, J = 7.3, 4.9 Hz, 1H) |
| 217 | 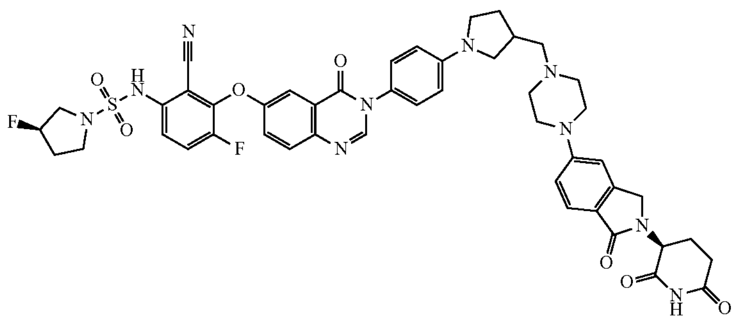 [SMILES: N#Cc1c(NS(=O)(=O)N2CC[C@@H](F)C2)ccc(F)c1Oc1ccc2ncn(-c3ccc(N4CCC(CN5CCN(c6ccc7c(c6)CN([C@H]6CCC(=O)NC6=O)C7=O)CC5)C4)cc3)c(=O)c2c1] | (3R)-N-(2-cyano-3-{[3-(4-{3-[(4-{2-[(3S)-2,6-dioxopiperidin-3-yl]-1-oxo-2,3-dihydro-1H-isoindol-5-yl}piperazin-1-yl)methyl]pyrrolidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.95 (s, 1H), 10.48-9.90 (m, 1H), 8.22 (s, 1H), 8.13 (s, 1H), 7.81 (d, J = 9.2 Hz, 1H), 7.69 (dd, J = 3.2, 8.8 Hz, 2H), 7.54 (d, J = 8.4 Hz, 1H), 7.44 (dd, J = 4.0, 9.2 Hz, 1H), 7.40 (d, J = 2.8 Hz, 1H), 7.26 (d, J = 8.8 Hz, 2H), 7.12-7.07 (m, 2H), 6.62 (d, J = 9.2 Hz, 2H), 5.39-5.20 (m, 1H), 5.05 (dd, J = 5.2, 13.2 Hz, 1H), 4.39-4.30 (m, 1H), 4.26-4.17 (m, 1H), 3.50-3.44 (m, 2H), 3.38 (s, 6H), 3.30-3.24 (m, 2H), 3.07 (dd, J = 6.4, 9.2 Hz, 1H), 2.96-2.87 (m, 1H), 2.83-2.66 (m, 5H), 2.65-2.54 (m, 4H), 2.42-2.34 (m, 1H), 2.22-2.08 (m, 2H), 2.07-2.01 (m, 1H), 1.99-1.93 (m, 1H), 1.83-1.73 (m, 1H) |

TABLE 1-continued

| Cmp. No. | Structure | IUPAC Name | ¹H NMR |
|---|---|---|---|
| 218 | 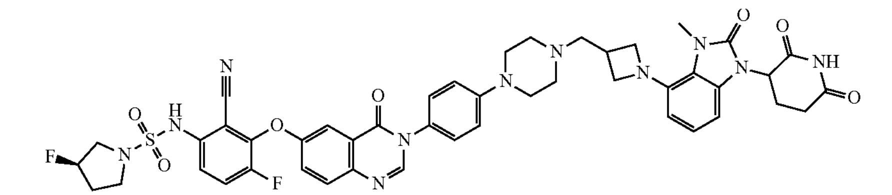 [SMILES: Cn1c(=O)n(C2CCC(=O)NC2=O)c2cccc(N3CC(CN4CCN(c5ccc(-n6cnc7ccc(Oc8c(F)ccc(NS(=O)(=O)N9CC[C@@H](F)C9)c8C#N)cc7c6=O)cc5)CC4)C3)c21] | (3R)-N-{2-cyano-3-[(3-{4-[4-({1-[1-(2,6-dioxopiperidin-3-yl)-3-methyl-2-oxo-2,3-dihydro-1H-1,3-benzodiazol-4-yl]azetidin-3-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 11.09 (s, 1H), 8.24 (s, 1H), 7.81 (d, J = 8.9 Hz, 1H), 7.67 (s, 1H), 7.55 (t, J = 9.7 Hz, 1H), 7.42-7.31 (m, 4H), 7.07 (d, J = 8.8 Hz, 2H), 6.96 (t, J = 8.0 Hz, 1H), 6.74 (d, J = 7.9 Hz, 1H), 6.67 (d, J = 8.2 Hz, 1H), 5.38-5.28 (m, 1H), 5.21 (s, 1H), 4.03-3.94 (m, 2H), 3.57 (d, J = 11.3 Hz, 6H), 3.31-3.26 (m, 9H), 3.20 (s, 2H), 2.99-2.86 (m, 2H), 2.82 (s, 5H), 2.71 (m, 1H), 2.65 (d, J = 9.4 Hz, 1H), 2.61 (d, J = 12.8 Hz, 1H), 2.06-1.95 (m, 1H) |
| 219 | 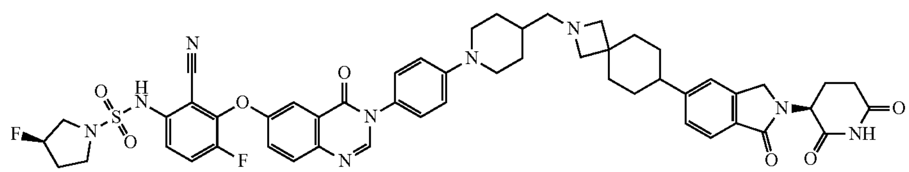 [SMILES: N#Cc1c(NS(=O)(=O)N2CC[C@@H](F)C2)ccc(F)c1Oc1ccc2ncn(-c3ccc(N4CCC(CN5CC6(CCC(c7ccc8c(c7)CN([C@H]7CCC(=O)NC7=O)C8=O)CC6)C5)CC4)cc3)c(=O)c2c1] | (3R)-N-(2-cyano-3-{[3-(4-{4-[(7-{2-[(3S)-2,6-dioxopiperidin-3-yl]-1-oxo-2,3-dihydro-1H-isoindol-5-yl}-2-azaspiro[3.5]nonan-2-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (300 MHz, DMSO) δ 10.98 (s, 1H), 8.22 (s, 1H), 7.81 (d, J = 2.4 Hz, 1H), 7.65 (d, J = 2.4 Hz, 2H), 7.81 (s, 1H), 7.39-7.28 (m, 6H), 7.06 (d, J = 9.0 Hz, 1H), 5.30 (s, 1H), 5.12-5.09 (m, 1H), 4.45-4.26 (m, 2H), 3.93-3.78 (m, 4H), 3.40-3.26 (m, 9H), 3.11-2.71 (m, 4H), 2.66-2.44 (m, 3H), 2.22-1.88 (m, 6H), 1.80-1.75 (m, 5H), 1.70-1.43 (m, 5H), 1.40-1.21 (m, 5H) |
| 220 | 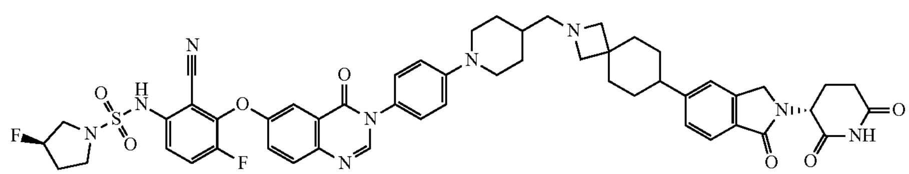 [SMILES: N#Cc1c(NS(=O)(=O)N2CC[C@@H](F)C2)ccc(F)c1Oc1ccc2ncn(-c3ccc(N4CCC(CN5CC6(CCC(c7ccc8c(c7)CN([C@@H]7CCC(=O)NC7=O)C8=O)CC6)C5)CC4)cc3)c(=O)c2c1] | (3R)-N-(2-cyano-3-{[3-(4-{4-[(7-{2-[(3R)-2,6-dioxopiperidin-3-yl]-1-oxo-2,3-dihydro-1H-isoindol-5-yl}-2-azaspiro[3.5]nonan-2-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (300 MHz, DMSO) δ 10.98 (s, 1H), 8.22 (s, 1H), 7.81 (d, J = 2.4 Hz, 1H), 7.65 (d, J = 2.4 Hz, 2H), 7.81 (s, 1H), 7.39-7.28 (m, 6H), 7.06 (d, J = 9.0 Hz, 1H), 5.30 (s, 1H), 5.12-5.09 (m, 1H), 4.45-4.26 (m, 2H), 3.93-3.78 (m, 4H), 3.40-3.26 (m, 9H), 3.11-2.71 (m, 4H), 2.66-2.44 (m, 3H), 2.22-1.88 (m, 6H), 1.80-1.75 (m, 5H), 1.70-1.43 (m, 5H), 1.40-1.21 (m, 5H) |

TABLE 1-continued

| Cmp. No. | Structure | IUPAC Name | ¹H NMR |
|---|---|---|---|
| 221 | 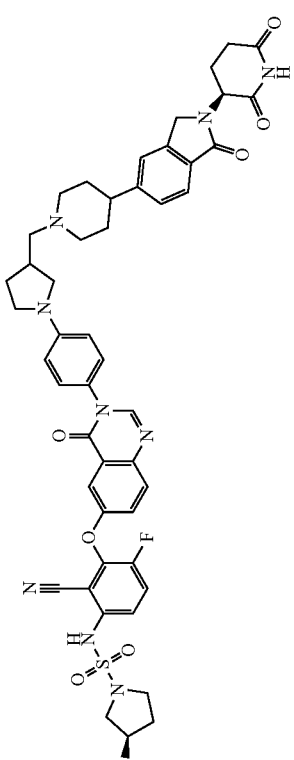 | (3R)-N-(2-cyano-3-{[3-(4-{3-[(4-{2-[(3S)-2,6-dioxopiperidin-3-yl]-1-oxo-2,3-dihydro-1H-isoindol-5-yl}piperidin-1-yl)methyl]pyrrolidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.99 (s, 1H), 8.21 (s, 1H), 8.13 (s, 1H), 7.80 (d, J = 8.8 Hz, 1H), 7.72-7.62 (m, 2H), 7.54-7.41 (m, 3H), 7.39-7.32 (m, 2H), 7.29 (d, J = 8.8 Hz, 2H), 6.64 (d, J = 8.8 Hz, 2H), 5.36-5.18 (m, 1H), 5.11 (dd, J = 4.8, 13.2 Hz, 1H), 4.49 - 4.40 (m, 1H), 4.37-4.27 (m, 1H), 3.58-3.47 (m, 2H), 3.45-3.36 (m, 3H), 3.27 (s, 2H), 3.23-3.15 (m, 2H), 3.14-3.05 (m, 2H), 2.98-2.85 (m, 3H), 2.83-2.71 (m, 2H), 2.63-2.57 (m, 1H), 2.42-2.38 (m, 1H), 2.29-2.15 (m, 2H), 2.06-1.84 (m, 8H) |
| 222 | 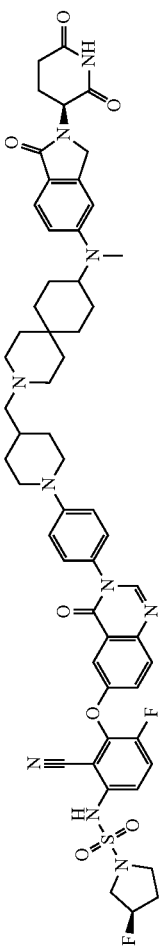 | (3R)-N-[2-cyano-3-({3-[4-(4-{[9-({2-[(3S)-2,6-dioxopiperidin-3-yl]-1-oxo-2,3-dihydro-1H-isoindol-5-yl}(methyl)amino)-3-azaspiro[5.5]undecan-3-yl]methyl}piperidin-1-yl]phenyl)-4-oxo-3,4-dihydroquinazolin-6-yl]oxy}-4-fluorophenyl]-3-fluoropyrrolidine-1-sulfonamide | 1H NMR (400 MHz, DMSO) δ 10.93 (s, 1H), 8.57 (s, 1H), 8.25 (s, 1H), 7.83 (d, J = 8.9 Hz, 1H), 7.73-7.68 (m, 2H), 7.56-7.38 (m, 3H), 7.33 (d, J = 8.6 Hz, 2H), 7.07 (d, J = 9.0 Hz, 2H), 6.93-6.87 (m, 2H), 5.40-5.20 (m, 1H), 5.04 (m, 1H), 4.31 (d, J = 16.7 Hz, 1H), 4.19 (d, J = 16.8 Hz, 1H), 3.92-3.70 (m, 3H), 3.69-3.57 (m, 1H), 3.53-3.43 (d, J = 8.9 Hz, 1H), 3.41-3.36 (m, 2H), 3.28 (d, J = 8.9 Hz, 1H), 3.16-3.11 (m, 1H), 3.04 (s, 3H), 2.96-2.89 (m, 1H), 2.83 (d, J = 8.6 Hz, 2H), 2.61 (d, J = 17.0 Hz, 5H), 2.56 (d, J = 3.5 Hz, 1H), 2.40-2.31 (m, 1H), 2.28-2.08 (m, 3H), 2.05-1.93 (m, 2H), 1.92-1.87 (m, 2H), 1.86 (d, J = 12.5 Hz, 2H), 1.74 (d, J = 32.3 Hz, 3H), 1.52 (d, J = 12.8 Hz, 5H), 1.40-1.32 (m, 2H), 1.31-0.91 (m, 10H), 0.91-0.78 (m, 1H), 0.75 (s, 1H) |

TABLE 1-continued

| Cmp. No. | Structure | IUPAC Name | 1H NMR |
|---|---|---|---|
| 223 | 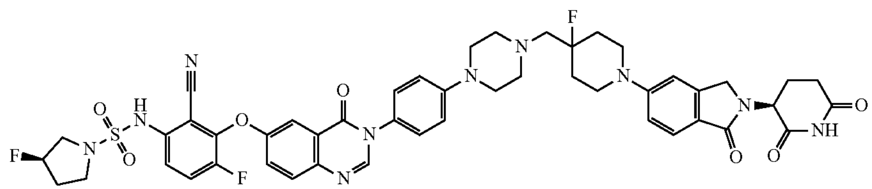 [SMILES: N#Cc1c(NS(=O)(=O)N2CC[C@@H](F)C2)ccc(F)c1Oc1ccc2ncn(-c3ccc(N4CCN(CC5(F)CCN(c6ccc7c(c6)CN([C@H]6CCC(=O)NC6=O)C7=O)CC5)CC4)cc3)c(=O)c2c1] | (3R)-N-(2-cyano-3-{[3-(4-{4-[(1-{2-[(3S)-2,6-dioxopiperidin-3-yl]-1-oxo-2,3-dihydro-1H-isoindol-5-yl}-4-fluoropiperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.94 (s, 1H), 10.32 (s, 1H), 8.26 (s, 1H), 7.86-7.73 (m, 2H), 7.70 (dd, J = 3.2, 8.8 Hz, 1H), 7.55-7.45 (m, 2H), 7.41 (d, J = 2.8 Hz, 1H), 7.32 (d, J = 8.8 Hz, 2H), 7.13-7.08 (m, 2H), 7.05 (d, J = 8.8 Hz, 2H), 5.39-5.22 (m, 1H), 5.04 (dd, J = 5.4, 13.4 Hz, 1H), 4.37-4.28 (m, 1H), 4.26-4.13 (m, 1H), 3.75-3.66 (m, 2H), 3.51-3.46 (m, 1H), 3.45-3.38 (m, 2H), 3.28-3.12 (m, 7H), 2.95-2.85 (m, 1H), 2.72-2.62 (m, 5H), 2.62-2.54 (m, 2H), 2.40-2.31 (m, 1H), 2.13 (s, 2H), 2.00-1.91 (m, 3H), 1.87-1.69 (m, 2H) |
| 224 | 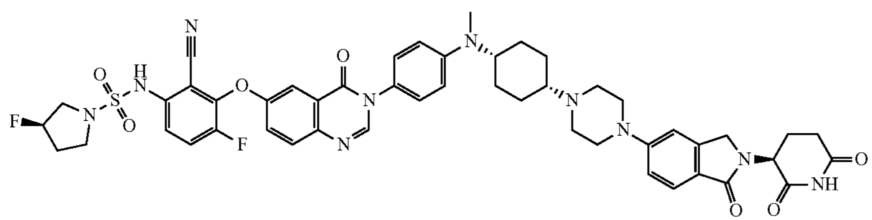 [SMILES: CN(c1ccc(-n2cnc3ccc(Oc4c(F)ccc(NS(=O)(=O)N5CC[C@@H](F)C5)c4C#N)cc3c2=O)cc1)[C@H]1CC[C@@H](N2CCN(c3ccc4c(c3)CN([C@H]3CCC(=O)NC3=O)C4=O)CC2)CC1] | (3R)-N-(2-cyano-4-fluoro-3-{[3-(4-{methyl[(1r,4r)-4-(4-{2-[(3S)-2,6-dioxopiperidin-3-yl]-1-oxo-2,3-dihydro-1H-isoindol-5-yl}piperazin-1-yl)cyclohexyl]amino}phenyl)-4-oxo-3,4-dihydroquinazolin-6-yl]oxy}phenyl)-3-fluoropyrrolidine-1-sulfonamide | 1H NMR (300 MHz, DMSO) δ 10.96 (s, 1H), 8.23 (s, 2H), 7.81 (d, J = 5.7 Hz, 1H), 7.68 (d, J = 0.9 Hz, 1H), 7.65-7.56 (m, 2H), 7.53-7.50 (m, 2H), 7.40-7.39 (m, 2H), 7.26-7.13 (m, 3H), 6.96-6.95 (m, 2H), 5.36 (q, J = 5.7, 5.2 Hz, 1H), 5.08-5.00 (m, 1H), 4.56-4.32 (m, 2H), 3.89-3.86 (m, 1H), 3.39-3.36 (m, 1H), 3.13-3.03 (m, 7H), 2.96-2.94 (m, 3H), 2.74 (s, 3H), 2.74-2.71 (m, 2H), 2.21-1.85 (m, 7H), 1.72-1.45 (m, 4H), 1.23-1.03 (m, 4H) |
| 225 | 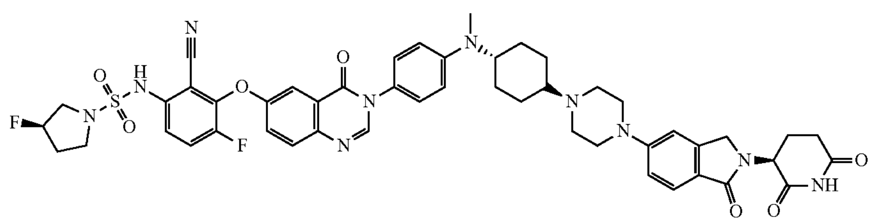 | (3R)-N-(2-cyano-4-fluoro-3-{[3-(4-{methyl[(1s,4s)-4-(4-{2-[(3S)-2,6-dioxopiperidin-3-yl]-1-oxo-2,3-dihydro-1H-isoindol-5-yl}piperazin-1-yl)cyclohexyl]amino}phenyl)-4-oxo-3,4-dihydroquinazolin-6-yl]oxy}phenyl)-3-fluoropyrrolidine-1-sulfonamide | 1H NMR (300 MHz, DMSO) δ 10.96 (s, 1H), 8.23 (s, 2H), 7.81 (d, J = 5.7 Hz, 1H), 7.68 (d, J = 0.9 Hz, 1H), 7.65-7.56 (m, 2H), 7.53-7.50 (m, 2H), 7.40-7.39 (m, 2H), 7.26-7.13 (m, 3H), 6.96-6.95 (m, 2H), 5.36 (q, J = 5.7, 5.2 Hz, 1H), 5.08-5.00 (m, 1H), 4.56-4.32 (m, 2H), 3.89-3.86 (m, 1H), 3.39-3.36 (m, 1H), 3.13-3.03 (m, 7H), 2.96-2.94 (m, 3H), 2.74 (s, 3H), 2.74-2.71 (m, 2H), 2.21-1.85 (m, 7H), 1.72-1.45 (m, 4H), 1.23-1.03 (m, 4H) |

TABLE 1-continued

| Cmp. No. | Structure | IUPAC Name | ¹H NMR |
|---|---|---|---|
| 226 | 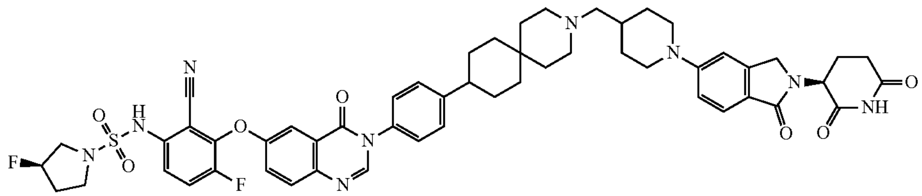 [SMILES: N#Cc1c(NS(=O)(=O)N2CC[C@@H](F)C2)ccc(F)c1Oc1ccc2ncn(-c3ccc(C4CCC5(CC4)CCN(CC4CCN(c6ccc7c(c6)CN([C@H]6CCC(=O)NC6=O)C7=O)CC4)CC5)cc3)c(=O)c2c1] | (3R)-N-(2-cyano-3-{[3-(4-{3-[(1-{2-[(3S)-2,6-dioxopiperidin-3-yl]-1-oxo-2,3-dihydro-1H-isoindol-5-yl]piperidin-4-yl]methyl]-3-azaspiro[5.5]undecan-9-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.96 (s, 1H), 8.28 (s, 1H), 8.14 (s, 1H), 7.81 (d, J = 8.8 Hz, 1H), 7.67 (dd, J = 3.2, 8.8 Hz, 1H), 7.53 (d, J = 8.8 Hz, 1H), 7.45 (s, 4H), 7.39 (d, J = 2.8 Hz, 2H), 7.33-7.26 (m, 1H), 7.12-7.04 (m, 2H), 5.40-5.14 (m, 1H), 5.05 (dd, J = 5.2, 13.2 Hz, 1H), 4.39-4.27 (m, 1H), 4.26-4.14 (m, 1H), 3.92 (br d, J = 11.2 Hz, 2H), 3.28-3.12 (m, 5H), 3.01-2.79 (m, 6H), 2.59 (br dd, J = 2.4, 14.8 Hz, 3H), 2.45-2.28 (m, 2H), 2.19-1.88 (m, 6H), 1.81 (br d, J = 11.2 Hz, 2H), 1.75-1.44 (m, 8H), 1.37-1.15 (m, 4H) |
| 227 | 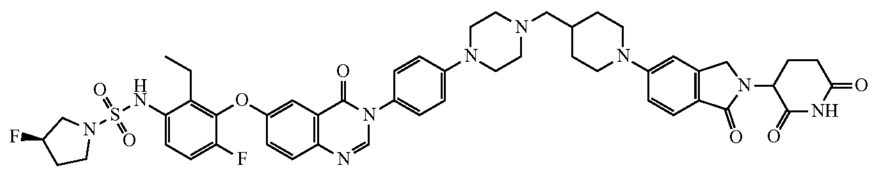 [SMILES: CCc1c(NS(=O)(=O)N2CC[C@@H](F)C2)ccc(F)c1Oc1ccc2ncn(-c3ccc(N4CCN(CC5CCN(c6ccc7c(c6)CN(C6CCC(=O)NC6=O)C7=O)CC5)CC4)cc3)c(=O)c2c1] | (3R)-N-{3-[(3-{4-[4-({1-[2-(2,6-dioxopiperidin-3-yl)-1-oxo-2,3-dihydro-1H-isoindol-5-yl]methyl}piperazin-1-yl]phenyl)-4-oxo-3,4-dihydroquinazolin-6-yl}oxy]-2-ethyl-4-fluorophenyl}-3-fluoropyrrolidine-1-sulfonamide | ¹H NMR (300 MHz, DMSO) δ 10.94 (s, 1H), 7.80 (d, J = 9.0 Hz, 1H), 7.63 (dd, J = 8.9, 3.1 Hz, 1H), 7.51 (d, J = 8.9 Hz, 1H), 7.37-7.24 (m, 5H), 7.05 (d, J = 8.6 Hz, 5H), 5.26 (s, 1H), 4.30 (s, 1H), 4.23 (s, 2H), 3.89 (d, J = 12.2 Hz, 2H), 3.53 (d, J = 8.3 Hz, 3H), 3.44 (s, 5 H), 2.85 (s, 3H), 2.72 (s, 3H), 2.51 (s, 1H), 2.32 (s, 1H), 2.01 (s, 4H), 1.82 (d, J = 11.6 Hz, 2H), 1.64 (s, 3H), 1.36 (t, J = 7.2 Hz, 14H), 1.06 (t, J = 7.2 Hz, 5H), 0.95 (s, 2H) |

TABLE 1-continued

| Cmp. No. | Structure | IUPAC Name | ¹H NMR |
|---|---|---|---|
| 228 | 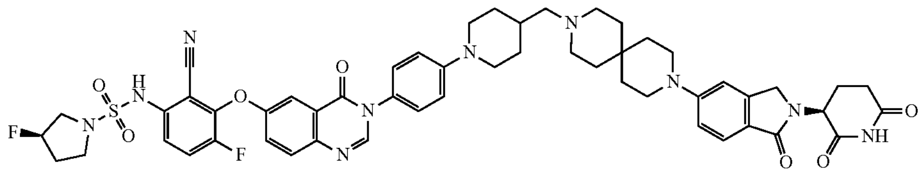 [SMILES: N#Cc1c(NS(=O)(=O)N2CC[C@@H](F)C2)ccc(F)c1Oc1ccc2ncn(-c3ccc(N4CCC(CN5CCC6(CC5)CCN(c5ccc7c(c5)CN([C@H]5CCC(=O)NC5=O)C7=O)CC6)CC4)cc3)c(=O)c2c1] | (3R)-N-(2-cyano-3-{[3-(4-{[9-(2-[(3S)-2,6-dioxopiperidin-3-yl]-1-oxo-2,3-dihydro-1H-isoindol-5-yl}-3,9-diazaspiro[5.5]undecan-3-yl)methyl]piperidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.93 (s, 1H), 8.21 (s, 1H), 8.13 (s, 1H), 7.79 (d, J = 9.2 Hz, 1H), 7.64 (dd, J = 2.8, 8.8 Hz, 1H), 7.51 (d, J = 8.8 Hz, 1H), 7.41-7.29 (m, 4H), 7.08-7.02 (m, 4H), 5.38-5.15 (m, 1H), 5.04 (dd, J = 5.6, 13.2 Hz, 1H), 4.38-4.26 (m, 1H), 4.24-4.14 (m, 1H), 3.89 - 3.76 (m, 2H), 3.29 (s, 8H), 3.24 (dt, J = 2.0, 6.4 Hz, 2H), 3.19-3.10 (m, 2H), 2.92-2.85 (m, 2H), 2.83-2.73 (m, 2H), 2.63-2.53 (m, 2H), 2.43 (s, 1H), 2.02-1.87 (m, 4H), 1.85-1.75 (m, 3H), 1.69-1.51 (m, 6H), 1.40-1.20 (m, 3H) |
| 229 | 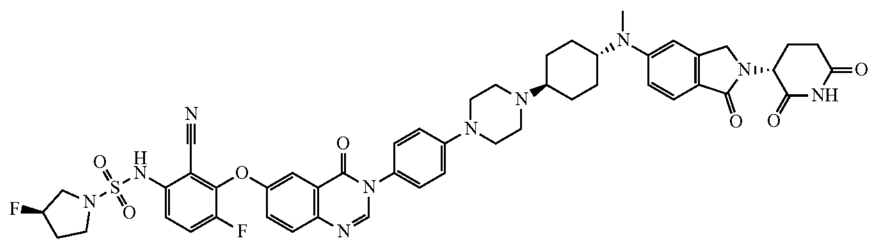 [SMILES: CN(c1ccc2c(c1)CN([C@@H]1CCC(=O)NC1=O)C2=O)[C@H]1CC[C@H](N2CCN(c3ccc(-n4cnc5ccc(Oc6c(F)ccc(NS(=O)(=O)N7CC[C@@H](F)C7)c6C#N)cc5c4=O)cc3)CC2)CC1] | (3R)-N-(2-cyano-4-fluoro-3-{[4-oxo-3-(4-{4-[(1r,4r)-4-({2-[(3R)-2,6-dioxopiperidin-3-yl]-1-oxo-2,3-dihydro-1H-isoindol-5-yl}(methyl)amino)cyclohexyl]piperazin-1-yl}phenyl)-3,4-dihydroquinazolin-6-yl]oxy}phenyl)-3-fluoropyrrolidine-1-sulfonamide | ¹H NMR (400 MHz, DMSO) δ 10.95 (s, 1H), 9.97 (b, 1H), 8.25 (s, 1H), 7.82 (d, J = 8.8 Hz, 1H), 7.81-7.80 (m, 1H), 7.70-7.68 (m, 1H), 7.52 (d, J = 9.6 Hz, 1H), 7.49-7.38 (m, 4H), 7.11 (d, J = 8.8 Hz, 2H), 6.92 (s, 2H), 5.32 (d, J = 42 Hz, 1H), 5.05-5.01 (m, 1H), 4.29-4.22 (q, 2H), 3.85 (s, 1H), 3.55-3.33 (m, 3H), 3.33-3.31 (m, 2H), 3.10-3.06 (m, 4H), 2.99-2.89 (m, 2H), 2.85 (s, 3H), 2.71-2.61 (m, 1H), 2.55-2.36 (m, 1H), 2.22-1.82 (m, 5H), 1.80-1.62 (m, 6H) |
| 230 | 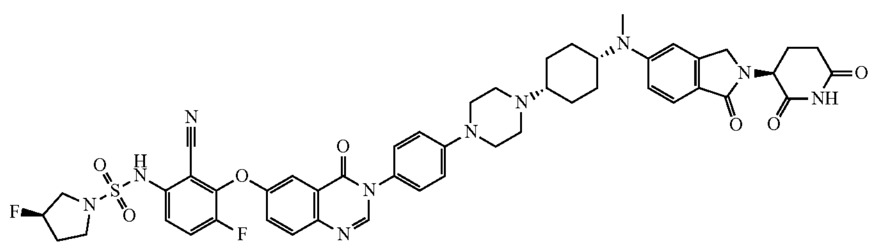 [SMILES: CN(c1ccc2c(c1)CN([C@H]1CCC(=O)NC1=O)C2=O)[C@H]1CC[C@@H](N2CCN(c3ccc(-n4cnc5ccc(Oc6c(F)ccc(NS(=O)(=O)N7CC[C@@H](F)C7)c6C#N)cc5c4=O)cc3)CC2)CC1] | (3R)-N-(2-cyano-4-fluoro-3-{[4-oxo-3-(4-{4-[(1r,4r)-4-({2-[(3S)-2,6-dioxopiperidin-3-yl]-1-oxo-2,3-dihydro-1H-isoindol-5-yl}(methyl)amino)cyclohexyl]piperazin-1-yl}phenyl)-3,4-dihydroquinazolin-6-yl]oxy}phenyl)-3-fluoropyrrolidine-1-sulfonamide | ¹H NMR (400 MHz, DMSO) δ 10.95 (s, 1H), 9.97 (b, 1H), 8.25 (s, 1H), 7.82 (d, J = 8.8 Hz, 1H), 7.81-7.80 (m, 1H), 7.70-7.68 (m, 1H), 7.52 (d, J = 9.6 Hz, 1H), 7.49-7.38 (m, 4H), 7.11 (d, J = 8.8 Hz, 2H), 6.92 (s, 2H), 5.32 (d, J = 42 Hz, 1H), 5.05-5.01 (m, 1H), 4.29-4.22 (q, 2H), 3.85 (s, 1H), 3.55-3.33 (m, 3H), 3.33-3.31 (m, 2H), 3.10-3.06 (m, 4H), 2.99-2.89 (m, 2H), 2.85 (s, 3H), 2.71-2.61 (m, 1H), 2.55-2.36 (m, 1H), 2.22-1.82 (m, 5H), 1.80-1.62 (m, 6H) |

TABLE 1-continued

| Cmp. No. | Structure | IUPAC Name | ¹H NMR |
|---|---|---|---|
| 231 | 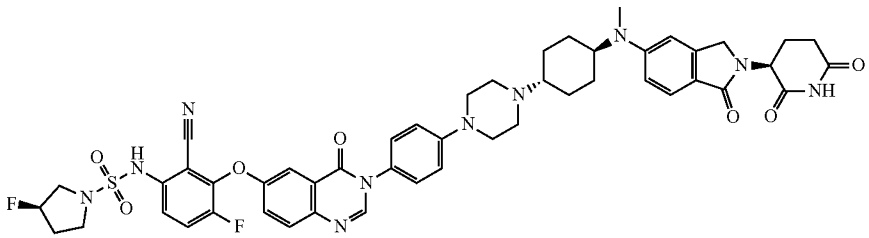 [SMILES: CN(c1ccc2c(c1)CN([C@H]1CCC(=O)NC1=O)C2=O)[C@H]1CC[C@H](N2CCN(c3ccc(-n4cnc5ccc(Oc6c(F)ccc(NS(=O)(=O)N7CC[C@@H](F)C7)c6C#N)cc5c4=O)cc3)CC2)CC1] | (3R)-N-(2-cyano-4-fluoro-3-{[4-oxo-3-(4-{4-[(1s,4s)-4-({2-[(3S)-2,6-dioxopiperidin-3-yl]-1-oxo-2,3-dihydro-1H-isoindol-5-yl}(methyl)amino)cyclohexyl]piperazin-1-yl}phenyl)-3,4-dihydroquinazolin-6-yl]oxy}phenyl)-3-fluoropyrrolidine-1-sulfonamide | ¹H NMR (400 MHz, DMSO) δ 10.95 (s, 1H), 9.97 (b, 1H), 8.25 (s, 1H), 7.82 (d, J = 8.8 Hz, 1H), 7.81-7.80 (m, 1H), 7.70-7.68 (m, 1H), 7.52 (d, J = 9.6 Hz, 1H), 7.49-7.38 (m, 4H), 7.11 (d, J = 8.8 Hz, 2H), 6.92 (s, 2H), 5.32 (d, J = 42 Hz, 1H), 5.05-5.01 (m, 1H), 4.29-4.22 (q, 2H), 3.85 (s, 1H), 3.55-3.33 (m, 3H), 3.33-3.31 (m, 2H), 3.10-3.06 (m, 4H), 2.99-2.89 (m, 2H), 2.85 (s, 3H), 2.71-2.61 (m, 1H), 2.55-2.36 (m, 1H), 2.22-1.82 (m, 5H), 1.80-1.62 (m, 6H) |
| 232 | 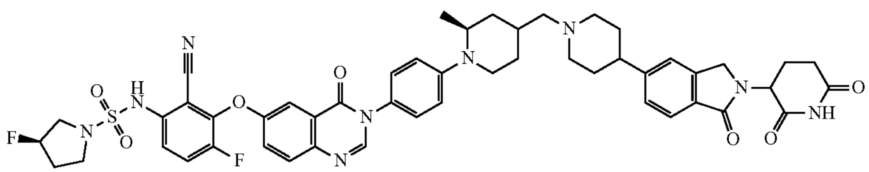 [SMILES: C[C@H]1CC(CN2CCC(c3ccc4c(c3)CN(C3CCC(=O)NC3=O)C4=O)CC2)CCN1c1ccc(-n2cnc3ccc(Oc4c(F)ccc(NS(=O)(=O)N5CC[C@@H](F)C5)c4C#N)cc3c2=O)cc1] | (3R)-N-{2-cyano-3-[(3-{4-[(2S)-4-({4-[2-(2,6-dioxopiperidin-3-yl)-1-oxo-2,3-dihydro-1H-isoindol-5-yl]piperidin-1-yl}methyl)-2-methylpiperidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.98 (s, 1H), 8.23 (s, 1H), 7.80 (d, J = 8.8 Hz, 1H), 7.74-7.62 (m, 2H), 7.56-7.24 (m, 7H), 7.01 (d, J = 8.8 Hz, 2H), 5.39-5.17 (m, 1H), 5.11 (dd, J = 5.2, 13.6 Hz, 1H), 4.50-4.40 (m, 1H), 4.39-4.27 (m, 2H), 3.67-3.54 (m, 1H), 3.46-3.38 (m, 1H), 3.37-3.33 (m, 2H), 3.29-3.25 (m, 2H), 3.25-3.12 (m, 2H), 3.05 - 2.78 (m, 5H), 2.61 (d, J = 16.4 Hz, 1H), 2.40 (dd, J = 4.4, 12.8 Hz, 1H), 2.07 (s, 3H), 2.03-1.91 (m, 6H), 1.80-1.69 (m, 1H), 1.56-1.42 (m, 1H), 1.36-1.14 (m, 2H), 1.08 (d, J = 6.4 Hz, 3H) |

| Cmp. No. | Structure | IUPAC Name | ¹H NMR |
|---|---|---|---|
| 233 | 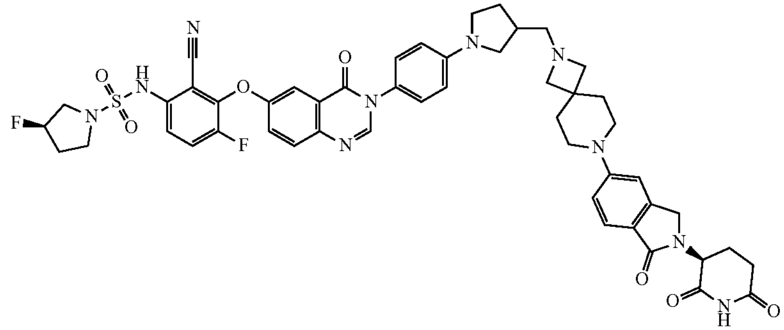 [SMILES: N#Cc1c(NS(=O)(=O)N2CC[C@@H](F)C2)ccc(F)c1Oc1ccc2ncn(-c3ccc(N4CCC(CN5CC6(CCN(c7ccc8c(c7)CN([C@H]7CCC(=O)NC7=O)C8=O)CC6)C5)C4)cc3)c(=O)c2c1] | (3R)-N-(2-cyano-3-{[3-(4-{3-[(7-{2-[(3S)-2,6-dioxopiperidin-3-yl]-1-oxo-2,3-dihydro-1H-isoindol-5-yl}-2,7-diazaspiro[3.5]nonan-2-yl)methyl]pyrrolidin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.94 (s, 1H), 8.20 (s, 1H), 8.13 (s, 1H), 7.80 (d, J = 8.8 Hz, 1H), 7.67 (dd, J = 3.0, 8.8 Hz, 1H), 7.55-7.44 (m, 2H), 7.33 (s, 2H), 7.29 (d, J = 8.8 Hz, 2H), 7.12-7.06 (m, 2H), 6.63 (d, J = 8.8 Hz, 2H), 5.36-5.19 (m, 1H), 5.04 (dd, J = 5.2, 13.2 Hz, 1H), 4.35-4.28 (m, 1H), 4.24-4.15 (m, 1H), 3.95 (s, 4H), 3.51-3.42 (m, 2H), 3.39 (d, J = 3.2 Hz, 4H), 3.30-3.25 (m, 4H), 3.25-3.15 (m, 2H), 3.10-3.03 (m, 1H), 2.96-2.85 (m, 1H), 2.60 (d, J = 2.4 Hz, 1H), 2.58-2.55 (m, 2H), 2.43-2.34 (m, 1H), 2.24-2.08 (m, 2H), 2.07-1.93 (m, 3H), 1.89 (s, 4H), 1.82-1.74 (m, 1H) |
| 234 | 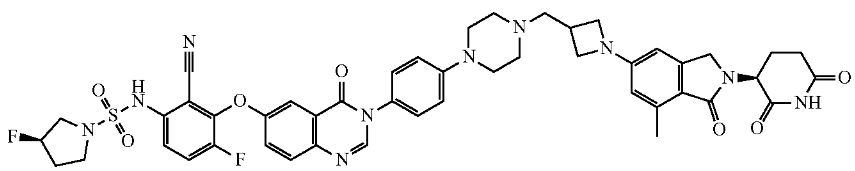 [SMILES: Cc1cc(N2CC(CN3CCN(c4ccc(-n5cnc6ccc(Oc7c(F)ccc(NS(=O)(=O)N8CC[C@@H](F)C8)c7C#N)cc6c5=O)cc4)CC3)C2)cc2c1C(=O)N([C@H]1CCC(=O)NC1=O)C2] | (3R)-N-(2-cyano-3-{[3-(4-{4-[(1-{2-[(3S)-2,6-dioxopiperidin-3-yl]-7-methyl-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.94 (s, 1H), 10.16 (s, 1H), 8.26 (s, 1H), 7.83 (d, J = 8.9 Hz, 1H), 7.73-7.68 (m, 2H), 7.47-7.41 (m, 2H), 7.36 (d, J = 8.8 Hz, 2H), 7.09 (d, J = 9.0 Hz, 2H), 6.38-6.22 (m, 2H), 5.39-5.22 (m, 1H), 5.04-5.47 (m, 1H), 4.24 (d, J = 16.9 Hz, 1H), 4.18-4.01 (m, 3H), 3.67-3.57 (m, 2H), 3.49-3.43 (m, 1H), 3.41-3.38 (m, 2H), 3.26 (d, J = 9.0 Hz, 2H), 3.08 (d, J = 6.9 Hz, 1H), 2.96-2.73 (m, 6H), 2.59 (d, J=16.6 Hz, 1H), 2.55-2.52 (m, 6H), 2.40-2.29 (m, 1H), 2.17-2.09 (m, 1H), 2.07 (d, J = 12.6 Hz, 1H), 1.98-1.89 (m, 1H), 1.24 (s, 1H) |

TABLE 1-continued

| Cmp. No. | Structure | IUPAC Name | ¹H NMR |
|---|---|---|---|
| 235 | 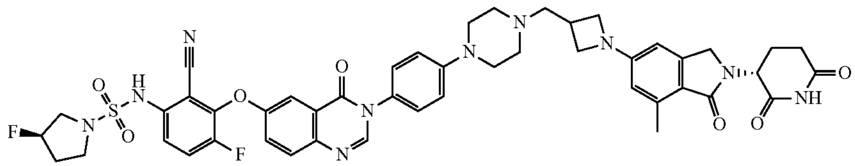 [SMILES: Cc1cc(N2CC(CN3CCN(c4ccc(-n5cnc6ccc(Oc7c(F)ccc(NS(=O)(=O)N8CC[C@@H](F)C8)c7C#N)cc6c5=O)cc4)CC3)C2)cc2c1C(=O)N([C@@H]1CCC(=O)NC1=O)C2] | (3R)-N-(2-cyano-3-{[3-(4-{4-[(1-{[2-[(3R)-2,6-dioxopiperidin-3-yl]-7-methyl-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.94 (s, 1H), 10.16 (s, 1H), 8.26 (s, 1H), 7.83 (d, J = 8.9 Hz, 1H), 7.73-7.68 (m, 2H), 7.47-7.41 (m, 2H), 7.36 (d, J = 8.8 Hz, 2H), 7.09 (d, J = 9.0 Hz, 2H), 6.38-6.22 (m, 2H), 5.39-5.22 (m, 1H), 5.04-5.47 (m, 1H), 4.24 (d, J = 16.9 Hz, 1H), 4.18-4.01 (m, 3H), 3.67-3.57 (m, 2H), 3.49-3.43 (m, 1H), 3.41-3.38 (m, 2H), 3.26 (d, J = 9.0 Hz, 2H), 3.08 (d, J = 6.9 Hz, 1H), 2.96-2.73 (m, 6H), 2.59 (d, J = 16.6 Hz, 1H), 2.55-2.52 (m, 6H), 2.40-2.29 (m, 1H), 2.17-2.09 (m, 1H), 2.07 (d, J = 12.6 Hz, 1H), 1.98-1.89 (m, 1H), 1.24 (s, 1H) |
| 236 | 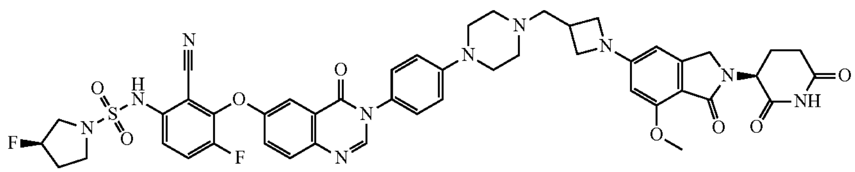 [SMILES: COc1cc(N2CC(CN3CCN(c4ccc(-n5cnc6ccc(Oc7c(F)ccc(NS(=O)(=O)N8CC[C@@H](F)C8)c7C#N)cc6c5=O)cc4)CC3)C2)cc2c1C(=O)N([C@H]1CCC(=O)NC1=O)C2] | (3R)-N-(2-cyano-3-{[3-(4-{4-[(1-{[2-[(3S)-2,6-dioxopiperidin-3-yl]-7-methoxy-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (300 MHz, DMSO) δ 10.89 (d, J = 3.9 Hz, 1H), 8.25 (d, J = 4.3 Hz, 1H), 7.83 (dd, J = 8.9, 4.1 Hz, 1H), 7.74-7.64 (m, 2H), 7.38 (dt, J = 22.2, 3.9 Hz, 4H), 7.08 (d, J = 8.2 Hz, 2H), 6.08 (s, 1H), 5.94 (s, 1H), 5.39 (s, 1H), 5.01-4.90 (m, 1H), 4.21 (d, J = 16.7 Hz, 1H), 4.09 (d, J = 7.0 Hz, 3H), 3.82 (d, J = 4.2 Hz, 3H), 3.64 (s, 3H), 3.47 (s, 1H), 3.24 (s, 3H), 3.07 (s, 2H), 2.87 (d, J = 13.8 Hz, 4H), 2.49 (s, 4H), 2.13 (s, 2H), 2.04 (s, 1H), 1.91 (s, 1H), 1.24 (s, 1H), 0.83 (s, 1H) |
| 237 | 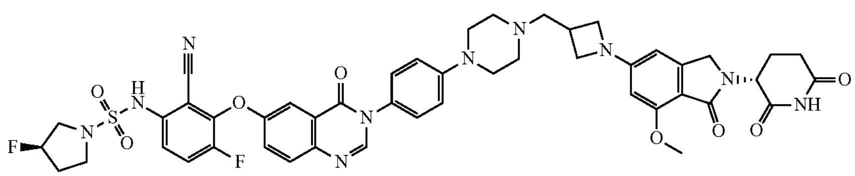 [SMILES: COc1cc(N2CC(CN3CCN(c4ccc(-n5cnc6ccc(Oc7c(F)ccc(NS(=O)(=O)N8CC[C@@H](F)C8)c7C#N)cc6c5=O)cc4)CC3)C2)cc2c1C(=O)N([C@@H]1CCC(=O)NC1=O)C2] | (3R)-N-(2-cyano-3-{[3-(4-{4-[(1-{[2-[(3R)-2,6-dioxopiperidin-3-yl]-7-methoxy-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (300 MHz, DMSO) δ 10.90 (d, J = 4.2 Hz, 1H), 9.98 (s, 1H), 8.25 (d, J = 4.4 Hz, 1H), 7.83 (dd, J = 8.9, 4.3 Hz, 1H), 7.71 (td, J = 8.5, 3.5 Hz, 2H), 7.44-7.36 (dd, J = 8.8, 4.0 Hz, 4H), 7.09 (t, J = 6.6 Hz, 2H), 6.09 (d, J = 3.8 Hz, 1H), 5.95 (d, J = 4.2 Hz, 1H), 5.39 (s, 1H), 5.21 (s, 1H), 4.95 (dd, J = 13.2, 5.0 Hz, 1H), 4.07 (dd, J = 11.7, 5.2 Hz, 3H), 3.82 (d, J = 4.3 Hz, 3H), 3.64 (s, 2H), 3.48 (s, 1H), 3.37 (s, 3H), 3.08 (s, |

| Cmp. No. | Structure | IUPAC Name | 1H NMR |
|---|---|---|---|
| | | | 2H), 2.88 (s, 3H), 2.75 (s, 4H), 2.49 (s, 1H), 2.14 (s, 3H), 2.04 (s, 1H), 1.91 (s, 1H), 1.64 (s, 1H) |
| 238 | 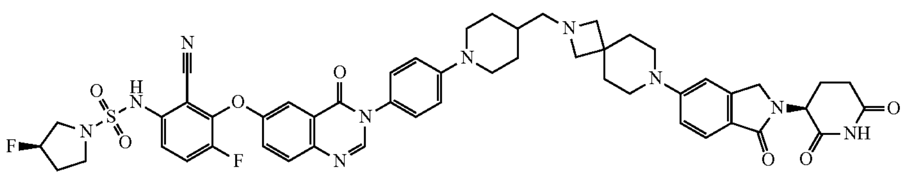 [SMILES: N#Cc1c(NS(=O)(=O)N2CC[C@@H](F)C2)ccc(F)c1Oc1ccc2ncn(-c3ccc(N4CCC(CN5CC6(CCN(c7ccc8c(c7)CN([C@H]7CCC(=O)NC7=O)C8=O)CC6)C5)CC4)cc3)c(=O)c2c1] | (3R)-N-(2-cyano-3-{[3-(4-{4-[(7-{2-[(3S)-2,6-dioxopiperidin-3-yl]-1-oxo-2,3-dihydro-1H-isoindol-5-yl}-2,7-diazaspiro[3.5]nonan-2-yl)methyl]piperidin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.93 (s, 1H), 8.21 (s, 1 H), 8.13 (s, 1 H), 7.79 (d, J = 9.2 Hz, 1 H), 7.64 (dd, J = 8.8, 2.8 Hz, 1 H), 7.51 (d, J = 8.4 Hz, 1 H), 7.34-7.43 (m, 2 H), 7.25-7.34 (m, 3 H), 6.97-7.14 (m, 4 H), 5.14-5.38 (m, 1 H), 5.04 (dd, J = 13.2, 5.2 Hz, 1 H), 4.13-4.38 (m, 2 H), 3.72-3.98 (m, 6 H), 3.39-3.47 (m, 2 H), 3.17-3.26 (m, 4 H), 3.14 (d, J = 7.6 Hz, 1 H), 3.05-3.12 (m, 2 H), 2.83-2.95 (m, 1 H), 2.75 (t, J = 11.2 Hz, 2 H), 2.52-2.63 (m, 2 H), 2.33-2.44 (m, 1 H), 2.02-2.18 (m, 1 H), 1.92-2.01 (m, 2 H), 1.88 (s, 4 H), 1.70-1.82 (m, 3 H), 1.21-1.40 (m, 2 H) |
| 239 | 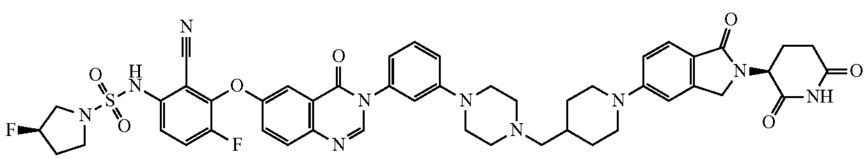 | (3R)-N-(2-cyano-3-{[3-(3-{4-[(1-{2-[(3S)-2,6-dioxopiperidin-3-yl]-1-oxo-2,3-dihydro-1H-isoindol-5-yl}piperidin-4-yl)methyl]piperazin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO) δ 10.94 (s, 1H), 10.38-9.50 (m, 1H), 8.27 (s, 1H), 8.13 (s, 1H), 7.83 (d, J = 8.8 Hz, 1H), 7.74-7.63 (m, 2H), 7.50 (d, J = 8.8 Hz, 1H), 7.47-7.32 (m, 3H), 7.14-7.03 (m, 4H), 6.91 (d, J = 8.0 Hz, 1H), 5.39-5.20 (m, 1H), 5.04 (dd, J = 5.1, 13.2 Hz, 1H), 4.36-4.27 (m, 1H), 4.23-4.15 (m, 1H), 3.89 (d, J = 12.4 Hz, 2H), 3.50-3.40 (m, 2H), 3.37 (s, 4H), 3.26 (s, 2H), 2.91 (s, 7H), 2.60 (d, J = 2.0 Hz, 1H), 2.57-2.54 (m, 2H), 2.41-2.37 (m, 1H), 2.15-2.08 (m, 1H), 2.07-2.00 (m, 1H), 1.88 (s, 2H), 1.82 (d, J = 12.8 Hz, 2H), 1.30-1.17 (m, 2H) |

TABLE 1-continued

| Cmp. No. | Structure | IUPAC Name | ¹H NMR |
|---|---|---|---|
| 240 | 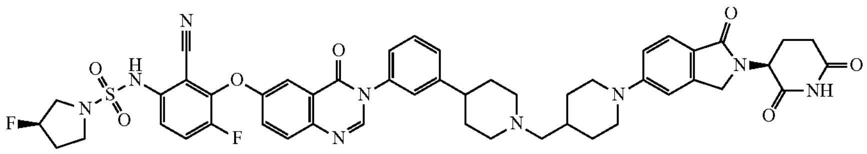 [SMILES: N#Cc1c(NS(=O)(=O)N2CC[C@@H](F)C2)ccc(F)c1Oc1ccc2ncn(-c3cccc(C4CCN(CC5CCN(c6ccc7c(c6)CN([C@H]6CCC(=O)NC6=O)C7=O)CC5)CC4)c3)c(=O)c2c1] | (3R)-N-(2-cyano-3-{[3-(3-{1-[(1-{2-[(3S)-2,6-dioxopiperidin-3-yl]-1-oxo-2,3-dihydro-1H-isoindol-5-yl}piperidin-4-yl)methyl]piperidin-4-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO) δ 10.0 (s, 1H), 8.2 (s, 1H), 8.2 (s, 1H), 7.6 (d, J = 9.0 Hz, 1H), 7.6 (dd, J = 3.0, 8.9 Hz, 1H), 7.60-7.20 (m, 8H), 7.20-6.80 (m, 2H), 5.2-5.2 (m, 1H), 4.80 (dd, J = 5.0, 13.3 Hz, 1H), 4.4-4.0 (m, 1H), 4.2-4.0 (m, 1H), 3.6 (d, J = 13.1 Hz, 2H), 3.60-3.20 (m, 4H), 3.20-3.20 (m, 4H), 2.80-2.80 (m, 7H), 2.4-2.4 (m, 1H), 2.4-2.0 (m, 1H), 2.4-1.6 (m, 8H), 2.0 (d, J = 11.9 Hz, 2H), 1.20-1.20 (m, 2H) |
| 241 | 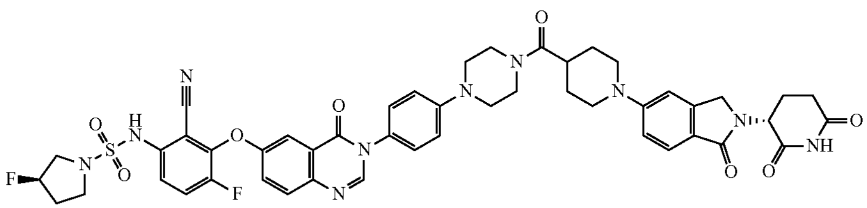 [SMILES: N#Cc1c(NS(=O)(=O)N2CC[C@@H](F)C2)ccc(F)c1Oc1ccc2ncn(-c3ccc(N4CCN(C(=O)C5CCN(c6ccc7c(c6)CN([C@@H]6CCC(=O)NC6=O)C7=O)CC5)CC4)cc3)c(=O)c2c1] | (3R)-N-{2-cyano-3-[(3-{4-[4-(1-{2-[(3R*)-2,6-dioxopiperidin-3-yl]-1-oxo-2,3-dihydro-1H-isoindol-5-yl}piperidine-4-carbonyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.96 (s, 1H), 10.36 (s, 1H), 8.27 (s, 1H), 7.96-7.80 (m, 2H), 7.72 (dd, J = 3.2, 8.9 Hz, 1H), 7.57-7.47 (m, 2H), 7.42 (d, J = 2.8 Hz, 1H), 7.36 (d, J = 8.8 Hz, 2H), 7.13-7.03 (m, 4H), 5.43-5.21 (m, 1H), 5.09-5.00 (m, 1H), 4.37-4.29 (m, 1H), 4.25-4.16 (m, 1H), 3.92 (d, J = 13 Hz, 2H), 3.73 (d, J = 4.4 Hz, 2H), 3.55-3.49 (m, 1H), 3.48-3.38 (m, 3H), 3.27 (s, 2H), 3.23-3.17 (m, 2H), 3.01-2.94 (m, 2H), 2.92-2.85 (m, 1H), 2.69-2.55 (m, 2H), 2.39-2.31 (m, 1H), 2.17-1.93 (m, 3H), 1.77-1.61 (m, 4H) |

TABLE 1-continued

| Cmp. No. | Structure | IUPAC Name | ¹H NMR |
|---|---|---|---|
| 242 | 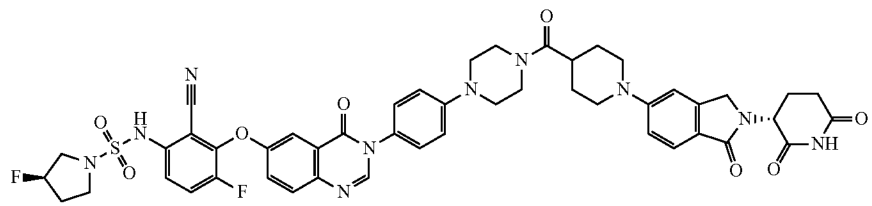 [SMILES: N#Cc1c(NS(=O)(=O)N2CC[C@@H](F)C2)ccc(F)c1Oc1ccc2ncn(-c3ccc(N4CCN(C(=O)C5CCN(c6ccc7c(c6)CN([C@@H]6CCC(=O)NC6=O)C7=O)CC5)CC4)cc3)c(=O)c2c1] | (3R)-N-{2-cyano-3-[(3-(4-[4-(1-{2-[(3R*)-2,6-dioxopiperidin-3-yl]-1-oxo-2,3-dihydro-1H-isoindol-5-yl}piperidine-4-carbonyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.96 (s, 1H), 10.36 (s, 1H), 8.27 (s, 1H), 7.92-7.81 (m, 2H), 7.72 (dd, J = 3.0, 9.0 Hz, 1H), 7.54-7.49 (m, 2H), 7.42 (d, J = 2.8 Hz, 1H), 7.36 (d, J = 9 Hz, 2H), 7.14-7.01 (m, 4H), 5.43-5.21 (m, 1H), 5.05 (dd, J = 4.8, 13.3 Hz, 1H), 4.38-4.29 (m, 1H), 4.25-4.15 (m, 1H), 3.92 (d, J = 12.4 Hz, 2H), 3.73 (s, 2H), 3.63 (s, 2H), 3.52 (s, 1H), 3.49-3.37 (m, 3H), 3.27 (s, 2H), 3.20 (s, 2H), 3.03 - 2.95 (m, 2H), 2.92-2.85 (m, 1H), 2.73-2.54 (m, 2H), 2.43-2.29 (m, 1H), 2.19-1.92 (m, 3H), 1.80-1.60 (m, 4H) |
| 243 | 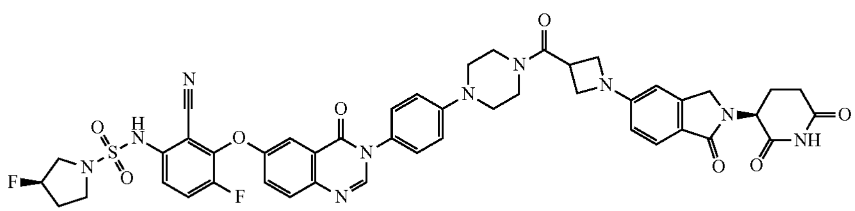 [SMILES: N#Cc1c(NS(=O)(=O)N2CC[C@@H](F)C2)ccc(F)c1Oc1ccc2ncn(-c3ccc(N4CCN(C(=O)C5CN(c6ccc7c(c6)CN([C@H]6CCC(=O)NC6=O)C7=O)C5)CC4)cc3)c(=O)c2c1] | (3R)-N-{2-cyano-3-[(3-{4-[4-(1-{2-[(3S)-2,6-dioxopiperidin-3-yl]-1-oxo-2,3-dihydro-1H-isoindol-5-yl}azetidine-3-carbonyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO) δ 10.93 (s, 1H), 10.33 (s, 1H), 8.26 (s, 1H), 7.90-7.80 (m, 2H), 7.71 (dd, J = 3.2, 9.2 Hz, 1H), 7.56-7.47 (m, 2H), 7.42 (d, J = 2.8 Hz, 1H), 7.36 (d, J = 8.8 Hz, 2H), 7.09 (d, J = 9.2 Hz, 2H), 6.60-6.47 (m, 2H), 5.46-5.19 (m, 1H), 5.03 (dd, J = 5.2, 13.2 Hz, 1H), 4.36-4.26 (m, 1H), 4.23-4.10 (m, 3H), 4.07-4.00 (m, 2H), 4.00-3.92 (m, 1H), 3.65 (d, J = 5.2 Hz, 2H), 3.55-3.48 (m, 3H), 3.48-3.40 (m, 2H), 3.39-3.33 (m, 1H), 3.29-3.21 (m, 4H), 2.95-2.83 (m, 1H), 2.59 (d, J = 2.8 Hz, 1H), 2.45-2.34 (m, 1H), 2.19-2.01 (m, 2H), 2.00-1.89 (m, 1H) |

TABLE 1-continued

| Cmp. No. | Structure | IUPAC Name | 1H NMR |
|---|---|---|---|
| 244 | 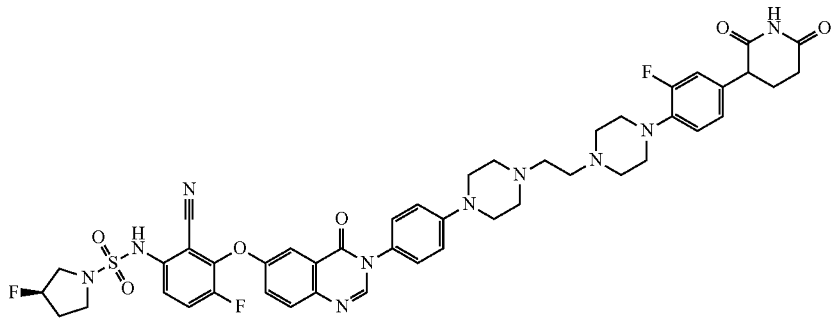 [SMILES: N#Cc1c(NS(=O)(=O)N2CC[C@@H](F)C2)ccc(F)c1Oc1ccc2ncn(-c3ccc(N4CCN(CCN5CCN(c6ccc(C7CCC(=O)NC7=O)cc6F)CC5)CC4)cc3)c(=O)c2c1] | (3R)-N-{2-cyano-3-[(3-(4-[4-(2-{4-(2,6-dioxopiperidin-3-yl)-2-fluorophenyl]piperazin-1-yl}ethyl)piperazin-1-yl]phenyl}-4-oxo-3,4-dihydroquinazolin-6-yl)oxy]-4-fluorophenyl}-3-fluoropyrrolidine-1-sulfonamide | 1H NMR (400 MHz, DMSO) δ 10.82 (s, 1H), 8.23 (s, 1H), 7.80 (d, J = 9.0 Hz, 1H), 7.67-7.65 (m, 1H), 7.51 (s, 1H), 7.42-7.31 (m, 4H), 7.10 (d, J = 2.2 Hz, 1H), 7.08-7.02 (m, 2H), 7.01-6.94 (m, 2H), 5.34-5.12 (m, 1H), 4.88 Hz,1H), 3.81-3.62(m,1H), 3.42-3.41 (m, 11H), 3.32-3.12 (m, 5H), 3.29-3.19 (m, 4H), 3.19 - 3.08 (m, 4H), 2.72-2.59 (m, 2H), 2.28-2.15 (m, 2H), 2.06 (m, 5H) |
| 245 | 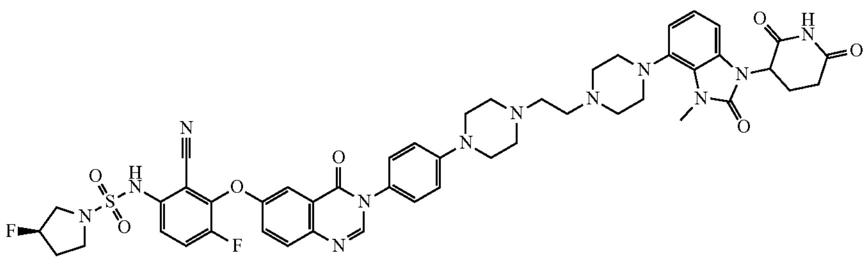 [SMILES: Cn1c(=O)n(C2CCC(=O)NC2=O)c2cccc(N3CCN(CCN4CCN(c5ccc(-n6cnc7ccc(Oc8c(F)ccc(NS(=O)(=O)N9CC[C@@H](F)C9)c8C#N)cc7c6=O)cc5)CC4)CC3)c21] | (3R)-N-{2-cyano-3-[(3-{4-[4-(2-{4-[1-(2,6-dioxopiperidin-3-yl)-3-methyl-2-oxo-2,3-dihydro-1H-1,3-benzodiazol-4-yl]piperazin-1-yl}ethyl)piperazin-1-yl]phenyl}-4-oxo-3,4-dihydroquinazolin-6-yl)oxy]-4-fluorophenyl}-3-fluoropyrrolidine-1-sulfonamide | 1H NMR (300 MHz, DMSO) δ 11.10 (s, 1H), 8.23 (s, 1H), 7.81 (d, J = 8.9 Hz, 1H), 7.67-7.57 (m, 1H), 7.49 (t, J = 9.9 Hz, 1H), 7.43-7.28 (m, 4H), 7.09 (d, J = 8.9 Hz, 2H), 7.06-6.87 (m, 3H), 5.36 (q, J = 5.7, 5.2 Hz, 1H), 5.28-5.18 (d, J = 30 Hz, 1H), 3.43-3.33 (m, 4H), 3.34-3.11 (m, 5H), 2.84 (s, 11H), 2.74-2.51 (m, 4H), 2.31 (s, 9H), 2.20-1.96 (m, 4H) |
| 246 | 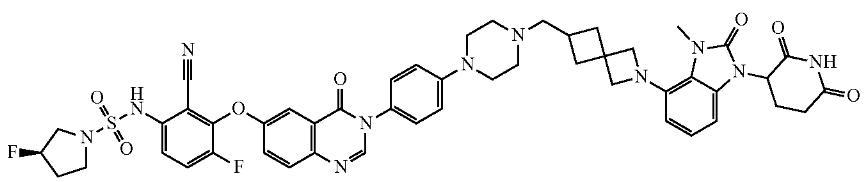 [SMILES: Cn1c(=O)n(C2CCC(=O)NC2=O)c2cccc(N3CC4(CC(CN5CCN(c6ccc(-n7cnc8ccc(Oc9c(F)ccc(NS(=O)(=O)N%10CC[C@@H](F)C%10)c9C#N)cc8c7=O)cc6)CC5)C4)C3)c21] | (3R)-N-{2-cyano-3-[(3-{4-[4-({2-[1-(2,6-dioxopiperidin-3-yl)-3-methyl-2-oxo-2,3-dihydro-1H-1,3-benzodiazol-4-yl]-2-azaspiro[3.3]heptan-6-yl}methyl)piperazin-1-yl]phenyl}-4-oxo-3,4-dihydroquinazolin-6-yl)oxy]-4-fluorophenyl}-3-fluoropyrrolidine-1-sulfonamide | 1H NMR (400 MHz, DMSO) δ 11.09 (s, 1H), 8.24 (s, 1H), 7.81 (d, J = 8.8 Hz, 1H), 7.67 (m, 1H), 7.51 (t, J = 9.9 Hz, 1H), 7.47-7.32 (m, 4H), 7.09 (d, J = 8.8 Hz, 2H), 6.95 (t, J = 8.0 Hz, 1H), 6.73 (d, J = 7.9 Hz, 1H), 6.61 (d, J = 8.2 Hz, 1H), 5.38-5.22 (m, 2H), 3.87 (s, 2H), 3.74 (s, 2H), 3.58 (s, 3H), 3.43 (m, 1H), 3.29 (m, 3H), 3.20 (m, 1H), 3.00-2.80 (m, 6H), 2.80-2.63 (m, 3H), 2.38-2.30 (m, 2H), 2.16-2.03 (m, 1H), 2.06-1.95 (m, 4H), 1.24 (s, 1H) |

TABLE 1-continued

| Cmp. No. | Structure | IUPAC Name | ¹H NMR |
|---|---|---|---|
| 251 | 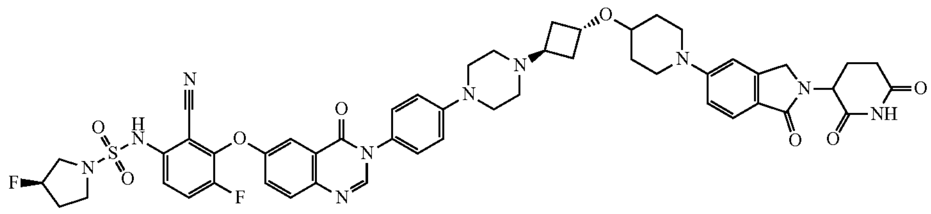 [SMILES: N#Cc1c(NS(=O)(=O)N2CC[C@@H](F)C2)ccc(F)c1Oc1ccc2ncn(-c3ccc(N4CCN([C@H]5C[C@H](OC6CCN(c7ccc8c(c7)CN(C7CCC(=O)NC7=O)C8=O)CC6)C5)CC4)cc3)c(=O)c2c1] | (3R)-N-(2-cyano-4-fluoro-3-{[4-oxo-3-(4-{4-[(1r,3r)-3-({1-[2-(2,6-dioxopiperidin-3-yl)-1-oxo-2,3-dihydro-1H-isoindol-5-yl]piperidin-4-yl}oxy)cyclobutyl]piperazin-1-yl}phenyl)-3,4-dihydroquinazolin-6-yl]oxy}phenyl)-3-fluoropyrrolidine-1-sulfonamide | ¹H NMR (400 MHz, DMSO-d6) δ 10.95 (s, 1H), 10.14 (s, 1H), 8.25 (s, 1H), 7.82 (d, 1H), 7.69 (dd, 2H), 7.50 (d, 1H), 7.41 (t, 2H), 7.35 (d, 2H), 7.12–7.02 (m, 4H), 5.36 (s, 1H), 5.23 (s, 1H), 5.05 (dd, 1H), 4.32-4.15 (m, 3H), 3.70 (d, 2H), 3.51 (m, 1H), |
| 252 | 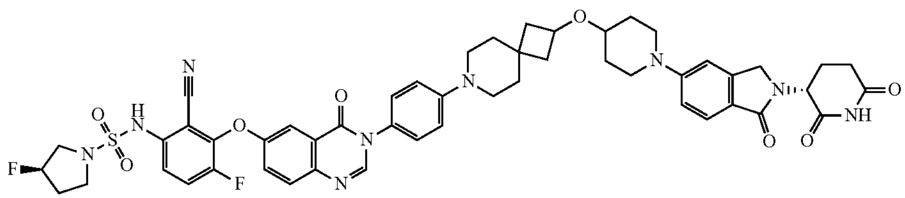 [SMILES: N#Cc1c(NS(=O)(=O)N2CC[C@@H](F)C2)ccc(F)c1Oc1ccc2ncn(-c3ccc(N4CCC5(CC4)CC(OC4CCN(c6ccc7c(c6)CN([C@@H]6CCC(=O)NC6=O)C7=O)CC4)C5)cc3)c(=O)c2c1] | (3R)-N-(2-cyano-3-{[3-(4-{2-[(1-{[(3R)-2,6-dioxopiperidin-3-yl]-1-oxo-2,3-dihydro-1H-isoindol-5-yl]piperidin-4-yl}oxy)-7-azaspiro[3.5]nonan-7-yl]phenyl)-4-oxo-3,4-dihydroquinazolin-6-yl]oxy}-4-fluorophenyl)-3-fluoropyrrolidine-1-sulfonamide | ¹H NMR (400 MHz, DMSO-d6) δ 10.95 (s, 1H), 10.35 (s, 1H), 8.25 (s, 1H), 7.87-7.78 (m, 2H), 7.71 (s, 1H), 7.51-7.49 (m, J = 8.9, 3.9 Hz, 2H), 7.42 (d, J = 3.0 Hz, 1H), 7.29 (d, J = 8.7 Hz, 2H), 7.09-7.00 (m, 4H), 5.41-5.35 (d, J =24 Hz, 1H), 5.25 (s, 1H), 5.05 ( |
| 253 | 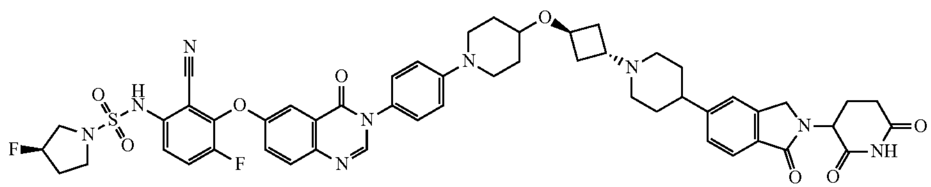 [SMILES: N#Cc1c(NS(=O)(=O)N2CC[C@@H](F)C2)ccc(F)c1Oc1ccc2ncn(-c3ccc(N4CCC(O[C@H]5C[C@H](N6CCC(c7ccc8c(c7)CN(C7CCC(=O)NC7=O)C8=O)CC6)C5)CC4)cc3)c(=O)c2c1] | (3R)-N-(2-cyano-4-fluoro-3-{[4-oxo-3-(4-{4-[(1r,3r)-3-{[4-[2-(2,6-dioxopiperidin-3-yl)-1-oxo-2,3-dihydro-1H-isoindol-5-yl]piperidin-1-yl]cyclobutoxy]piperidin-1-yl}phenyl)-3,4-dihydroquinazolin-6-yl]oxy}phenyl)-3-fluoropyrrolidine-1-sulfonamide | ¹H NMR (400 MHz, DMSO-d6) δ 11.00 (s, 1H), 9.97 (s, 1H), 8.24 (s, 1H), 7.81 (d, J = 8.9 Hz, 1H), 7.73-7.63 (m, 2H), 7.50 (m, 2H), 7.44-7.36 (m, 3H), 7.32 (d, J = 8.5 Hz, 2H), 7.07 (d, J = 8.6 Hz, 2H), 5.34 (m, 1H), 5.12 (dd, J = 13.3, 5.1 Hz, 1H), 4.4 |

| Cmp. No. | Structure | IUPAC Name | ¹H NMR |
|---|---|---|---|
| 254 | 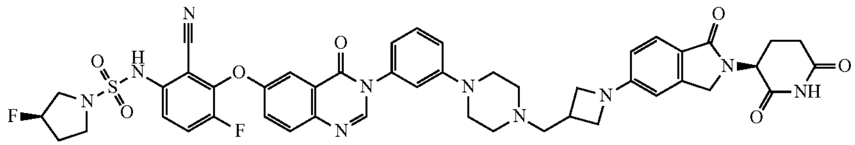 [SMILES: N#Cc1c(NS(=O)(=O)N2CC[C@@H](F)C2)ccc(F)c1Oc1ccc2ncn(-c3cccc(N4CCN(CC5CN(c6ccc7c(c6)CN([C@H]6CCC(=O)NC6=O)C7=O)C5)CC4)c3)c(=O)c2c1] | (3R)-N-(2-cyano-3-{[3-(3-{4-[(1-{2-[(3S)-2,6-dioxopiperidin-3-yl]-1-oxo-2,3-dihydro-1H-isoindol-5-yl}azetidin-3-yl)methyl]piperazin-1-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d6) δ 10.93 (s, 1H), 8.32-8.23 (m, 1H), 8.13 (s, 1H), 7.83 (d, J = 8.8 Hz, 1H), 7.77-7.62 (m, 2H), 7.49 (d, J = 8.4 Hz, 1H), 7.44 (dd, J = 4.0, 9.2 Hz, 1H), 7.42-7.34 (m, 2H), 7.16-7.03 (m, 2H), 6.97-6.84 (m, 1H), 6.52 (s, |
| 255 | 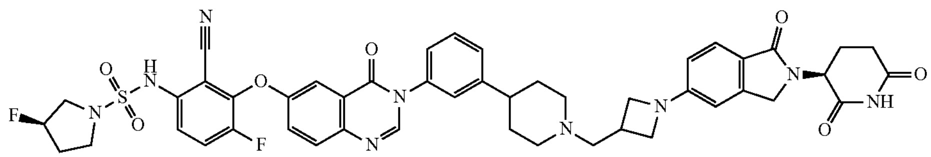 [SMILES: N#Cc1c(NS(=O)(=O)N2CC[C@@H](F)C2)ccc(F)c1Oc1ccc2ncn(-c3cccc(C4CCN(CC5CN(c6ccc7c(c6)CN([C@H]6CCC(=O)NC6=O)C7=O)C5)CC4)c3)c(=O)c2c1] | (3R)-N-(2-cyano-3-{[3-(3-{1-[(1-{2-[(3S)-2,6-dioxopiperidin-3-yl]-1-oxo-2,3-dihydro-1H-isoindol-5-yl}azetidin-3-yl)methyl]piperidin-4-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d6) δ 10.0 (s, 1H), 8.4 (s, 1H), 8.13 (s, 1H), 7.6-7.2 (m, 1H), 7.6-7.2 (m, 7H), 7.2 (dd, J = 3.6, 9.2 Hz, 1H), 6.4-6.4 (m, 2H), 5.2-4.8 (m, 1H), 5.2-4.8 (m, 1H), 4.4-4.0 (m, 1H), 4.2-4.0 (m, 1H), 4.4 |
| 256 | 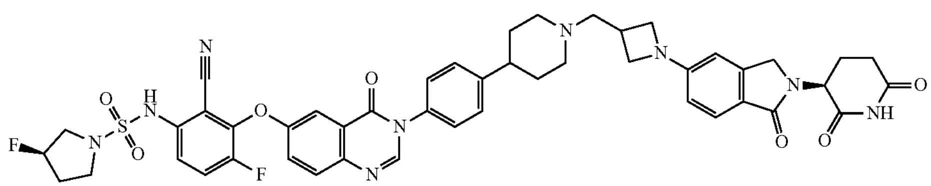 [SMILES: N#Cc1c(NS(=O)(=O)N2CC[C@@H](F)C2)ccc(F)c1Oc1ccc2ncn(-c3ccc(C4CCN(CC5CN(c6ccc7c(c6)CN([C@H]6CCC(=O)NC6=O)C7=O)C5)CC4)cc3)c(=O)c2c1] | (3R)-N-(2-cyano-3-{[3-(4-{1-[(1-{2-[(3S)-2,6-dioxopiperidin-3-yl]-1-oxo-2,3-dihydro-1H-isoindol-5-yl}azetidin-3-yl)methyl]piperidin-4-yl}phenyl)-4-oxo-3,4-dihydroquinazolin-6-yl]oxy}-4-fluorophenyl)-3-fluoropyrrolidine-1-sulfonamide | ¹H NMR (400 MHz, DMSO-d6) δ 10.94 (s, 1H), 10.35-9.58 (m, 1H), 8.29 (s, 1H), 8.14 (s, 1H), 7.83 (d, J = 8.8 Hz, 1H), 7.68 (dd, J = 3.2, 8.8 Hz, 1H), 7.56-7.47 (m, 4H), 7.47-7.41 (m, 3H), 7.40-7.32 (m, 1H), 6.58-6.49 (m, 2H), 5.39-5.15 (m, 1H), |

TABLE 1-continued

| Cmp. No. | Structure | IUPAC Name | ¹H NMR |
|---|---|---|---|
| 257 | 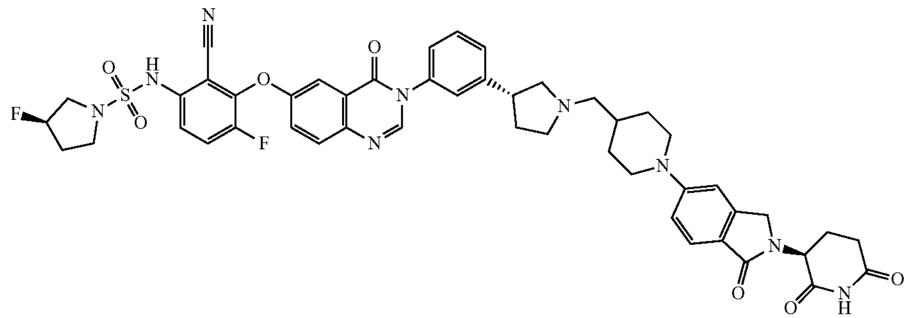 [SMILES: N#Cc1c(NS(=O)(=O)N2CC[C@@H](F)C2)ccc(F)c1Oc1ccc2ncn(-c3cccc([C@H]4CCN(CC5CCN(c6ccc7c(c6)CN([C@H]6CCC(=O)NC6=O)C7=O)CC5)C4)c3)c(=O)c2c1] | (3R)-N-{2-cyano-3-[(3-{3-[(3R*)-1-{(1-{2-[(3S)-2,6-dioxopiperidin-3-yl]-1-oxo-2,3-dihydro-1H-isoindol-5-yl}piperidin-4-yl)methyl]pyrrolidin-3-yl}phenyl)-4-oxo-3,4-dihydroquinazolin-6-yl]oxy]-4-fluorophenyl}-3-fluoropyrrolidine-1-sulfonamide | ¹H NMR (400 MHz, DMSO-d6) δ 10.98 (s, 1H), 8.30 (s, 1H), 8.13 (s, 1H), 7.84-7.82 (d, J = 8.8 Hz, 1H), 7.69 (dd, J = 3.2, 9.2 Hz, 1H), 7.59-7.37 (m, 8H), 7.31 (dd, J = 4.2, 9.2 Hz, 1H), 7.09-7.03 (m, 2H), 5.36-5.16 (m, 1H), 5.08-4.99 (m, 1H), 4.3 |
| 258 | 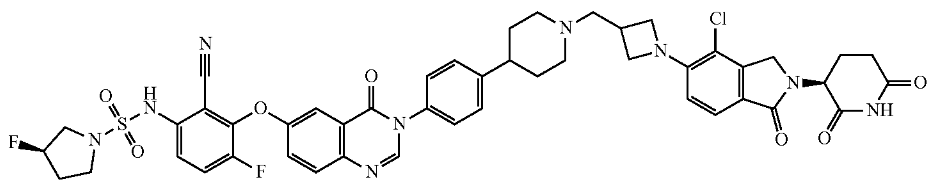 [SMILES: N#Cc1c(NS(=O)(=O)N2CC[C@@H](F)C2)ccc(F)c1Oc1ccc2ncn(-c3ccc(C4CCN(CC5CN(c6ccc7c(c6Cl)CN([C@H]6CCC(=O)NC6=O)C7=O)C5)CC4)cc3)c(=O)c2c1] | (3R)-N-(3-{[3-(4-{[1-{(1-{4-chloro-2-[(3S)-2,6-dioxopiperidin-3-yl]-1-oxo-2,3-dihydro-1H-isoindol-5-yl}azetidin-3-yl)methyl]piperidin-4-yl}phenyl)-4-oxo-3,4-dihydroquinazolin-6-yl]oxy}-2-cyano-4-fluorophenyl)-3-fluoropyrrolidine-1-sulfonamide | ¹H NMR (400 MHz, DMSO-d6) δ 10.96 (s, 1H), 8.28 (s, 1H), 8.13 (s, 1H), 7.81 (d, J = 8.8 Hz, 1H), 7.67 (dd, J = 3.2, 8.8 Hz, 1H), 7.52 (d, J = 8.4 Hz, 1H), 7.51-7.47 (m, 2H), 7.46 (s, 2H), 7.43-7.38 (m, 2H), 7.33 (dd, J = 4.4, 9.6 Hz, 1H), 6.74-6.59 |
| 259 | 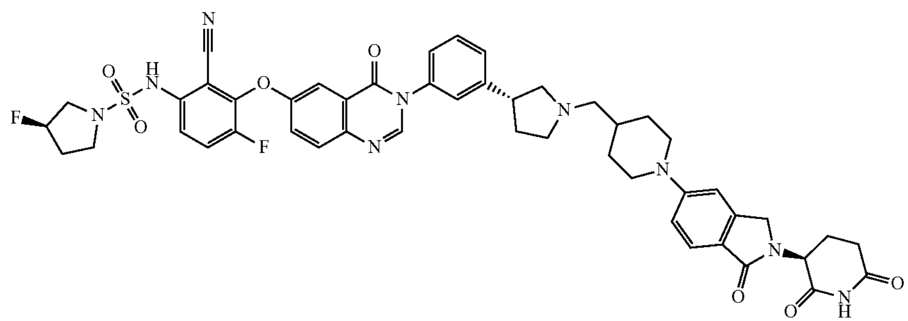 [SMILES: N#Cc1c(NS(=O)(=O)N2CC[C@@H](F)C2)ccc(F)c1Oc1ccc2ncn(-c3cccc([C@H]4CCN(CC5CCN(c6ccc7c(c6)CN([C@H]6CCC(=O)NC6=O)C7=O)CC5)C4)c3)c(=O)c2c1] | (3R)-N-{2-cyano-3-[(3-{3-[(3R*)-1-{(1-{2-[(3S)-2,6-dioxopiperidin-3-yl]-1-oxo-2,3-dihydro-1H-isoindol-5-yl}piperidin-4-yl)methyl]pyrrolidin-3-yl}phenyl)-4-oxo-3,4-dihydroquinazolin-6-yl]oxy]-4-fluorophenyl}-3-fluoropyrrolidine-1-sulfonamide | ¹H NMR (400 MHz, DMSO-d6) δ 10.95 (s, 1H), 8.0 (s, 1H), 8.2 (s, 1H), 7.83 (d, J = 2.9, 8.8 Hz, 1H), 7.69 (dd, J = 2.9, 8.8 Hz, 1H), 7.6-7.2 (m, 8H), 7.2 (dd, J = 2.8, 4.3 Hz, 1H), 7.2-6.8 (m, 2H), 5.6-5.2 (m, 1H), 5.00 (s, 1H), 4.4-4.0 (m, 1H), 4.4-4 |

TABLE 1-continued

| Cmp. No. | Structure | IUPAC Name | 1H NMR |
|---|---|---|---|
| 260 | 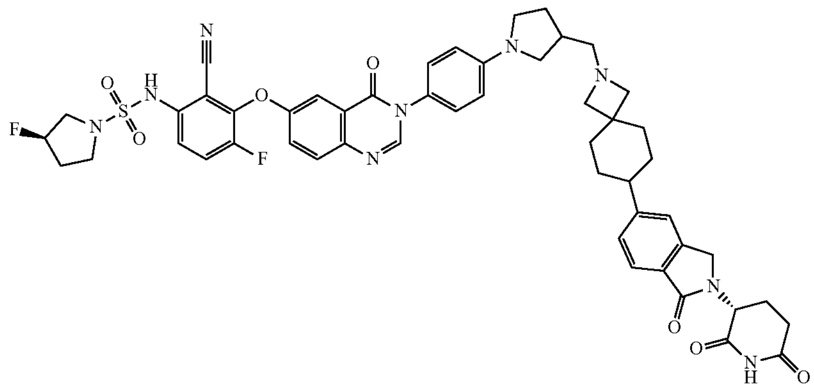 [SMILES: N#Cc1c(NS(=O)(=O)N2CC[C@@H](F)C2)ccc(F)c1Oc1ccc2ncn(-c3ccc(N4CCC(CN5CC6(CCC(c7ccc8c(c7)CN([C@@H]7CCC(=O)NC7=O)C8=O)CC6)C5)C4)cc3)c(=O)c2c1] | (3R)-N-(2-cyano-3-{[3-(4-{3-[(7-{2-[(3R*)-2,6-dioxopiperidin-3-yl]-1-oxo-2,3-dihydro-1H-isoindol-5-yl]-2-azaspiro[3.5]nonan-2-yl}methyl]pyrrolidin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO-d6) δ 10.98 (s, 1H), 8.19 (s, 1H), 8.14 (s, 1H), 7.79 (d, J = 8.8 Hz, 1H), 7.69-7.62 (m, 2H), 7.47 (s, 1H), 7.39 (d, J = 8.0 Hz, 1H), 7.37-7.31 (m, 2H), 7.31-7.24 (m, 3H), 6.63 (d, J = 8.8 Hz, 2H), 5.35-5.15 (m, 1H), 5.10 (dd |
| 261 | 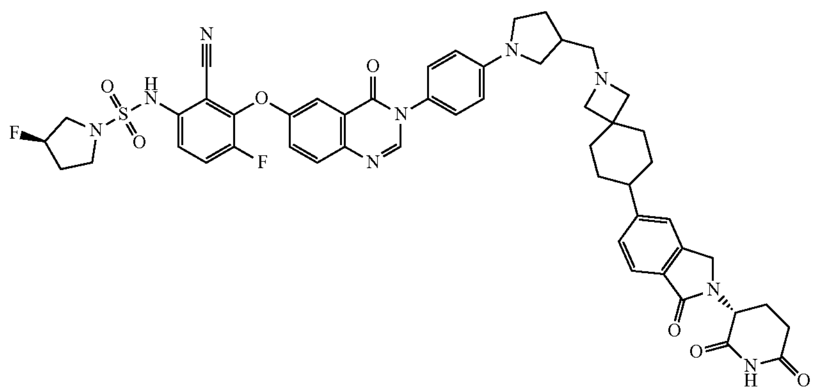 [SMILES: N#Cc1c(NS(=O)(=O)N2CC[C@@H](F)C2)ccc(F)c1Oc1ccc2ncn(-c3ccc(N4CCC(CN5CC6(CCC(c7ccc8c(c7)CN([C@@H]7CCC(=O)NC7=O)C8=O)CC6)C5)C4)cc3)c(=O)c2c1] | (3R)-N-(2-cyano-3-{[3-(4-{3-[(7-{2-[(3R*)-2,6-dioxopiperidin-3-yl]-1-oxo-2,3-dihydro-1H-isoindol-5-yl]-2-azaspiro[3.5]nonan-2-yl}methyl]pyrrolidin-1-yl}phenyl)-4-oxo-3,4-dihydroquinazolin-6-yl]oxy}-4-fluorophenyl)-3-fluoropyrrolidine-1-sulfonamide | 1H NMR (400 MHz, DMSO-d6) δ 10.98 (s, 1H), 8.19 (s, 1H), 8.14 (s, 1H), 7.79 (d, J = 8.8 Hz, 1H), 7.67-7.62 (m, 2H), 7.47 (s, 1H), 7.39 (d, J = 8.0 Hz, 1H), 7.32 (s, 2H), 7.31-7.24 (m, 3H), 6.63 (d, J = 8.8 Hz, 2H), 5.35-5.16 (m, 1H), 5.10 (dd, J = 4 |

TABLE 1-continued

| Cmp. No. | Structure | IUPAC Name | $^1$H NMR |
|---|---|---|---|
| 262 | 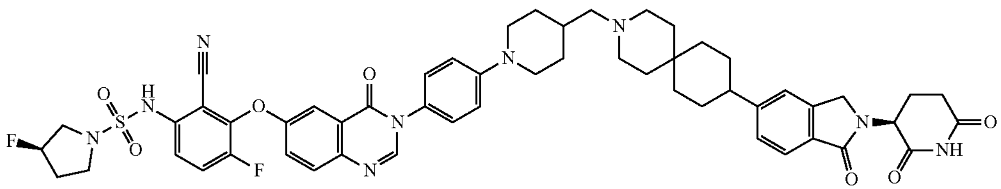 [SMILES: N#Cc1c(NS(=O)(=O)N2CC[C@@H](F)C2)ccc(F)c1Oc1ccc2ncn(-c3ccc(N4CCC(CN5CCC6(CCC(c7ccc8c(c7)CN([C@H]7CCC(=O)NC7=O)C8=O)CC6)CC5)CC4)cc3)c(=O)c2c1] | (3R)-N-(2-cyano-3-{[3-(4-{4-[(9-{2-[(3S)-2,6-dioxopiperidin-3-yl]-1-oxo-2,3-dihydro-1H-isoindol-5-yl}-3-azaspiro[5.5]undecan-3-yl)methyl]piperidin-1-yl}phenyl)-4-oxo-3,4-dihydroquinazolin-6-yl]oxy}-4-fluorophenyl)-3-fluoropyrrolidine-1-sulfonamide | $^1$H NMR (400 MHz, DMSO-d6) δ 10.97 (s, 1H), 8.2 (s, 1H), 8.2 (s, 1H), 8.0 (d, J = 8.8 Hz, 1H), 7.8-7.6 (m, 2H), 7.6 (s, 1H), 7.4 (d, J = 8.4 Hz, 1H), 7.4-7.2 (m, 5H), 7.2 (d, J = 9.2 Hz, 2H), 5.4-5.2 (m, 1H), 5.10 (dd, J = 5.2, 13.2 Hz, 1H), 4.4-4. |
| 263 | 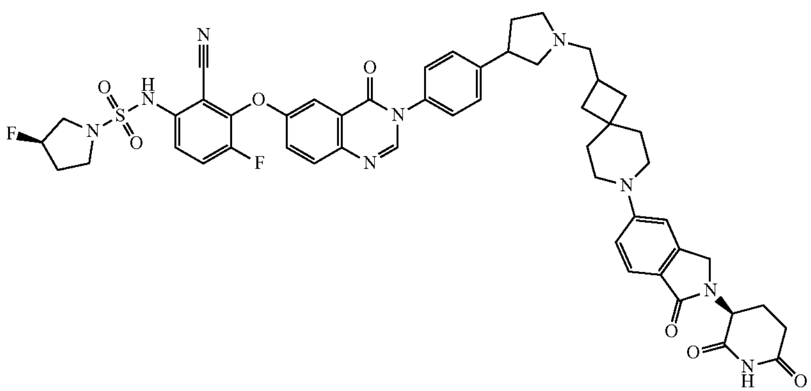 [SMILES: N#Cc1c(NS(=O)(=O)N2CC[C@@H](F)C2)ccc(F)c1Oc1ccc2ncn(-c3ccc(C4CCN(CC5CC6(CCN(c7ccc8c(c7)CN([C@H]7CCC(=O)NC7=O)C8=O)CC6)C5)C4)cc3)c(=O)c2c1] | (3R)-N-(2-cyano-3-{[3-(4-{1-[(7-{2-[(3S)-2,6-dioxopiperidin-3-yl]-1-oxo-2,3-dihydro-1H-isoindol-5-yl}-7-azaspiro[3.5]nonan-2-yl)methyl]pyrrolidin-3-yl}phenyl)-4-oxo-3,4-dihydroquinazolin-6-yl]oxy}-4-fluorophenyl)-3-fluoropyrrolidine-1-sulfonamide | $^1$H NMR (400 MHz, DMSO-d6) δ 10.94 (s, 1H), 8.26 (s, 1H), 8.14 (s, 1H), 7.81 (d, J = 8.8 Hz, 1H), 7.67 (dd, J = 3.0, 8.8 Hz, 1H), 7.57-7.46 (m, 5H), 7.43-7.33 (m, 2H), 7.32-7.27 (m, 1H), 7.09-7.01 (m, 2H), 5.35-5.16 (m, 1H), 5.04 (dd, J = 5.1, 13 |

TABLE 1-continued

| Cmp. No. | Structure | IUPAC Name | ¹H NMR |
|---|---|---|---|
| 264 | 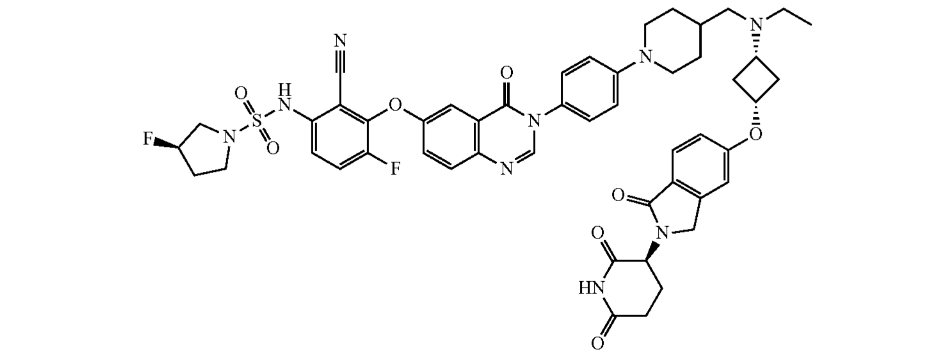 [SMILES: CCN(CC1CCN(c2ccc(-n3cnc4ccc(Oc5c(F)ccc(NS(=O)(=O)N6CC[C@@H](F)C6)c5C#N)cc4c3=O)cc2)CC1)[C@H]1C[C@@H](Oc2ccc3c(c2)CN([C@H]2CCC(=O)NC2=O)C3=O)C1] | (3R)-N-{2-cyano-3-[(3-{4-[4-({ethyl[(1r,3r)-3-({(3S)-2,6-dioxopiperidin-3-yl}oxy)cyclobutyl]amino}methyl)piperidin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d6) δ 10.96 (s, 1H), 8.23 (s, 1H), 7.80 (d, J = 9.2 Hz, 1H), 7.70-7.48 (m, 3H), 7.43-7.35 (m, 2H), 7.31 (d, J = 8.8 Hz, 2H), 7.09-7.02 (m, 3H), 7.01-6.94 (m, 1H), 5.39-5.16 (m, 1H), 5.07 (dd, J = 5.2, 13.2 Hz, 1H), 4.88 (s, |
| 265 | 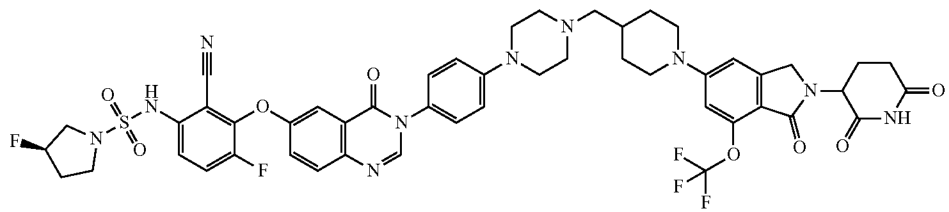 [SMILES: N#Cc1c(NS(=O)(=O)N2CC[C@@H](F)C2)ccc(F)c1Oc1ccc2ncn(-c3ccc(N4CCN(CC5CCN(c6cc7c(c(OC(F)(F)F)c6)C(=O)N(C6CCC(=O)NC6=O)C7)CC5)CC4)cc3)c(=O)c2c1] | (3R)-N-{2-cyano-3-[(3-{4-[4-({1-[2-(2,6-dioxopiperidin-3-yl)-1-oxo-7-(trifluoromethoxy)-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d6) δ 10.98 (s, 1H), 9.96 (s, 1H), 8.25 (s, 1H), 7.83 (d, J = 8.9 Hz, 1H), 7.76-7.63 (m, 2H), 7.50-7.39 (m, 2H), 7.36 (d, J = 8.4 Hz, 2H), 7.14-7.02 (m, 3H), 6.89 (s, 1H), 5.39 (d, J = 3.2 Hz, 1H), 5.21 (t, J = 2.8 Hz, 1H), 5.01 (m, 2H), 4.3 |
| 266 | 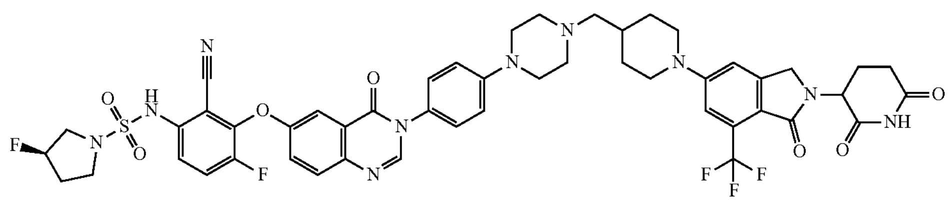 [SMILES: N#Cc1c(NS(=O)(=O)N2CC[C@@H](F)C2)ccc(F)c1Oc1ccc2ncn(-c3ccc(N4CCN(CC5CCN(c6cc7c(c(C(F)(F)F)c6)C(=O)N(C6CCC(=O)NC6=O)C7)CC5)CC4)cc3)c(=O)c2c1] | (3R)-N-{2-cyano-3-[(3-{4-[4-({1-[2-(2,6-dioxopiperidin-3-yl)-1-oxo-7-(trifluoromethyl)-2,3-dihydro-1H-isoindol-5-yl]piperidin-4-yl}methyl)piperazin-1-yl]phenyl}-4-oxo-3,4-dihydroquinazolin-6-yl)oxy]-4-fluorophenyl}-3-fluoropyrrolidine-1-sulfonamide | ¹H NMR (400 MHz, DMSO-d6) δ 10.98 (s, 1H), 9.96 (s, 1H), 8.25 (s, 1H), 7.83 (d, J = 8.9 Hz, 1H), 7.76-7.63 (m, 2H), 7.50-7.39 (m, 2H), 7.36 (d, J = 8.4 Hz, 2H), 7.14 (m, 2H), 7.02 (m, 2H), 5.39 (d, J = 3.2 Hz, 1H), 5.01 (m, 1H), 4.36 (m, 3H), 4.23 (d, J = 17.3 Hz |

TABLE 1-continued

| Cmp. No. | Structure | IUPAC Name | $^1$H NMR |
|---|---|---|---|
| 267 | 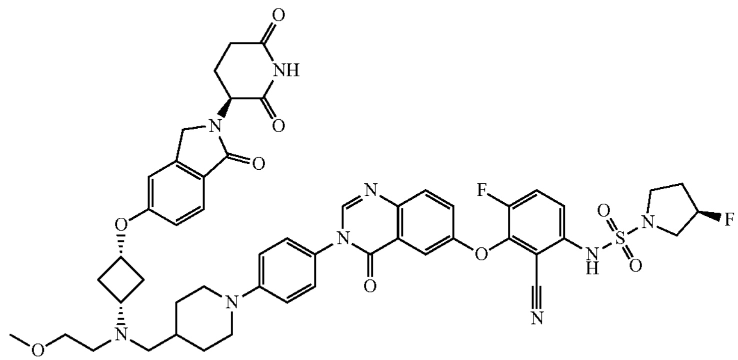 [SMILES: COCCN(CC1CCN(c2ccc(-n3cnc4ccc(Oc5c(F)ccc(NS(=O)(=O)N6CC[C@@H](F)C6)c5C#N)cc4c3=O)cc2)CC1)[C@H]1C[C@@H](Oc2ccc3c(c2)CN([C@H]2CCC(=O)NC2=O)C3=O)C1] | (3R)-N-[2-cyano-4-fluoro-3-{3-[4-{[(2-methoxyethyl)]((1r,3r)-3-({2-[(3S)-2,6-dioxopiperidin-3-yl]-1-oxo-2,3-dihydro-1H-isoindol-5-yl}oxy)cyclobutyl]amino]methyl]piperidin-1-yl}phenyl]-4-oxo-3,4-dihydroquinazolin-6-yl}oxy)phenyl]-3-fluoropyrrolidine-1-sulfonamide | $^1$H NMR (400 MHz, DMSO-d6) δ 8 10.96 (s, 1H), 8.27-8.19 (m, 1H), 7.85-7.77 (m, 1H), 7.68 (dd, J = 2.8, 8.8 Hz, 1H), 7.66-7.60 (m, 1H), 7.46-7.37 (m, 2H), 7.33-7.24 (m, 2H), 7.06-6.99 (m, 3H), 6.96 (d, J = 8.4 Hz, 1H), 5.41-5.20 (m, 1H), 5.12- |
| 268 | 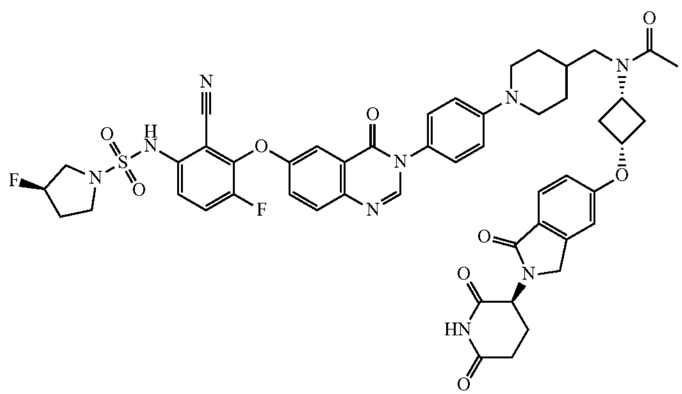 [SMILES: CC(=O)N(CC1CCN(c2ccc(-n3cnc4ccc(Oc5c(F)ccc(NS(=O)(=O)N6CC[C@@H](F)C6)c5C#N)cc4c3=O)cc2)CC1)[C@H]1C[C@@H](Oc2ccc3c(c2)CN([C@H]2CCC(=O)NC2=O)C3=O)C1] | N-[1-(4-{6-[2-cyano-6-fluoro-3-{[(3R)-3-fluoropyrrolidin-1-yl]sulfonyl}amino)phenoxy]-4-oxo-3,4-dihydroquinazolin-3-yl}piperidin-4-yl]methyl]-N-((1r,3r)-3-{[2-[(3S)-2,6-dioxopiperidin-3-yl]-1-oxo-2,3-dihydro-1H-isoindol-5-yl}oxy)cyclobutyl]acetamide | $^1$H NMR (400 MHz, DMSO-d6) δ 10.96 (s, 1H), 10.33 (s, 1H), 8.26 (d, J = 4.4 Hz, 1H), 7.91-7.78 (m, 2H), 7.71 (dd, J = 3.2, 8.9 Hz, 1H), 7.64 (dd, J = 3.2, 8.4 Hz, 1H), 7.52 (dd, J = 4.4, 9.2 Hz, 1H), 7.43 (d, J = 2.8 Hz, 1H), 7.30 (d, J = 8.8 Hz, 2H), 7. |

TABLE 1-continued

| Cmp. No. | Structure | IUPAC Name | $^1$H NMR |
|---|---|---|---|
| 269 | 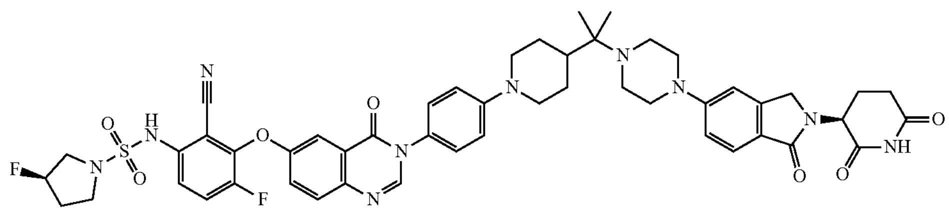 [SMILES: CC(C)(C1CCN(c2ccc(-n3cnc4ccc(Oc5c(F)ccc(NS(=O)(=O)N6CC[C@@H](F)C6)c5C#N)cc4c3=O)cc2)CC1)N1CCN(c2ccc3c(c2)CN([C@H]2CCC(=O)NC2=O)C3=O)CC1] | (3R)-N-(2-cyano-3-{[3-(4-{4-[2-(4-{2-[(3S)-2,6-dioxopiperidin-3-yl]-1-oxo-2,3-dihydro-1H-isoindol-5-yl}piperazin-1-yl)propan-2-yl]piperidin-1-yl}phenyl)-4-oxo-3,4-dihydroquinazolin-6-yl]oxy}-4-fluorophenyl)-3-fluoropyrrolidine-1-sulfonamide | $^1$H NMR (400 MHz, DMSO-d6) δ 10.95 (s, 1H), 10.51-10.12 (m, 1H), 8.25 (s, 1H), 8.13 (s, 1H), 7.82 (d, J = 9.2 Hz, 1H), 7.78-7.65 (m, 2H), 7.54 (d, J = 8.8 Hz, 1H), 7.46 (dd, J = 4.0, 9.2 Hz, 1H), 7.41 (d, J = 3.2 Hz, 1H), 7.31 (d, J = 8.8 Hz, 2H), 7.12 |

Biological Assays
Target Protein Degradation
A. T-Rex 293 Cells (96 well format)

T-Rex 293 cells were purchased from Invitrogen (#R71007), and stably transfected with a pcDNA4/TO_HA-B-RAF_V600E construct, using 400 ug Zeocin for selection. V600e cells are plated in ulbecco's Modified Eagle Medium (DMEM; Gibco #11965118) containing 10% fetal bovine serum (FBS; Gibco #16000044) and 1 ng/mL doxycycline (Selleckchem #4163) at a density of 5,000 cells/well in 50 µl on poly-D-lysine (PDL) coated, black clear bottom 96-well plates (Corning #354640) and incubated for 24 hours at 37° C. with 5% $CO_2$. The following day 50 ul of tested compound was added at 2× concentration in DMEM with a final concentration ranging from 1 µM to 0.1 nM in 0.1% dimethylsulfoxide (DMSO), and incubated for 24 hours at 37° C. with 5% $CO_2$. At the end of the experimental treatment, the media was flicked off and cells washed once with phosphate-buffered saline (PBS)++(PBS with CaCl and MgCl) and gently replacing with 200 µl PBS++ per well. The PBS++ was removed and 50 uL 4% paraformaldehyde (PFA; EMS #15710) in PBS++ was added, and incubate at room temperature for 15 minutes. Cells were washed once with PBS++ and 50 uL 0.1% Triton X-100 (Fisher #BP151-500) in PBS++ was added. Plate was incubate for 5 minutes at room temperature. Cells were was once with PBS++. Cells were blocked with 100 uL Licor blocking buffer (Licor #927-50000) for 1 hour at room temperature. Next, 50 uL of HA antibody (CST #3724) at 1:1000 in Licor blocking buffer was added, and the plate icubate overnight at 4° C. The plates were parafilmed to prevent evaporation. Plate was washed three times with 200 uL PBS++. Fifty microliters of HCS secondary antibody solution [1:1000 Hoechst (Invitrogen #H3570), 1:1000 phalloidin (Invitrogen #A22287) and 1:5000 Alexa fluor (Invitrogen #A11008)] was added and incubated for 1 hour. Plate was wash three times with 200 uL PBS++, and imaged on a high content reader (ImageXpress Micro XLS, Molecular Devices).

B. T-Rex 293 Cells (96 Well Format)

T-Rex 293 cells were purchased from Invitrogen (#R71007), and stably transfected with a pcDNA4/TO_HA-B-RAF_G466V construct, using 400 ug Zeocin for selection. G466V cells are plated in ulbecco's Modified Eagle Medium (DMEM; Gibco #11965118) containing 10% fetal bovine serum (FBS; Gibco #16000044) and 0.75 ng/mL doxycycline (Selleckchem #4163) at a density of 5,000 cells/well in 50 µl on poly-D-lysine (PDL) coated, black clear bottom 96-well plates (Corning #354640) and incubated for 24 hours at 37° C. with 5% $CO_2$. The following day 50 ul of tested compound was added at 2× concentration in DMEM with a final concentration ranging from 30 nM to 3 pM in 0.1% dimethylsulfoxide (DMSO), and incubated for 24 hours at 37° C. with 5% $CO_2$. At the end of the experimental treatment, the media was flicked off and cells washed once with phosphate-buffered saline (PBS)++(PBS with CaCl and MgCl) and gently replacing with 200 µl PBS++ per well. The PBS++ was removed and 50 uL 4% paraformaldehyde (PFA; EMS #15710) in PBS++ was added, and incubate at room temperature for 15 minutes. Cells were washed once with PBS++ and 50 uL 0.1% Triton X-100 (Fisher #BP151-500) in PBS++ was added. Plate was incubate for 5 minutes at room temperature. Cells were was once with PBS++. Cells were blocked with 100 uL Licor blocking buffer (Licor #927-50000) for 1 hour at room temperature. Next, 50 uL of HA antibody (CST #3724) at 1:1000 in Licor blocking buffer was added, and the plate icubate overnight at 4° C. The plates were parafilmed to prevent evaporation. Plate was washed three times with 200 uL PBS++. Fifty microliters of HCS secondary antibody solution [1:1000 Hoechst (Invitrogen #H3570), 1:1000 phalloidin (Invitrogen #A22287) and 1:5000 Alexa fluor (Invitrogen #A11008)] was added and incubated for 1 hour. Plate was wash three times with 200 uL PBS++, and imaged on a high content reader (ImageXpress Micro XLS, Molecular Devices).

C. T-Rex 293 Cells (384 Well Format)

T-Rex 293 cells were purchased from Invitrogen (#R71007), and stably transfected with a pcDNA4/TO_HA-BRAF_V600E construct, using 400 ug Zeocin for selection. V600E cells are plated in DMEM media (Gibco #11965118) containing 10% FBS (Gibco #16000044), 1% penicillin-streptomycin (ThermoFisher #15140122), 1:250 zeocin (Invitrogen #R-25005), and 1 ng/mL doxycycline (Selleckchem #4163) at a density of 7,500 cells/well in 45 µl on PDL coated, black clear bottom 384 well plates (Corning #354663) and incubated at 37° C.+5% $CO_2$ for 24 hours. The following day, PROTAC compounds in a 1:3 11 point dilution are diluted into DMEM media using an Agilent Bravo. 5 ul of PROTACs suspended in DMEM media are added to the cells, with a final assay concentration ranging from 300 nM to 5 pM in 0.5% DMSO. Plates are incubated at 37° C.+5% CO2 for 24 hours. At the end of treatment, media is aspirated, and cells are fixed in 50 uL 4% PFA (EMS #15710) in PBS++(PBS, 1 mM CaCl, 1 mM MgCl) at RT for 15 minutes. Cells are washed 2× with 60 uL PBS++ and permeabilized in 50 uL 1% Triton X-100 (Sigma #93443) in PBS++ for 5 minutes at RT. Cells are washed in PBS++ prior to blocking with 50 uL Licor blocking buffer (Licor #927-60001) for 1 hour at RT. HA-tagged BRAF was stained using 50 uL HA antibody (CST #3724) at 1:1000 in Licor blocking buffer for two hours at RT. Primary is aspirated before adding 50 ul of secondary antibody solution containing 1:1000 Hoechst (ThermoFisher #62249), 1:1000 HCS CellMask Deep Red Stain (ThermoFisher #H32721), and 1:5000 goat anti-rabbit IgG Alexa-Fluor 488 (ThermoFisher #A32731) in PBS++ for 1 hr at RT. Plates are washed 4× with 60 uL PBS++, then sealed with Adhesive Black Light Absorbing Film (VWR #89087-692) and imaged on the ThermoFisher CX7 PRO high content instrument. BRAF intensity is quantified in HCS Studio software (ThermoFisher), using a custom script, exported, analyzed using KNIME, and curve curation is performed in an ELN (Scilligence). Cell toxicity is measured via comparing number of nuclei in PROTAC treated wells to DMSO controls.

D. T-Rex 293 Cells (384 Well Format)

T-Rex 293 cells were purchased from Invitrogen (#R71007), and stably transfected with a pcDNA4/TO_HA-BRAF_G466V construct, using 400 ug Zeocin for selection. G466V cells are plated in DMEM media (Gibco #11965118) containing 10% FBS (Gibco #16000044), 1% penicillin-streptomycin (ThermoFisher #15140122), 1:250 zeocin (Invitrogen #R-25005), and 1 ng/mL doxycycline (Selleckchem #4163) at a density of 7,500 cells/well in 45 µl on PDL coated, black clear bottom 384 well plates (Corning #354663) and incubated at 37° C.+5% CO2 for 24 hours. The following day, PROTAC compounds in a 1:3 11 point dilution are diluted into DMEM media using an Agilent Bravo. 5 ul of PROTACs suspended in DMEM media are added to the cells, with a final assay concentration ranging from 300 nM to 5 pM in 0.5% DMSO. Plates are incubated at 37° C.+5% CO2 for 24 hours. At the end of treatment, media is aspirated, and cells are fixed in 50 uL 4% PFA (EMS #15710) in PBS++(PBS, 1 mM CaCl, 1 mM MgCl) at RT for 15 minutes. Cells are washed 2× with 60 uL PBS++ and permeabilized in 50 uL 1% Triton X-100 (Sigma #93443) in PBS++ for 5 minutes at RT. Cells are washed in PBS++ prior to blocking with 50 uL Licor blocking buffer (Licor #927-60001) for 1 hour at RT. HA-tagged BRAF was stained using 50 uL HA antibody (CST #3724) at 1:1000 in Licor blocking buffer for two hours at RT. Primary is aspirated before adding 50 ul of secondary antibody solution containing 1:1000 Hoechst (ThermoFisher #62249), 1:1000 HCS CellMask Deep Red Stain (ThermoFisher #H32721), and 1:5000 goat anti-rabbit IgG Alexa-Fluor 488 (ThermoFisher #A32731) in PBS++ for 1 hr at RT. Plates are washed 4× with 60 uL PBS++, then sealed with Adhesive Black Light Absorbing Film (VWR #89087-692) and imaged on the ThermoFisher CX7 PRO high content instrument. BRAF intensity is quantified in HCS Studio software (ThermoFisher), using a custom script, exported, analyzed using KNIME, and curve curation is performed in an ELN (Scilligence). Cell toxicity is measured via comparing number of nuclei in PROTAC treated wells to DMSO controls.

The concentration of an exemplary compound that leads to half maximal degradation ($DC_{50}$) as well as the maximum degradation observed ($D_{max}$, conventionally expressed as a percentage of control) is shown below in Table 2.

TABLE 2

| Cmp No. | B-RAF V600E $DC_{50}$ (nM) | B-RAF V600E $D_{Max}$ (%) | B-RAF G466V $DC_{50}$ (nM) | B-RAF G466V $D_{Max}$ (%) |
|---|---|---|---|---|
| 1 | B | B | A | B |
| 2 | C | C | A | B |
| 3 | C | C | B | B |
| 4 | B | B | B | B |
| 5 | D | NT | D | NT |
| 6 | D | NT | A | C |
| 7 | D | B | C | B |
| 8 | C | B | B | C |
| 9 | C | B | D | NT |
| 10 | D | NT | D | NT |
| 11 | B | B | D | NT |
| 12 | B | B | D | NT |
| 13 | B | B | D | NT |
| 14 | C | B | D | NT |
| 15 | D | NT | D | NT |
| 30 | C | C | B | B |
| 31 | D | NT | D | NT |
| 32 | C | B | D | NT |
| 65 | D | NT | C | B |
| 66 | C | B | D | NT |
| 67 | C | B | D | NT |
| 68 | C | B | B | B |
| 69 | C | B | B | B |
| 70 | C | B | B | C |
| 71 | D | NT | D | NT |
| 72 | D | NT | D | NT |
| 73 | B | B | B | B |
| 74 | C | B | B | C |
| 75 | C | B | B | C |
| 76 | B | B | B | C |
| 77 | C | B | B | B |
| 78 | B | B | B | B |
| 79 | C | B | A | B |
| 80 | C | B | B | B |
| 81 | C | B | NT | NT |
| 82 | C | B | B | C |
| 83 | C | B | A | C |
| 84 | B | B | A | B |
| 85 | B | B | B | B |
| 86 | B | B | A | C |
| 87 | D | NT | D | NT |
| 88 | B | C | A | B |
| 89 | B | B | B | C |
| 90 | C | B | B | B |
| 91 | B | B | B | C |
| 92 | C | C | C | C |
| 93 | C | B | B | C |
| 94 | B | B | B | C |
| 95 | B | B | B | C |
| 96 | B | B | B | C |
| 97 | C | B | B | B |
| 98 | C | B | B | B |
| 99 | C | B | B | B |
| 100 | C | B | B | B |
| 101 | C | B | B | B |
| 102 | C | B | D | NT |
| 103 | B | B | B | B |
| 104 | B | B | B | B |
| 105 | B | B | B | C |
| 106 | C | B | B | C |
| 107 | B | B | B | B |
| 108 | B | B | B | C |
| 109 | C | B | B | B |
| 110 | C | B | D | NT |
| 111 | C | B | B | B |
| 112 | B | B | B | B |
| 113 | C | B | B | B |
| 114 | C | C | B | B |
| 115 | C | B | NT | NT |
| 116 | C | C | NT | NT |
| 117 | C | B | NT | NT |
| 118 | D | NT | NT | NT |
| 119 | D | NT | NT | NT |
| 120 | B | C | NT | NT |
| 121 | C | B | NT | NT |
| 127 | C | B | D | NT |
| 128 | C | C | B | B |
| 129 | C | B | B | B |
| 130 | D | NT | C | C |
| 131 | C | B | B | C |
| 132 | C | B | A | B |
| 133 | C | B | B | B |
| 134 | C | B | B | B |
| 135 | D | NT | D | NT |
| 136 | B | C | B | B |
| 137 | D | NT | D | C |
| 138 | C | C | B | C |
| 139 | B | C | D | NT |
| 140 | C | C | D | NT |
| 141 | C | C | B | C |
| 142 | B | B | A | C |
| 143 | A | B | D | NT |
| 144 | B | C | C | C |
| 145 | C | B | B | B |
| 146 | B | B | B | B |
| 147 | B | B | B | B |
| 148 | C | C | D | NT |
| 149 | B | C | C | B |
| 150 | A | B | A | C |
| 151 | B | B | B | B |
| 152 | C | B | B | C |
| 153 | C | B | D | NT |
| 154 | C | C | C | C |
| 155 | D | NT | B | C |
| 156 | C | B | D | NT |
| 157 | C | B | D | NT |
| 158 | C | C | A | C |
| 159 | C | B | B | C |
| 160 | C | C | D | NT |
| 161 | C | B | B | C |
| 162 | B | B | A | C |
| 163 | C | B | C | C |
| 164 | C | B | A | C |
| 165 | A | C | D | C |
| 166 | D | NT | B | C |
| 167 | C | B | B | C |
| 168 | C | C | C | B |
| 169 | C | B | B | C |
| 170 | B | C | B | C |
| 171 | C | B | B | B |
| 172 | C | B | B | C |
| 173 | C | B | D | NT |

TABLE 2-continued

| Cmp No. | B-RAF V600E DC$_{50}$ (nM) | B-RAF V600E D$_{Max}$ (%) | B-RAF G466V DC$_{50}$ (nM) | B-RAF G466V D$_{Max}$ (%) |
|---|---|---|---|---|
| 174 | C | B | B | C |
| 175 | B | B | B | B |
| 176 | C | B | B | B |
| 177 | B | B | B | B |
| 178 | C | B | C | B |
| 179 | C | A | B | A |
| 180 | C | B | D | B |
| 181 | C | B | B | C |
| 182 | C | C | B | B |
| 183 | C | B | D | NT |
| 184 | C | C | D | NT |
| 185 | C | B | C | C |
| 186 | C | B | C | C |
| 187 | C | A | B | C |
| 188 | C | B | B | B |
| 189 | C | B | B | B |
| 190 | C | B | B | B |
| 191 | C | B | B | B |
| 192 | C | B | B | B |
| 193 | C | B | B | B |
| 194 | C | C | B | B |
| 195 | C | C | B | C |
| 196 | C | B | B | B |
| 197 | C | C | B | B |
| 198 | C | C | B | B |
| 199 | C | B | B | B |
| 200 | C | B | B | B |
| 201 | C | B | B | B |
| 202 | C | B | B | B |
| 203 | C | B | B | B |
| 204 | C | B | B | C |
| 205 | C | C | B | C |
| 206 | C | A | B | C |
| 207 | C | A | B | B |
| 208 | B | B | B | C |
| 209 | C | B | C | B |
| 210 | C | B | C | B |
| 211 | C | B | B | B |
| 212 | C | C | B | B |
| 213 | C | C | B | C |
| 214 | D | NT | C | C |
| 215 | C | B | B | C |
| 216 | C | B | B | C |
| 217 | C | B | B | C |
| 218 | C | B | B | B |
| 219 | C | B | B | B |
| 220 | C | B | C | B |
| 221 | C | B | B | B |
| 222 | C | B | B | B |
| 223 | C | B | B | B |
| 224 | C | C | C | B |
| 225 | D | NT | C | B |
| 226 | C | C | B | B |
| 227 | C | C | C | C |
| 228 | C | B | B | B |
| 229 | C | B | B | B |
| 230 | C | B | B | B |
| 231 | C | B | B | B |
| 232 | C | B | B | B |
| 233 | C | B | C | B |
| 234 | C | B | B | B |
| 235 | C | B | B | B |
| 236 | C | B | C | A |
| 237 | C | B | B | A |
| 238 | C | A | B | A |
| 239 | C | A | B | A |
| 240 | B | A | B | A |
| 241 | D | NT | D | B |
| 242 | D | NT | C | C |
| 243 | D | NT | C | B |
| 244 | C | B | B | C |
| 245 | C | A | B | B |
| 246 | C | B | B | B |
| 247 | C | A | B | B |
| 248 | C | A | B | A |
| 249 | D | NT | B | B |
| 250 | C | B | B | B |
| 251 | C | B | B | B |
| 252 | B | C | B | B |
| 253 | C | B | B | B |
| 254 | C | B | B | A |
| 255 | C | B | B | A |
| 256 | C | B | B | A |
| 257 | C | B | B | B |
| 258 | C | B | B | B |
| 259 | C | B | B | B |
| 260 | C | B | B | A |
| 261 | C | B | B | A |
| 262 | B | A | B | A |
| 263 | C | A | B | A |
| 264 | C | B | B | B |
| 265 | C | B | C | B |
| 266 | C | B | D | NT |
| 267 | C | B | C | B |
| 268 | D | NT | C | C |
| 269 | C | B | C | A |

Assays A and B were used in Examples 1-82
Assays C and D were used in Examples 83-269
*DC$_{50}$ V600E (nM) D > 500; 50 < C ≤ 500; 5 < B ≤ 50; A ≤ 5
*DC$_{50}$ G446V (nM) A ≤ 1; 1 < B ≤ 10; 10 < C ≤ 30; D > 30
**D$_{Max}$ (%): C ≤ 35; 35 < B < 70; A ≥ 70
NT = not tested Tumor Growth Inhibition Studies H1666 was obtained from ATCC (CRL-5885) and maintained in RPMI-1640 medium (Gibco 21870-076) supplemented by 10% fetal bovine serum (Gibco 26140-079). Female CB17SCID mice were inoculated subcutaneously in the right flank with H1666 cells (5×10$^6$) in 0.2 ml of phenol-red free RPMI (Gibco 11835030) supplemented with Matrigel at a 1:3 ratio for tumor development. Tumor volume was measured twice weekly by calipers, and volume (mm$^3$) was calculated by formula: V=0.5a×b$^2$ in which a and b are the long and short diameters of the tumor in mm, respectively. The animals were randomized into treatment groups once the tumors reached an average volume of 150 mm$^3$, around 21 days after implantation, and the treatment began on Day 0.

Figure 2:
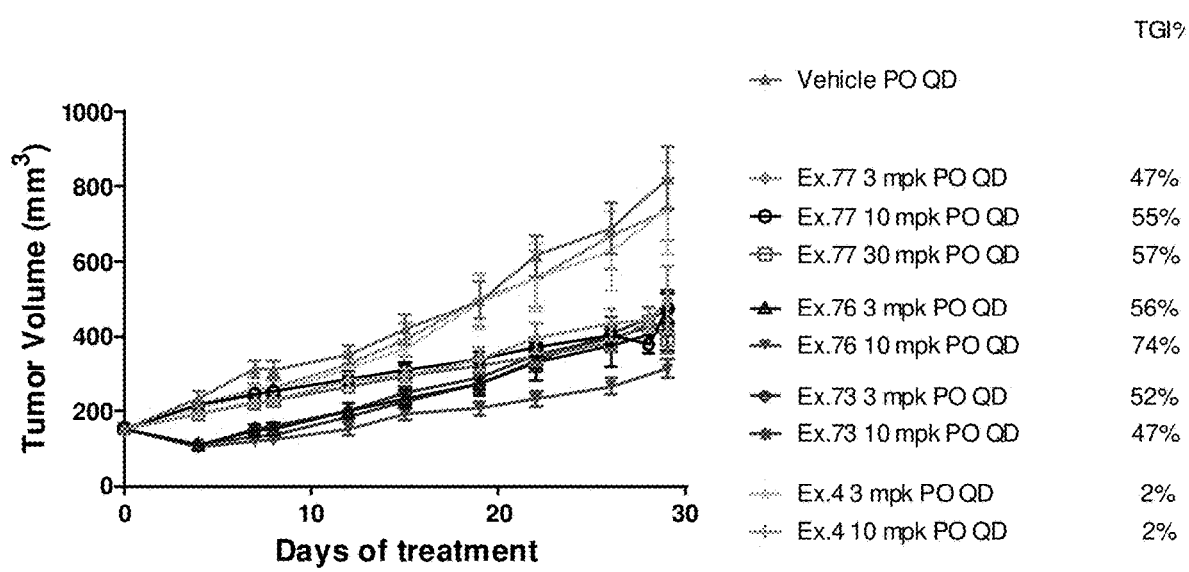
FIG. 2 shows tumor growth inhibition results in H1666 tumors using compounds 74, 73, 76, and 77 of the present disclosure.
Figure 3:
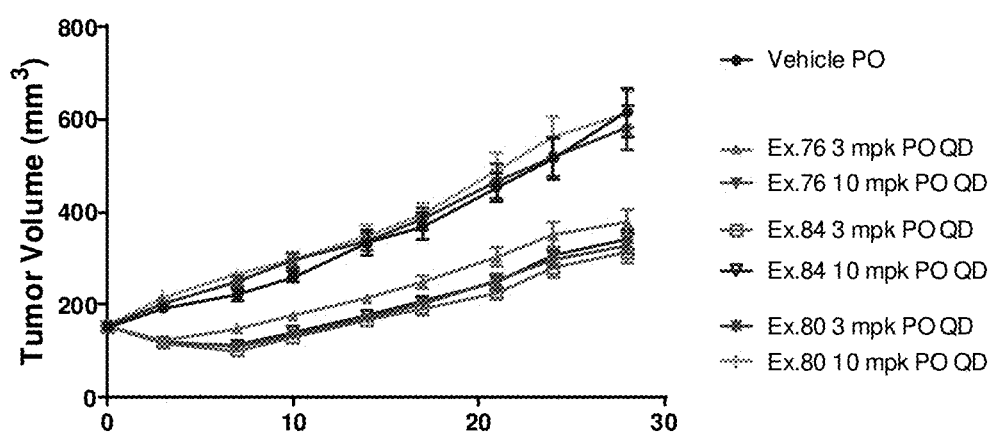
FIG. 3 shows tumor growth inhibition results in H1666 tumors using compounds 76, 80, and 84 of the present disclosure.
Figure 4:
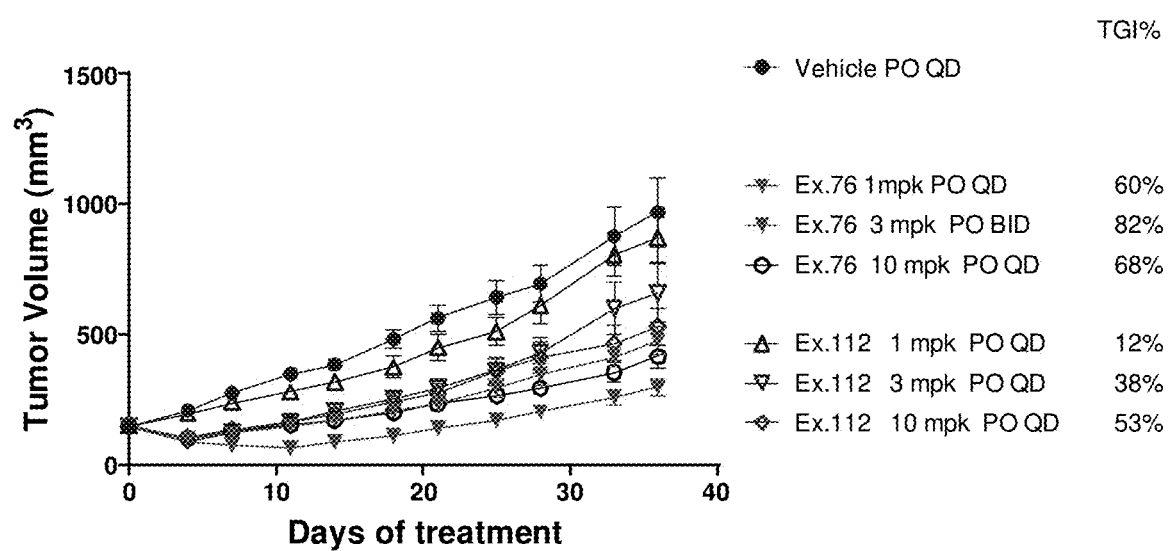
FIG. 4 shows tumor growth inhibition results in H1666 tumors using compounds 76 and 112 of the present disclosure.
Figure 5:
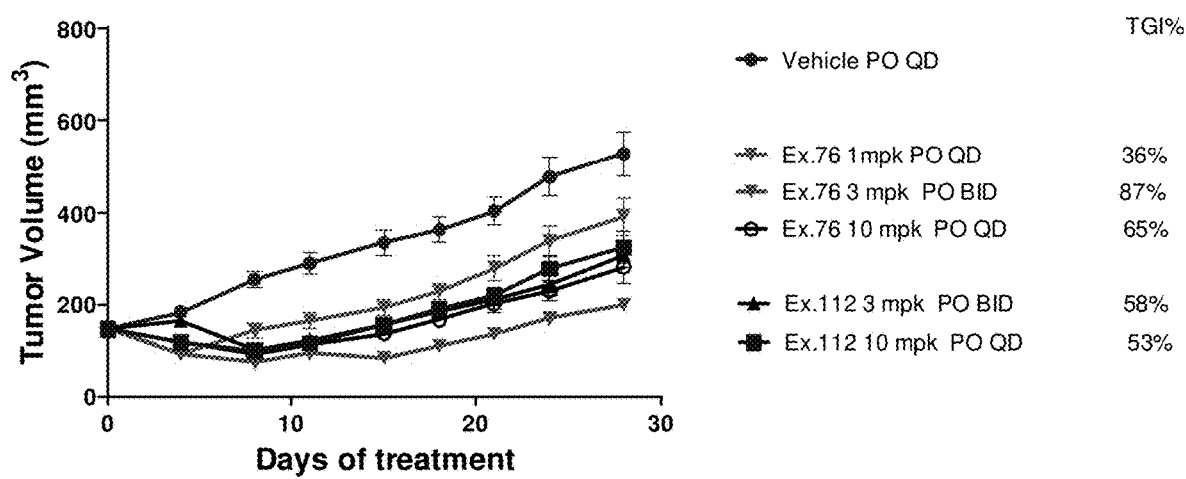
FIG. 5 shows tumor growth inhibition results in H1666 tumors using compounds 76 and 112 of the present disclosure.

Compounds were administrated to mice bearing H1666 tumors orally (PO), daily (QD), or twice a day (BID), at indicated concentrations, for 20-36 days. All compounds were formulated in 30% SBE-B-CD in 10 mM Citrate (pH 3.0) as vehicle and dosed at a volume of 5 ml/kg. Body weight and tumor volumes were measured twice per week and reported as Mean±SEM. Percentage of tumor growth inhibition (% TGI) was calculated with the formula: [1-(Tf-Ti)/(Cf-Ci)]*100 (T: treatment; C: vehicle; f: final point; i: initial point). Results are shown in FIGS. 1 to 5.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example. a The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:
1. A compound represented by the structural formula:

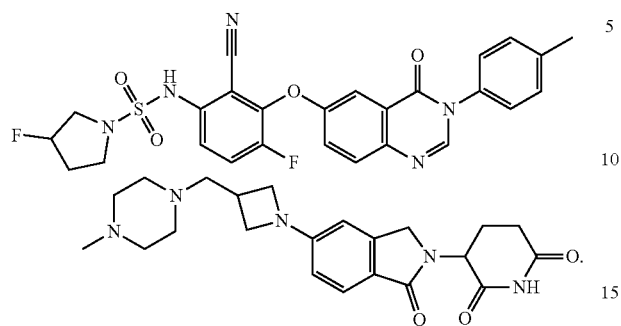

2. A compound represented by the structural formula:

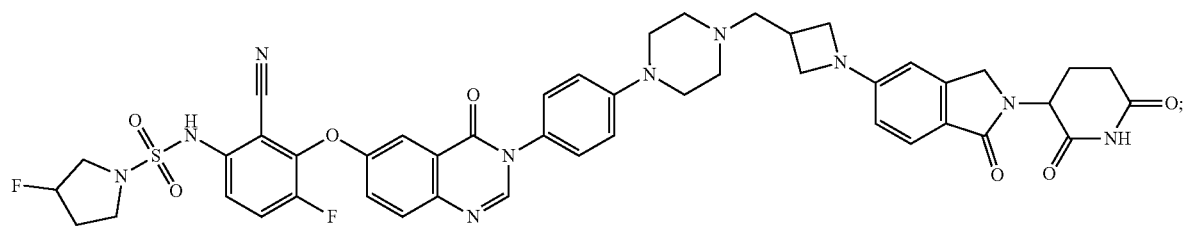 [SMILES: N#Cc1c(NS(=O)(=O)N2CCC(F)C2)ccc(F)c1Oc1ccc2ncn(-c3ccc(N4CCN(CC5CN(c6ccc7c(c6)CN(C6CCC(=O)NC6=O)C7=O)C5)CC4)cc3)c(=O)c2c1]

or a pharmaceutically acceptable salt thereof.

3. A pharmaceutical composition comprising a compound represented by the structural formula:

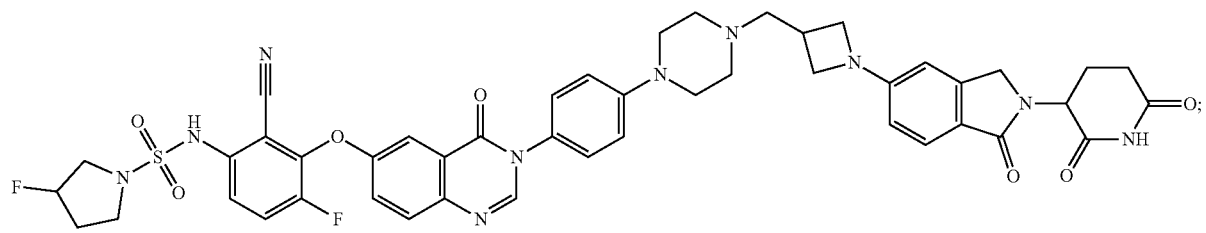 [SMILES: N#Cc1c(NS(=O)(=O)N2CCC(F)C2)ccc(F)c1Oc1ccc2ncn(-c3ccc(N4CCN(CC5CN(c6ccc7c(c6)CN(C6CCC(=O)NC6=O)C7=O)C5)CC4)cc3)c(=O)c2c1]

or a pharmaceutically acceptable salt thereof; and a pharmaceutically acceptable carrier.

4. The compound of claim 1, wherein the compound is represented by the structural formula:

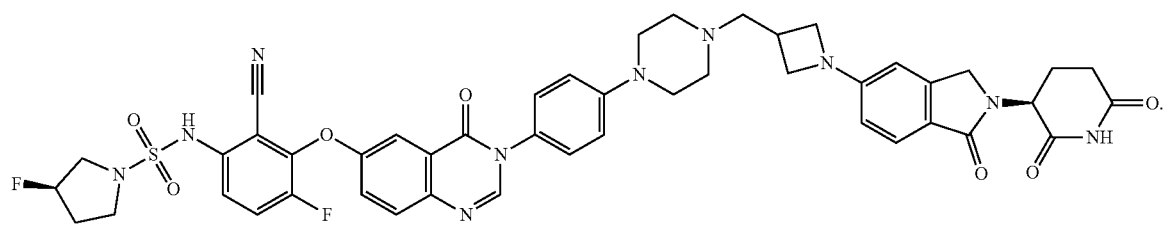 [SMILES: N#Cc1c(NS(=O)(=O)N2CC[C@@H](F)C2)ccc(F)c1Oc1ccc2ncn(-c3ccc(N4CCN(CC5CN(c6ccc7c(c6)CN([C@H]6CCC(=O)NC6=O)C7=O)C5)CC4)cc3)c(=O)c2c1]

5. The compound of claim 2, wherein the compound is represented by the structural formula:
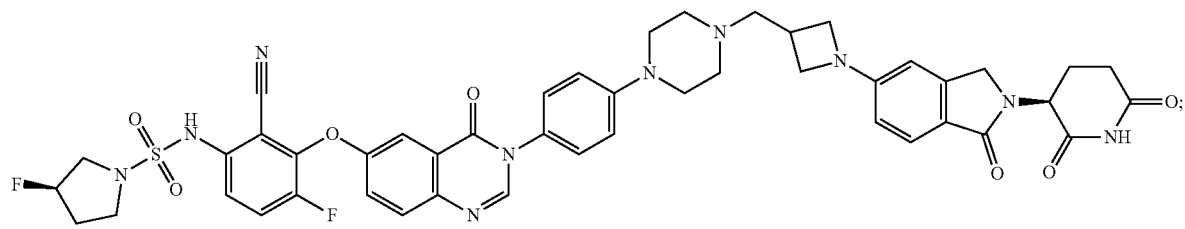 [SMILES: N#Cc1c(NS(=O)(=O)N2CC[C@@H](F)C2)ccc(F)c1Oc1ccc2ncn(-c3ccc(N4CCN(CC5CN(c6ccc7c(c6)CN([C@H]6CCC(=O)NC6=O)C7=O)C5)CC4)cc3)c(=O)c2c1]
or a pharmaceutically acceptable salt thereof.
6. The pharmaceutical composition of claim 1, wherein the compound is represented by the structural formula:
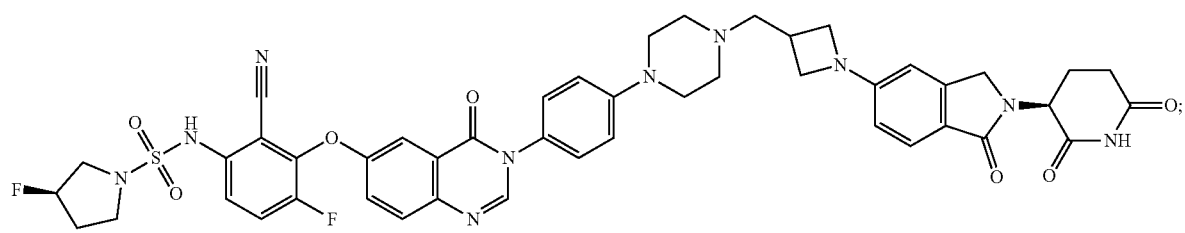 [SMILES: N#Cc1c(NS(=O)(=O)N2CC[C@@H](F)C2)ccc(F)c1Oc1ccc2ncn(-c3ccc(N4CCN(CC5CN(c6ccc7c(c6)CN([C@H]6CCC(=O)NC6=O)C7=O)C5)CC4)cc3)c(=O)c2c1]
or a pharmaceutically acceptable salt thereof.
* * * * *

UNITED STATES PATENT AND TRADEMARK OFFICE
CERTIFICATE OF CORRECTION

Page 1 of 1

PATENT NO. : 11,957,759 B1
APPLICATION NO. : 18/243177
DATED : April 16, 2024
INVENTOR(S) : Keith R. Hornberger It is certified that error appears in the above-identified patent and that said Letters Patent is hereby corrected as shown below:

In the Claims

In Claim 1, Column 449, Line numbers 5-15, please replace the structure "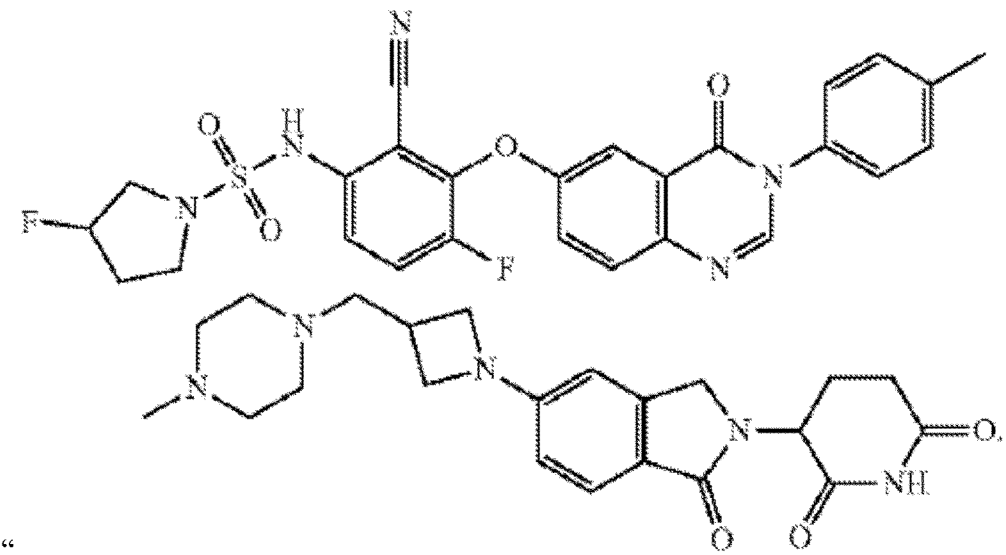" with the structure --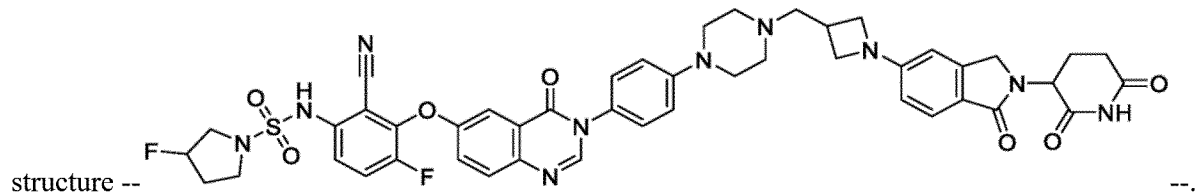--.

In Claim 6, Column 501, Line number 16, please replace the phrase "of claim 1" with the phrase --of claim 3--.

Signed and Sealed this
Twenty-first Day of May, 2024

Katherine Kelly Vidal
*Director of the United States Patent and Trademark Office*